(12) United States Patent
Josien et al.

(10) Patent No.: US 12,178,842 B2
(45) Date of Patent: Dec. 31, 2024

(54) PCSK9 ANTAGONIST COMPOUNDS

(71) Applicant: MERCK SHARP & DOHME LLC, Rahway, NJ (US)

(72) Inventors: Hubert Josien, Jersey City, NJ (US); Abbas Walji, Lansdale, PA (US); Harold B. Wood, Westfield, NJ (US); Fa-Xiang Ding, Staten Island, NY (US); Jian Liu, Edison, NJ (US); Thomas Joseph Tucker, North Wales, PA (US); Michael Man-Chu Lo, Bedminster, NJ (US); Liangqin Guo, Monroe, NJ (US)

(73) Assignee: MERCK SHARP & DOHME LLC, Rahway, NJ (US)

( * ) Notice: Subject to any disclaimer, the term of this patent is extended or adjusted under 35 U.S.C. 154(b) by 0 days.

(21) Appl. No.: 18/051,250

(22) Filed: Oct. 31, 2022

(65) Prior Publication Data

US 2023/0165932 A1 Jun. 1, 2023

Related U.S. Application Data

(62) Division of application No. 17/005,686, filed on Aug. 28, 2020, now Pat. No. 11,484,565.

(60) Provisional application No. 62/950,690, filed on Dec. 19, 2019, provisional application No. 62/894,286, filed on Aug. 30, 2019.

(51) Int. Cl.
| | |
|---|---|
| *A61K 38/00* | (2006.01) |
| *A61K 38/12* | (2006.01) |
| *A61P 3/06* | (2006.01) |
| *C07K 9/00* | (2006.01) |

(52) U.S. Cl.
CPC .............. *A61K 38/12* (2013.01); *A61P 3/06* (2018.01); *C07K 9/006* (2013.01)

(58) Field of Classification Search
None
See application file for complete search history.

(56) References Cited

U.S. PATENT DOCUMENTS

| | | | |
|---|---|---|---|
| 4,393,046 | A | 7/1983 | Baylis et al. |
| 2010/0041102 | A1 | 2/2010 | Sitlani et al. |
| 2012/0219558 | A1 | 8/2012 | Ni et al. |
| 2013/0158021 | A1 | 6/2013 | Dong et al. |
| 2013/0281366 | A1 | 10/2013 | Pingali et al. |
| 2017/0081383 | A1 | 3/2017 | Gruber |
| 2017/0189470 | A1 | 7/2017 | Wang et al. |
| 2018/0023071 | A1 | 1/2018 | Basak |
| 2023/0144324 | A1* | 5/2023 | Josien ............... C07K 7/64 |
| | | | 530/317 |
| 2023/0159592 | A1* | 5/2023 | Wood ............... A61P 3/06 |
| | | | 514/7.4 |

FOREIGN PATENT DOCUMENTS

| | | |
|---|---|---|
| WO | WO 2010/144038 A1 | 12/2010 |
| WO | WO 2012/040259 A2 | 3/2012 |
| WO | WO 2017/181061 A1 | 10/2017 |
| WO | WO 2017/220701 A1 | 12/2017 |
| WO | WO 2018/053517 A1 | 3/2018 |
| WO | WO 2019/246349 A1 | 12/2019 |
| WO | WO 2019/246352 A1 | 12/2019 |
| WO | WO 2019/246386 A1 | 12/2019 |
| WO | WO 2019/246387 A1 | 12/2019 |
| WO | WO 2019/246405 A1 | 12/2019 |

(Continued)

OTHER PUBLICATIONS

Chaudhary et al., "PCSK9 inhibitors: A new era of lipid lowering therapy", *World Journal of Cardiology* 9(2):76-91 (2017).

(Continued)

*Primary Examiner* — Aradhana Sasan
*Assistant Examiner* — Mercy H Sabila
(74) *Attorney, Agent, or Firm* — LATHROP GPM LLP; Brian C. Trinque

(57) ABSTRACT

Disclosed are compounds of Formula A, or a pharmaceutically acceptable salt thereof:

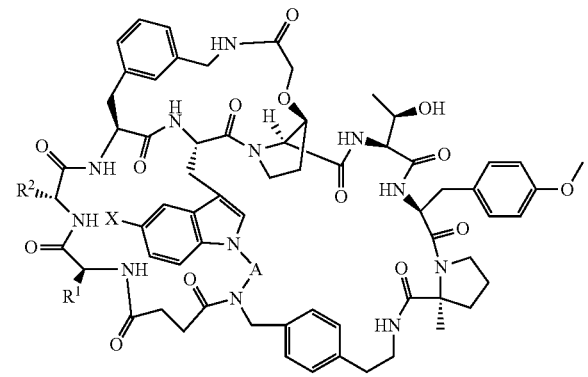

where A, X, $R^1$, and $R^2$ are as defined herein, which compounds have properties for antagonizing PCSK9. Also described are pharmaceutical formulations comprising the compounds of Formula I or their salts, and methods of treating cardiovascular disease and conditions related to PCSK9 activity, e.g. atherosclerosis, hypercholesterolemia, coronary heart disease, metabolic syndrome, acute coronary syndrome, or related cardiovascular disease and cardiometabolic conditions.

18 Claims, No Drawings

(56) References Cited

FOREIGN PATENT DOCUMENTS

WO     WO 2020/009805 A3     1/2020

OTHER PUBLICATIONS

Elbitar et al., "Proprotein convertase subtilisin/kexin 9 (PCSK9) inhibitors and the future of dyslipidemia therapy: an updated patent review (2011-2015)", *Expert Opinion on Therapeutic Patents* 26(12):1377-1392 (2016).

He et al., "Lowering serum lipids via PCSK9-targeting drugs: current advances and future perspectives", *ACTA Pharmacologica Sinica* 38:301-311 (2017).

International Search Report and Written Opinion in related PCT Application No. PCT/US2019/038220, mailed Nov. 5, 2019, 11 pages.

International Search Report and Written Opinion in related PCT Application No. PCT/US2019/038155, mailed Nov. 15, 2019, 6 pages.

International Search Report and Written Opinion in related PCT Application No. PCT/US2019/038221, mailed Nov. 18, 2019, 12 pages.

International Search Report and Written Opinion in related PCT Application No. PCT/US2019/038247, mailed Apr. 20, 2020, 13 pages.

International Search Report and Written Opinion in related PCT Application No. PCT/US2019/038250, mailed Sep. 17, 2019, 7 pages.

International Search Report and Written Opinion in related PCT Application No. PCT/US2019/038158, mailed Dec. 26, 2019, 7 pages.

International Search Report and Written Opinion in related PCT Application No. PCT/US2020/048342, mailed Nov. 18, 2020, 11 pages.

International Search Report and Written Opinion in related PCT Application No. PCT/US2020/066046, mailed Mar. 2, 2021, 3 pages.

Umemura et al., "Characterization of the biosynthetic gene cluster for the ribosomally synthesized cyclic peptide ustiloxin B in Aspergillus flavus", *Fungal Genetics and Biology* 68:23-30 (2014).

Zhang et al., "Identification of a Small Peptide That Inhibits PCSK9 Protein Binding to the Low Density Lipoprotein Receptor", *The Journal of Biological Chemistry* 289(2):942-955 (2014).

U.S. Appl. No. 17/253,764, 2022-0348610 A1, filed Dec. 18, 2020, Nov. 3, 2022, Alonso Ricardo.

U.S. Appl. No. 17/253,774, 2022-0089640 A1, filed Dec. 18, 2020, Mar. 24, 2022, Alonso Ricardo.

U.S. Appl. No. 17/253,783, 2021-0163538 A1, now U.S. Pat. No. 11,505,575, filed Dec. 18, 2020, Jun. 3, 2021, Nov. 22, 2022, Alonso Ricardo.

U.S. Appl. No. 17/898,220, filed Aug. 29, 2022, Alonso Ricardo.

U.S. Appl. No. 17/253,864, 2021-0284694 A1, now U.S. Pat. No. 11,530,244, filed Dec. 18, 2020, Sep. 16, 2021, Dec. 20, 2022, Alonso Ricardo.

U.S. Appl. No. 17/935,726, filed Sep. 27, 2022, Alonso Ricardo.

U.S. Appl. No. 16/446,940, 2019-0389909 A1, now U.S. Pat. No. 11,427,616, filed Jun. 20, 2019, Dec. 26, 2019, Aug. 30, 2022, Harold B. Wood.

U.S. Appl. No. 17/854,379, filed Jun. 30, 2022, Harold B. Wood.

U.S. Appl. No. 17/253,815, 2021-0214395 A1, now U.S. Pat. No. 11,306,125, filed Dec. 18, 2020, Jul. 15, 2021, Apr. 19, 2022, Yusheng Xiong.

U.S. Appl. No. 17/005,686, 2021-0069288 A1, now U.S. Pat. No. 11,484,565, filed Aug. 28, 2020, Mar. 11, 2021, Nov. 1, 2022, Hubert Josien.

U.S. Appl. No. 18/051,250, filed Oct. 31, 2022, Hubert Josien.

U.S. Appl. No. 17/757,622, filed Jun. 17, 2022, Hubert Josien.

\* cited by examiner

PCSK9 ANTAGONIST COMPOUNDS

RELATED APPLICATIONS

This application claims the benefit of priority to U.S. Provisional Patent Application No. 62/894,286, filed Aug. 30, 2019, and U.S. Provisional Patent Application No. 62/950,690, filed Dec. 19, 2019. The contents of both of these applications are incorporated herein by reference in their entireties.

BACKGROUND OF THE INVENTION

The identification of compounds and/or agents effective in the treatment of cardiovascular affliction is highly desirable. In clinical trials, reductions in LDL cholesterol levels have been directly related to the rate of coronary events; Law et al., 2003 *BMJ* 326:1423-1427. The moderate lifelong reduction in plasma LDL cholesterol levels was found to correlate with a substantial reduction in the incidence of coronary events; Cohen et al., 2006 *N Engl. J. Med.* 354:1264-1272. This was the case even in populations with a high prevalence of non-lipid-related cardiovascular risk factors; supra. Accordingly, there is great benefit to be reaped from the managed control of LDL cholesterol levels.

Proprotein convertase subtilisin-kexin type 9 (hereinafter called "PCSK9"), also known as neural apoptosis-regulated convertase 1 ("NARC-1"), is a proteinase K-like subtilase identified as the $9^{th}$ member of the secretory subtilase family; see Seidah et al., 2003 *PNAS* 100:928-933. PCSK9 belongs to the mammalian proprotein convertase family of serine proteases and contains an N-terminal signal sequence, prodomain, catalytic domain, and C-terminal domain; see Seidah et al., 2012 *Nat. Rev. Drug Discov.* 11:367-383. A study of PCSK9 transcriptional regulation demonstrated that it is regulated by sterol regulatory element-binding proteins ("SREBP"), as seen with other genes involved in cholesterol metabolism; Maxwell et al., 2003 *J. Lipid Res.* 44:2109-2119, as is typical of other genes implicated in lipoprotein metabolism; Dubuc et al., 2004 *Arterioscler. Thromb. Vasc. Biol.* 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

While in the endoplasmic reticulum, PCSK9 performs as its only catalytic activity an autocleavage between residues Gln-152 and Ser-153; see Naureckiene et al., 2003 *Arch. Biochem. Biophys.* 420:55-67; Seidah et al., 2003 Proc. Natl. Acad. Sci. U.S.A. 100:928-933. The prodomain remains tightly associated with the catalytic domain during subsequent trafficking through the trans-Golgi network. The maturation via autocleavage has been demonstrated to be critical for PCSK9 secretion and subsequent extracellular function (see Benjannet et al., 2012 *J. Biol. Chem.* 287:33745-33755). Accordingly, several lines of evidence demonstrate that PCSK9, in particular, lowers the amount of hepatic LDLR protein and thus compromises the liver's ability to remove LDL cholesterol from the circulation.

Adenovirus-mediated overexpression of PCSK9 in the livers of mice results in the accumulation of circulating LDL-C due to a dramatic loss of hepatic LDLR protein, with no effect on LDLR mRNA levels; Benjannet et al., 2004 *J. Biol. Chem.* 279:48865-48875; Maxwell & Breslow, 2004 *PNAS* 101:7100-7105; Park et al., 2004 *J. Biol. Chem.* 279:50630-50638; and Lalanne et al., 2005 *J. Lipid Res.* 46:1312-1319. The effect of PCSK9 overexpression on raising circulating LDL-C levels in mice is completely dependent on the expression of LDLR, again, indicating that the regulation of LDL-C by PCSK9 is mediated through downregulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid et al., 2005 *PNAS* 102:5374-5379; and Graham et al., 2007 *J. Lipid Res.* 48(4):763-767. In addition, lowering PCSK9 levels in cultured human hepatocytes by siRNA also results in higher LDLR protein levels and an increased ability to take up LDL-C; Benjannet et al., 2004 *J. Biol. Chem.* 279:48865-48875; and Lalanne et al., 2005 *J. Lipid Res.* 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *J. Nature Genetics* 34:154-156; Timms et al., 2004 *J. Hum. Genet.* 114:349-353; Leren, 2004 *J. Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Engl. J. Med.* 354:1264-1272.

Thus, identification of compounds and/or agents effective in the treatment of cardiovascular affliction is highly desirable, including antagonism of PCSK9's role in LDL regulation. In general, because PCSK9 circulates in blood and has modest binding affinity to cell surface LDL receptors prior attempts to utilize this mechanism in treatment of diseases related to high serum LDL levels have been focused on the use of large biomolecules, for example, antibodies. Accordingly, there is scant publication reflecting activity toward this target using small peptides or small molecules to inhibit PCSK9, see for example, Zhang et al., 2014 J. Biol. Chemistry, 289(2): 942-955. Moreover, there is a paucity of compounds which are amenable to formulation into a dosage form for utilizing an oral administration route of dosing such compounds, a route which would be highly desirable for the provision of therapy for conditions in which regulation of the activities of PCSK9 could play a role.

The present invention advances these interests by providing antagonists of PCSK9 that are believed to be of use for inhibiting the activities of PCSK9 and the corresponding role PCSK9 plays in various conditions for which the administration of a PCSK9 antagonist provides therapy. Compounds of the instant invention have been optimized to provide an increased half-life over compounds in co-pending application PCT/US19/38155, filed on Jun. 20, 2019. Compounds of the instant invention also have an improved pharmacokinetic profile and prolonged pharmaceutical action over compounds of the co-pending application.

SUMMARY OF THE INVENTION

In one aspect the invention provides a compound of Formula A:

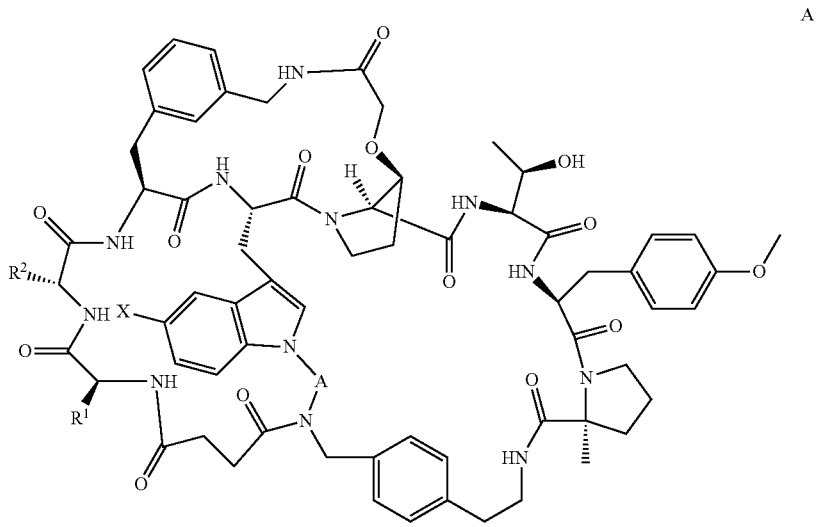

wherein:

X is H, F, Cl, or Br;

R is independently selected from H or $C_{1-6}$ alkyl;

$R^a$ is independently selected from H, $-CR_2-S(O)_2OR^9$, or $-C(O)OR^9$;

$R^b$ is independently selected from H, $C_{1-6}$ alkyl, or $C_{1-6}$ alkyl-$N^+(CH_3)_2$;

$R^d$ is independently selected from H or $-C(O)OR^9$;

$R^1$ is selected from:
(a) $-H$,
(b) $C_{1-6}$ alkyl,
(c) $-(CR_2)_z-NR^b-C(O)R^{10}$, and
(d) $-(CR_2)_z-NR-C(O)-(CR_2)_z[O(CR_2)_n]_r-N^+(CH_3)_3$;

$R^2$ is selected from:
(a) $-H$,
(b) $C_{1-6}$ alkyl,
(c) $-(CR_2)_z-NR^b-C(O)R^{10}$, and
(d) $-(CR_2)_z-NR-C(O)-(CR_2)_z[O(CR_2)_n]_r-N^+(CH_3)_3$;

provided that at least one of $R^1$ and $R^2$ is $-(CR_2)_z-NR^b-C(O)R^{10}$;

$R^4$ is

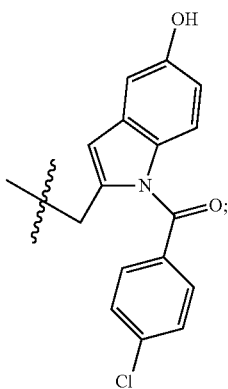 [SMILES: *Cc1cc2cc(O)ccc2n1C(=O)c1ccc(Cl)cc1]

$R^5$ is independently selected from $-(CR^a_2)_x-$, $-(CR^a_2)_xO(CR^a_2)_x-$, and $C_{1-8}$alkyl;

$R^6$ is independently selected from $-(CR^a_2)_xNRC(O)-$, $-(CR_2)_xNRS(O)_2-$, and $-(CR^a_2)_nO(CR^a_2)_qNRC(O)-$;

$R^9$ is independently selected from H or $C_{1-6}$ alkyl;

$R^{10}$ is independently selected from:
a) $-(R^5-N^+(CH_3)_2-R^6)_u-(R^{20})_n-(R^6)_m-R^{12}$,
b) $-(R^{20})_n-(R^6)_m-R^5-N^+(CH_3)_2-R^6-R^{12}$,
c) $-(R^{20})_n-R^5-N^+(CH_3)_2-(R^{20})_s-(R^6)_q-R^{12}$,
d) $-R^6-R^{20}-N^+(CH_3)_2-(R^{20})_n-(R^6)_m-R^{12}$,
e) $-R^{20}-N^+(CH_3)_2-(R^6)_m-(R^{20})_n-(R^6)_q-R^{12}$,
f) $-(R^{20})_n-(R^6)_m-R^{12}$, g) —R⁵—N⁺(CH₃)₂—(R²⁰)ₙ—(R⁶)ₘ—R⁵—[NRC(O)—R⁵]_q,
h) —R²⁰—N⁺(CH₃)₂—(R⁶)ₘ—R⁵,
i) —R⁵—N⁺(CH₃)₂—(R²⁰)ₙ—(R⁶)ₘR⁵,
j) —R⁵—N⁺(CH₃)₂—(R²⁰)ₙ—(R⁶)ₘ—R¹²,
k) —(R²⁰)ₙ—N⁺(CH₃)₂—(R²⁰)ₙ—(R⁶)_q—R¹²,
l) —R⁶—R⁵—N⁺(CH₃)₂—(R²⁰)ₙ—(R⁶)_q—R¹²,
m) —(R²⁰)ₙ—N⁺(CH₃)₂—(R⁶)_q—R¹²,
n) —(R²⁰)ₙ—(R⁶)ₘ—R²⁰—N⁺(CH₃)₂—(R²⁰)_s—(R⁶)_q—R¹²,
o) —R²⁰—N⁺(CH₃)₂—(R⁶)ₘR⁴, In a further embodiment, the invention provides a compound of Formula A, wherein X is F, or a pharmaceutically acceptable salt of any thereof.

In one embodiment the present invention provides pharmaceutical compositions comprising a compound of the invention, for example, a compound of Formula A, and at least one pharmaceutical excipient, preferably a composition directed to oral administration.

In another aspect, the invention provides a compound of Formula I:

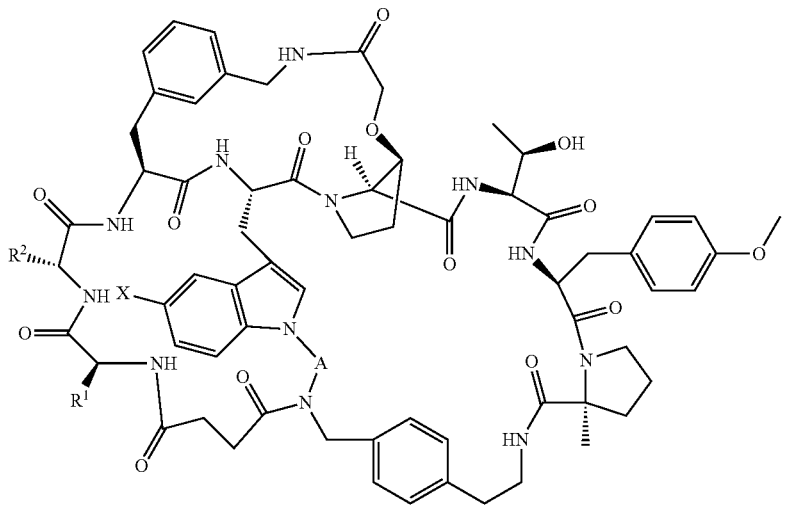

I p) —(R²⁰)ₙ—N⁺(CH₃)₂—(R⁶)_q—(R²⁰)ₙ—(R⁶)ₘR¹²,
q) —R²⁰—N⁺(CH₃)₂—(R⁶)ₘ—(R²⁰)ₙ—N⁺(CH₃)₂—(R²⁰)ₙ—(R⁶)_q—R¹²,
r) —R⁵—N⁺(CH₃)₂—(R⁶)ₘ—R⁵—N⁺(CH₃)₂—(R²⁰)ₙ—(R⁶)_q—R¹², and
s) —CR^b₂—(R²⁰)ₙ—(R⁶)ₘ—R¹²;

R¹² is independently selected from —C₁₁₋₂₀ alkyl-R^d, —(CR₂)_x—O—(CR₂)_x—R^d, —C₁₁₋₂₀ alkyl-C(O)NR—(CR^d₂)₂H, and C₂₋₁₆ alkenyl;

R²⁰ is independently selected from
a) —(CR^a₂)_t O(CR^a₂)_q O—(CR^a₂)_t—,
b) —(CR^a₂)_t O(CR^a₂)_q O—(CR^a₂)_t—NRC(O)—,
c) —(CR^a₂)_t O(CR^a₂)_q—NRC(O)—(CR^a₂)_n O(CR^a₂)_n O—,
d) —(CR^a₂)_t—NRC(O)—(CR^a₂)_q O(CR^a₂)_q O—(CR^a₂)_t—,
e) —(CR^a₂)_t O(CR^a₂)_q O—(CR^a₂)_t—, and
f) —(CR^a₂)_t—O—(CR^a₂)_q O(CR^a₂)_q O—(CR^a₂)_t—;

A is selected from C₂₋₆ alkyl or C₂₋₆ alkenyl;
m is independently selected from 0, 1, 2, 3, or 4;
m is independently selected from 1, 2, or 3;
q is independently selected from 1, 2, 3, or 4;
r is independently selected from 0, 1, 2, 3, or 4;
s is independently selected from 0, 1, 2, or 3;
t is independently selected from 0, 1, 2, or 3;
u is 1 or 2;
x is independently selected from 1, 2, 3, 4, 5, 6, 7, or 8;
z is independently selected from 1, 2, 3, 4, 5, or 6;
or a pharmaceutically acceptable salt of any thereof.

wherein:

X is H, F, Cl, or Br;

R is independently selected from H or C₁₋₆ alkyl;

R^a is independently selected from H, —CR₂—S(O)₂OR⁹, or —C(O)OR⁹;

R^b is independently selected from H, C₁₋₆ alkyl, or C₁₋₆ alkyl-N⁺(CH₃)₂;

R^d is independently selected from H or —C(O)OR⁹;

R¹ is selected from:
(a) —H,
(b) C₁₋₆ alkyl,
(c) —(CR₂)_z—NR^b—C(O)R¹⁰, and
(d) —(CR₂)_z—NR—C(O)—(CR₂)_z[O(CR₂)_n]_r—N⁺(CH₃)₃;

R² is selected from:
(a) —H,
(b) C₁₋₆ alkyl,
(c) —(CR₂)_z—NR^b—C(O)R¹⁰, and
(d) —(CR₂)_z—NR—C(O)—(CR₂)_z[O(CR₂)_n]_r—N⁺(CH₃)₃;

provided that at least one of R¹ and R² is —(CR₂)_z—NR^b—C(O)R¹⁰;

$R^4$ is

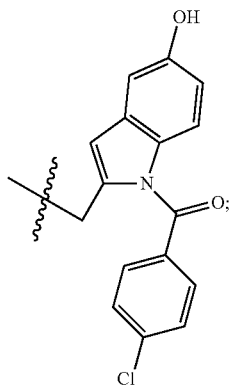 [SMILES: *Cc1cc2cc(O)ccc2n1C(=O)c1ccc(Cl)cc1]

$R^5$ is independently selected from —$(CR^a{}_2)_x$—, —$(CR^a{}_2)_xO(CR^a{}_2)_x$—, and $C_{1-8}$alkyl;
$R^6$ is independently selected from —$(CR^a{}_2)_xNRC(O)$—, —$(CR_2)_xNRS(O)_2$—, and —$(CR^a{}_2)_nO(CR^a{}_2)_qNRC(O)$—;
$R^9$ is independently selected from H or $C_{1-6}$ alkyl;
$R^{10}$ is independently selected from:
  a) —$(R^5$—$N^+(CH_3)_2$—$R^6)_u$—$(R^{20})_n$—$(R^6)_m$—$R^{12}$,
  b) —$(R^{20})_n$—$(R^6)_m$—$R^5$—$N^+(CH_3)_2$—$R^6$—$R^{12}$,
  c) —$(R^{20})_n$—$R^5$—$N^+(CH_3)_2$—$(R^{20})_s$—$(R^6)_q$—$R^{12}$,
  d) —$R^6$—$R^{20}$—$N^+(CH_3)_2$—$(R^{20})_n$—$(R^6)_m$—$R^{12}$,
  e) —$R^{20}$—$N^+(CH_3)_2$—$(R^6)_m$—$(R^{20})_n$—$(R^6)_q$—$R^{12}$,
  f) —$(R^{20})_n$—$(R^6)_m$—$R^{12}$,
  g) —$R^5$—$N^+(CH_3)_2$—$(R^{20})_n$—$(R^6)_m$—$R^5$—$[NRC(O)$—$R^5]_q$,
  h) —$R^{20}$—$N^+(CH_3)_2$—$(R^6)_m$—$R^5$,
  i) —$R^5$—$N^+(CH_3)_2$—$(R^{20})_n$—$(R^6)_mR^5$,
  j) —$R^5$—$N^+(CH_3)_2$—$(R^{20})_n$—$(R^6)_m$—$R^{12}$,
  k) —$(R^{20})_n$—$N^+(CH_3)_2$—$(R^{20})_n$—$(R^6)_q$—$R^{12}$,
  l) —$R^6$—$R^5$—$N^+(CH_3)_2$—$(R^{20})_n$—$(R^6)_q$—$R^{12}$,
  m) —$(R^{20})_n$—$N^+(CH_3)_2$—$(R^6)_q$—$R^{12}$,
  n) —$(R^{20})_n$—$(R^6)_m$—$R^{20}$—$N^+(CH_3)_2$—$(R^{20})_s$—$(R^6)_q$—$R^{12}$,
  o) —$R^{20}$—$N^+(CH_3)_2$—$(R^6)_mR^4$,
  p) —$(R^{20})_n$—$N^+(CH_3)_2$—$(R^6)_q$—$(R^{20})_n$—$(R^6)_mR^{12}$,
  q) —$R^{20}$—$N^+(CH_3)_2$—$(R^6)_m$—$(R^{20})_n$—$N^+(CH_3)_2$—$(R^{20})_n$—$(R^6)_q$—$R^{12}$,
  r) —$R^5$—$N^+(CH_3)_2$—$(R^6)_m$—$R^5$—$N^+(CH_3)_2$—$(R^{20})_n$—$(R^6)_q$—$R^{12}$, and
  s) —$CR^b{}_2$—$(R^{20})_n$—$(R^6)_m$—$R^{12}$;
$R^{12}$ is independently selected from —$C_{11-20}$ alkyl-$R^d$, —$(CR_2)_x$—O—$(CR_2)_x$—$R^d$, —$C_{11-20}$ alkyl-$C(O)NR$—$(CR^d{}_2)_2H$, and $C_{2-16}$ alkenyl;
$R^{20}$ is independently selected from
  a) —$(CR^a{}_2)_tO(CR^a{}_2)_qO$—$(CR^a{}_2)_t$—,
  b) —$(CR^a{}_2)_tO(CR^a{}_2)_qO$—$(CR^a{}_2)_t$—NRC(O)—,
  c) —$(CR^a{}_2)_tO(CR^a{}_2)_q$—NRC(O)—$(CR^a{}_2)_nO(CR^a{}_2)_nO$—,
  d) —$(CR^a{}_2)_t$—NRC(O)—$(CR^a{}_2)_qO(CR^a{}_2)_qO$—$(CR^a{}_2)_t$—,
  e) —$(CR^a{}_2)_tO(CR^a{}_2)_qO$—$(CR^a{}_2)_t$—, and
  f) —$(CR^a{}_2)_t$—O—$(CR^a{}_2)_qO(CR^a{}_2)_qO$—$(CR^a{}_2)_t$—;
A is selected from $C_{2-6}$ alkyl or $C_{2-6}$ alkenyl;
m is independently selected from 0, 1, 2, 3, or 4;
n is independently selected from 1, 2, or 3;
q is independently selected from 1, 2, 3, or 4;
r is independently selected from 0, 1, 2, 3, or 4;
s is independently selected from 0, 1, 2, or 3;
t is independently selected from 0, 1, 2, or 3;
u is 1 or 2;
x is independently selected from 1, 2, 3, 4, 5, 6, 7, or 8;
z is independently selected from 1, 2, 3, 4, 5, or 6;
or a pharmaceutically acceptable salt of any thereof.

In a further embodiment, the invention provides a compound of Formula I, wherein X is F, or a pharmaceutically acceptable salt of any thereof.

In one embodiment the present invention provides pharmaceutical compositions comprising a compound of the invention, for example, a compound of Formula I, and at least one pharmaceutical excipient, preferably a composition directed to oral administration.

In another aspect the present invention provides a method of antagonizing PCSK9 in the provision of therapy for disease states related to PCSK9 activity, for example, atherosclerosis, hypercholesterolemia, coronary heart disease, metabolic syndrome, acute coronary syndrome, or related cardiovascular disease and cardiometabolic conditions, by administering to a subject in need thereof a therapeutically effective amount of a compound of Formula A, or a salt thereof, preferably in the form of a pharmaceutical composition.

In one aspect the present invention provides a method of antagonizing PCSK9 in the provision of therapy for disease states related to PCSK9 activity, for example, atherosclerosis, hypercholesterolemia, coronary heart disease, metabolic syndrome, acute coronary syndrome, or related cardiovascular disease and cardiometabolic conditions, by administering to a subject in need thereof a therapeutically effective amount of a compound of Formula I, or a salt thereof, preferably in the form of a pharmaceutical composition.

DETAILED DESCRIPTION OF THE INVENTION

In the description that follows conventional structural representation is employed and includes conventional stereochemical notation for certain asymmetric carbon centers. Thus, structural representation of compounds of the invention includes conventional stereochemical notation for some asymmetric carbon centers shown in the example compounds. Accordingly, in such instances, solid black "wedge" bonds represent bonds projecting from the plane of the reproduction medium, "hashed wedge" bonds representing descending bonds into the plane of the reproduction medium, and a "wavy" line appended to a carbon bearing a double bond indicates both possible cis and trans orientations are included. As is conventional, plain solid lines represent all spatial configurations for the depicted bonding. Accordingly, where no specific stereochemical notation is supplied, the representation contemplates all stereochemical and spatial orientations of the structural features.

As is shown in the examples of the invention, and mentioned above, particular asymmetric carbon centers are structurally represented using conventional "Solid Wedge" and "Hash Wedge" bonding representation. For the most part, absolute configuration has not been determined for the example compounds, but has been assigned by analogy to specific example compounds of known stereochemical configurations (determined by X-ray crystallography) prepared using the same or analogous reaction conditions and starting reagents and isolated under the same chromatographic conditions. Accordingly, specific assignment of the configurations structurally represented herein is meant to identify the specific compounds prepared has having an excess of one particular stereoisomer and is not put forth herein necessarily as being a statement of the absolute determination of the stereochemical structure of said compound unless otherwise noted in the data presented.

It will be appreciated that where isomeric mixtures are obtained, the preparation of individual stereoisomers in significant percentages of enantiomeric excess can be carried out, if desired, by separation of the mixture using customary methods, for example by chromatography or crystallization, or by the use of stereochemically uniform starting materials for the synthesis described, or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product.

Where indicated herein, absolute stereochemistry is determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. The present invention is meant to include all suitable isotopic variations of the compounds of Formula I.

Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$, and $^{125}I$. It wiill be appreciated that other isotopes may be incorporated by known means also.

In particular, certain isotopically-labeled compounds of the invention (e.g., those labeled with $^3H$, $^{11}C$, and $^{14}C$) are recognized as being particularly useful in compound and/or substrate tissue distribution assays using a variety of known techniques. Additionally, compounds of the invention contemplate isotopic substitution include different isotopic forms of hydrogen (H), including protium ($^1H$) and deuterium ($^2H$ or D). Protium is the predominant hydrogen isotope found in nature.

Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

Where a wavy line terminates a conventional bond (as opposed to connecting two atoms within a structure) it indicates a point of bonding to a structure, e.g.:

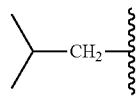

indicates a the secondary-butyl moiety is bonded via the methylene group via the bond terminated with the wavy line. Where an alphabetical notation is used to depict a substituent moiety, a dash is employed to indicate the point of bonding to the indicated substrate, e.g.: —$CH_2$—C(O)—$CH_2Cl$ indicates the acetyl chloride moiety is bonded via the methylene portion of the moiety.

When any variable (e.g., n, R, $R^a$, $R^6$, etc.) occurs more than one time in any constituent or in Formula I, its definition on each occurrence is independent of its definition at every other occurrence unless otherwise specified at the point of definition. One of ordinary skill in the art will recognize that choice of combinations of the various substituents defined in a structural representation, i.e. R, $R^6$, $R^{20}$, etc., are to be chosen in conformity with well-known principles of chemical structure connectivity and stability, and combinations of substituents and/or variables are permissible only if such combinations result in stable compounds. For example, if $R^{10}$ is defined as "—$R^5$—$N^+$($CH_3$)$_2$—($R^{20}$)$_n$—($R^6$)$^m$—$R^{12}$", integer n can be selected from 1, 2 or 3 and integer m can be selected from 0, 1, 2, 3, or 4. If integer n in this example is 3 and integer m is 4, then each of the three $R^{20}$ substitutions and each of the four $R^6$ substitutions is independently selected from the list of definitions provided herein.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

Where any variable or moiety is expressed in the form of a range, e.g. (—$CH_2$)$_{0-4}$, both of the extremes of the specified range are included (i.e. 0 and 4 in the example) as well as all of the whole number values in between (i.e. 1, 2 and 3 in the example).

The term "halogen" includes fluorine, chlorine, bromine and iodine unless specified otherwise at the point of use.

As the term is used herein, "subjects" (alternatively "patients") refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In some embodiments the subject is preferably a human. As used herein, the term "administration" and variants thereof (e.g., "administering" a compound) in reference to a compound of Formula I means providing the compound, or a pharmaceutically acceptable salt thereof, to a subject in need of treatment.

As mentioned above, in one aspect the present invention includes the provision of compounds of Formula A, or a pharmaceutically acceptable salt thereof, which have properties that antagonize PCSK9 function. Thus, in one aspect the invention provides a compound of Formula A:

A

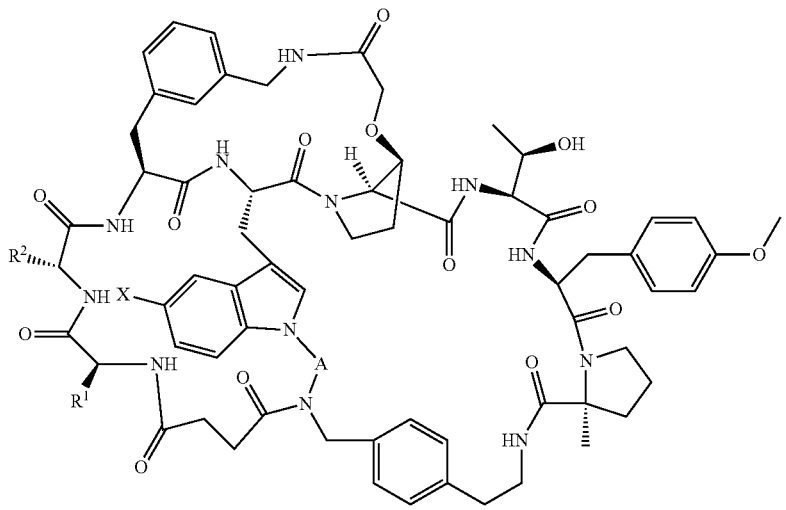

wherein:
X is H, F, Cl, or Br;
R is independently selected from H or $C_{1-6}$ alkyl;
$R^a$ is independently selected from H, $-CR_2-S(O)_2OR^9$, or $-C(O)OR^9$;
$R^b$ is independently selected from H, $C_{1-6}$ alkyl, or $C_{1-6}$ alkyl-$N^+(CH_3)_2$;
$R^d$ is independently selected from H or $-C(O)OR^9$;
$R^1$ is selected from:
 (a) $-H$,
 (b) $C_{1-6}$ alkyl,
 (c) $-(CR_2)_z-NR^b-C(O)R^{10}$, and
 (d) $-(CR_2)_z-NR-C(O)-(CR_2)_z[O(CR_2)_n]_r-N^+(CH_3)_3$;
$R^2$ is selected from:
 (a) $-H$,
 (b) $C_{1-6}$ alkyl,
 (c) $-(CR_2)_z-NR^b-C(O)R^{10}$, and
 (d) $-(CR_2)_z-NR-C(O)-(CR_2)_z[O(CR_2)_n]_r-N^+(CH_3)_3$;
provided that at least one of $R^1$ and $R^2$ is $-(CR_2)_z-NR^b-C(O)R^{10}$;
$R^4$ is

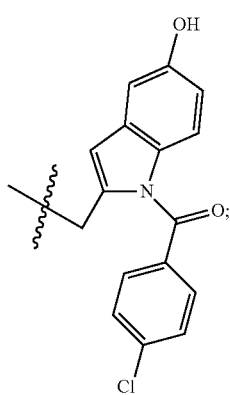 [SMILES: *Cc1cc2cc(O)ccc2n1C(=O)c1ccc(Cl)cc1]

$R^5$ is independently selected from $-(CR^a_2)_x-$, $-(CR^a_2)_xO(CR^a_2)_x-$, and $C_{1-8}$alkyl;

$R^6$ is independently selected from $-(CR^a_2)_xNRC(O)-$, $-(CR_2)_xNRS(O)_2-$, and $-(CR^a_2)_nO(CR^a_2)_qNRC(O)-$;
$R^9$ is independently selected from H or $C_{1-6}$ alkyl;
$R^{10}$ is independently selected from:
 a) $-(R^5-N^+(CH_3)_2-R^6)_u-(R^{20})_n-(R^6)_m-R^{12}$,
 b) $-(R^{20})_n-(R^6)_m-R^5-N^+(CH_3)_2-R^6-R^{12}$,
 c) $-(R^{20})_n-R^5-N^+(CH_3)_2-(R^{20})_s-(R^6)_q-R^{12}$,
 d) $-R^6-R^{20}-N^+(CH_3)_2-(R^{20})_n-(R^6)_m-R^{12}$,
 e) $-R^{20}-N^+(CH_3)_2-(R^6)_m-(R^{20})_n-(R^6)_q-R^{12}$,
 f) $-(R^{20})_n-(R^6)_m-R^{12}$,
 g) $-R^5-N^+(CH_3)_2-(R^{20})_n-(R^6)_m-R^5-[NRC(O)-R^5]_q$,
 h) $-R^{20}-N^+(CH_3)_2-(R^6)_m-R^5$,
 i) $-R^5-N^+(CH_3)_2-(R^{20})_n-(R^6)_mR^5$,
 j) $-R^5-N^+(CH_3)_2-(R^{20})_n-(R^6)_m-R^{12}$,
 k) $-(R^{20})_n-N^+(CH_3)_2-(R^{20})_n-(R^6)_q-R^{12}$,
 l) $-R^6-R^5-N^+(CH_3)_2-(R^{20})_n-(R^6)_q-R^{12}$,
 m) $-(R^{20})_n-N^+(CH_3)_2-(R^6)_q-R^{12}$,
 n) $-(R^{20})_n-(R^6)_m-R^{20}-N^+(CH_3)_2-(R^{20})_s-(R^6)_q-R^{12}$,
 o) $-R^{20}-N^+(CH_3)_2-(R^6)_mR^4$,
 p) $-(R^{20})_n-N^+(CH_3)_2-(R^6)_q-(R^{20})_n-(R^6)_mR^{12}$,
 q) $-R^{20}-N^+(CH_3)_2-(R^6)_m-(R^{20})_n-N^+(CH_3)_2-(R^{20})_n-(R^6)_q-R^{12}$,
 r) $-R^5-N^+(CH_3)_2-(R^6)_m-R^5-N^+(CH_3)_2-(R^{20})_n-(R^6)_q-R^{12}$, and
 s) $-CR^b_2-(R^{20})_n-(R^6)_m-R^{12}$;
$R^{12}$ is independently selected from $-C_{11-20}$ alkyl-$R^d$, $-(CR_2)_x-O-(CR_2)_x-R^d$, $-C_{11-20}$ alkyl-C(O)NR-$(CR^a_2)_2$H, and $C_{2-16}$ alkenyl;
$R^{20}$ is independently selected from
 a) $-(CR^a_2)_tO(CR^a_2)_qO-(CR^a_2)_t-$,
 b) $-(CR^a_2)_tO(CR^a_2)_qO-(CR^a_2)_t-NRC(O)-$,
 c) $-(CR^a_2)_tO(CR^a_2)_q-NRC(O)-(CR^a_2)_nO(CR^a_2)_nO-$,
 d) $-(CR^a_2)_t-NRC(O)-(CR^a_2)_qO(CR^a_2)_qO-(CR^a_2)_t-$,
 e) $-(CR^a_2)_tO(CR^a_2)_qO-(CR^a_2)_t-$, and
 f) $-(CR^a_2)_t-O-(CR^a_2)_qO(CR^a_2)_qO-(CR^a_2)_t-$;
A is selected from $C_{2-6}$ alkyl or $C_{2-6}$ alkenyl;
m is independently selected from 0, 1, 2, 3, or 4;
n is independently selected from 1, 2, or 3;
q is independently selected from 1, 2, 3, or 4;
r is independently selected from 0, 1, 2, 3, or 4;
s is independently selected from 0, 1, 2, or 3;
t is independently selected from 0, 1, 2, or 3;
u is 1 or 2;

x is independently selected from 1, 2, 3, 4, 5, 6, 7, or 8;
z is independently selected from 1, 2, 3, 4, 5, or 6;
or a pharmaceutically acceptable salt of any thereof.

In a further embodiment, the invention provides a compound of Formula A, wherein X is F, or a pharmaceutically acceptable salt of any thereof.

As mentioned above, in one aspect the present invention includes the provision of compounds of Formula I, or a pharmaceutically acceptable salt thereof, which have properties that antagonize PCSK9 function.

In one embodiment of the invention, the present invention comprises a compound of Formula I:

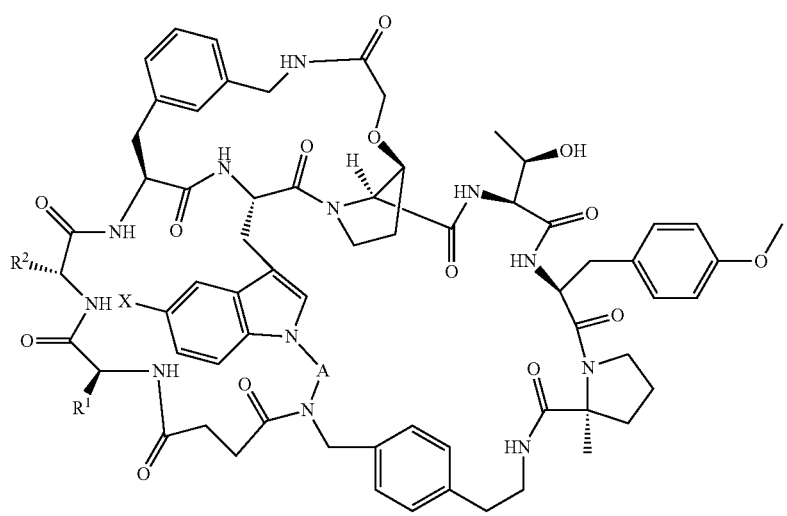

I

In an embodiment of the compounds of Formula A, $R^1$ is selected from $C_{1-6}$ alkyl, $-(CR_2)_z-NR^b-C(O)R^{10}$, and $-(CR_2)_z-NR-C(O)-(CR_2)_z[O(CR_2)_n]_r-N^+(CH_3)_3$. In a further embodiment of Formula I, $R^1$ is $C_{1-6}$ alkyl and $R^2$ is $-(CH_2)_z-NH-C(O)R^{10}$.

In an embodiment of the compounds of Formula A, $R^2$ is selected from $C_{1-6}$ alkyl, $-(CR_2)_z-NR^b-C(O)R^{10}$, and $-(CR_2)_z-NR-C(O)-(CR_2)_z[O(CR_2)_n]_r-N^+(CH_3)_3$. In another embodiment, $R^2$ is $-(CR_2)_z-NR^b-C(O)R^{10}$. In a further embodiment, $R^2$ is $-(CH_2)_z-NH-C(O)R^{10}$.

In an embodiment of the compounds of Formula A, $R^5$ is $C_{1-8}$ alkyl.

In an embodiment of the compound of Formula A, $R^6$ is $-(CR^a{}_2)_xNRC(O)-$. In a further embodiment, $R^6$ is independently selected from:

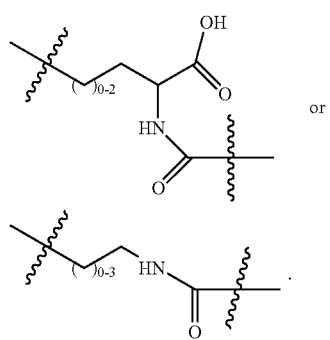

In one embodiment the present invention provides pharmaceutical compositions comprising a compound of the invention, for example, a compound of Formula A, and at least one pharmaceutical excipient, preferably a composition directed to oral administration.

wherein:
X is H, F, Cl, or Br;
R is independently selected from H or $C_{1-6}$ alkyl;
$R^a$ is independently selected from H, $-CR_2-S(O)_2OR^9$, or $-C(O)OR^9$;
$R^b$ is independently selected from H, $C_{1-6}$ alkyl, or $C_{1-6}$ alkyl-$N^+(CH_3)_2$;
$R^d$ is independently selected from H or $-C(O)OR^9$;
$R^1$ is selected from:
  (a) $-H$,
  (b) $C_{1-6}$ alkyl,
  (c) $-(CR_2)_z-NR^b-C(O)R^{10}$, and
$R^2$ is selected from:
  (a) $C_{1-6}$ alkyl, and
  (b) $-(CR_2)_z-NR^b-C(O)R^{10}$;
provided that at least one of $R^1$ and $R^2$ is $-(CR_2)_z-NR^b-C(O)R^{10}$;
$R^4$ is

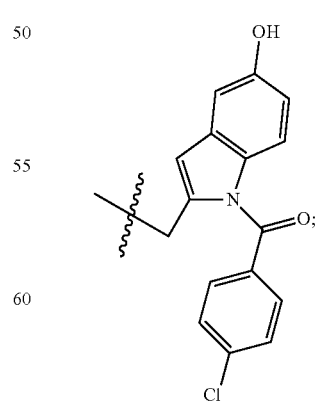

$R^5$ is independently selected from $-(CR^a{}_2)_x-$, $-(CR^a{}_2)_xO(CR^a{}_2)_x-$, and $C_1$-alkyl;

$R^6$ is independently selected from —$(CR^a{}_2)_x$NRC(O)— and —$(CR^a{}_2)_n$O$(CR^a{}_2)_q$NRC(O)—;

$R^9$ is independently selected from H or $C_{1-6}$ alkyl;

$R^{10}$ is independently selected from:
 a) —$(R^5$—$N^+(CH_3)_2$—$R^6)_u$—$(R^{20})_n$—$(R^6)_m$—$R^{12}$,
 b) —$(R^{20})_n$—$(R^6)_m$—$R^5$—$N^+(CH_3)_2$—$R^6$—$R^{12}$,
 c) —$(R^{20})_n$—$R^5$—$N^+(CH_3)_2$—$(R^{20})_s$—$(R^6)_q$—$R^{12}$,
 d) —$R^6$—$R^{20}$—$N^+(CH_3)_2$—$(R^{20})_n$—$(R^6)_m$—$R^{12}$,
 e) —$R^{20}$—$N^+(CH_3)_2$—$(R^6)_m$—$(R^{20})_n$—$(R^6)_q$—$R^{12}$,
 f) —$(R^{20})_n$—$(R^6)_m$—$R^{12}$,
 g) —$R^5$—$N^+(CH_3)_2$—$(R^{20})_n$—$(R^6)_m$—$R^5$—[NRC(O)—$R^5]_q$,
 h) —$R^{20}$—$N^+(CH_3)_2$—$(R^6)_m$—$R^5$,
 i) —$R^5$—$N^+(CH_3)_2$—$(R^{20})_n$—$(R^6)_m R^5$,
 j) —$R^5$—$N^+(CH_3)_2$—$(R^{20})_n$—$(R^6)_m$—$R^{12}$,
 k) —$(R^{20})_n$—$N^+(CH_3)_2$—$(R^{20})_n$—$(R^6)_q$—$R^{12}$,
 l) —$R^6$—$R^5$—$N^+(CH_3)_2$—$(R^{20})_n$—$(R^6)_q$—$R^{12}$,
 m) —$(R^{20})_n$—$N^+(CH_3)_2$—$(R^6)_q$—$R^{12}$,
 n) —$(R^{20})_n$—$(R^6)_m$—$R^{20}$—$N^+(CH_3)_2$—$(R^{20})_s$—$(R^6)_q$—$R^{12}$,
 o) —$R^{20}$—$N^+(CH_3)_2$—$(R^6)_m R^4$,
 p) —$(R^{20})_n$—$N^+(CH_3)_2$—$(R^6)_q$—$(R^{20})_n$—$(R^6)_m R^{12}$,
 q) —$R^{20}$—$N^+(CH_3)_2$—$(R^6)_m$—$(R^{20})_n$—$N^+(CH_3)_2$—$(R^{20})_n$—$(R^6)_q$—$R^{12}$,
 r) —$R^5$—$N^+(CH_3)_2$—$(R^6)_m$—$R^5$—$N^+(CH_3)_2$—$(R^{20})_n$—$(R^6)_q$—$R^{12}$, and
 s) —$CR^b{}_2$—$(R^{20})_n$—$(R^6)_m$—$R^{12}$;

$R^{12}$ is independently selected from —$C_{11-20}$ alkyl-$R^d$, —$(CR_2)_x$—O—$(CR_2)_x$—$R^d$, —$C_{11-20}$ alkyl-C(O)NR—$(CR^d{}_2)_2$H, and $C_{2-16}$ alkenyl;

$R^{20}$ is independently selected from
 a) —$(CR^a{}_2)_t$O$(CR^a{}_2)_q$O—$(CR^a{}_2)_t$—,
 b) —$(CR^a{}_2)_t$O$(CR^a{}_2)_q$O—$(CR^a{}_2)_t$—NRC(O)—,
 c) —$(CR^a{}_2)_t$O$(CR^a{}_2)_q$—NRC(O)—$(CR^a{}_2)_n$O$(CR^a{}_2)_n$O—,
 d) —$(CR^a{}_2)_t$—NRC(O)—$(CR^a{}_2)_q$O$(CR^a{}_2)_q$O—$(CR^a{}_2)_t$—,
 e) —$(CR^a{}_2)_t$O$(CR^a{}_2)_q$O—$(CR^a{}_2)_t$—, and
 f) —$(CR^a{}_2)_t$—O—$(CR^a{}_2)_q$O$(CR^a{}_2)_q$O—$(CR^a{}_2)_t$—;

A is selected from $C_{2-6}$ alkyl or $C_{2-6}$ alkenyl;

m is independently selected from 0, 1, 2, 3 or 4;
n is independently selected from 1, 2 or 3;
q is independently selected from 1, 2, 3 or 4;
r is independently selected from 0, 1, 2, 3 or 4;
s is independently selected from 0, 1 or 2;
t is independently selected from 0, 1, 2 or 3;
u is 1 or 2;
x is independently selected from 1, 2, 3, 4, 5, 6, 7, or 8;
z is independently selected from 1, 2, 3, 4, 5 or 6;
or a pharmaceutically acceptable salt of any thereof.

In another embodiment, the compounds of Formula I have the structure of Formula IA:

wherein $R^1$, $R^{10}$ and A are as defined above in Formula I, or a pharmaceutically acceptable salt thereof.

In an embodiment, the compounds of Formula I have the structure of Formula II:

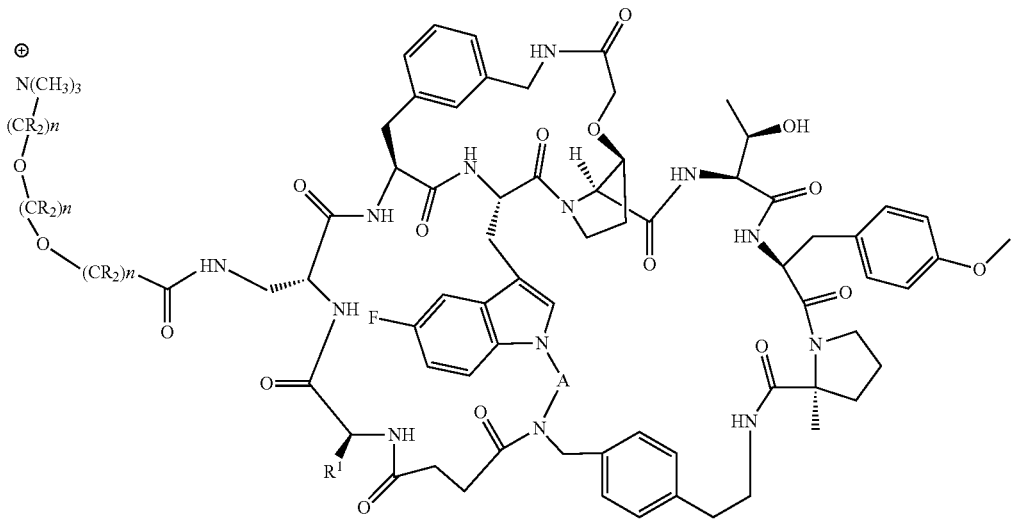

wherein $R^1$ is —$(CR_2)_z$—$NR^b$—$C(O)R^{10}$, A and $R^{10}$ are as defined above in Formula I,
or a pharmaceutically acceptable salt thereof.

In an embodiment, the compounds of Formula I have the structure of Formula IIA:

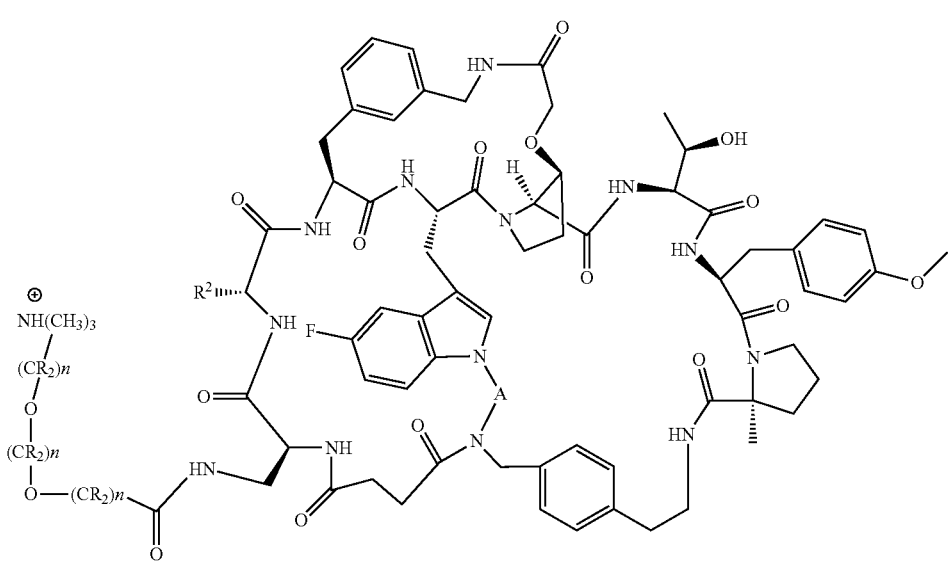

wherein $R^2$ is —$(CR_2)_z$—$NR^b$—$C(O)R^{10}$, A and $R^{10}$ are as defined above in Formula I,
or a pharmaceutically acceptable salt thereof.

In an embodiment of the compounds of Formula I, IA, or II, $R^1$ is selected from $C_{1-6}$ alkyl, —$(CR_2)_z$—$NR^b$—$C(O)R^{10}$, and —$(CR_2)_z$—NR—C(O)—$(CR_2)_z$[$O(CR_2)_n$]$_r$—$N^+(CH_3)_3$. In a further embodiment of Formula I, $R^1$ is $C_{1-6}$ alkyl and $R^2$ is —$(CH_2)_z$—NH—$C(O)R^{10}$.

In an embodiment of the compounds of Formula I or IIA, $R^2$ is selected from $C_{1-6}$ alkyl, —$(CR_2)_z$—$NR^b$—$C(O)R^{10}$, and —$(CR_2)_z$—NR—C(O)—$(CR_2)_z$[$O(CR_2)_n$]$_r$—$N^+(CH_3)_3$. In another embodiment, $R^2$ is —$(CR_2)_z$—$NR^b$—$C(O)R^{10}$. In a further embodiment, $R^2$ is —$(CH_2)_z$—NH—C(O)$R^{10}$.

In an embodiment of the compounds of Formula I, IA, II, or IIA, $R^5$ is $C_{1-8}$ alkyl.

In an embodiment of the compound of Formula I, IA, II or IIA, $R^6$ is —$(CR^a_2)_x$NRC(O)—. In a further embodiment, $R^6$ is independently selected from:

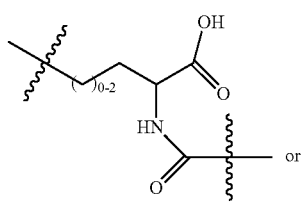

-continued

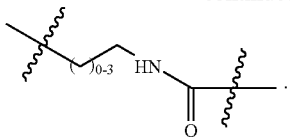

In an embodiment of the compounds of Formula I, IA, II or IIA, $R^{10}$ is independently selected from
a) $-R^6-R^{20}-N^+(CH_3)_2-(R^{20})_n-(R^6)_m-R^{12}$,
b) $-R^{20}-N^+(CH_3)_2-(R^6)_m-(R^{20})_n-(R^6)_q-R^{12}$,
c) $-(R^{20})_n-(R^6)_m-R^{12}$,
d) $-R^5-N^+(CH_3)_2-(R^{20})_n-(R^6)_m-R^{12}$,
e) $-(R^{20})_n-N^+(CH_3)_2-(R^{20})_n-(R^6)_q-R^{12}$,
f) $-(R^{20})_n-N^+(R^6)_q-R^{12}$, and
g) $-(R^{20})_n-(R^6)_m-R^{20}-N^+(CH_3)_2-(R^{20})_s(R^6)_q-R^{12}$.

In another embodiment of the compounds of Formula I, IA, II or IIA, $R^{10}$ is independently selected from
a) $-R^6-R^{20}-N^+(CH_3)_2-(R^{20})_n-(R^6)_m-R^{12}$,
b) $-R^5-N^+(CH_3)_2-(R^{20})_n-(R^6)_m-R^{12}$,
c) $-(R^{20})_n-N^+(CH_3)_2-(R^{20})_n-(R^6)_q-R^{12}$, and
d) $-(R^{20})_n-(R^6)_m-R^{20}-N^+(CH_3)_2-(R^{20})_n(R^6)_q-R^{12}$.

In further embodiment, $R^{10}$ is $-(R^{20})_n-N^+(CH_3)_2-(R^{20})_n-(R^6)_q-R^{12}$.

In an embodiment of the compound of Formula I, IA, II or IIA, A is
(a) $-(CH_2)_{4-6}$, or
(b) a moiety of the formula:

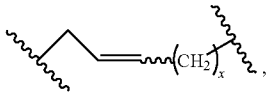

wherein x is 1 to 3. In a further embodiment, A is $-(CH_2)_6$.

It is understood that reference to "Formula I" also encompasses compounds of Formula IA, Formula II and Formula IIA, unless indicated otherwise.

Also provided herein are compounds of Formula A, selected from Ex-1, Ex-2, Ex-3, Ex-4, Ex-5, Ex-6, Ex-7, Ex-8, Ex-9, Ex-10, Ex-11, Ex-12, Ex-13, Ex-14, Ex-15, Ex-16, Ex-17, Ex-18, Ex-19, Ex-20, Ex-21, Ex-22, Ex-23, Ex-24, Ex-25, Ex-26, Ex-27, Ex-28, Ex-29, Ex-31, Ex-35, Ex-36, Ex-38, Ex-39, Ex-40, Ex-41, Ex-44, Ex-47, Ex-48, Ex-49, Ex-50, Ex-51, Ex-52, Ex-53, Ex-54, Ex-55, Ex-56, Ex-57, Ex-58, Ex-59, Ex-60, Ex-61, Ex-62, Ex-63, Ex-64, Ex-65, Ex-66, Ex-67, and Ex-68 or any pharmaceutically acceptable salt thereof.

Also provided herein are compounds of Formula I, selected from Ex-1, Ex-2, Ex-3, Ex-4, Ex-5, Ex-6, Ex-7, Ex-8, Ex-9, Ex-10, Ex-11, Ex-12, Ex-13, Ex-14, Ex-15, Ex-16, Ex-17, Ex-18, Ex-19, Ex-20, Ex-21, Ex-22, Ex-23, Ex-24, Ex-25, Ex-26, Ex-27, Ex-28, Ex-29, Ex-31, Ex-35, Ex-36, Ex-38, Ex-39, Ex-40, Ex-41, Ex-44, Ex-47, Ex-48, Ex-49, Ex-50, Ex-51, Ex-52, Ex-53, Ex-54, Ex-55, Ex-56, Ex-57, Ex-58, Ex-59, Ex-60, Ex-61, Ex-62, Ex-63 and Ex-64 or any pharmaceutically acceptable salt thereof.

An embodiment of the invention comprises compounds selected from Ex-2, Ex-4, Ex-8, Ex-9, Ex-10, Ex-22, Ex-34, Ex-44, Ex-48, Ex-49, and Ex-58, or a pharmaceutically acceptable salt thereof. A further embodiment of the invention comprises compounds selected from Ex-4, Ex-8, Ex-9, Ex-10, Ex-22, Ex-34, Ex-48 and Ex-49, or a pharmaceutically acceptable salt thereof.

The compounds shown below in Table 1 are also referred to herein as "compounds of the invention". In Table 1, the * denotes that the compound includes "A⁻", which represents any pharmaceutically acceptable counter ion, including those depicted in the experimental section.

TABLE 1
| Ex No | Structure |
|---|---|
| Ex-1* | A' 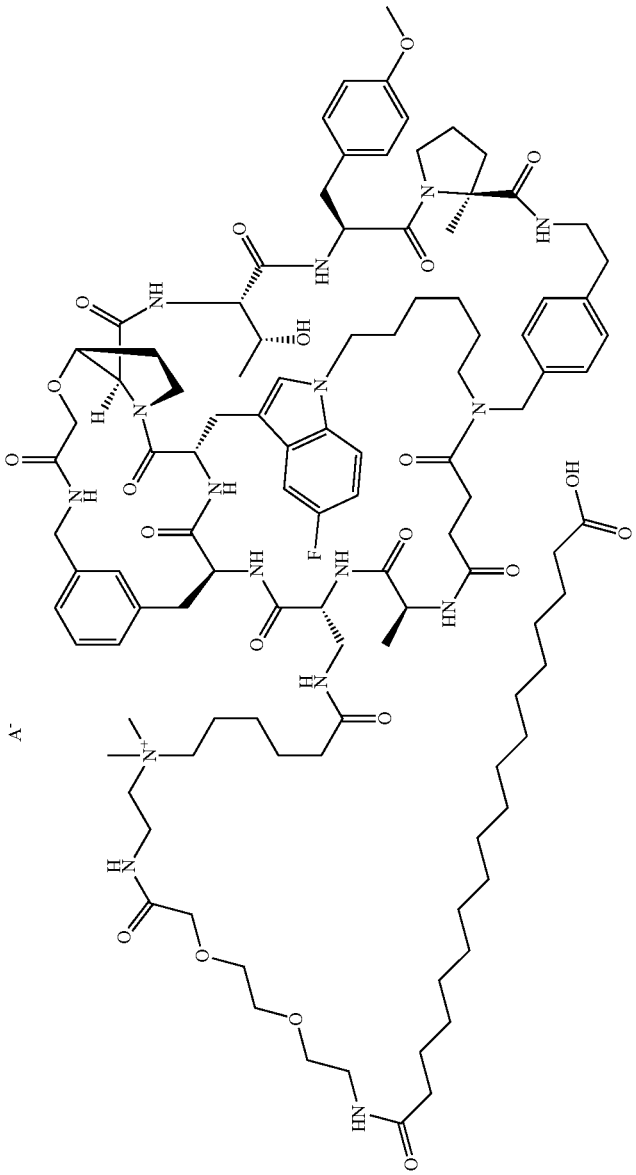 |

TABLE 1-continued
| Ex No | Structure |
|---|---|
| Ex-2* | 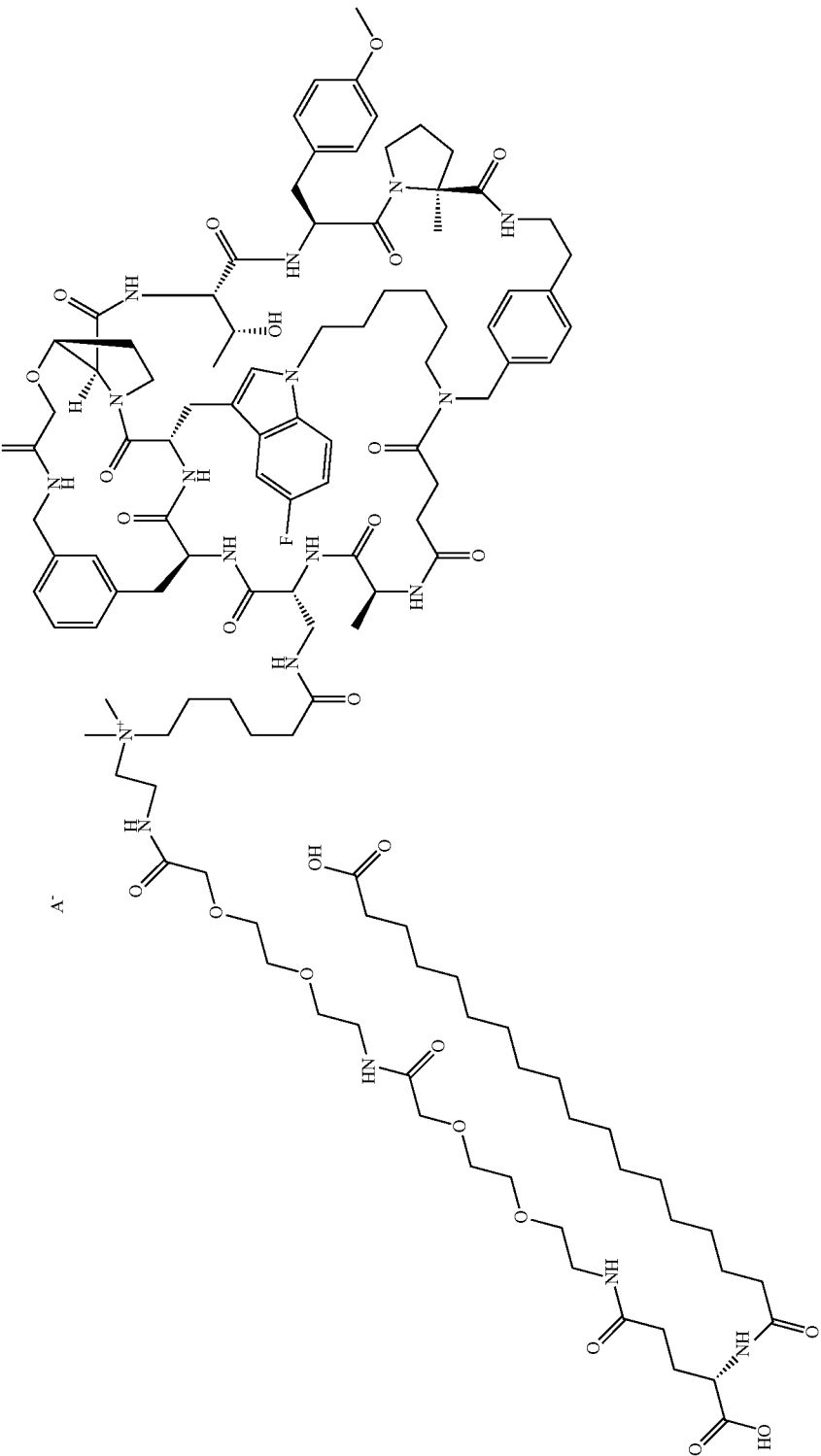 |

TABLE 1-continued
| Ex No | Structure |
|---|---|
| Ex-3* | 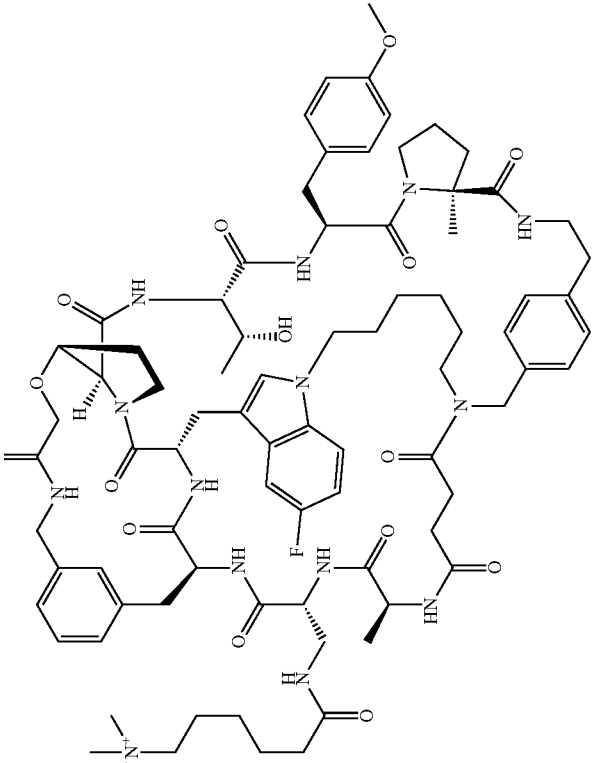 |

TABLE 1-continued
| Ex No | Structure |
|---|---|
| Ex-4* | 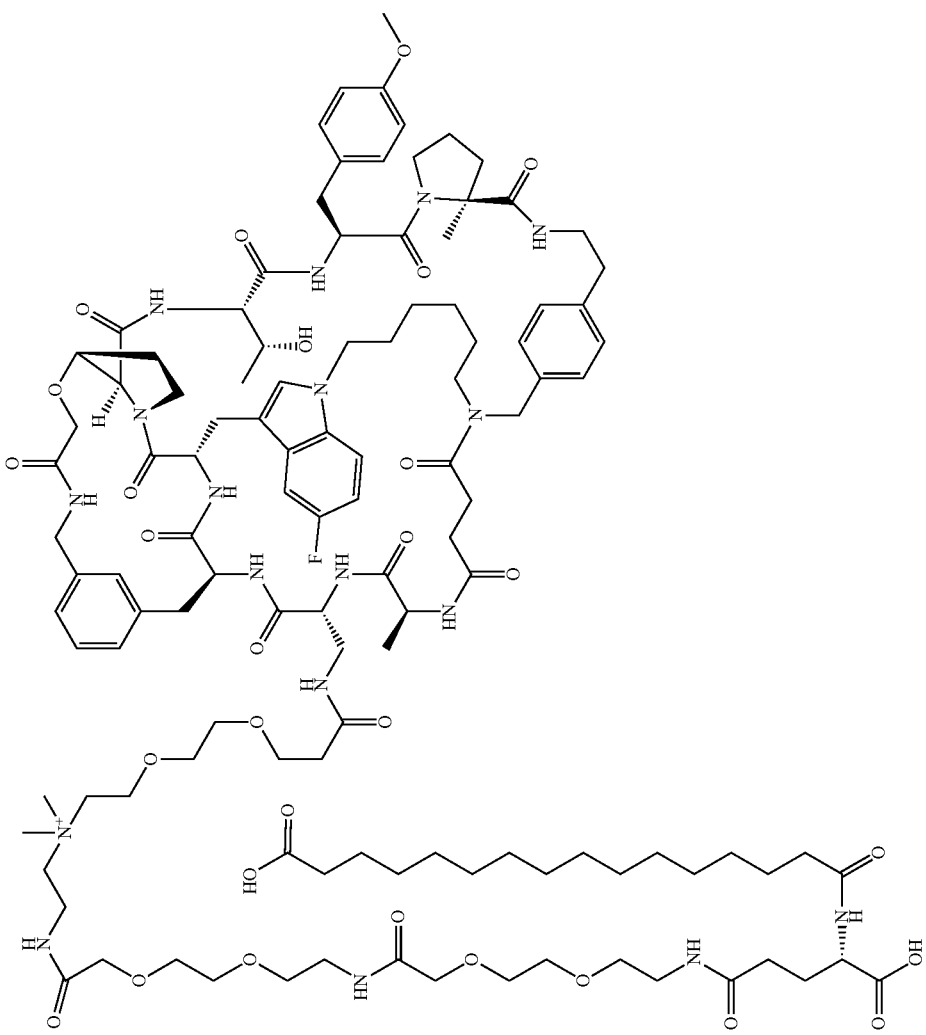 |

TABLE 1-continued
| Ex No | Structure |
|---|---|
| Ex-5* | 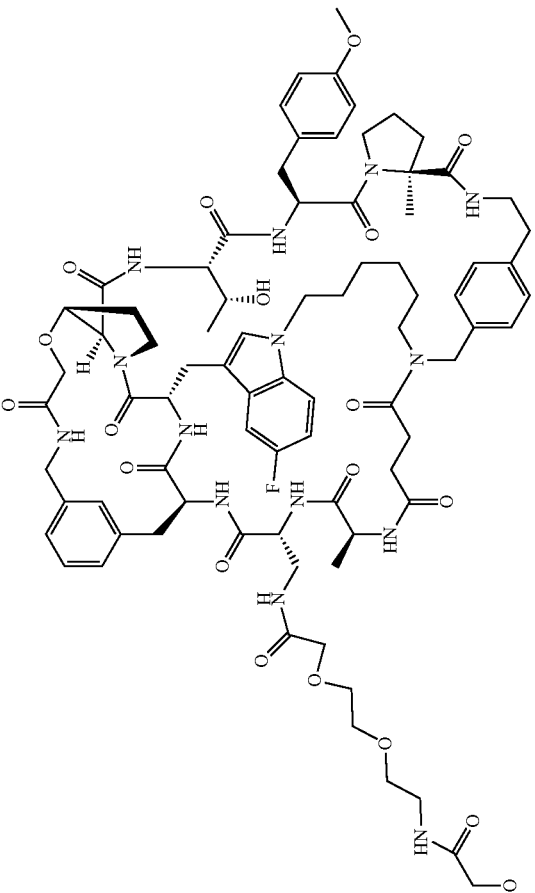 |

TABLE 1-continued
| Ex No | Structure |
|---|---|
| Ex-6* | 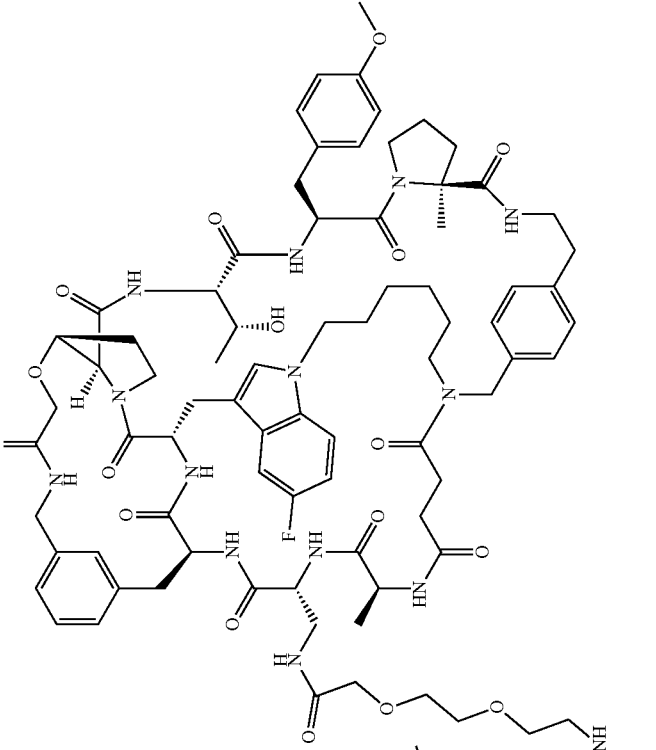 |

TABLE 1-continued
| Ex No | Structure |
|---|---|
| Ex-7* | 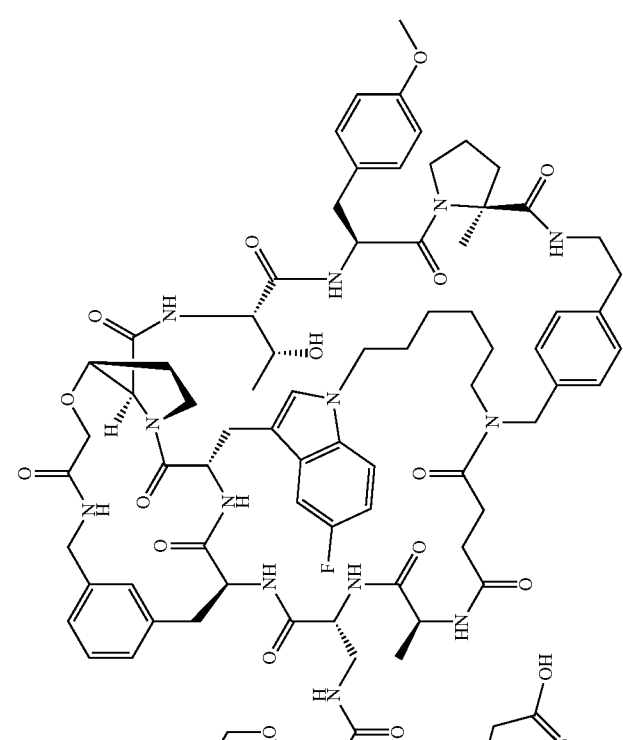 |

TABLE 1-continued
| Ex No | Structure |
|---|---|
| Ex-8* | 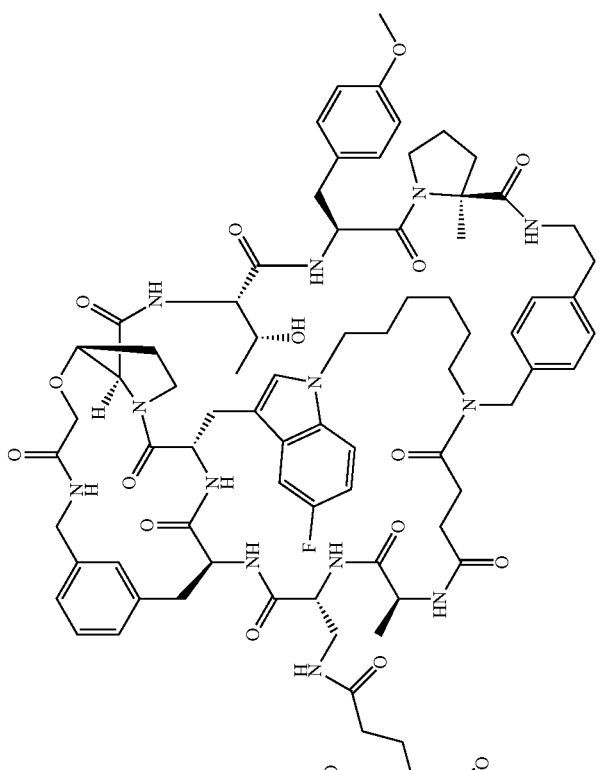 |

TABLE 1-continued
| Ex No | Structure |
|---|---|
| Ex-9* | 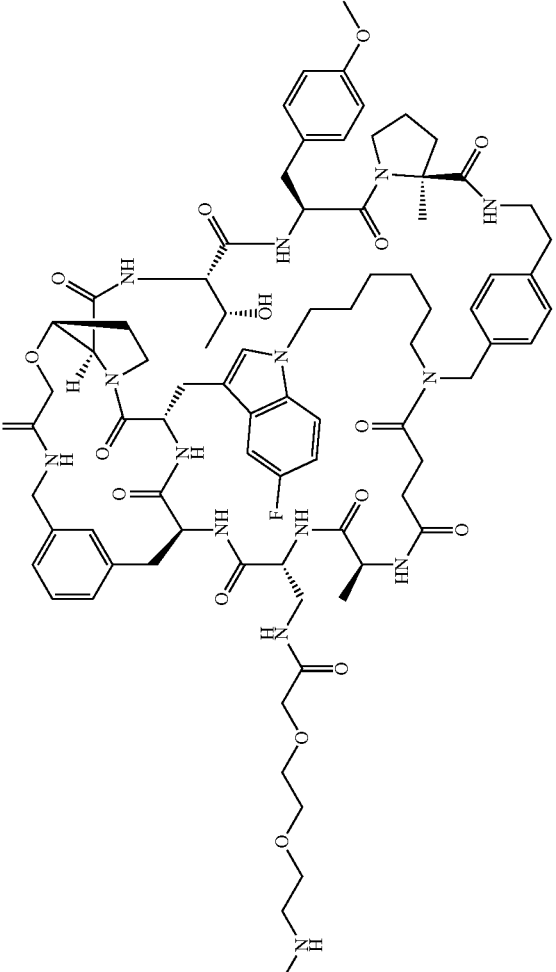 |

TABLE 1-continued
Structure
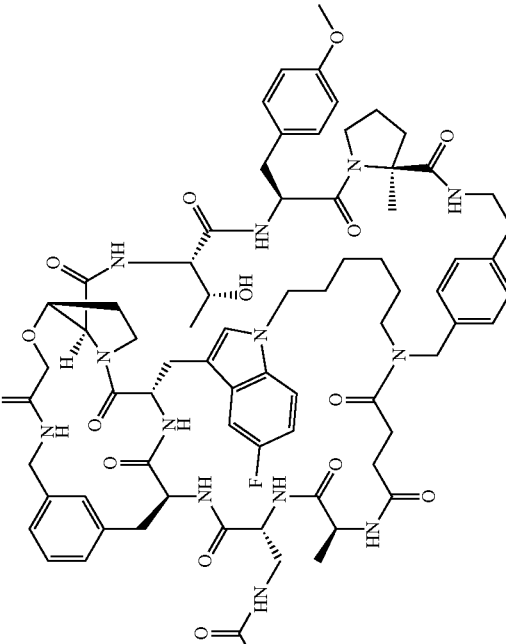
| Ex No |
|---|
| Ex-10* |

TABLE 1-continued
| Ex No | Structure |
|---|---|
| Ex-11* | 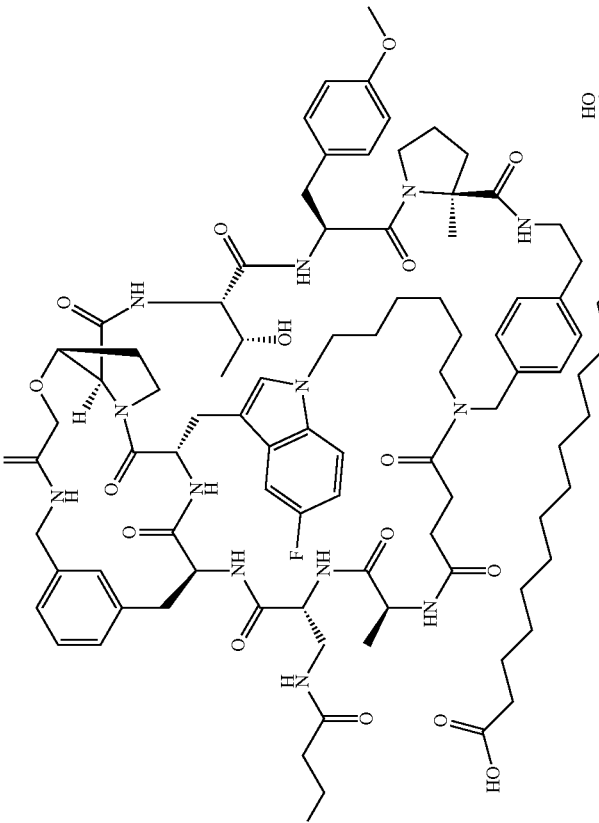 |

TABLE 1-continued
| Ex No | Structure |
|---|---|
| Ex-12* | 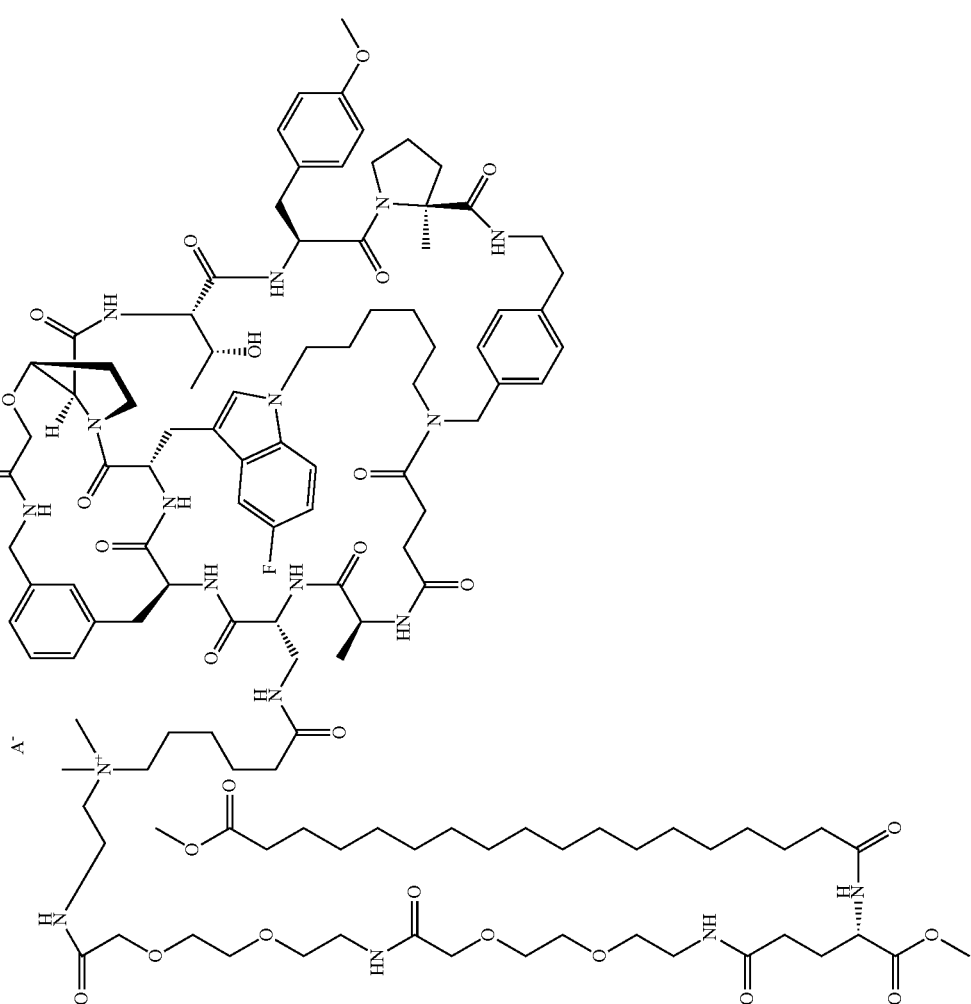 |

TABLE 1-continued
| Ex No | Structure |
|---|---|
| Ex-13* | 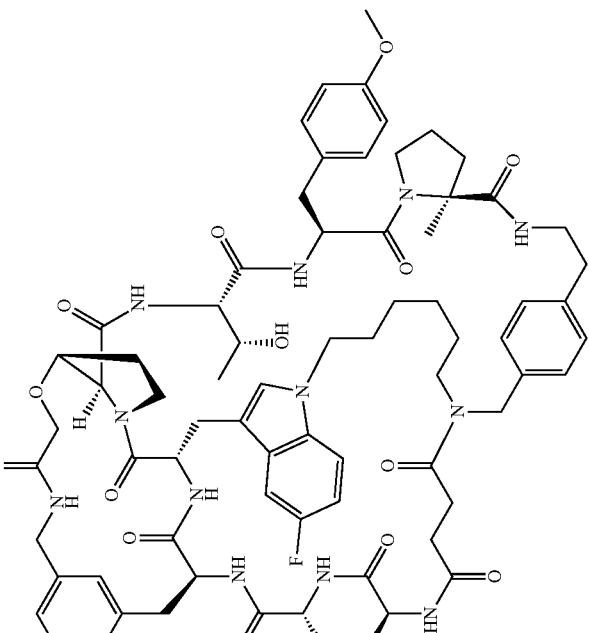 |

TABLE 1-continued
| Ex No | Structure |
|---|---|
| Ex-14* | 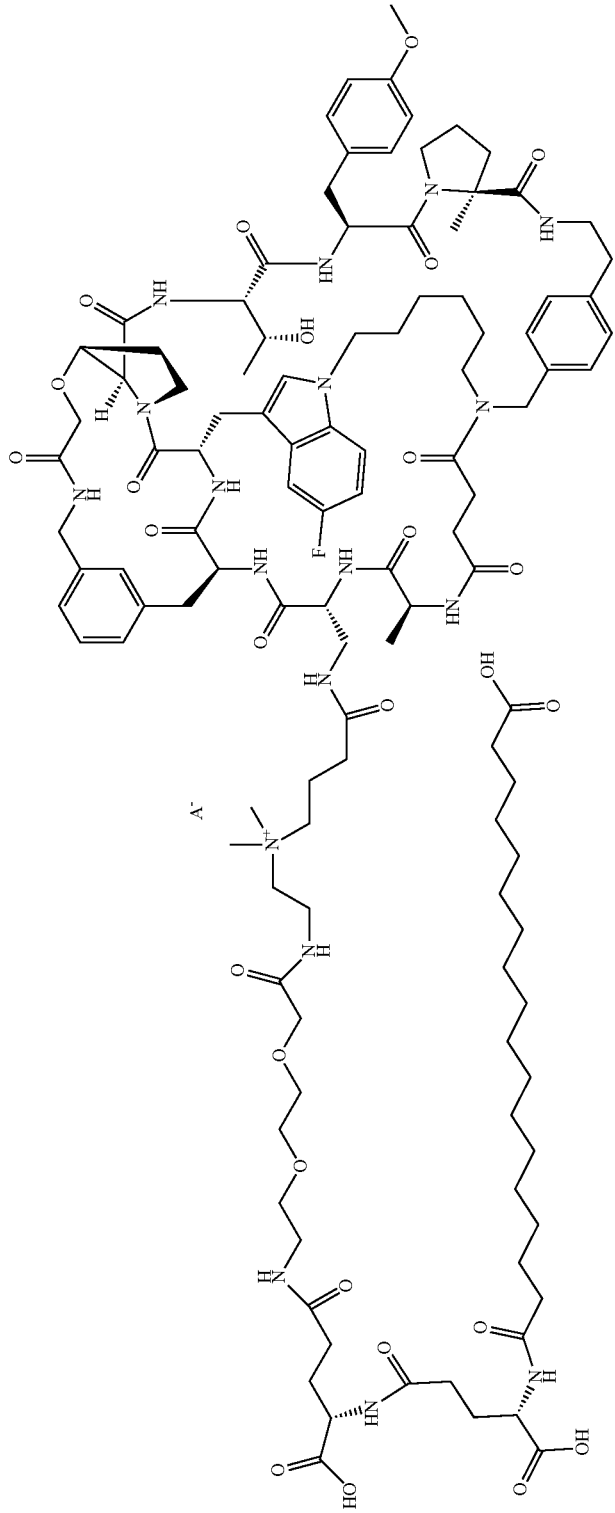 |

TABLE 1-continued
| Ex No | Structure |
|---|---|
| Ex-15* | 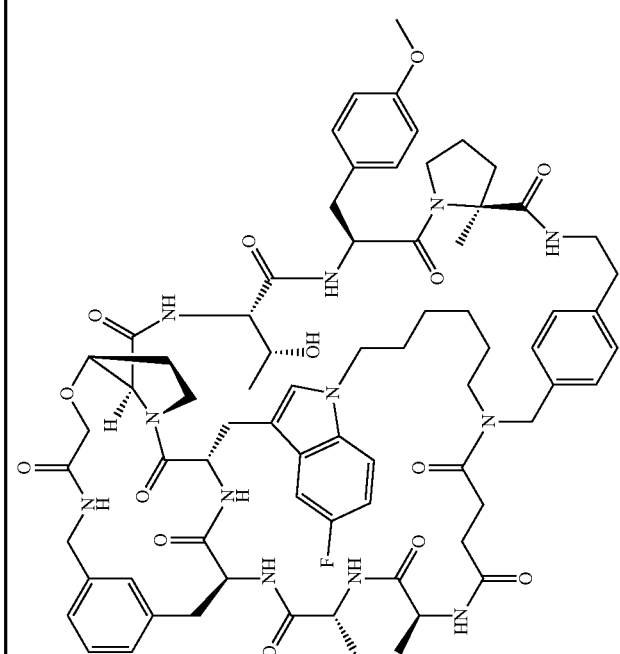 |

TABLE 1-continued
| Ex No | Structure |
|---|---|
| Ex-16* | 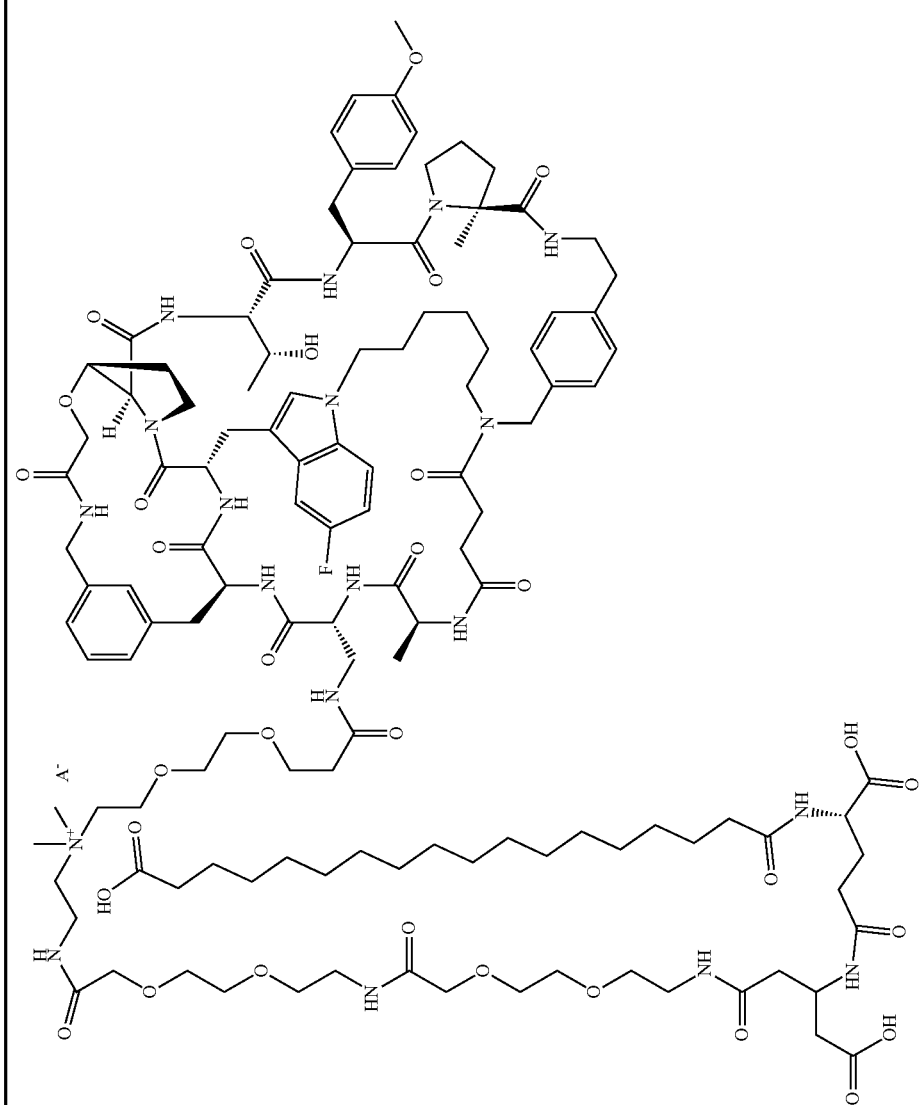 |

TABLE 1-continued
| Ex No | Structure |
|---|---|
| Ex-17* | 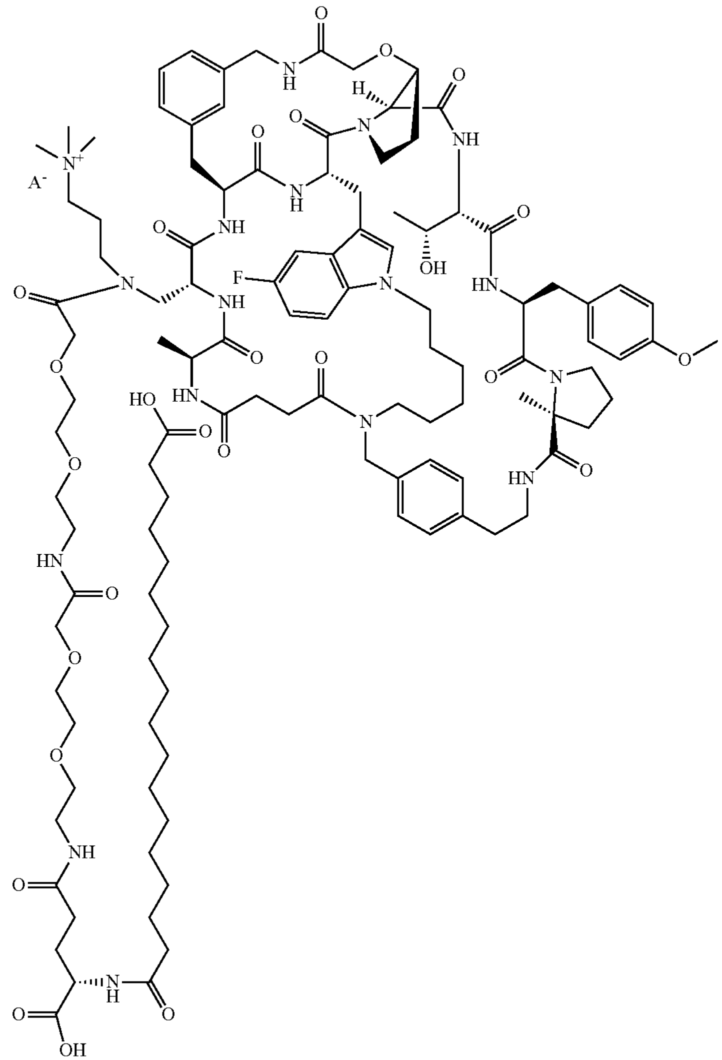 |

TABLE 1-continued
| Ex No | Structure |
|---|---|
| Ex-18 | 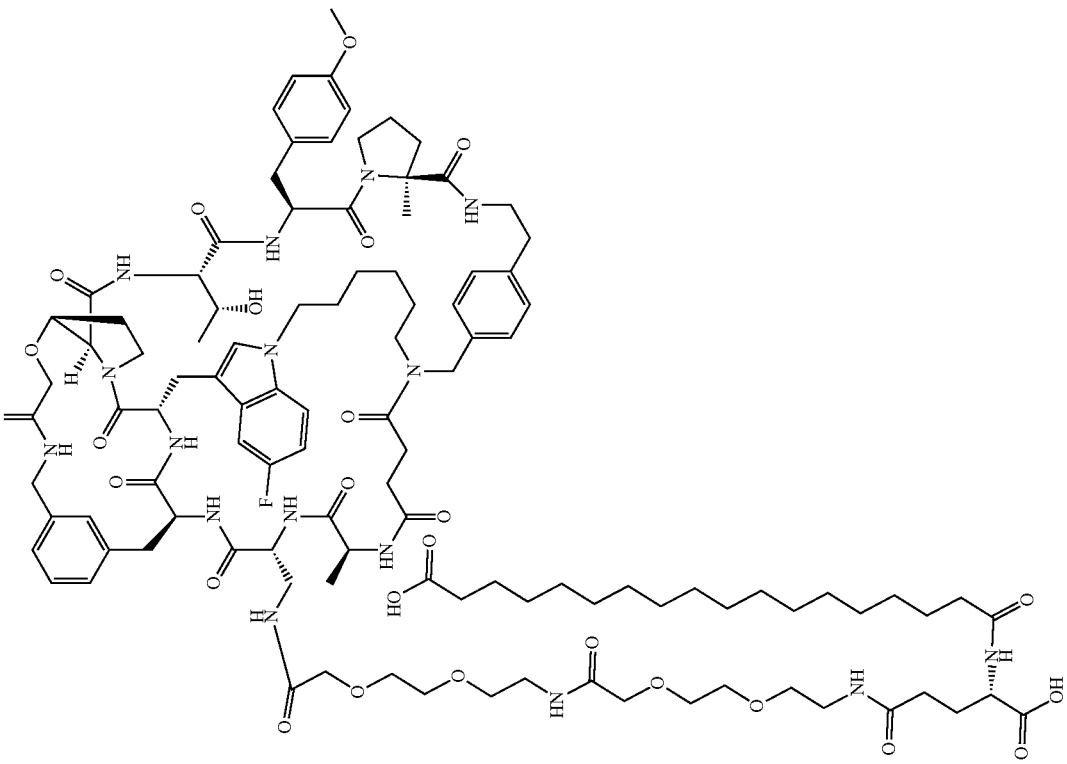 |

TABLE 1-continued
| Ex No | Structure |
|---|---|
| Ex-19* | 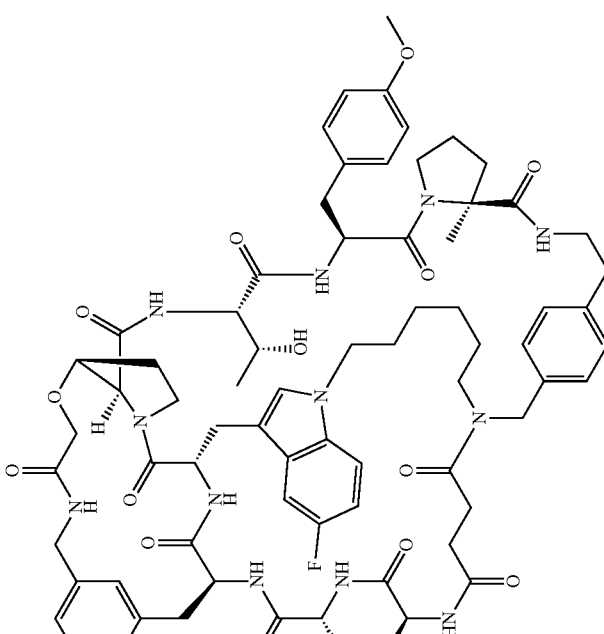 |

TABLE 1-continued
| Ex No | Structure |
|---|---|
| Ex-20* | 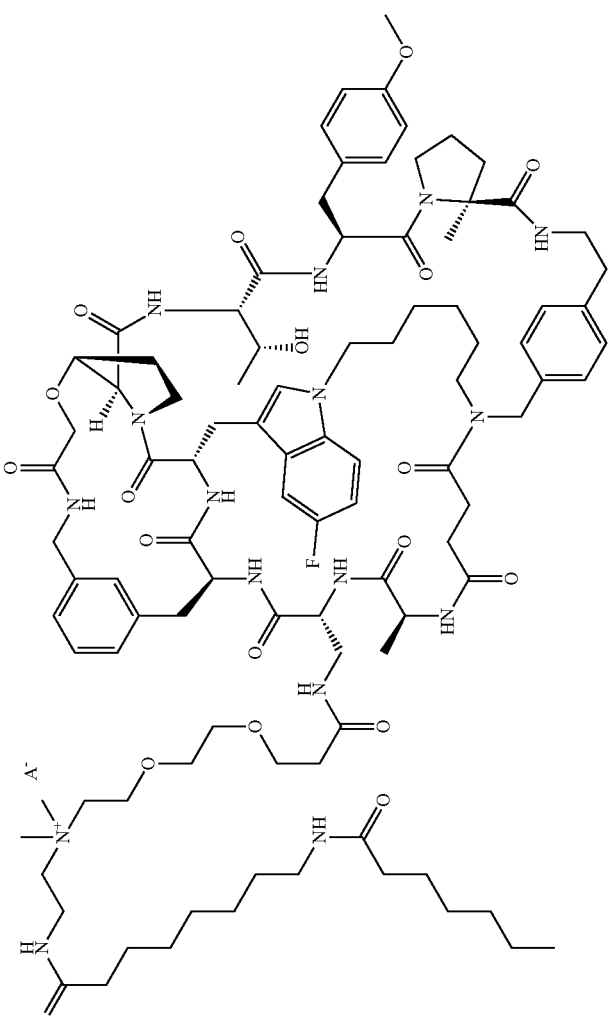 |

TABLE 1-continued
| Ex No | Structure |
|---|---|
| Ex-21* | 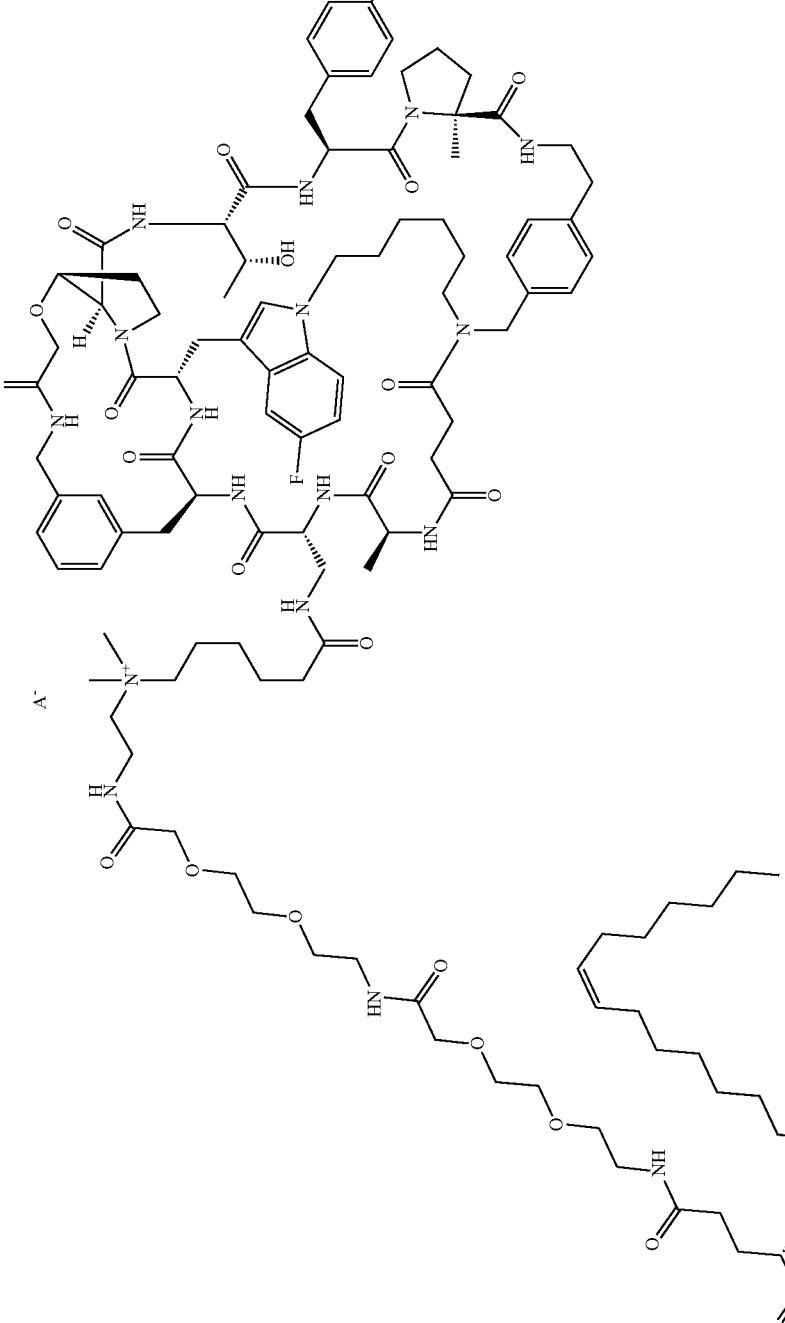 |

TABLE 1-continued
| Ex No | Structure |
|---|---|
| Ex-22* | 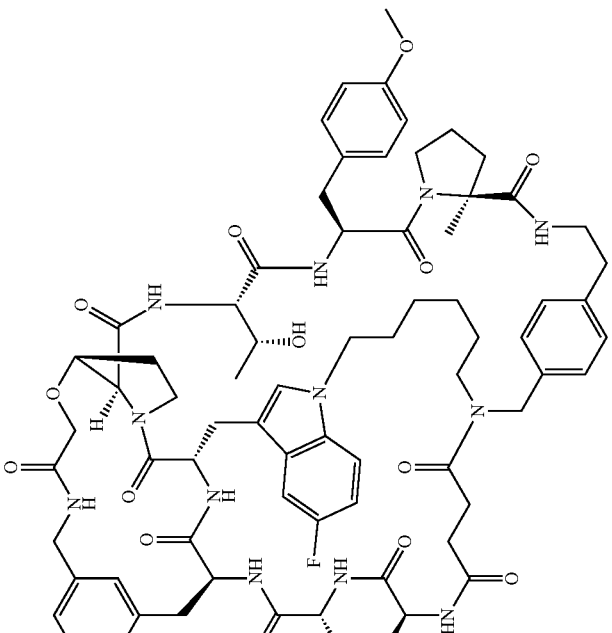 |

TABLE 1-continued
| Ex No | Structure |
|---|---|
| Ex-23* | 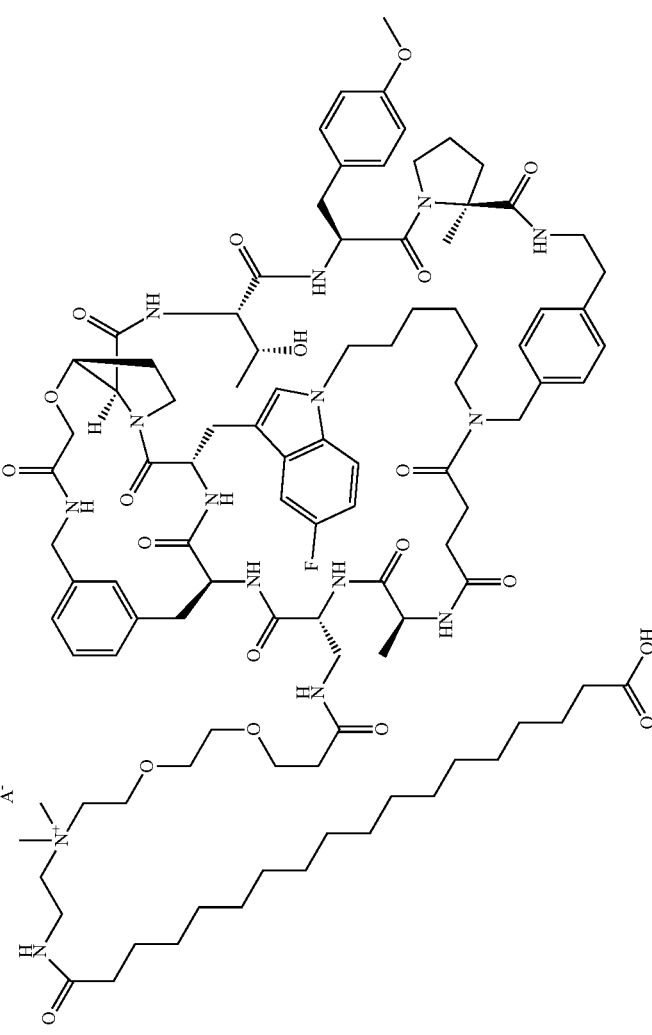 |

TABLE 1-continued
| Ex No | Structure |
|---|---|
| Ex-24 | 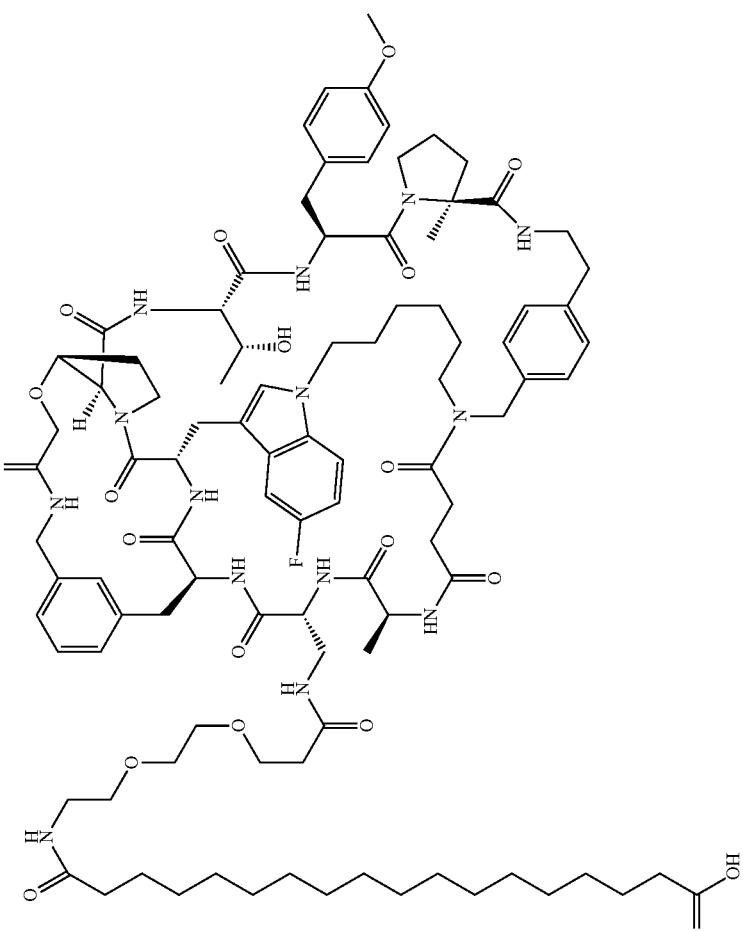 |

TABLE 1-continued
| Ex No | Structure |
|---|---|
| Ex-25* | 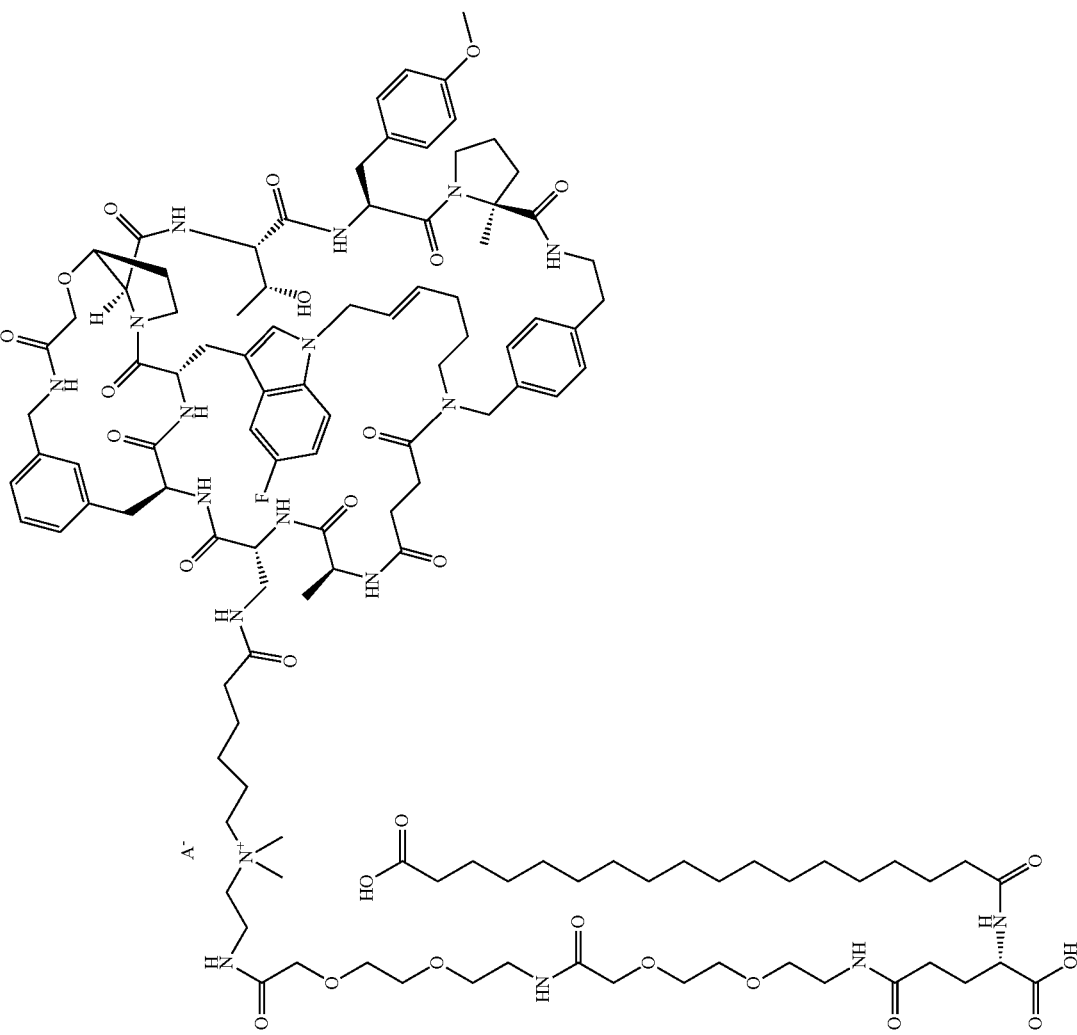 |

TABLE 1-continued
| Ex No | Structure |
|---|---|
| Ex-26* | 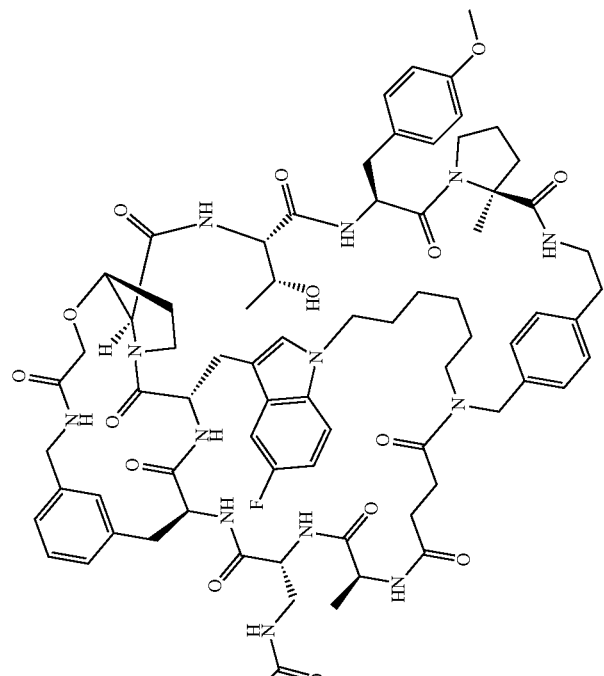 |

TABLE 1-continued
| Ex No | Structure |
|---|---|
| Ex-27* | 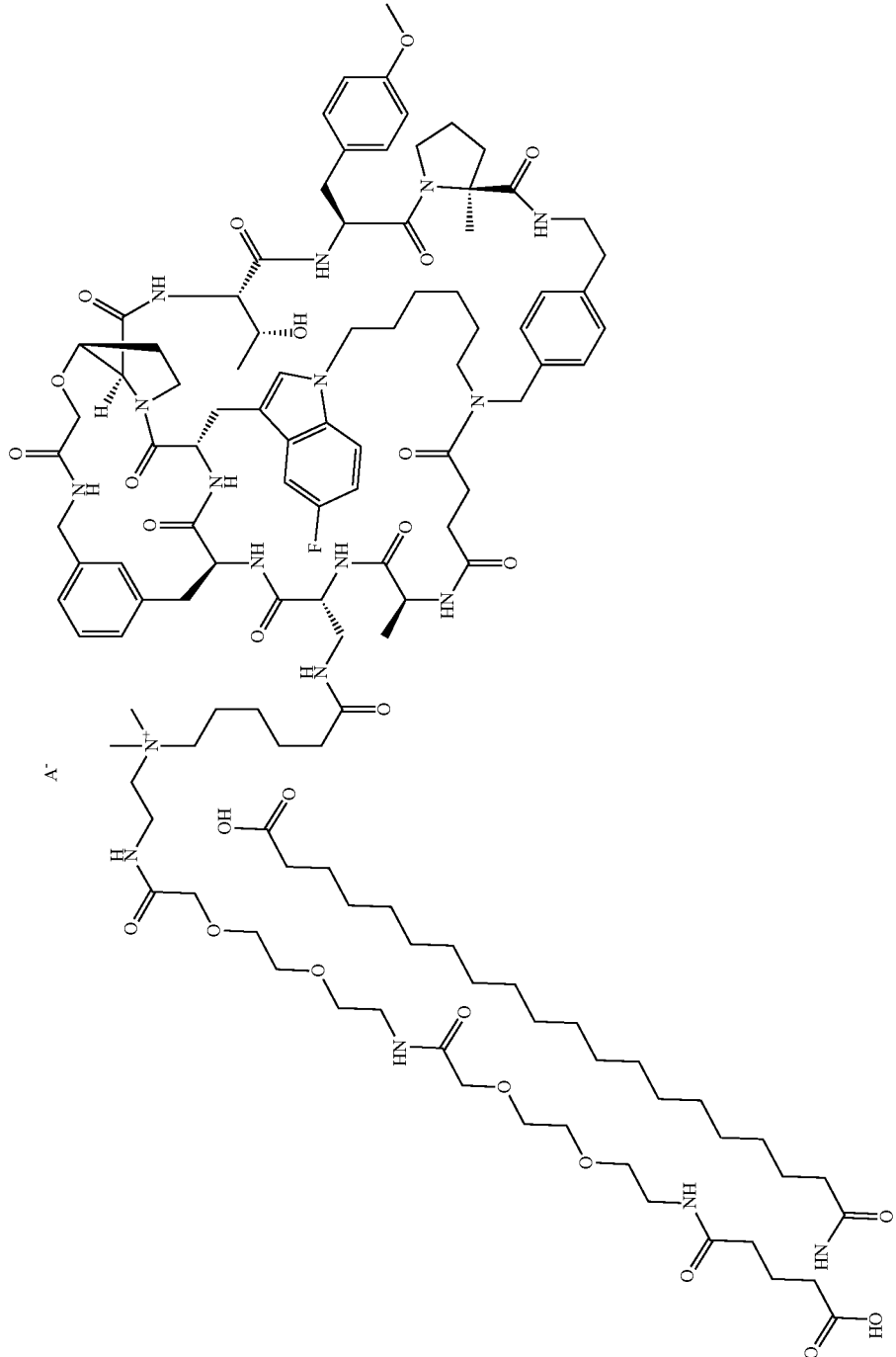 |

TABLE 1-continued
| Ex No | Structure |
|---|---|
| Ex-28* | 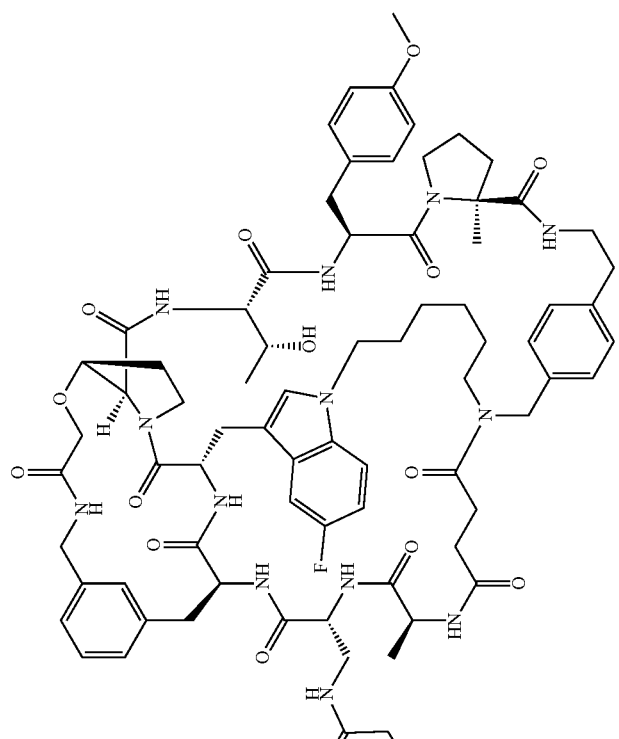 |

| Ex No | Structure |
|---|---|
| Ex-29* | 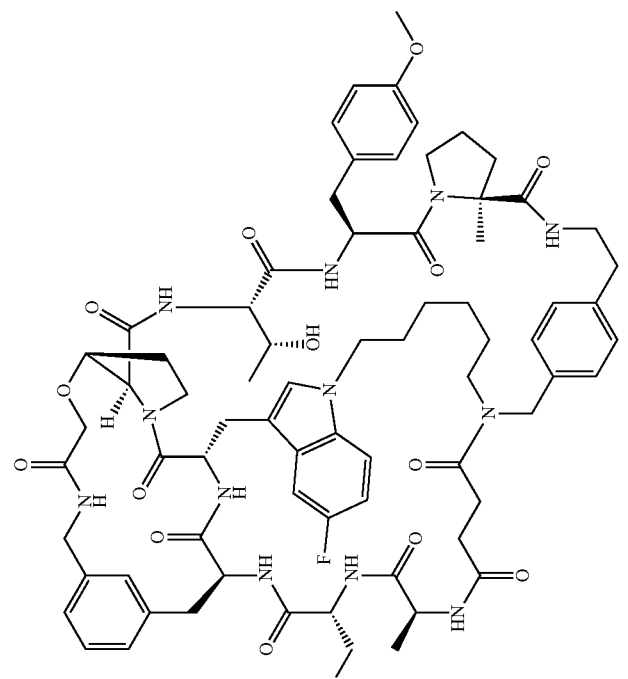 |

TABLE 1-continued
| Ex No | Structure |
|---|---|
| Ex-30* | 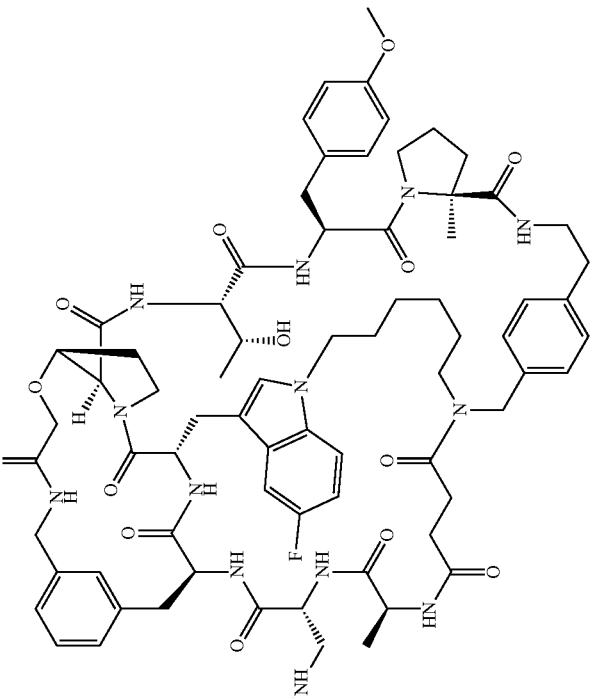 |

TABLE 1-continued
| Ex No | Structure |
|---|---|
| Ex31* | 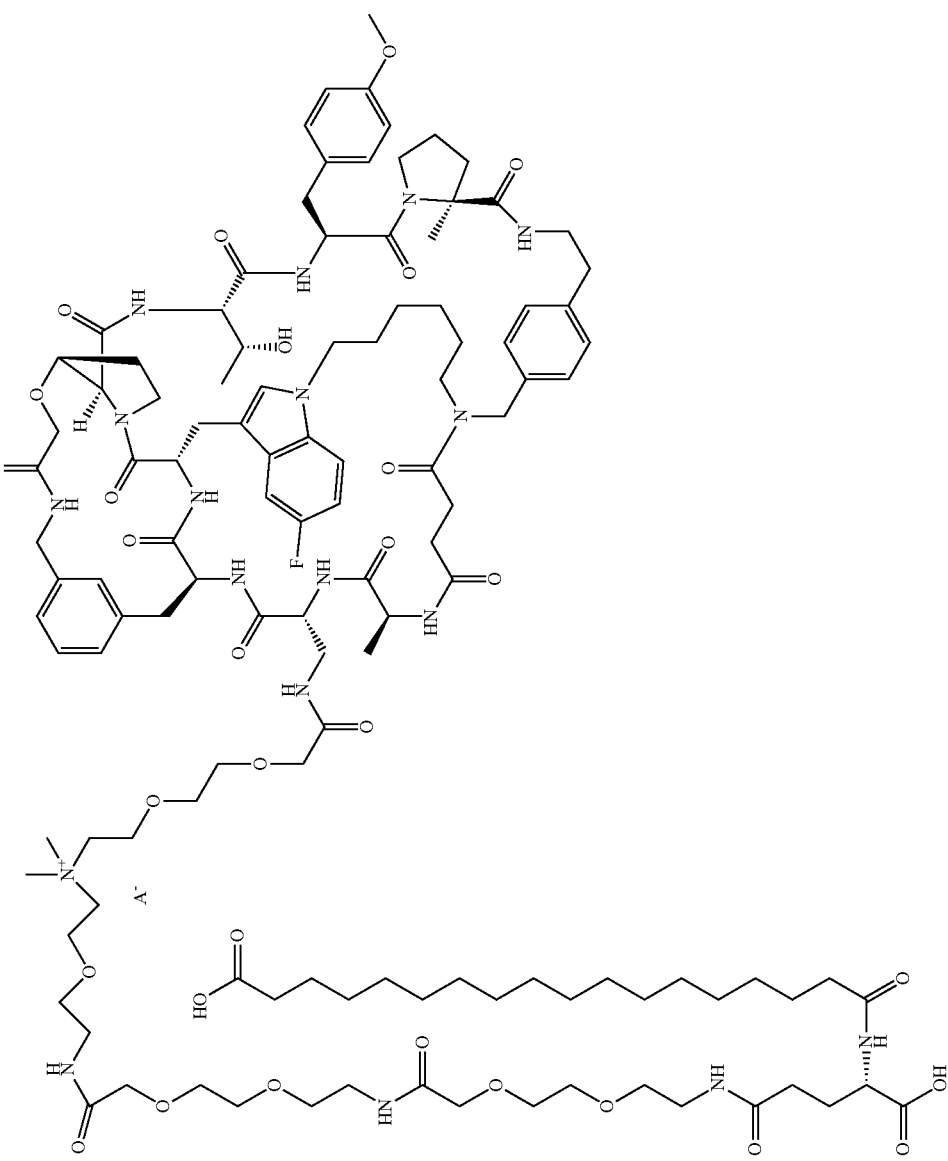 |

TABLE 1-continued
| Ex No | Structure |
|---|---|
| Ex-32* | 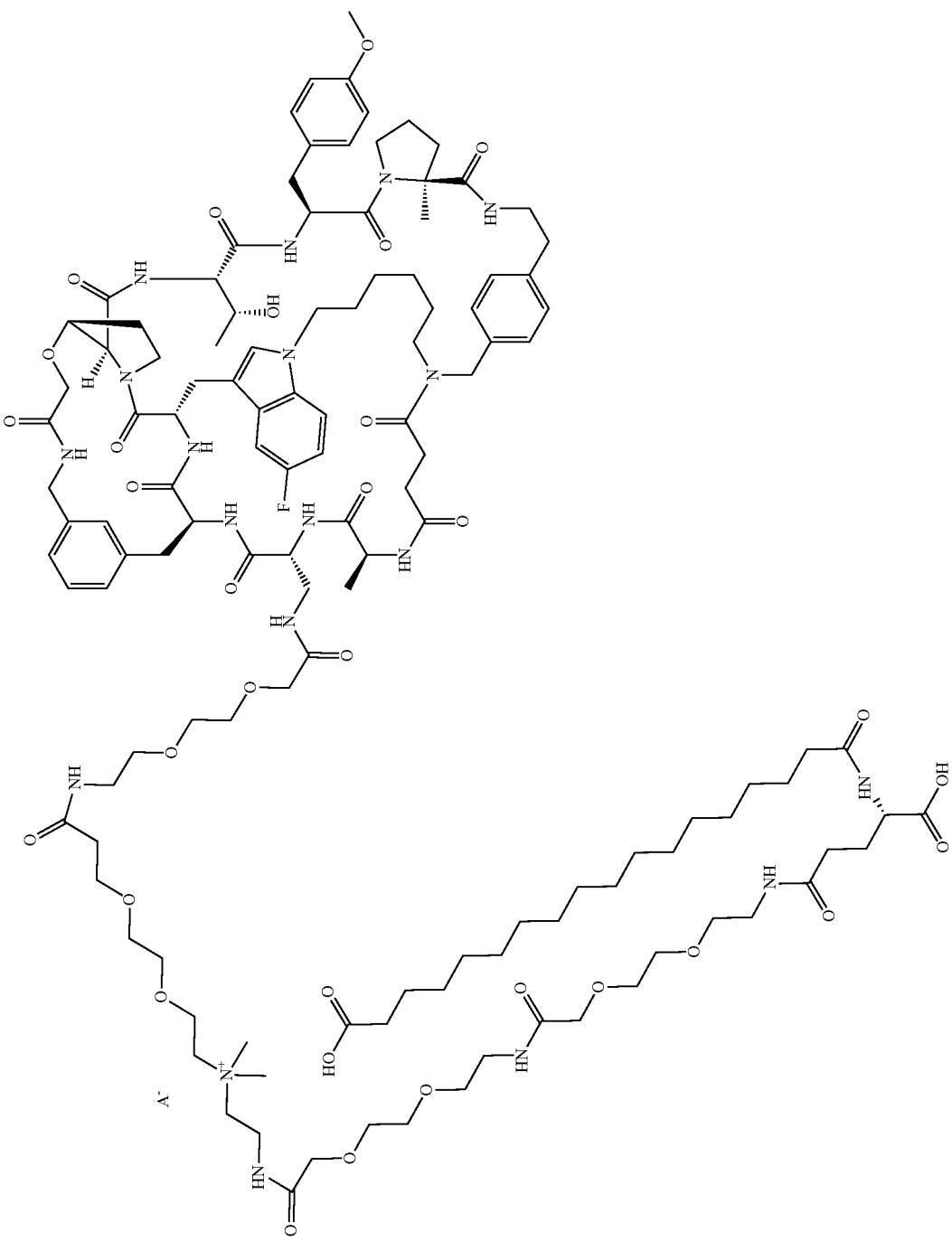 |

TABLE 1-continued
| Ex No | Structure |
|---|---|
| Ex-33* | 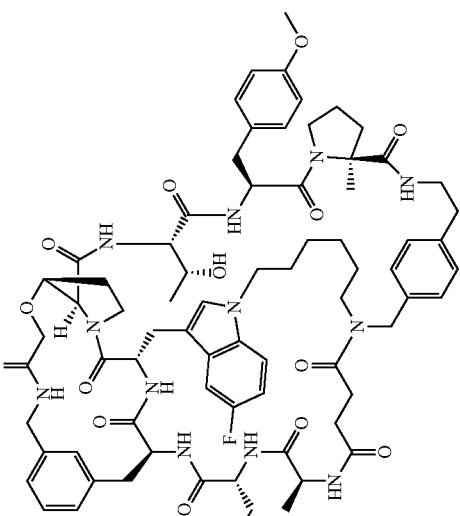 |

TABLE 1-continued
| Ex No | Structure |
|---|---|
| Ex-34* | 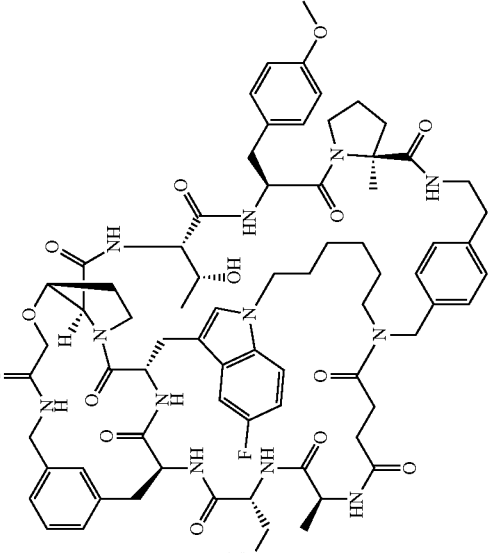 |

TABLE 1-continued
| Ex No | Structure |
|---|---|
| Ex-35* | 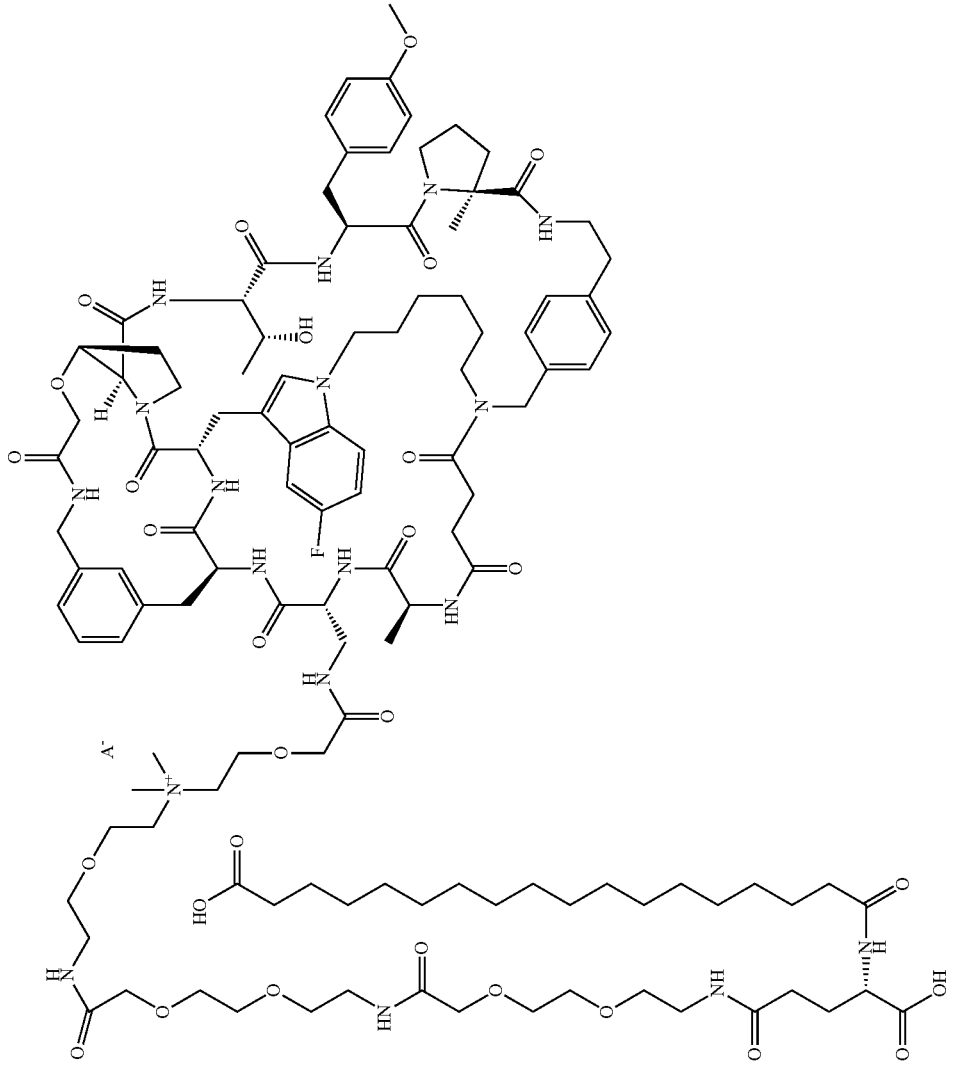 |

TABLE 1-continued

| Ex No | Structure |
|---|---|
| Ex-36* | 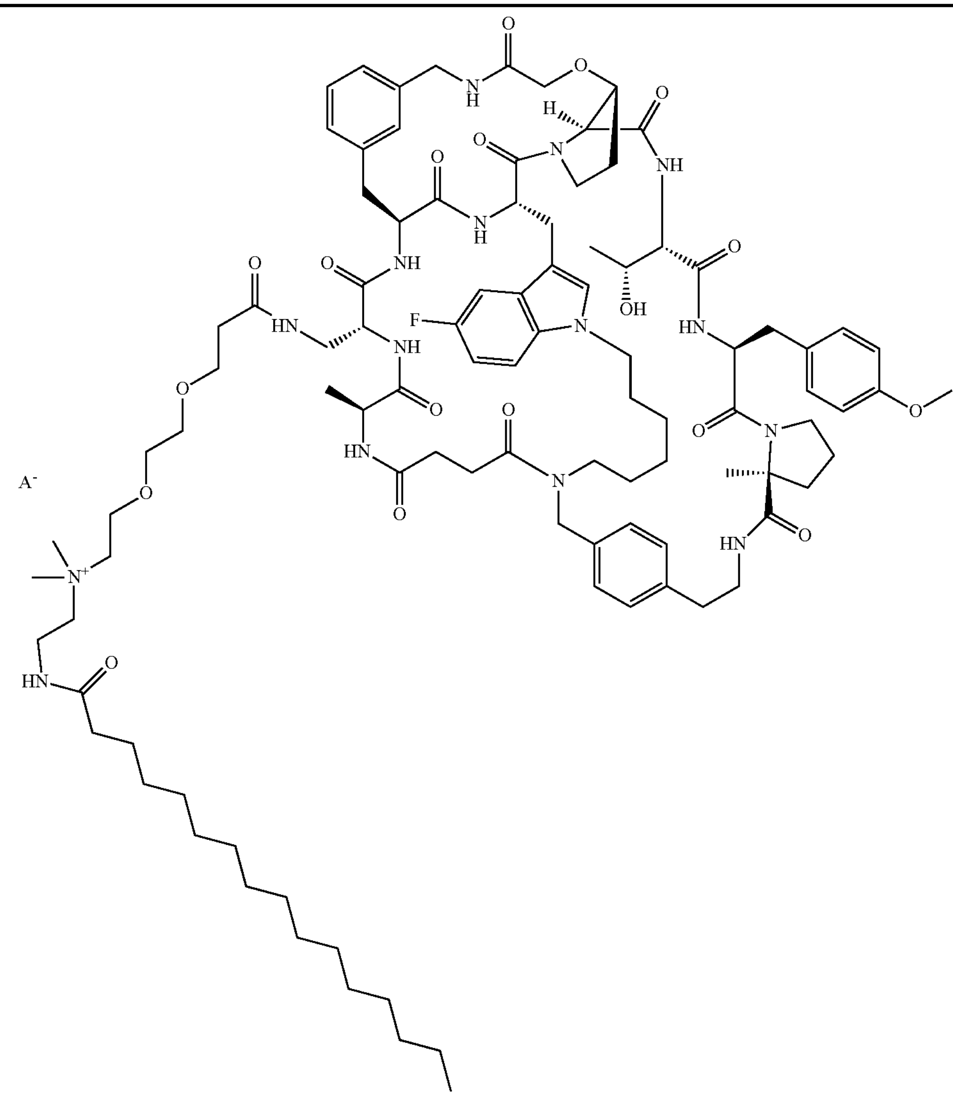 |

TABLE 1-continued
| Ex No | Structure |
|---|---|
| Ex-37* | 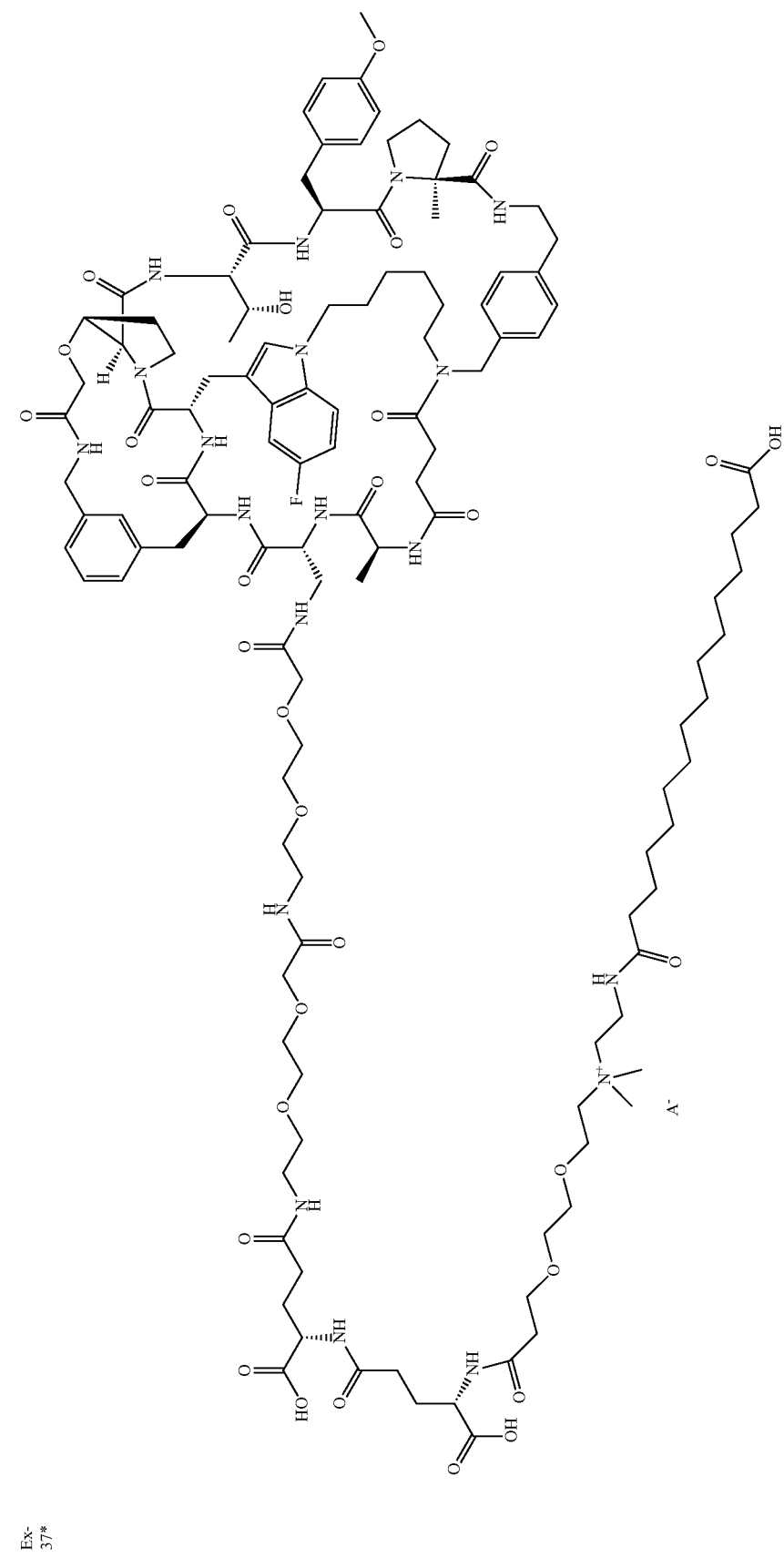 |

TABLE 1-continued
| Ex No | Structure |
|---|---|
| Ex-38* | 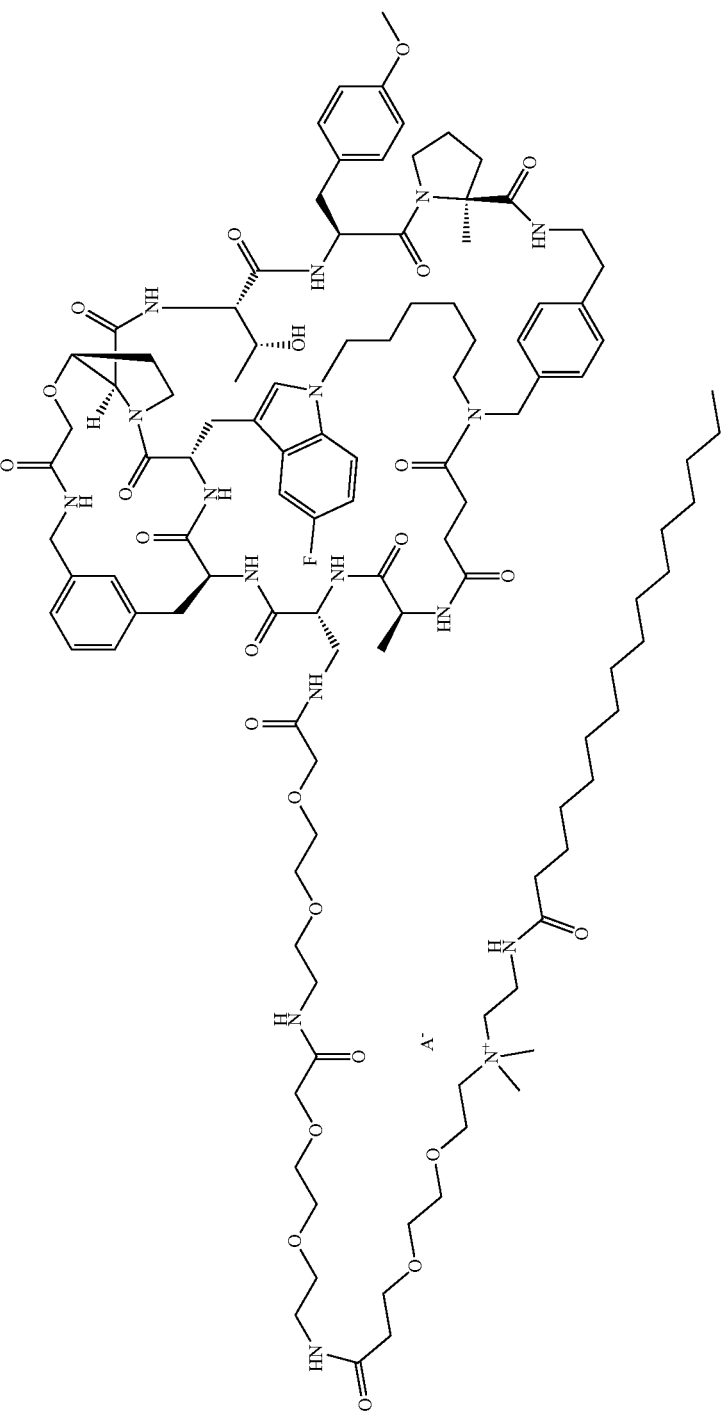 |

| Ex No | Structure |
|---|---|
| Ex-39* | 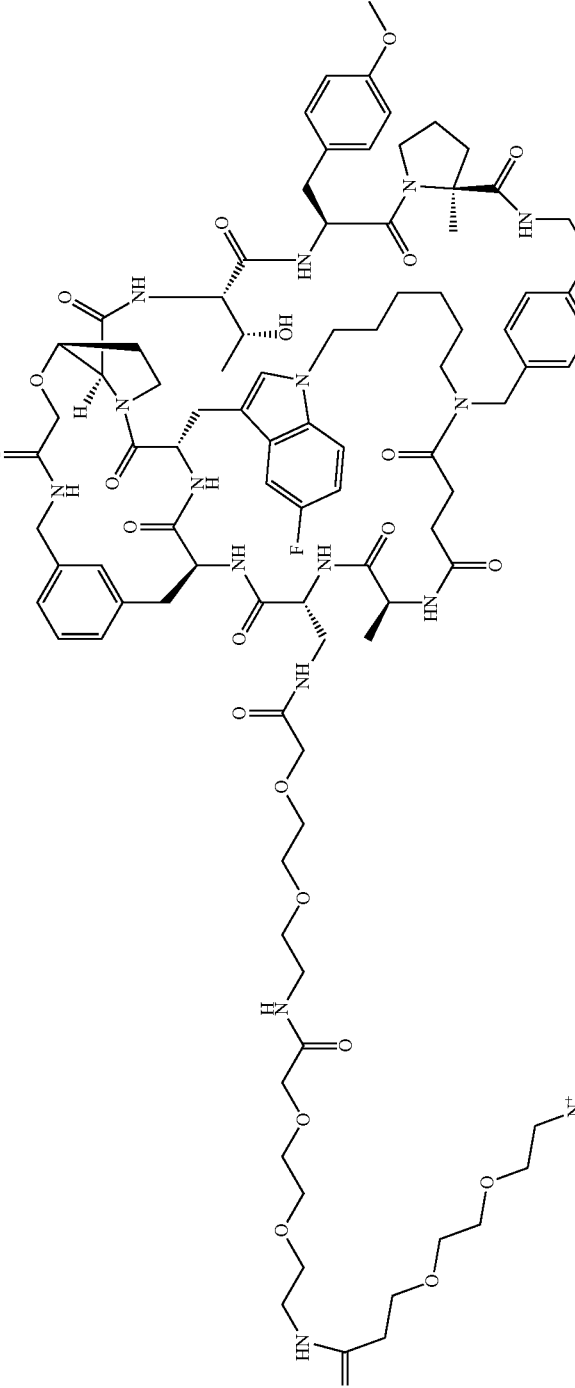 |

TABLE 1-continued

| Ex No | Structure |
|---|---|
| Ex-40* | 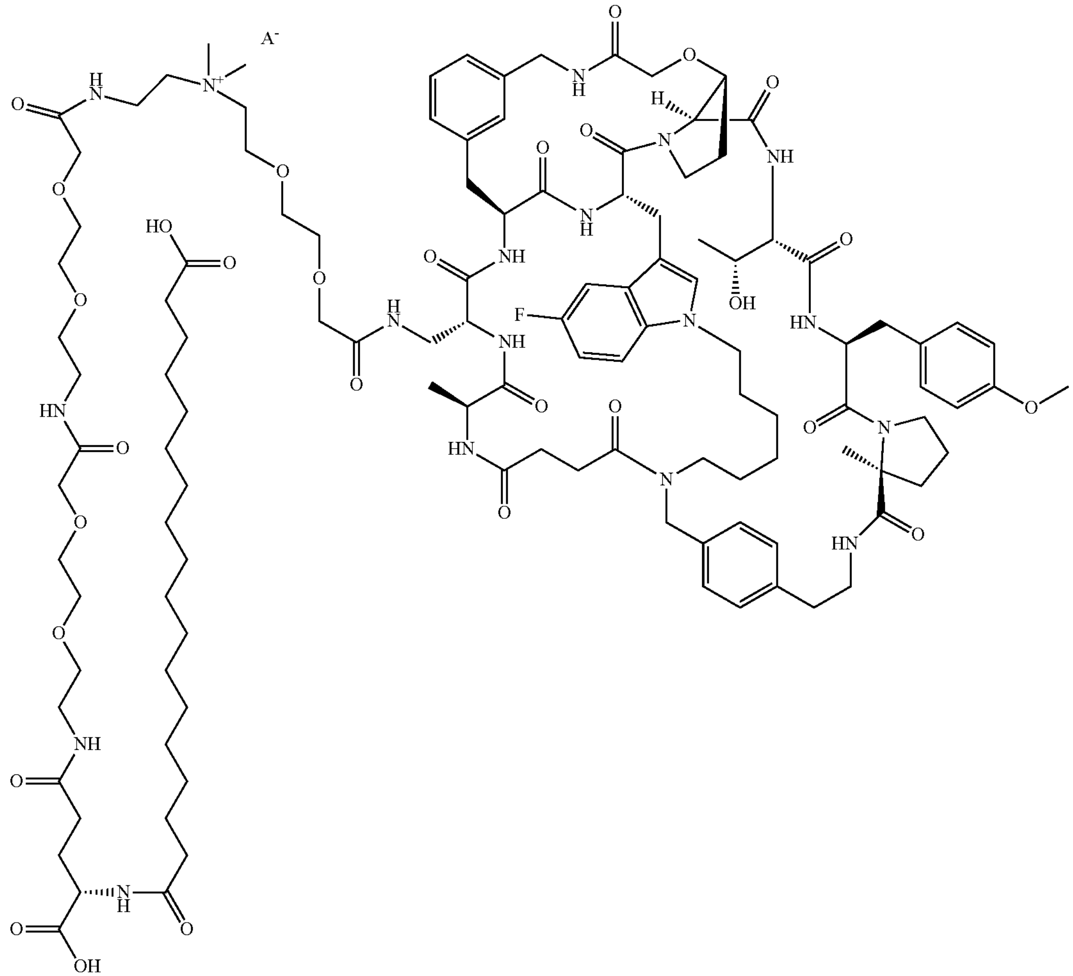 |

TABLE 1-continued
| Ex No | Structure |
|---|---|
| Ex-41 | 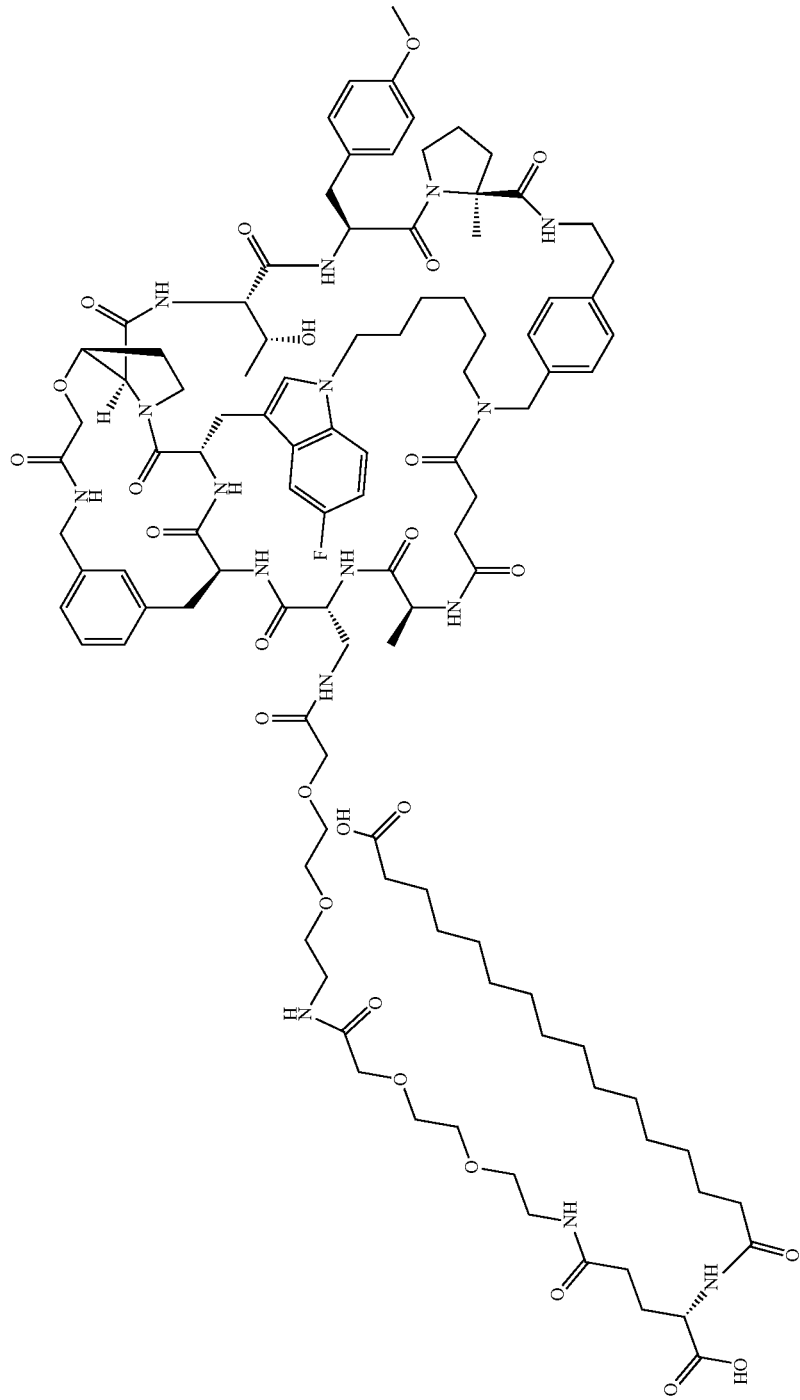 |

TABLE 1-continued
| Ex No | Structure |
|---|---|
| Ex-42 | 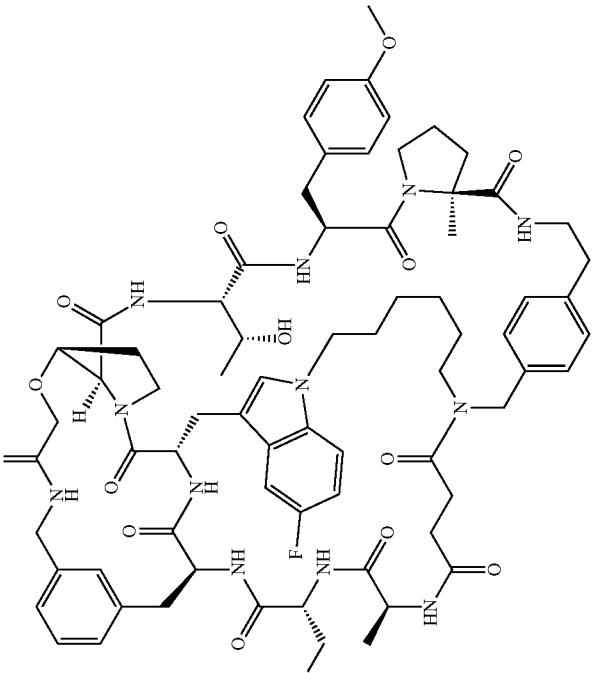 |

TABLE 1-continued
Structure
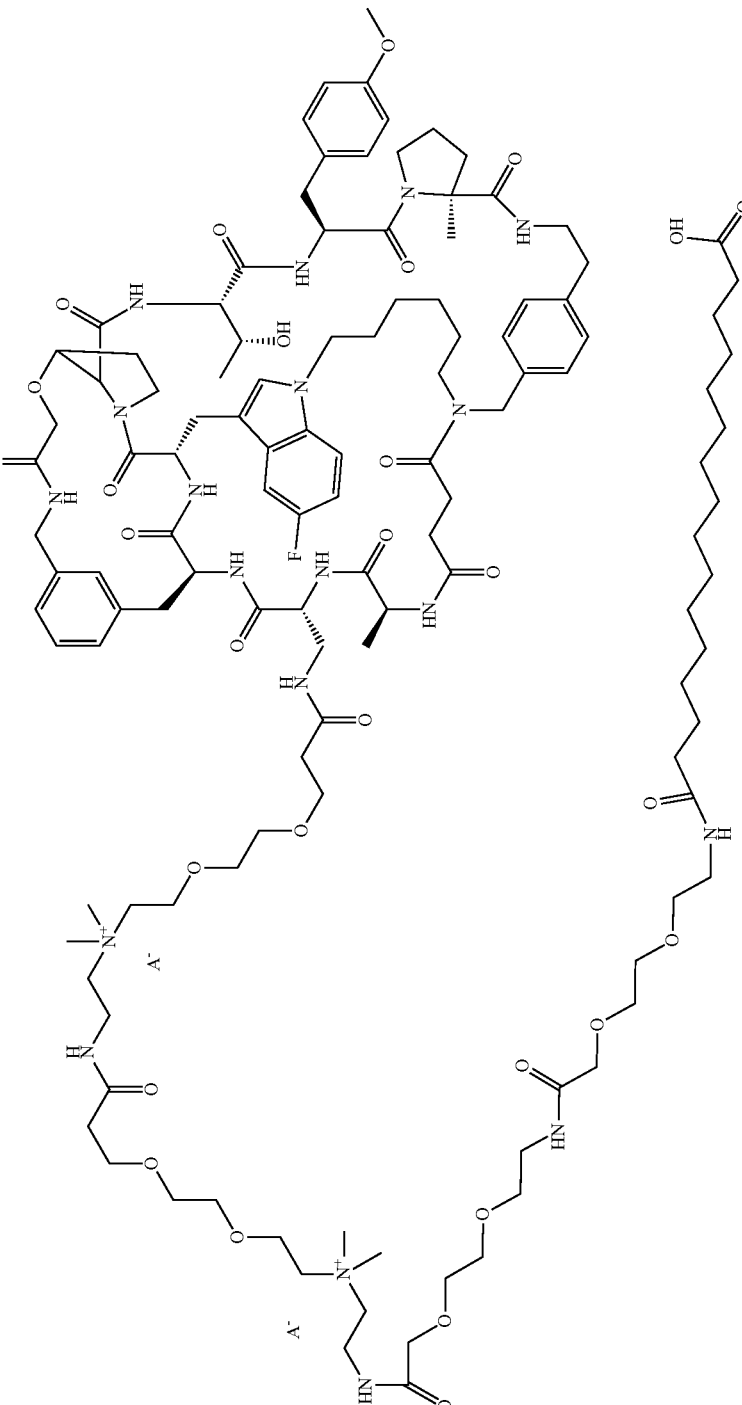
Ex No: Ex-43*

TABLE 1-continued
| Ex No | Structure |
|---|---|
| Ex-44* | 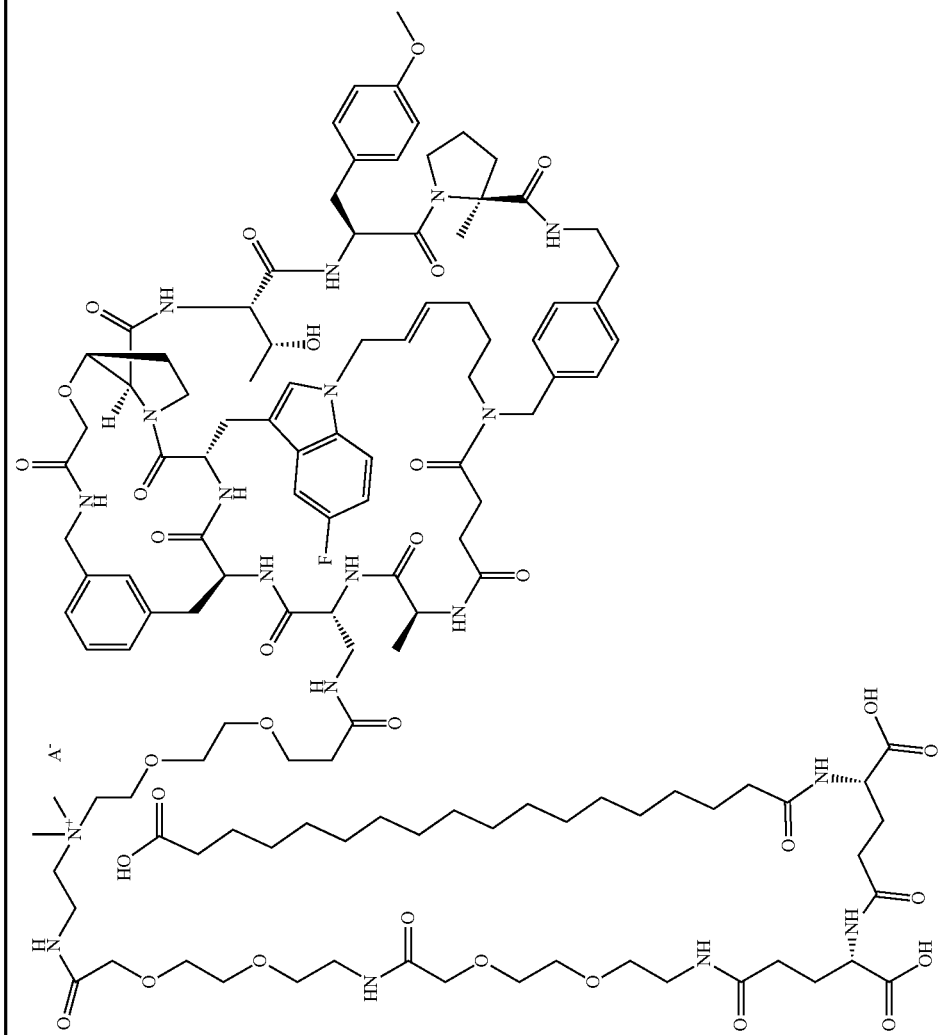 |

TABLE 1-continued

| Ex No | Structure |
|---|---|
| Ex-45* | 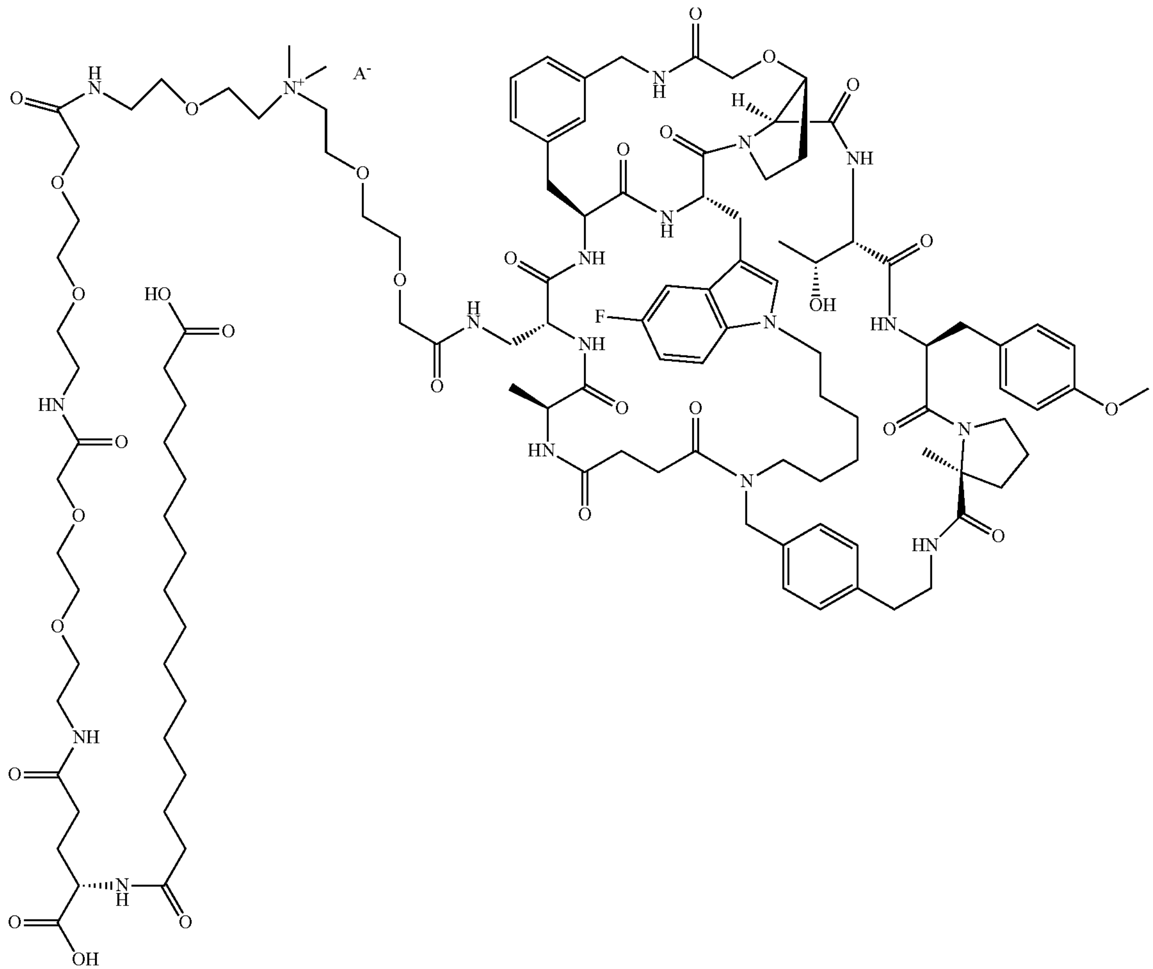 |

TABLE 1-continued
| Ex No | Structure |
|---|---|
| Ex-46* | 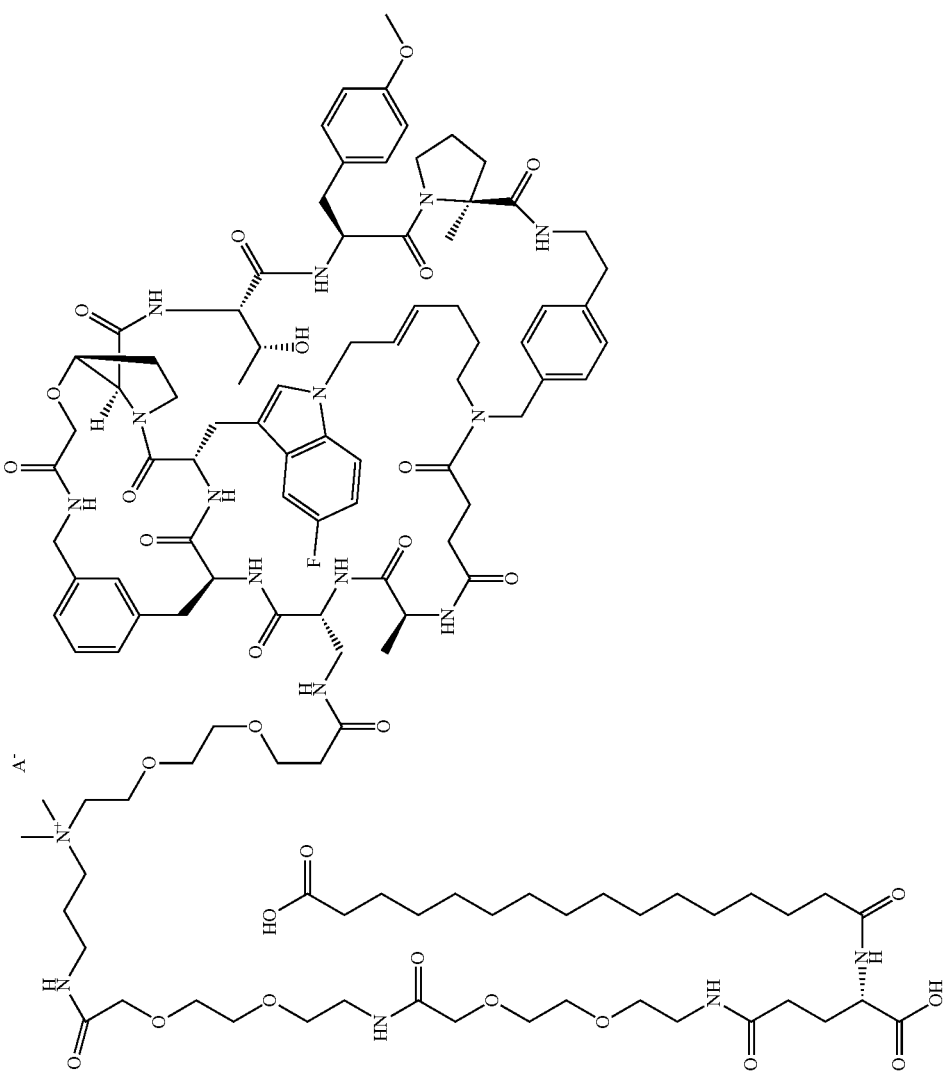 |

TABLE 1-continued
| Ex No | Structure |
|---|---|
| Ex-47* | 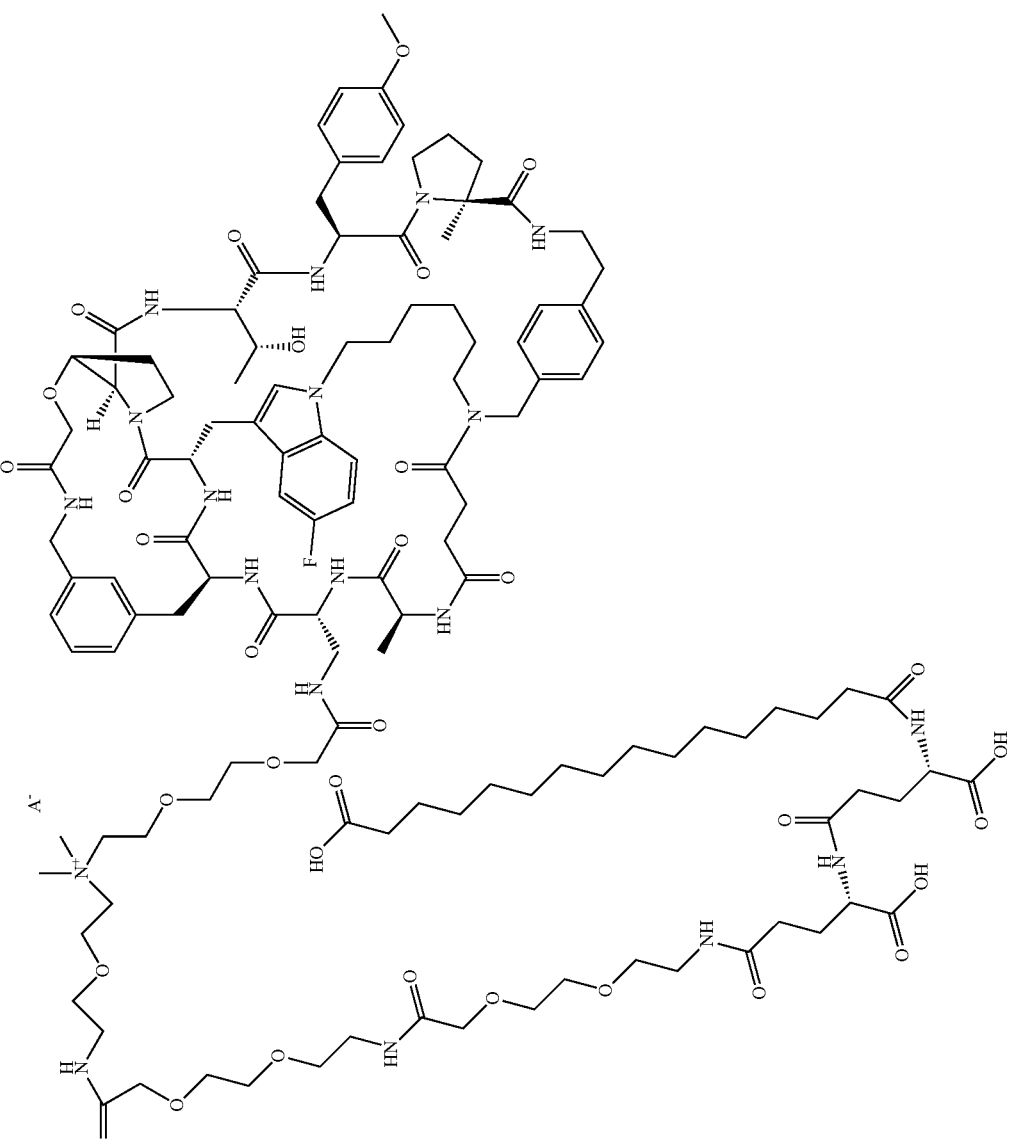 |

TABLE 1-continued
| Ex No | Structure |
|---|---|
| Ex-48* | 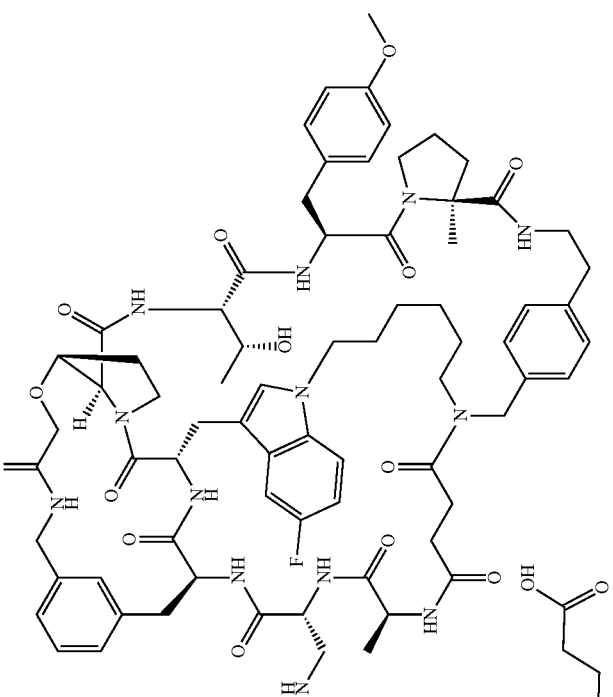 |

TABLE 1-continued
| Ex No | Structure |
|---|---|
| Ex-49* | 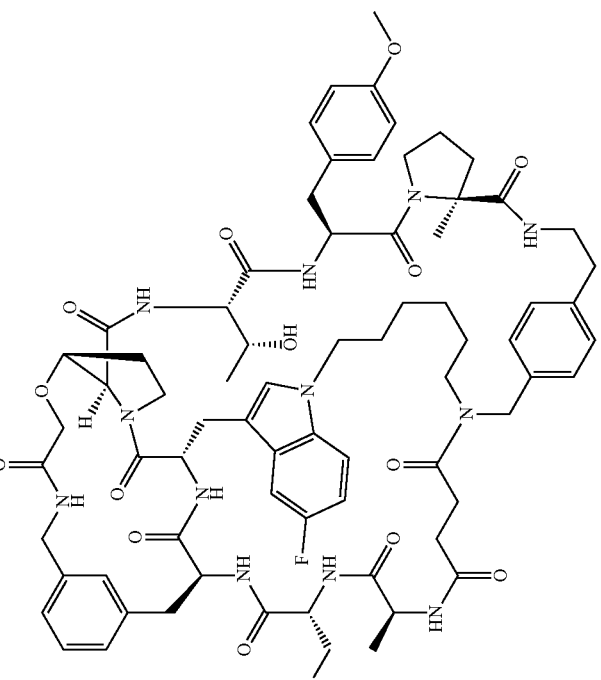 |

TABLE 1-continued
Structure
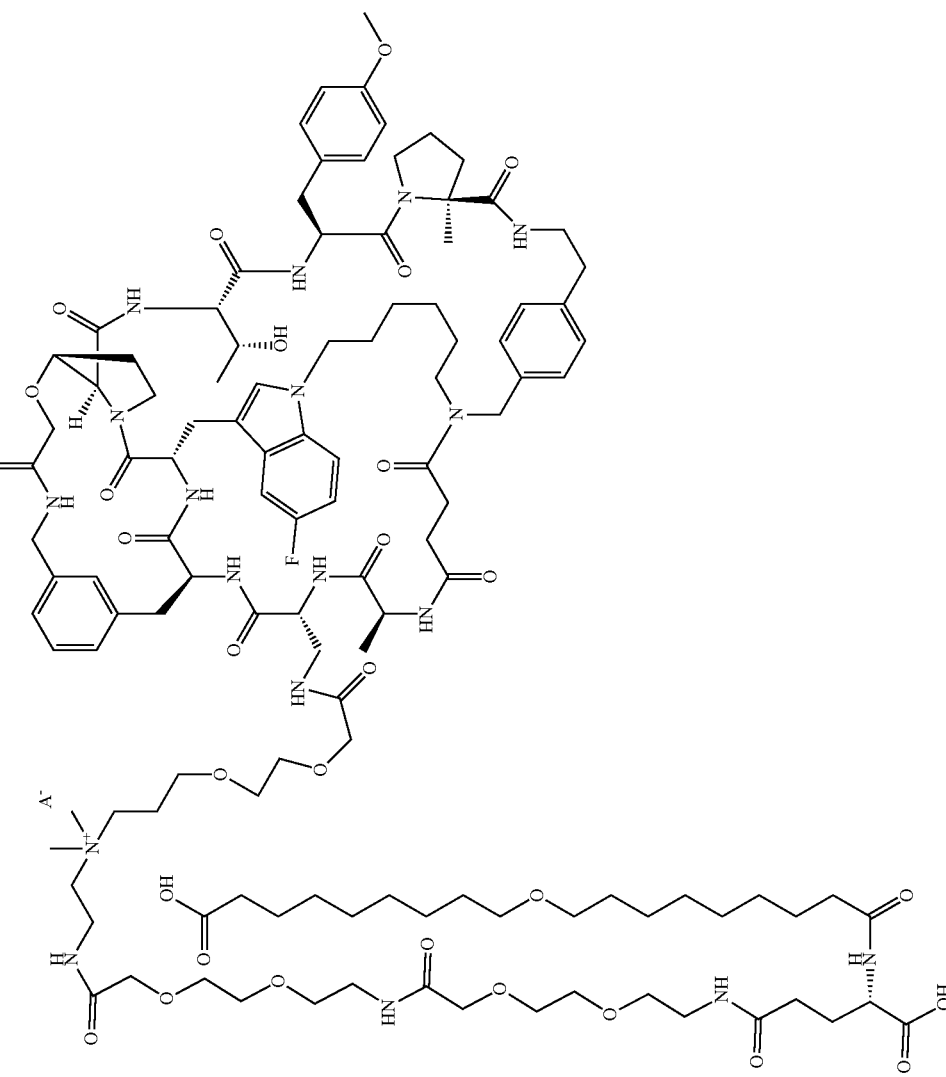
| Ex No |
|---|
| Ex-50* |

TABLE 1-continued
| Ex No | Structure |
|---|---|
| Ex-51* | 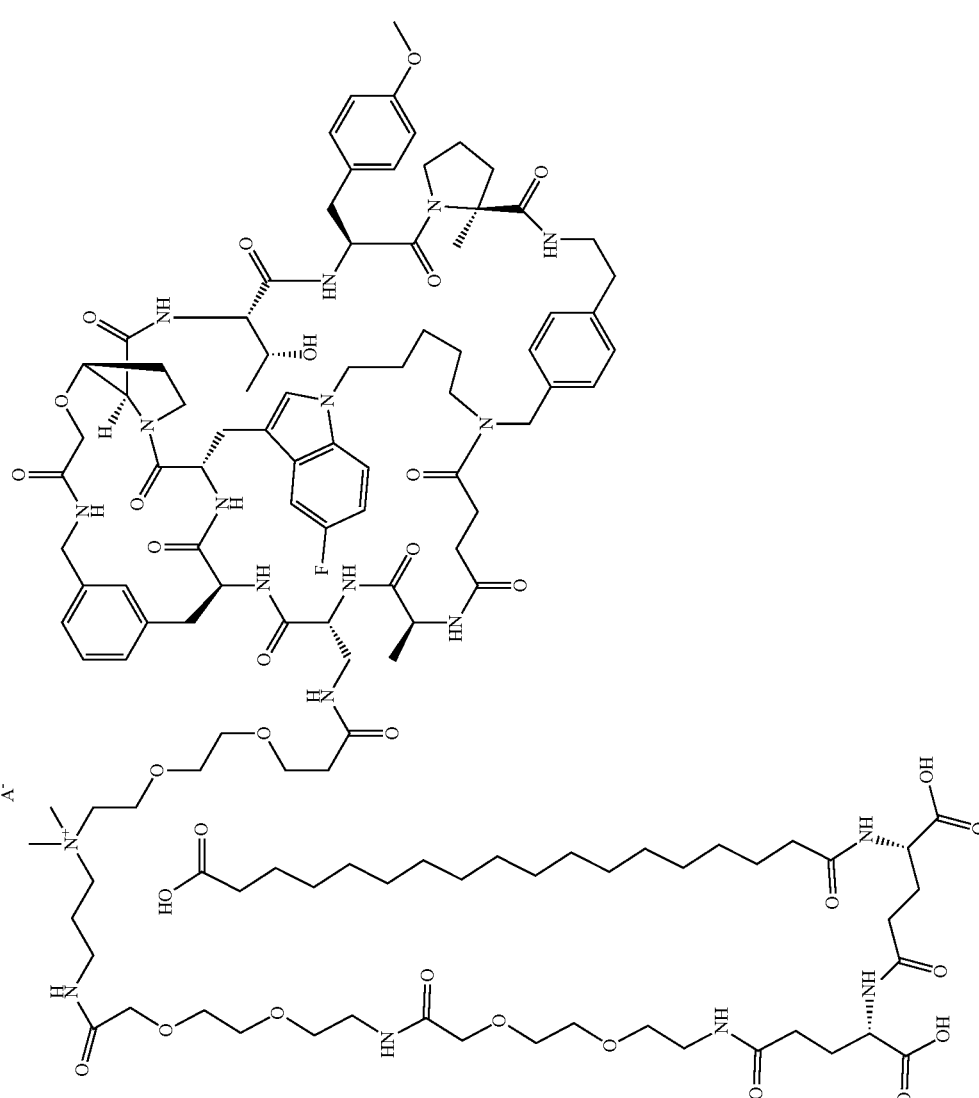 |

TABLE 1-continued
| Ex No | Structure |
|---|---|
| Ex-52* | 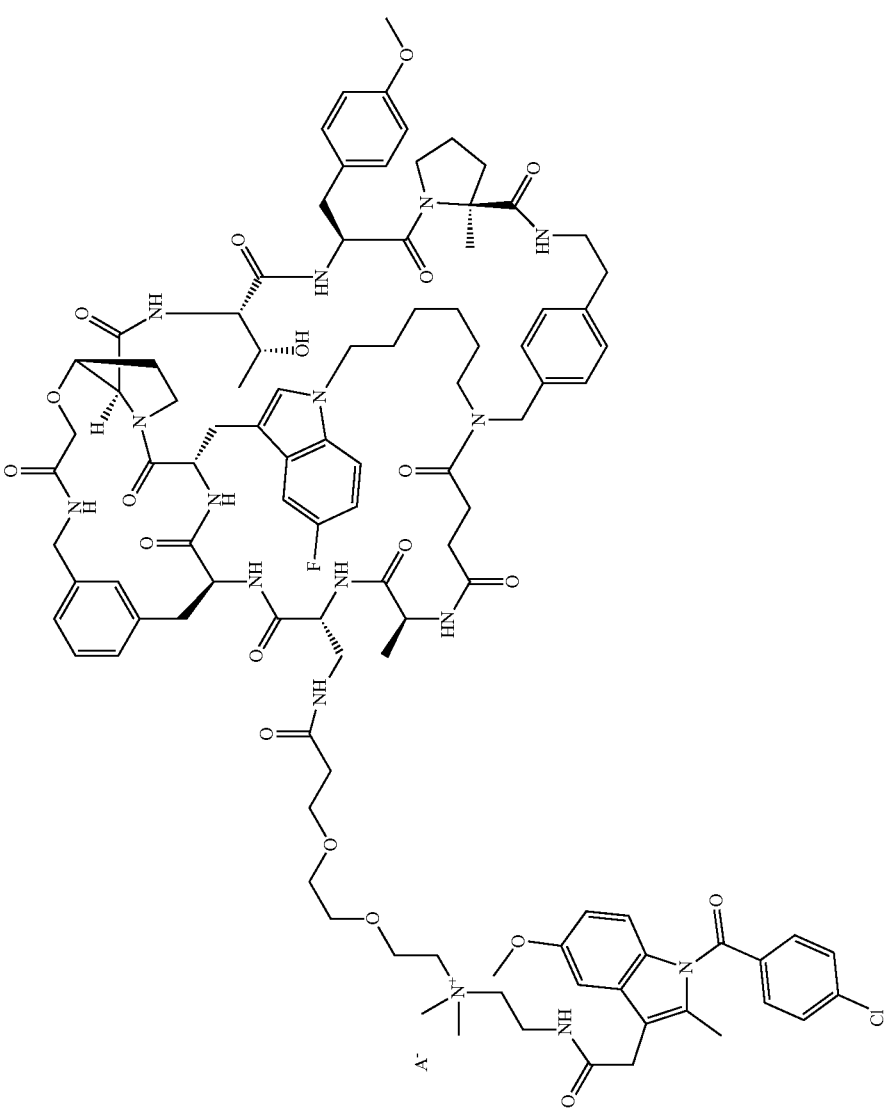 |

TABLE 1-continued
| Ex No | Structure |
|---|---|
| Ex-53* | 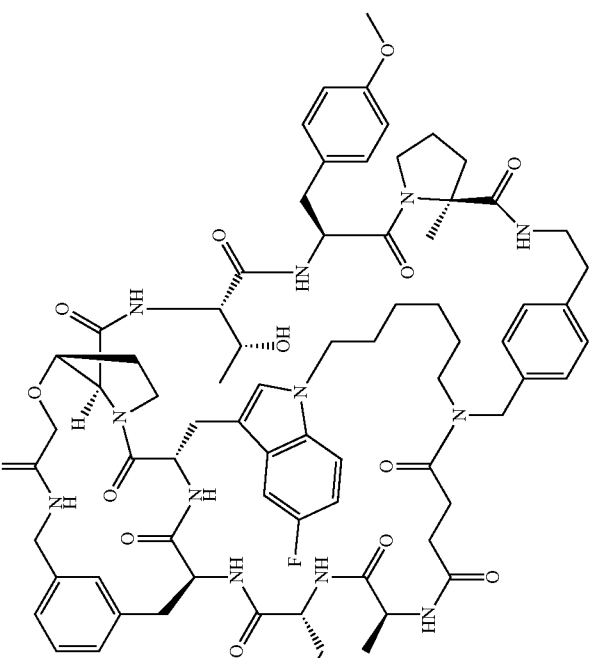 |

TABLE 1-continued
| Ex No | Structure |
|---|---|
| Ex-54* | 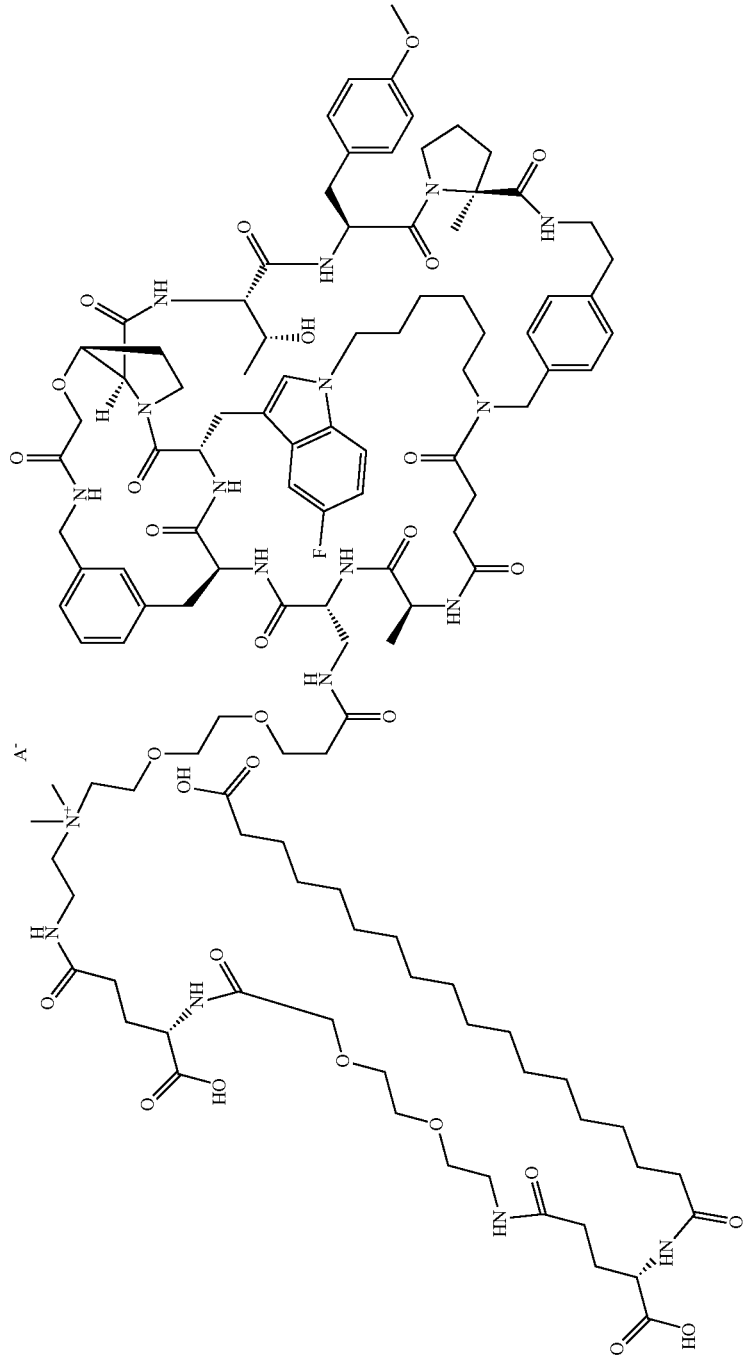 |

TABLE 1-continued
| Ex No | Structure |
|---|---|
| Ex-55* | 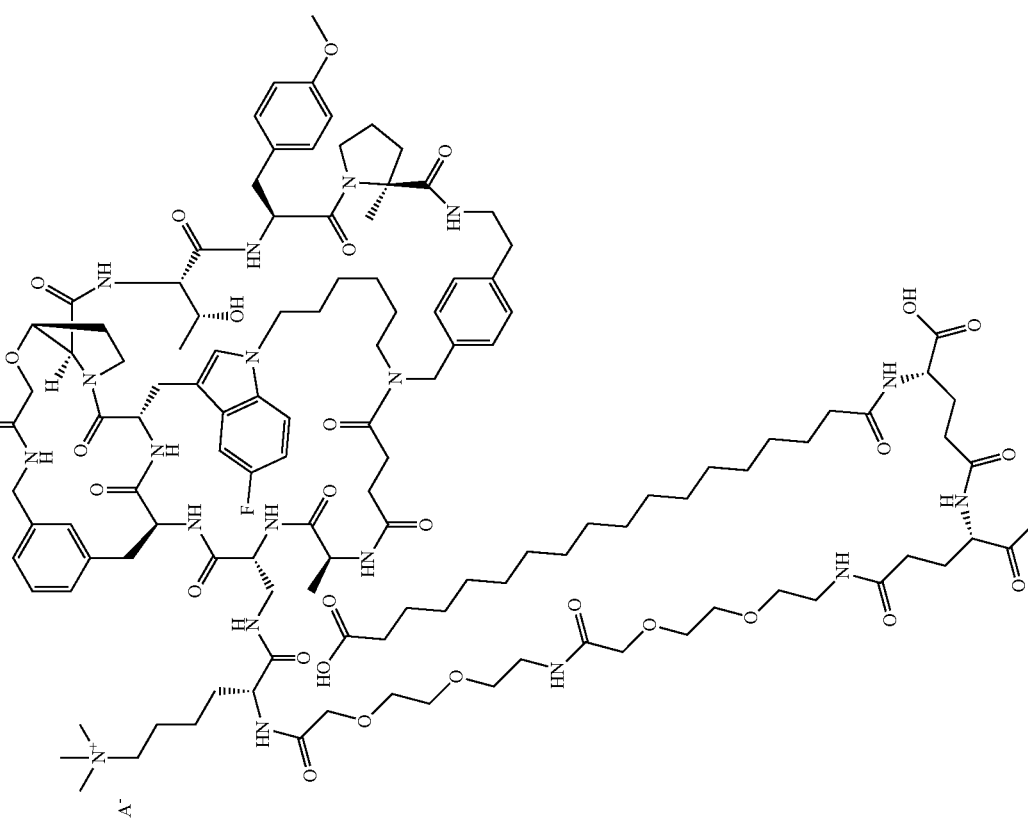 |

TABLE 1-continued
| Ex No | Structure |
|---|---|
| Ex-56* | 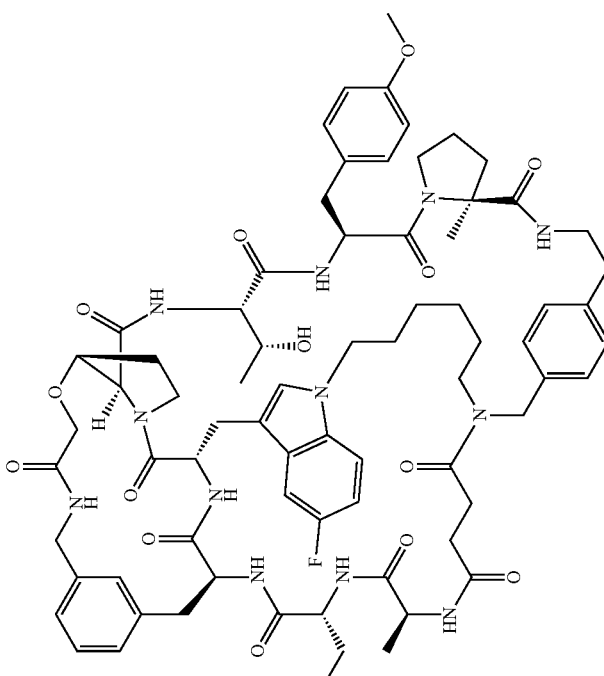 |

TABLE 1-continued

| Ex No | Structure |
|---|---|
| Ex-57* | 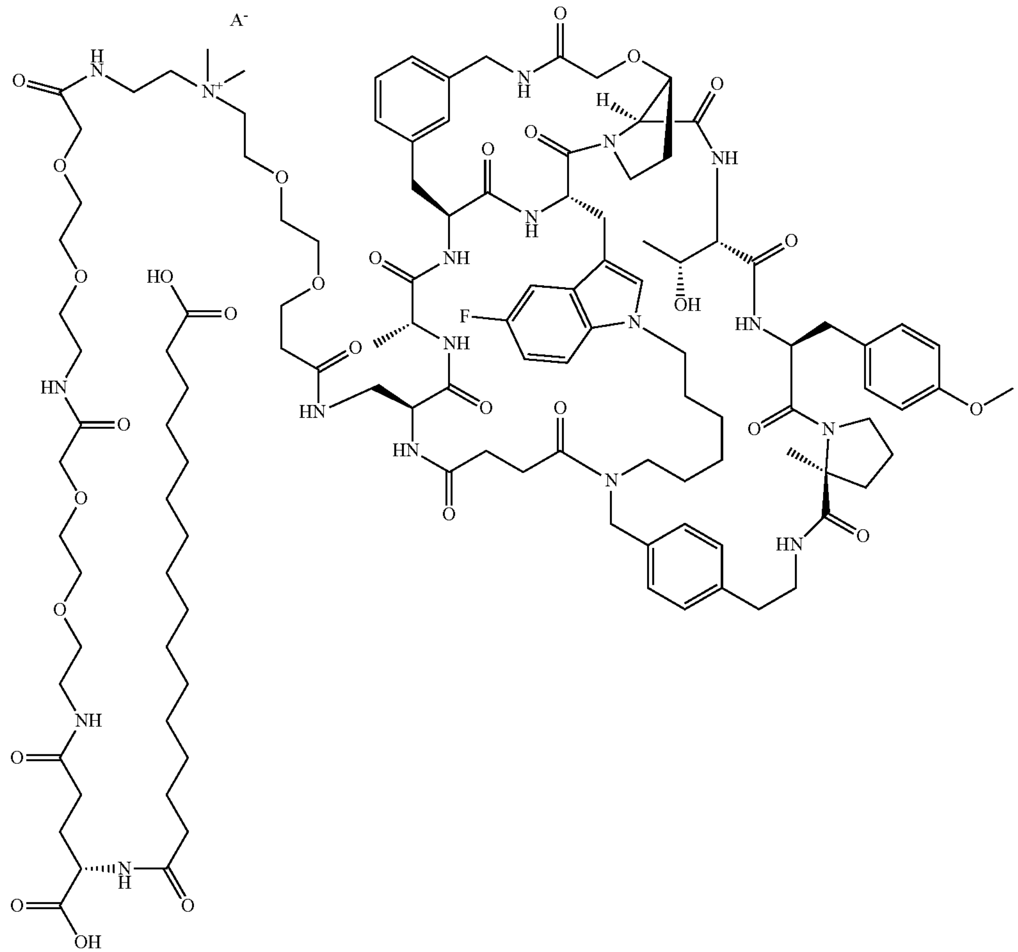 |

TABLE 1-continued
| Ex No | Structure |
|---|---|
| Ex-58* | 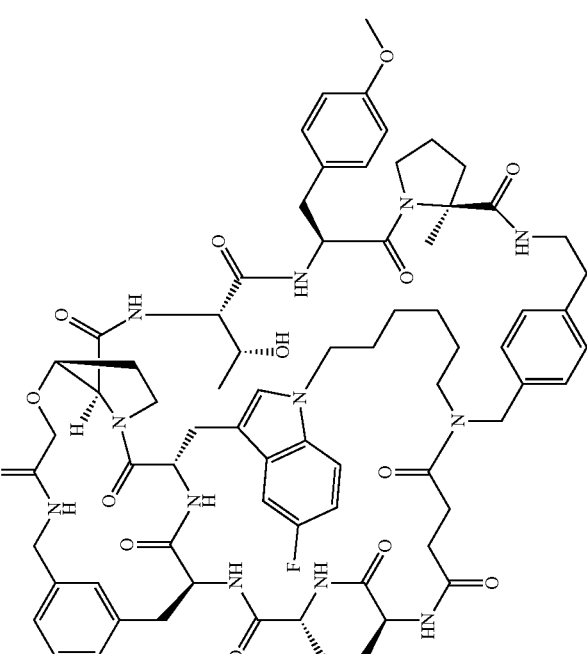 |

TABLE 1-continued
| Ex No | Structure |
|---|---|
| Ex-59* | 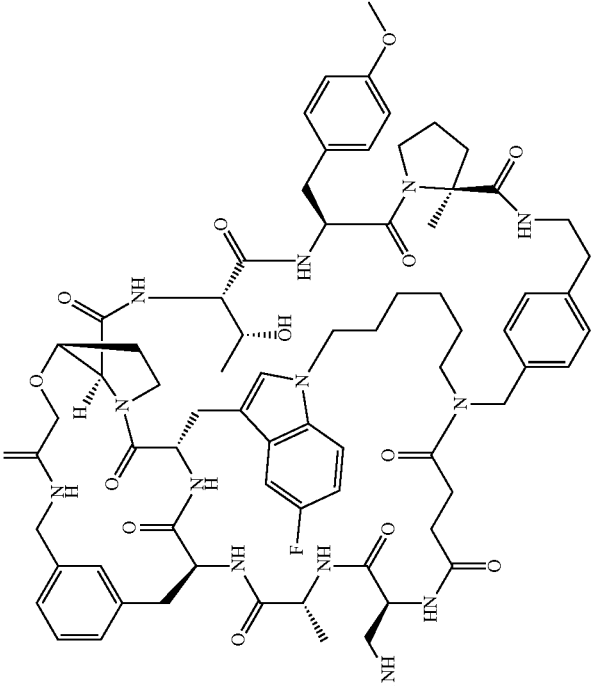 |

TABLE 1-continued
| Ex No | Structure |
|---|---|
| Ex-60* | 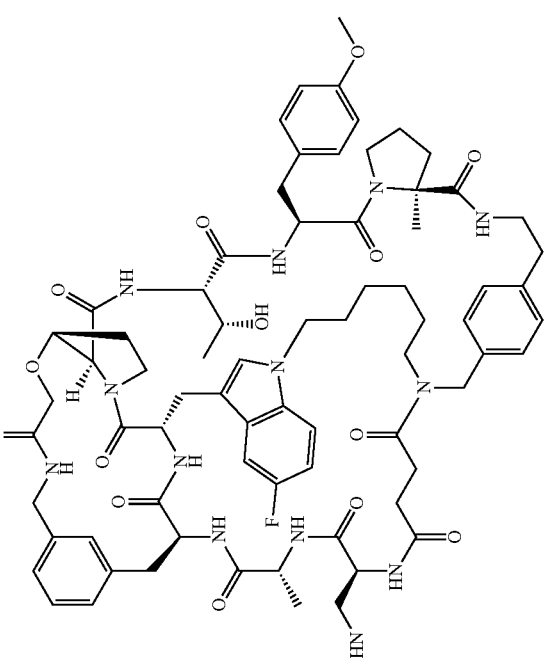 |

TABLE 1-continued
Structure
| Ex No |
|---|
| Ex-61* |
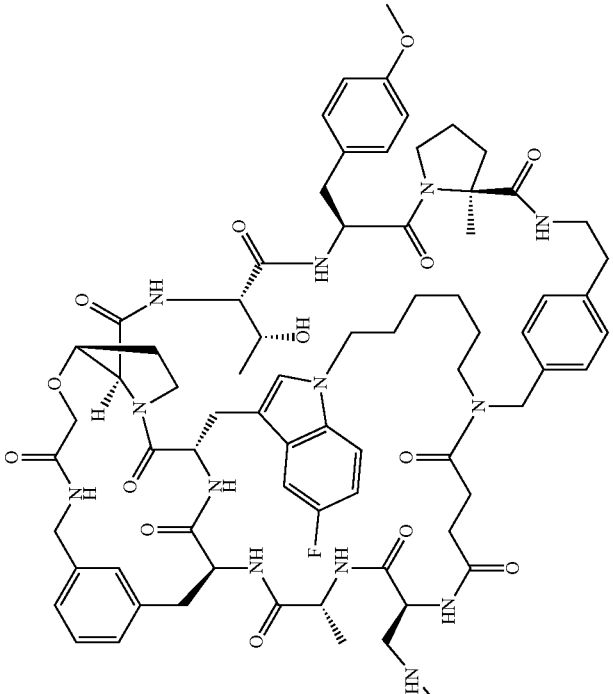

TABLE 1-continued
| Ex No | Structure |
|---|---|
| Ex-62* | 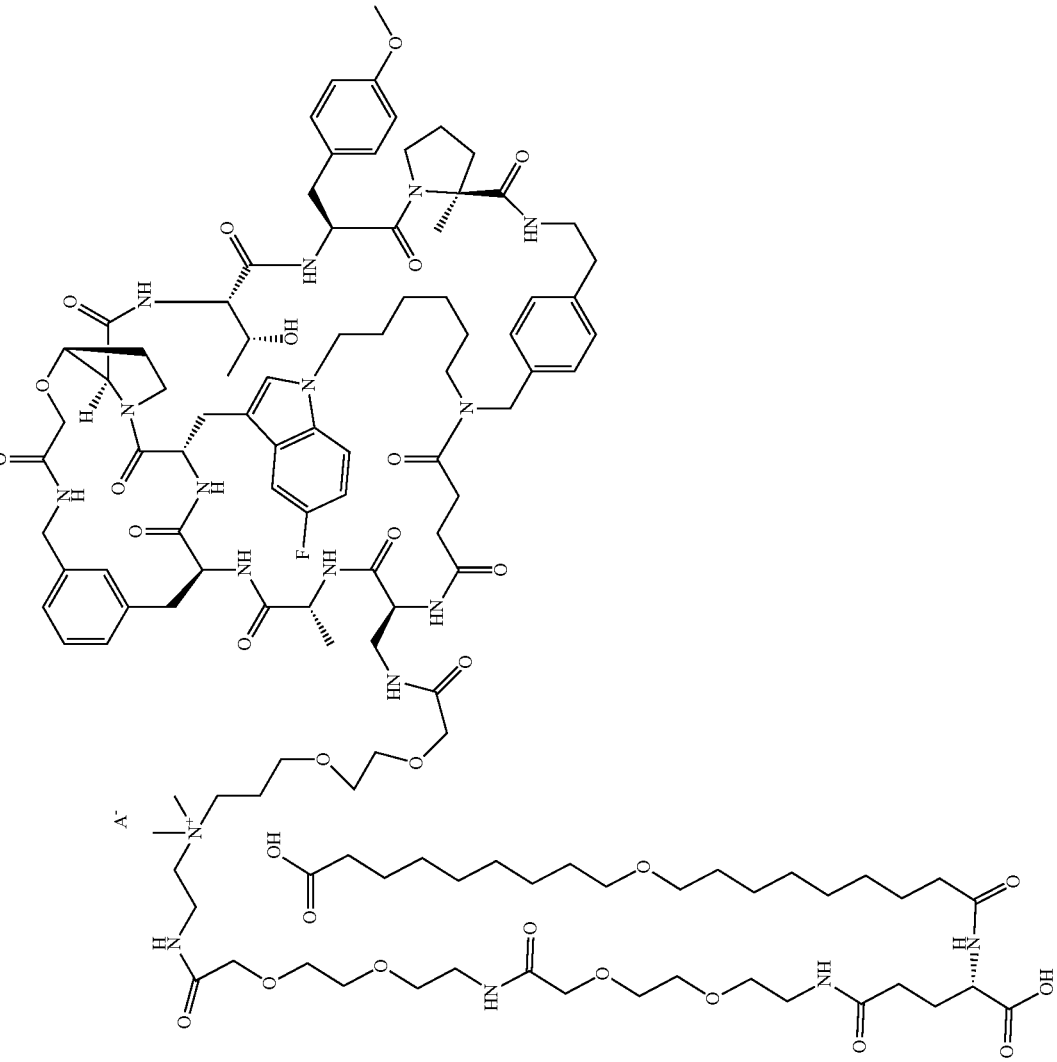 |

TABLE 1-continued

| Ex No | Structure |
|---|---|
| Ex-63* | 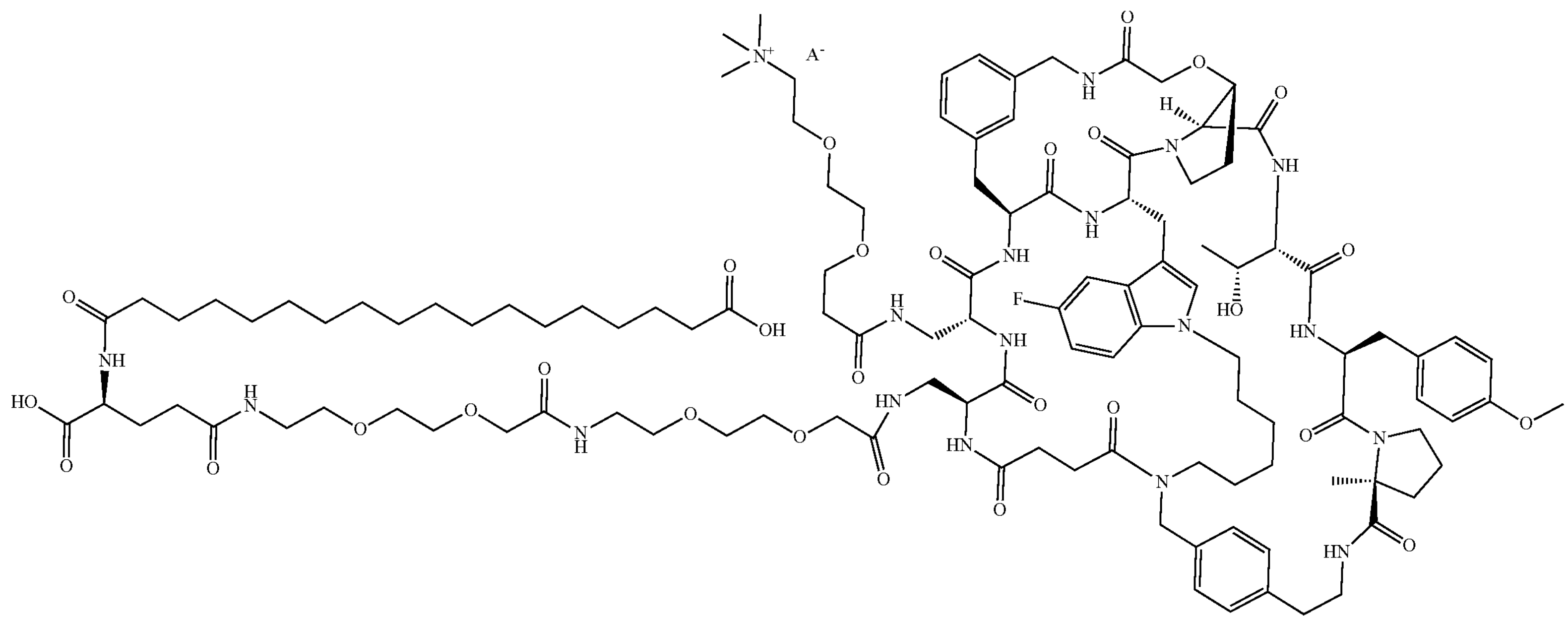 |

TABLE 1-continued
| Ex No | Structure |
|---|---|
| Ex-64* | 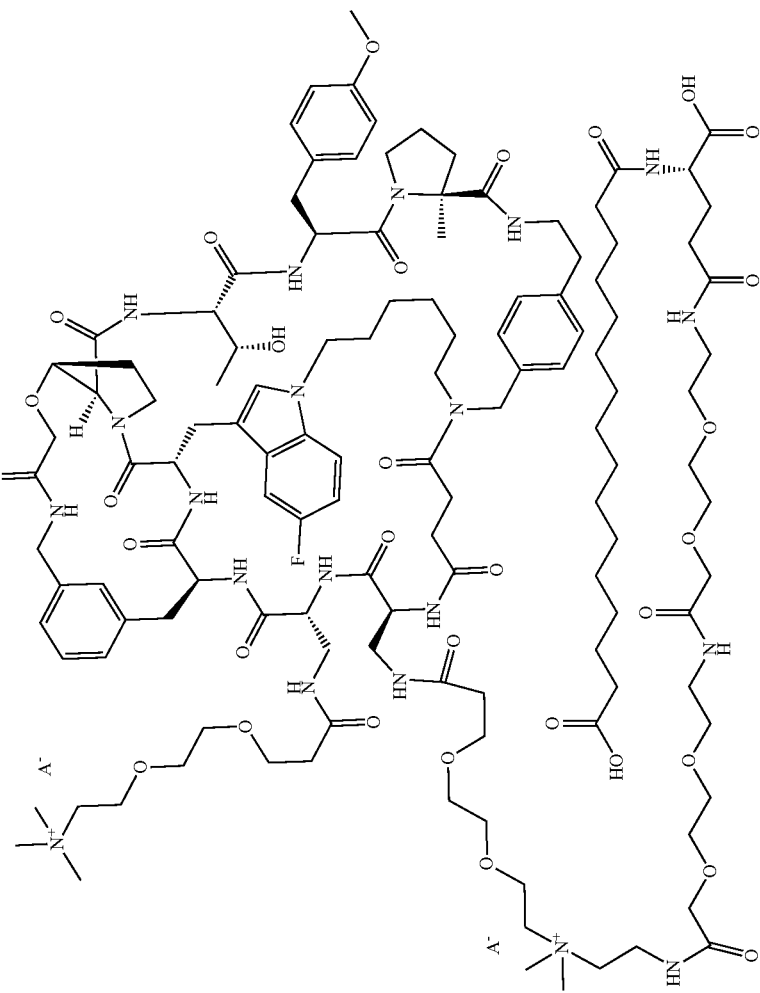 |

TABLE 1-continued
| Ex No | Structure |
|---|---|
| Ex-65 | 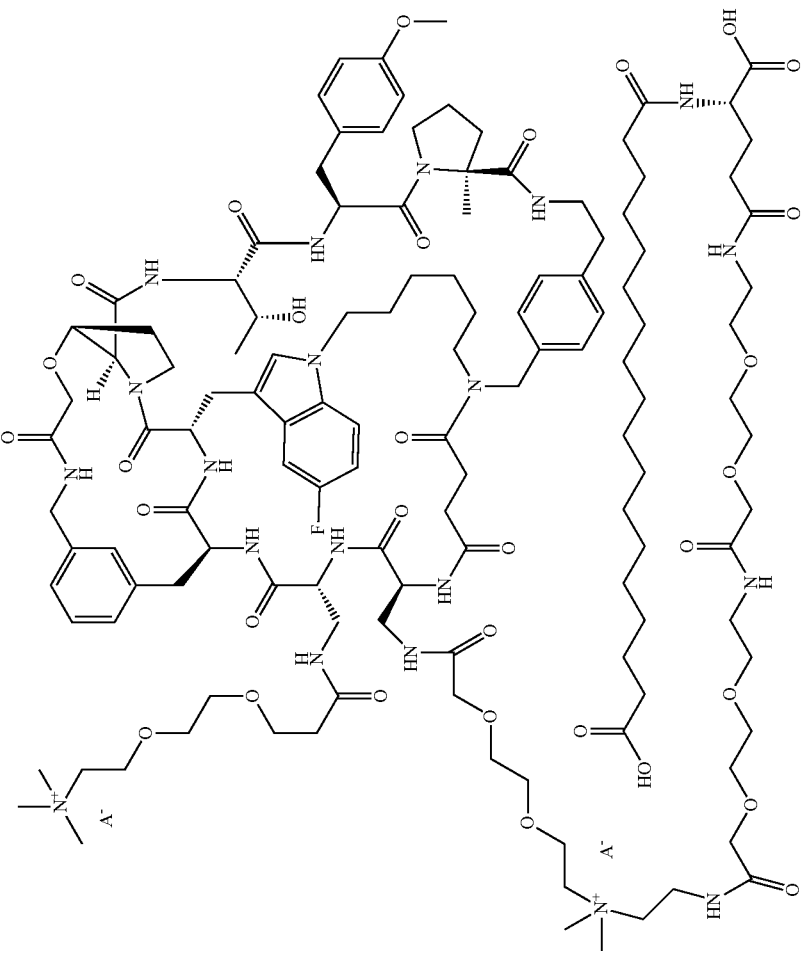 |

TABLE 1-continued

| Ex No | Structure |
|---|---|
| Ex-66 | 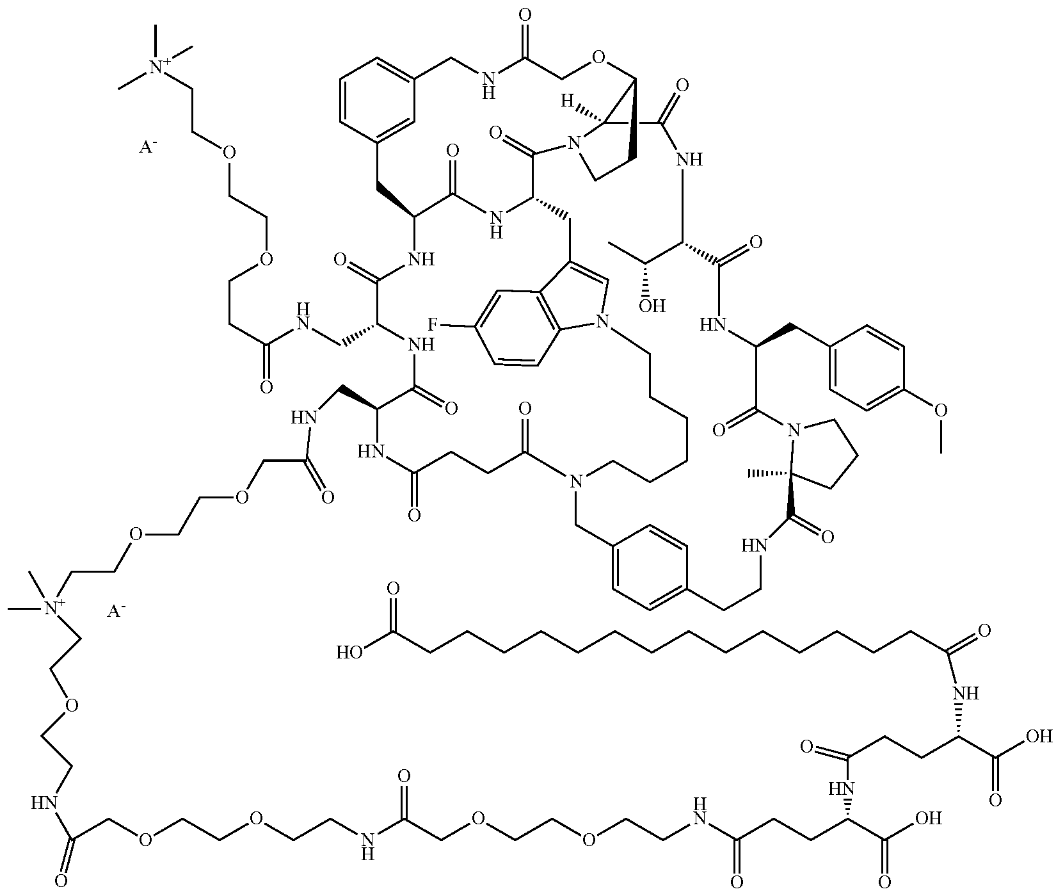 |

TABLE 1-continued
| Ex No | Structure |
|---|---|
| Ex-67 | 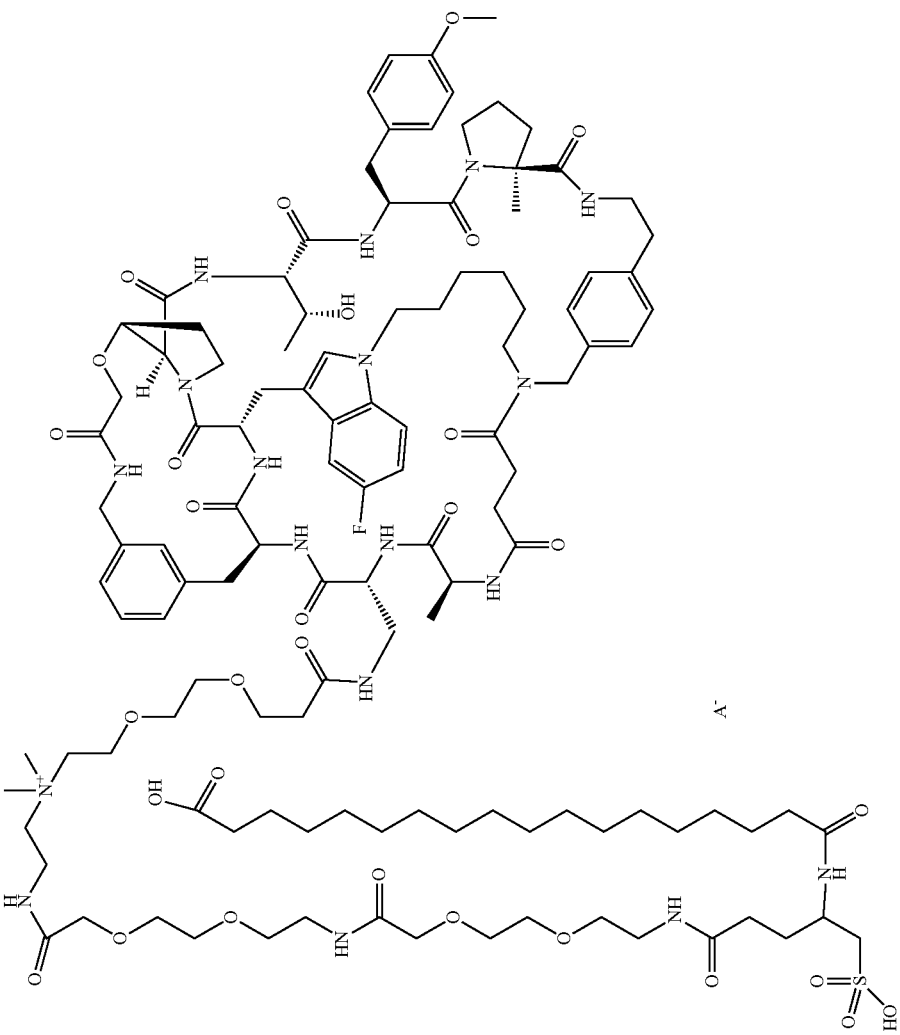 |

TABLE 1-continued
| Ex No | Structure |
|---|---|
| Ex-68 | 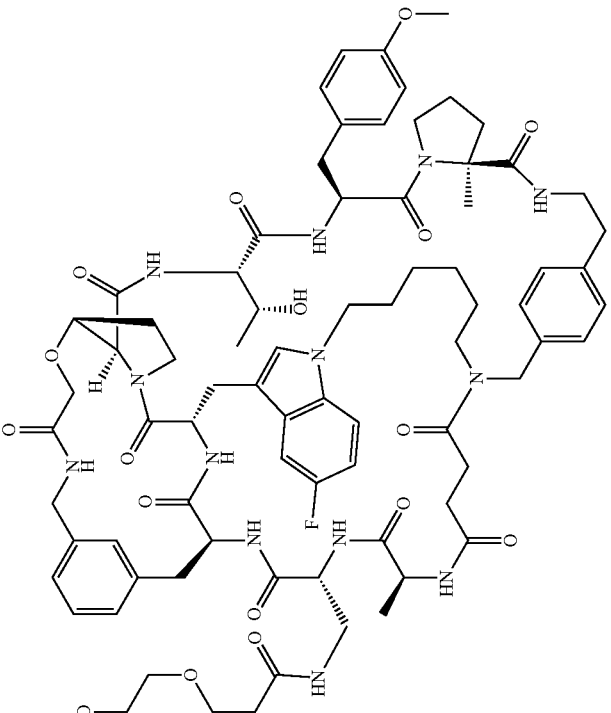 | or a pharmaceutically acceptable salt thereof.

The term "salt(s)", and its use in the phrase "pharmaceutically acceptable salts" employed herein, includes any of the following: acidic salts formed with inorganic and/or organic acids, basic salts formed with inorganic and/or organic bases, zwitterionic and quaternary ammonium complexes. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization. As used herein, a pharmaceutically acceptable salt of the compounds of Table 1 may be different from the compound associated with a counter ion (A-).

Compounds of the invention contain tri-coordinate nitrogen atoms, for example, primary, secondary or tertiary amino moieties, wherein, as is known, the lone pair of electrons residing on the nitrogen atom may be protonated with an appropriate acid or alkylated with an appropriate reagent, for example, alkyl bromide, under the appropriate reaction conditions to provide tetracoordinate charged nitrogen stabilized by an anion generated in the process, for example, a halogen ion or conjugate base. Accordingly, compounds of the invention may be prepared in the form of a free-base or isolated in the form of a quaternary complex or a salt complex. In some instances where there is an appropriate acidic proton proximal to a basic nitrogen, formation of a zwitterionic complex is possible. As the term is employed herein, salts of the inventive compounds, are included in the scope of the invention, whether acidic salts formed with inorganic and/or organic acids, basic salts formed with inorganic and/or organic bases, salts formed which include zwitterionic character (for example, where a compound contains both a basic moiety, for example, but not limited to, a nitrogen atom, for example, an amine, pyridine or imidazole, and an acidic moiety, for example, but not limited to a carboxylic acid), and quaternary ammonium complexes.

Accordingly, structural representation of compounds of the invention, whether in a free-base form, a salt form, a zwitterionic form or a quaternary ammonium form, also include all other forms of such compounds discussed above. Thus, one aspect of the invention is the provision of compounds of the invention in the form of a pharmaceutically acceptable salt, zwitterionic complex or quaternary ammonium complex. Those skilled in the art will recognize those instances in which the compounds of the invention may form such complexes, including where a tetracoordinate nitrogen can be quaternized or protonated and the charged nitrogen form stabilized by an associated anion. The term "pharmaceutically acceptable salt" refers to a salt (including a quaternary ammonium complex and an inner salt such as a zwitterion complex) which possesses effectiveness similar to or greater than a free-base form of the compound and which is not biologically or otherwise undesirable (e.g., is neither toxic nor otherwise deleterious to the recipient thereof).

The formation of pharmaceutically useful salts from basic (or acidic) pharmaceutical compounds are discussed, for example, by S. Berge et al., Journal of Pharmaceutical Sciences (1977) 66 (1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates both freebase forms of the compounds of the invention and all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". As will be appreciated, freebase compounds may be prepared by controlling the conditions of isolation of the compound during synthesis or by neutralization and ion exchange from salt forms of compounds of the invention.

Examples of pharmaceutically acceptable acid salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Further examples of pharmaceutically acceptable salts that may be used with the instant invention include, but are not limited to, fluoride, chloride, bromide and iodide.

In general, salts of compounds are intended to be pharmaceutically acceptable salts within the scope of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan. Compounds of the invention include any form of the compound including in situ in a reaction mixture as well as in isolated and purified form obtained by routine techniques. Also included are polymorphic forms of the compounds of the invention and solvates and prodrugs thereof.

Certain compounds of the invention may exist in different tautomeric forms, for example, but are not limited to, ketone/enol tautomeric forms, imine-enamine tautomeric forms, and for example heteroaromatic forms such as the following moieties:

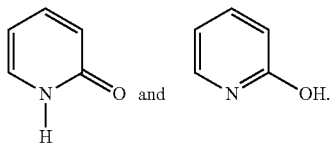 [SMILES: O=c1cccc[nH]1 ; Oc1ccccn1]

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention.

In another aspect, the present invention provides pharmaceutical compositions comprising one or more compounds of the invention. As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts.

As will be appreciated by the ordinarily skilled artisan, excipients are any constituent which adapts the composition to a particular route of administration or aids the processing of a composition into a dosage form without itself exerting an active pharmaceutical effect. In general compositions comprise more than one excipient depending upon the route of administration and the characteristics of the active being administered. Examples of excipients which impart to the composition properties which make it easier to handle or process include, but are not limited to, lubricants or pressing aids in powdered medicaments intended to be tableted, and emulsion stabilizers in compositions in which the active is present in the form of an emulsion. Examples of excipients which adapt a composition to a desired route of administration are, for example, but not limited to, for oral administration, absorption enhancers promoting absorption from the gastrointestinal tract, for transdermal or transmucosal administration, penetration enhancers, for example, those employed in adhesive skin "patch" or compositions for buccal administration.

Notwithstanding the function excipients perform in a composition, excipients are collectively termed herein "a carrier". Typically, formulations may comprise up to about 95 percent active ingredient and the balance carrier, although formulations with different ratios may be prepared. In general, acceptable pharmaceutical compositions contain a suitable concentration of the active that an effective amount of the PCSK9 antagonist can be provided in an individual dosage form of acceptable volume based upon the route of administration such that it can provide a therapeutic serum level of the active for an acceptable period of time in a subject to whom the composition is administered and the composition will retain biological activity during storage within an acceptable temperature range for an acceptable period of time.

Pharmaceutical composition, as used herein, refers both to a bulk composition, that is, formulated material that has not yet been formed into individual dosage units for administration, and the composition contained within individual dosage units.

While compositions of the invention may be employed in bulk form, it will be appreciated that for most applications compositions will be incorporated into a dosage form providing individual units suitable for administration to a patient, each dosage form comprising an amount of the selected composition which contains an effective amount of said one or more compounds of Formula I. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachet or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; (vi) a dosage form adapted for intravenous (IV) infusion, for example, over a prolonged period using an I.V. infusion pump; (vii) a dosage form adapted for intramuscular administration (IM), for example, an injectable solution or suspension, and which may be adapted to form a depot having extended release properties; (viii) a dosage form adapted for drip intravenous administration (IV), for example, a solution or suspension, for example, as an IV solution or a concentrate to be injected into a saline IV bag; (ix) a dosage form adapted for subcutaneous administration, including administration over an extended time period by implanting a rod or other device which diffuses the compound into the surround tissue and thereby provides a continuous serum therapeutic level; or (x) a dosage form adapted for delivery via rectal or vaginal mucosa, for example, a suppository.

Pharmaceutical compositions can be solid, semi-solid or liquid. Solid, semi-solid and liquid form preparations can be adapted to a variety of modes of administration, examples of which include, but are not limited to, powders, dispersible granules, mini-tablets, beads, which can be used, for example, for tableting, encapsulation, or direct administration. In addition, liquid form preparations include, but are not limited to, solutions, suspensions and emulsions which for example, but not exclusively, can be employed in the preparation of formulations intended for ingestion, inhalation or intravenous administration (IV), for example, but not limited to, administration via drip IV or infusion pump, intramuscular injection (IM), for example, of a bolus which is released over an extended duration, direct IV injection, or adapted to subcutaneous routes of administration.

Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in a solid oral dosage form, for example, a tablet or quick-melt mouth-dissolving formulation are preferable routes of administration for a compound of the invention or a salt thereof, a composition of the invention may be formulated for administration via other routes mentioned above. Examples include aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, MD Additional examples of publications addressing formulation issues may be found in: Pharmaceutical compositions may be formulated by any number of strategies known in the art, see, e.g., McGoff and Scher, 2000 *Solution Formulation of Proteins/Peptides*: In—McNally, E. J., ed. Protein Formulation and Delivery. New York, NY: Marcel Dekker; pp. 139-158; Akers & Defilippis, 2000, *Peptides and Proteins as Parenteral Solutions*. In—Pharmaceutical Formulation Development of Peptides and Proteins. Philadelphia, PA: Taylor and Francis; pp. 145-177; Akers et al., 2002, *Pharm. Biotechnol.* 14:47-127.

In another aspect the present invention provides methods of employing PCSK9-specific antagonist compounds described herein for antagonizing PCSK9 function; said methods of which are further described below. Use of the term "antagonizing" throughout the present application refers to providing to the affected tissue(s) a substance which opposes the action of, inhibits, counteracts, neutralizes or curtails one or more functions of PCSK9 in the affected tissues. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen relative to the activity observed when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. In some embodiments of the present invention include such methods wherein the cell is a human cell. Additional embodiments of the present invention include such methods wherein the cell is a murine cell.

In one aspect, the present invention provides a method for antagonizing the activity of PCSK9 in a subject, which comprises administering to the subject a therapeutically effective amount of a PCSK9-specific antagonist of the present invention. In some embodiments, the methods for antagonizing PCSK9 function are for the treatment, as defined herein, of a PCSK9-associated disease, disorder or condition or, alternatively, for providing therapy in a disease, disorder or condition that could benefit from the effects of a PCSK9 antagonist.

The present invention, thus, contemplates the use of PCSK9-specific antagonists described herein in various methods of treatment where antagonizing PCSK9 function is desirable. As used herein, the term "method of treatment" relates to a course of action resulting in a change in at least one symptom of a disease state which can be prophylactic or therapeutic in nature. In some embodiments, the present invention relates to a method of treatment for a condition associated with and/or attributed to PCSK9 activity, or a condition where the functioning of PCSK9 is contraindicated for a particular subject, the method comprising administering to the subject a therapeutically effective amount of a PCSK9-antagonist compound of Formula I, or pharmaceutically acceptable salt thereof. In some embodiments, the condition may be atherosclerosis, hypercholesterolemia, coronary heart disease, metabolic syndrome, acute coronary syndrome or related cardiovascular disease and cardiometabolic conditions, or may be a disease state or condition in which PCSK9 activity is contraindicated.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic and/or prophylactic effect for the period of time desired. The desired effect may be, for example, the alleviation, amelioration, reduction or cessation of at least one symptom associated with the treated condition. These amounts will vary, as the skilled artisan will appreciate, according to various factors, including but not limited to the disease state, age, sex, and weight of the individual, and the ability of the PCSK9-specific antagonist to elicit the desired effect in the individual. The response may be documented by in vitro assay, in vivo non-human animal studies, and/or further supported from clinical trials.

In some embodiments it is preferred to administer a PCSK9 antagonist compound of the invention in the form of a pharmaceutical composition as described herein.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors, for example, but not limited to, those mentioned above, including the condition of the patient, the area being treated, the route of administration, and the treatment desired, for example, prophylaxis or acute treatment and the like. A physician or veterinarian of ordinary skill can readily determine and prescribe the effective therapeutic amount of the antagonist.

The subject may be in need of, or desire, treatment for an existing disease or medical condition. As used herein, the subject "in need" of treatment of an existing condition encompasses both a determination of need by a medical professional as well as the desire of the subject for such treatment. When a compound or a salt thereof is provided in combination with one or more other active agents, "administration" and its variants are each understood to include provision of the compound or its salt and the other agents contemporaneously or simultaneously or over a course of separate administrations over a period of time. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" means the amount of active compound sufficient to antagonize PCSK9 and thereby elicit the response being sought (i.e., induce a therapeutic response in the treatment or management of conditions associated with or impacted by PCSK9 function, including, but not limited to atherosclerosis, hypercholesterolemia, coronary heart disease, metabolic syndrome, acute coronary syndrome, and related cardiovascular disease and cardiometabolic conditions in an animal or human).

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, NJ 07645-1742, USA), the Physician's Desk Reference, 56th Edition, 2002 (published by Medical Economics company, Inc. Montvale, NJ 07645-1742), or the Physician's Desk Reference, 57th Edition, 2003 (published by Thompson P D R, Montvale, NJ 07645-1742); the disclosures of which is incorporated herein by reference thereto. For convenience, the total daily dosage may be divided and administered in portions during the day as required or delivered continuously.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), or administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the subject in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives, peptidyl amino diols and peptidyl beta-aminoacyl aminodiol carbamates, and small molecule renin inhibitors (including diol sulfonamides and sulfinyls), N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), crivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the treatment of the above-mentioned conditions or disorders including the free-acid, free-base, and pharmaceutically acceptable salt forms of the above active agents where chemically possible.

The compounds of the present invention can be readily prepared according to the following reaction schemes and examples, or modifications thereof, using readily available starting materials, reagents and conventional synthesis procedures. In these reactions, it is also possible to make use of known variants. For purification of the compounds using reverse phase chromatography (either HPLC or MPLC, as noted below), a C18 column was used. Other methods for preparing compounds of the invention will be readily apparent to the person of ordinary skill in the art in light of the following reaction schemes and examples. Abbreviations listed below may be used in the exemplary schemes and/or examples herein.

Abbreviations

ACN is acetonitrile; AcOH is acetic acid; Boc is t-butoxycarbonyl; Boc$_2$O is di-tert-butyl dicarbonate; BnBr is benzyl bromide; BzCl is benzoyl chloride; CBr$_4$ is perbromomethane or tetrabromomethane; Cbz-Cl is benzyl chloroformate; Cbz-OSu is is N-(benzyloxycarbonyloxy)succinimide; Cs$_2$CO$_3$ is cesium carbonate; DCE is 1,2-dichloroethane; DCM is dichloromethane; DIEA or DIPEA is N,N-diisopropylethylamine; DMF is N,N-dimethylformamide; DMAP is 4-dimethylaminopyridine; DMSO is dimethyl sulfoxide; DIAD is (E)-diisopropyl diazene-1,2-dicarboxylate; DMP is Dess-Martin periodinane; Et$_3$N is triethylamine; EA or EtOAc is ethyl acetate; Et$_2$O is diethyl ether; EtOH is ethanol; Fmoc is fluorenylmethyloxycarbonyl protecting group; Fmoc-Cl is (9H-fluoren-9-yl)methyl carbonochloridate; Fmoc-Osu is Fmoc N-hydroxysuccinimide ester; HATU is 1-[bis(dimethylamino)methylene]-1H-1,2,3-triazolo[4,5-b]pyridinium 3-oxid hexafluorophosphate; HPLC is high pressure liquid chromatography; Im is imidazole; IPA is isopropyl alcohol; IPAc is isopropyl acetate; LC/MS is liquid chromatography mass spectrometry; LiOH is lithium hydroxide; Me is methyl; MeOH is methanol; MeI is methyl iodide; MgSO$_4$ is magnesium sulfate; MPLC is medium pressure liquid chromatography; Na$_2$SO$_4$ is sodium sulfate; NaHCO$_3$ is sodium bicarbonate; Na$_2$CO$_3$ is sodium carbonate; NaBH$_3$CN is sodium cyanoborohydride; NaBH(OAc)$_3$ is sodium triacetoxyborohydride; NaN$_3$ is sodium azide; NH$_4$Cl is ammonium chloride; NH$_4$HCO$_3$ is ammonium bicarbonate; NMR is Nuclear Magnetic Resonance; NsCl is 4-nitrobenzene-1-sulfonyl chloride; Oxyma is ethyl 2-cyano-2-(hydroxyimino)acetate; Pd/C is palladium on carbon; PE is petroleum ether; Pd$_2$(dba)$_3$(HCCl$_3$) is tris(dibenzylideneacetone)dipalladium(0)-chloroform adduct; PPh$_3$ or Ph$_3$P is triphenylphosphine; Pd(dppf)Cl$_2$·CH$_2$Cl$_2$ is dichloro[1,1'-bis(diphenylphosphino)ferrocene]palladium (II) dichloromethane adduct; Pd(PPh$_3$)$_4$ is tetrakis(triphenylphosphine)palladium; RT or r.t. or rt is room temperature; S-Phos is 2-dicyclohexylphosphino-2',6'-dimethoxybiphenyl; TBAB is tetrabutylammonium bromide; TBAF is tetrabutylammonium fluoride; TBAHS is tetrabutylammonium hydrogenosulfate; TEA is triethylamine; TFA is trifluoroacetic acid; THF is tetrahydrofuran; Tf$_2$O is trifluoromethanesulfonic anhydride; TMS-diazomethane is trimethylsilyl-diazomethane; Teoc-OSu is 1-[2-(Trimethylsilyl) ethoxy carbonyloxy] pyrrolidin-2,5-dione.

The compounds of the present invention can be readily prepared according to the following reaction schemes and examples, or modifications thereof, in conjunction with readily available starting materials, reagents and conventional synthesis procedures. Alternate salt forms for products and intermediates may also be present in the invention. Alternate methods for preparing compounds of the invention will be readily apparent to the person of ordinary skill in the art in light of the following reaction schemes and examples. For example, in these reactions it is possible to make use of known variants. Immediately following is a section describing the preparation of intermediates useful in the preparation of example compounds of the invention. Unless otherwise noted, reagents used in the preparation of intermediates and examples are commercially available or can be prepared by known methods.

Preparation of Intermediates Useful in the Preparation of Examples of the Invention Preparation of Intermediate A

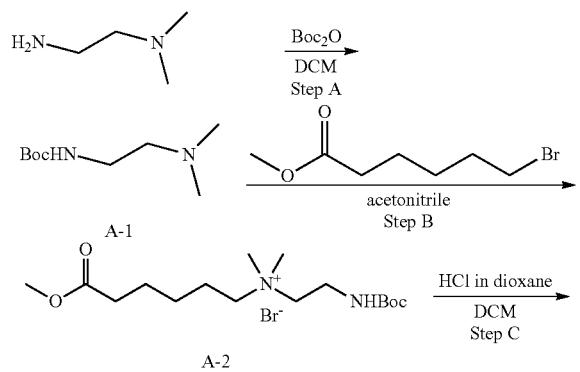

-continued

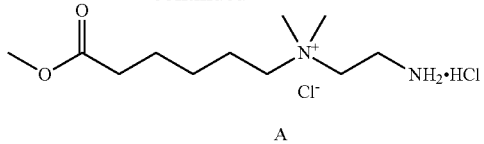

Step A—Synthesis of Intermediate A-1

To a solution of N,N-dimethylethane-1,2-diamine (1.00 g, 11.3 mmol) in DCM (20 mL) was added Boc2O (3.42 mL, 14.8 mmol) at 0° C. The mixture was stirred at RT for 1 h then concentrated under reduced pressure and the residue was purified by MPLC over silica gel (eluting with a gradient of 1%-15% MeOH in DCM). The fractions containing the desired product were combined and concentrated to afford A-1. LC/MS: [M+H]$^+$=189.2.

Step B—Synthesis of Intermediate A-2

To a solution of A-1 (500 mg, 2.66 mmol) in acetonitrile (2 mL) was added methyl 6-bromohexanoate (1.67 g, 7.97 mmol). The reaction mixture was stirred at 50° C. for 16 h then concentrated under reduced pressure. The residue was diluted with Et$_2$O, stirred at RT for 1 h, filtered, washed with Et$_2$O and dried to afford A-2. LC/MS: [M]$^+$=317.2.

Step C—Synthesis of Intermediate A

A solution of A-2 (800 mg, 2.01 mmol) in 4 M HCl in dioxane (10 mL) was stirred at RT for 4 h. The final mixture was concentrated under reduced pressure, diluted with Et$_2$O, and stirred at RT for 2 h. The solid was filtered, rinsed with Et$_2$O and dried to provide intermediate A. LC/MS: [M]$^+$=217.2. $^1$H NMR (400 MHz, DMSO-d$_6$): δ 8.64 (s, 3H), 3.68-3.56 (m, 5H), 3.40-3.33 (m, 2H), 3.33-3.22 (br, 2H), 3.12 (s, 6H), 2.36 (t, J=7.4 Hz, 2H), 1.79-1.66 (m, 2H), 1.65-1.54 (m, 2H), 1.36-1.25 (m, 2H).

Preparation of Intermediate B

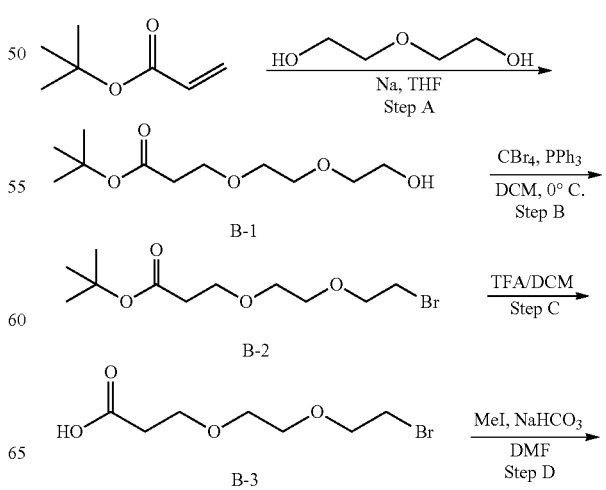

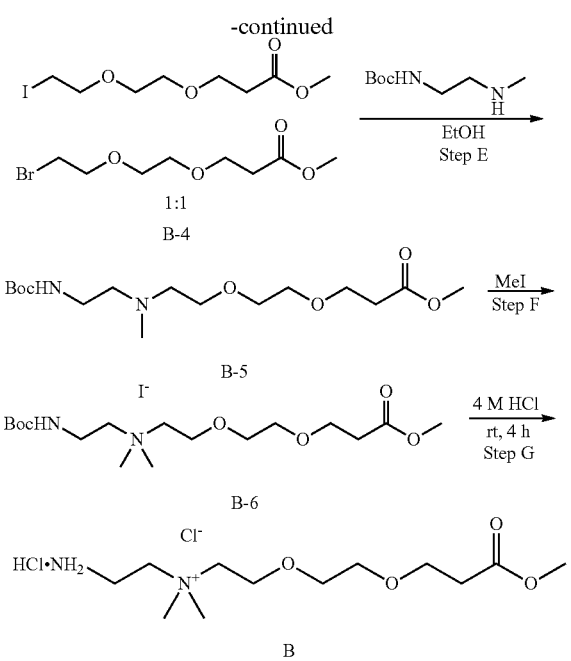

Step A—Synthesis of Intermediate B-1

To a mixture of 2,2'-oxydiethanol (24.8 g, 234 mmol) in THF (150 mL) was added sodium (0.054 g, 2.34 mmol) at RT followed by addition of tert-butyl acrylate (10 g, 78 mmol) until the sodium was dissolved. The resulting mixture was stirred for 16 h at RT then quenched by the addition of saturated NH$_4$Cl in water (100 mL). The mixture was extracted with EtOAc, the organic extracts were combined, washed with brine, dried over anhydrous Na$_2$SO$_4$ and concentrated. The residue was purified by MPLC over silica gel (eluting with a gradient of 40%-60% EtOAc in PE) to provide B-1. $^1$H NMR (300 MHz, CDCl$_3$): δ 3.79-3.70 (m, 4H), 3.68-3.56 (m, 6H), 2.51 (t, J=6.3 Hz, 2H), 2.37 (s, 1H), 1.45 (s, 9H).

Step B—Synthesis of Intermediate B-2

To a mixture of B-1 (5.00 g, 21.3 mmol) and carbon tetrabromide (21.2 g, 64.0 mmol) in DCM (50 mL) at 0° C. was added triphenylphosphine (16.8 g, 64.0 mmol). The mixture was stirred at 0° C. for 2 h then quenched by addition of water (100 mL). The solid was removed by filtration and the filtrate was extracted with EtOAc. The organic extracts were combined, washed with brine, dried over Na$_2$SO$_4$ and concentrated. The residue was purified by MPLC over silica gel (eluting with a gradient of 20%-50% EtOAc in PE) to give B-2. $^1$H NMR (400 MHz, CD$_3$OD): δ 3.81 (t, J=6.0 Hz, 2H), 3.73 (t, J=6.4 Hz, 2H), 3.68-3.60 (m, 4H), 3.52 (t, J=6.0 Hz, 2H), 2.50 (t, J=6.2 Hz, 2H), 1.48 (s, 9H).

Step C—Synthesis of Intermediate B-3

To a mixture of B-2 (4.90 g, 16.49 mmol) in DCM (25 mL) at 0° C. was added TFA (25 mL). The mixture was stirred for 2 h at RT then concentrated to provide B-3. $^1$H NMR (300 MHz, DMSO-d$_6$): δ 3.78-3.70 (m, 2H), 3.67-3.48 (m, 8H), 2.46 (t, J=6.3 Hz, 2H).

Step D—Synthesis of Intermediate B-4

To a mixture of B-3 (3.50 g, 14.5 mmol) and NaHCO$_3$ (4.88 g, 58.1 mmol) in DMF (20 mL) at 0° C. was added MeI (8.24 g, 58.1 mmol). The mixture was stirred at RT for 16 h then quenched with water (200 mL). The mixture was extracted with EtOAc, and the organic extracts were combined, washed with brine, dried over Na$_2$SO$_4$ and concentrated. The residue was purified by MPLC over silica gel (eluting with a gradient of 20%-45% EtOAc in PE) to give B-4 as a mixture of methyl-3-(2-(2-bromoethoxy)ethoxy)propanoate and methyl-3-(2-(2-iodoethoxy)ethoxy)propanoate (1:1). LC/MS (bromide): [M+H]$^+$=255.1 and 257.1; LC/MS (iodide): [M+H]$^+$=303.0.

Step E—Synthesis of Intermediate B-5

To a solution of B-4 (400.0 mg, 1.436 mmol) in EtOH (4 mL) at RT was added tert-butyl (2-(methylamino)ethyl) carbamate (1251 mg, 7.18 mmol). The mixture was stirred for 16 h then concentrated and the residue was purified by MPLC over silica gel (eluting with a gradient of 0%-5% MeOH in DCM) to afford B-5. LC/MS: [M+H]$^+$=349.3. $^1$H NMR (400 MHz, CDCl$_3$): δ 3.57 (t, J=6.5 Hz, 2H), 3.50 (s, 3H), 3.47-3.34 (m, 6H), 3.02 (q, J=6.1, 5.6 Hz, 2H), 2.42 (q, J=6.3, 5.7 Hz, 4H), 2.35 (t, J=6.1 Hz, 2H), 2.11 (s, 3H), 1.25 (s, 9H).

Step F—Synthesis of Intermediate B-6

To a solution of B-5 (440.0 mg, 1.263 mmol) in acetonitrile (10 mL) at RT was added MeI (0.395 mL, 6.31 mmol) and the reaction mixture was stirred for 36 h. The final mixture was concentrated to afford B-6. LC/MS: [M]$^+$=363.3.

Step G—Synthesis of Intermediate B

A solution of B-6 (600 mg, 1.224 mmol) in 4 M HCl in dioxane (12 mL) was stirred at RT for 4 h. The mixture was concentrated under reduced pressure and the residue was dissolved in Et$_2$O. The slurry was stirred at RT for 2 h then filtered and the solid was rinsed with Et$_2$O and dried to afford intermediate B. LC/MS: [M]$^+$=263.3.

Preparation of Intermediate C

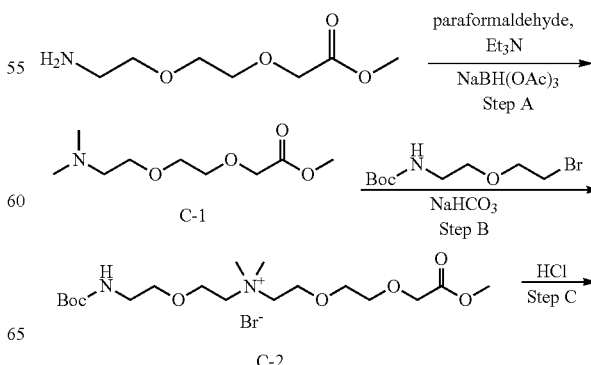

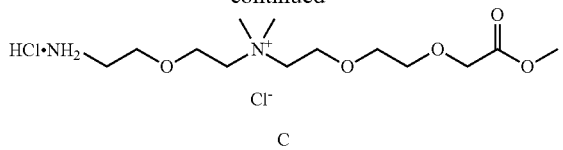

C

Step A—Synthesis of Intermediate C-1

To a solution of methyl 2-(2-(2-aminoethoxy)ethoxy)acetate (1.28 g, 7.22 mmol) and paraformaldehyde (0.433 g, 14.5 mmol) in DCE (20 mL) at RT were added MgSO$_4$ (8.69 g, 72.2 mmol) and TEA (3.02 mL, 21.7 mmol) and the reaction was stirred for 30 min. NaBH(OAc)$_3$ (4.59 g, 21.7 mmol) was added to the mixture and the reaction was stirred at RT for 16 h. The reaction mixture was filtered, the filtrate was concentrated under reduced pressure, and the residue was purified by MPLC over silica gel (eluting with a gradient of 1%-16% MeOH in DCM) to afford C-1.
LC/MS: [M+H]$^+$=206.2. $^1$H NMR (300 MHz, CD$_3$OD): δ 4.18 (s, 2H), 3.75 (s, 3H), 3.74-3.65 (m, 6H), 3.05-2.92 (m, 2H), 2.63 (s, 6H).

Step B—Synthesis of Intermediate C-2

To a solution of C-1 (600 mg, 2.92 mmol) in acetonitrile (12 mL) at RT were added tert-butyl (2-(2-bromoethoxy)ethyl)carbamate (6.27 g, 23.4 mmol) and NaHCO$_3$ (737 mg, 8.77 mmol). The mixture was stirred at 50° C. for 16 h then allowed to cool down to RT and filtered. The filtrate was concentrated under reduced pressure and the residue was purified by MPLC over silica gel (eluting with a gradient of 10%-20% MeOH in DCM) to give C-2. LC/MS: [M]$^+$=393.3.

Step C—Synthesis of Intermediate C

To a solution of 2 M HCl in EtOAc (4 mL) at RT was added C-2 (330 mg, 0.700 mmol) and the reaction was stirred for 1.5 h. The solvent was concentrated under reduced pressure, the material dissolved in DCM, then concentrated under reduced pressure to provide intermediate C. LC/MS: [M]$^+$=293.3.

Preparation of Intermediate D

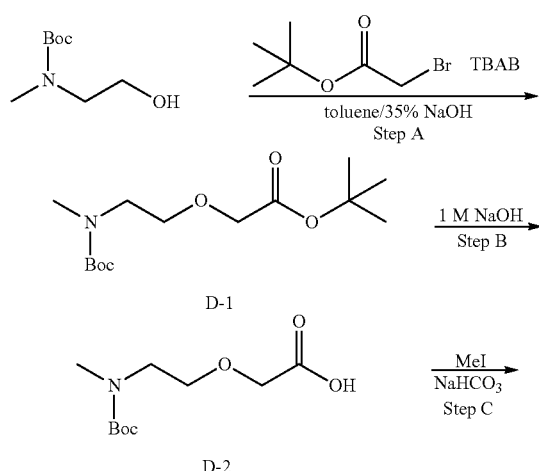

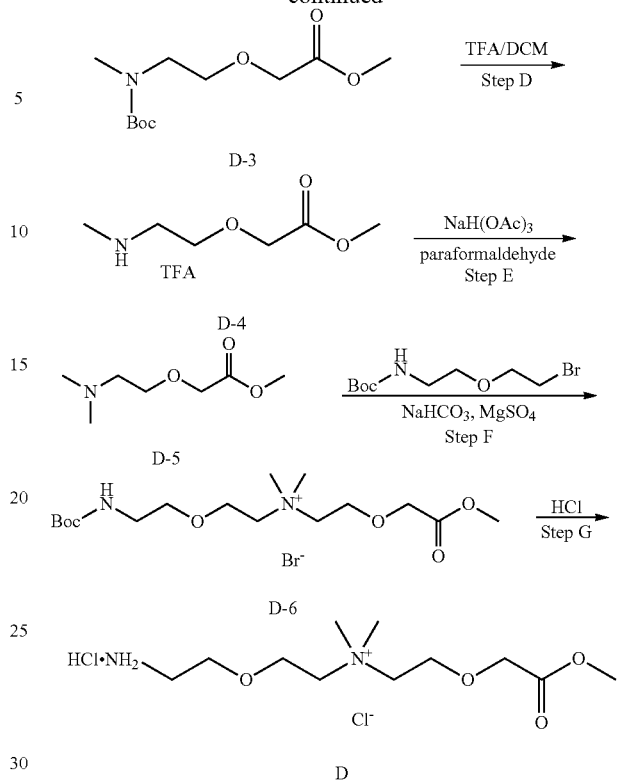

Step A—Synthesis of Intermediate D-1

To a solution of tert-butyl (2-hydroxyethyl)(methyl)carbamate (2.0 g, 11.41 mmol) in toluene (200 mL) and 35% aqueous NaOH (200 mL, 11.41 mmol) at 10° C. were added TBAB (1.10 g, 3.42 mmol) and tert-butyl 2-bromoacetate (2.23 g, 11.41 mmol), then the reaction was stirred at RT for 30 min. The final mixture was diluted with Et$_2$O, washed with brine, 0.1 N aqueous HCl, and brine, then dried over anhydrous MgSO$_4$ and filtered. The filtrate was concentrated under reduced pressure to afford D-1. LC/MS: [M+H]$^+$=290.2.

Step B—Synthesis of Intermediate D-2

To a solution of D-1 (3.2 g, 11.06 mmol) in THF (32 mL) at RT was added 1 M aqueous NaOH (1.769 g, 44.2 mmol) then the mixture was warmed to 40° C. and stirred for 24 h. The solution was quenched with 1 M aqueous HCl (45 mL) at 0° C. and diluted with Me-THF (100 mL). The organic layer was washed with brine, dried over anhydrous MgSO$_4$ and filtered. The filtrate was concentrated under reduced pressure to afford D-2. LC/MS: [M+H]$^+$=234.1.

Step C—Synthesis of Intermediate D-3

To a solution of D-2 (2.80 g, 12.00 mmol) in DMF (28 mL) at RT were added NaHCO$_3$ (5.04 g, 60.0 mmol) and MeI (3.00 mL, 48.0 mmol) and the reaction was stirred for 24 h. The mixture was diluted with brine, extracted with EA, washed with brine, dried over anhydrous MgSO$_4$ and filtered. The filtrate was concentrated under reduced pressure and the residue was purified by MPLC over silica gel (eluting with a gradient of 1%-50% EtOAc in PE) to give D-3. LC/MS: [M+H]⁺=248.2.

Step D—Synthesis of Intermediate D-4

To a solution of D-3 (2.00 g, 8.09 mmol) in DCM (30 mL) at 0° C. was added TFA (10 mL) then the mixture was stirred at RT for 3 h. The final solution was concentrated under reduced pressure to afford D-4. LC/MS: [M+H]⁺=148.2.

Step E—Synthesis of Intermediate D-5

To a solution of D-4 (1.7 g, 6.51 mmol) in DCE (17 mL) at RT was added paraformaldehyde (3.91 g, 65.1 mmol). The reaction was treated with MgSO₄ and stirred at RT for 30 mins, then NaBH(OAc)₃ (6.90 g, 32.5 mmol) was added to the solution. The mixture was stirred at RT for 16 h then filtered. The filtrate was concentrated under reduced pressure and the residue was purified by MPLC over silica gel (eluting with a gradient of 0%-15% MeOH (+10% ammonia in water) in DCM) to afford D-5. ¹H NMR (400 MHz, CD₃OD): δ 4.15 (s, 2H), 3.75 (s, 3H), 3.69 (t, J=5.6 Hz, 2H), 2.63 (t, J=5.6 Hz, 2H), 2.33 (s, 6H).

Step F—Synthesis of Intermediate D-6

To a solution of D-5 (800 mg, 4.96 mmol) in acetonitrile (10 mL) at RT were added tert-butyl (2-(2-bromoethoxy)ethyl)carbamate (6.65 g, 24.81 mmol) and NaHCO₃ (2.09 g, 24.81 mmol) then the reaction was stirred at 55° C. for 16 h. The final mixture was cooled down, filtered, the filtrate was concentrated under reduced pressure and the residue was purified by MPLC over silica gel (eluting with a gradient of 0%-20% MeOH in DCM) to give D-6. LC/MS: [M]⁺=349.1. ¹H NMR (300 MHz, CD₃OD): δ 4.23 (s, 2H), 4.06-3.89 (m, 4H), 3.79-3.70 (m, 7H), 3.56 (t, J=5.4 Hz, 2H), 3.31-3.21 (m, 8H), 1.46 (s, 9H).

Step G—Synthesis of Intermediate D

To a solution of 2 M HCl in EtOAc (30 mL) at RT was added D-6 (1.3 g, 3.03 mmol) and the reaction was stirred for 1 h. The solvent was concentrated under reduced pressure to provide intermediate D. LC/MS: [M]⁺=249.2.

Preparation of Intermediate E

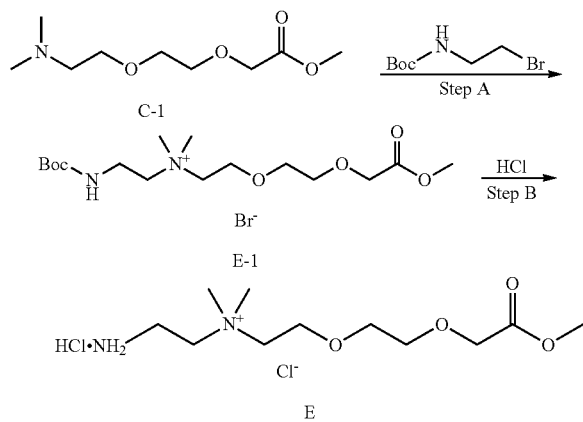

Step A—Synthesis of Intermediate E-1

To a solution of C-1 (1.00 g, 4.87 mmol) in acetonitrile (15 mL) at RT was added tert-butyl (2-bromoethyl)carbamate (6.55 g, 29.2 mmol) then the solution was stirred at 50° C. for 16 h. The final mixture was cooled down, filtered, the filtrate was concentrated under reduced pressure and the residue was purified by MPLC over silica gel (eluting with a gradient of 0%-10% MeOH in DCM) to give E-1. LC/MS: [M]⁺=349.1. ¹H NMR (400 MHz, CD₃OD): δ 4.20 (s, 2H), 4.01-3.99 (m, 2H), 3.77-3.75 (m, 4H), 3.73-3.72 (m, 4H), 3.69-3.66 (m, 2H), 3.55 (s, 3H), 3.25 (s, 6H), 1.34 (s, 9H).

Step B—Synthesis of Intermediate E

To a solution of 2 M HCl in EtOAc (4 mL) at RT was added E-1 (330 mg, 0.780 mmol) and the reaction was stirred for 1.5 h. The solvent was concentrated under reduced pressure, the material was dissolved in DCM, then concentrated under reduced pressure to provide intermediate E. LC/MS: [M]⁺=249.1.

Preparation of Intermediate F

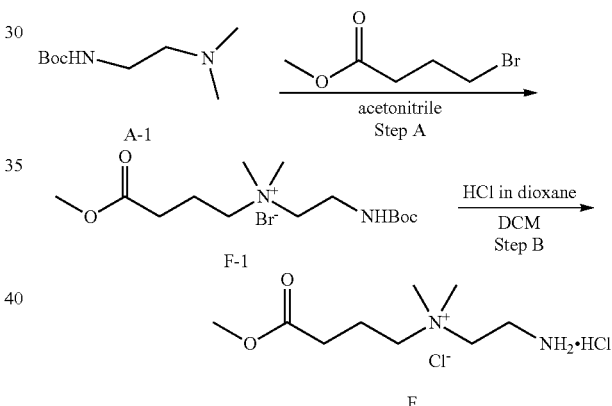

Step A—Synthesis of Intermediate F-1

To a solution of A-1 (4.90 g, 26 mmol) in acetonitrile (20 ml) at RT was added methyl 4-bromobutyrate (7.24 ml, 57.2 mmol) and the mixture was warmed to 50° C. and stirred overnight. The reaction was concentrated and the residue was diluted with Et₂O. The slurry was stirred at RT for 2 h, and the solid was filtered, rinsed with Et₂O and dried to provide F-1. LC/MS: [M]⁺=289.14.

Step B—Synthesis of Intermediate F

A solution of F-1 (8.92 g, 24.15 mmol) in 4 N HCl in dioxane (60.4 ml, 242 mmol) was stirred for 2 h. The reaction was concentrated, diluted with Et₂O, stirred for 2 h then concentrated to give intermediate F. ¹H NMR (400 MHz, DMSO-d₆): δ 8.54 (s, 3H), 3.65-3.45 (m, 5H), 3.40-3.20 (m, 4H), 3.12 (s, 6H), 2.41 (t, J=7.4 Hz, 2H), 2.00-1.90 (m, 2H).

Preparation of Intermediate G

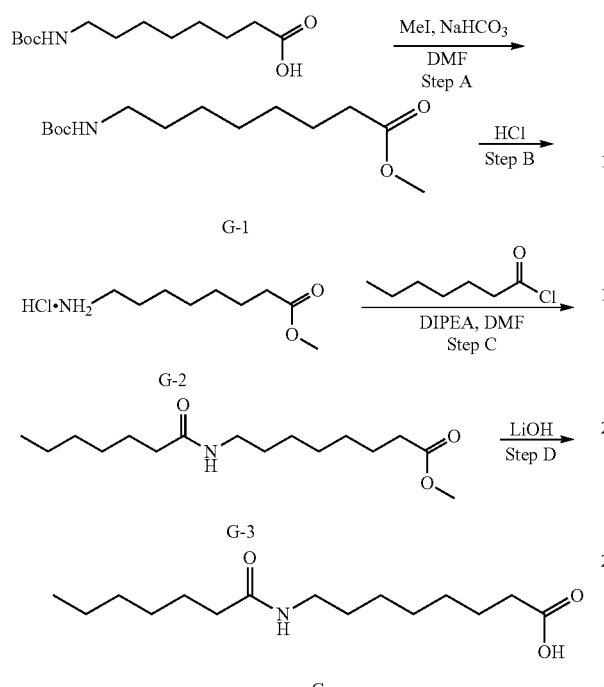

Step A—Synthesis of Intermediate G-1

To a solution of 8-((tert-butoxycarbonyl)amino)octanoic acid (5.00 g, 19.28 mmol) in DMF (100 mL) at RT were added NaHCO$_3$ (8.10 g, 96 mmol) and MeI (4.82 mL, 77 mmol) and the mixture was stirred for 24 h. The solution was diluted with brine, extracted with EtOAc, washed with brine, dried over MgSO$_4$ and filtered. The filtrate was concentrated and the residue was purified by MPLC over silica gel (eluting with a gradient of 1%-25% EtOAc in PE) to provide G-1. LC/MS: [M+H]$^+$=274.2.

Step B—Synthesis of Intermediate G-2

A solution of G-1 (3.9 g, 14.27 mmol) in 4 M HCl in dioxane (40 mL) was stirred at RT for 2 h then concentrated under reduced pressure. The residue was dissolved in DCM (50 mL) and concentrated under reduced pressure to give G-2. LC/MS: [M+H]$^+$=174.2.

Step C—Synthesis of Intermediate G-3

To a solution of G-2 (2.6 g, 12.40 mmol) in DMF (30 mL) at 0° C. were added DIPEA (4.81 g, 37.2 mmol) and heptanoyl chloride (1.843 g, 12.40 mmol) and the mixture was stirred at 0° C. for 1 h. The solution was diluted with brine, extracted with DCM, washed with brine, dried over anhydrous MgSO$_4$ and filtered. The filtrate was concentrated and the residue was purified by MPLC over silica gel (eluting with a gradient of 1%-30% EtOAc in PE) to provide G-3. LC/MS: [M+H]$^+$=286.3.

Step D—Synthesis of Intermediate G

To a solution of G-3 (2.00 g, 7.01 mmol) in THF (20 mL) at RT was added 2M aqueous LiOH (14.01 mL, 28.0 mmol) and the mixture was stirred for 16 h. The solution was quenched with 1 M aqueous HCl (28 mL), diluted with brine, extracted with EtOAc, washed with brine, dried over MgSO$_4$ and filtered. The filtrate was concentrated and the residue was dissolved in Et$_2$O (20 mL) and stirred at RT for 1 h. The solid was filtered, washed with Et$_2$O and dried to give intermediate G. LC/MS: [M+H]$^+$=272.2. $^1$H NMR (400 MHz, CDCl$_3$): δ 2.97 (td, J=6.6, 6.2, 1.9 Hz, 2H), 2.10 (t, J=7.4 Hz, 2H), 1.98 (t, J=7.5 Hz, 2H), 1.41 (tt, J=9.8, 5.6 Hz, 4H), 1.31 (p, J=7.0 Hz, 2H), 1.25-1.05 (m, 12H), 0.81-0.67 (m, 3H).

Preparation of Intermediate H

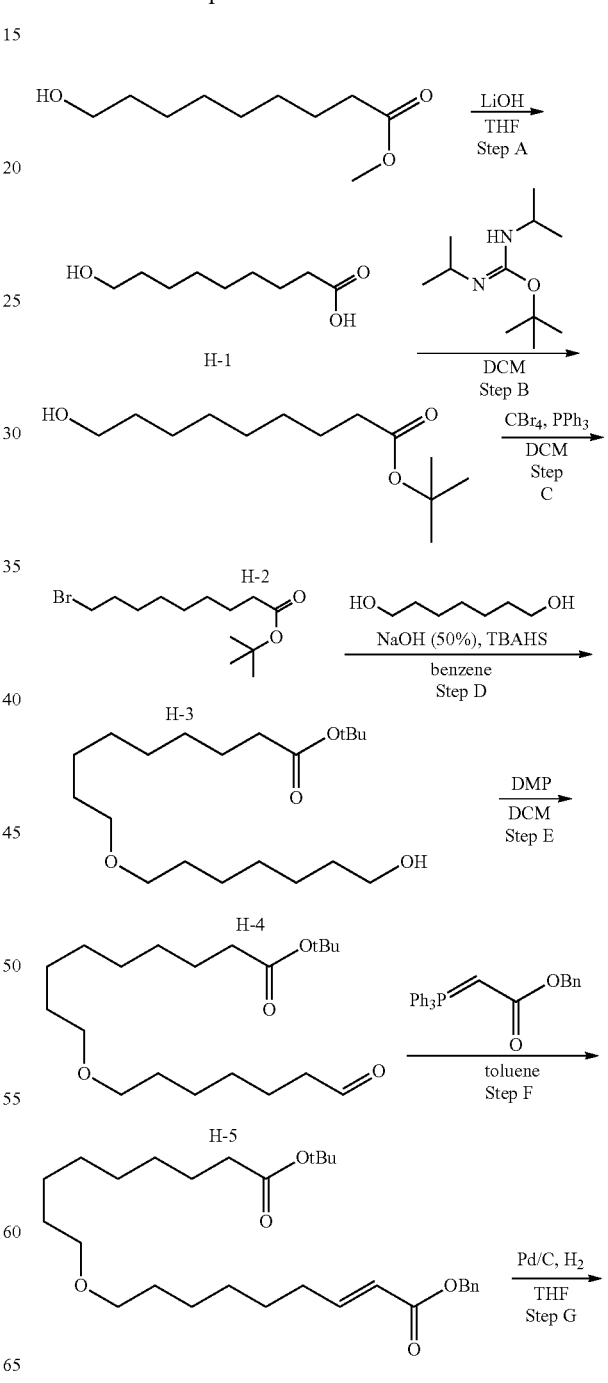

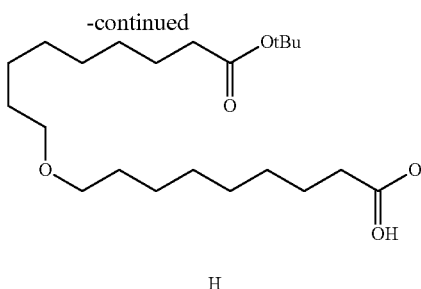

Step A—Synthesis of Intermediate H-1

To a solution of methyl 9-hydroxynonanoate (5 g, 26.6 mmol) in THF (50 mL) at RT was added 1 M aqueous LiOH (53.1 mL, 53.1 mmol) then the solution was stirred for 1 h. The solution was adjusted to pH 2 with 1 N aqueous HCl then extracted with EA (2×100 mL). The combined organic layers were washed with brine, dried over anhydrous $Na_2SO_4$ and filtered. The filtrate was concentrated under reduced pressure to give H-1. $^1$H NMR (400 MHz, $CDCl_3$): δ 3.64 (t, J=6.6 Hz, 2H), 2.34 (t, J=7.5 Hz, 2H), 1.66-1.52 (m, 4H), 1.38-1.29 (m, 8H).

Step B—Synthesis of Intermediate H-2

To a solution of H-1 (4.6 g, 26.4 mmol) in DCM (50 mL) at RT was added tert-butyl N,N'-diisopropylcarbamimidate (26.4 g, 132 mmol) then the solution was stirred at 50° C. for 5 h. The final mixture was concentrated under reduced pressure and the residue was purified by MPLC over silica gel (eluting with a gradient of 1%-30% EtOAc in PE) to provide H-2. $^1$H NMR (400 MHz, $CDCl_3$): δ 3.64 (t, J=6.6 Hz, 2H), 2.20 (t, J=7.5 Hz, 2H), 1.61-1.52 (m, 4H), 1.44 (s, 9H), 1.36-1.27 (m, 8H).

Step C—Synthesis of Intermediate H-3

To a solution of H-2 (3 g, 13.0 mmol) in DCM (10 mL) at 0° C. were added $CBr_4$ (8.64 g, 26.0 mmol) and $Ph_3P$ (5.12 g, 19.5 mmol) then the reaction was stirred at RT for 2 h. The final mixture was concentrated under reduced pressure and the residue was purified by MPLC over silica gel (eluting with a gradient of 1%-10% EtOAc in PE) to provide H-3. $^1$H NMR (400 MHz, $CDCl_3$): δ 3.41 (t, J=6.8 Hz, 2H), 2.20 (t, J=7.5 Hz, 2H), 1.90-1.80 (m, 2H), 1.61-1.39 (m, 13H), 1.36-1.26 (m, 6H).

Step D—Synthesis of Intermediate H-4

To a solution of H-3 (3.3 g, 11.2 mmol) and heptane-1,7-diol (2.98 g, 22.5 mmol) in benzene (40 mL) at 0° C. were added 50% aqueous NaOH (16 mL) and TBAHS (3.82 g, 11.25 mmol) then the reaction mixture was stirred at RT for 16 h. The final solution was diluted with water, extracted with EtOAc, and the combined organic layers were washed with brine, dried over anhydrous $Na_2SO_4$ and filtered. The filtrate was concentrated under reduced pressure and the residue was purified by MPLC over silica gel (eluting with a gradient of 1%-30% EtOAc in PE) to give H-4. $^1$H NMR (400 MHz, $CDCl_3$): δ 3.64 (t, J=6.6 Hz, 2H), 3.45-3.33 (m, 4H), 2.20 (t, J=7.5 Hz, 2H), 1.59-1.55 (m, 8H), 1.44 (s, 9H), 1.39-1.25 (m, 14H).

Step E—Synthesis of Intermediate H-5

To a solution of H-4 (1.9 g, 5.5 mmol) in DCM (20 mL) at 0° C. was added DMP (4.68 g, 11.0 mmol) then the reaction mixture was stirred at RT for 2 h. The final solution was quenched by saturated aqueous $Na_2S_2O_3$/$NaHCO_3$ solution (100 mL) and extracted with EtOAc (2×50 mL). The combined organic layers were washed with brine, dried with anhydrous $Na_2SO_4$ and filtered. The filtrate was concentrated under reduced pressure and the residue was purified by a silica gel column chromatography (eluting with a gradient of 1%-10% EtOAc in PE) to give H-5. $^1$H NMR (400 MHz, $CDCl_3$): δ 9.76 (t, J=1.8 Hz, 1H), 3.45-3.29 (m, 4H), 2.47-2.38 (m, 2H), 2.20 (t, J=7.5 Hz, 2H), 1.68-1.53 (m, 8H), 1.44 (s, 9H), 1.40-1.26 (m, 12H).

Step F—Synthesis of Intermediate H-6

To a solution of H-5 (1.2 g, 3.50 mmol) in toluene (20 mL) at RT was added benzyl (triphenyl phosphoranylidene) acetate (2.88 g, 7.01 mmol) then the reaction was stirred for 16 h. The final solution was concentrated under reduced pressure and the residue was purified by MPLC over silica gel (eluting with a gradient of 1%-5% EtOAc in PE) to provide H-6. $^1$H NMR (400 MHz, $CDCl_3$): δ 7.42-7.28 (m, 5H), 7.01 (dt, J=15.7, 7.0 Hz, 1H), 5.86 (dt, J=15.7, 1.6 Hz, 1H), 5.17 (s, 2H), 3.38 (td, J=6.7, 1.0 Hz, 4H), 2.26-2.14 (m, 4H), 1.61-1.53 (m, 6H), 1.50-1.41 (s, 11H), 1.38-1.24 (m, 12H).

Step G—Synthesis of Intermediate H

To a solution of H-6 (900 mg, 1.90 mmol) in THF (20 mL) at RT under nitrogen atmosphere was added 10% Pd/C (100 mg, 0.094 mmol). The mixture was degassed with hydrogen 3 times and stirred at RT for 16 h under hydrogen (1.5 atm). The final mixture was filtered over Celite and the filtrate was concentrated under reduced pressure to give intermediate H. $^1$H NMR (400 MHz, $CDCl_3$): δ 3.39 (t, J=6.7 Hz, 4H), 2.35 (t, J=7.5 Hz, 2H), 2.20 (t, J=7.5 Hz, 2H), 1.67-1.49 (m, 8H), 1.44 (s, 9H), 1.38-1.26 (m, 16H).

Preparation of Intermediate I

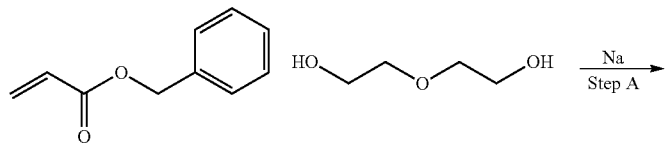

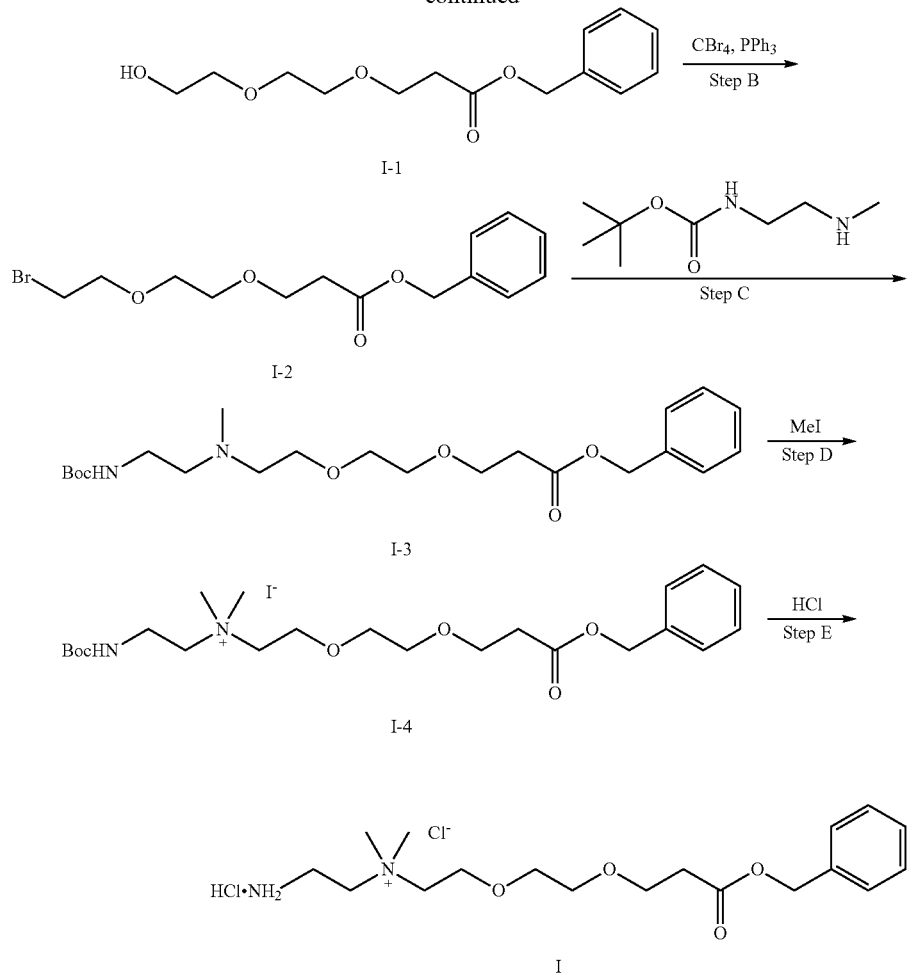

Step A—Synthesis of Intermediate I-1

To a solution of 2,2′-oxybis(ethan-1-ol) (35.1 ml, 370 mmol) in THF (247 ml) at RT under nitrogen was added sodium (0.085 g, 3.70 mmol), followed by benzyl acrylate (18.87 ml, 123 mmol) and the resulting mixture was stirred at RT overnight. The final mixture was quenched with saturated aqueous NH$_4$Cl, extracted with EtOAc, washed with brine, dried over MgSO$_4$, filtered and concentrated. The residue was purified by MPLC over silica gel (eluting with a gradient of 0%-80% EtOAc in hexanes) to give I-1. LC/MS: [M+H]$^+$=269.23.

Step B—Synthesis of Intermediate I-2

To a solution of I-1 (1.69 g, 6.30 mmol) and carbon tetrabromide (6.27 g, 18.90 mmol) in DCM (15.75 ml) at 0° C. was added triphenylphosphine (4.96 g, 18.90 mmol) portion wise over 10 min then the resulting mixture was stirred at 0° C. for 2 h. The final mixture was quenched with water, extracted with DCM, dried over MgSO$_4$ and filtered. The filtrate was concentrated and the residue was purified by MPLC over silica gel (eluting with a gradient of 0%-60% EtOAc in hexanes) to provide I-2. LC/MS: [M+H]$^+$=331.2, 333.2.

Step C—Synthesis of Intermediate I-3

To a solution of I-2 (3.17 g, 9.57 mmol) in EtOH (9.57 ml) at RT was added tert-butyl 2-(methylamino)ethylcarbamate (8.34 g, 47.9 mmol) and sodium iodide (0.072 g, 0.479 mmol) then the reaction mixture was stirred at RT for 72 h. The final mixture was concentrated and the residue was purified by MPLC over silica gel (eluting with a gradient of 0%-10% MeOH in DCM) to provide I-3. LC/MS: [M+H]$^+$=425.4.

Step D—Synthesis of Intermediate I-4

To a solution of I-3 (1.48 g, 3.49 mmol) in acetonitrile (11.62 ml) at RT was added iodomethane (1.085 ml, 17.43 mmol). The reaction mixture was stirred at RT overnight then concentrated to give I-4. LC/MS: [M]$^+$=439.4.

Step E—Synthesis of Intermediate I

To a solution of I-4 (1.97 g, 3.48 mmol) in DCM (17.39 ml) at RT was added 4 M HCl in dioxane (3.48 ml, 13.91 mmol) and the mixture was stirred at RT for 2.5 h. The final solution was concentrated then the residue was taken in acetonitrile:water 1:1 and lyophilized to give intermediate I. LC/MS: [M]$^+$=339.4.

Preparation of Intermediate J

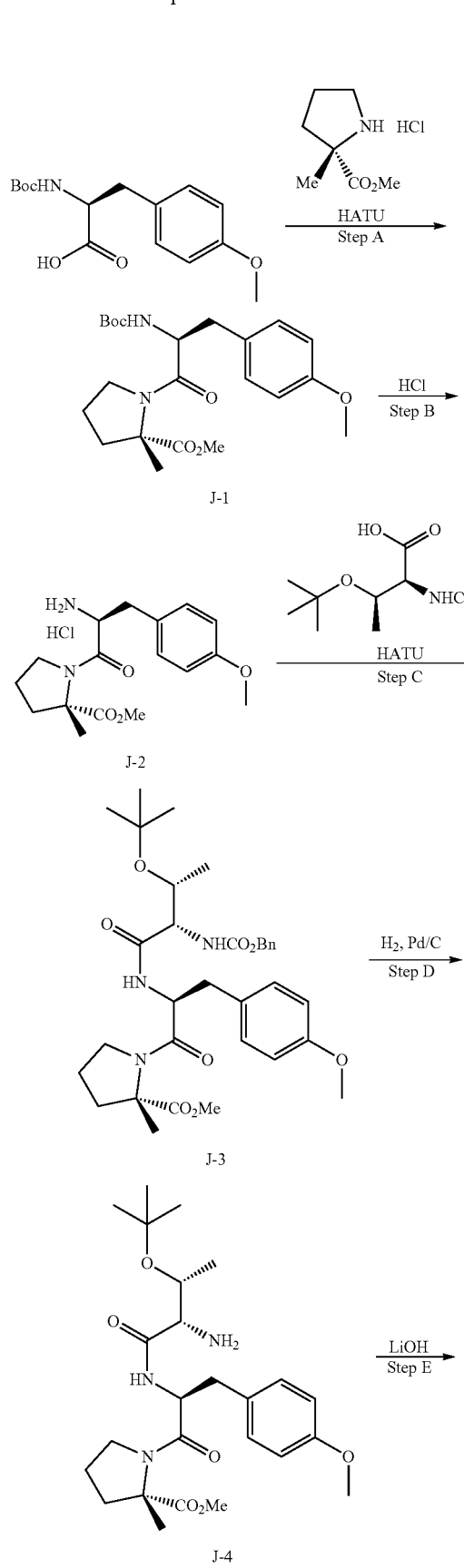

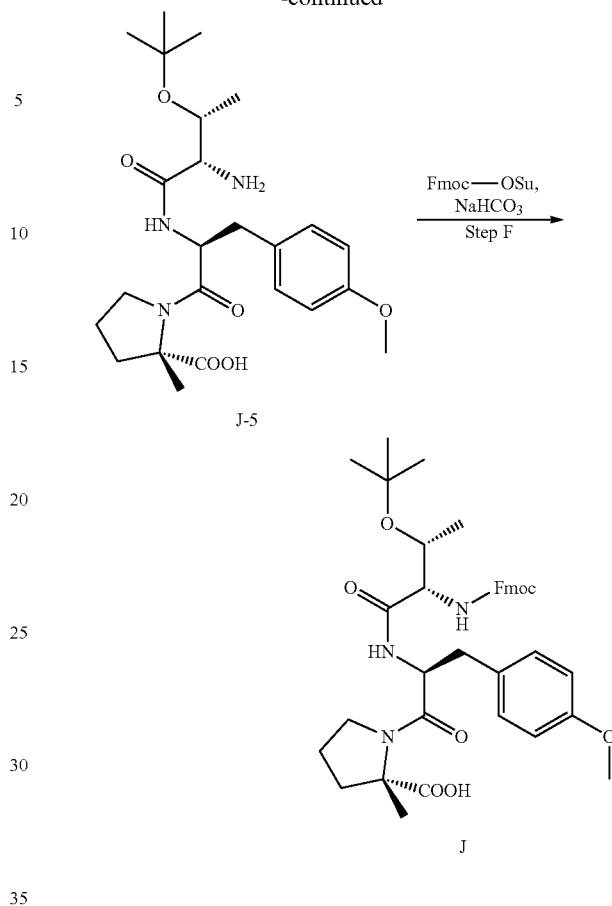

Step A—Synthesis of Intermediate J-1

To a solution of methyl (S)-2-methylpyrrolidine-2-carboxylate hydrochloride (7.00 g, 39 mmol) and (S)-2-((tert-butoxycarbonyl)amino)-3-(4-methoxyphenyl)propanoic acid (12.08 g, 40.9 mmol) in DMF (100 ml) at 0° C. was added DIPEA (17.01 ml, 97.0 mmol) followed by HATU (19.26 g, 50.7 mmol) and the resulting mixture was allowed to warm to RT and stirred overnight. The reaction was quenched with 10% aqueous LiCl solution and extracted with EtOAc. The combined organic layers were washed with 10% aqueous LiCl, dried over MgSO$_4$ and filtered. The filtrate was concentrated under reduced pressure and the residue was purified by MPLC over silica gel (eluting with a gradient of 20%-60% EtOAc in hexanes) to provide J-1. LC/MS: [M+H]$^+$=421.3.

Step B—Synthesis of Intermediate J-2

To a solution of J-1 (16.4 g, 39.0 mmol) in EtOAc (100 ml) was added 4 N HCl in dioxane (48.8 ml, 195 mmol). The resulting mixture was stirred at room temperature for 18 h and was concentrated under reduced pressure to give J-2.

Step C—Synthesis of Intermediate J-3

To a solution of J-2 (13.2 g, 37.0 mmol) and N-((benzyloxy)carbonyl)-O-(tert-butyl)-L-threonine (18.15 g, 37.0 mmol) in DMF at 0° C. was added DIPEA (16.15 ml, 92 mmol) followed by HATU (18.28 g, 48.1 mmol) and the resulting mixture was allowed to warm to RT and stirred overnight. The reaction was quenched with 10% aqueous LiCl solution and extracted with EtOAc. The combined organic layers were washed with 10% aqueous LiCl, dried over MgSO₄ and filtered. The filtrate was concentrated under reduced pressure and the residue was purified by MPLC over silica gel (eluting with a gradient of 20%-60% EtOAc in hexanes) to provide J-3.

Step D—Synthesis of Intermediate J-4

To a solution of J-3 (16.5 g, 27.0 mmol) in MeOH was added a slurry of 10% Pd/C and the mixture was hydrogenated at 20 psi for 4 h. The reaction mixture was filtered over Celite and the filtrate was concentrated under reduced pressure. The crude product was then re-dissolved in DCM and the solution was filtered through a 2 um filter and concentrated to give J-4.

Step E—Synthesis of Intermediate J-5

To a solution of J-4 (10.34 g, 21.65 mmol) in THF (100 ml) at RT was added 2 N lithium hydroxide monohydrate (43.3 ml, 87 mmol) and the mixture was warmed to 45° C. and stirred overnight to give J-5 as crude solution. LC/MS: [M+H]⁺=464.3. The reaction mixture was cooled to 0° C. and treated with 1 M aqueous HCl (40 mL). The resulting J-5 solution was directly used in the next step without further purification.

Step F—Synthesis of Intermediate J

To the crude J-5 solution prepared in the previous step was added NaHCO₃ (1.725 g, 20.54 mmol) and Fmoc-OSu (3.81 g, 11.30 mmol) at 0° C. The reaction mixture was stirred at 0° C. for 2 h, then treated with 1 M aqueous HCl (20.5 mL), and extracted with EtOAc (2×200 mL). The combined organic layers were washed with brine (2×100 mL), dried over Na₂SO₄, filtered and the filtrate was concentrated under reduced pressure. The residue was purified by MPLC over silica gel (eluting with a gradient of 2%-5% MeOH in DCM) to afford intermediate J. LC/MS: [M+H]⁺ =686.4.

Preparation of Intermediate K

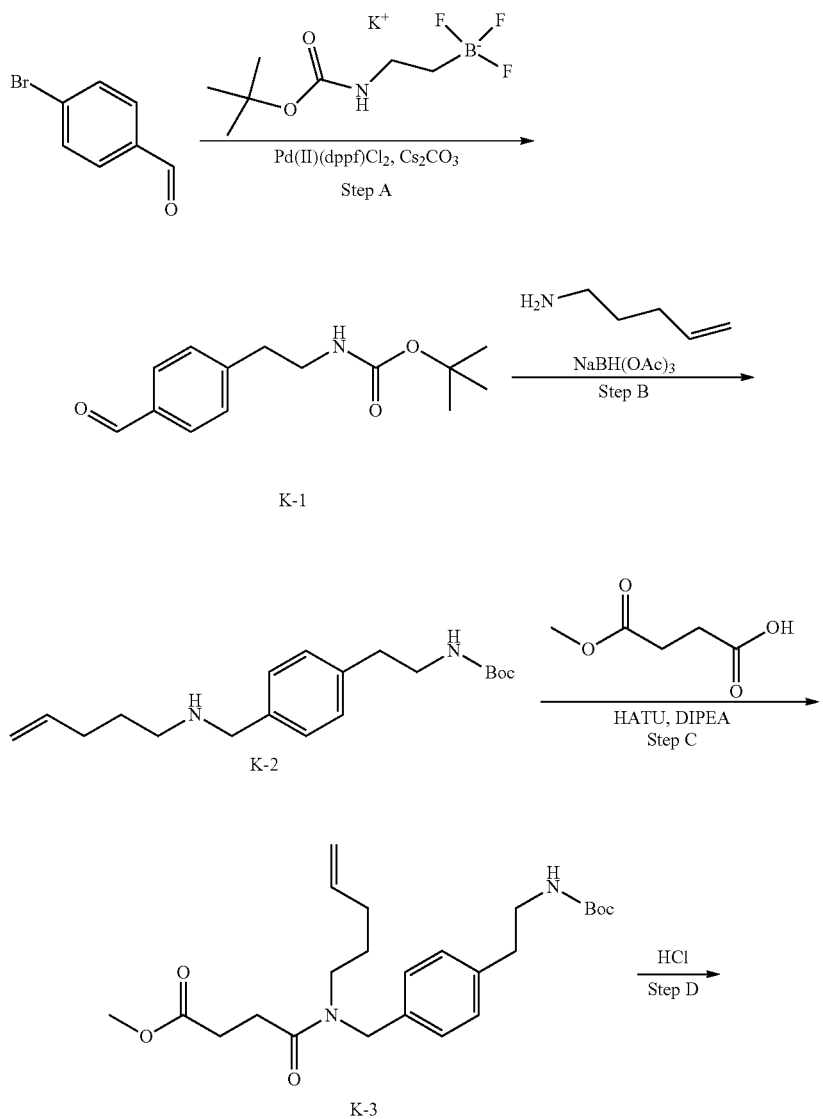

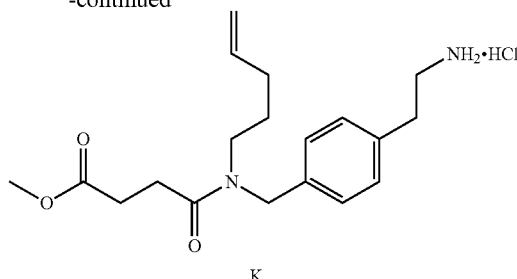

K

Step A—Synthesis of Intermediate K-1

A solution of 4-bromobenzaldehyde (15.00 g, 81 mmol), potassium tert-butyl N-[2-(trifluoroboranuidy)ethyl]carbamate (20.97 g, 84 mmol), cesium carbonate (52.8 g, 162 mmol) and 1,1'-bis(diphenylphosphino)ferrocene-palladium (II)dichloride dichloromethane complex (1.99 g, 2.43 mmol) in degassed toluene (250 ml) and water (85 ml) was warmed to 76° C. and stirred overnight. The mixture was quenched at RT with half-saturated aqueous $NH_4Cl$ and extracted with EtOAc. The combined organic fractions were washed with brine, dried over $Na_2SO_4$, filtered and the filtrate was concentrated in vacuo. The residue was purified by MPLC over silica gel (eluting with a gradient of EtOAc in DCM) to give K-1. LC/MS: $[M-56]^+=193.0$.

Step B—Synthesis of Intermediate K-2

To a solution of K-1 (12.9 g, 51.7 mmol) and pent-4-en-1-amine (6.61 g, 78 mmol) in DCM (120 ml) and AcOH (3 ml) at RT in a water bath was added sodium triacetoxy borohydride (32.9 g, 155 mmol) portion wise and the mixture was stirred for 30 min. The reaction was slowly quenched at 0° C. with water (3 ml), poured into 1 N aqueous NaOH (500 ml), stirred for 15 min then extracted with DCM, dried over $Na_2SO_4$, and concentrated. The residue was purified by MPLC over silica gel (eluting with a gradient of MeOH in DCM) to give K-2. LC/MS: $[M+H]^+=319.2$.

Step C—Synthesis of Intermediate K-3

To a solution of K-2 (8.48 g, 20.77 mmol) and 4-methoxy-4-oxobutanoic acid (3.02 g, 22.85 mmol) in DMF (40 ml) were added HATU (9.48 g, 24.92 mmol) and DIPEA (8.71 ml, 49.8 mmol). The resulting solution was stirred at RT for 1 h, then quenched with aqueous saturated $NaHCO_3$ (10 mL). The mixture was partitioned between EtOAc (500 mL) and aqueous saturated $NaHCO_3$ (200 mL), the organic phase was washed with brine (3×200 mL), dried over $Na_2SO_4$, concentrated and the residue was purified by MPLC over silica gel (eluting with a gradient of EtOAc in hexanes) to give K-3. LC/MS: $[M+H]^+=433.4$.

Step D—Synthesis of Intermediate K

To a solution of K-3 (2.9 g, 6.70 mmol) in DCM (15 mL) at RT was added 4 M HCl in dioxane (10 mL) and the reaction mixture was stirred at RT for 1 h. The mixture was concentrated under reduced pressure to give intermediate K. LC/MS: $[M+H]^+=333.3$.

Preparation of Intermediate L

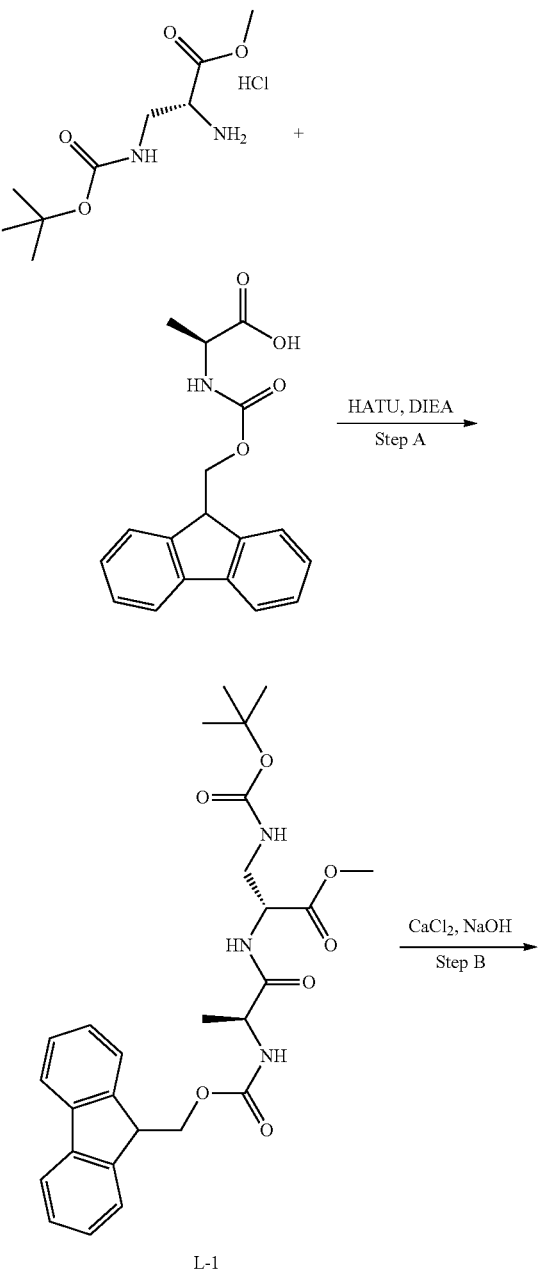

L-1

Step A—Synthesis of Intermediate L-1

To a solution of D-Dap(Boc)-OMe HCl salt (4.10 g, 16.10 mmol), Fmoc-Ala-OH (5.01 g, 16.10 mmol) and HATU (6.43 g, 16.90 mmol) in DMF (40 ml) at 0° C. was added DIPEA (7.03 ml, 40.2 mmol) and the mixture was stirred at 0° C. for 2 h then kept in the refrigerator overnight. The mixture was quenched at RT with water and extracted with EtOAc. The combined organic fractions were washed with half brine, dried over Na$_2$SO$_4$, filtered and the filtrate was concentrated in vacuo. The residue was purified by MPLC over silica gel (eluting with a gradient of EtOAc in hexanes) to give L-1. LC/MS: [M+H]$^+$=512.3.

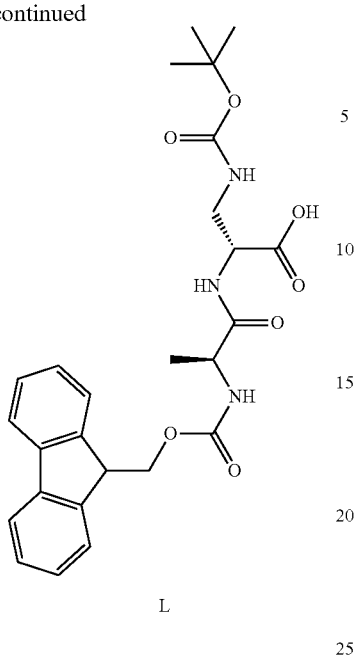

L

Step B—Synthesis of Intermediate L

To a solution of L-1 (8.03 g, 15.70 mmol) and 0.8 N calcium chloride (19.62 ml, 15.70 mmol) in water (40 ml) and 2-propanol (120 ml) at RT was added solid sodium hydroxide (0.691 g, 17.27 mmol). The mixture was stirred at room temperature overnight. The final mixture was concentrated, acidified with 0.5 N aqueous HCl to pH ~2 (~40 mL), extracted three times with EtOAc, washed with brine, dried over Na$_2$SO$_4$ and concentrated. The residue was purified by reverse phase MPLC over C18 (eluting with a gradient of acetonitrile in water (+0.1% TFA)) to give intermediate L. LC/MS: [M+H]$^+$=498.2.

Preparation of Intermediate M

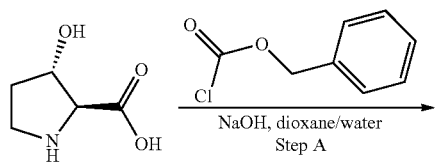

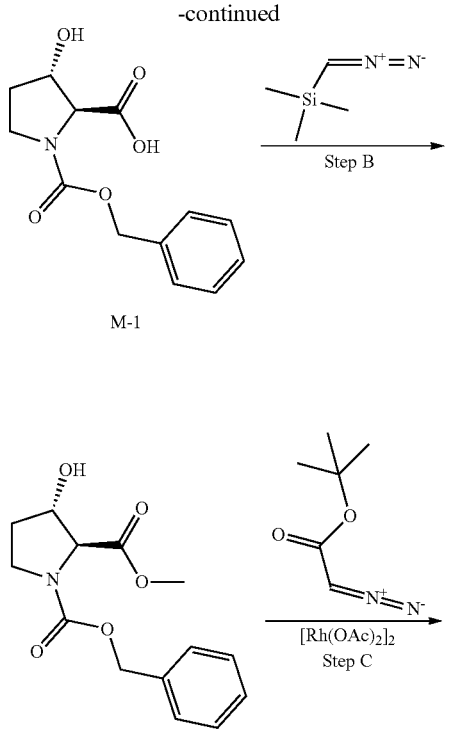

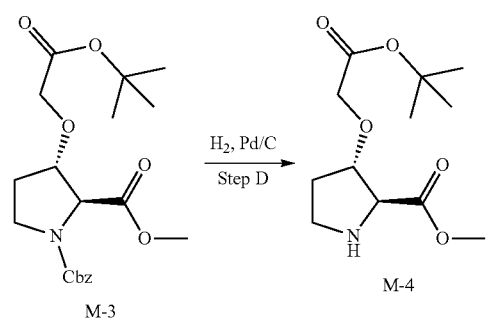

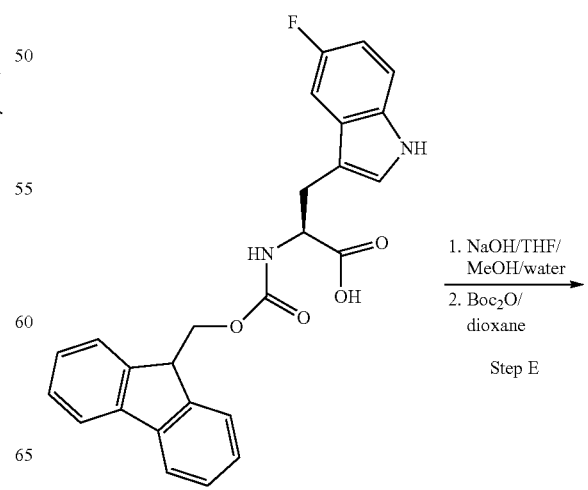

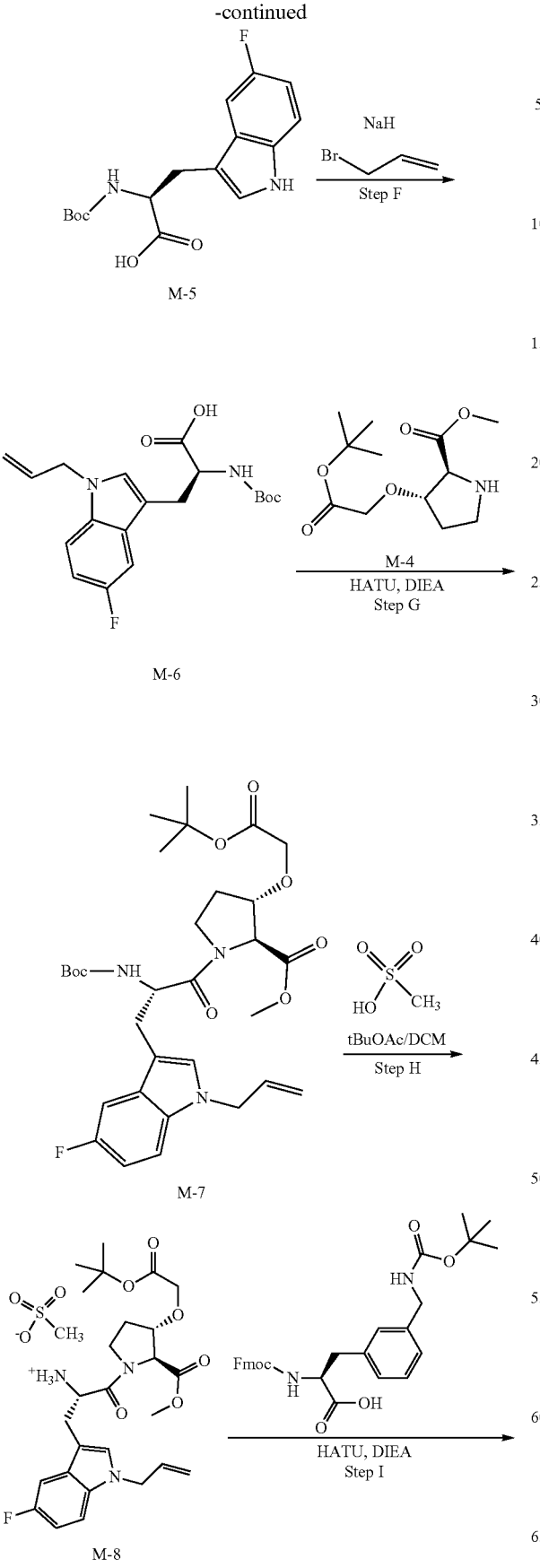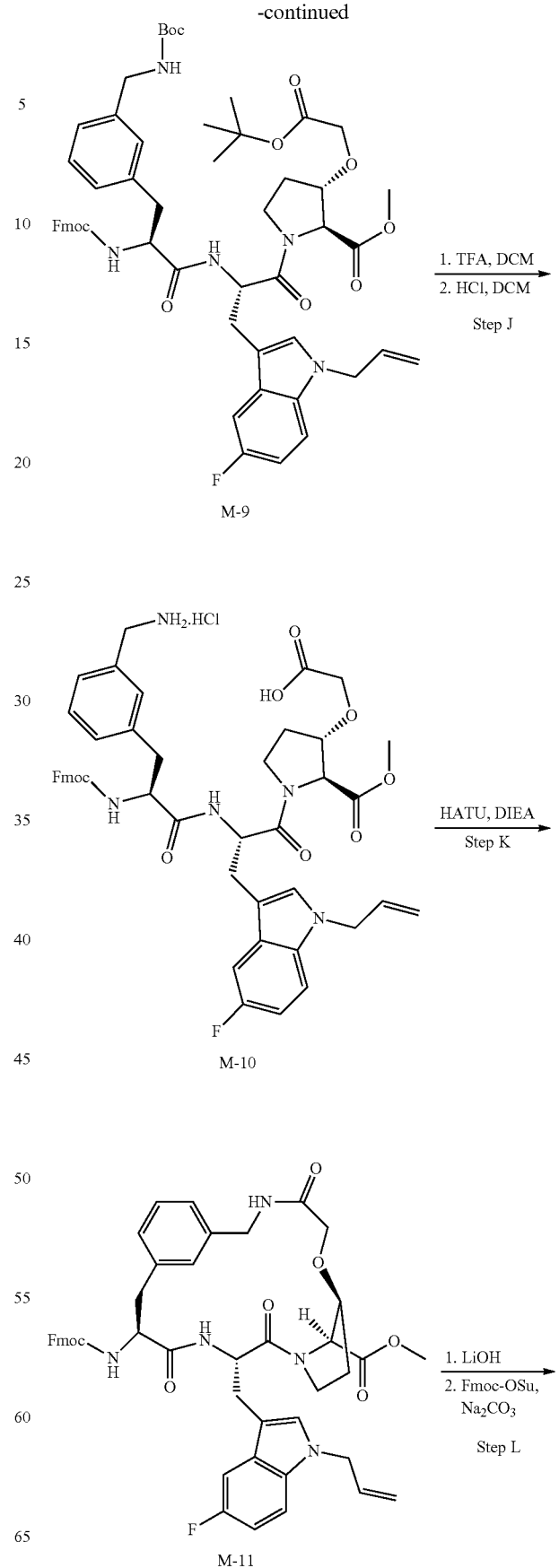

191

-continued

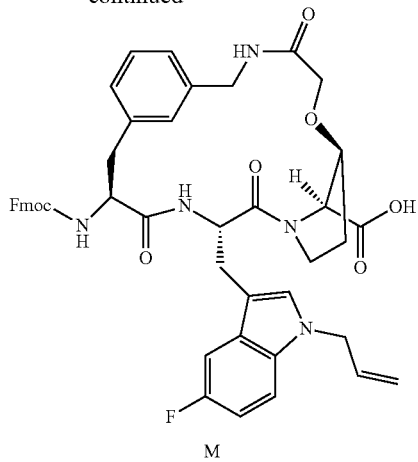

M

Step A—Synthesis of Intermediate M-1

To a suspension of (2S,3S)-3-hydroxypyrrolidine-2-carboxylic acid (5.32 g, 40.6 mmol) in dioxane (100 ml) at 0° C. was added 1N aqueous NaOH (122 ml, 122 mmol), followed by addition of benzyl chloroformate (6.50 ml, 44.6 mmol) dropwise then the resulting suspension was stirred at 0° C. for 5 h. The solution was concentrated, the aqueous layer was acidified to pH 3, partitioned between 30% IPA in DCM (200 mL) and brine (50 mL), and the aqueous phase was further extracted with 30% IPA in DCM (2×100 mL). The combined organic layers were dried over $Na_2SO_4$, filtered and the filtrate was concentrated to give M-1. LC/MS: $[M+H]^+=266.1$.

Step B—Synthesis of Intermediate M-2

To a solution of M-1 (7.48 g, 28.2 mmol) in MeOH (80 ml) was added TMS-diazomethane (70.5 ml, 141 mmol) dropwise, and the resulting solution was stirred at RT for 10 min, then quenched by addition of acetic acid (ca. 400 uL) dropwise. The solution was concentrated, and the residue was purified by MPLC over silica gel (eluting with a gradient of EtOAc in hexanes) to give M-2. LC/MS: $[M+H]^+=280.1$.

Step C—Synthesis of Intermediate M-3

A solution of M-2 (4.81 g, 17.22 mmol) in DCM (200 mL) was bubbled with nitrogen for 30 min, followed by addition of rhodium(ii) acetate dimer (0.761 g, 1.722 mmol). The mixture was cooled in an ice-water bath, and tert-butyl diazoacetate (3.58 mL, 25.8 mmol) was added at 0° C. dropwise. The resulting mixture was stirred at 0° C. for 1.5 h. The final reaction was quenched by addition of water (100 mL), the mixture was extracted with DCM (3×100 mL), and the combined organic layers was dried over $Na_2SO_4$ and filtered. The filtrate was concentrated and the residue was purified by reverse phase MPLC over C18 (eluting with a gradient of acetonitrile (+0.05% TFA) in water (+0.05% TFA)). The fraction containing the product was concentrated and the resulting aqueous phase was extracted with DCM (2×100 mL). The combined organic phase was dried over $Na_2SO_4$, filtered and concentrated to give M-3. LC/MS: $[M+H]^+=394.2$.

Step D—Synthesis of Intermediate M-4

To a solution of M-3 (3.72 g, 9.46 mmol) in MeOH (80 ml) was added 10% Pd/C (0.805 g, 0.756 mmol) and the

192 resulting mixture was hydrogenated using a balloon filled with hydrogen at RT for 2 h. The final mixture was filtered over Celite and the filtrate was concentrated to give M-4. LC/MS: $[M+H]^+=259.9$.

Step E—Synthesis of Intermediate M-5

To a solution of (S)-2-((((9H-fluoren-9-yl)methoxy)carbonyl)amino)-3-(5-fluoro-1H-indol-3-yl)propanoic acid (3 g, 6.75 mmol) in THF (20 ml), MeOH (10 mL), and water (20.00 ml) at 0° C. was added 1N aqueous NaOH (20.25 ml, 20.25 mmol), and the resulting solution was stirred at RT for 4 h then concentrated. To the aqueous mixture was added dioxane (50 ml) and water (20 mL), the resulting solution was cooled to 0° C. and Boc2O (1.881 ml, 8.10 mmol) was added. The resulting solution was stirred at 0° C. for 3 h, then concentrated and the aqueous phase was extracted with $Et_2O$ (3×40 mL), acidified to pH 3, then extracted with DCM (3×100 mL), followed by extraction with 30% IPA in DCM (2×80 mL). The combined organic layers were dried over $Na_2SO_4$, filtered and concentrated to give M-5. LC/MS: $[M+H]^+=322.9$.

Step F—Synthesis of Intermediate M-6

To a solution of M-5 (2.079 g, 6.45 mmol) in DMF (40 ml) at 0° C. was added 60% NaH in hexane (0.568 g, 14.19 mmol), and the resulting solution was stirred at 0° C. for 50 min followed by addition of allyl bromide (1.172 mL, 13.54 mmol) dropwise. The resulting solution was stirred at 0° C. for 1.5 h, then quenched by addition of 1N aqueous HCl (ca. 3.68 mL). The solution was then partitioned between EtOAc (200 mL) and water (100 mL), the organic phase was washed with brine (2×100 mL), dried over $Na_2SO_4$, filtered and concentrated and the residue was purified by MPLC over silica gel (eluting with a gradient of MeOH in DCM) to give M-6. LC/MS: $[M+H]^+=363.0$.

Step G—Synthesis of Intermediate M-7

To a solution of M-6 (2.239 g, 6.18 mmol) and M-4 (1.842 g, 7.11 mmol) in DMF (30 ml) were added HATU (2.82 g, 7.41 mmol) and DIEA (2.59 ml, 14.83 mmol) and the resulting solution was stirred at RT for 1 h. The mixture was partitioned between EtOAc (200 mL) and brine (100 mL), the organic phase was washed with brine (3×100 mL), dried over $Na_2SO_4$, filtered and concentrated and the residue was purified by MPLC over silica gel (eluting with a gradient of EtOAc in hexanes) to give M-7. LC/MS: $[M+H]^+=604.2$.

Step H—Synthesis of Intermediate M-8

To a solution of M-7 (2.83 g, 4.69 mmol) in DCM (20 ml) and tBuOAc (30 ml) at 0° C. was added methanesulfonic acid (1.218 ml, 18.75 mmol) and the resulting solution was stirred at 0° C. for 16.5 h, then at RT for 2.5 h. The solution containing the product M-8 was used in the next step without further purification. LC/MS: $[M+H]^+=504.2$.

Step I—Synthesis of Intermediate M-9

To a solution of (S)-2-((((9H-fluoren-9-yl)methoxy)carbonyl)amino)-3-(3-(((tert-butoxycarbonyl)amino)methyl)phenyl)propanoic acid (2.66 g, 5.16 mmol) in DMF (10 ml) was added HATU (1.961 g, 5.16 mmol) and DIEA (5.32 ml, 30.5 mmol), and the resulting solution was stirred at RT for 30 min, then added to an ice-cold bath of the above prepared solution containing M-8. The resulting solution was stirred at RT for 1 h then concentrated under reduced pressure. The residue was purified by reverse phase MPLC over C18

(eluting with a gradient of acetonitrile (+0.05% TFA) in water (+0.05% TFA)) to provide M-9. LC/MS: [M+H]$^+$=1002.1.

Step J—Synthesis of Intermediate M-10

To a solution of M-9 (3.235 g, 3.23 mmol) in DCM (4 ml) was added TFA (7.46 ml, 97 mmol), and the resulting solution was stirred at RT for 1 h, then concentrated. The residue was dissolved in DCM (10 mL), treated with 4 N HCl in dioxane (3.23 ml, 12.91 mmol), and concentrated. The residue was dissolved in acetonitrile (100 mL) and water (50 mL) and lyophilized to provide M-10.
LC/MS: [M+H]$^+$=846.1.

Step K—Synthesis of Intermediate M-11

To a solution of M-10 (2.85 g, 3.23 mmol) in DMF (45 ml) was added HATU (1.474 g, 3.88 mmol), and the resulting solution was stirred at RT for 30 min, then diluted with DCM (600 ml) followed by addition of DIEA (1.692 ml, 9.69 mmol) dropwise. The resulting solution was stirred at ambient temperature for 1 h. The final solution was concentrated, and the residue was purified by reverse phase MPLC over C18 (eluting with a gradient of acetonitrile (+0.05% TFA) in water (+0.05% TFA). The fractions containing the product were concentrated and the aqueous layer was partitioned between DCM (200 mL) and saturated NaHCO$_3$ (200 mL). The aqueous phase was further extracted with DCM (2×100 mL) and the combined organic layers were dried over Na$_2$SO$_4$, filtered and concentrated to give M-11. LC/MS: [M+H]$^+$=828.1.

Step L—Synthesis of Intermediate M

To a solution of M-11 (1.93 g, 2.331 mmol) in THF (60 ml), MeOH (30 ml), and water (20 ml) at 0° C. was added 1N aqueous LiOH (9.9 ml, 9.90 mmol) dropwise, and the resulting solution was stirred at 0° C. for 16 h then quenched by addition of 1N aqueous HCl (9.9 mL). The mixture was concentrated under reduced pressure and to the resulting solution at 0° C. were added acetone (60 ml), sodium carbonate (0.371 g, 3.50 mmol), and Fmoc-Osu (0.802 g, 2.378 mmol). The resulting solution was stirred at 0° C. for 6 h, concentrated under reduced pressure, then the aqueous phase was acidified to pH 4 and extracted with 30% IPA in DCM (3×100 mL). The combined organic layers were dried over Na$_2$SO$_4$, filtered and concentrated and the residue was purified by MPLC over silica gel (eluting with a gradient of MeOH in DCM) to give intermediate M. LC/MS: [M+H]$^+$=814.2.

Preparation of Intermediate N

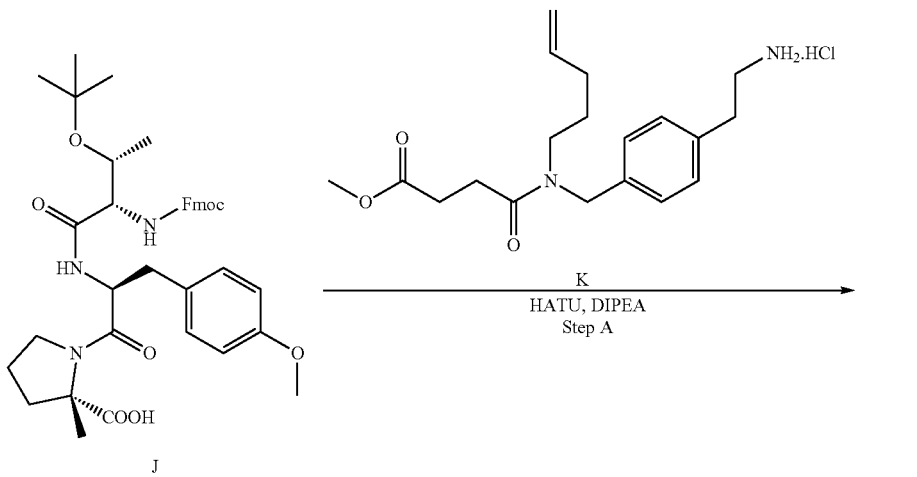

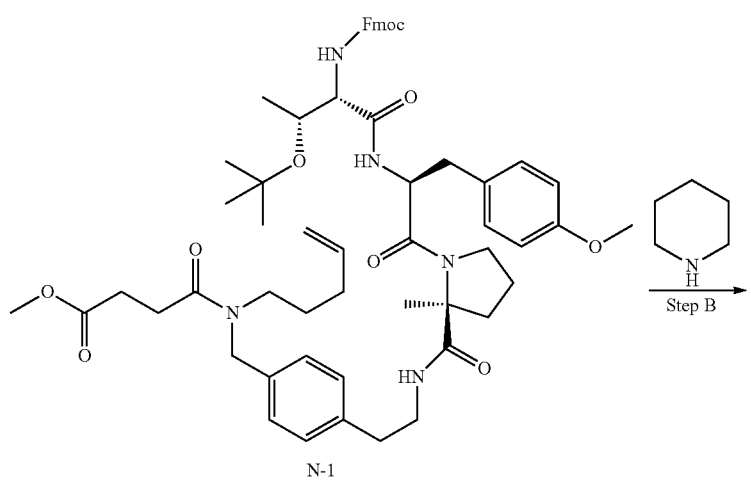

-continued
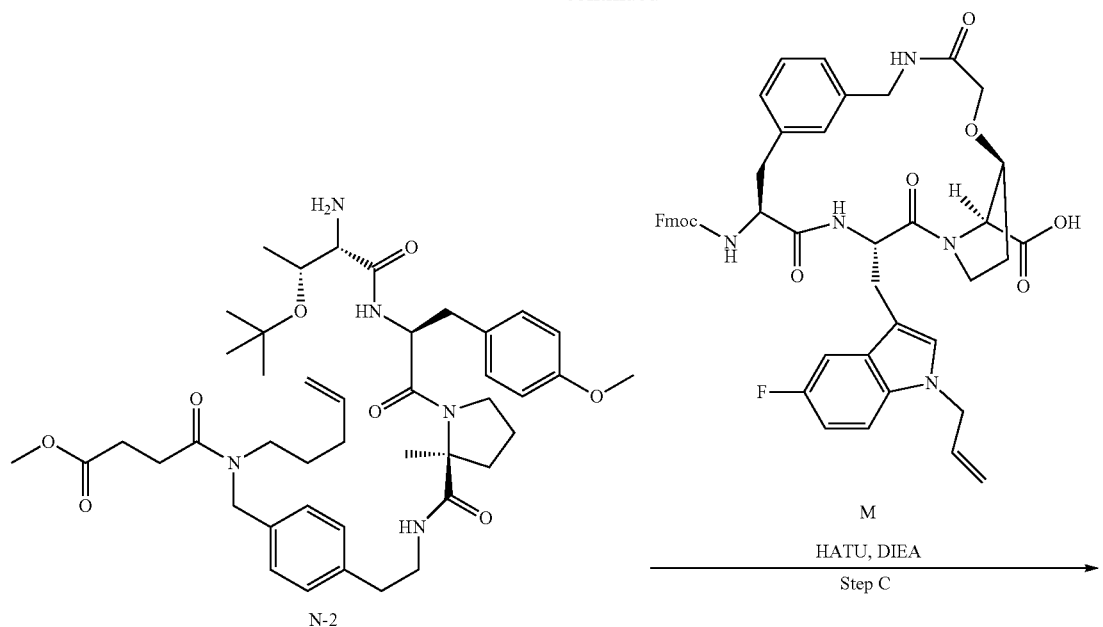
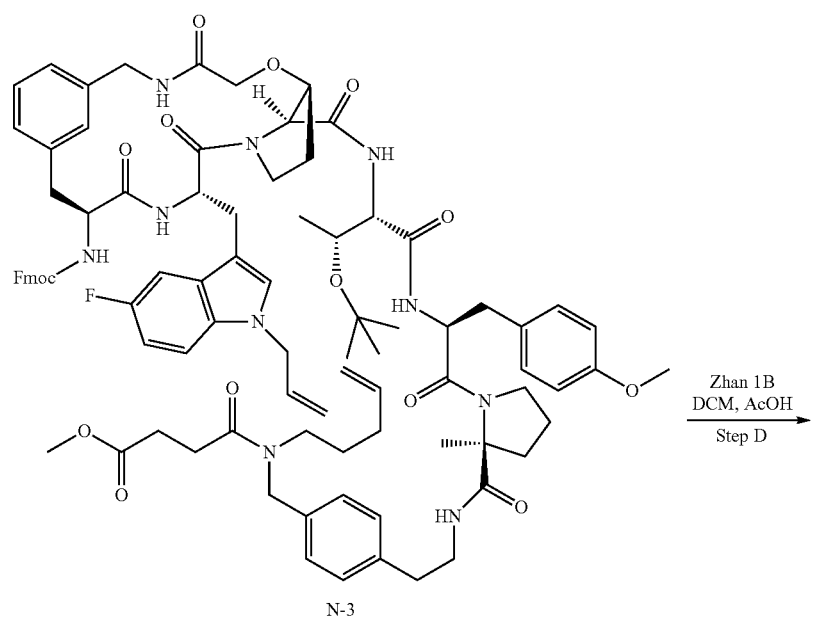

197
-continued
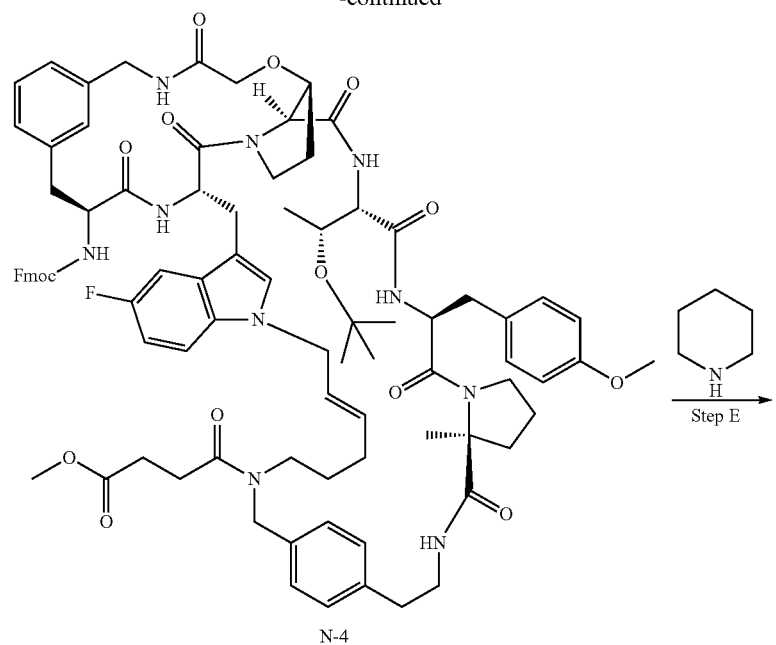
198
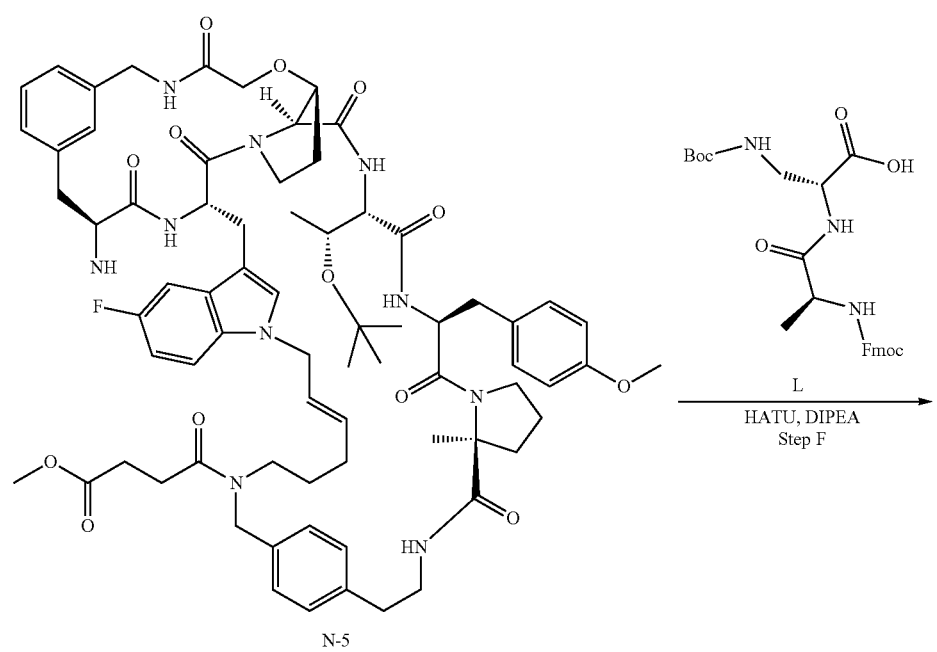

-continued
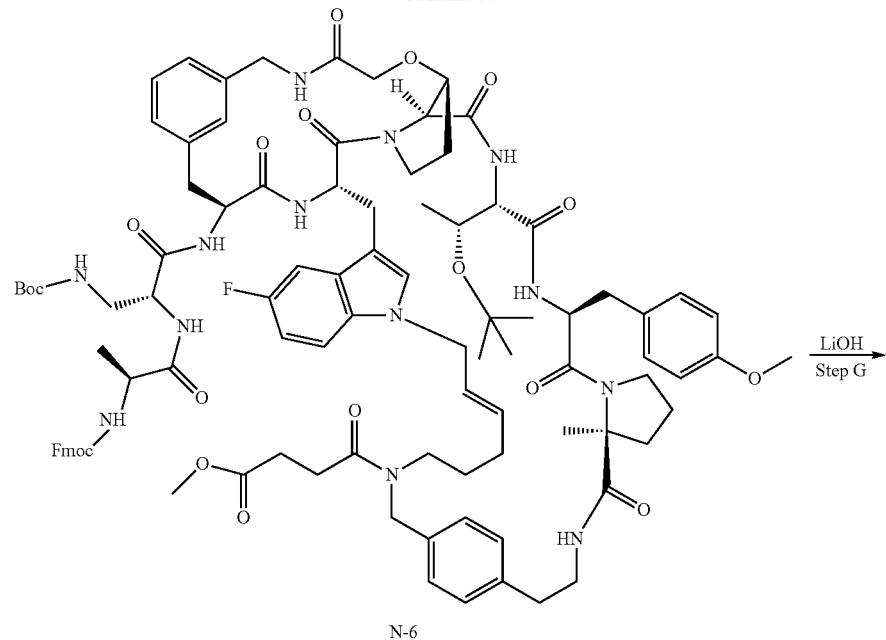
N-6
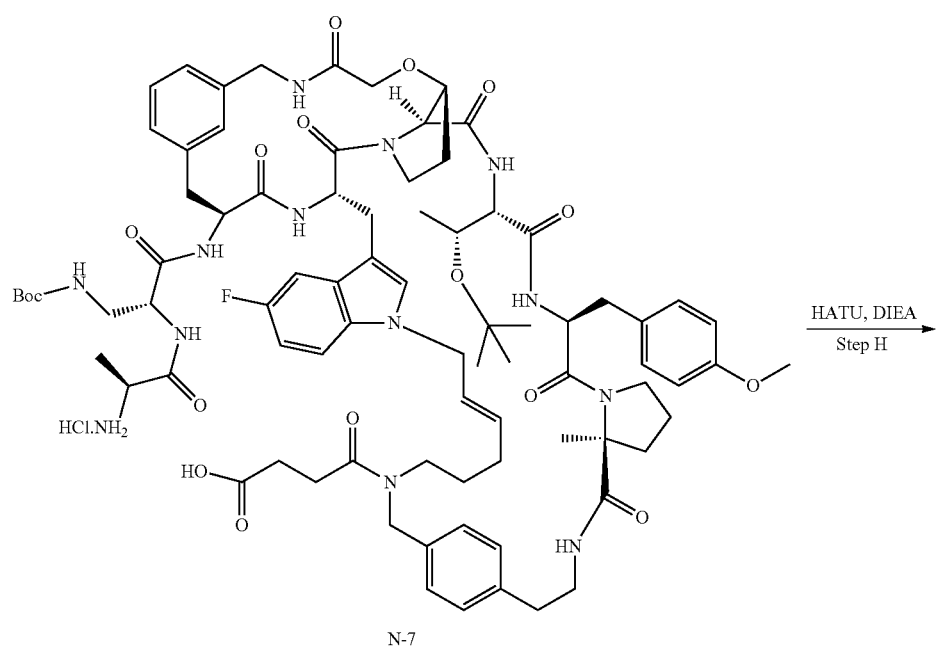
N-7

-continued
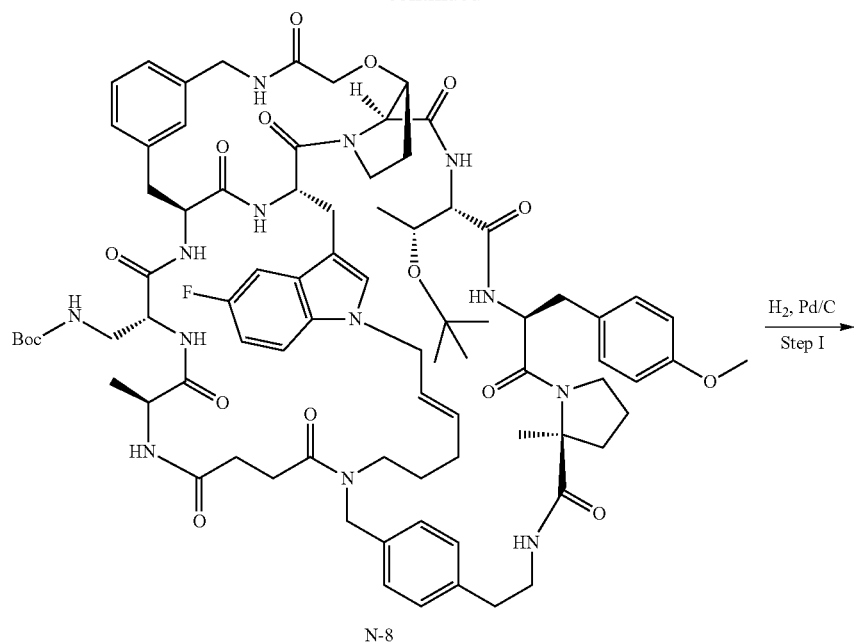
N-8
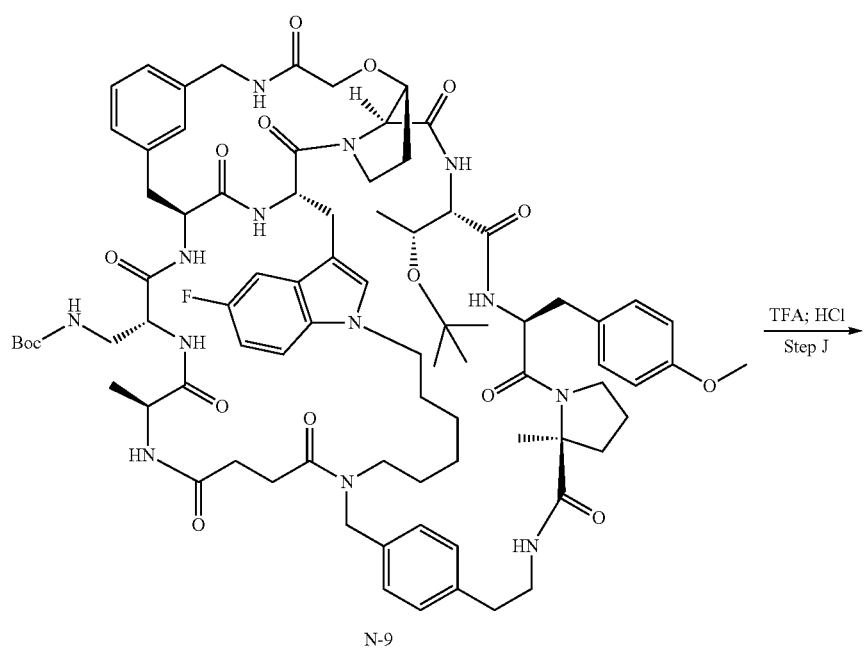
N-9

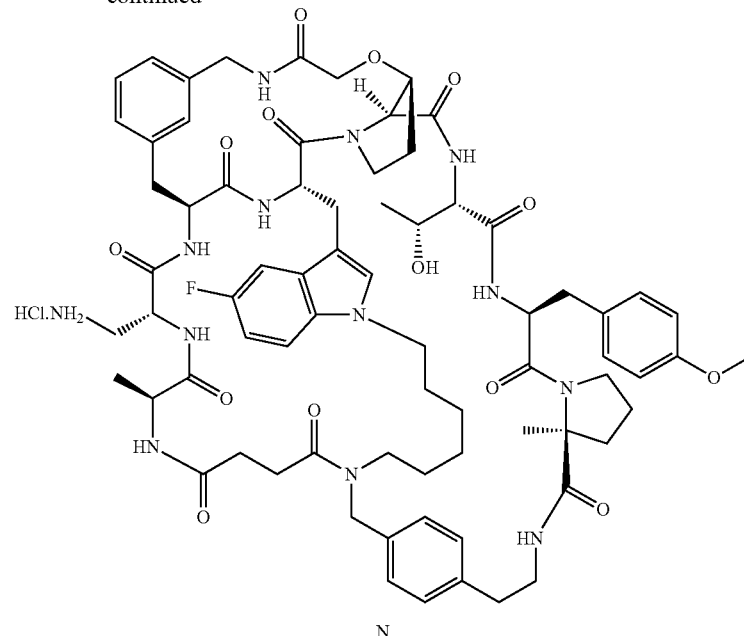

Step A—Synthesis of Intermediate N-1

To a solution of intermediate J (7.09 g, 10.33 mmol) in DMF (45 ml) at 0° C. were added intermediate K (3.63 g, 9.84 mmol) and HATU (3.74 g, 9.84 mmol)) followed by DIPEA (6.87 ml, 39.4 mmol) and the mixture was allowed to warm to RT and stirred for 1 h. The final mixture was quenched at 0° C. with brine and extracted with EtOAc. The combined organic fractions were washed with brine, dried over $MgSO_4$, filtered and concentrated in vacuo. The residue was purified by MPLC over silica gel (eluting with a gradient of 1%-80% EtOAc in PE) to give N-1. LC/MS: $[M+H]^+=1000.5$.

Step B—Synthesis of Intermediate N-2

To a solution of N-1 (3.48 g, 3.48 mmol) in acetonitrile (50 ml) was added piperidine (1.72 ml, 17.40 mmol), and the resulting solution was stirred at RT for 3 h. The mixture was concentrated, the residue was re-dissolved in DCM:acetonitrile 1:1 (20 mL), concentrated again and the residue was dried under vacuum to give N-2. LC/MS: $[M+H]^+=778.5$.

Step C—Synthesis of Intermediate N-3

To a solution of intermediate M (2.45 g, 3.01 mmol) and N-2 (2.69 g, 3.46 mmol) in DMF (70 ml) at 0° C. was added HATU (1.37 g, 3.61 mmol) followed by DIEA (1.05 ml, 6.02 mmol) then the resulting solution was stirred at RT for 50 min. The final mixture was partitioned between EtOAc (500 mL) and brine (200 mL). The organic phase was washed with brine (2×200 mL), dried over $Na_2SO_4$, filtered and concentrated and the residue was purified by MPLC over silica gel (eluting with a gradient of 1%-5% MeOH in DCM) to give N-3. LC/MS: $[M+H]^+=1574.7$.

Step D—Synthesis of Intermediate N-4

A solution of N-3 (1.91 g, 1.21 mmol) in DCM (1500 ml) and acetic acid (30 mL) at RT was bubbled with nitrogen for 30 min followed by addition of Zhan's catalyst-1B (0.445 g, 0.607 mmol). The resulting mixture was further bubbled at RT with nitrogen for 30 min, then heated at 55° C. for 5 h. After cooling to RT, the mixture was filtered over Celite, the filtrate was concentrated, and the residue was purified by MPLC over silica gel (eluting with a gradient of 1%-5% MeOH in DCM) to give N-4 (as a mixture of cis and trans olefins). LC/MS: $[M+H]^+=1546.8$.

Step E—Synthesis of Intermediate N-5

To a solution of N-4 (as a mixture of cis and trans olefins) (5.49 g, 3.55 mmol) in DCM (20 ml) and acetonitrile (50 ml) was added piperidine (1.76 ml, 17.8 mmol). The resulting solution was stirred at RT for 2 h, then concentrated and the residue was suspended in acetonitrile (20 ml) and concentrated again. The residue was then dried under vacuum to give N-5 (as a mixture of cis and trans olefins). LC/MS: $[M+H]^+=1323.8$.

Step F—Synthesis of Intermediate N-6

To a solution of N-5 (as a mixture of cis and trans olefins) (4.70 g, 3.55 mmol) and intermediate L (2.21 g, 4.44 mmol) in DMF (70 ml) at 0° C. were added HATU (1.76 g, 4.62 mmol) and DIEA (1.55 ml, 8.88 mmol). The resulting solution was warmed to RT and stirred for 1 h, then partitioned between EtOAc (300 mL) and brine (200 mL). The aqueous phase was extracted with EtOAc (200 mL), and the combined organic layers were washed with brine, dried over $Na_2SO_4$, filtered and concentrated. The residue was purified by MPLC over silica gel (eluting with a gradient of 1%-5% MeOH in DCM) to give N-6 (as a mixture of cis and trans olefins). LC/MS: $[M+H]^+=1802.8$.

Step G—Synthesis of Intermediate N-7

To a solution of N-6 (as a mixture of cis and trans olefins) (5.41 g, 3.00 mmol) in THF (100 ml), MeOH (30 ml), and water (30 ml) at 0° C. was added 1 N aqueous LiOH (24.0 ml, 24.0 mmol) dropwise, and the resulting solution was stirred at 0° C. for 3 h. The mixture was neutralized at 0° C. by addition of 1N aqueous HCl, the reaction was concentrated, and the aqueous layer was further brought to pH 5 by addition of 1 N aqueous HCl. The mixture was then frozen and lyophilized, and the residue was purified by reverse phase MPLC over C18 (eluting with a gradient of acetonitrile (0.05% TFA) in water (0.05% TFA)) to give N-7 (as a mixture of cis and trans olefins) as a TFA salt. To the N-7 TFA salt thus obtained (as a mixture of cis and trans olefins) in acetonitrile (750 mL) and water (450 mL) at 0° C. was added 0.1N aqueous HCl (150 ml, 15.00 mmol) dropwise. The resulting solution was stirred at 0° C. for 5 min, frozen and lyophilized to N-7 as a HCl salt (as a mixture of cis and trans olefins). LC/MS: [M+H]$^+$=1566.6.

Step H—Synthesis of Intermediate N-8

To a solution of N-7 HCl salt (as a mixture of cis and trans olefins) (1.01 g, 0.630 mmol) in DMF (50 ml) and DCM (1300 ml) were added DIEA (0.330 ml, 1.890 mmol) and HATU (0.287 g, 0.756 mmol) and the resulting solution was stirred at RT for 2 h. The mixture was concentrated, and the residue was partitioned between EtOAc (400 mL) and brine (200 mL). The aqueous phase was extracted with EtOAc (300 mL), the combined organic layers were washed with brine (3×100 mL), dried over Na$_2$SO$_4$, filtered and concentrated. The residue was purified by MPLC over silica gel (eluting with a gradient of 1%-10% MeOH in DCM) to give N-8 (as a mixture of cis and trans olefins). LC/MS: [M+H]$^+$=1548.8.

Step I—Synthesis of Intermediate N-9

To a solution of N-8 (as a mixture of cis and trans olefins) (1.22 g, 0.788 mmol) in MeOH (100 ml) was added 10% Pd/C (0.645 g, 0.607 mmol), and the resulting mixture was hydrogenated at RT using a balloon filled with hydrogen for 7 h. The reaction mixture was filtered over Celite, the filtrate was concentrated, and the residue was purified by MPLC over silica gel (eluting with a gradient of 1%-10% MeOH in DCM) to give N-9. LC/MS: [M+H]$^+$=1550.9.

Step J—Synthesis of Intermediate N

To a solution of N-9 (1.14 g, 0.735 mmol) in DCM (6 ml) at RT was added TFA (12 ml, 156 mmol) and the resulting solution was stirred for 30 min. The mixture was concentrated, the residue was re-dissolved in DCM (20 mL) and toluene (20 mL) and concentrated. The residue was re-dissolved in DCM (20 mL), treated with 4N HCl in dioxane (0.919 ml, 3.68 mmol) and the resulting mixture was concentrated. The resulting solid was re-dissolved in acetonitrile (200 mL) and water (100 mL) and treated at 0° C. with 1N aqueous HCl (3.68 ml, 3.68 mmol) dropwise. The resulting solution was stirred at 0° C. for 2 min, then frozen and lyophilized to give intermediate N as HCl salt. LC/MS: [M+H]$^+$=1394.7.

Preparation of Intermediate O

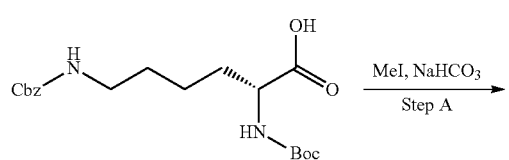

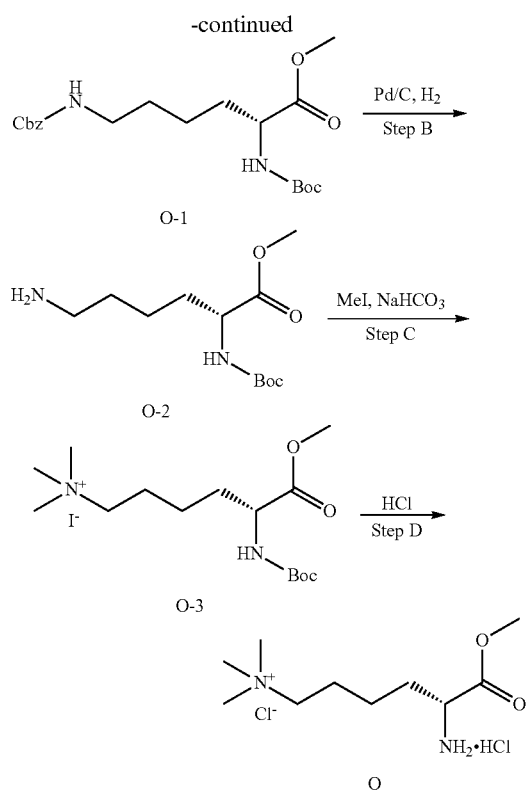

Step A—Synthesis of Intermediate O-1

To a solution of (R)-6-(((benzyloxy)carbonyl)amino)-2-((tert-butoxycarbonyl)amino)hexanoic acid (5 g, 13.14 mmol) in DMF (50 mL) at RT were added NaHCO$_3$ (5.52 g, 65.7 mmol) and MeI (4.11 mL, 65.7 mmol) and the solution was stirred for 24 h. The reaction was quenched with water, extracted with EtOAc and the combined organic layers were washed with brine, dried over anhydrous Na$_2$SO$_4$, filtered and concentrated. The residue was purified by MPLC over silica gel (eluting with a gradient of 0%-50% EtOAc in PE) to provide O-1. LC/MS: [M+Na]$^+$=417.2.

Step B—Synthesis of Intermediate O-2

To a solution of O-1 (5 g, 12.68 mmol) in THF (80 mL) was added 10% Pd/C (1.5 g, 1.268 mmol), and the resulting mixture was hydrogenated at RT using a balloon filled with hydrogen for 6 h. The resulting mixture was filtered and the filtrate was concentrated under reduced pressure to afford O-2. LC/MS: [M+H]$^+$=261.2.

Step C—Synthesis of Intermediate O-3

To a solution of O-2 (3.2 g, 12.29 mmol) in MeOH (80 mL) at RT were added NaHCO$_3$ (5.16 g, 61.5 mmol) and MeI (7.69 mL, 123 mmol) and the solution was stirred for 14 h. The resulting mixture was filtered, the filtrate was concentrated under reduced pressure and the residue was purified by MPLC over silica gel (eluting with a gradient of 0%-13% MeOH in DCM) to give O-3. LC/MS: [M]$^+$=303.2. $^1$H NMR (300 MHz, CD$_3$OD): δ 4.14 (dd, J=9.0, 5.1 Hz, 1H), 3.72 (s, 3H), 3.44-3.34 (m, 2H), 3.15 (s, 9H), 1.98-1.64 (m, 5H), 1.55-1.47 (m, 1H), 1.44 (s, 9H).

Step D—Synthesis of Intermediate O

To a solution of O-3 (1.1 g, 2.56 mmol) in DCM (5 mL) at RT was added 4 M HCl in dioxane (20 mL) and the reaction mixture was stirred for 2 h. The final solution was concentrated under reduced pressure to afford intermediate O. LC/MS: $[M]^+$=203.2.

Preparation of Intermediate P

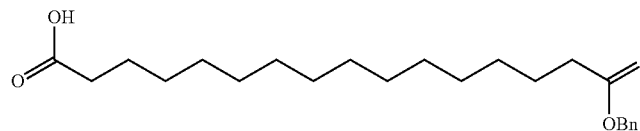 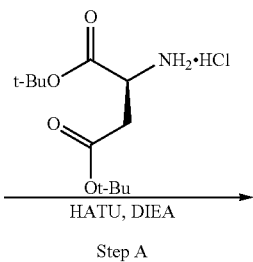

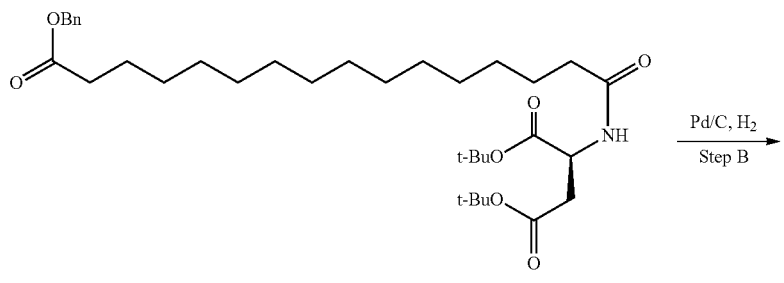

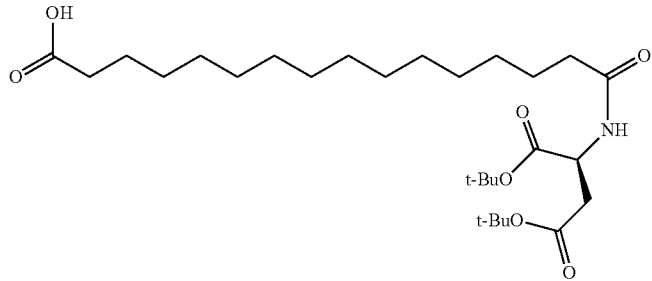

Step A—Synthesis of Intermediate P-1

To a solution of 16-(benzyloxy)-16-oxohexadecanoic acid (1.1 g, 2.92 mmol) in DMF (12 mL) at 0° C. were added (S)-di-tert-butyl 2-aminosuccinate hydrochloride (0.91 g, 3.21 mmol), HATU (1.22 g, 3.21 mmol) and DIEA (2.55 mL, 14.61 mmol) and the reaction mixture was stirred at 0° C. for 1 h. The resulting solution was quenched with water (2 mL) and purified by reverse phase MPLC over C18 (eluting with a gradient of acetonitrile in water (0.05% TFA)) to afford P-1. LC/MS: $[M+H]^+$=604.5.

Step B—Synthesis of Intermediate P

To a solution of P-1 (650 mg, 1.08 mmol) in EtOH (18 mL) at RT was added 10% Pd/C (115 mg, 0.108 mmol), and the resulting mixture was hydrogenated at RT using a balloon filled with hydrogen for 2 h. The final mixture was filtered, the filtrate was concentrated under reduced pressure and the residue was purified by reverse phase MPLC over C18 (eluting with a gradient of acetonitrile in water (0.05% TFA)) to give intermediate P. LC/MS: $[M+H]^+$=514.3. $^1$H NMR (300 MHz, CD$_3$OD): δ 4.62 (dd, J=7.2, 5.4 Hz, 1H), 2.82-2.57 (m, 2H), 2.32-2.18 (m, 4H), 1.66-1.55 (m, 4H), 1.48 (s, 9H), 1.46 (s, 9H), 1.36-1.21 (m, 20H).

Using the synthetic schemes and intermediates described above and, as will be appreciated, in some instances with appropriate substitution of certain intermediates with different spacers apparent to those skilled in the art, the following intermediates were prepared.

TABLE 2

Additional Intermediates of the Invention.

| Intermediate | Structure | LC/MS Observed [M + H]+ |
|---|---|---|
| Q | 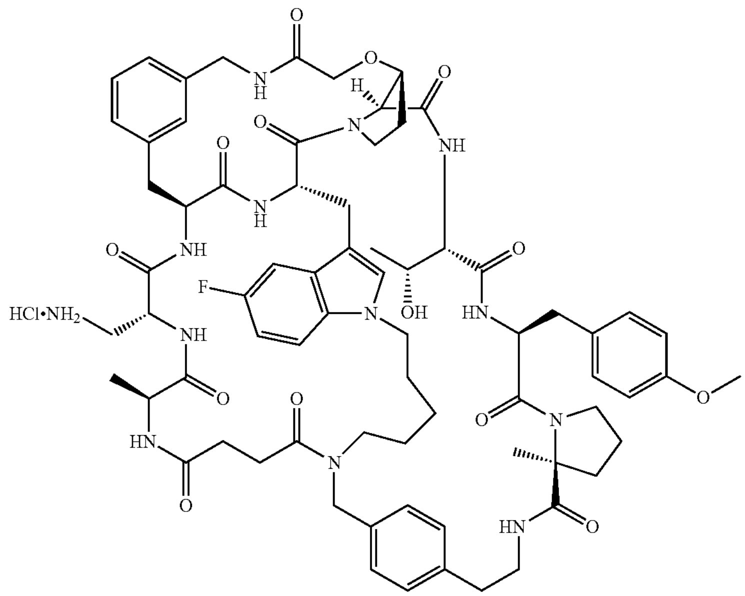 | 1381.5 |
| R | 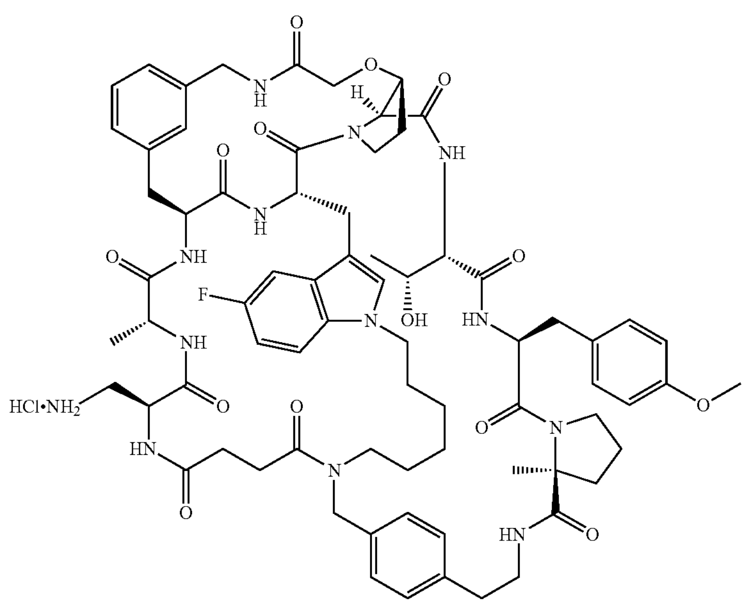 | 1394.4 |

Preparation of Intermediate S
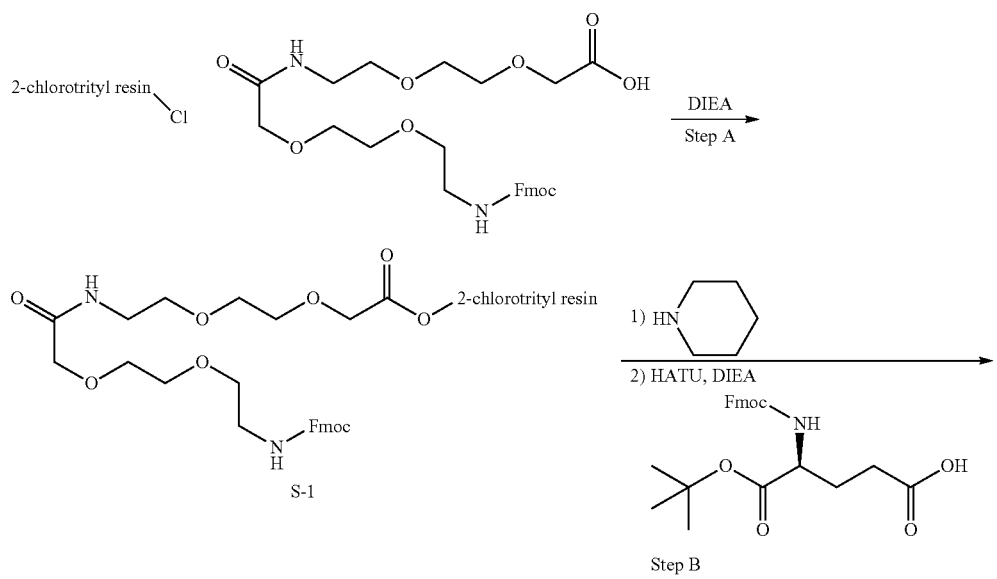
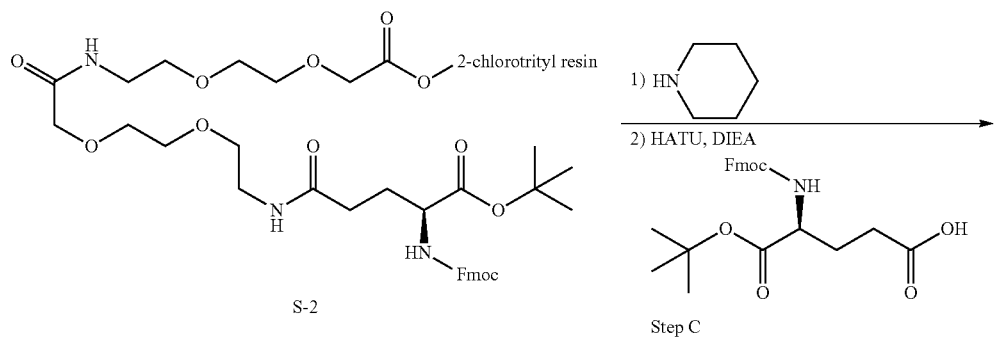
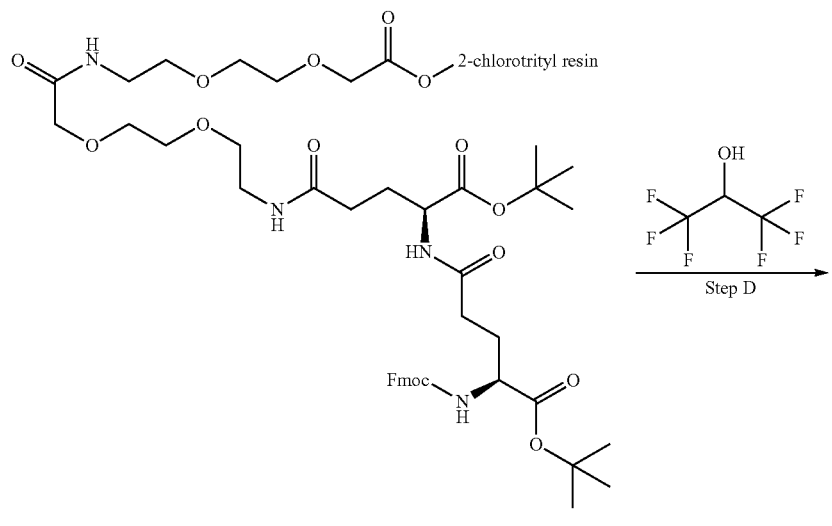

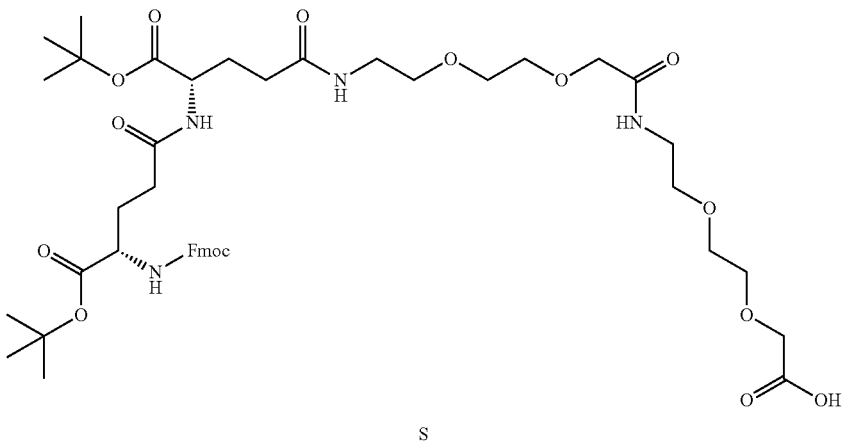

S

Step A—Synthesis of Intermediate S-1

To 2-chlorotrityl chloride resin (0.5 g, about 1 mmol/g loading) was added dry DCM (3 mL) and the resin was allowed to stand at RT for 20 min. A solution of 17-(9-fluorenylmethyloxycarbonyl-amino)-9-aza-3,6,12,15-tetraoxa-10-on-heptadecanoic acid, CAS 560088-89-3 (332 mg, 0.625 mmol) and DIPEA (0.109 mL, 0.625 mmol) in DCM (1.5 mL) was added slowly, followed by more DIPEA (0.25 mL). The resin was shaken at RT for 2 h then filtered and rinsed with DCM three times. The resin was then quenched with 5% DIPEA and 10% MeOH in DCM (5 mL) and shaken for 2 h at RT. The resin was filtered, rinsed with DCM three times, DMF three times, DCM three times then dried under vacuum to give resin S-1 which was used as is in the next step.

Step B—Synthesis of Intermediate S-2

Resin S-1, from step A, was treated with 20% piperidine in DMF (4 mL), shaken for 30 min at RT, filtered and rinsed with DMF three times, DCM three times, and DMF three times. The resin was then treated with a solution of Fmoc-L-Glu-OtBu (0.851 g, 2.00 mmol), HATU (0.760 g, 2.00 mmol) and DIPEA (0.699 mL, 4.00 mmol) in DMF (5 mL) and shaken for 75 min at RT. The resin was filtered and rinsed with DMF three times, DCM three times, and DMF three times to afford resin S-2 which was used as is in the next step.

Step C—Synthesis of Intermediate S-3

Resin S-2, from Step B, was treated with 20% piperidine in DMF (4 mL), shaken for 30 min at RT, filtered and rinsed with DMF three times, DCM three times, and DMF three times. The resin was then treated with a solution of Fmoc-L-Glu-OtBu (0.851 g, 2.00 mmol), HATU (0.760 g, 2.00 mmol) and DIPEA (0.699 mL, 4.00 mmol) in DMF (5 mL) and shaken for 75 min at RT. The resin was filtered and rinsed with DMF three times, DCM three times, DMF three times, and DCM three times to afford resin S-3 which was used as is in the next step.

Step D—Synthesis of Intermediate S

Resin S-3, from Step C, was treated with 25% hexafluoroisopropanol in DCM (5 mL), shaken for 75 min at RT then filtered. The filtrate was concentrated under vacuum to provide intermediate S. LC/MS: $[M+H]^+=901.0$. $^1$H NMR (400 MHz, DMSO-$d_6$): δ 8.14 (m, 1H), 7.90 (m, 2H), 7.70-7.75 (m, 2H), 7.64 (m, 1H), 7.40-7.45 (m, 2H), 7.30-7.35 (m, 2H), 4.32 (m, 1H), 4.20-4.28 (m, 2H), 4.05 (m, 1H), 3.99 (s, 2H), 3.90 (m, 1H), 3.98 (s, 2H), 3.50-3.60 (m, 6H), 3.37-3.45 (m, 4H), 3.24-3.35 (m, 6H), 3.17-3.22 (m, 2H), 2.22 (m, 2H), 2.15 (m, 2H), 1.85-1.98 (m, 2H), 1.70-1.82 (m, 2H), 1.39 (s, 18H).

Preparation of Intermediate T

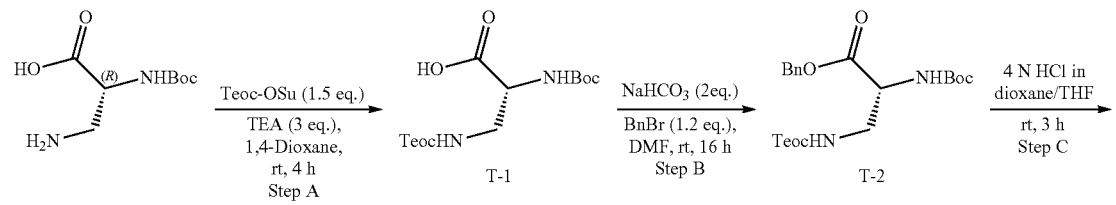

-continued
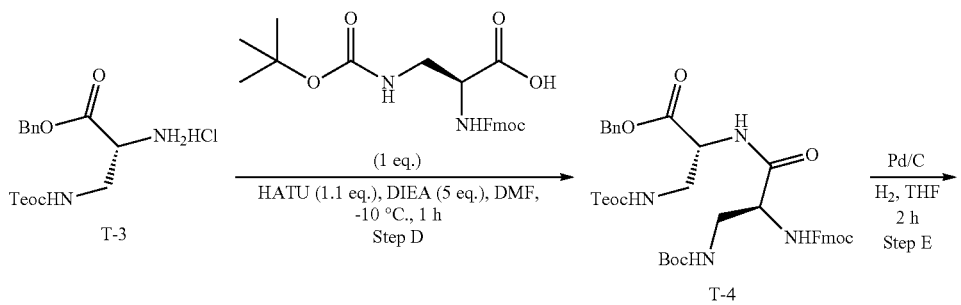
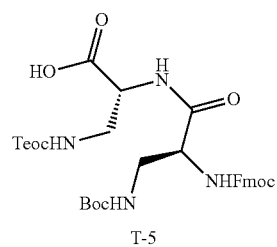
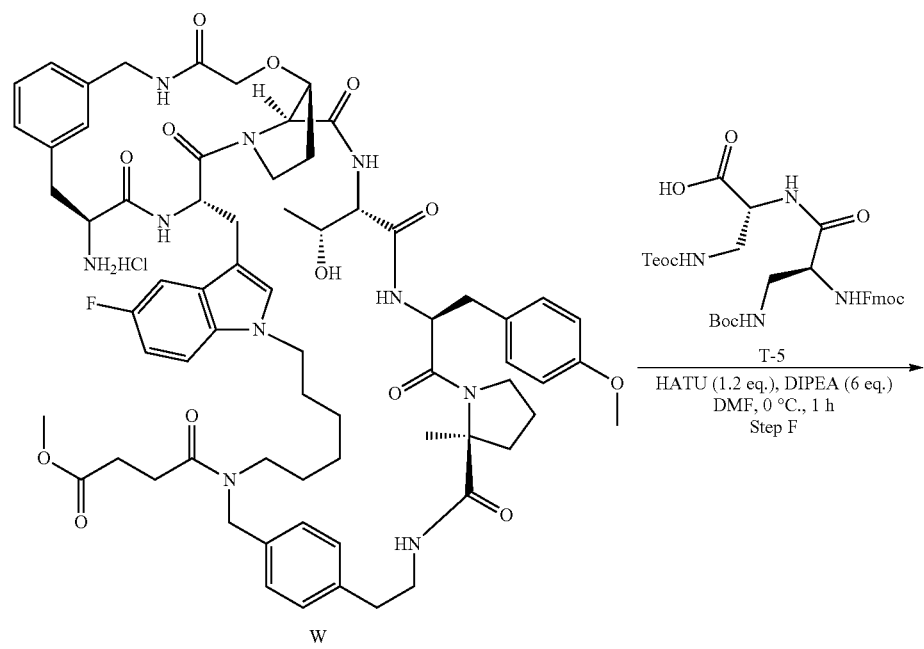

-continued
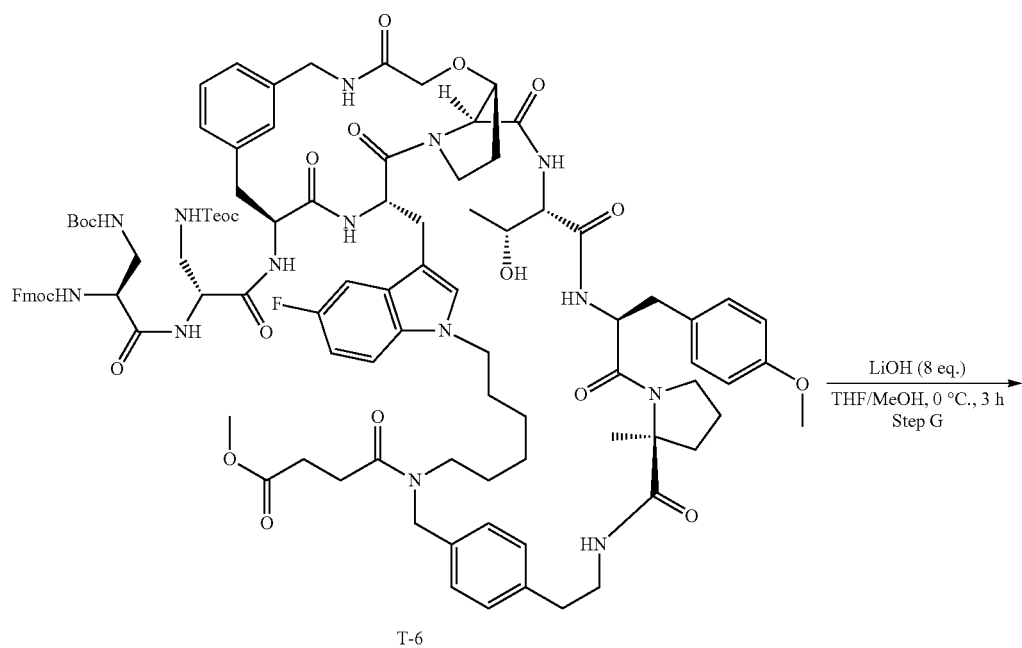
T-6
LiOH (8 eq.)
THF/MeOH, 0 °C., 3 h
Step G
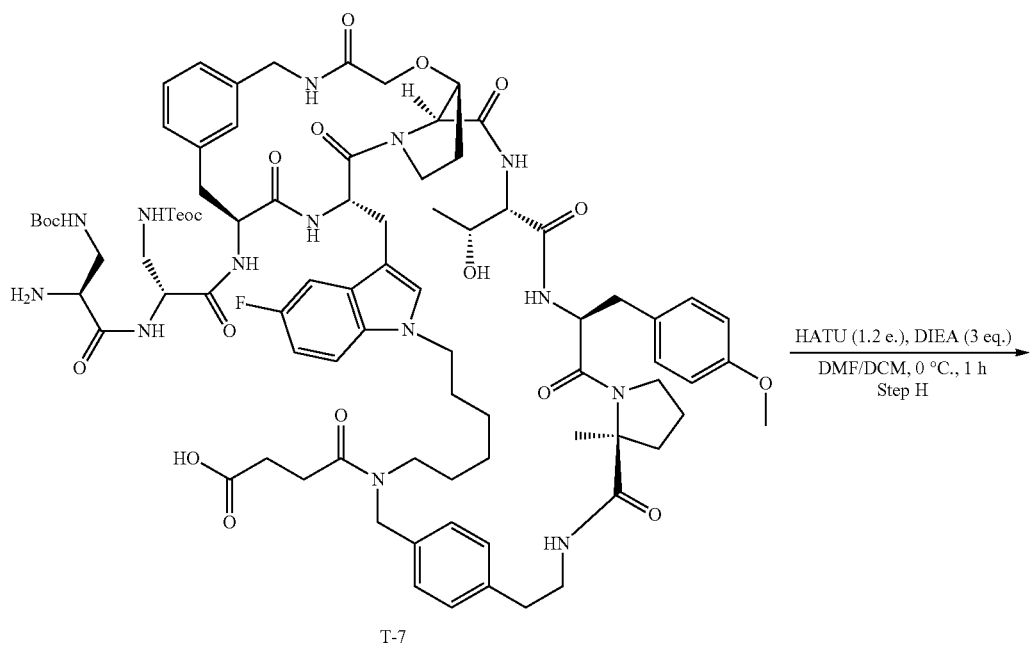
T-7
HATU (1.2 e.), DIEA (3 eq.)
DMF/DCM, 0 °C., 1 h
Step H -continued
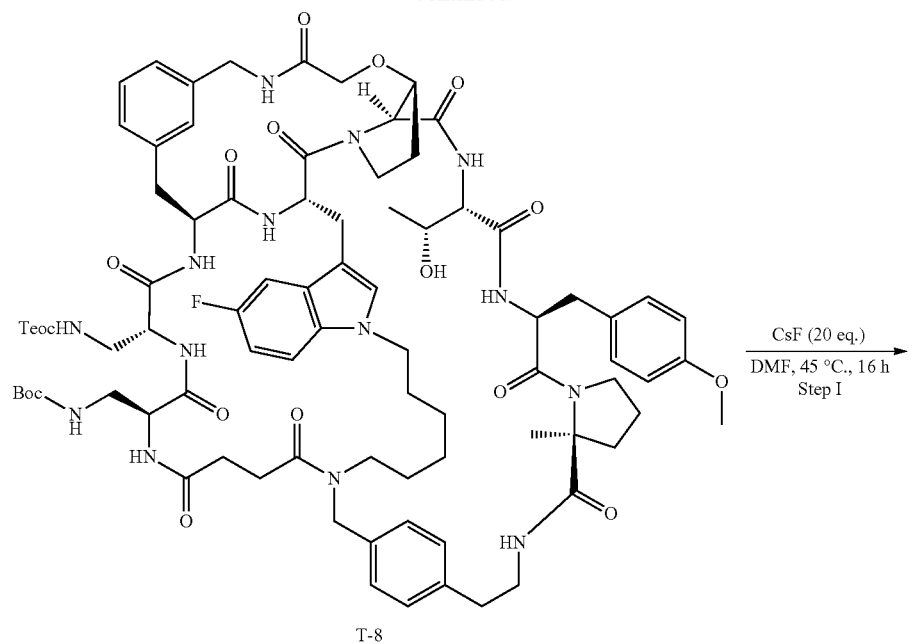
T-8
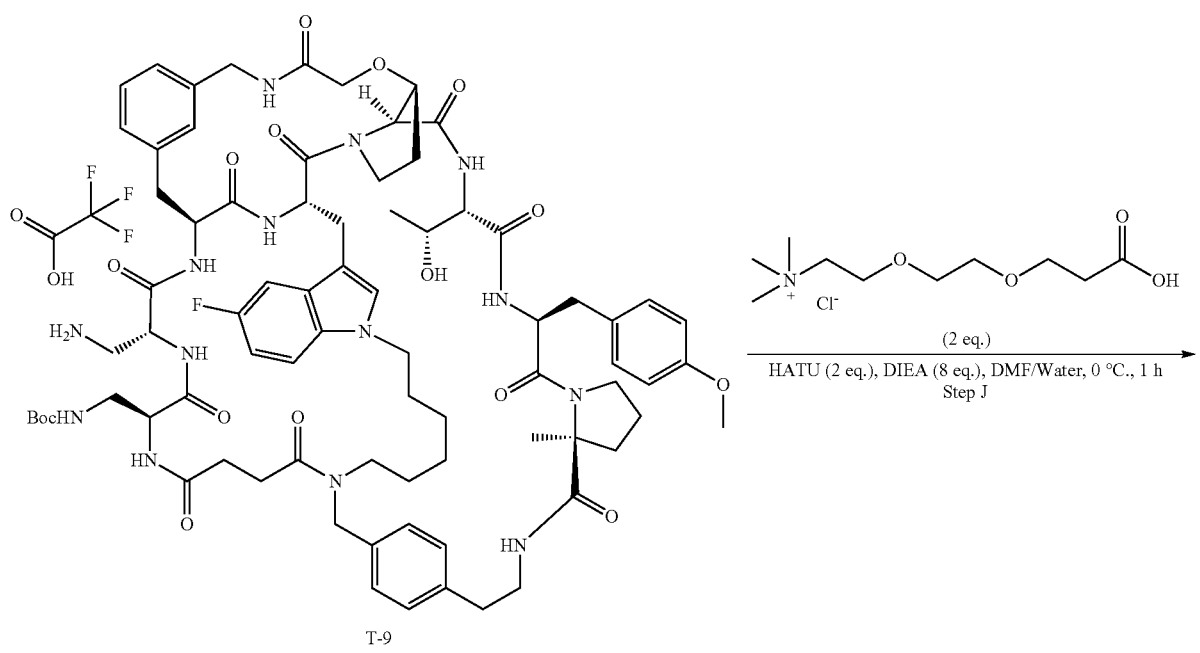
T-9

-continued
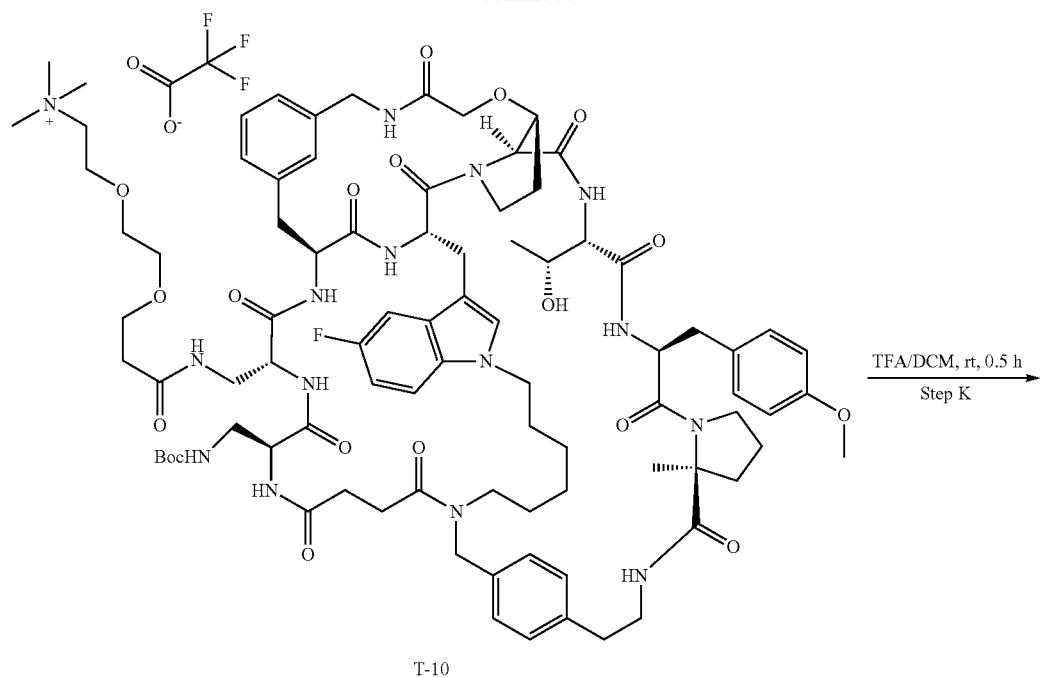
T-10
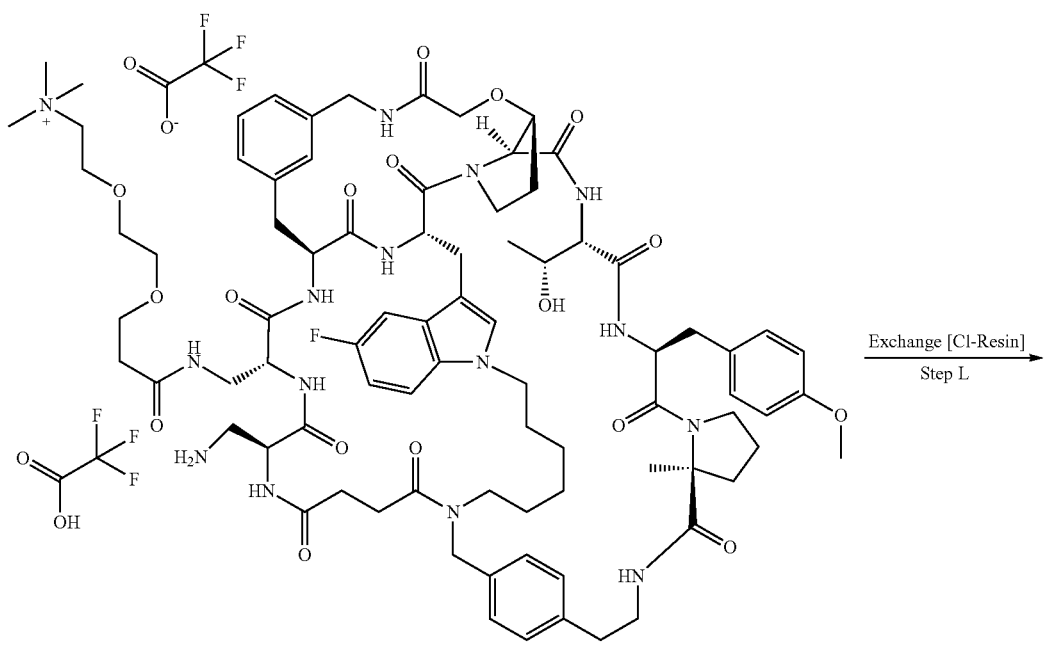
T-11

-continued

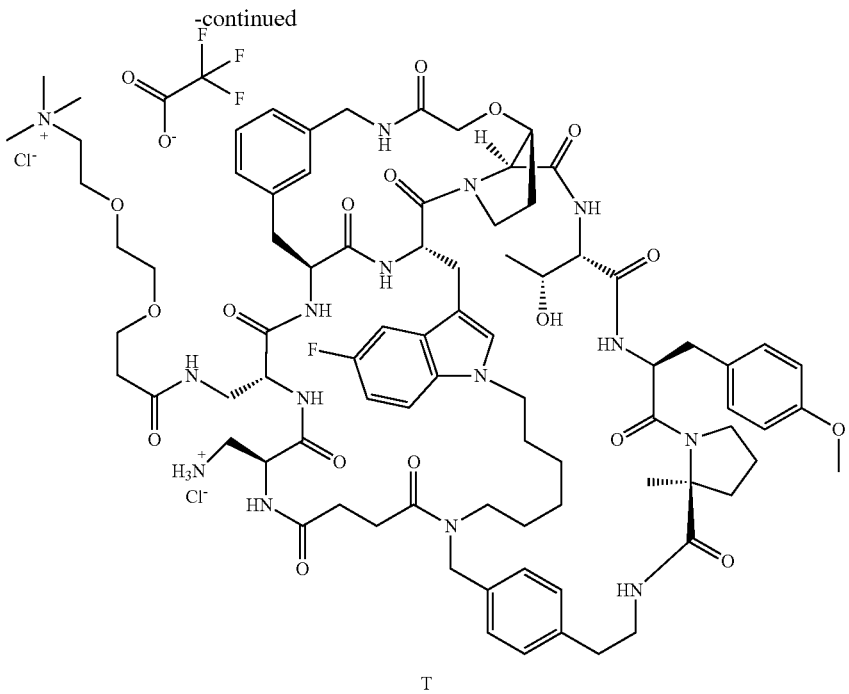

T

Step A—Synthesis of (R)-2-((tert-butoxycarbonyl)amino)-3-(((2-(trimethylsilyl)ethoxy)carbonyl)amino)propanoic acid T-1

To a solution of (R)-3-amino-2-((tert-butoxycarbonyl)amino)propanoic acid (800 mg, 3.92 mmol) in 1,4-dioxane (20 mL) were added Teoc-OSu (1.52 g, 5.88 mmol) and TEA (1.2 g, 11.75 mmol) at room temperature. The reaction solution was stirred at room temperature for 4 h. The resulting solution was concentrated under reduced pressure. The residue was purified by silica gel column chromatography, eluted with a gradient of 0%-10% MeOH in DCM. The fractions containing the desired product were combined and concentrated under reduced pressure to afford (R)-2-((tert-butoxycarbonyl)amino)-3-(((2-(trimethylsilyl)ethoxy)carbonyl)amino) propanoic acid T-1. LCMS (ESI) calc'd for $C_{14}H_{28}N_2O_6Si$ [M+Na]$^+$: 371.2, found 371.2.

Step B—Synthesis of (R)-benzyl 2-((tert-butoxycarbonyl)amino)-3-(((2-(trimethylsilyl)ethoxy)carbonyl)amino)propanoate T-2

To a stirred solution of (R)-2-((tert-butoxycarbonyl)amino)-3-(((2-(trimethylsilyl)ethoxy)carbonyl)amino)propanoic acid T-1 (1.20 g, 3.44 mmol) in DMF (15 mL) were added NaHCO$_3$ (0.579 g, 6.89 mmol) and BnBr (0.707 g, 4.13 mmol) at room temperature.

The solution was stirred at room temperature for 16 h. The resulting solution was diluted with H$_2$O (100 mL) and extracted with EA (2×100 mL). The combined organic layer was washed with brine (3×100 mL), dried over anhydrous Na$_2$SO$_4$ and filtered. The filtrate was concentrated under reduced pressure. The residue was purified by silica gel column chromatography, eluted with a gradient of 0%-30% EA in PE. The fractions containing the desired product were combined and concentrated under reduced pressure to afford (R)-benzyl 2-((tert-butoxycarbonyl)amino)-3-(((2-(trimethylsilyl)ethoxy)carbonyl)amino)propanoate T-2. LCMS (ESI) calc'd for $C_{21}H_{34}N_2O_6Si$ [M+H]$^+$: 439.2, found 439.3. $^1$H NMR (300 MHz, CDCl$_3$) δ 7.42-7.35 (m, 5H), 5.49 (br, 1H), 5.21 (s, 2H), 4.89 (s, 1H), 4.41 (s, 1H), 4.21-4.09 (m, 2H), 3.64-3.57 (m, 2H), 1.46 (s, 9H), 1.04-0.92 (m, 2H), 0.05 (s, 9H).

Step C—Synthesis of (R)-benzyl 2-amino-3-(((2-(trimethylsilyl)ethoxy)carbonyl)amino)propanoate hydrochloride T-3

To a stirred solution of (R)-benzyl 2-((tert-butoxycarbonyl)amino)-3-(((2-(trimethylsilyl)ethoxy)carbonyl)amino)propanoate T-2 (800 mg, 1.824 mmol) in THF (8 mL) was added 4 N HCl in 1,4-dioxane (8 mL) at room temperature. The reaction mixture was stirred at room temperature for 3 h. The resulting solution was concentrated under reduced pressure to afford (R)-benzyl 2-amino-3-(((2-(trimethylsilyl)ethoxy)carbonyl)amino) propanoate hydrochloride T-3. LCMS (ESI) calc'd for $C_{16}H_{27}ClN_2O_4Si$ [M−HCl+H]$^+$: 339.2, found 339.2.

Step D—Synthesis of (R)-benzyl 2-((S)-2-((((9H tert-butoxycarbonyl)amino)propanamido)-3-(((2-(trimethylsilyl)ethoxy)carbonyl)amino)propanoate T-4

To a stirred solution of (S)-2-(((((9H-fluoren-9-yl)methoxy)carbonyl)amino)-3-((tert-butoxycarbonyl)amino) propanoic acid T-3 (796 mg, 1.87 mmol) in DMF (10 mL) were added HATU (781 mg, 2.05 mmol), (R)-benzyl 2-amino-3-(((2-(trimethylsilyl)ethoxy)carbonyl)amino)propanoate hydrochloride (700 mg, 1.87 mmol) and DIEA (1.63 mL, 9.33 mmol) at −10° C. under nitrogen atmosphere. The reaction solution was stirred at −10° C. for 1 h. The reaction was quenched with water (100 mL), extracted with EA (3×100 mL). The combined organic layer was washed with brine (3×100 mL), dried over anhydrous Na$_2$SO$_4$ and filtered. The crude mixture was purified by silica gel column chromatography, eluted with a gradient of 0%-50% EA in PE, to afford (R)-benzyl 2-((S)-2-((((9H-fluoren-9-yl)methoxy)carbonyl)amino)-3-((tert-butoxycarbonyl)amino)propanamido)-3-(((2-(trimethylsilyl)ethoxy)carbonyl)amino)propanoate T-4. LCMS (ESI) calc'd for $C_{39}H_{50}N_4O_9Si$ [M+H]$^+$: 747.3, found 747.3. $^1$H NMR (400 MHz, CD$_3$OD) δ 7.84 (d, J=7.5 Hz, 2H), 7.70 (d, J=7.5 Hz, 2H), 7.48-7.28 (m, 9H), 5.25-5.09 (m, 2H), 4.62-4.53 (m, 1H), 4.41-4.21 (m, 4H), 4.08 (t, J=8.4 Hz, 2H), 3.65-3.35 (m, 4H), 1.45 (s, 9H), 0.93 (t, J=8.6 Hz, 2H), 0.02 (s, 9H).

Step E—Synthesis of (R)-2-((S)-2-((((9H-fluoren-9-yl)methoxy)carbonyl)amino)-3-((tert-butoxycarbonyl)amino)propanamido)-3-(((2-(trimethylsilyl)ethoxy)carbonyl)amino)propanoic acid T-5

To a solution of (R)-benzyl 2-((S)-2-((((9H-fluoren-9-yl)methoxy)carbonyl)amino)-3-((tert-butoxycarbonyl)amino)propanamido)-3-(((2-(trimethylsilyl)ethoxy)carbonyl)amino)propanoate T-4 (900 mg, 1.205 mmol) in THF (30 mL) was added 10% Pd/C (128 mg, 0.12 mmol, dry, 10% wt) at room temperature under nitrogen atmosphere. The reaction mixture was degassed with hydrogen for three times and stirred at room temperature for 2 h. The resulting mixture was filtered and the filtrate was concentrated under reduced pressure to afford (R)-2-((S)-2-((((9H-fluorenyl)methoxy)carbonyl)amino)-3-((tert-butoxycarbonyl)amino)propanamido)-3-(((2-(trimethylsilyl)ethoxy)carbonyl)amino)propanoic acid T-5. LCMS (ESI) calc'd for $C_{32}H_{44}N_4O_9Si$ [M+H]$^+$: 657.3, found 657.3. $^1$H NMR (300 MHz, CD$_3$OD) δ 7.80 (d, J=7.5 Hz, 2H), 7.73-7.64 (m, 2H), 7.45-7.26 (m, 4H), 4.56-4.46 (m, 1H), 4.43-4.20 (m, 4H), 4.13-4.00 (m, 2H), 3.72-3.34 (m, 4H), 1.44 (s, 9H), 0.91 (t, J=8.4 Hz, 2H), 0.00 (s, 9H).

Step F—Synthesis of T-6

To a stirred solution of intermediate W (100 mg, 0.077 mmol), T-5 (50.3 mg, 0.077 mmol), HATU (34.9 mg, 0.092 mmol) and DIEA (59.4 mg, 0.459 mmol) at 0° C. The reaction mixture was stirred at 0° C. for 1 h. The resulting mixture was diluted with brine (50 mL), extracted with EA (2×50 mL), washed with brine (2×50 mL), dried over anhydrous Na$_2$SO$_4$ and filtered, then the filtrate was concentrated under reduced pressure. The residue was purified by silica gel column chromatography, eluted with a gradient 1%-6% MeOH in DCM. The fractions containing the desired product were combined and concentrated to afford T-6. LCMS (ESI) calc'd for $C_{100}H_{127}FN_{14}O_{21}Si$ [M+H]$^+$: 1907.9, found 1908.6.

Step G—Synthesis of T-7

To a solution of T-6 (110 mg, 0.058 mmol) in THF (2 mL) and MeOH (0.4 mL) was added 1 M aqueous LiOH (0.461 mL, 0.461 mmol) at 0° C. The reaction mixture was stirred at 0° C. for 3 h. The resulting mixture was quenched with 1 M aqueous HCl (0.5 mL) and the mixture was purified by reverse phase flash chromatography (Column: Flash C$^{18}$ 80 g; Mobile Phase A: water (0.1% TFA), Mobile Phase B: ACN; Flow rate: 65 mL/min; Gradient: 2% B to 2% B in 5 min, 30% B to 50% B in 20 min; Detector: UV 220 nm; Rt=18 min) to afford T-7. LCMS (ESI) calc'd for $C_{84}H_{115}FN_{24}O_{19}Si$ [M+H]$^+$: 1671.8, found 1671.5.

Step H—Synthesis of T-8

To a solution of T-7 (68 mg, 0.041 mmol) in DMF (6 mL) and DCM (75 mL) were added DIEA (15.8 mg, 0.122 mmol), HATU (18.6 mg, 0.049 mmol) at 0° C. The reaction mixture was stirred at room temperature for 1 h. The resulting solution was concentrated under reduced pressure to remove DCM and diluted with brine (50 mL), extracted with EA (2×50 mL), washed brine (2×50 mL), dried over anhydrous Na$_2$SO$_4$ and filtered. The filtrate was concentrated under reduced pressure. The residue was purified by silica gel column chromatography, eluted with a gradient of 1%-10% MeOH in DCM. The fractions containing the desired product were combined and concentrated to afford T-8. LCMS (ESI) calc'd for $C_{84}H_{113}FN_{14}O_{18}Si$ [(M/2+H)]$^+$: 827.4, found 827.6.

Step I—Synthesis of T-9

To a solution of T-8 (110 mg, 0.065 mmol) in DMF (2 mL) was added CsF (198 mg, 1.31 mmol) at room temperature. The mixture was stirred at 45° C. for 16 h. The reaction solution was purified by reverse phase flash chromatography (Column: Flash C$^{18}$ 40 g; Mobile Phase A: water (0.1% TFA), Mobile Phase B: ACN; Flow rate: 45 mL/min; Gradient: 2% B to 2% B in 5 min, 20% B to 50% B in 15 min; Detector: UV 220 nm; Rt=17 min). The fractions containing the desired product were combined and concentrated under reduced pressure. The residue was re-dissolved in ACN (5 mL) and water (5 mL), and lyophilized to afford T-9. LCMS (ESI) calc'd for $C_{80}H_{102}F_4N_{14}O_{18}$ [(M-TFA)/2+H]$^+$: 755.4, found 755.7.

Step J—Synthesis of T-10

To a solution of T-9 (80 mg, 0.049 mmol) in DMF (300 μL) and water (30 μL) were added 2-(2-(2-carboxyethoxy)ethoxy)-N,N,N-trimethylethanaminium chloride (25.2 mg, 0.099 mmol), HATU (37.5 mg, 0.099 mmol) and DIEA (68.8 μL, 0.394 mmol) at 0° C. The mixture was stirred at 0° C. for 1 h. The reaction solution was quenched with water (100 μL) and purified by reverse phase flash chromatography (Column: Flash C$^{18}$ 80 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 220 nm; Rt=15 min). The fractions containing the desired product were combined and concentrated under reduced pressure. The residue was re-dissolved in ACN (5 mL) and water (5 mL), and lyophilized to afford T-10. LCMS (ESI) calc'd for $C_{90}H_{121}F_4N_{15}O_{21}$ [(M-TFA$^-$)/2]$^+$: 855.4, found 856.6.

Step K—Synthesis of T-11

To a suspension of T-10 (60 mg, 0.033 mmol) in DCM (1 mL) was added TFA (200 μL, 2.60 mmol) at 0° C. The reaction mixture was stirred at room temperature for 0.5 h. The resulting solution was concentrated under reduced pressure and the residue was purified by reverse phase flash chromatography (Column: Flash C$^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 210 nm; Rt=15 min). The fractions containing the desired product were combined and concentrated under reduced pressure. The residue was re-dissolved in ACN (3 mL) and water (6 mL), treated with 1 M aqueous HCl (33 μL) and lyophilized to afford T-11. LCMS (ESI) calc'd for $C_{87}H_{114}F_7N_{15}O_{21}$ [(M-TFA-TFA$^-$)/2]$^+$: 805.4, found 806.4.

Step L—Synthesis of Intermediate T 5 g of AG MP-1 Resin (cat #141-1841 BIO-RAD) was packed in a column. The column was washed with water (2×10 mL), followed by 20% ACN in water (2×10 mL). A solution of T-11 (45 mg, 0.026 mmol) in 40% ACN in water (20 mL) was loaded onto the resin column, then the column was eluted with 40% ACN in water (3×20 mL). The eluents were combined and lyophilized to afford intermediate T.
LCMS (ESI) calc'd for $C_{83}H_{114}Cl_2FN_{15}O_{17}$ [(M-Cl$^-$—HCl)/2]$^+$: 805.4, found 806.4.
Preparation of Intermediate U
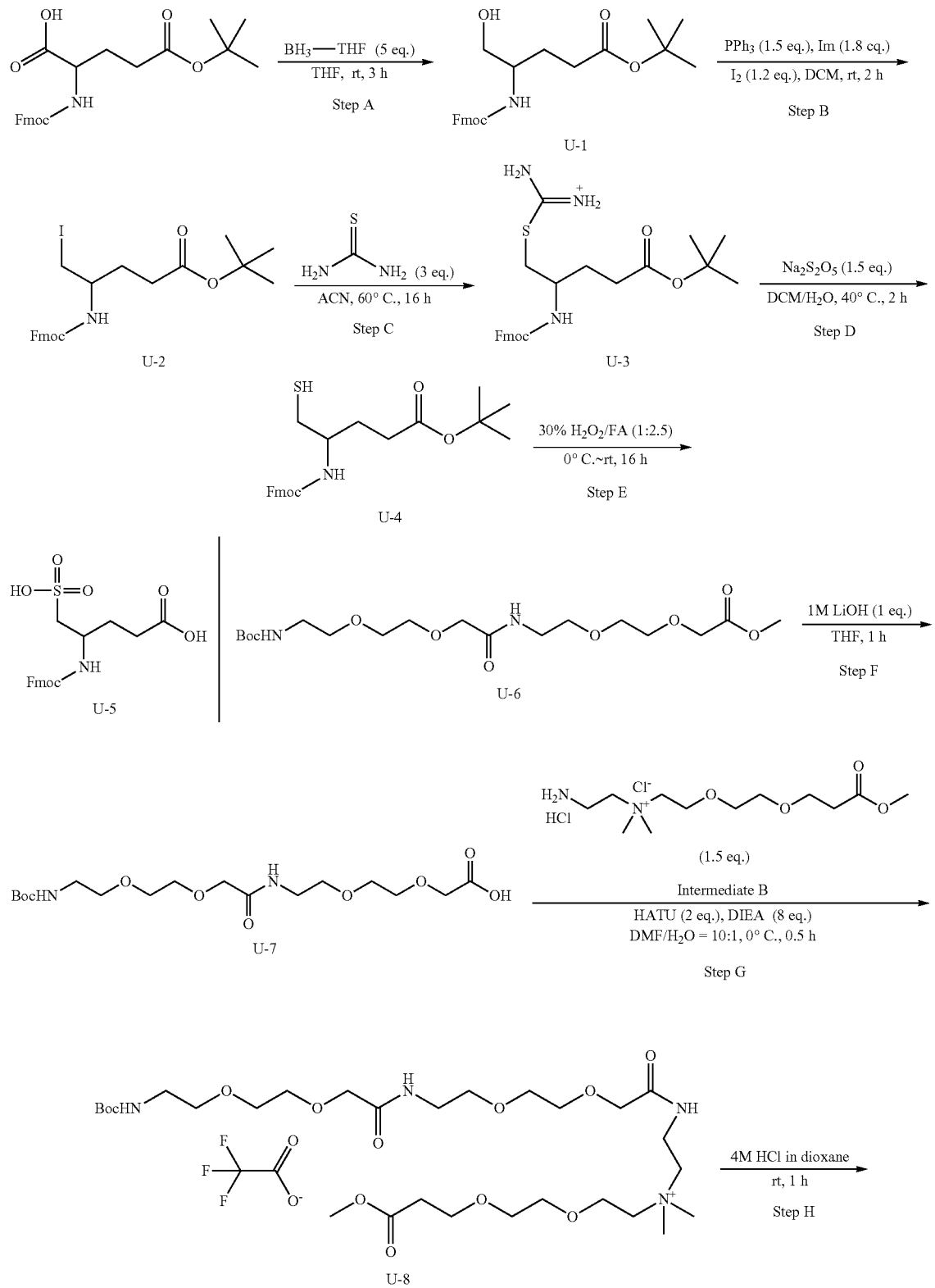

-continued
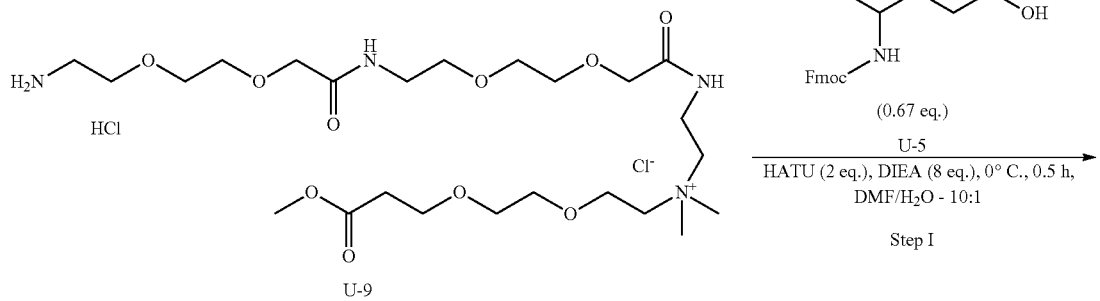
Step I
U-5
HATU (2 eq.), DIEA (8 eq.), 0° C., 0.5 h,
DMF/H₂O - 10:1
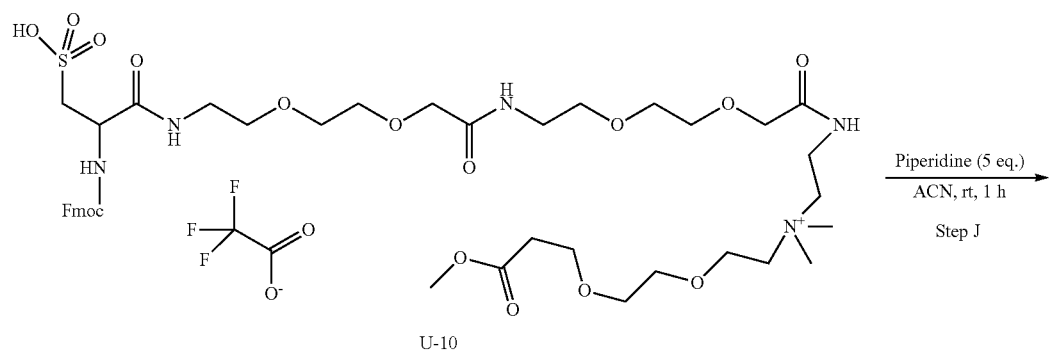
Step J
Piperidine (5 eq.)
ACN, rt, 1 h
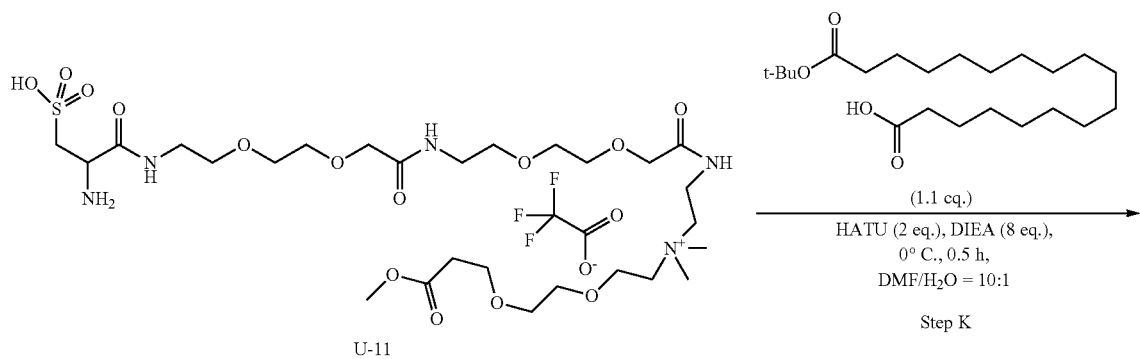
Step K
(1.1 eq.)
HATU (2 eq.), DIEA (8 eq.),
0° C., 0.5 h,
DMF/H₂O = 10:1
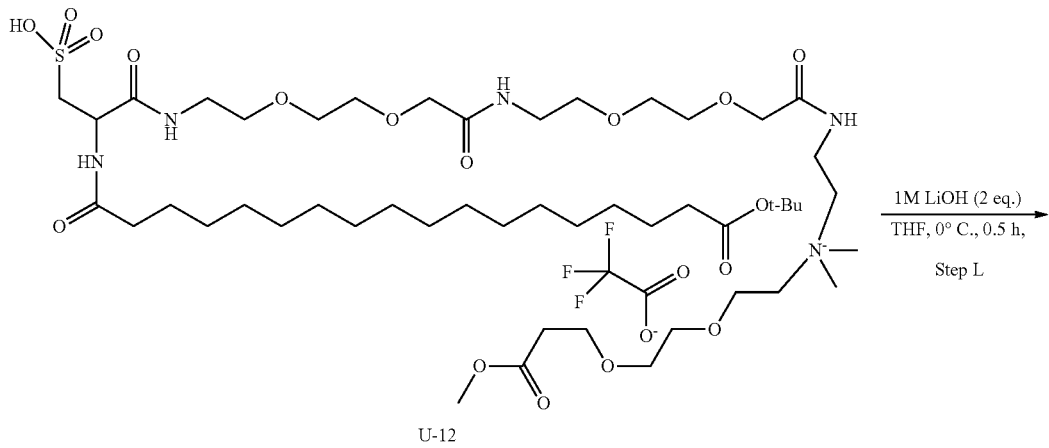
Step L
1M LiOH (2 eq.)
THF, 0° C., 0.5 h,

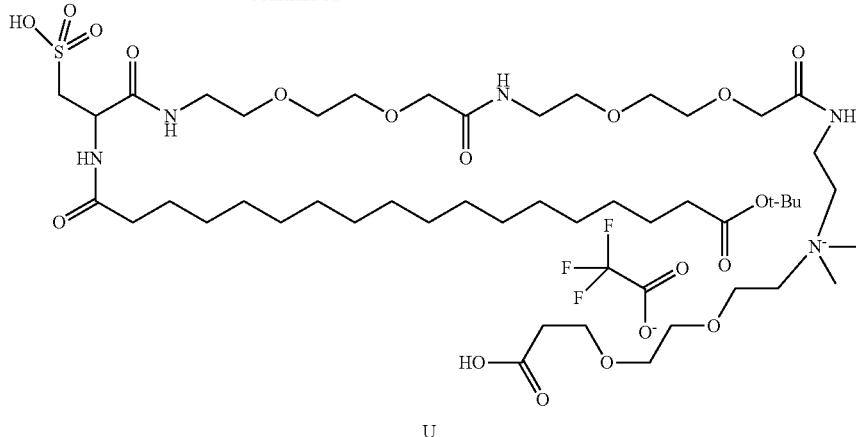

U

Step A—Synthesis of tert-butyl 4-((((9H-fluoren-9-yl)methoxy)carbonyl)amino)-5-hydroxypentanoate U-1

To a solution of 2-((((9H-fluoren-9-yl)methoxy)carbonyl)amino)-5-(tert-butoxy)-5-oxopentanoic acid (2 g, 4.70 mmol) in THF (20 mL) was added $BH_3$-THF (23.5 mL, 23.5 mmol) at 0° C. The mixture was stirred at room temperature for 3 h. The resulting mixture was concentrated under reduced pressure and the residue was purified by silica gel column chromatography, eluted with a gradient of 0-47% EA in PE. The fractions containing the desired product were combined and concentrated to afford tert-butyl 4-((((9H-fluoren-9-yl)methoxy)carbonyl)amino) hydroxypentanoate U-1 LCMS (ESI) calc'd for $C_{24}H_{29}NO_5$ [M+H]$^+$: 412.2, found 412.2; $^1$H NMR (300 MHz, $CD_3OD$) δ 7.82 (d, J=7.4 Hz, 2H), 7.68 (d, J=7.5 Hz, 2H), 7.46-7.28 (m, 4H), 4.66-4.29 (m, 2H), 4.23 (t, J=6.9 Hz, 1H), 3.62 (s, 2H), 3.53-3.41 (m, 2H), 2.29 (t, J=7.6 Hz, 2H), 2.01-1.78 (m, 2H), 1.46 (d, J=1.3 Hz, 9H).

Step B—Synthesis of tert-butyl 4-((((9H-fluoren-9-yl)methoxy)carbonyl)amino)-5-iodopentanoate U-2

To a solution of tert-butyl 4-((((9H-fluoren-9-yl)methoxy)carbonyl)amino)-5-hydroxypentanoate U-1 (100 mg, 0.243 mmol) in DCM (2 mL) were added $PPh_3$ (96 mg, 0.365 mmol), Im (29.8 mg, 0.437 mmol) and I2 (74 mg, 0.292 mmol) at room temperature. The mixture was stirred at room temperature for 2 h. The resulting mixture was concentrated under reduced pressure and the residue was purified by silica gel column chromatography, eluted with a gradient of 0-15% EA in PE. The fractions containing the desired product were combined and concentrated to afford tert-butyl 4-((((9H-fluoren-9-yl)methoxy)carbonyl)amino)-5-iodopentanoate U-2. LCMS (ESI) calc'd for $C_{24}H_{28}INO_4$ [M+H]$^+$: 522.1, found 522.1; $^1$H NMR (400 MHz, $CD_3OD$) δ 7.82 (d, J=7.5 Hz, 2H), 7.73-7.62 (m, 2H), 7.41 (t, J=7.4 Hz, 2H), 7.37-7.29 (m, 2H), 4.49-4.32 (m, 2H), 4.25 (t, J=6.9 Hz, 1H), 3.62-3.53 (m, 1H), 3.43-3.20 (m, 2H), 2.29 (t, J=7.4 Hz, 2H), 2.04-1.61 (m, 2H), 1.47 (s, 9H).

Step C—Synthesis of 2-(2-((((9H-fluoren-9-yl)methoxy)carbonyl)amino)-5-(tert-butoxy)-5-oxopentyl)isothiouronium U-3

To a solution of tert-butyl 4-((((9H-fluoren-9-yl)methoxy)carbonyl)amino)-5-iodopentanoate U-2 (50 mg, 0.096 mmol) in ACN (1 mL) was added thiourea (21.9 mg, 0.288 mmol) at room temperature. The mixture was stirred at 60° C. for 16 h. The resulting mixture was concentrated under reduced pressure to afford 2-(2-((((9H-fluoren-9-yO-methoxy)carbonyl)amino)-5-(tert-butoxy)-5-oxopentyl)isothiouronium U-3. LCMS (ESI) calc'd for $C_{25}H_{32}N_3O_4S$ [M]$^+$: 470.2, found 470.3.

Step D—Synthesis of Tert-butyl 4-((((9H-fluoren-9-yl)methoxy)carbonyl)amino)-5-mercaptopentanoate U-4

To a solution of 2-(2-((((9H-fluoren-9-yl)methoxy)carbonyl)amino)-5-(tert-butoxy)-5-oxopentyl)isothiouronium U-3 (1.8 g, 1.912 mmol) in DCM (20 mL) and water (4 mL) was added $Na_2S_2O_5$ (545 mg, 2.87 mmol) at room temperature. The mixture was stirred at 40° C. for 2 h. The reaction was diluted with water (50 mL), extracted with EA (2×100 mL). The combined organic layer was washed with brine (100 mL), dried over anhydrous $Na_2SO_4$ and filtered. The filtrate was concentrated under reduced pressure and the residue was purified by silica gel column chromatography, eluted with a gradient of 0-25% EA in PE. The fractions containing the desired product were combined and concentrated to afford tert-butyl 4-((((9H-fluoren-9-yl)methoxy)carbonyl)amino)-5-mercaptopentanoate U-4 LCMS (ESI) calc'd for $C_{24}H_{29}NO_4S$ [M+Na]$^+$: 450.2, found 450.2; $^1$H NMR (400 MHz, $CD_3OD$) δ 7.82 (d, J=7.5 Hz, 2H), 7.69 (d, J=7.5 Hz, 2H), 7.41 (t, J=7.4 Hz, 2H), 7.37-7.29 (m, 2H), 4.46-4.38 (m, 2H), 4.24 (t, J=6.7 Hz, 1H), 3.66-3.58 (m, 1H), 2.65-2.54 (m, 2H), 2.26 (t, J=7.5 Hz, 2H), 2.00-1.85 (m, 1H), 1.75-1.59 (m, 1H), 1.46 (s, 9H).

Step E—Synthesis of 4-((((9H-fluoren-9-yl)methoxy)carbonyl)amino)-5-sulfopentanoic acid U-5

To a solution of 30% $H_2O_2$ (50 mL) was dissolved in 98% formic acid (100 mL) at 0° C. and the mixture was stirred at this temperature for 1 h to afford performic acid. tert-butyl 4-((((9H-fluoren-9-yl)methoxy)carbonyl)amino)-5-mercaptopentanoate U-4 (635 mg, 1.485 mmol) in 98% formic acid (25 mL) solution was added dropwise to the performic acid solution and the resulting reaction mixture was stirred at room temperature for 16 h. The resulting mixture was concentrated under reduced pressure and extracted with EA (2×100 mL). The combined organic layer was washed with brine (100 mL), dried over anhydrous $Na_2SO_4$ and filtered. The filtrate was concentrated under reduced pressure and the residue was purified by reverse phase flash chromatography (Column: Flash $C^{18}$ 120 g; Mobile Phase A: water (0.05% TFA), Mobile Phase B: ACN; Flow rate: 85 mL/min; Gradient: 2% B to 2% B in 10 min, 30% B to 70% B in 20 min; Detector: UV 220 nm; RT: 21 min) to afford 4-((((9H-fluoren-9-yl)methoxy)carbonyl)amino)-5-sulfopentanoic acid U-5 LCMS (ESI) calc'd for $C_{20}H_{21}NO_7S$ [M+H]$^+$: 420.1, found 420.1.

Step F—Synthesis of 2,2-Dimethyl-4,13-dioxo-3,8,11,17,20-pentaoxa-5,14-diazadocosan-22-oic acid U-7

To a solution of methyl 2,2-dimethyl-4,13-dioxo-3,8,11,17,20-pentaoxa-5,14-diazadocosan-22-oate (400 mg, 0.947 mmol) in THF (5 mL) was added 1 M aqueous LiOH (0.947 mL, 0.947 mmol) at 0° C. The mixture was stirred at 0° C. for 0.5 h. The reaction solution was quenched with 1 M aqueous HCl (0.74 mL) and purified by reverse phase flash chromatography (Column: Flash $C^{18}$ 80 g; Mobile Phase A: water (0.05% TFA), Mobile Phase B: ACN; Flow rate: 60 mL/min; Gradient: 2% B to 40% B in 30 min; Detector: UV 220 nm; RT: 15 min). The fractions containing the desired product were combined and concentrated to afford 2,2-dimethyl-4,13-dioxo-3,8,11,17,20-pentaoxa-5,14-diazadocosan-22-oic acid U-7. LCMS (ESI) calc'd for $C_{17}H_{32}N_2O_9$ [M+H]+: 409.2, found 409.2. Step G—Synthesis of N-(2-(2-(3-methoxy-3-oxopropoxy)ethoxy)ethyl)-N,N,2,2-tetramethyl-4,13,22-trioxo-3,8,11,17,20-pentaoxa-5,14,23-triazapentacosan-25-aminium 2,2,2-trifluoroacetate U-8

To a stirred solution of 2,2-dimethyl-4,13-dioxo-3,8,11,17,20-pentaoxa-5,14-diazadocosan-22-oic acid U-7 (360 mg, 0.881 mmol) in DMF (3 mL) were added HATU (369 mg, 0.970 mmol) and DIEA (0.924 mL, 5.29 mmol) at 0° C. 2-Amino-N-(2-(2-(3-methoxy-3-oxopropoxy)ethoxy)ethyl)-N,N-dimethylethanaminium chloride hydrochloride intermediate B (591 mg, 1.763 mmol) in DMF (1 mL) and water (0.3 mL) solution was added to the solution and the resulting reaction mixture was stirred at 0° C. for 0.5 h. The reaction solution was quenched with water (2 mL) and purified by reverse phase flash chromatography (Column: Flash $C^{18}$ 80 g; Mobile Phase A: water (0.05% TFA), Mobile Phase B: ACN; Flow rate: 65 mL/min; Gradient: 2% B to 10% B in 10 min, 10% B to 30% B in 20 min; Detector: UV 220 nm; RT: 20 min) to afford N-(2-(2-(3-methoxy-3-oxopropoxy)ethoxy)ethyl)-N,N,2,2-tetramethyl-4,13,22-trioxo-3,8,11,17,20-pentaoxa-5,14,23-triazapentacosan-25-aminium 2,2,2-trifluoroacetate U-8. LCMS (ESI) calc'd for $C_{31}H_{57}F_3N_4O_{14}$ [M–TFA$^-$]$^+$: 653.4, found 653.4.

Step H—Synthesis of 20-Amino-N-(2-(2-(3-methoxy-3-oxopropoxy)ethoxy)ethyl)-N,N-dimethyl-4,13-dioxo-6,9,15,18-tetraoxa-3,12-diazaicosan-1-aminium chloride hydrochloride U-9

To a solution of N-(2-(2-(3-methoxy-3-oxopropoxy)ethoxy)ethyl)-N,N,2,2-tetramethyl-4,13,22-trioxo-3,8,11,17,20-pentaoxa-5,14,23-triazapentacosan-25-aminium 2,2,2-trifluoroacetate U-8 (340 mg, 0.443 mmol) was added HCl (4 M) in dioxane (10 mL) at room temperature. The reaction mixture was stirred for 1 h at room temperature. The resulting solution was concentrated under reduced pressure to afford 20-amino-N-(2-(2-(3-methoxy-3-oxopropoxy)ethoxy)ethyl)-N,N-dimethyl-4,13-dioxo-6,9,15,18-tetraoxa-3,12-diazaicosan-1-aminium chloride hydrochloride U-9. LCMS (ESI) calc'd for $C_{24}H_{50}Cl_2N_4O_{10}$ [M—HCl—Cl$^-$]$^+$: 553.4, found 553.4.

Step I—Synthesis of 1-(9H-fluoren-9-yl)-N-(2-(2-(3-methoxy-3-oxopropoxy)ethoxy)ethyl)-N,N-dimethyl-3,8,17,26-tetraoxo-5-(sulfomethyl)-2,12,15,21,24-pentaoxa-4,9,18,27-tetraazanonacosan-29-aminium 2,2,2-trifluoroacetate U-10

To a stirred solution of 4-((((9H-fluoren-9-yl)methoxy)carbonyl)amino)-5-sulfopentanoic acid U-5 (120 mg, 0.286 mmol) in DMF (4 mL) were added HATU (120 mg, 0.315 mmol) and DIEA (0.4 mL, 2.289 mmol) at 0° C. 20-Amino-N-(2-(2-(3-methoxy-3-oxopropoxy)ethoxy)ethyl)-N,N-dimethyl-4,13-dioxo-6,9,15,18-tetraoxa-3,12-diazaicosan-1-aminium chloride hydrochloride U-9 (215 mg, 0.343 mmol) in DMF (1 mL) and water (0.5 mL) was added to the solution and stirred at 0° C. for 0.5 h. The reaction solution was quenched with water (1 mL) and purified by reverse phase flash chromatography (Column: Flash $C^{18}$ 80 g; Mobile Phase A: water (0.05% TFA), Mobile Phase B: ACN; Flow rate: 65 mL/min; Gradient: 2% B to 2% B in 10 min, 2% B to 50% B in 25 min; Detector: UV 220 nm; RT: 24 min) to afford 1-(9H-fluoren-9-yl)-N-(2-(2-(3-methoxy-3-oxopropoxy)ethoxy)ethyl)-N,N-dimethyl-3,8,17,26-tetraoxo-5-(sulfomethyl)-2,12,15,21,24-pentaoxa-4,9,18,27-tetraazanonacosan-29-aminium 2,2,2-trifluoroacetate U-10. LCMS (ESI) calc'd for $C_{46}H_{68}F_3N_5O_{18}S$ [M–TFA$^-$]$^+$: 954.4, found 954.3; $^1$H NMR (400 MHz, $CD_3OD$) δ 7.82 (d, J=7.4 Hz, 2H), 7.69 (t, J=6.4 Hz, 2H), 7.41 (t, J=7.4 Hz, 2H), 7.34 (t, J=7.4 Hz, 2H), 4.37 (d, J=7.2 Hz, 2H), 4.24 (t, J=6.8 Hz, 1H), 4.10-3.99 (m, 6H), 3.93 (br, 2H), 3.81-3.56 (m, 27H), 3.48-3.35 (m, 4H), 3.22 (s, 6H), 3.13-2.93 (m, 2H), 2.57 (t, J=6.0 Hz, 1H), 2.30-2.17 (m, 2H), 1.97-1.82 (m, 2H).

Step J—Synthesis of 25-Amino-N-(2-(2-(3-methoxy-3-oxopropoxy)ethoxy)ethyl)-N,N-dimethyl-4,13,22-trioxo-26-sulfo-6,9,15,18-tetraoxa-3,12,21-triazahexacosan-1-aminium 2,2,2-trifluoroacetate U-11

To a solution of 1-(9H-fluoren-9-yl)-N-(2-(2-(3-methoxy-3-oxopropoxy)ethoxy)ethyl)-N,N-dimethyl-3,8,17,26-tetraoxo-5-(sulfomethyl)-2,12,15,21,24-pentaoxa-4,9,18,27-tetraazanonacosan-29-aminium 2,2,2-trifluoroacetate U-10 (90 mg, 0.084 mmol) in ACN (2 mL) was added piperidine (35.9 mg, 0.421 mmol) at room temperature. The reaction mixture was stirred for 1 h at room temperature. The resulting solution was concentrated under reduced pressure to afford 25-amino-N-(2-(2-(3-methoxy-3-oxopropoxy)ethoxy)ethyl)-N,N-dimethyl-4,13,22-trioxo-26-sulfo-6,9,15,18-tetraoxa-3,12,21-triazahexacosan-1-aminium 2,2,2-trifluoroacetate U-11. LCMS (ESI) calc'd for $C_{31}H_{58}F_3N_5O_{16}S$ [M–TFA$^-$]$^{-+}$: 732.4, found 732.3.

Step K—Synthesis of N-(2-(2-(3-methoxy-3-oxopropoxy)ethoxy)ethyl)-N,N,46,46-tetramethyl-4,13,22,27,44-pentaoxo-25-(sulfomethyl)-6,9,15,18,45-pentaoxa-3,12,21,26-tetraazaheptatetracontan-1-aminium 2,2,2-trifluoroacetate U-12

To a stirred solution of 18-(tert-butoxy)-18-oxooctadecanoic acid (28.9 mg, 0.078 mmol) in DMF (2 mL) were added HATU (32.4 mg, 0.085 mmol) and DIEA (0.074 mL, 0.426 mmol) at 0° C. 25-Amino-N-(2-(2-(3-methoxy-3- oxopropoxy)ethoxy)ethyl)-N,N-dimethyl-4,13,22-trioxo-26-sulfo-6,9,15,18-tetraoxa-3,12,21-triazahexacosan-1-aminium 2,2,2-trifluoroacetate U-11 (60 mg, 0.071 mmol) in DMF (1 mL) and Water (0.2 mL) was added to the solution and stirred at 0° C. for 0.5 h. The reaction solution was quenched with water (1 mL) and purified by reverse phase flash chromatography (Column: Flash $C^{18}$ 80 g; Mobile Phase A: water (0.05% TFA), Mobile Phase B: ACN; Flow rate: 65 mL/min; Gradient: 2% B to 2% B in 10 min, 2% B to 50% B in 25 min; Detector: UV 220 nm; RT: 29 min) to afford N-(2-(2-(3-methoxy-3-oxopropoxy)ethoxy)ethyl)-N,N,46,46-tetramethyl-4,13,22,27,44-pentaoxo-25-(sulfomethyl)-6,9,15,18,45-pentaoxa-3,12,21,26-tetraazaheptatetracontan-1-aminium 2,2,2-trifluoroacetate U-12. LCMS (ESI) calc'd for $C_{53}H_{98}F_3N_5O_{19}S$ [M−TFA⁻]⁺: 1084.65, found 1084.75.

Step L—Synthesis of N-(2-(2-(2-carboxyethoxy)ethoxy)ethyl)-N,N,46,46-tetramethyl-4,13,22,27,44-pentaoxo-25-(sulfomethyl)-6,9,15,18,45-pentaoxa-3,12,21,26-tetraazaheptatetracontan-1-aminium U To a solution of N-(2-(2-(3-methoxy-3-oxopropoxy)ethoxy)ethyl)-N,N,46,46-tetramethyl-4,13,22,27,44-pentaoxo-25-(sulfomethyl)-6,9,15,18,45-pentaoxa-3,12,21,26-tetraazaheptatetracontan-1-aminium 2,2,2-trifluoroacetate U-12 (70 mg, 0.058 mmol) in THF (1 mL) was added lithium hydroxide (0.117 mL, 0.117 mmol) at 0° C. The mixture was stirred at 0° C. for 0.5 h. The reaction solution was quenched with 1 M aqueous HCl (0.12 mL) and purified by reverse phase flash chromatography (Column: Flash $C^{18}$ 40 g; Mobile Phase A: water (5 mmol $NH_4HCO_3$), Mobile Phase B: ACN; Flow rate: 40 mL/min; Gradient: 1% B to 30% B in 10 min, 30% B to 70% B in 20 min; Detector: UV 220 nm; RT: 25 min). The fractions containing the desired product were combined and concentrated to afford N-(2-(2-(2-carboxyethoxy)ethoxy)ethyl)-N,N,46,46-tetramethyl-4,13,22,27,44-pentaoxo-25-(sulfomethyl)-6,9,15,18,45-pentaoxa-3,12,21,26-tetraazaheptatetracontan-1-aminium intermediate U. LCMS (ESI) calc'd for $C_{51}H_{97}N_5O_{20}S$ [M−HCO₃⁻]⁺: 1070.6, found 1070.9; ¹H NMR (400 MHz, $CD_3OD$) δ 4.36-4.26 (m, 1H), 4.07 (s, 2H), 4.03 (s, 2H), 3.97 (br, 2H), 3.84-3.55 (m, 24H), 3.49 (t, J=5.5 Hz, 2H), 3.40 (q, J=5.5 Hz, 2H), 3.25 (s, 6H), 3.12-2.93 (m, 2H), 2.55 (t, J=6.0 Hz, 2H), 2.35-2.11 (m, 7H), 1.9-1.81 (m, 1H), 1.70-1.51 (m, 4H), 1.46 (s, 9H), 1.41-1.26 (m, 24H).

Preparation of Intermediate V

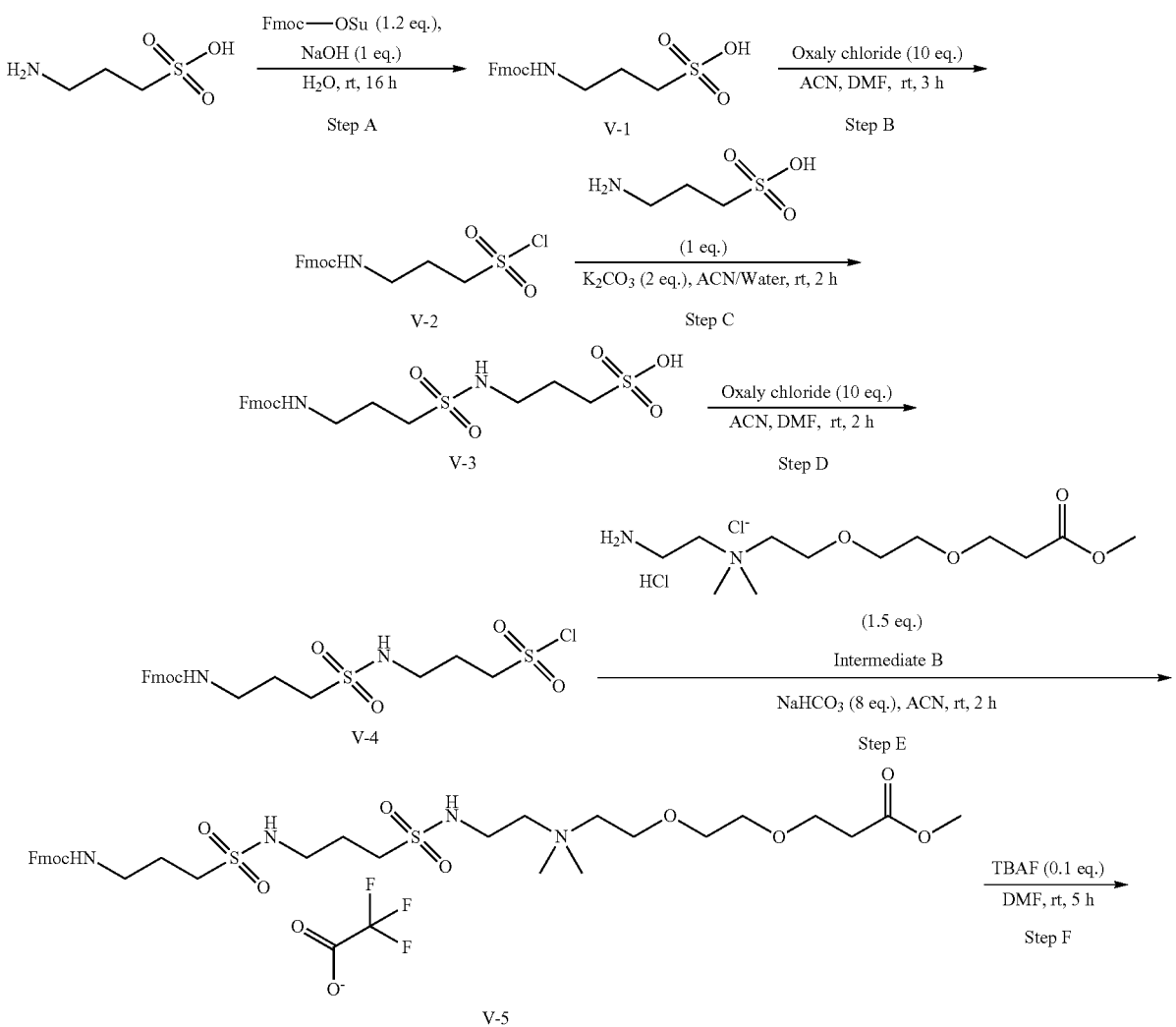

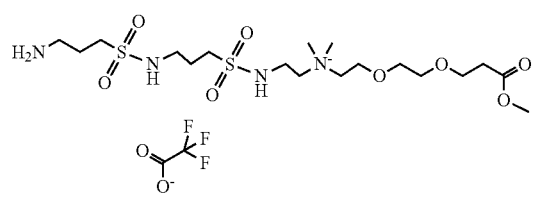
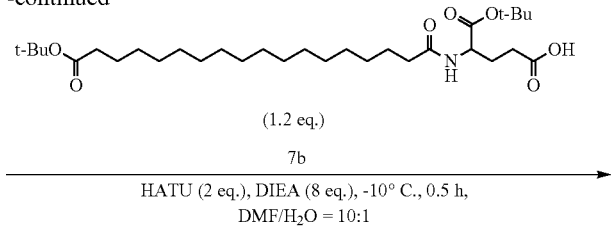
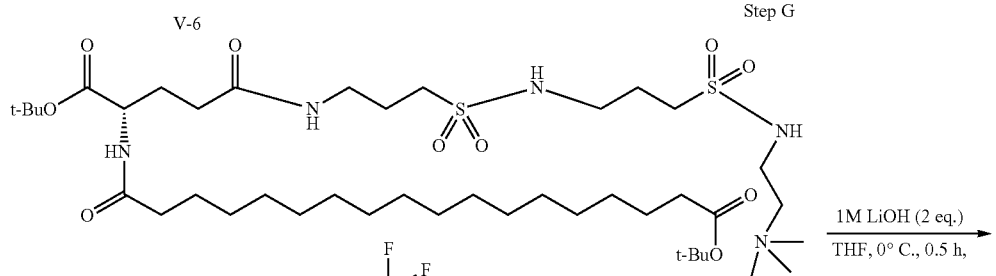
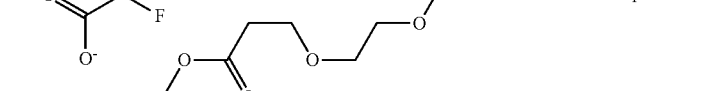
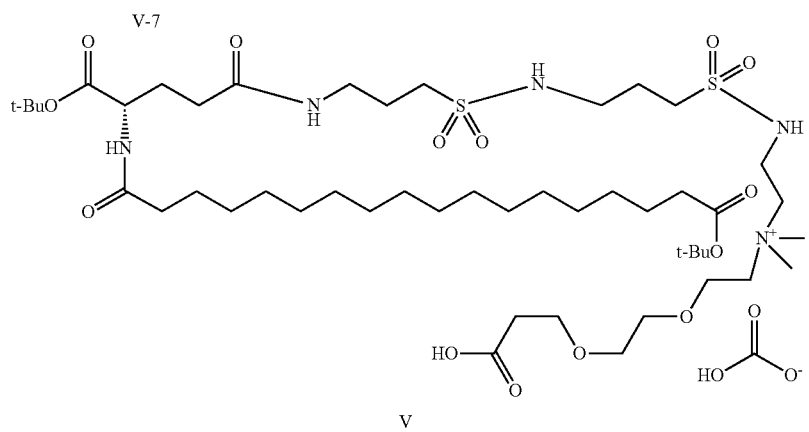

Step A—Synthesis of 3-((((9H-fluoren-9-yl)methoxy)carbonyl)amino)propane-1-sulfonic acid V-1

To a solution of 3-aminopropane-1-sulfonic acid (2 g, 14.37 mmol) in water (60 mL) were added NaOH (0.58 g, 14.37 mmol) and Fmoc-OSu (5.82 g, 17.24 mmol) at 0° C. The mixture reaction was stirred at room temperature for 16 h. The filtrate was concentrated under reduced pressure and the residue was purified by reverse phase flash chromatography (Column: Flash $C^{18}$ 330 g; Mobile Phase A: water; Mobile Phase B: ACN; Flow rate: 80 mL/min; 2%-2% in 10 min; 2%-25% in 5 min; 25%-55% in 15 min; Detector: UV 210 nm; RT: 30 min) to afford 3-((((9H-fluoren-9-yl)methoxy)carbonyl)amino)propane-1-sulfonic acid V-1. LCMS (ESI) calc'd for $C_{18}H_{19}NO_5S$ [M+H]$^+$: 362.1, found 362.0; $^1$H NMR (400 MHz, CD$_3$OD) δ 7.79 (d, J=7.5 Hz, 2H), 7.65 (d, J=7.5 Hz, 2H), 7.38 (t, J=7.4 Hz, 2H), 7.31 (td, J=7.4, 1.2 Hz, 2H), 4.59-4.32 (m, 2H), 4.26-4.18 (m, 1H), 3.26-3.22 (m, 2H), 2.86-2.80 (m, 2H), 2.01-1.92 (m, 2H).

Step B—Synthesis of (9H-fluoren-9-yl)methyl(3-(chlorosulfonyl)propyl)carbamate V-2

To a solution of 3-((((9H-fluoren-9-yl)methoxy)carbonyl)amino)propane-1-sulfonic acid V-1 (2 g, 5.53 mmol) in ACN (40 mL) were added oxalyl dichloride (4.68 mL, 55.3 mmol) and a catalytic amount of DMF at 0° C. The mixture was stirred at room temperature for 3 h. The filtrate was concentrated under reduced pressure and the residue was purified by silica gel column chromatography, eluted with a gradient of 0-55% EA in PE, to afford (9H-fluoren-9-yl)methyl (3-(chlorosulfonyl)propyl)carbamate V-2. LCMS (ESI) calc'd for $C_{18}H_{18}ClNO_4S$ [M+Na]$^+$: 402.1, found 402.1; $^1$H NMR (400 MHz, CD$_3$OD) δ 7.79 (d, J=7.5 Hz, 2H), 7.64 (d, J=7.5 Hz, 2H), 7.39 (t, J=7.4 Hz, 2H), 7.34-7.28 (m, 2H), 4.44-4.39 (m, 2H), 4.23-4.17 (m, 1H), 3.89-3.81 (m, 2H), 3.26-3.21 (m, 2H), 2.19-2.09 (m, 2H).

Step C—Synthesis of 3-((3-((((9H-fluoren-9-yl)methoxy)carbonyl)amino)propyl)sulfonamido)propane-1-sulfonic acid V-3

To a solution of 3-aminopropane-1-sulfonic acid (0.550 g, 3.95 mmol) in water (15 mL) were added K$_2$CO$_3$ (1.092 g, 7.90 mmol) and (9H-fluoren-9-yl)methyl (3-(chlorosulfonyl)propyl)carbamate V-2 (1.5 g, 3.95 mmol) at 0° C. The reaction was stirred at room temperature for 2 h. The filtrate was concentrated under reduced pressure and the residue was purified by reverse phase flash chromatography (Column: Flash C$^{18}$ 330 g; Mobile Phase A: water (0.05% TFA); Mobile Phase B: ACN; Flow rate: 80 mL/min; 2%-2% in 10 min; 2%-30% in 5 min; 30%-70% in 20 min; Detector, UV 210 nm; RT: 35 min) to afford 3-((3-((((9H-fluoren-9-yl)methoxy)carbonyl)amino)propyl)sulfonamido)propane-1-sulfonic acid V-3. LCMS (ESI) calc'd for $C_{21}H_{26}N_2O_7S_2$ [M+H]$^+$: 483.1, found 483.1; $^1$H NMR (400 MHz, CD$_3$OD) δ 7.79 (d, J=7.5 Hz, 2H), 7.65 (d, J=7.5 Hz, 2H), 7.39 (t, J=7.4 Hz, 2H), 7.31 (t, J=7.5 Hz, 2H), 4.37 (d, J=6.8 Hz, 2H), 4.21 (d, J=7.0 Hz, 1H), 3.24-3.21 (m, 2H), 3.19-3.15 (m, 2H), 3.06-3.02 (m, 2H), 2.90-2.84 (m, 2H), 2.03-1.89 (m, 4H).

Step D—Synthesis of (9H-fluoren-9-yl)methyl (3-(N-(3-(chlorosulfonyl)propyl)sulfamoyl)propyl)carbamate V-4

To a solution of 3-((3-((((9H-fluoren-9-yl)methoxy)carbonyl)amino)propyl)sulfonamido)propane-1-sulfonic acid V-3 (190 mg, 0.394 mmol) in ACN (4 mL) were added oxalyl dichloride (0.333 mL, 3.94 mmol) and a catalytic amount of DMF at 0° C. The mixture was stirred at room temperature for 2 h and concentrated under reduced pressure. The residue was purified by silica gel column chromatography, eluted with a gradient of 0-55% EA in PE, to afford (9H-fluoren-9-yl)methyl(3-(N-(3-(chlorosulfonyl)propyl)sulfamoyl)propyl)carbamate V-4. LCMS (ESI) calc'd for $C_{21}H_{25}ClN_2O_6S_2$ [M+H]$^+$: 501.1, found 501.1; $^1$H NMR (300 MHz, CD$_3$OD) δ 7.80 (d, J=7.5 Hz, 2H), 7.64 (d, J=7.4 Hz, 2H), 7.35 (dt, J=23.9, 7.2 Hz, 4H), 4.38 (d, J=6.8 Hz, 2H), 4.22 (d, J=6.8 Hz, 1H), 4.01-3.93 (m, 2H), 3.26-3.18 (m, 4H), 3.09-3.01 (m, 2H), 2.24-2.15 (m, 2H), 1.99-1.90 (m, 2H).

Step E—Synthesis of 2-((3-((3-((((9H-fluoren-9-yl)methoxy)carbonyl)amino)propyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-5

To a solution of 2-amino-N-(2-(2-(3-methoxy-3-oxopropoxy)ethoxy)ethyl)-N,N-dimethylethanaminium chloride hydrochloride intermediate B (100 mg, 0.299 mmol) in ACN (2 mL) were added NaHCO$_3$ (134 mg, 1.597 mmol) and (9H-fluoren-9-yl)methyl (3-(N-(3-(chlorosulfonyl)propyl)sulfamoyl)propyl)carbamate V-4 (100 mg, 0.200 mmol) at 0° C. The reaction was stirred at room temperature for 2 h. The filtrate was concentrated under reduced pressure and the residue was purified by reverse phase flash chromatography (Column: Flash C$^{18}$ 40 g; Mobile Phase A: water; Mobile Phase B: ACN; Flow rate: 45 mL/min; 2%-2% in 5 min; 2%-30% in 5 min; 30%-75% in 20 min; Detector: UV 210 nm; RT: 30 min) to afford 2-((3-((3-((((9H-fluoren-9-yl)methoxy)carbonyl)amino)propyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-5. LCMS (ESI) calc'd for $C_{35}H_{51}F_3N_4O_{12}S_2$ [M-TFA$^-$]$^+$: 727.3, found 727.3.

Step F—Synthesis of 2-((3-((3-(3-aminopropyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-6

To a solution of 2-((3-((3-((((9H-fluoren-9-yl)methoxy)carbonyl)amino)propyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-5 (45 mg, 0.054 mmol) in DMF (1 mL) was added TBAF (1.688 mg, 5.35 μmol) at 0° C. The mixture was stirred at room temperature for 5 h. The mixture was concentrated under reduced pressure to afford 2-((3-((3-aminopropyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-6. LCMS (ESI) calc'd for $C_{20}H_{41}F_3N_4O_{10}S_2$ [M-TFA$^-$]$^+$: 505.2, found 505.15.

Step G—Synthesis of (S)-2-((3-((3-(5-(tert-butoxy)-4-(18-(tert-butoxy)-18-oxooctadecanamido)-5-oxopentanamido)propyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-7

To a solution of 2-((3-((3-aminopropyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-6 (32 mg, 0.052 mmol) (crude) in DMF (500 μL) and water (50 μL) were added HATU (39.3 mg, 0.103 mmol), DIEA (68.4 μL, 0.414 mmol) and (S)-5-(tert-butoxy)-4-(18-(tert-butoxy)-18-oxooctadecanamido)-5-oxopentanoic acid 7b (34.5 mg, 0.062 mmol; the synthesis of which is described in Example 7) at −10° C. The resulted mixture was stirred at −10° C. for 0.5 h and directly purified by reverse phase flash chromatography (Column: Flash C$^{18}$ 40 g; Mobile Phase A: water (0.05% TFA); Mobile Phase B: ACN; Flow rate: 45 mL/min; 2%-2% in 5 min; 2%-30% in 5 min; 30%-65% in 10 min; 60%-95% in 15 min; Detector: UV 210 nm; RT: 35 min) to afford (S)-2-((3-((3-(5-(tert-butoxy)-4-(18-(tert-butoxy)-18-oxooctadecanamido)-5-oxopentaanamido)propyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-7. LCMS (ESI) calc'd for $C_{51}H_{96}F_3N_5O_{16}S_2$ [M-TFA$^-$]$^+$: 1042.6, found 1042.5.

Step H—Synthesis of (S)-2-((3-((3-(5-(tert-butoxy)-4-(18-(tert-butoxy)-18-oxooctadecanamido)-5-oxopentanamido)propyl)sulfonamido)propyl)sulfonamido)-N-(2-(2-(2-carboxyethoxy)ethoxy)ethyl)-N,N-dimethylethan-1-aminium hydrogen carbonate V To a solution of (S)-2-((3-((3-(5-(tert-butoxy)-4-(18-(tert-butoxy)-18-oxooctadecanamido)-5-oxopentanamido)propyl)sulfonamido)propyl)sulfonamido)-N-(2-(2-(3-methoxy-3-oxopropoxy)ethoxy)ethyl)-N,N-dimethylethan-1-aminium 2,2,2-trifluoroacetate V-7 (80 mg, 0.069 mmol) in THF (1 mL) was added 1 M aqueous LiOH (0.138 mL, 0.138 mmol) at 0° C. The reaction mixture was stirred at 0° C. for 0.5 h. The reaction mixture was cooled to 0° C. and treated with 1 M aqueous HCl (0.140 mL), then directly purified by reverse phase flash chromatography (Column: Flash C$^{18}$ 40 g; Mobile Phase A: water (5 mM NH$_4$HCO$_3$); Mobile Phase B: ACN; Flow rate: 50 mL/min; 2%-2% in 5 min; 2%-30% in 5 min; 30%-65% in 8 min; 65%-95% in 12 min; Detector: UV 210 nm; RT: 35 min) to afford (S)-2-((3-((3-(5-(tert-butoxy)-4-(18-(tert-butoxy)-18-oxooctadecanamido)-5-oxopentanamido)propyl)sulfonamido)propyl)sulfonamido)-N-(2-(2-(2-carboxyethoxy)ethoxy)ethyl)-N,N-dimethylethan-1-aminium hydrogen carbonate V. LCMS (ESI) calc'd for $C_{49}H_{95}N_5O_{17}S2$[M−HCO$_3^-$]$^+$: 1028.6, found 1028.6; $^1$H NMR (400 MHz, CD$_3$OD) δ 4.23 (dd, J=9.1, 5.1 Hz, 1H), 3.94 (d, J=5.2 Hz, 2H), 3.73 (t, J=5.9 Hz, 2H), 3.68-3.57 (m, 10H), 3.34-3.10 (m, 12H), 3.11-3.05 (m, 2H), 2.40 (t, J=5.9 Hz, 2H), 2.31-2.17 (m, 6H), 2.15-1.82 (m, 6H), 1.70-1.56 (m, 4H), 1.45 (d, J=9.8 Hz, 18H), 1.29 (d, J=4.9 Hz, 24H).
Preparation of Intermediate W
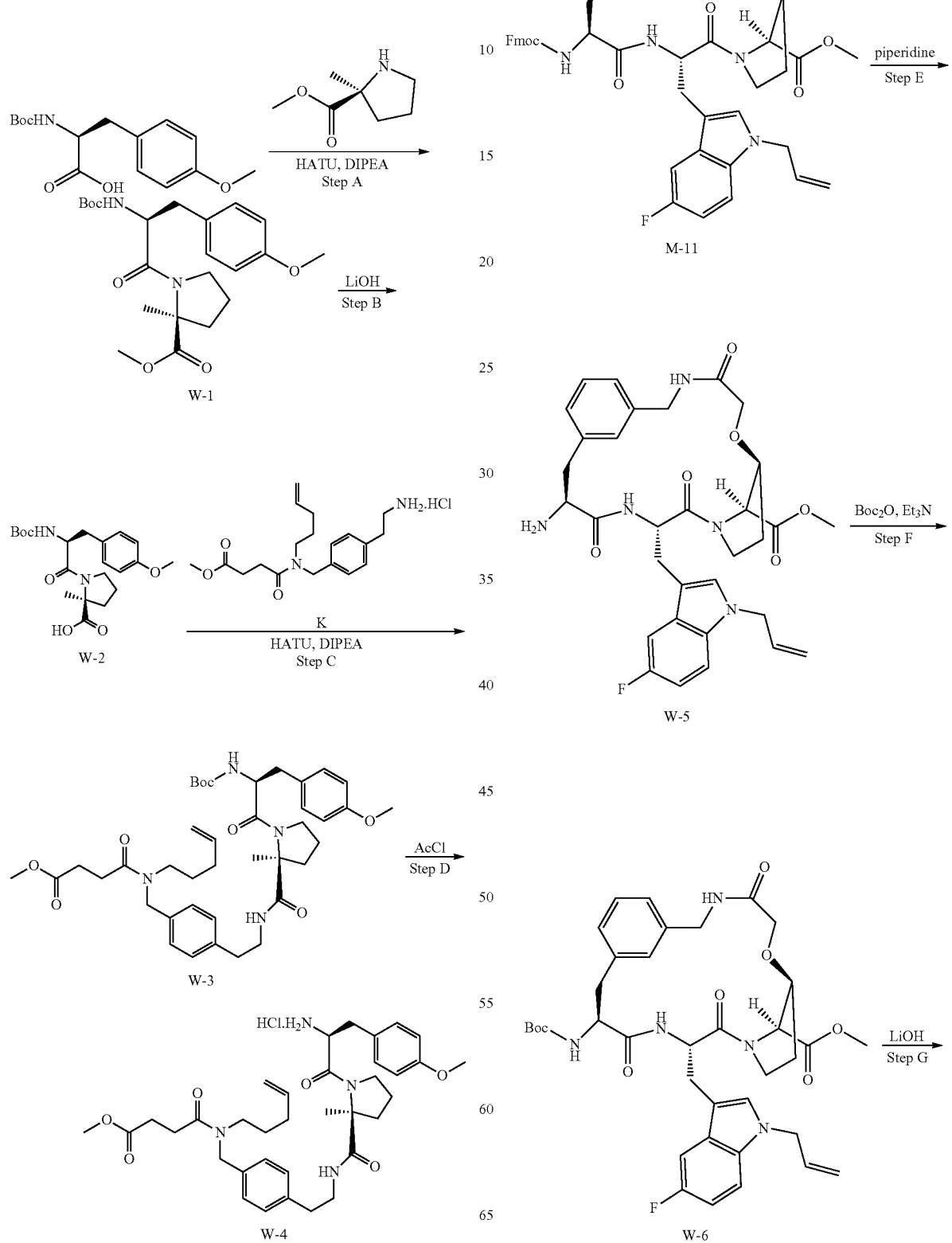

243
-continued
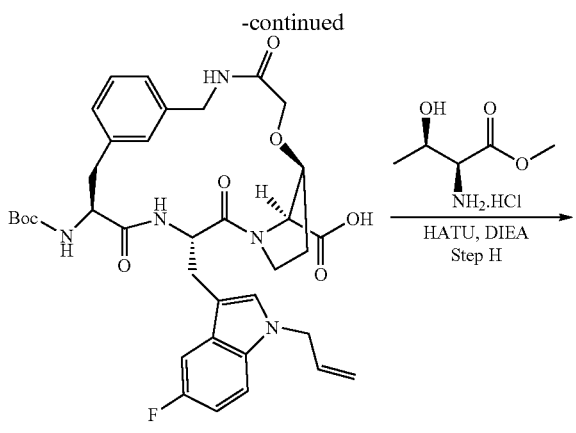
W-7
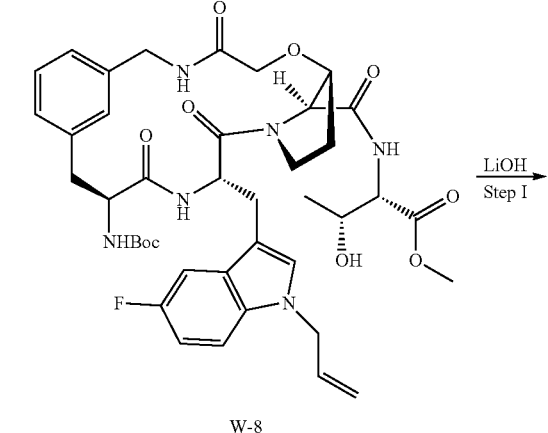
W-8
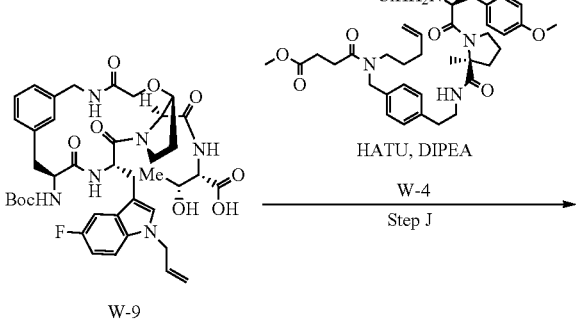
W-9
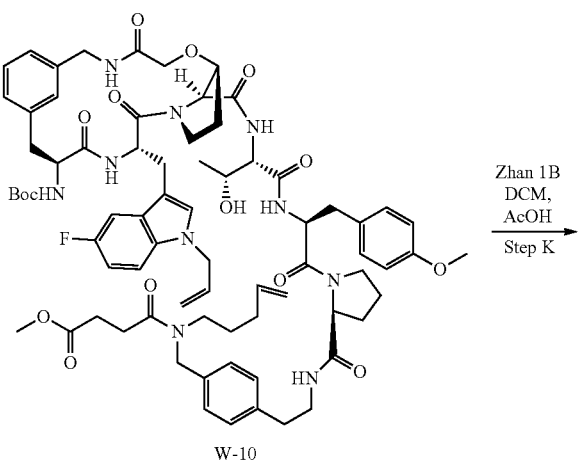
W-10
244
-continued
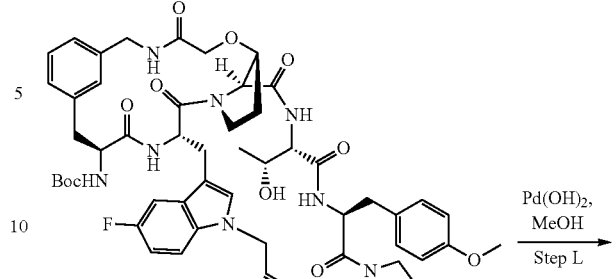
W-11
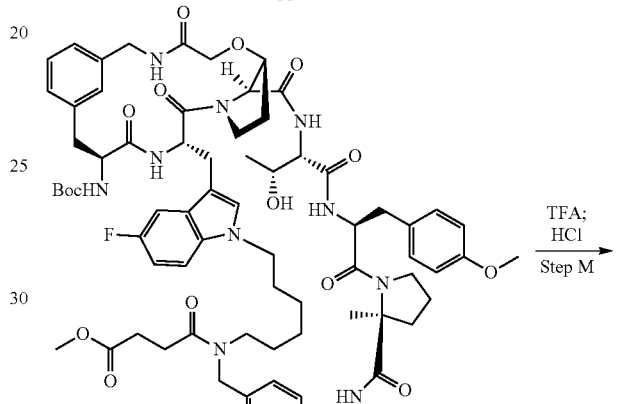
W-12
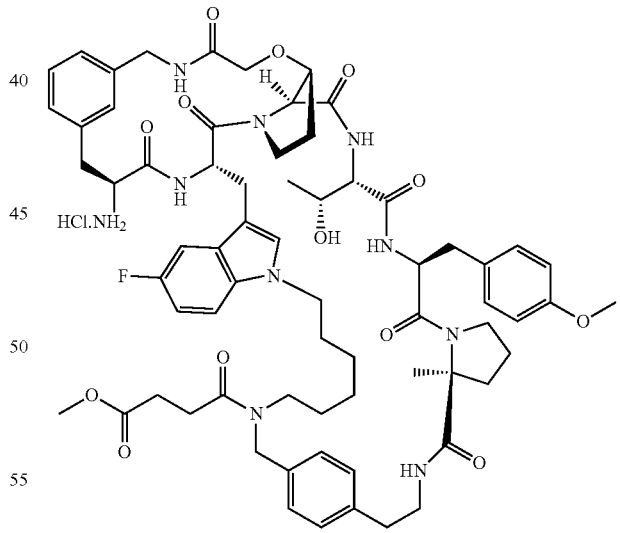
W
Step A—Synthesis of Intermediate W-1
To a solution of (S)-2-((tert-butoxycarbonyl)amino)-3-(4-methoxyphenyl)propanoic acid (3 g, 10.16 mmol) and HATU (3.86 g, 10.16 mmol) in DMF (50 ml) at −40° C. were added DIEA (7.10 ml, 40.6 mmol) and (S)-methyl 2-methylpyrrolidine-2-carboxylate (1.60 g, 11.2 mmol). The mixture was stirred at −40° C. for 2 h then quenched with water (50 mL) and extracted with EA (2×50 mL). The combined organic layers were washed with brine, dried over anhydrous $Na_2SO_4$, filtered and concentrated. The residue was purified by MPLC over silica gel (eluting with a gradient of 40%-350% EA in PE) to afford W-1. LC/MS: $[M+H]^+=421.3$.

Step B—Synthesis of Intermediate W-2

To a solution of W-1 (1.2 g, 2.71 mmol) in THF (18 mL) at RT was added 2N aqueous LiOH (5.42 mL, 10.84 mmol). The reaction was then stirred at 45° C. for 48 h. The pH value of the solution was adjusted to 4 with 1 N aqueous HCl and the solution was extracted with EA (3×50 mL). The combined organic layers were washed with brine, dried over anhydrous $Na_2SO_4$, filtered and concentrated to afford W-2. LC/MS: $[M+H]^+=407.2$. $^1H$ NMR (300 MHz, chloroform-d): δ 7.19-7.10 (m, 2H), 6.80 (d, J=8.6 Hz, 2H), 5.29 (d, J=7.2 Hz, 1H), 4.54 (d, J=7.8 Hz, 1H), 3.74 (s, 3H), 3.71-3.59 (m, 1H), 2.99 (dd, J=13.0, 7.3 Hz, 2H), 2.92-2.79 (m, 1H), 2.50-2.40 (m, 1H), 1.84 (d, J=16.8 Hz, 2H), 1.83-1.71 (m, 1H), 1.61 (s, 3H), 1.40 (s, 9H).

Step C—Synthesis of Intermediate W-3

To a solution of intermediate K (0.91 g, 2.46 mmol), W-2 (1.00 g, 2.46 mmol) and DIPEA (1.72 ml, 9.84 mmol) in DMF (20 ml) at 0° C. was added HATU (1.22 g, 3.20 mmol) and the reaction was allowed to warm to RT and stirred for 1 h. The reaction was diluted with EA and 10% aqueous LiCl, decanted and the organic layer was washed with 10% aqueous LiCl, dried over anhydrous $Na_2SO_4$, filtered and concentrated. The residue was purified by MPLC over silica gel (eluting with a gradient of 20%-70% of EA in hexanes) to provide W-3. LC/MS: $[M+H]^+=721.4$.

Step D—Synthesis of Intermediate W-4

To a solution of W-3 (38 g, 52.7 mmol) in MeOH (190 ml) at −10° C. was added acetyl chloride (7.50 ml, 105 mmol) dropwise over 30 min then the mixture was warmed to RT and stirred overnight. The reaction was concentrated and co-evaporated with AcN twice to provide W-4. LC/MS: $[M+H]^+=621.2$.

Step E—Synthesis of Intermediate W-5

To a solution of M-11 (10 g, 12.08 mmol) in DCM (50 ml) at 0° C. was added piperidine (10.28 g, 121 mmol) dropwise then the mixture was stirred at RT for 3 h. The mixture was concentrated then purified by MPLC over silica gel (eluting with DCM:MeOH 40:1) to afford W-5. LC/MS: $[M+H]^+=606.4$.

Step F—Synthesis of Intermediate W-6

To a solution of W-5 (4 g, 6.60 mmol) and triethylamine (1.93 ml, 13.84 mmol) in DCM (40 ml) was added di-tert-butyl dicarbonate (1.70 ml, 7.33 mmol) and the solution was stirred at RT overnight. The reaction mixture was washed with brine, dried over anhydrous $Na_2SO_4$, filtered and concentrated to provide W-6. LC/MS: $[M+H]^+=706.4$.

Step G—Synthesis of Intermediate W-7

To a solution of W-6 (2.1 g, 2.98 mmol) in THF (20 mL) at 0° C. was added 2 M aqueous LiOH (3 mL). The reaction mixture was stirred at 0° C. for 2 h then treated with 1N aqueous HCl (6 mL), and extracted with EA (3×50 ml). The combined organic layers were washed with brine, dried over anhydrous $Na_2SO_4$, filtered and concentrated to afford W-7. LC/MS: $[M+Na]^+=714.4$.

Step H—Synthesis of Intermediate W-8

To a solution of W-7 (8.75 g, 9.49 mmol), (2S,3S)-methyl 2-amino-3-hydroxybutanoate hydrochloride (2.41 g, 14.23 mmol) and HATU (4.69 g, 12.33 mmol) in DMF (88 ml) was added water (1.31 ml) followed by DIPEA (4.97 ml, 28.5 mmol) and the reaction was stirred for 1 h. The reaction was diluted with 10% aqueous LiCl solution, EA and water, decanted and the organic layer was washed with 10% aqueous LiCl, water, then brine, and dried over anhydrous $Na_2SO_4$, filtered and concentrated. The residue was purified by MPLC over silica gel (eluting with a gradient of 0-25% (20% MeOH/DCM) in DCM) to afford W-8.

Step I—Synthesis of Intermediate W-9

To a solution of W-8 (475 mg, 0.589 mmol) in MeOH (4.8 ml) was added 1N aqueous LiOH (2.36 ml, 2.36 mmol) and the reaction was stirred for 2 h. The mixture was concentrated, diluted with water, pH was adjusted to <4 via dropwise addition of 1 M aqueous HCl and the resulting solid was collected via filtration, rinsed with water and dried to provide W-9. LC/MS: $[M+H]^+=793.4$.

Step J—Synthesis of Intermediate W-10

To a solution of W-4 (30 g, 45.6 mmol) in DMF (300 ml) were added W-9 (36.2 g, 45.6 mmol) and DIEA (7.97 ml, 45.6 mmol). HATU (17.36 g, 45.6 mmol) was added at RT over 1 h then the mixture was stirred at RT for 1 h. The mixture was poured into water, filtered, and rinsed with water. The solid was dissolved in EA, and the organic layer was washed with brine, dried over anhydrous $Na_2SO_4$, filtered and concentrated. The residue was purified by MPLC over silica gel (eluting with a gradient of 2-5% MeOH in DCM) to give W-10. LC/MS: $[M+H_2O]^+=1413.5$.

Step K—Synthesis of Intermediate W-11

A solution of DCE (4.5 L) was bubbled with nitrogen for 30 min then heated to 70° C. Zhan's catalyst-1B (1.66 g, 2.26 mmol) was added followed by a solution of W-10 (45 g, 32.2 mmol) in DCE (900 ml, bubbled with nitrogen for 30 min), added dropwised at 70° C. over 30 mins. The mixture was then stirred at 70° C. for 1 h. The mixture was concentrated then purified by reverse phase flash chromatography (Column, C18-1 silica gel; mobile phase, ACN/$H_2O$ ($NH_4HCO_3$) (50-65% in 30 min, up to 100% in 15 min); Detector, UV 254 nm, 210 nm) to provide W-11. LC/MS: $[M+H]^+=1368.7$.

Step L—Synthesis of Intermediate W-12

To a solution of W-11 (30 g, 21.94 mmol) in MeOH (300 ml) was added $Pd(OH)_2$ (10 g, 14.24 mmol). The reaction was flushed three times with hydrogen then stirred overnight at RT under one atmosphere of hydrogen. The reaction was filtered then concentrated to provide W-12. LC/MS: $[M+H]^+=1370.1$.

Step M—Synthesis of Intermediate W

To a solution of W-12 (700 mg, 0.511 mmol) in DCM (30 mL) at 0° C. was added TFA (6 mL). The mixture was stirred at 0° C. for 2 h then concentrated under reduced pressure. The residue was dissolved in DCM (20 mL) and toluene (20 mL) and concentrated under reduced pressure. The residue was dissolved in DCM (20 mL) and HCl (4 M in dioxane, 0.7 mL) and concentrated again under reduced pressure. The residue was dissolved in ACN (30 mL) and water (30 mL), treated with 1 M aqueous HCl (0.7 mL) at 0° C. and lyophilized to afford intermediate W. LC/MS: [M+H]$^+$=1269.8.

Synthesis of Example 1

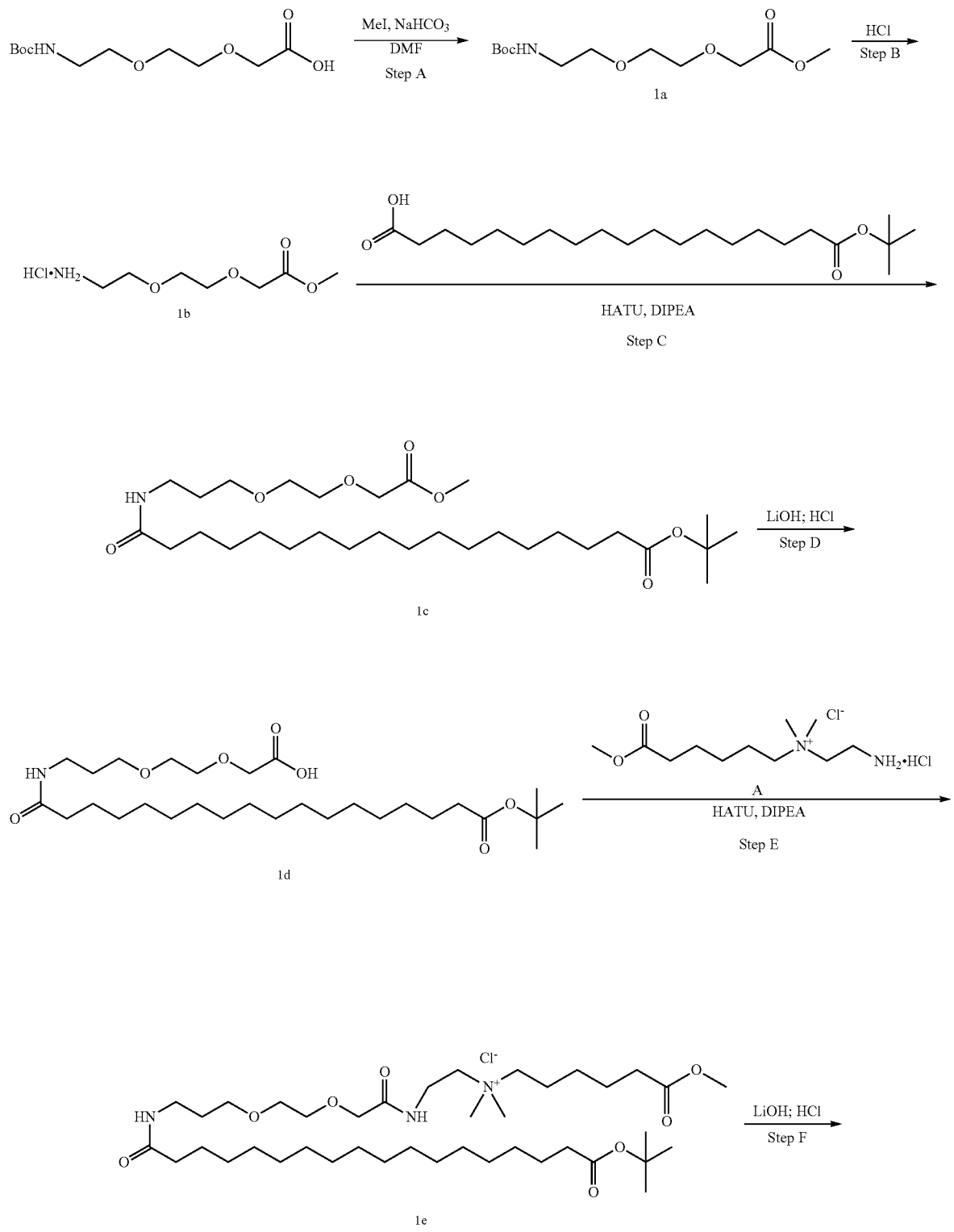

-continued
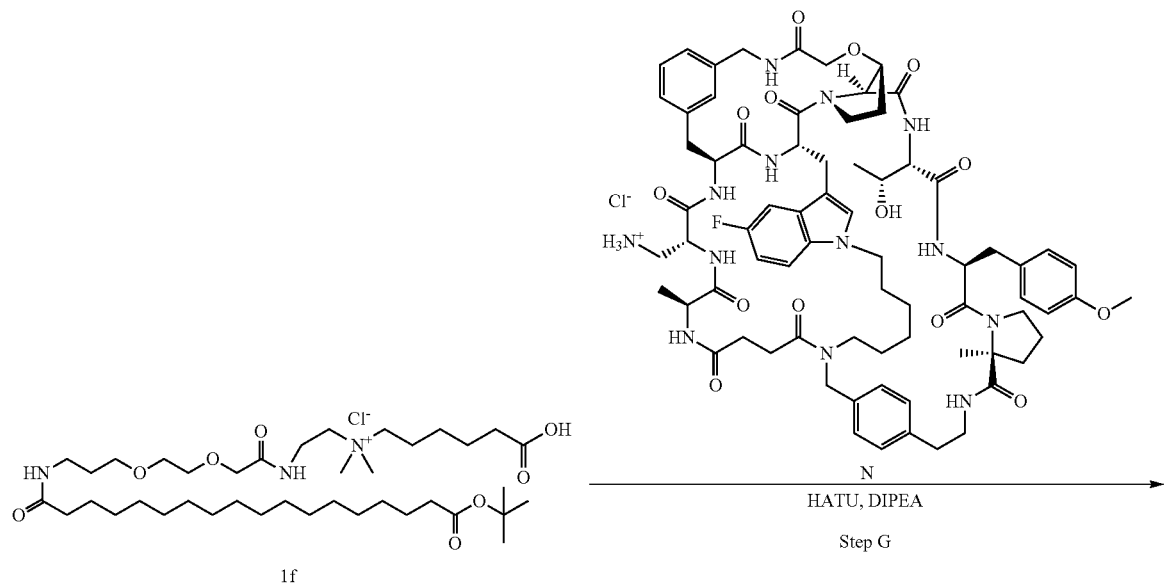
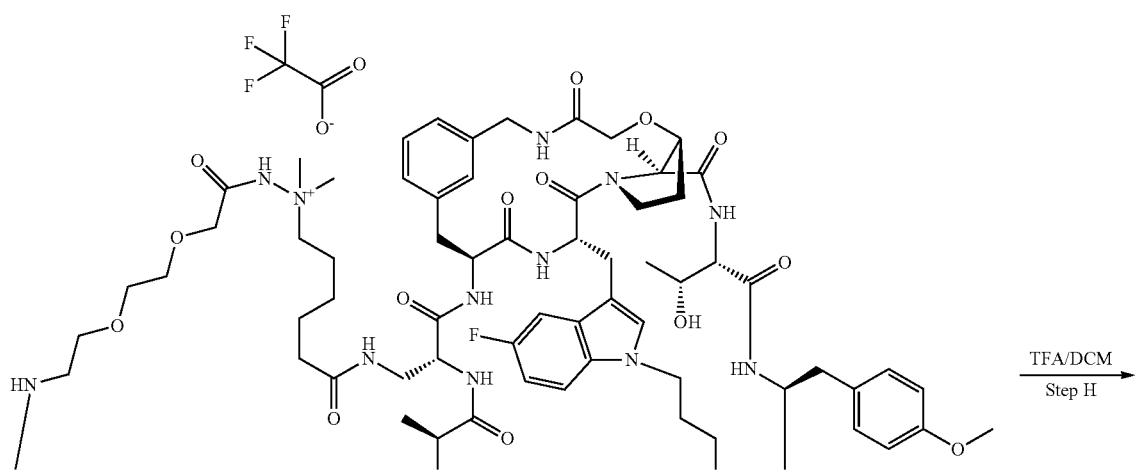
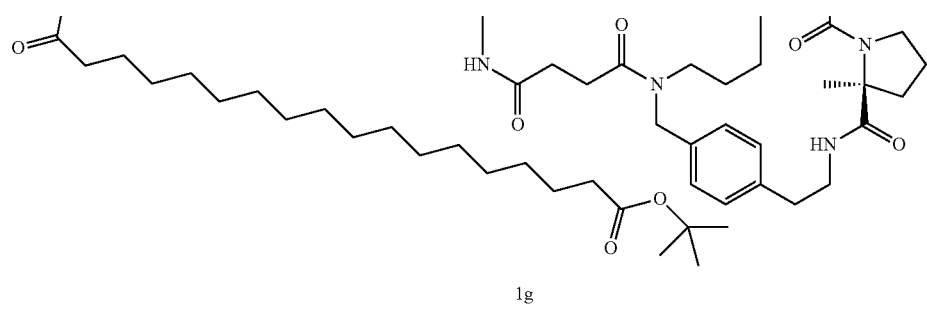

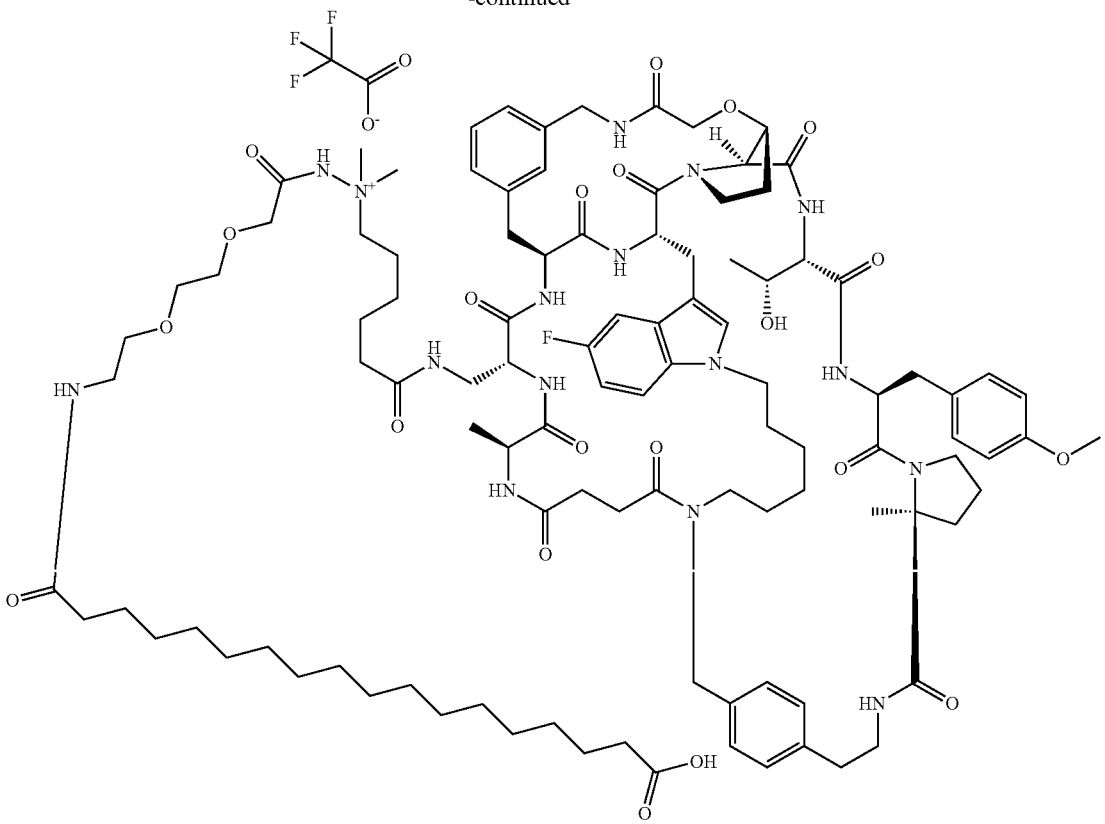

Example 1 (TFA salt)

Step A—Synthesis of Intermediate 1a

To a solution of 2,2-dimethyl-4-oxo-3,8,11-trioxa-5-azatridecan-13-oic acid (900 mg, 3.42 mmol) in DMF (10 mL) at RT were added NaHCO$_3$ (144 mg, 17.1 mmol) and MeI (0.641 mL, 10.3 mmol). The mixture was stirred for 24 h then diluted with brine and extracted with EtOAc. The combined organic layers were washed with brine, dried over MgSO$_4$ and filtered, and the filtrate was concentrated. The residue was purified by MPLC over silica gel (eluting with a gradient of 1%-50% EtOAc in PE) to give 1a. LC/MS: [M+H]$^+$=278.2.

Step B—Synthesis of Intermediate 1b

A solution of 1a (770 mg, 2.78 mmol) in 4 M HCl in dioxane (2 mL) was stirred at RT for 2 h then concentrated under reduced pressure. The residue was re-dissolved in DCM (5 mL) and concentrated under reduced pressure to 1b. LC/MS: [M+H]$^+$=178.2.

Step C—Synthesis of Intermediate 1c

To a solution of 18-(tert-butoxy)-18-oxooctadecanoic acid (347 mg, 0.936 mmol) in DMF (2 mL) at 0° C. were added 1b (200 mg, 0.936 mmol), HATU (356 mg, 0.936 mmol) and DIPEA (0.817 mL, 4.68 mmol) and the mixture was stirred at RT for 1 h. The solution was diluted with water and extracted with EtOAc. The combined organic layers were washed with brine, dried over MgSO$_4$, filtered and concentrated. The residue was purified by MPLC over silica gel (eluting with a gradient of 1%-5% MeOH in DCM) to provide 1c. LC/MS: [M+H]$^+$=530.5.

Step D—Synthesis of Intermediate 1d

To a solution of 1c (300 mg, 0.566 mmol) in THF (6 mL) at RT was added 0.5N aqueous LiOH (0.425 mL, 0.849 mmol) and the mixture was stirred for 1 h. The reaction was quenched with 1 M aqueous HCl (0.85 mL) and concentrated under reduced pressure. The residue was purified by MPLC over silica gel (eluting with a gradient of 1%-20% MeOH in DCM) to afford 1d. LC/MS: [M+H]$^+$=516.5.

Step E—Synthesis of Intermediate 1e

To a solution of 1d (260 mg, 0.504 mmol) in DMF (2 mL) and water (200 μL) at 0° C. were added intermediate A (292 mg, 1.01 mmol), HATU (383 mg, 1.01 mmol) and DIPEA (521 mg, 4.03 mmol) then the reaction was stirred at RT for 1 h. The solution was quenched with water (50 μL) and purified by reverse phase MPLC over C18 (eluting with a gradient of acetonitrile in water (0.05% TFA)). The fractions containing the desired product were combined and concentrated. The residue was re-dissolved in DCM (5 mL) and HCl (4N in dioxane, 0.2 mL). The resulting mixture was concentrated under reduced pressure, the residue was re-dissolved in acetonitrile (10 mL) and water (10 mL), treated with 1 N aqueous HCl (0.6 mL) at 0° C., then lyophilized to give 1e. LC/MS: [M]$^+$=714.6.

Step F—Synthesis of Intermediate 1f

To a solution of 1e (170 mg, 0.227 mmol) in THF (1.7 mL) at 0° C. was added 2 M aqueous LiOH (0.227 mL, 0.453 mmol) and the mixture was stirred at 0° C. for 2 h. The solution was quenched with 1 M aqueous HCl (450 μL) and purified by reverse phase MPLC over C18 (eluting with a gradient of acetonitrile in water). The fractions containing the desired product were combined and concentrated. The residue was re-dissolved in acetonitrile (5 mL) and water (5 mL), treated with 1 N aqueous HCl (0.2 mL) at 0° C. and lyophilized to afford 1f. LC/MS: [M]$^+$=700.6. $^1$H NMR (400 MHz, CDCl$_3$): δ 4.06 (s, 2H), 3.80-3.64 (m, 6H), 3.57 (t, J=5.7 Hz, 2H), 3.48 (t, J=6.8 Hz, 2H), 3.45-3.36 (m, 4H), 3.17 (s, 6H), 2.32 (t, J=7.2 Hz, 2H), 2.22 (td, J=7.5, 6.0 Hz, 4H), 1.90-1.80 (m, 2H), 1.77-1.67 (m, 2H), 1.66-1.54 (m, 4H), 1.53-1.42 (m, 11H), 1.38-1.29 (d, J=5.8 Hz, 24H).

Step G—Synthesis of Intermediate 1 g

To a solution of intermediate N (35.0 mg, 0.024 mmol) in DMF (200 μL) and water (100 μL) at 0° C. were added if (27.0 mg, 0.037 mmol), HATU (13.95 mg, 0.037 mmol) and DIPEA (21.36 μL, 0.122 mmol) then the reaction was stirred at RT for 1 h. The solution was quenched with water (200 μL) and purified by reverse phase MPLC over C18 (eluting with a gradient of acetonitrile in water (+0.05% TFA)) to afford 1 g. LC/MS: [(M+H)/2)]$^+$=1039.2.

Step H—Synthesis of Example 1 (TFA Salt)

To a solution of 1 g (35.0 mg, 0.016 mmol) in DCM (1 mL) at 0° C. was added TFA (1 mL)) then the reaction was stirred at RT for 1 h. The mixture was concentrated under reduced pressure and the residue was purified by reverse phase MPLC over C18 (eluting with a gradient of acetonitrile in water (+0.05% TFA)) to give Example 1 (TFA salt). LC/MS: [M]$^+$=2020.2.

Synthesis of Example 2

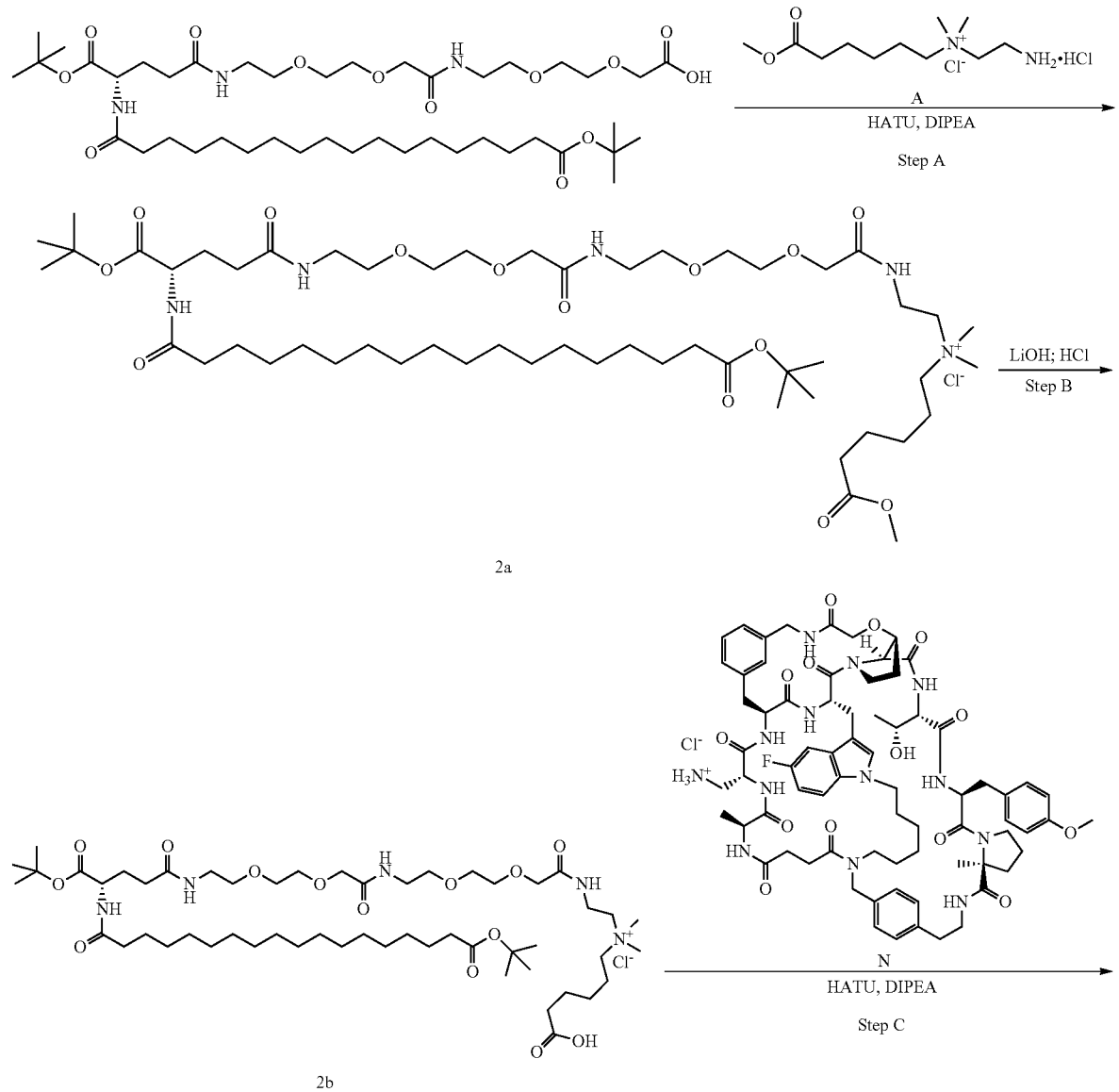

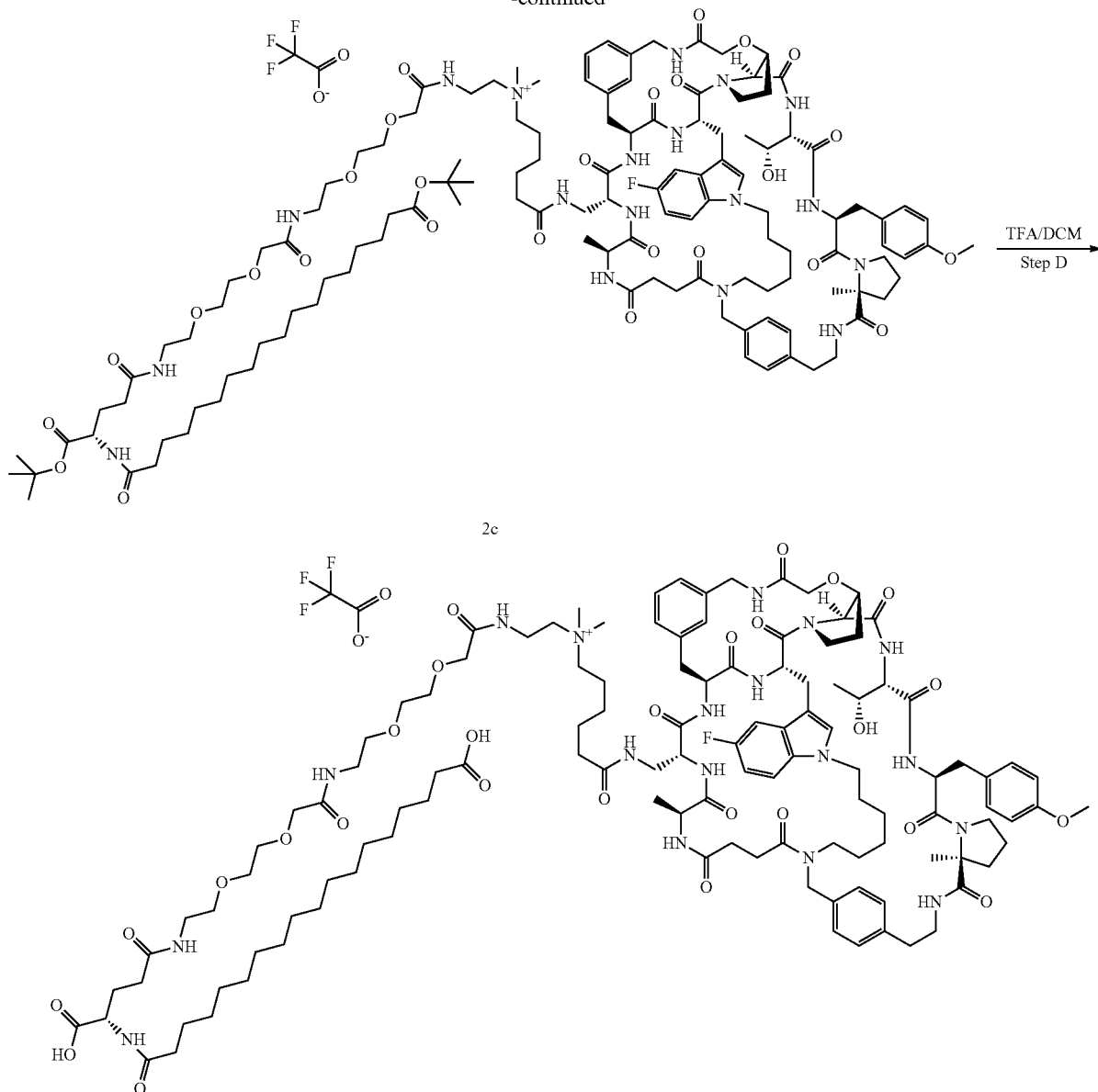

Example 2 (TFA salt)

Step A—Synthesis of Intermediate 2a

To a solution of (S)-22-(tert-butoxycarbonyl)-43,43-dimethyl-10,19,24,41-tetraoxo-3,6,12,15,42-pentaoxa-9,18,23-triazatetratetracontan-1-oic acid (250 mg, 0.295 mmol, the synthesis of which is described in Example 9, page 90, of WO 2009/115469) in DMF (300 μL) and water (50 μL) at 0° C. were added intermediate A (103 mg, 0.355 mmol), HATU (124 mg, 0.325 mmol) and DIPEA (153 mg, 1.18 mmol). The mixture was stirred at RT for 1 h then quenched with water (50 μL) and purified by reverse phase MPLC over C18 (eluting with a gradient of acetonitrile in water (+0.05% TFA)). The fractions containing the desired product were combined and concentrated. The residue was re-dissolved in DCM (5 mL) and 4 N HCl in dioxane (0.1 mL) then concentrated under reduced pressure. The residue was re-dissolved in acetonitrile (10 mL) and water (10 mL), treated with 1 N aqueous HCl (0.4 mL) at 0° C. and lyophilized to afford 2a. LC/MS: [M]$^+$=1044.7.

Step B—Synthesis of Intermediate 2b

To a solution of 2a (50.0 mg, 0.046 mmol) in THF (0.5 mL) at 0° C. was added aqueous LiOH (0.069 mL, 0.139 mmol, 2 N) and the mixture was stirred at RT for 2 h. The solution was quenched with 1 M aqueous HCl (140 μL) and purified by reverse phase MPLC over C18 (eluting with a gradient of acetonitrile in water (+0.05% TFA)). The fractions containing the desired product were combined and concentrated. The residue was re-dissolved in acetonitrile (5 mL) and water (5 mL), treated with 1 N aqueous HCl (0.1 mL) at 0° C. and lyophilized to afford 2b. LC/MS: [M]$^+$=1030.8.

Step C—Synthesis of Intermediate 2c

To a solution of intermediate N (20.0 mg, 0.014 mmol) in DMF (100 μL) and water (50 μL) at 0° C. were added 2b (22.4 mg, 0.021 mmol), HATU (7.97 mg, 0.021 mmol) and DIPEA (9.03 mg, 0.070 mmol). The mixture was stirred at RT for 1 h then quenched with water (50 μL) and purified by reverse phase MPLC over C18 (eluting with a gradient of acetonitrile in water (+0.05% TFA)) to provide 2c. LC/MS: [(M+H)/2)]$^+$=1204.3.

Step D—Synthesis of Example 2 (TFA Salt)

To a solution of 2c (12.0 mg, 4.76 μmol) in DCM (0.5 mL) at 0° C. was added TFA (0.5 mL) then the mixture was stirred at RT for 1 h. The solution was concentrated under reduced pressure and the residue was purified by reverse phase MPLC over C18 (eluting with a gradient of acetonitrile in water (+0.05% TFA)) to afford Example 2 (TFA salt). LC/MS: [M]$^+$=2294.3.

Synthesis of Example 3

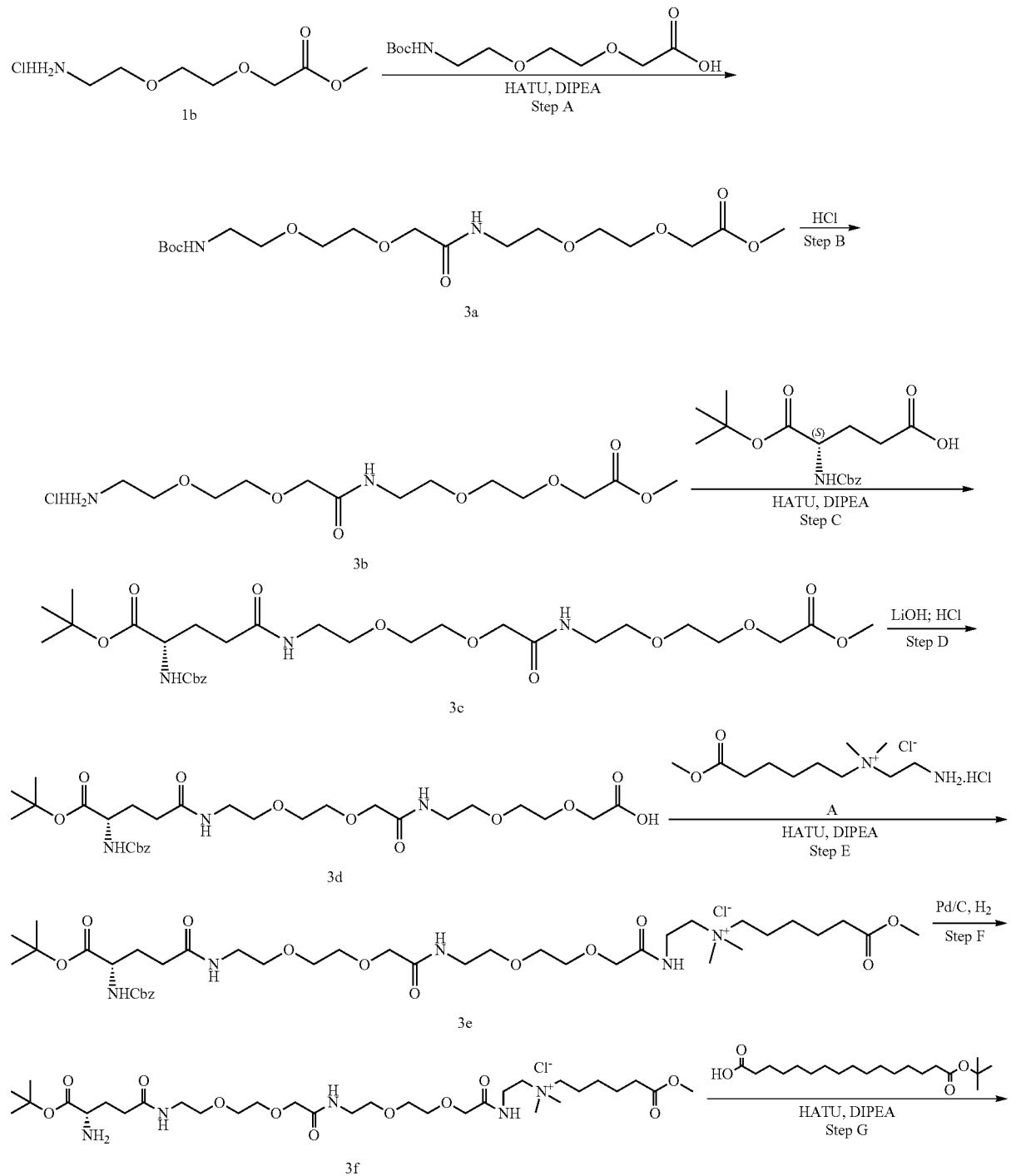

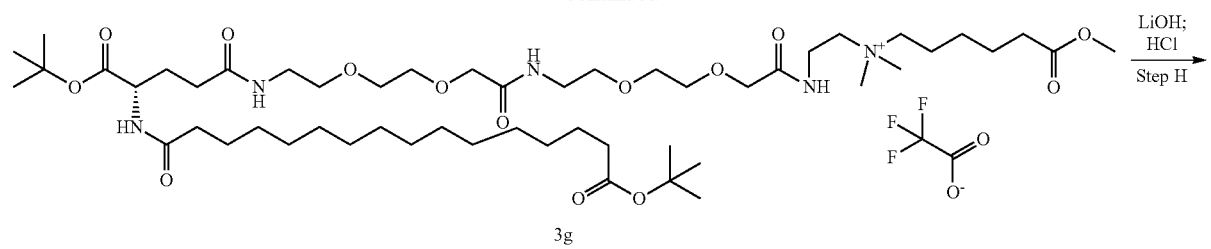
3g
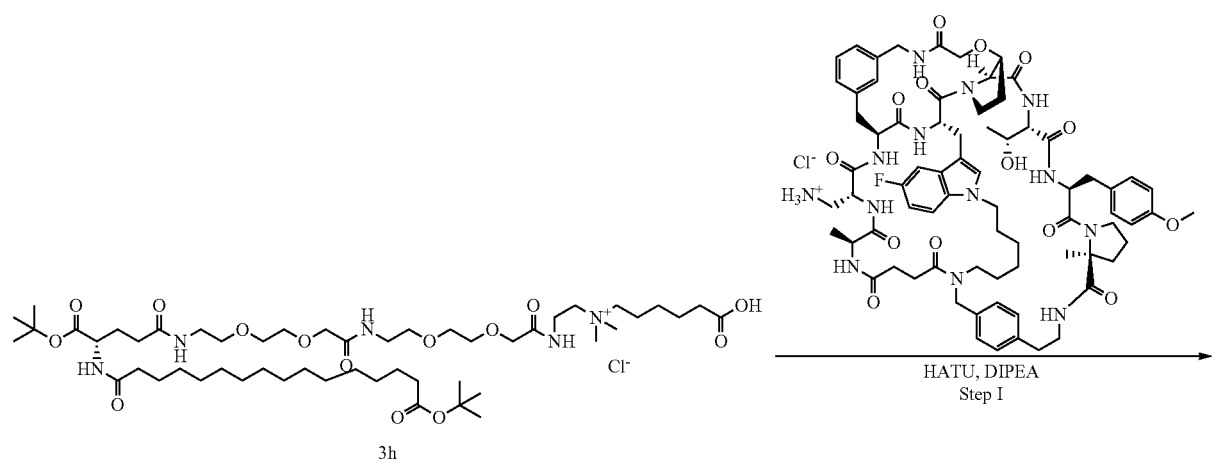
3h
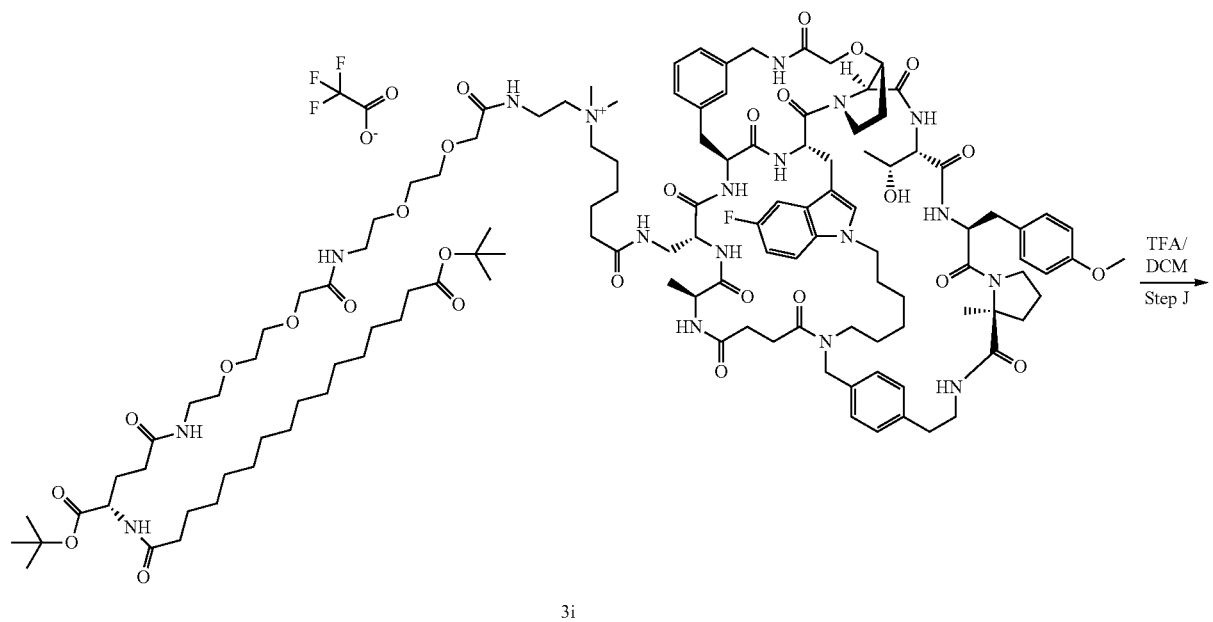
3i

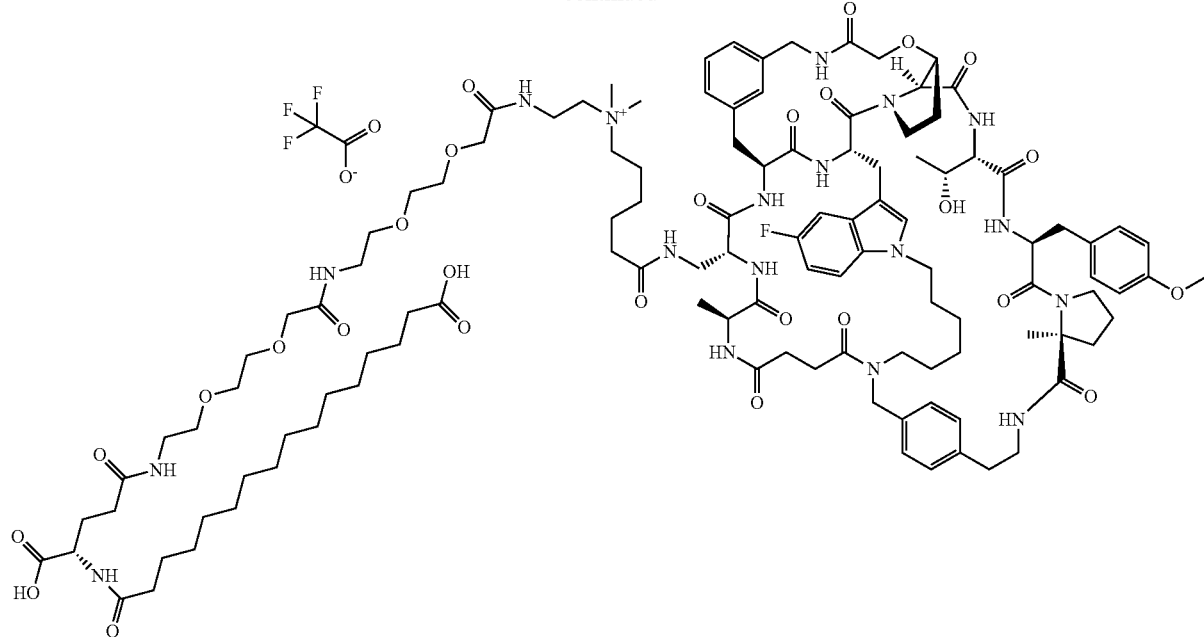

Example 3 (TFA salt)

Step A—Synthesis of Intermediate 3a

To a solution of 2,2-dimethyl-4-oxo-3,8,11-trioxa-5-aza-tridecan-13-oic acid (3.33 g, 12.6 mmol) in DMF (30 mL) at 0° C. were added 1b (2.70 g, 12.6 mmol), HATU (4.80 g, 12.6 mmol) and DIPEA (6.53 g, 50.5 mmol) then the solution was stirred at RT for 1 h. The mixture was diluted with brine, extracted with EtOAc, washed with brine, dried over $MgSO_4$ and filtered. The filtrate was concentrated under reduced pressure and the residue was purified by MPLC over silica gel (eluting with a gradient of 1%-8% MeOH in DCM) to provide 3a. LC/MS: $[M+H]^+$=445.3.

Step B—Synthesis of Intermediate 3b

A solution of 3a (3.00 g, 7.10 mmol) in 4 M HCl in dioxane (30 mL) was stirred at RT for 2 h then concentrated. The residue was re-dissolved in DCM (30 mL) and concentrated under reduced pressure to afford 3b. LC/MS: $[M+H]^+$=323.2.

Step C—Synthesis of Intermediate 3c

To a solution of (S)-4-(((benzyloxy)carbonyl)amino)-5-(tert-butoxy)-5-oxopentanoic acid (0.940 g, 2.79 mmol) in DMF (10 mL) at 0° C. were added 3b (1.00 g, 2.79 mmol), HATU (1.06 g, 2.79 mmol) and DIPEA (1.80 g, 13.9 mmol) then the mixture was stirred at RT for 1 h. The solution was diluted with brine, extracted with EtOAc, washed with brine, dried over $MgSO_4$ and filtered. The filtrate was concentrated under reduced pressure and the residue was purified by MPLC over silica gel (eluting with a gradient of 1%-8% MeOH in DCM) to provide 3c. LC/MS: $[M+H]^+$=642.3.

Step D—Synthesis of Intermediate 3d

To a solution of 3c (2.00 g, 3.12 mmol) in THF (20 mL) at 0° C. was added 2 M aqueous LiOH (3.12 mL, 6.23 mmol) and the mixture was stirred at 0° C. for 2 h. The solution was quenched with 1 M aqueous HCl (6.3 mL) and purified by reverse phase MPLC over C18 (eluting with a gradient of acetonitrile in water (+0.05% TFA)) to provide 3d. LC/MS: $[M+H]^+$=628.3.

Step E—Synthesis of Intermediate 3e

To a solution of 3d (1.70 g, 2.71 mmol) in DMF (10 mL) and water (1 mL) at 0° C. were added intermediate A (1.57 g, 5.42 mmol), HATU (2.06 g, 5.42 mmol) and DIPEA (2.80 g, 21.7 mmol) then the mixture was stirred at RT for 1 h. The reaction was quenched with water (2 mL) and purified by reverse phase MPLC over C18 (eluting with a gradient of acetonitrile in water (+0.05% TFA)). The fractions containing the desired product were combined and concentrated. The residue was re-dissolved in DCM (20 mL) and treated with 4 N HCl in dioxane (0.35 mL). The resulting mixture was concentrated, and the residue was re-dissolved in acetonitrile (30 mL) and water (30 mL), treated with 1 N aqueous HCl (1.3 mL) at 0° C. and lyophilized to afford 3e. LC/MS: $[M]^+$=826.5.

Step F—Synthesis of Intermediate 3f

A solution of 3e (1.10 g, 1.28 mmol) and 10% Pd—C (110 mg, 0.103 mmol) in THF (30 mL) was hydrogenated at 1.5 atm for 4 h. The mixture was filtered, and the filtrate was concentrated to give 3f. LC/MS: $[M]^+$=692.5.

Step G—Synthesis of Intermediate 3 g

To a solution of 16-(tert-butoxy)-16-oxohexadecanoic acid (127 mg, 0.371 mmol) in DMF (2 mL) and water (200 μL) at 0° C. were added 3f (180 mg, 0.247 mmol), HATU (188 mg, 0.494 mmol) and DIPEA (256 mg, 1.98 mmol) then the mixture was stirred at RT for 1 h. The solution was quenched with water (50 μL) and purified by reverse phase MPLC over C18 (eluting with a gradient of acetonitrile in water (+0.05% TFA)) to give 3 g. LC/MS: [M]+=1016.7.

Step H Synthesis of Intermediate 3 h

To a solution of 3 g (190 mg, 0.168 mmol) in THF (2 mL) 0° C. was added 2 M aqueous LiOH (0.252 mL, 0.504 mmol) and the mixture was stirred at 0° C. for 1 h. The solution was quenched with 1 M aqueous HCl (500 μL) and purified by reverse phase MPLC over C18 (eluting with a gradient of acetonitrile in water (+0.05% TFA)). The fractions containing the desired product were combined and concentrated. The residue was re-dissolved in acetonitrile (20 mL) and water (20 mL), treated with 1 N aqueous HCl (0.12 mL) at 0° C. and lyophilized to afford 3 h. LC/MS: [M]+=1002.8. $^1$H NMR (400 MHz, CD$_3$OD): δ 4.07 (t, J=6.9 Hz, 1H), 3.84 (dd, J=12.2, 3.0 Hz, 4H), 3.49 (d, J=9.4 Hz, 10H), 3.40 (dt, J=14.5, 4.8 Hz, 4H), 3.29 (s, 4H), 3.21 (s, 4H), 2.98 (d, J=2.9 Hz, 6H), 2.23-1.98 (m, 8H), 1.92 (s, 1H), 1.66 (s, 3H), 1.59-1.33 (m, 6H), 1.33-1.06 (m, 40H).

Step I—Synthesis of Intermediate 3i

To a solution of intermediate N (30.0 mg, 0.021 mmol) in DMF (200 μL) and water (100 μL) at 0° C. were added 3 h (32.7 mg, 0.031 mmol), HATU (12.0 mg, 0.031 mmol) and DIPEA (13.6 mg, 0.105 mmol) and the mixture was stirred at RT for 1 h. The solution was quenched with water (50 μL) and purified by reverse phase MPLC over C18 (eluting with a gradient of acetonitrile in water (+0.05% TFA)) to afford 3i. LC/MS: [(M+H)/2)]+=1190.4.

Step J—Synthesis of Example 3 (TFA Salt)

To a solution of 3i (25.0 mg, 10.0 μmol) in DCM (1 mL) at 0° C. was added TFA (1 mL) then the mixture was stirred at RT for 1 h. The solution was concentrated under reduced pressure and the residue was purified by reverse phase MPLC over C18 (eluting with a gradient of acetonitrile in water (+0.05% TFA)) to afford Example 3 (TFA salt). LC/MS: [M]+=2266.3.

Synthesis A of Example 4

265 -continued 266
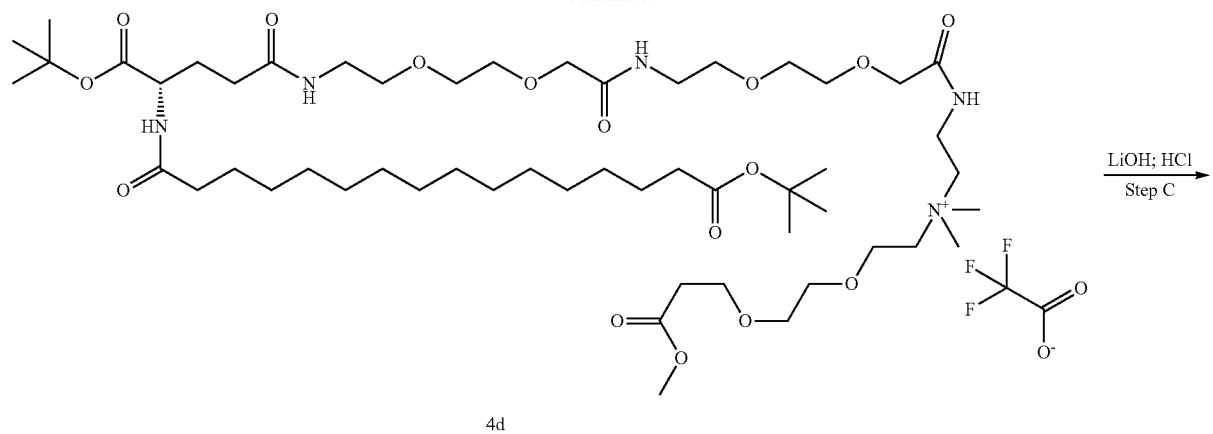
4d
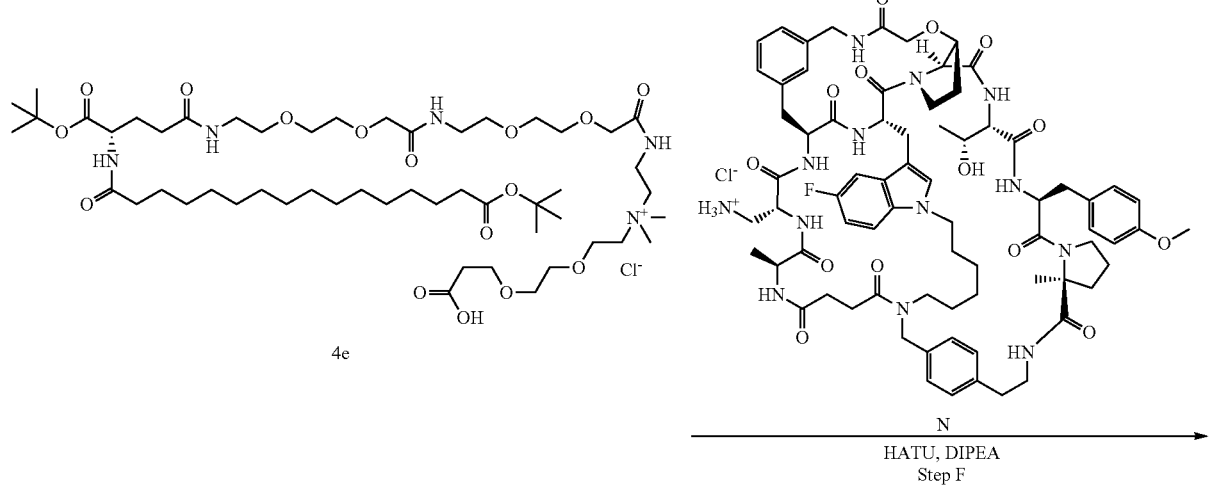
4e
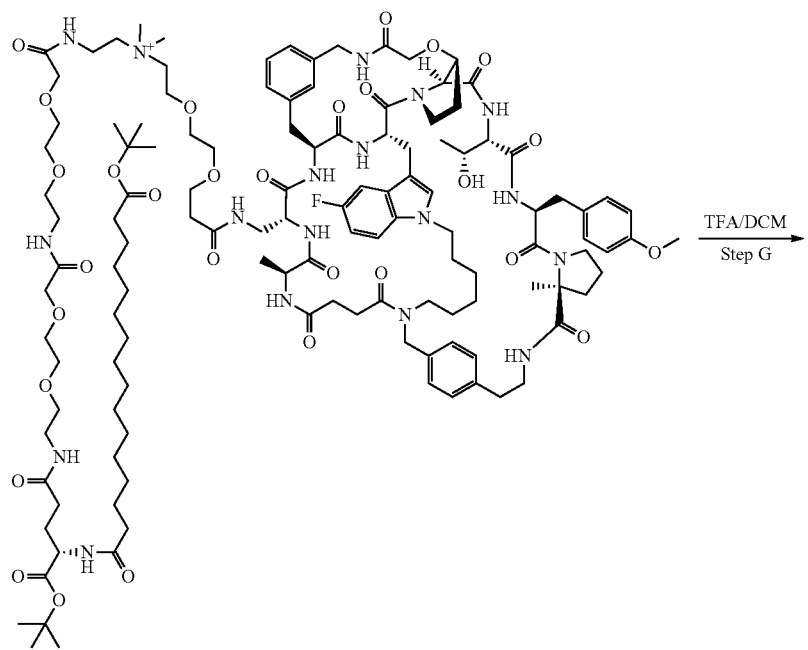
4f

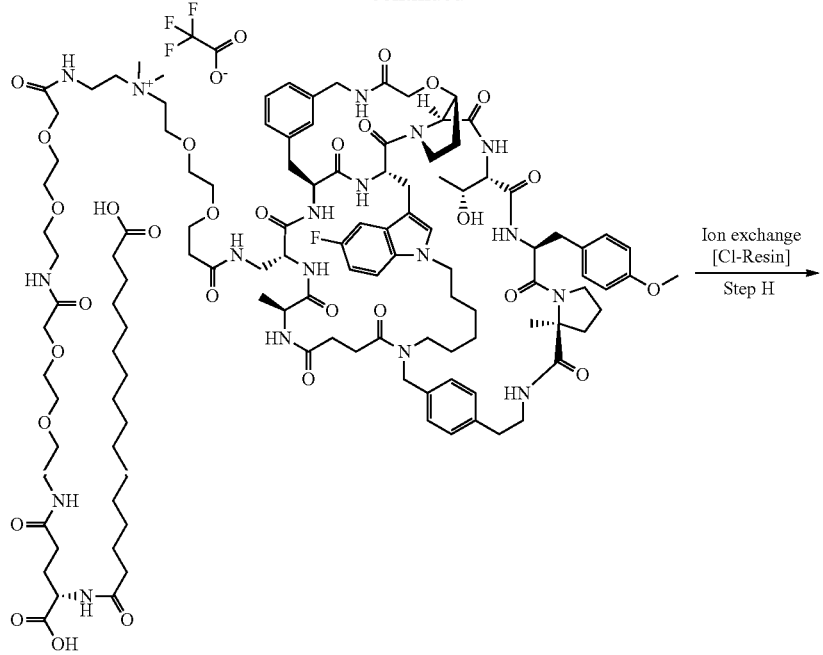

Example 4 (TFA salt)

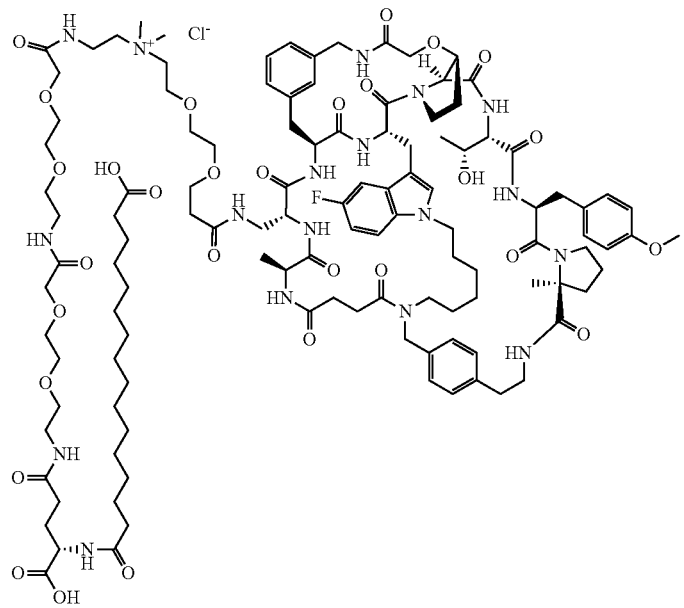

Example 4 (Cl salt)

Step A—Synthesis of Intermediate 4a

To a solution of 3c (700 mg, 1.091 mmol) in THF (20 mL) at RT was added 10% Pd/C (70 mg, 0.066 mmol) then the mixture was degassed with hydrogen 3 times and stirred at RT for 4 h under hydrogen at 1.5 atm. The final mixture was filtered over Celite and the filtrate was concentrated under reduced pressure to provide 4a. LC/MS: [M+H]$^+$=508.3.

Step B—Synthesis of Intermediate 4b

To a solution of 4a (510 mg, 1.005 mmol) in DMF (5 mL) at 0° C. were added 16-(tert-butoxy)-16-oxohexadecanoic acid (344 mg, 1.005 mmol), HATU (382 mg, 1.005 mmol) and DIEA (0.526 mL, 3.01 mmol) and the mixture was stirred at 0° C. for 1 h. The solution was quenched with water (1 mL) and purified by reverse phase MPLC over C18 (eluting with a gradient of acetonitrile in water (+0.05% TFA)) to afford 4b. LC/MS: [M+H]$^+$=832.6.

Step C—Synthesis of Intermediate 4c

To a solution of 4b (490 mg, 0.589 mmol) in THF (5 mL) at 0° C. was added 1 M aqueous LiOH (1.178 mL, 1.178 mmol) and the mixture was stirred at 0° C. for 1 h. The solution was quenched with 1 M aqueous HCl (1.2 mL) and purified by reverse phase MPLC over C18 (eluting with a gradient of acetonitrile in water) to give 4c. LC/MS: [M+H]$^+$ =818.6.

Step D—Synthesis of Intermediate 4d

To a solution of 4c (250 mg, 0.306 mmol) in DMF (2 mL) and water (0.2 mL) at 0° C. were added intermediate B (102 mg, 0.306 mmol), HATU (116 mg, 0.306 mmol) and DIEA (0.267 mL, 1.528 mmol) and the mixture was stirred at 0° C. for 1 h. The solution was diluted with water (500 μL) and purified by reverse phase MPLC over C18 (eluting with a gradient of acetonitrile in water (+0.05% TFA)). The fractions containing the desired product were combined and concentrated. The residue was re-dissolved in acetonitrile (10 mL) and water (10 mL), and lyophilized to afford 4d. LC/MS: [M]$^+$=1062.7.

Step E—Synthesis of Intermediate 4e

To a solution of 4d (240 mg, 0.204 mmol) in THF (2.5 mL) at 0° C. was added 1 M aqueous LiOH (0.408 mL, 0.408 mmol) and the mixture was stirred at 0° C. for 1 h. The solution was quenched with 1 M aqueous HCl (0.41 mL) and purified by reverse phase MPLC over C18 (eluting with a gradient of acetonitrile in water (+0.05% TFA)). The fractions containing the desired product were combined and concentrated. The residue was re-dissolved in acetonitrile (5 mL) and water (5 mL), treated with 1 N aqueous HCl (0.22 mL) at 0° C. and lyophilized to afford 4e. LC/MS: [M]$^+$=1048.7. $^1$H NMR (300 MHz, CD$_3$OD): δ 4.26 (dd, J=9.1, 5.1 Hz, 1H), 4.05 (s, 2H), 4.02 (s, 2H), 3.96 (s, 2H), 3.83-3.51 (m, 24H), 3.47 (t, J=5.5 Hz, 2H), 3.39 (t, J=5.6 Hz, 3H), 3.22 (s, 6H), 2.42 (t, J=6.1 Hz, 2H), 2.30 (t, J=7.9 Hz, 2H), 2.21 (t, J=7.6 Hz, 4H), 2.18-2.02 (m, 1H), 1.91 (dd, J=14.2, 8.5 Hz, 1H), 1.59 (dd, J=15.7, 8.0 Hz, 5H), 1.47 (s, 9H), 1.45 (s, 9H), 1.31 (s, 20H).

Step F—Synthesis of Intermediate 4f

To a solution of intermediate N (48 mg, 0.034 mmol) in DMF (500 μL) and water (250 μL) at 0° C. were added 4e (36.4 mg, 0.034 mmol), HATU (19.13 mg, 0.050 mmol) and DIEA (21.68 mg, 0.168 mmol) and the mixture was stirred at 0° C. for 1 h. The final solution was quenched with water (30 μL) and purified by reverse phase MPLC over C18 (eluting with a gradient of acetonitrile in water (+0.05% TFA)) to give 4f LC/MS: [(M+H)/2)]$^+$=1213.3.

Step G—Synthesis of Example 4 (TFA Salt)

To a solution of 4f (38 mg, 0.015 mmol) in DCM (6 mL) at 0° C. was added TFA (6 mL) then the mixture was stirred at RT for 1 h. The final solution was concentrated under reduced pressure and the residue was purified by reverse phase MPLC over C18 (eluting with a gradient of acetonitrile in water (+0.05% TFA)) to provide Example 4 (TFA salt). LC/MS: [(M+H)/2)]$^+$=1157.0.

Step H—Synthesis of Example 4 (Cl Salt)

5 g of AG-MP-1M Cl resin (Bio-RAD, cat #141-1841) was packed in a column and washed with water (2×10 mL) followed by 20% acetonitrile in water (2×10 mL). A solution of Example 4 (TFA salt) in 50% acetonitrile (10 mL) was loaded onto the column, then the compound was eluted with 50% acetonitrile (50 mL). The collected fractions were lyophilized to give Example 4 (Cl salt). LC/MS: [M]$^+$=2312.5.

Synthesis B of Example 4

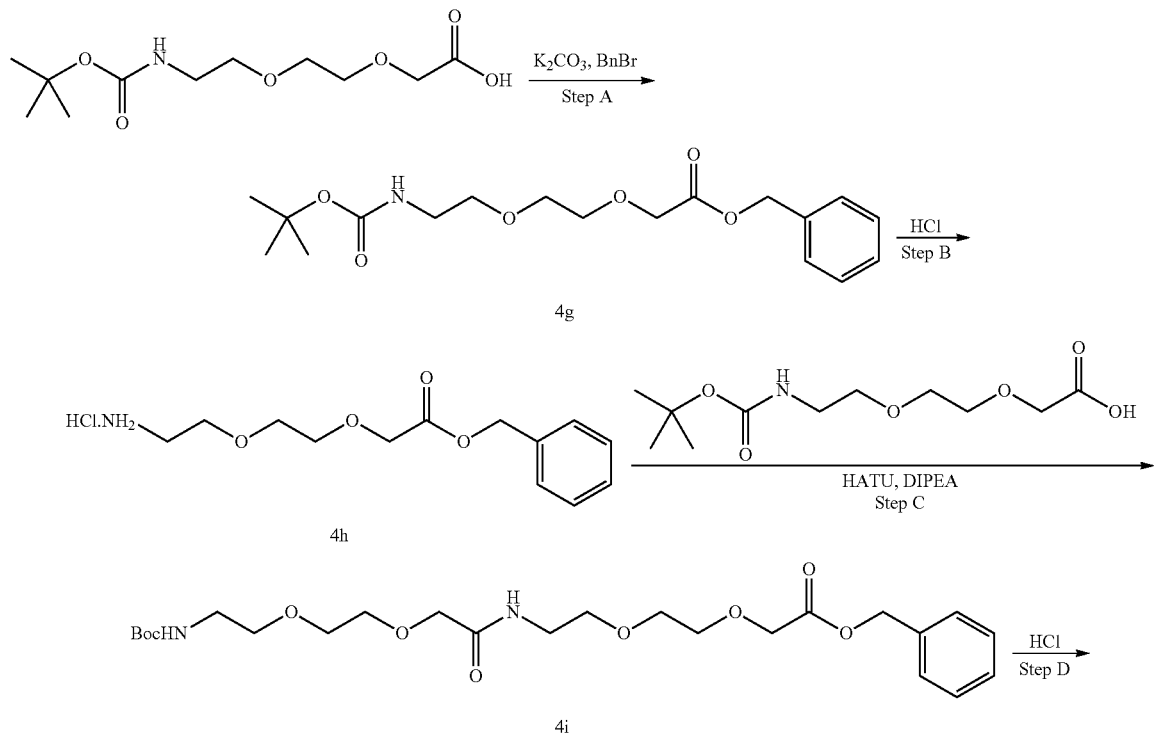

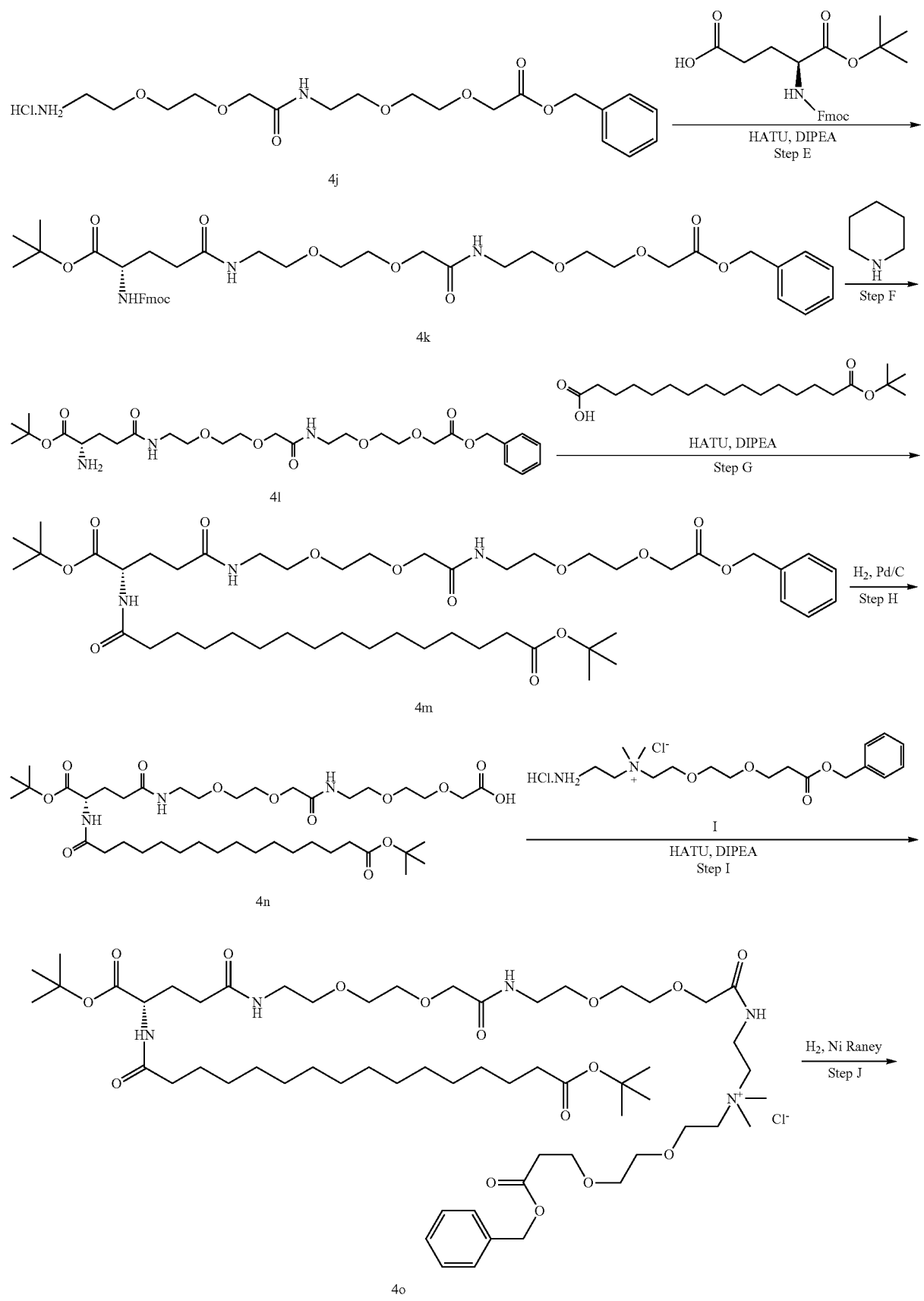

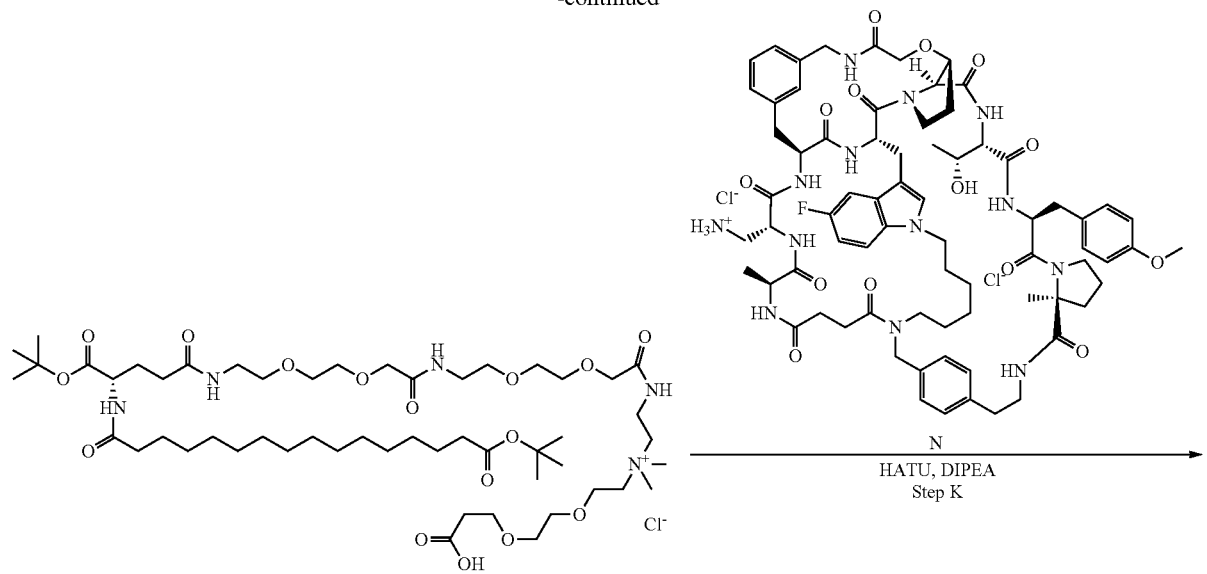
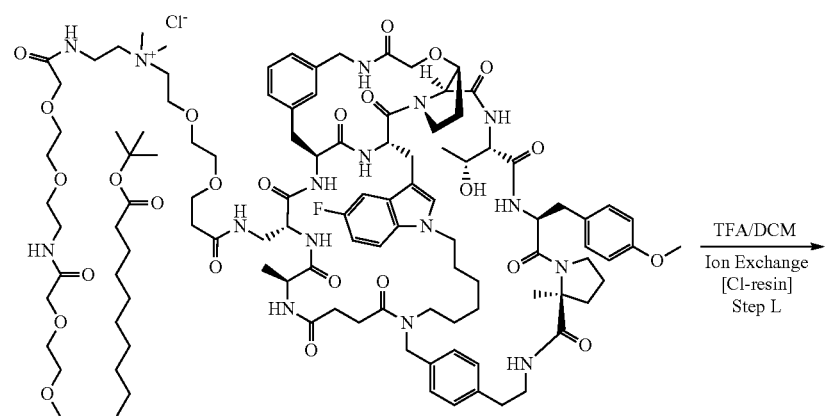
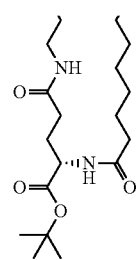

-continued

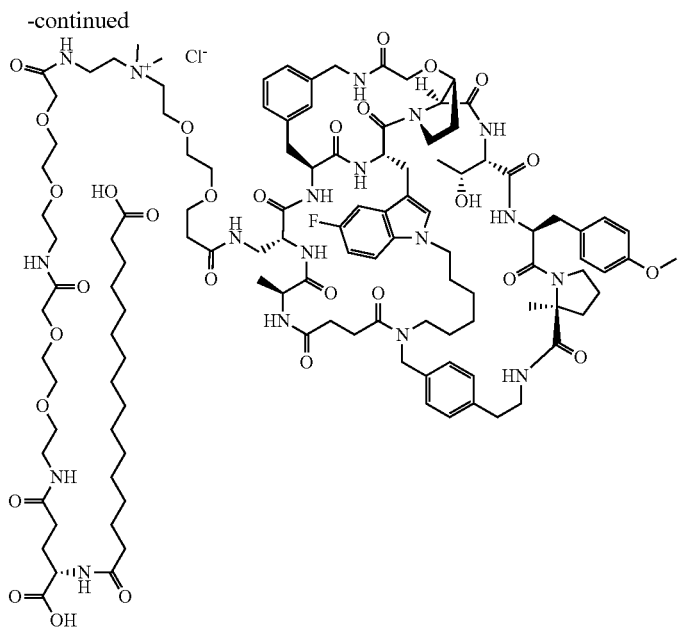

Example 4 (Cl salt)

Step A—Synthesis of Intermediate 4 g

To a solution of 2,2-dimethyl-4-oxo-3,8,11-trioxa-5-azatridecan-13-oic acid (8.55 g, 32.5 mmol) in acetone (125 ml) at RT was added potassium carbonate (11.9 g, 86 mmol) followed by benzyl bromide (5 ml, 42.0 mmol) and the reaction was heated at reflux for 1.5 h. The final mixture was filtered over Celite and concentrated. The residue was purified by MPLC over silica gel (eluting with a gradient of 0%-50% EtOAc in hexanes) to give 4 g. LC/MS: $[M+Na]^+=376.1$.

Step B—Synthesis of Intermediate 4 h

To a solution of 4 g (9.88 g, 28.0 mmol) in dioxane (120 ml) was added 4 N HCl in dioxane (28.0 ml, 112 mmol) then the reaction mixture was heated at 50° C. for 4 h and at 60° C. for another 1.5 h. The final mixture was concentrated to provide 4 h. LC/MS: $[M+H]^+=254.5$.

Step C—Synthesis of Intermediate 4i

To a solution of 4 h (6.8 g, 23.47 mmol) and 2,2-dimethyl-4-oxo-3,8,11-trioxa-5-azatridecan-13-oic acid (6.45 g, 24.50 mmol) in DMF (35 ml) and acetonitrile (105 ml) was added DIPEA (15 ml, 86 mmol). The reaction mixture was cooled to 5° C. and HATU (10.03 g, 26.4 mmol) was added portion wise. The solution was stirred at RT for 1.5 h then concentrated, diluted with water, and extracted with IPAc. The combined organic layers were washed with water, 5% LiCl aqueous solution, brine, dried over MgSO$_4$, filtered and concentrated. The residue was purified by MPLC over silica gel (eluting with a gradient of 10%-90% EtOAc in hexanes followed by a gradient of 60%-90% (EtOAc:EtOH 3:1) in hexanes) to give 4i. LC/MS: $[M+Na]^+=521.2$.

Step D—Synthesis of Intermediate 4j

To a solution of 4i (9.694 g, 19.44 mmol) in dioxane (50 ml) was added 4 N HCl in dioxane (5 mL, 20.00 mmol) then the reaction mixture was heated at 60° C. for 4 h. More 4 N HCl in dioxane (15 mL, 60.00 mmol) was added and the reaction mixture was heated for another 3 h. The final mixture was concentrated to provide 4j. LC/MS: $[M+H]^+=399.2$.

Step E—Synthesis of Intermediate 4k

To a solution of 4j (6.76 g, 15.55 mmol) and Fmoc-Glu-OtBu (7.282 g, 17.11 mmol) in acetonitrile (80 mL) and DMF (20 mL) was added DIEA (10.83 mL, 62.2 mmol). The reaction mixture was cooled to 5° C. and HATU (7.69 g, 20.22 mmol) was added portion wise. The solution was stirred for 1.5 h at RT then concentrated, diluted with water, and extracted with IPAc. The combined organic layers were washed with water, 5% LiCl aqueous solution, brine, dried over MgSO$_4$, filtered and concentrated. The residue was purified by MPLC over silica gel (eluting with a gradient of 30%-100% (EtOAc:EtOH 3:1) in hexanes) to provide 4k. LC/MS: $[M+Na]^+=828.3$.

Step F—Synthesis of Intermediate 4l

To a solution of 4k (4.82 g, 5.98 mmol) in acetonitrile (50 mL) at RT was added piperidine (3 mL, 30.4 mmol) and the reaction mixture was stirred for 3.5 h. The final mixture was diluted with acetonitrile and washed with hexanes, the acetonitrile layer was then concentrated, and the residue was taken in acetonitrile (50 mL) and water (50 mL) and lyophilized to give 4l. LC/MS: $[M+H]^+=584.2$.

Step G—Synthesis of Intermediate 4m

To a solution of 4l (3.49 g, 5.98 mmol) and 16-(tert-butoxy)-16-oxohexadecanoic acid (2.262 g, 6.60 mmol) in acetonitrile (40 mL) and DMF (10 mL) was added DIPEA (4 mL, 22.96 mmol). The reaction mixture was cooled to 5° C. and HATU (2.82 g, 7.42 mmol) was added portion wise then the solution was stirred at RT for 1.5 h. More 16-(tert-butoxy)-16-oxohexadecanoic acid (0.24 g, 2.505 mmol), DIPEA (0.5 mL, 9.19 mmol) and HATU (0.26 g, 2.78 mmol) were added and the mixture was stirred for 2 h. The final solution was concentrated, diluted with water, and extracted with IPAc.

The combined organic layers were washed with water, 5% LiCl aqueous solution, brine, dried over MgSO$_4$, filtered and concentrated. The residue was purified by MPLC over silica gel (eluting with a gradient of 20%-100% (EtOAc:EtOH 3:1) in hexanes) to give 4m. LC/MS: [M+H]$^+$=908.7.

Step H—Synthesis of Intermediate 4n

To a solution of 4m (4.896 g, 5.39 mmol) in MeOH (30 mL) at RT was added 10% Pd/C (0.066 g, 0.620 mmol). The mixture was degassed with hydrogen 3 times and stirred for 3 h at RT under hydrogen. The final mixture was filtered over Celite and the filtrate was concentrated under reduced pressure to provide 4n. LC/MS: [M+H]$^+$=819.8.

Step I—Synthesis of Intermediate 4o

To a solution of 4n (2.59 g, 3.17 mmol) in acetonitrile (30 mL) were added a suspension of intermediate I (1.436 g, 3.49 mmol) in DMF (6 mL) followed by DIEA (2.2 mL, 12.63 mmol). The reaction mixture was cooled to 5° C. and HATU (1.484 g, 3.90 mmol) was added portion wise. The solution was stirred for 1.5 h at RT then concentrated and washed with Et$_2$O. It was then diluted with DCM and further washed with brine:water 1:1. The aqueous layer was then extracted with dichloromethane, and the combined organic layers were washed with brine, dried over MgSO$_4$ and filtered. The filtrate was concentrated to afford 4o. LC/MS: [M]$^+$=1139.5.

Step J—Synthesis of Intermediate 4p

To a solution of 4o (3.20 mmol) in MeOH (99 mL) was added well shaken Raney Ni (2 mL). After 1 h, more well shaken Raney Ni (23 mL) was added as well as 0.1 M pH 4 potassium phosphate buffer (5 mL) and the resulting mixture was hydrogenated using a balloon filled with hydrogen for 3 h. More well shaken Raney Ni (8 mL) was then added as well as 0.1 M pH 4 potassium phosphate buffer (5 mL) and the mixture was further hydrogenated using a balloon filled with hydrogen for 6.5 h. The final mixture was filtered over Celite rinsing with DCM and the filtrate was concentrated to afford 4p. LC/MS: [M]$^+$=1048 [M]. $^1$H-NMR (CD$_3$CN, 500 MHz): δ 7.86 (s, 1H), 7.34 (s, 1H), 7.02 (d, J=7.6 Hz, 1H), 6.93 (s, 1H), 4.20-4.31 (m, 1H), 4.00 (s, 2H), 3.97 (s, 2H), 3.91 (s, 2H), 3.76-3.49 (m, 24H), 3.45 (q, J=5.2 Hz, 2H), 3.36 (q, J=5.4 Hz, 2H), 3.14 (s, 6H), 2.41 (t, J=6.0 Hz, 2H), 2.24 (t, J=7.3 Hz, 2H), 2.19 (t, J=7.4 Hz, 2H), 2.18 (t, J=7.4 Hz, 2H), 2.03 (dtd, J=5.2, 7.6, 13.0 Hz, 1H), 1.86 (dtd, J=4.8, 7.7, 13.7 Hz, 1H), 1.46 (s, 9H), 1.44 (s, 9H), 1.30 (s, 24H)

Step K—Synthesis of Intermediate 4q

Intermediate 4p (1.416 g, 1.305 mmol) was reacted with intermediate N and converted to 4q using conditions similar to those described in Synthesis of Example 9 Step C. LC/MS: [(M+H)/2]$^+$=1213.3

Step L—Synthesis of Example 4 (Cl Salt)

Intermediate 4q (3.44 g, 1.398 mmol) was converted to Example 4 (Cl salt) using conditions similar to those described in Synthesis A of Example 4, Steps G and H. LC/MS: [(M+H)/2]$^+$=1157.2.

Synthesis of Example 5

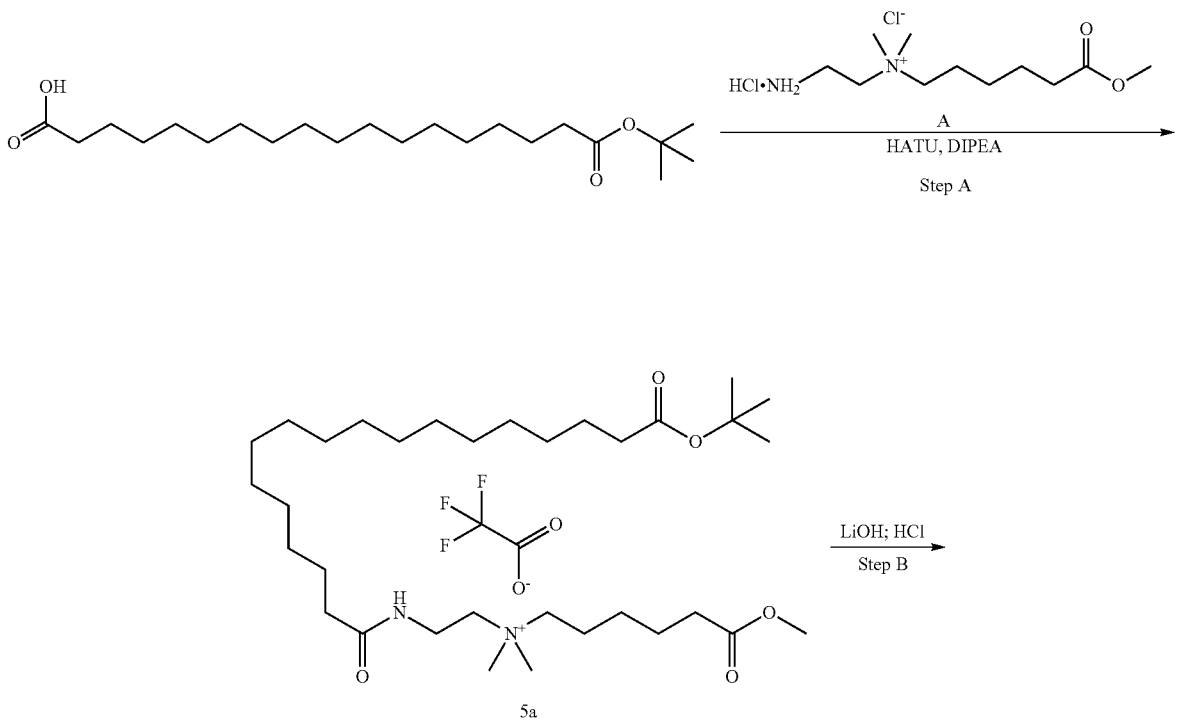

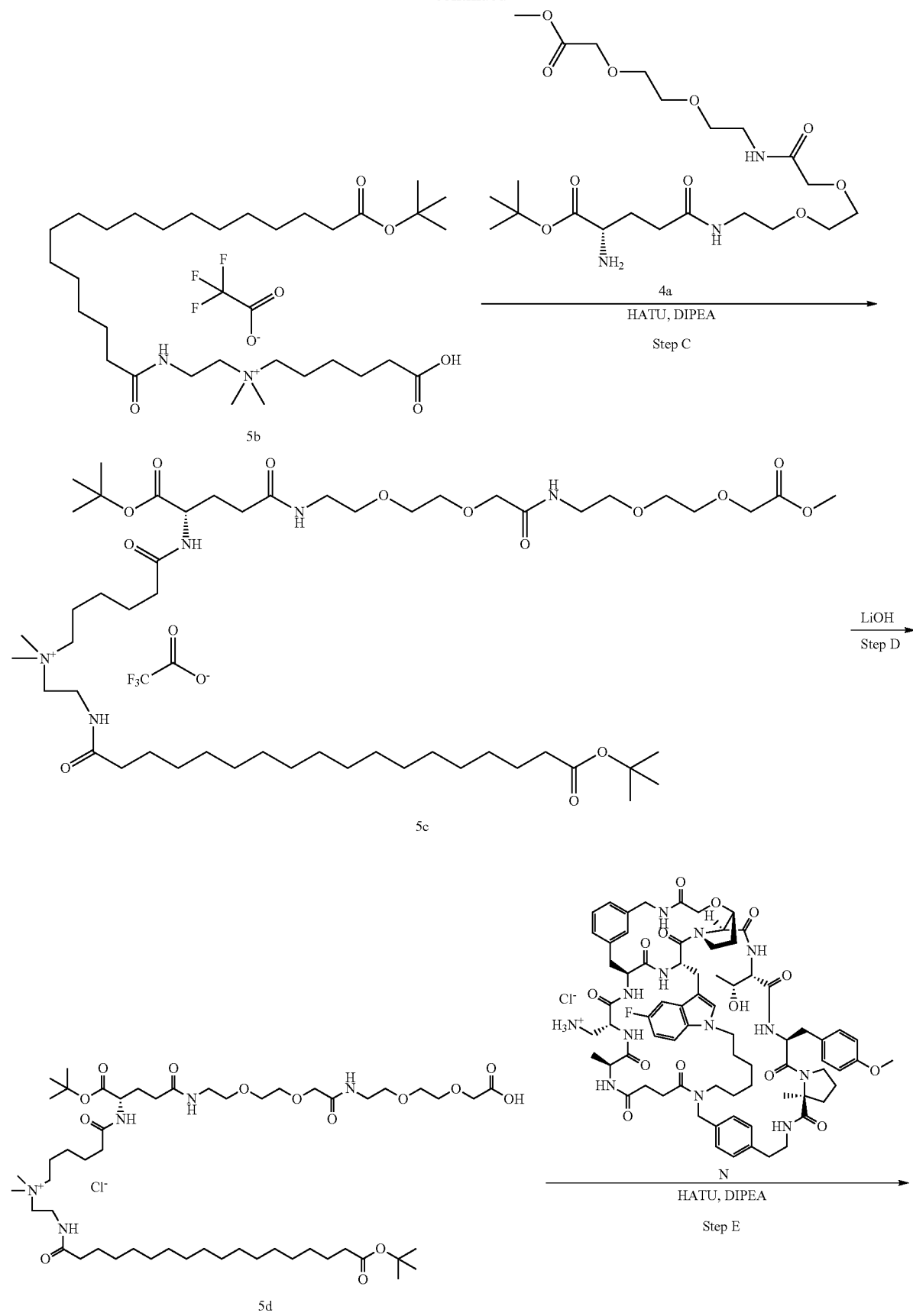

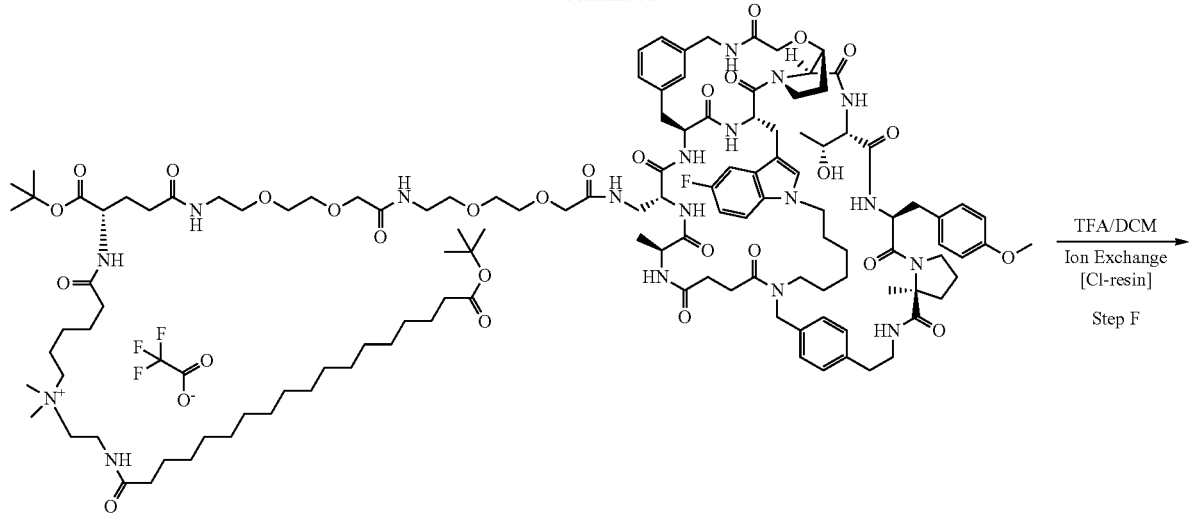

5e

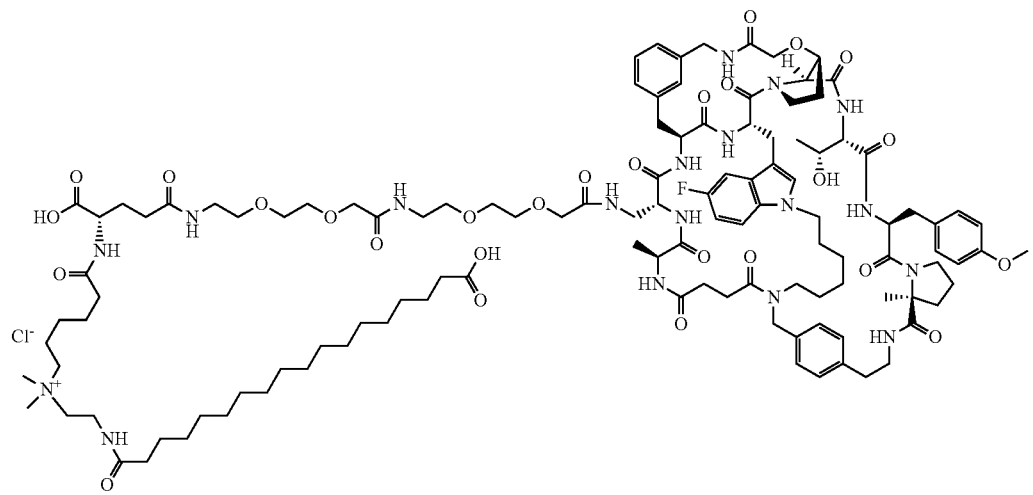

Example 5 (Cl salt)

Step A—Synthesis of Intermediate 5a

To a solution of 18-(tert-butoxy)-18-oxooctadecanoic acid (400 mg, 1.08 mmol) in DMF (5 mL) and water (0.5 mL) at 0° C. were added intermediate A (411 mg, 1.62 mmol), HATU (616 mg, 1.62 mmol) and DIPEA (1.51 mL, 8.64 mmol) and the solution was stirred at 0° C. for 1 h. The final mixture was quenched with water (1 mL) and purified by reverse phase MPLC over C18 (eluting with a gradient of acetonitrile in water (+0.05% TFA)) to give 5a. LC/MS: [M]$^+$=569.7.

Step B—Synthesis of Intermediate 5b

To a solution of 5a (380 mg, 0.56 mmol) in THF (4 mL) at 0° C. was added 1 M aqueous LiOH (1.12 mL, 1.12 mmol) and the solution was stirred at 0° C. for 1 h. The mixture was quenched with 1 M aqueous HCl (1.12 mL) and purified by reverse phase MPLC over C18 (eluting with a gradient of acetonitrile in water (+0.05% TFA)) to afford 5b. LC/MS: [M]$^+$=555.5. $^1$H NMR (300 MHz, CDCl$_3$): δ 8.84 (br, 1H), 8.03 (br, 1H), 3.72 (s, 2H), 3.57 (s, 2H), 3.39 (s, 2H), 3.17 (s, 6H), 2.41-2.32 (m, 2H), 2.28-2.16 (m, 4H), 1.89-1.51 (m, 8H), 1.46 (s, 9H), 1.35-1.20 (m, 26H).

Step C—Synthesis of Intermediate 5c

To a solution of 5b (250 mg, 0.37 mmol) in DMF (4 mL) and water (0.4 mL) at 0° C. were added HATU (213 mg, 0.56 mmol), 4a (190 mg, 0.37 mmol) and DIPEA (0.53 mL, 2.99 mmol) and the solution was stirred at 0° C. for 1 h. The final mixture was quenched with water (1 mL) and purified by reverse phase MPLC over C18 (eluting with a gradient of acetonitrile in water (+0.05% TFA)) to afford 5c. LC/MS: [M]$^+$=1044.7.

Step D—Synthesis of Intermediate 5d

To a solution of 5c (300 mg, 0.26 mmol) in THF (3 mL) at 0° C. was added 1 M aqueous LiOH (0.52 mL, 0.52 mmol) and the reaction was stirred for 1 h. The mixture was quenched with 1 M aqueous HCl (0.52 mL) and purified by reverse phase MPLC over C18 (eluting with a gradient of acetonitrile in water). The fractions containing the desired product were combined and concentrated. The residue was re-dissolved in acetonitrile (3 mL) and water (5 mL), treated with 1 N aqueous HCl (0.20 mL) at 0° C. and lyophilized to afford 5d. LC/MS: [M]$^+$=1030.6. $^1$H NMR (400 MHz, CDCl$_3$): δ 8.36 (br, 1H), 7.86 (br, 1H), 7.58 (br, 1H), 7.44 (br, 1H), 4.32 (d, J=6.3 Hz, 1H), 4.18 (s, 2H), 4.03 (s, 2H), 3.78-3.41 (m, 23H), 3.28 (s, 6H), 2.47-2.12 (m, 10H), 2.05-1.51 (m, 8H), 1.48 (s, 9H), 1.46 (s, 9H), 1.32-1.23 (m, 26H).

Step E—Synthesis of Intermediate 5e

To a solution of intermediate N (55 mg, 0.038 mmol) in DMF (550 µL) and water (55 µL) at 0° C. were added 5d (41.0 mg, 0.038 mmol), HATU (21.92 mg, 0.058 mmol) and DIEA (24.84 mg, 0.192 mmol) and the mixture was stirred at 0° C. for 1 h. The reaction solution was quenched with water (500 µL) and purified by reverse phase MPLC over C18 (eluting with a gradient of acetonitrile in water (+0.1% TFA)) to provide 5e. LC/MS: [(M+H)/2)]$^+$=1204.3.

Step F—Synthesis of Example 5 (Cl Salt)

To a solution of 5e (48.0 mg, 0.019 mmol) in DCM (10 mL) at 0° C. was added TFA (12.5 mL) then the mixture was stirred at RT for 3 h. The solution was concentrated under reduced pressure and the residue was purified by reverse phase MPLC over C18 (eluting with a gradient of acetonitrile in water (+0.1% TFA)) to provide Example 5 (TFA salt). 6 g of AG-MP-1M Cl resin (Bio-RAD, cat #141-1841) was packed in a column and washed with water (2×10 mL) followed by 20% acetonitrile in water (2×10 mL). Example 5 (TFA salt) was dissolved in 50% acetonitrile (2×2 mL) and loaded onto the column, and the compound was eluted with 65% acetonitrile (80 mL). The collected fractions were lyophilized to give Example 5 (Cl salt). LC/MS: [M]$^+$=2294.3.

Synthesis of Example 6

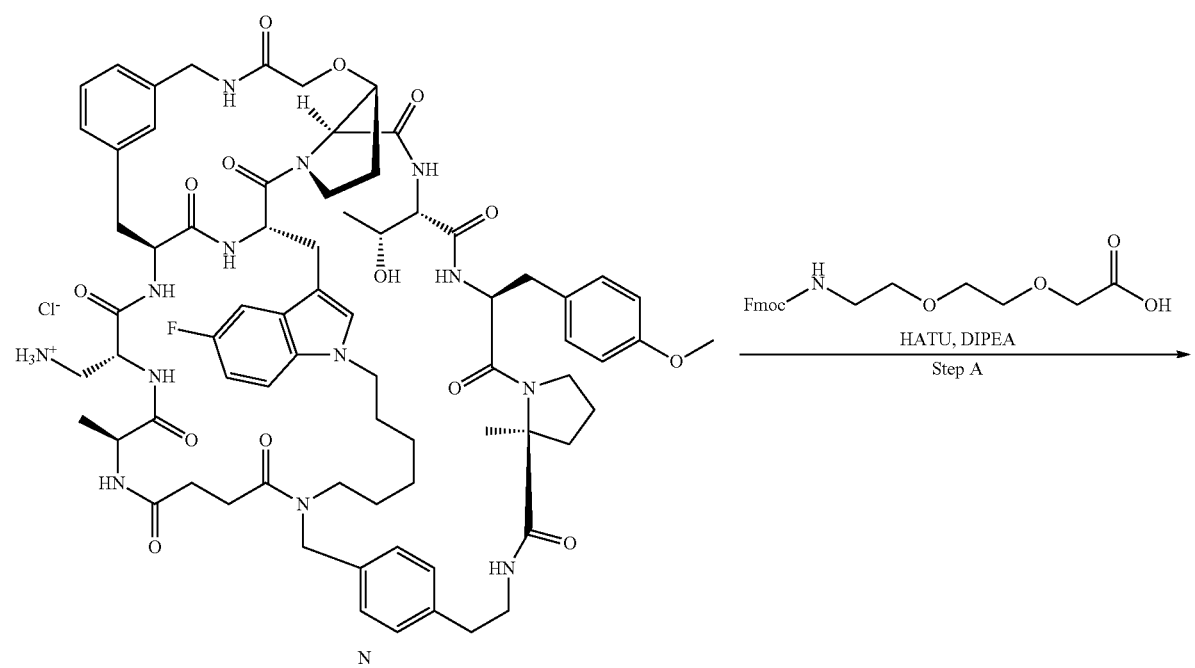

-continued
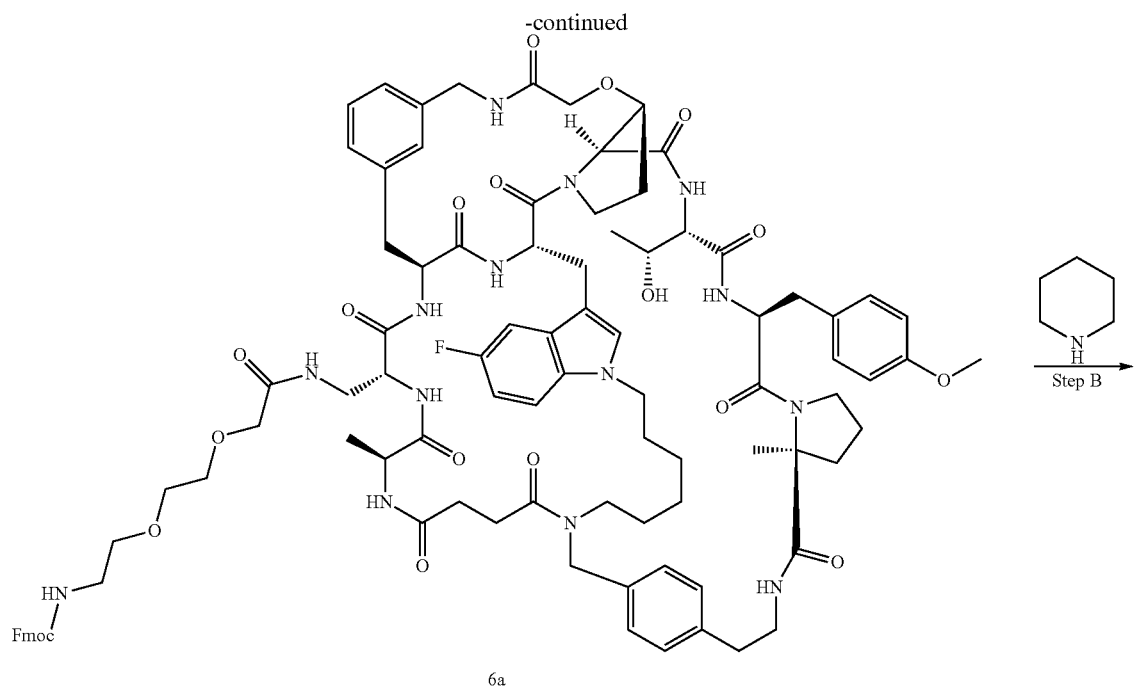
6a
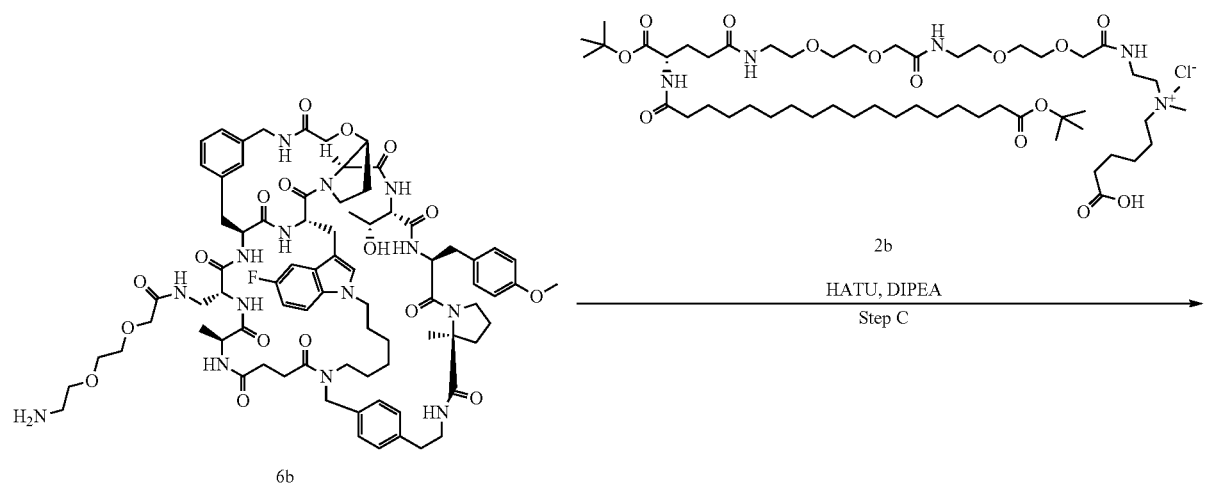
6b
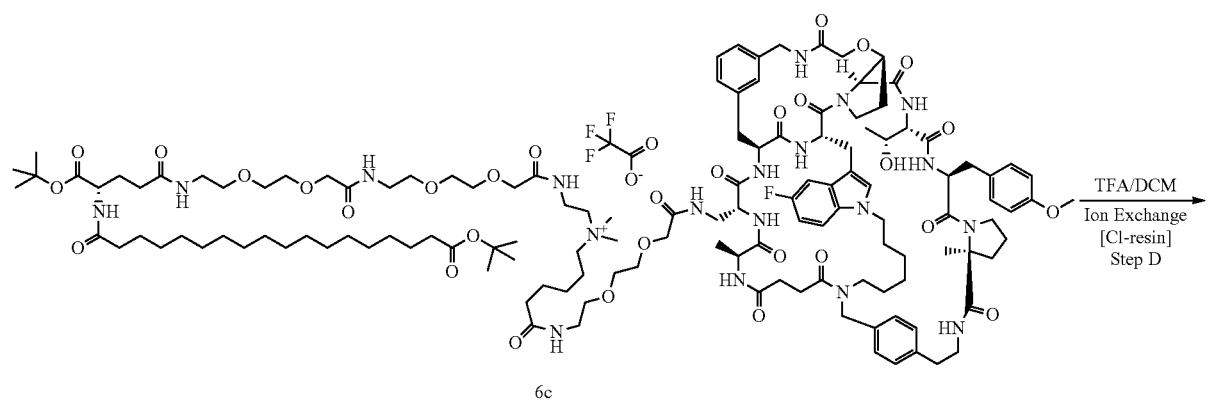
6c

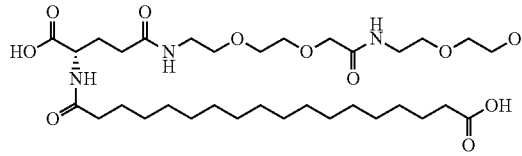
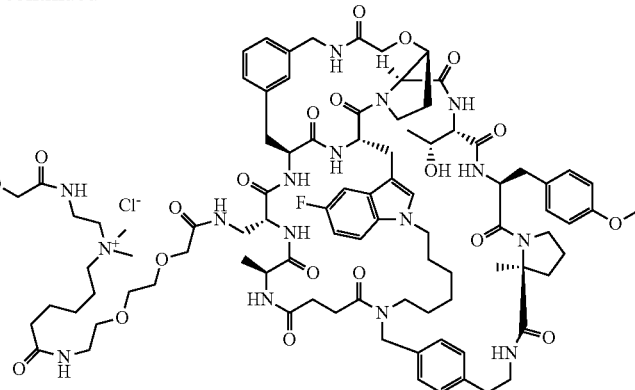

Example 6 (Cl salt)

Step A—Synthesis of Intermediate 6a

To a solution of intermediate N (70 mg, 0.049 mmol) and [2-[2-(fmoc-amino)ethoxy]ethoxy] acetic acid (20.74 mg, 0.054 mmol) in DMF (2 ml) and water (0.1 ml) at 0° C. were added HATU (20.46 mg, 0.054 mmol) and DIEA (0.034 ml, 0.196 mmol) and the resulting solution was stirred at 0° C. for 90 min. The final mixture was purified by reverse phase MPLC over C18 (eluting with a gradient of acetonitrile (+0.05% TFA) in water (+0.05% TFA)) to give 6a. LC/MS: [(M+2)/2]$^+$=881.7.

Step B—Synthesis of Intermediate 6b

To a solution of 6a (76 mg, 0.043 mmol) in DMF (2 ml) at RT was added piperidine (0.017 ml, 0.173 mmol) and the resulting solution was stirred at RT for 2 h. The final mixture was purified by reverse phase MPLC on C18 (eluting with a gradient of acetonitrile (+0.05% TFA) in water (+0.05% TFA)) to give the product as TFA salt. The salt was re-dissolved in acetonitrile/water 1:1 (15 mL), treated with 1 N aqueous HCl (0.216 ml, 0.216 mmol) and lyophilized to afford 6b. LC/MS: [(M+2)/2]$^+$=770.7.

Step C—Synthesis of Intermediate 6c

To a solution of 6b (59.6 mg, 0.038 mmol) and 2b (42.7 mg, 0.038 mmol) in DMF (3 mL) and water (0.15 mL) at 0° C. were added HATU (14.38 mg, 0.038 mmol) and DIEA (0.040 mL, 0.227 mmol) and the solution was stirred at 0° C. for 40 min. The final mixture was purified by reverse phase MPLC on C18 (eluting with a gradient of acetonitrile (+0.05% TFA) in water (+0.05% TFA)) to give 6c. LC/MS: [(M+H)/2)]$^+$=1277.0.

Step D—Synthesis of Example 6 (Cl Salt)

Intermediate 6c (94 mg, 0.035 mmol) was converted to Example 6 (TFA salt) using tert-butyl ester deprotection conditions similar to those described in Synthesis A of Example 4, Step G. LC/MS: [(M+H)/2)]$^+$=1220.9. Example 6 (TFA salt) was then converted to Example 6 (Cl salt) using resin exchange conditions similar to those described in Synthesis A of Example 4, Step H. LC/MS: [(M+H)/2)]$^+$=1220.7.

Synthesis of Example 7

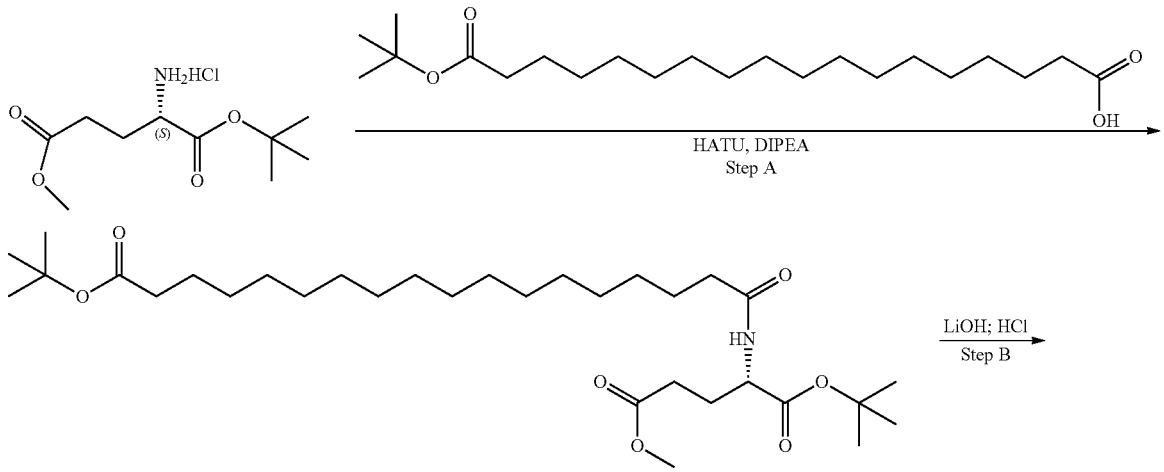

7a

-continued
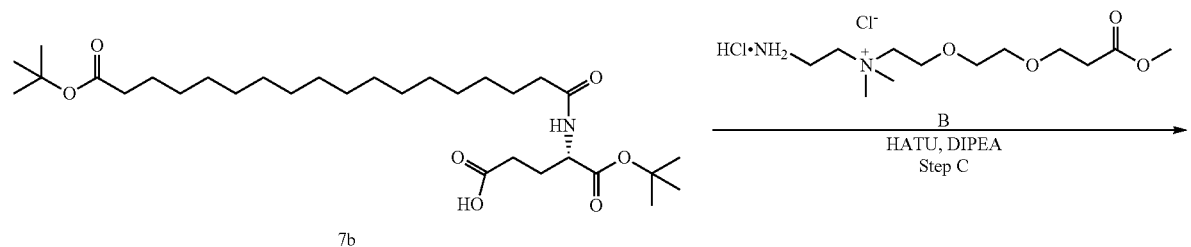
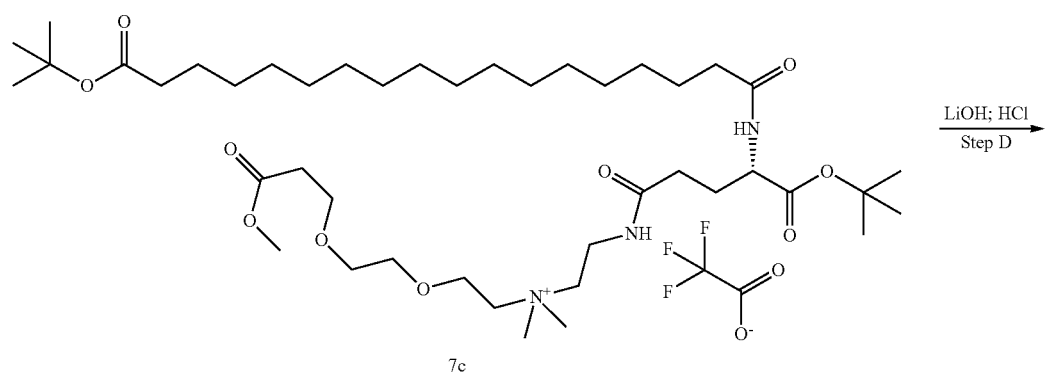
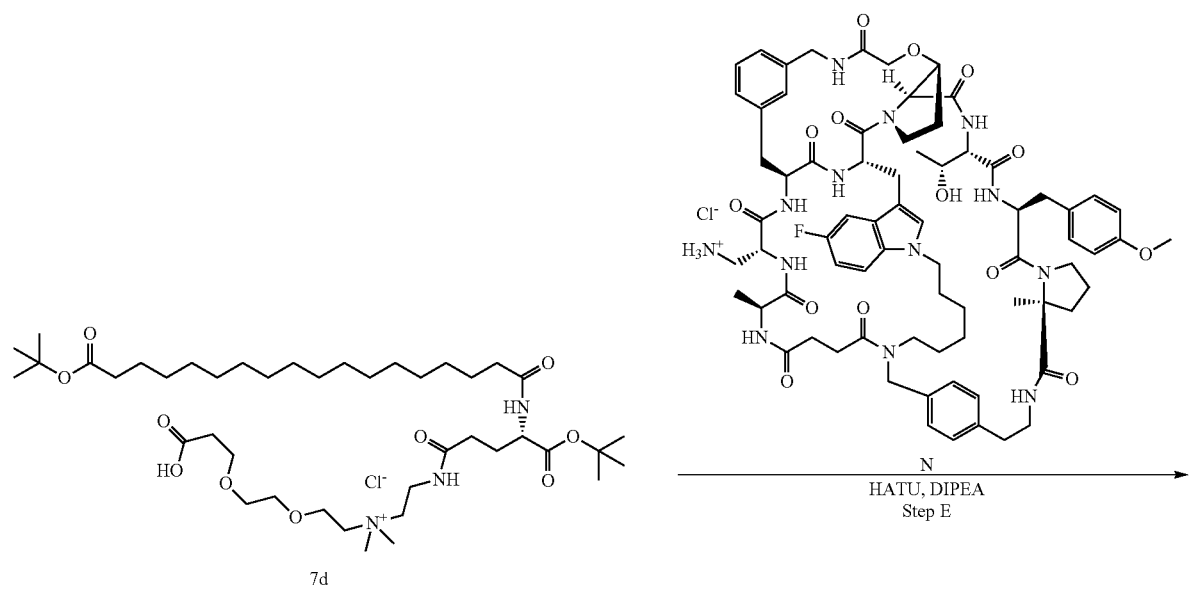

-continued

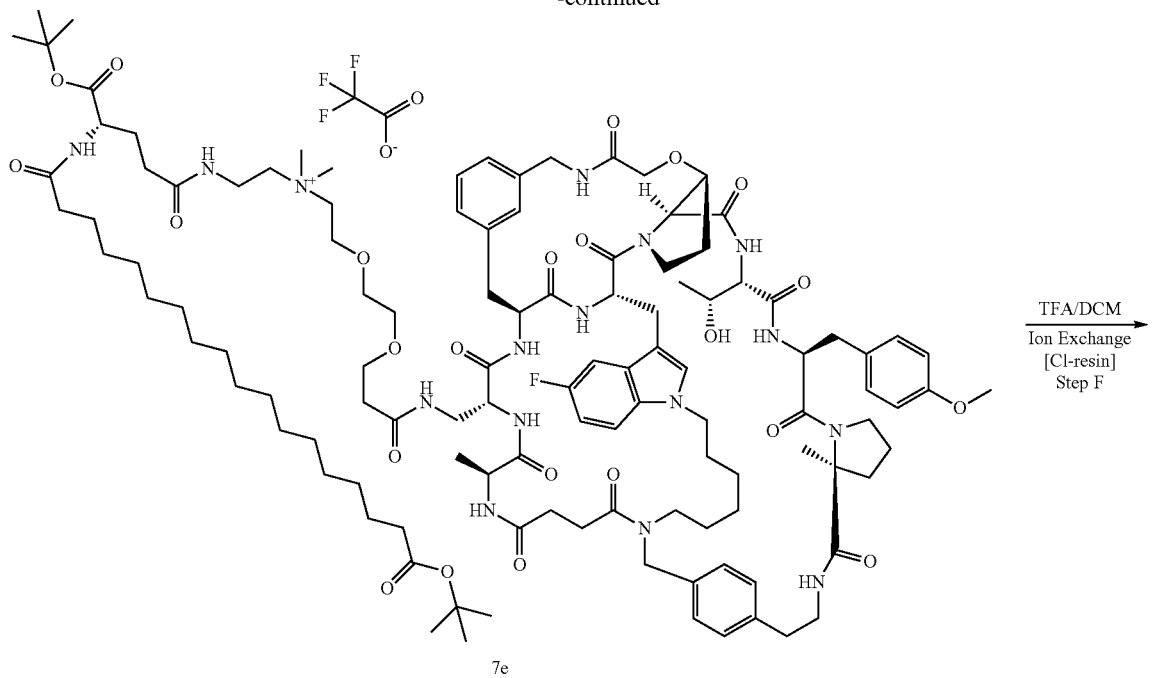

7e

↓ TFA/DCM
Ion Exchange
[Cl-resin]
Step F

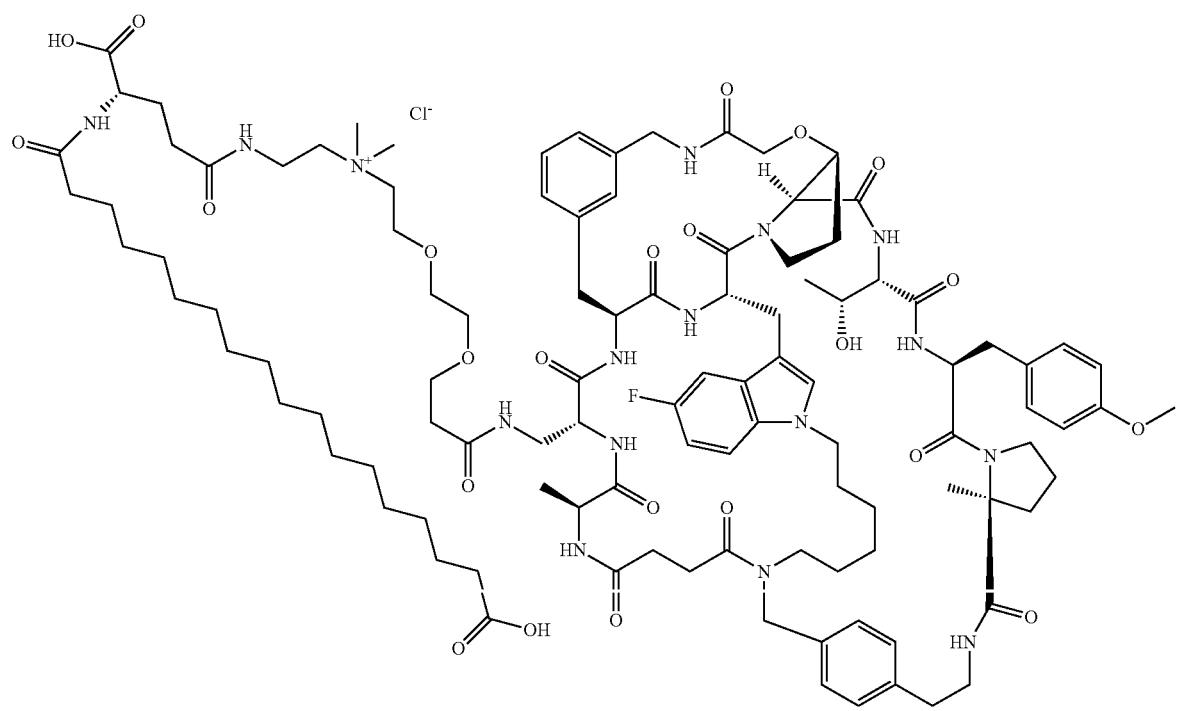

Example 7 (Cl salt)

Step A—Synthesis of Intermediate 7a

To a solution of 18-(tert-butoxy)-18-oxooctadecanoic acid (730 mg, 1.971 mmol) in DMF (5 mL) at 0° C. were added (S)-1-tert-butyl 5-methyl 2-aminopentanedioate hydrochloride (500 mg, 1.971 mmol), HATU (787 mg, 2.069 mmol) and DIEA (1273 mg, 9.85 mmol) then the mixture was stirred at 0° C. for 1 h. The mixture was diluted with brine (20 mL), extracted with EtOAc, washed with brine, dried over anhydrous MgSO$_4$ and filtered. The filtrate was concentrated under reduced pressure and the residue was purified by MPLC over silica gel (eluting with a gradient of 1%-40% EtOAc in PE) to give 7a. LC/MS: [M+H]$^+$=570.7. $^1$H NMR (400 MHz, CDCl$_3$): δ 6.08 (d, J=7.7 Hz, 1H), 4.59-4.44 (m, 1H), 3.68 (s, 3H), 2.54-2.25 (m, 2H), 2.26-2.10 (m, 5H), 2.02-1.90 (m, 1H), 1.60-1.55 (m, 4H), 1.47 (s, 9H), 1.44 (s, 9H), 1.36-1.20 (d, J=15.0 Hz, 24H).

Step B—Synthesis of Intermediate 7b

To a solution of 7a (780 mg, 1.369 mmol) in THF at 0° C. was added 2 M aqueous LiOH (1.369 mL, 2.74 mmol) and the mixture was stirred at 0° C. for 5 h. The solution was quenched with 1 M aqueous HCl (2.8 mL), diluted with brine (20 mL), extracted with EtOAc, and the combined organic layers were washed with brine, dried over anhydrous MgSO$_4$ and filtered. The filtrate was concentrated under reduced pressure and the residue was purified by MPLC over silica gel (eluting with a gradient of 1%-8% MeOH in DCM) to give 7b. LC/MS: [M+H]$^+$=556.4.

Step C—Synthesis of Intermediate 7c

To a solution of 7b (280 mg, 0.504 mmol) in DMF (3 mL) and water (0.6 mL) at 0° C. were added intermediate B (169 mg, 0.504 mmol), HATU (192 mg, 0.504 mmol) and DIEA (0.440 mL, 2.52 mmol) and the mixture was stirred at 0° C. for 1 h. The solution was quenched with water (600 µL) and purified by reverse phase MPLC over C18 (eluting with a gradient of acetonitrile in water (+0.05% TFA)). The fractions containing the desired product were combined and concentrated. The residue was re-dissolved in acetonitrile (10 mL) and water (10 mL), and lyophilized to afford 7c. LC/MS: [M]$^+$=800.7.

Step D—Synthesis of Intermediate 7d

To a solution of 7c (240 mg, 0.263 mmol) in THF (2.4 mL) at 0° C. was added 1 M aqueous LiOH (0.525 mL, 0.525 mmol) and the mixture was stirred at 0° C. for 1 h. The solution was quenched with 1 M aqueous HCl (0.53 mL) and purified by reverse phase MPLC over C18 (eluting with a gradient of acetonitrile in water). The fractions containing the desired product were combined and concentrated. The residue was re-dissolved in acetonitrile (10 mL) and water (10 mL), treated with 1 N aqueous HCl (0.25 mL) at 0° C. and lyophilized to afford 7d. LC/MS: [M]$^+$=786.6. $^1$H NMR (400 MHz, CD$_3$OD): δ 4.29 (dd, J=9.3, 5.2 Hz, 1H), 3.97 (d, J=5.7 Hz, 2H), 3.76 (t, J=5.9 Hz, 2H), 3.74-3.58 (m, 8H), 3.53 (t, J=6.7 Hz, 2H), 3.23 (s, 6H), 2.57 (t, J=5.9 Hz, 2H), 2.41-2.30 (m, 2H), 2.30-2.18 (m, 4H), 2.20-2.11 (m, 1H), 2.01-1.82 (m, 1H), 1.69-1.53 (m, 4H), 1.49 (s, 9H), 1.47 (s, 9H), 1.42-1.25 (m, 24H).

Step E—Synthesis of Intermediate 7e

To a solution of intermediate N (65 mg, 0.045 mmol) in DMF (600 µL) and water (60 µL) at 0° C. were added 7d (37.4 mg, 0.045 mmol), HATU (25.9 mg, 0.068 mmol) and DIEA (29.4 mg, 0.227 mmol) and the mixture was stirred at 0° C. for 1 h. The solution was quenched with water (500 µL) and purified by reverse phase MPLC over C18 (eluting with a gradient of acetonitrile in water (+0.1% TFA)) to afford 7e. LC/MS: [(M+H)/2)]$^+$=1082.1.

Step F—Synthesis of Example 7 (Cl Salt)

Intermediate 7e (58.0 mg, 0.025 mmol) was converted to Example 7 (TFA salt) using tert-butyl ester deprotection conditions similar to those described in Synthesis A of Example 4, Step G. LC/MS: [(M+H)/2)]$^+$=1026.1. Example 7 (TFA salt) was then converted to Example 7 (Cl salt) using resin exchange conditions similar to those described in Synthesis A of Example 4, Step H. LC/MS: [M]$^+$=2050.1.

Synthesis of Example 8

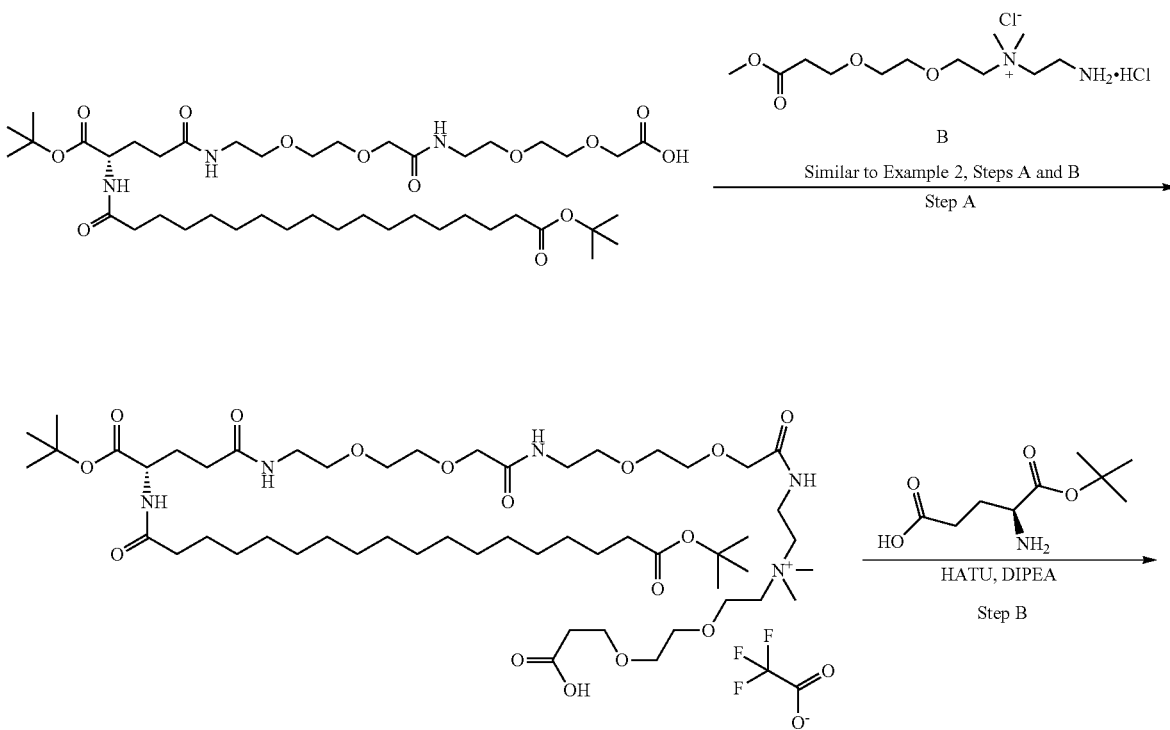

8a

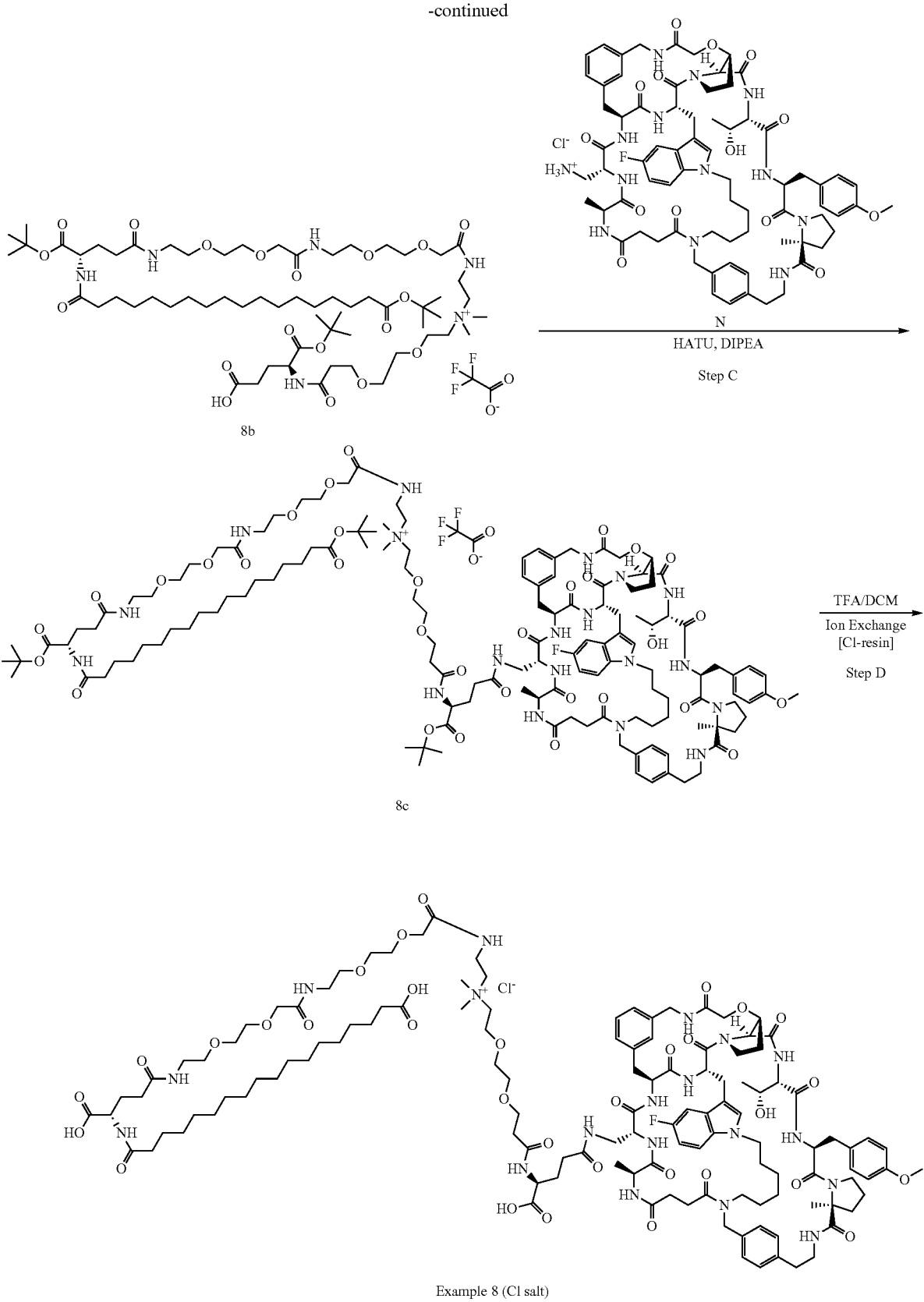

Step A—Synthesis of Intermediate 8a (S)-22-(tert-butoxycarbonyl)-43,43-dimethyl-10,19,24,41-tetraoxo-3,6,12,15,42-pentaoxa-9,18,23-triazatetratetracontan-1-oic acid (3.00 g, 3.55 mmol, the synthesis of which is described in Example 9, page 90, of WO 2009/115469) was coupled with intermediate B (1.329 g, 4.43 mmol) following conditions similar to those described in Example 2, Step A then hydrolyzed following conditions similar to those described in Example 2, Step B to afford 8a. LC/MS: $[M]^+=1076.5$.

Step B—Synthesis of Intermediate 8b

To a solution of 8a (130 mg, 0.111 mmol) in DMF (1.0 ml) at RT were added HATU (46.3 mg, 0.122 mmol) and DIPEA (0.087 ml, 0.498 mmol) and the mixture was stirred for 10 min. H-Glu-OtBu (25.8 mg, 0.127 mmol) as a slurry in NMP (1.5 ml)) was then added at RT and the mixture was stirred for 30 min. The mixture was quenched slowly at 0° C. with 0.5 N aqueous HCl (0.85 ml) then purified by reverse phase MPLC over C18 (eluting with a gradient of acetonitrile (+0.05% TFA) in water (+0.05% TFA)) to give 8b. LC/MS: $[M]^+=1261.9$.

Step C—Synthesis of Intermediate 8c

To a solution of intermediate N (40 mg, 0.028 mmol) and 8b (38.0 mg, 0.028 mmol) in DMF (3 ml) at 0° C. were added HATU (10.63 mg, 0.028 mmol) and DIEA (0.029 ml, 0.168 mmol) then the resulting solution was stirred at 0° C. for 1 h. The final mixture was purified by reverse phase MPLC over C18 (eluting with a gradient of acetonitrile (+0.05% TFA) in water (+0.05% TFA)) to afford 8c. LC/MS: $[(M+H)/2)]^+=1320.0$.

Step D—Synthesis of Example 8 (Cl Salt)

Intermediate 8c (63 mg, 0.024 mmol) was converted to Example 8 (TFA salt) using tert-butyl ester deprotection conditions similar to those described in Synthesis A of Example 4, Step G. LC/MS: $[(M+H)/2)]^+=1235.5$. Example 8 (TFA salt) was then converted to Example 8 (Cl salt) using resin exchange conditions similar to those described in Example 4 Step H. LC/MS: $[(M+H)/2)]^+=1235.3$.

Synthesis of Example 9

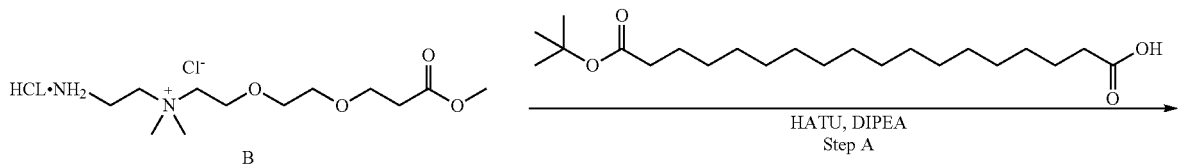

B

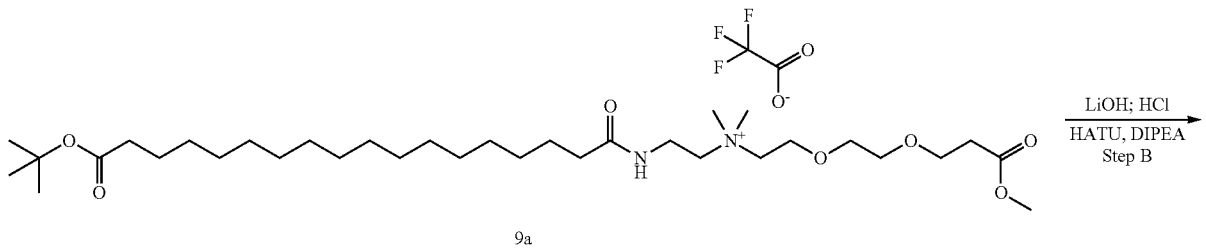

9a

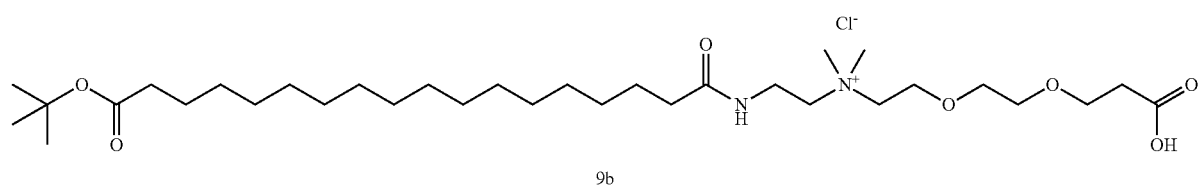

9b

-continued
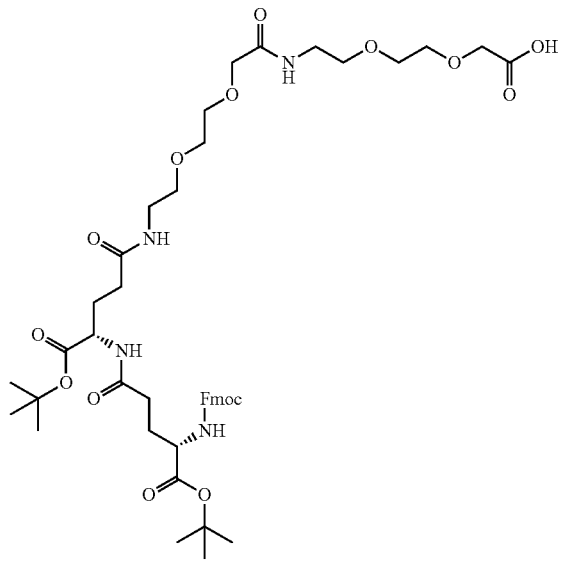
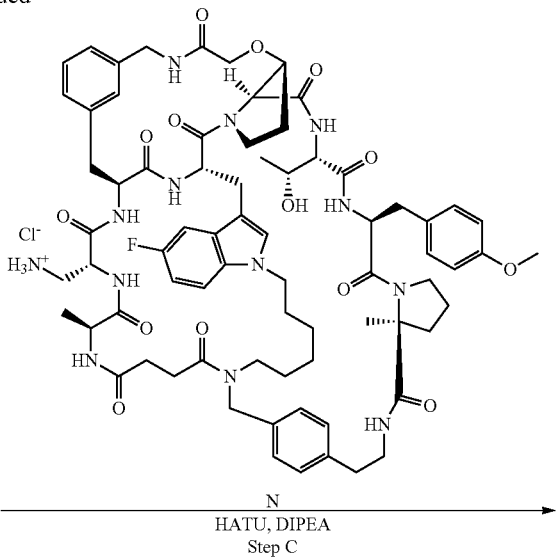
HATU, DIPEA
Step C
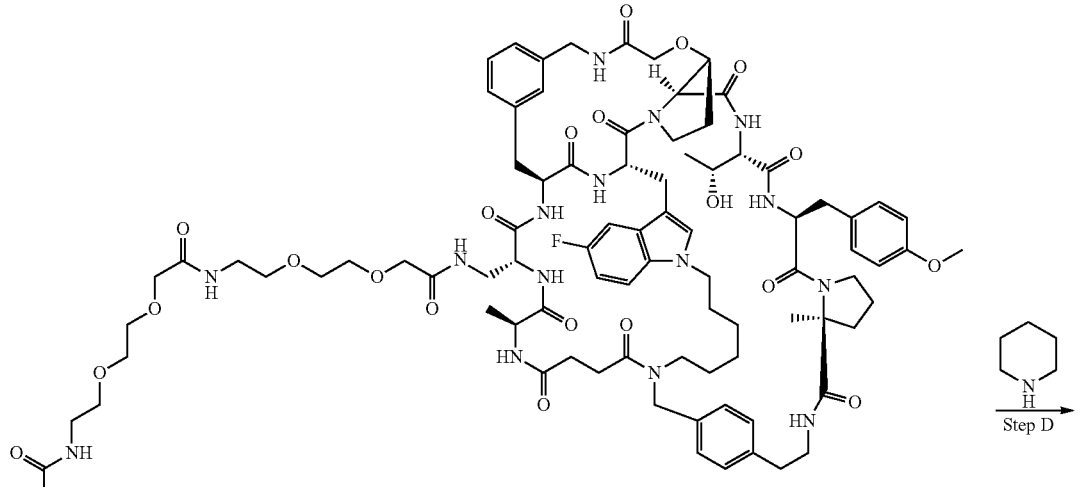
piperidine
Step D
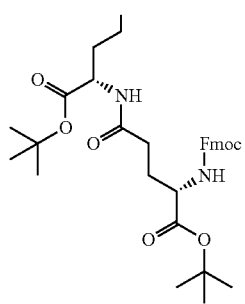
9c

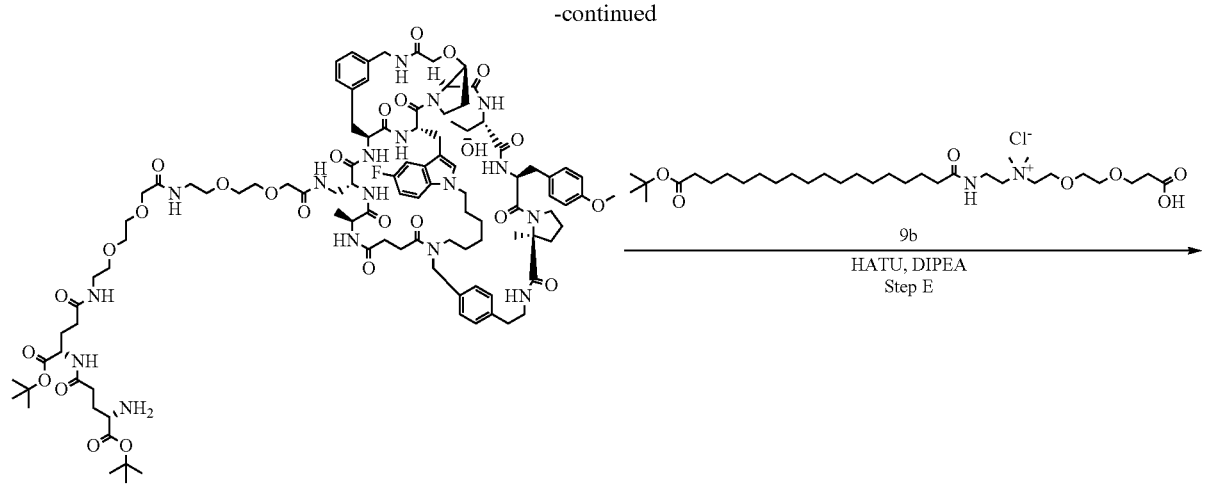
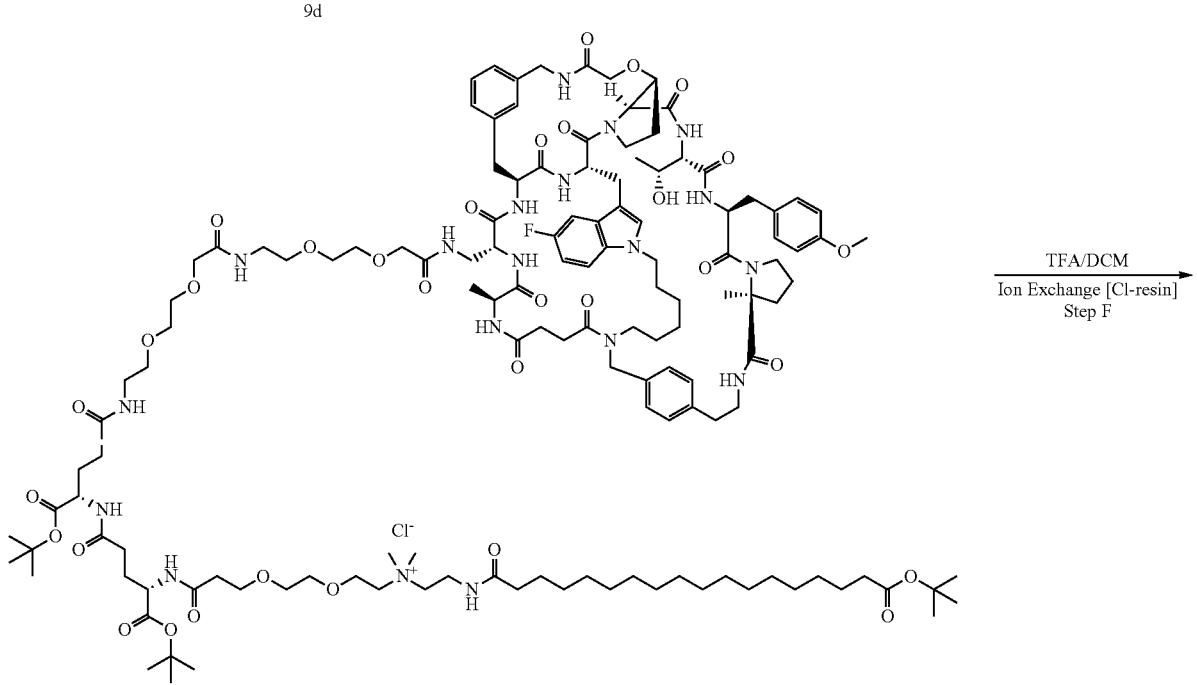
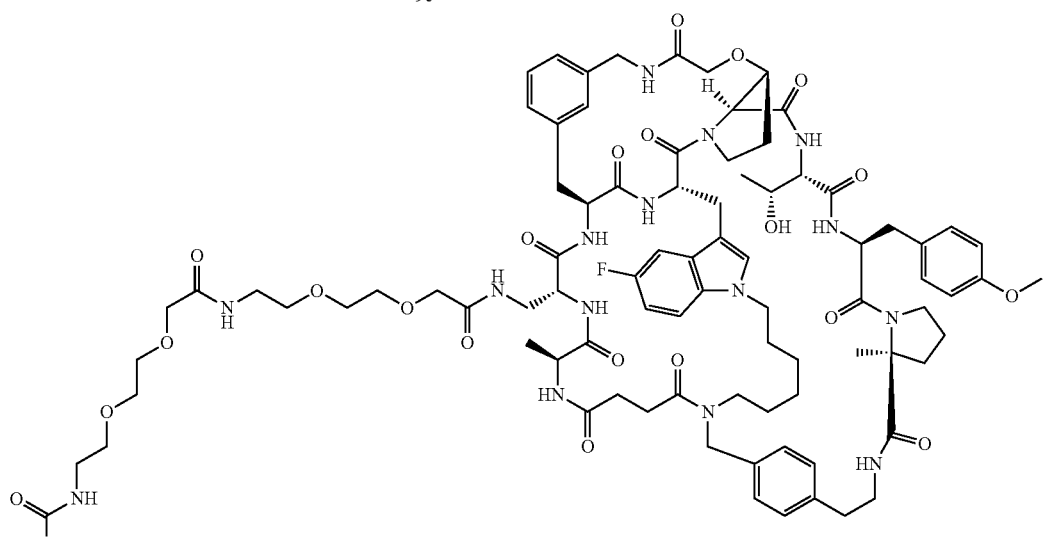

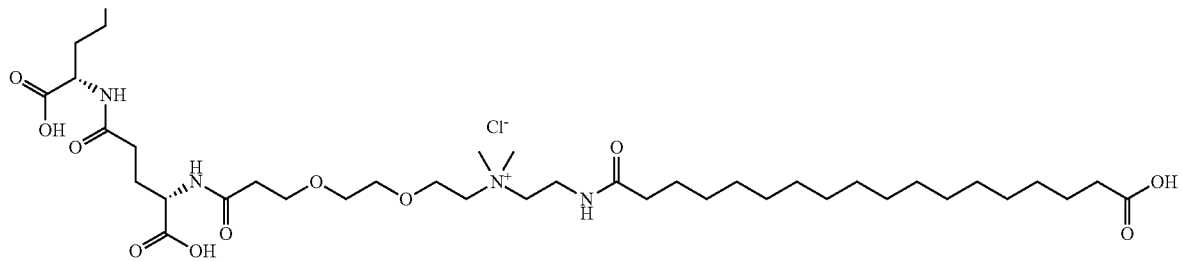

Example 9 (Cl salt)

Step A—Synthesis of Intermediate 9a

To a solution of 18-(tert-butoxy)-18-oxooctadecanoic acid (350 mg, 0.944 mmol) in DMF (2.0 mL) and water (0.15 mL) at 0° C. were added intermediate B (390 mg, 1.133 mmol), HATU (413 mg, 1.086 mmol) and DIPEA (0.99 mL, 5.67 mmol) then the mixture was stirred at RT for 90 min. The reaction was quenched with 0.5N aqueous HCl (2 mL) then purified by reverse phase MPLC over C18 (eluting with a gradient of acetonitrile in water (+0.05% TFA)) to provide 9a. LC/MS: [M]$^+$=615.4.

Step B—Synthesis of Intermediate 9b

To a solution of 9a (434 mg, 0.608 mmol) in THF (7 mL) at RT was added aqueous LiOH 1N (0.912 mL, 0.912 mmol) and the mixture was stirred for 1 h. The mixture was quenched with 0.5 N aqueous HCl (2.0 mL), concentrated then taken up in 50% acetonitrile in water and lyophilized to provide 9b. LC/MS: [M]$^+$=601.4.

Step C—Synthesis of Intermediate 9c

To a solution of intermediate N (140 mg, 0.098 mmol) and intermediate S (93 mg, 0.103 mmol) in acetonitrile (2 mL) and DMF (0.2 mL) at 0° C. were added HATU (39.1 mg, 0.103 mmol) and DIPEA (0.068 mL, 0.391 mmol) then the mixture was stirred at RT for 45 min. The solution was slowly dripped into a centrifuge tube filled with IPAc/cyclopentylmethyl ether 1:1 (30 mL). The tube was chilled at −78° C. for 5 min then centrifuged for 15 min. The solution was decanted, IPAc/cyclopentylmethyl ether 1:1 (20 ml) was added, the tube shaken, chilled at −78° C. for 5 min then centrifuged for 15 min. The solution was decanted and the solid dried under vacuum to give 9c.
LC/MS: [(M+2)/2]$^+$=1139.4.

Step D—Synthesis of Intermediate 9d

To a solution of 9c (226 mg, 0.099 mmol) in acetonitrile (2 mL) and DMF (0.2 mL) at RT was added piperidine (0.039 mL, 0.397 mmol) and the mixture was stirred for 1 h. The solution was slowly dripped into a centrifuge tube filled with IPAc/cyclopentylmethyl ether 1:1 (30 mL). The tube was chilled at −78° C. for 5 min then centrifuged for 15 min. The solution was decanted, IPAc/cyclopentylmethyl ether 1:1 (20 ml) was added, the tube shaken, chilled at −78° C. for 5 min then centrifuged for 15 min. The solution was decanted and the solid dried under vacuum to give 9d.

LC/MS: [(M+2)/2]$^+$=1028.1.

Step E—Synthesis of Intermediate 9e

To a solution of 9d (75 mg, 0.036 mmol) and 9b (31.9 mg, 0.046 mmol) in acetonitrile (1.0 mL) and DMF (0.15 mL) at 0° C. was added HATU (15.96 mg, 0.042 mmol) and DIPEA (0.025 mL, 0.146 mmol) then the mixture was stirred at RT for 30 min. The solution was slowly dripped into a centrifuge tube filled with IPAc/cyclopentylmethyl ether 1:1 (30 mL). The tube was chilled at −78° C. for 5 min then centrifuged for 20 min. The solution was decanted, IPAc/cyclopentylmethyl ether 1:1 (20 ml) was added, the tube shaken, chilled at −78° C. for 5 min then centrifuged for 15 min. The solution was decanted and the solid dried under vacuum to give 9e. LC/MS: [(M+H)/2]$^+$=1319.4.

Step F—Synthesis of Example 9 (Cl Salt)

Intermediate 9e (81 mg, 0.029 mmol) was converted to Example 9 (TFA salt) using tert-butyl ester deprotection conditions similar to those described in Synthesis A of Example 4, Step G. LC/MS: [(M+H)/2]$^+$=1235.4. Example 9 (TFA salt) was then converted to Example 9 (Cl salt) using resin exchange conditions similar to those described in Synthesis A of Example 4, Step H. LC/MS: [(M+H)/2]$^+$=1235.5.

Synthesis A of Example 10
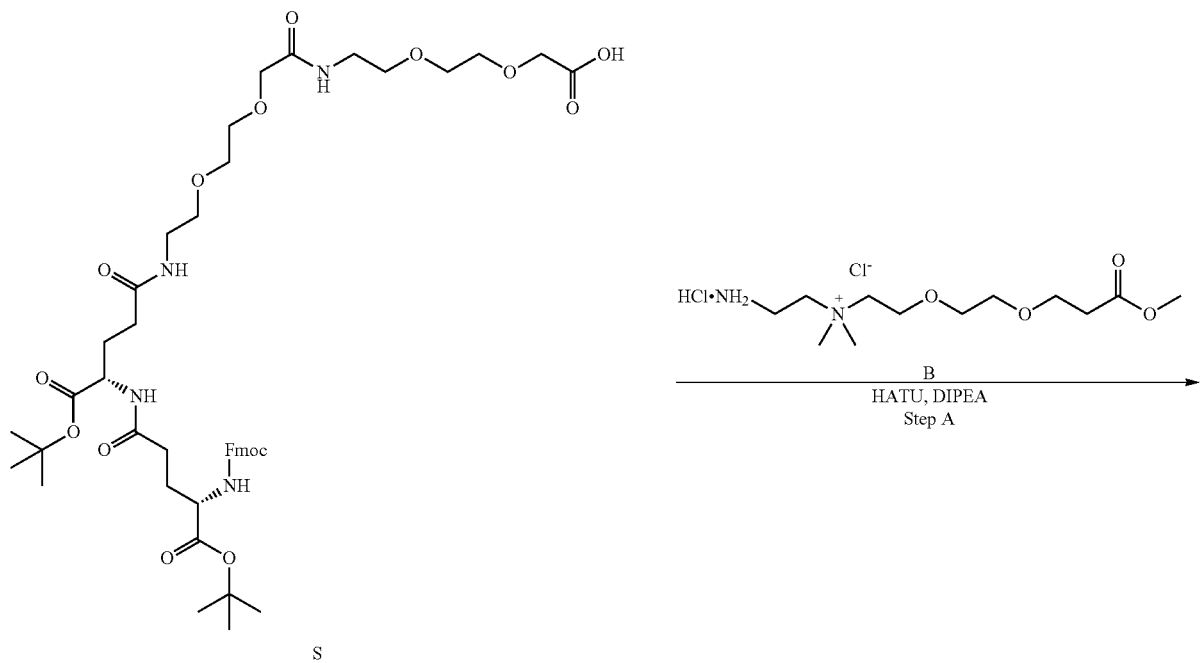
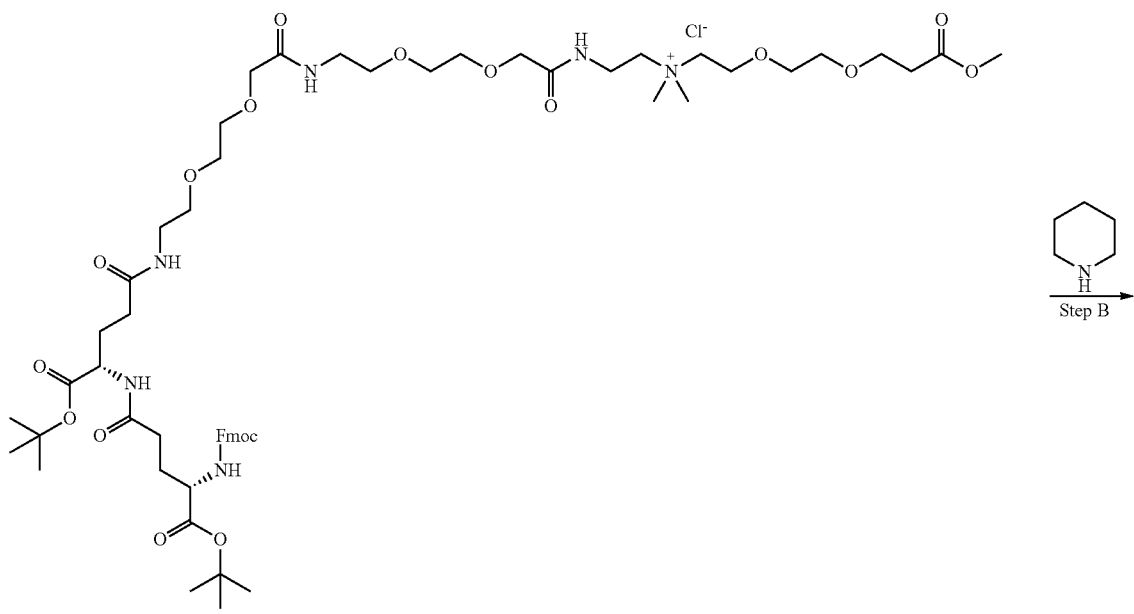

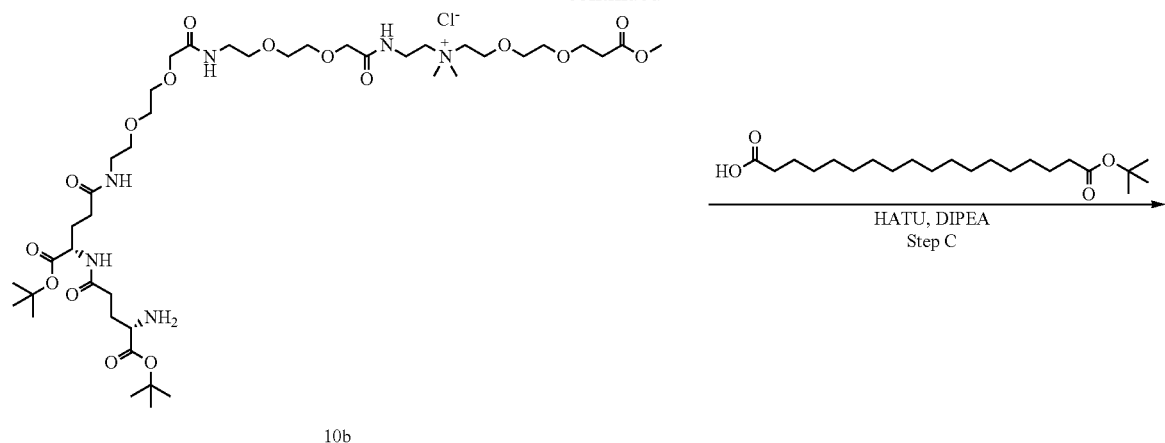
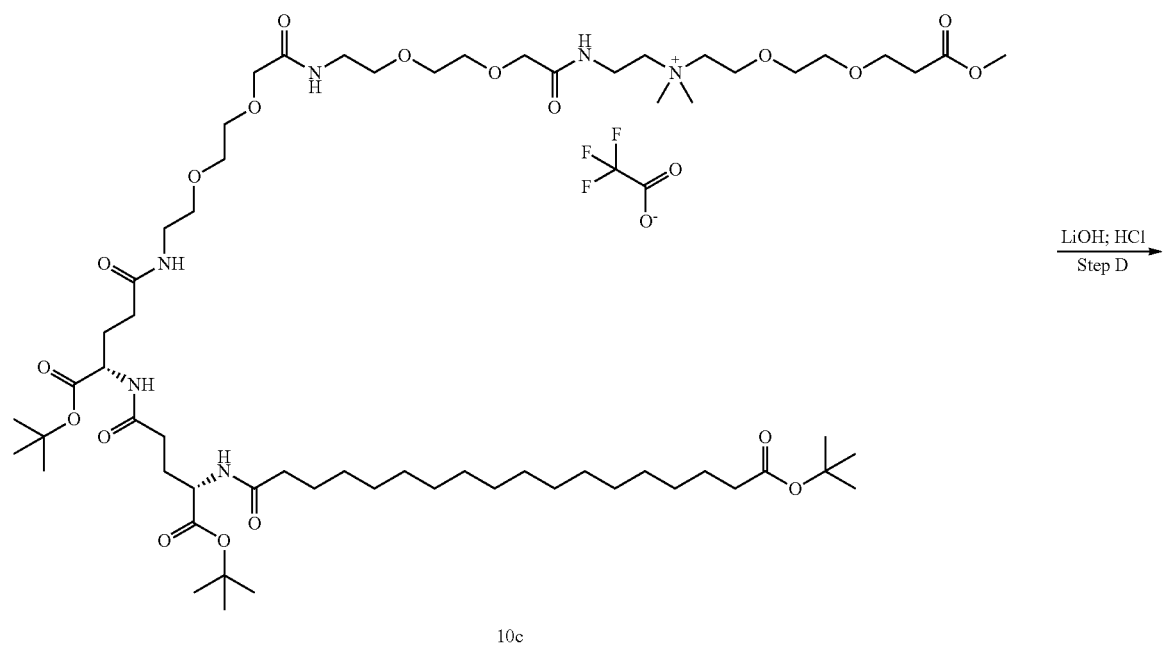
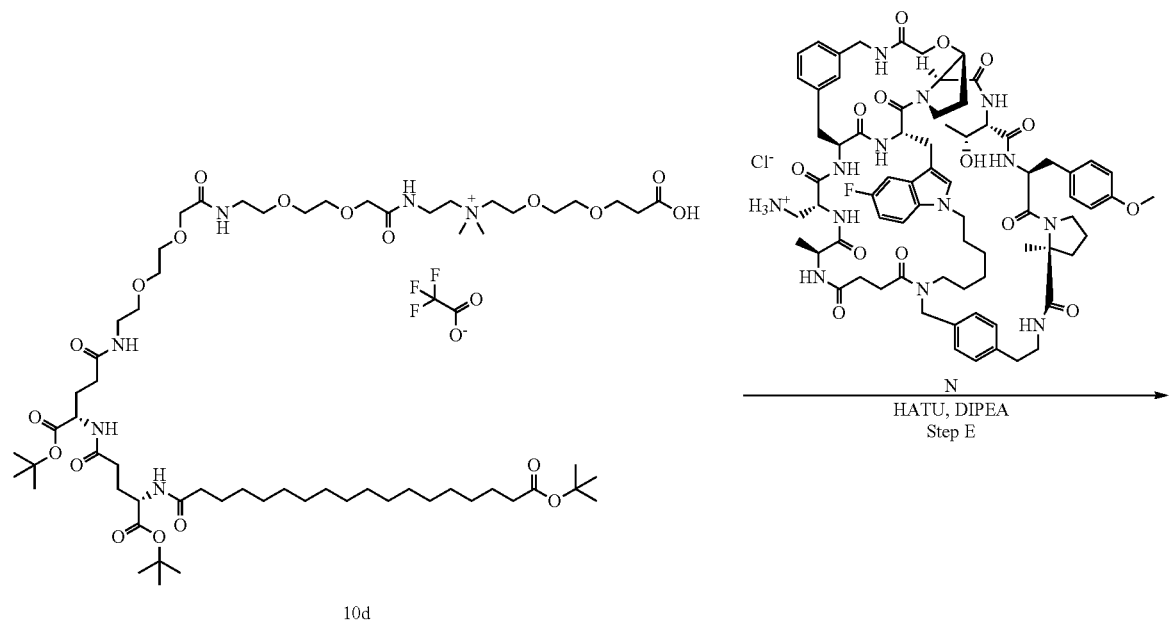

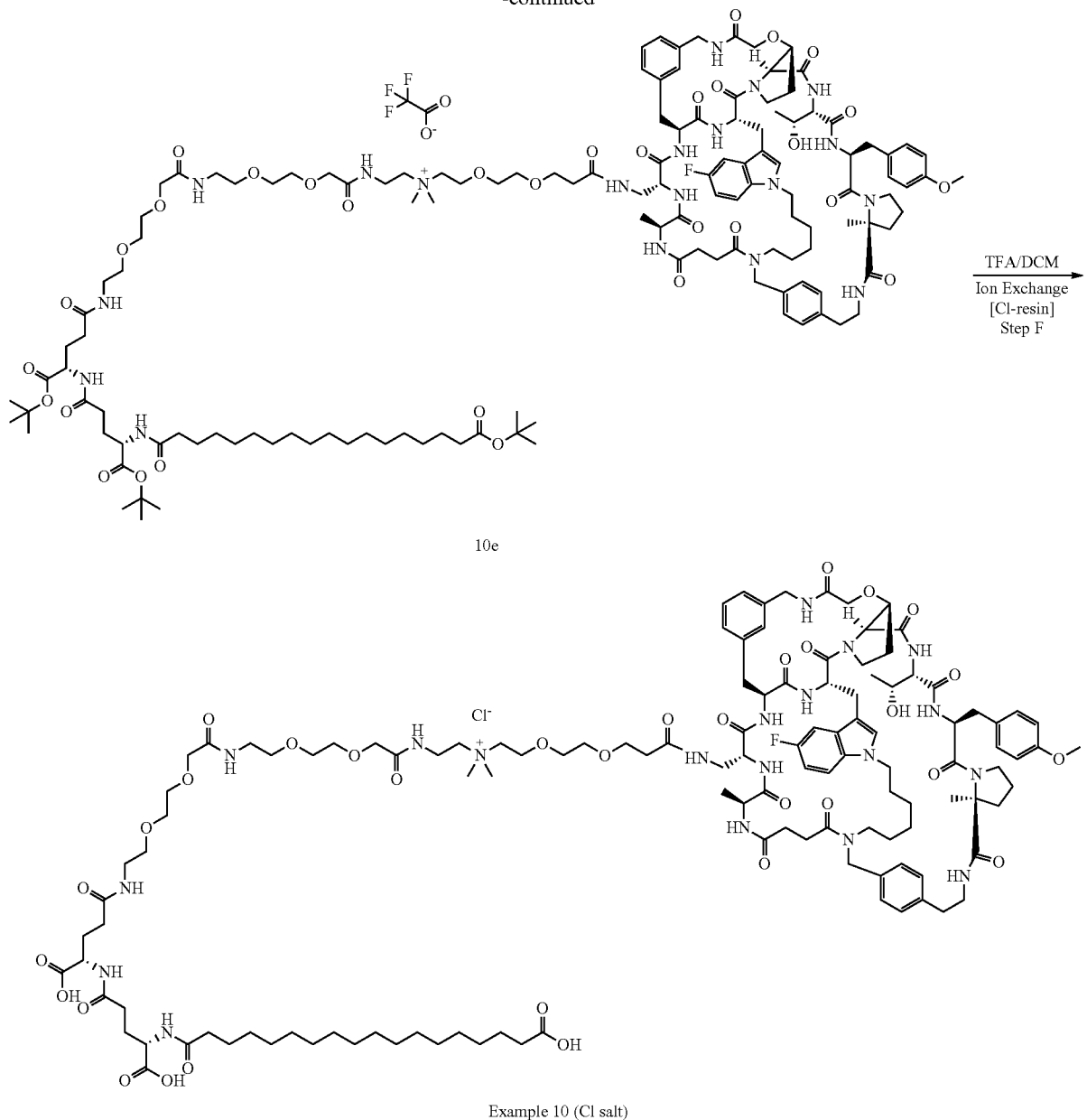

Example 10 (Cl salt)

Step A—Synthesis of Intermediate 10a

To a solution of intermediate S (300 mg, 0.333 mmol) and intermediate B (169 mg, 0.400 mmol) in DMF (4 ml) at RT were added HATU (146 mg, 0.383 mmol) and DIEA (0.465 ml, 2.66 mmol) and the solution was stirred at RT for 2 h. The final mixture was purified by reverse phase MPLC over C18 (eluting with a gradient of acetonitrile (+0.05% TFA) in water (+0.05% TFA)) to give 10a. LC/MS: $[M]^+=1145.4$.

Step B—Synthesis of Intermediate 10b

To a solution of 10a (327 mg, 0.285 mmol) in acetonitrile (5 ml) was added piperidine (0.085 ml, 0.856 mmol) and the solution was stirred at RT for 3 h. The final mixture was concentrated, the residue was dissolved in acetonitrile/water 2:1 (20 mL) then lyophilized to give 10b. LC/MS: $[M]^+=923.3$.

Step C—Synthesis of Intermediate 10c

To a solution of 10b (132 mg, 0.143 mmol) in DMF (4 ml) were added 18-(tert-butoxy)-18-oxooctadecanoic acid (74.1 mg, 0.200 mmol), HATU (76 mg, 0.200 mmol), and DIEA (0.100 ml, 0.571 mmol) and the solution was stirred at RT for 1 h. The final mixture was purified by reverse phase MPLC over C18 (eluting with a gradient of acetonitrile (+0.05% TFA) in water (+0.05% TFA)) to give 10c. LC/MS: $[M]^+=1275.6$.

Step D—Synthesis of Intermediate 10d

To a solution of 10c (161 mg, 0.117 mmol) in THF (2.5 ml) at 0° C. was added 1N aqueous LiOH (0.135 ml, 0.135 mmol) then the solution was stirred at RT for 2 h. The final mixture was quenched at 0° C. with 1 N aqueous HCl (100 uL), concentrated and the residue was purified by reverse phase MPLC over C18 (eluting with a gradient of acetonitrile (+0.05% TFA) in water (+0.05% TFA)) to provide 10d. LC/MS: $[M]^+$=1261.5. $^1$H NMR (500 MHz, CD$_3$OD): δ 4.29-4.23 (m, 2H), 4.05 (s, 2H), 4.01 (s, 2H), 3.98-3.93 (m, 2H), 3.78-3.53 (m, 24H), 3.46 (t, J=5.6 Hz, 2H), 3.39 (td, J=5.6, 4.0 Hz, 2H), 3.21 (s, 6H), 2.40 (t, J=6.1 Hz, 2H), 2.37-2.09 (m, 10H), 1.93-1.82 (m, 2H), 1.68-1.51 (m, 4H), 1.469 (s, 9H), 1.467 (s, 9H), 1.44 (s, 9H), 1.36-1.26 (m, 24H).

Step E—Synthesis of Intermediate 10e

To a solution of intermediate N (60 mg, 0.042 mmol) and 10d (68.5 mg, 0.050 mmol) in DMF (3 ml) and water (0.15 ml) at 0° C. were added HATU (17.54 mg, 0.046 mmol) and DIEA (0.044 ml, 0.252 mmol) and the solution was stirred at 0° C. for 1 h. The final mixture was purified by reverse phase MPLC over C18 (eluting with a gradient of acetonitrile (+0.05% TFA) in water (+0.05% TFA)) to provide 10e. LC/MS: $[(M+H)/2]^+$=1320.2.

Step F—Synthesis of Example 10 (Cl Salt)

Intermediate 10e (113 mg, 0.041 mmol) was converted to Example 10 (TFA salt) using tert-butyl ester deprotection conditions similar to those described in Synthesis A of Example 4, Step G. LC/MS: $[(M+H)/2]^+$=1236.0. Example 10 (TFA salt) was then converted to Example 10 (Cl salt) using resin exchange conditions similar to those described in Synthesis A of Example 4, Step H. LC/MS: $[(M+H)/2]^+$=1235.9.

Synthesis B of Example 10

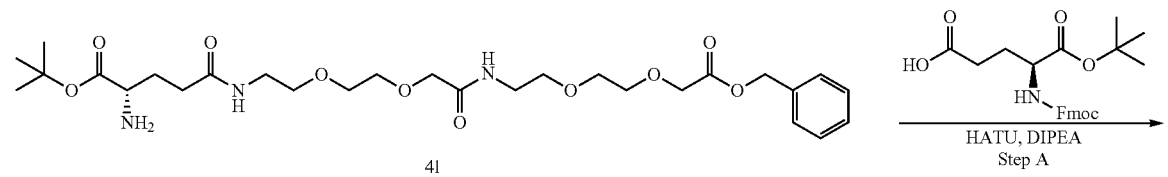

41

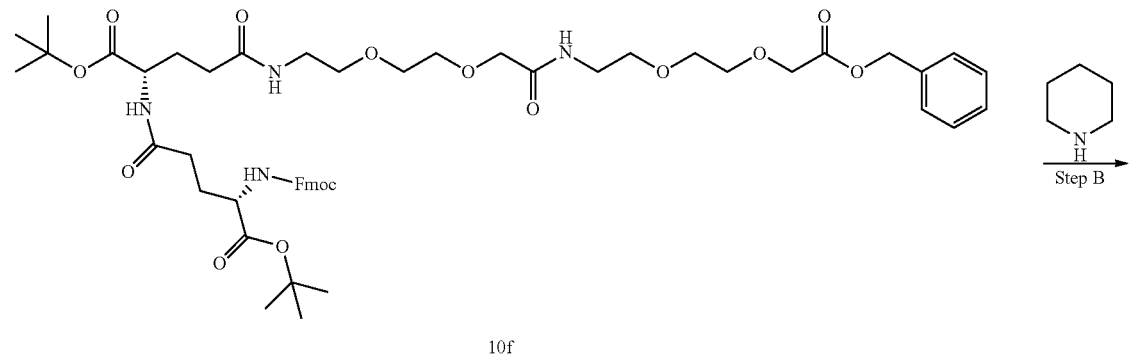

10f

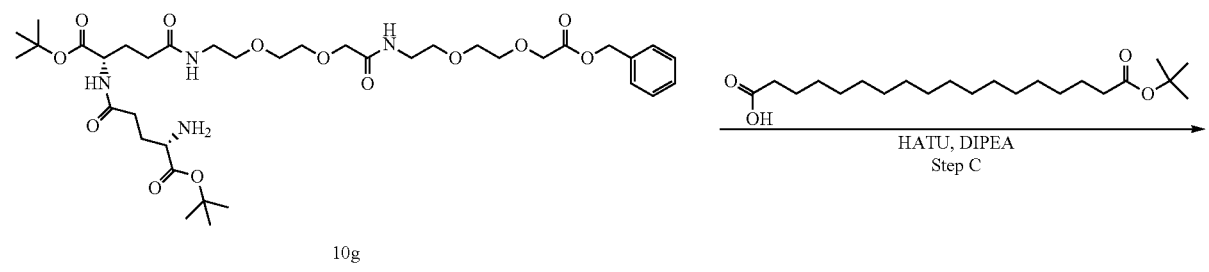

10g

313
314
-continued
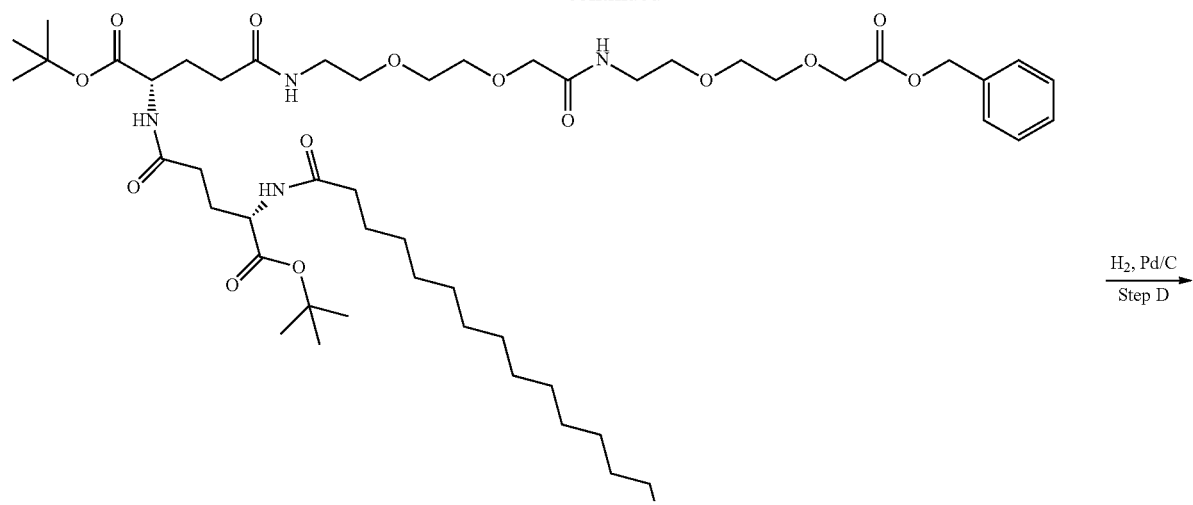
H₂, Pd/C
―――――→
Step D
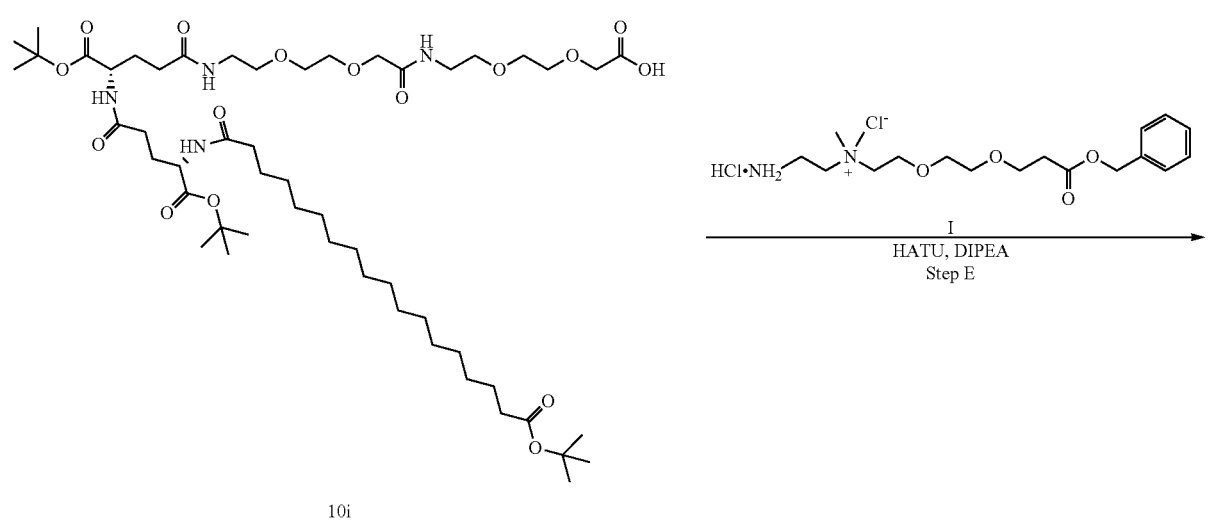
HATU, DIPEA
―――――→
Step E

315
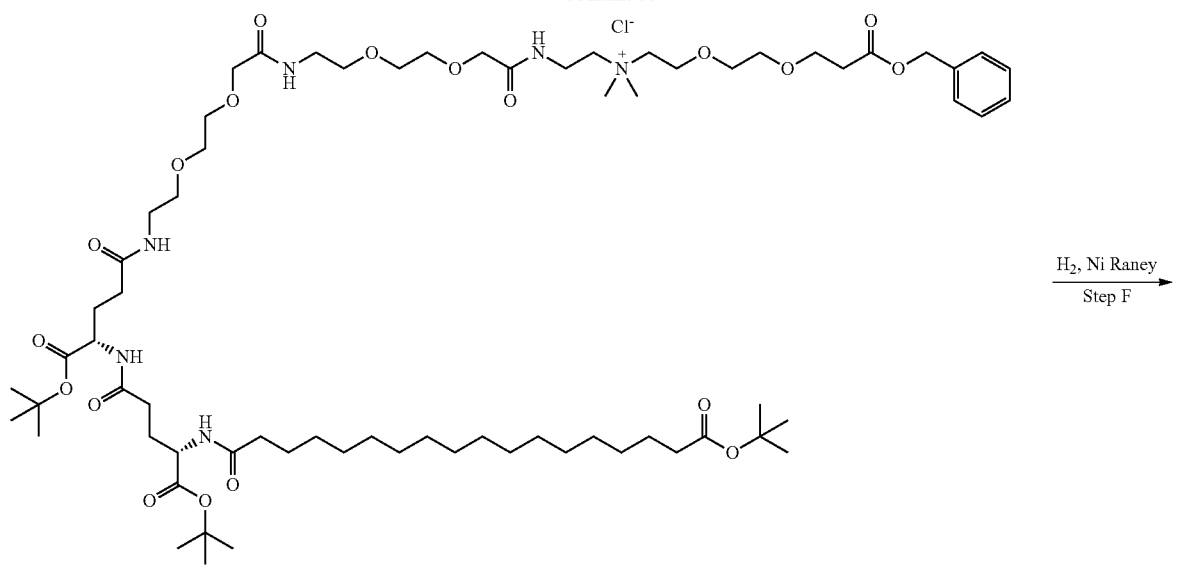
10j
316
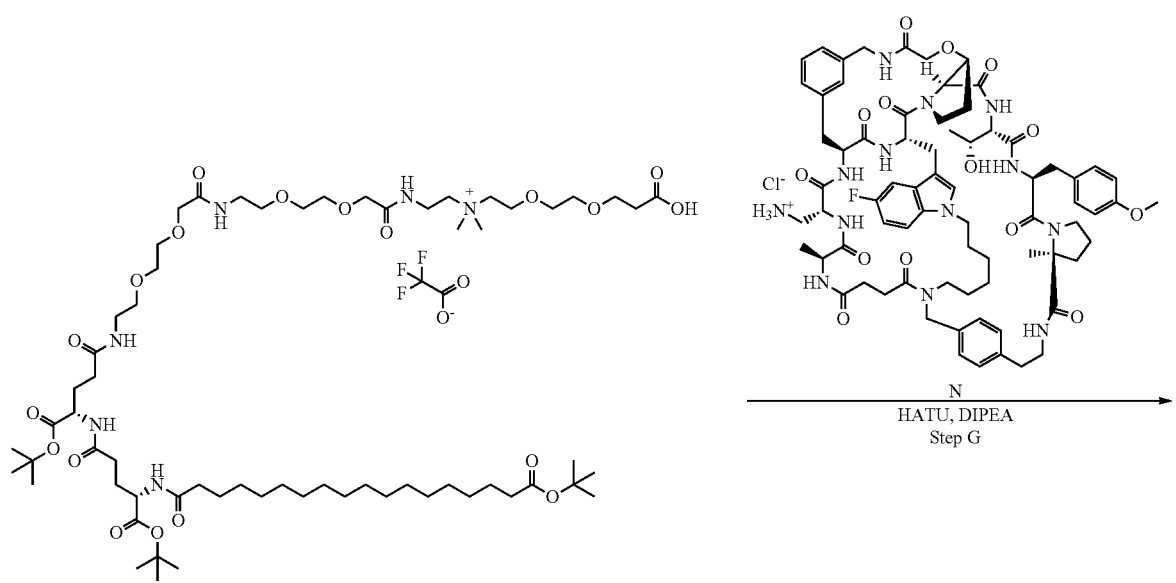
10k

-continued

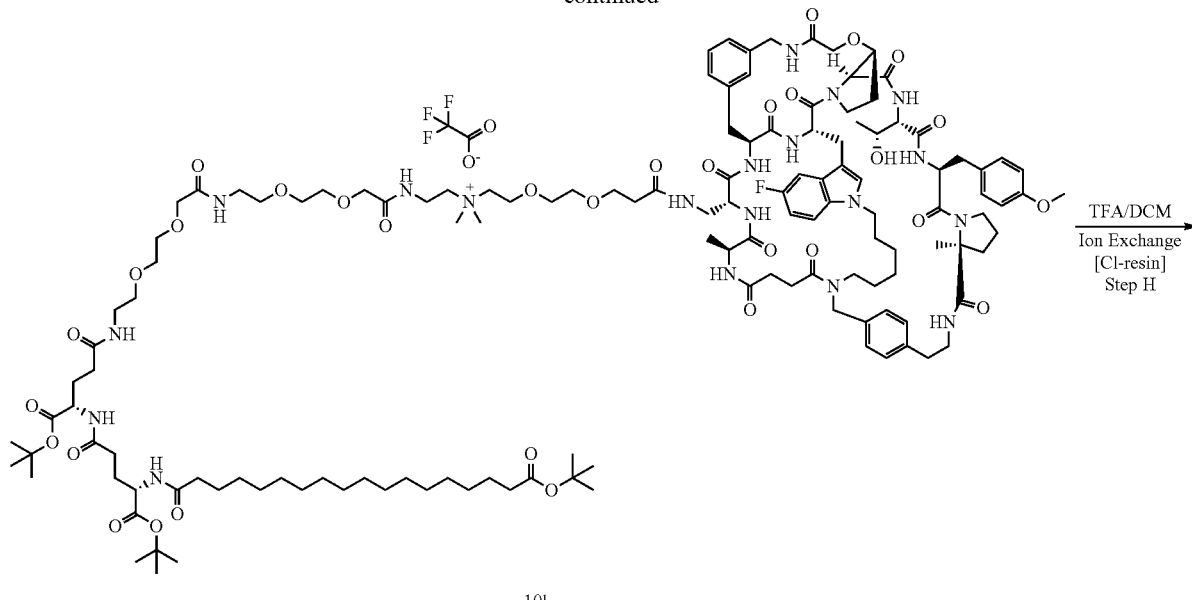

101

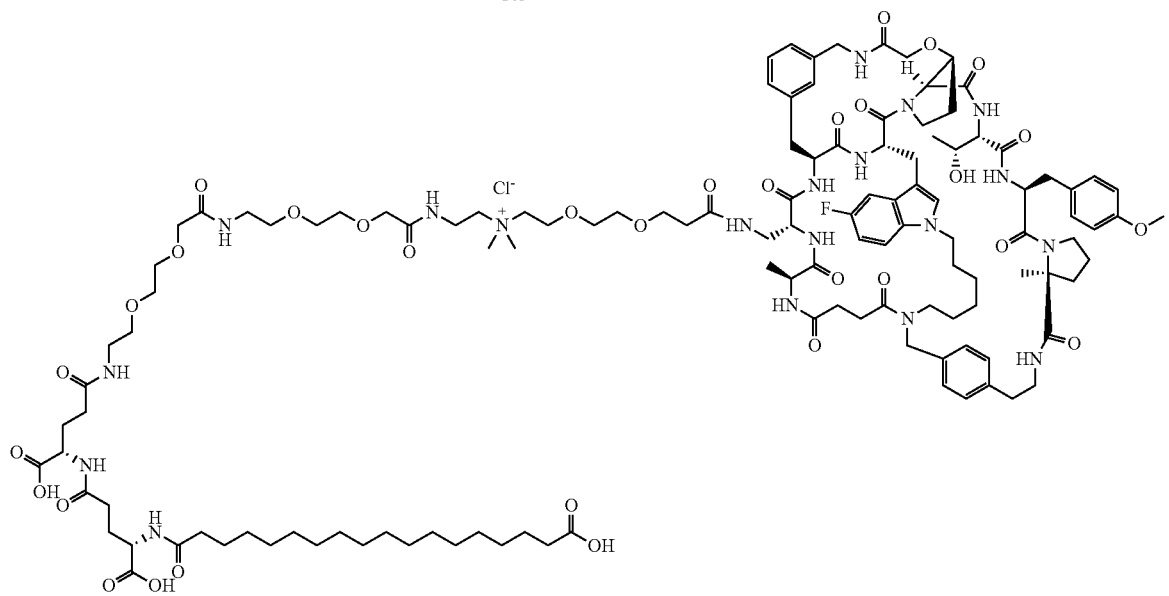

Example 10 (Cl salt)

Step A—Synthesis of Intermediate 10f

To a solution of 4l (2.411 g, 4.13 mmol) and Fmoc-Glu-OtBu (2.109 g, 4.96 mmol) in DMF (15 ml) and acetonitrile (40.00 ml) at 0° C. were added HATU (1.884 g, 4.96 mmol) and DIEA (2.89 ml, 16.52 mmol), then the resulting solution was stirred at RT for 2 h. The final mixture was diluted with brine and extracted with EtOAc. The organic layer was washed with brine, dried over $Na_2SO_4$ and filtered. The filtrate was concentrated and the residue was purified by MPLC over silica gel (eluting with a gradient of MeOH in DCM) to provide 10f. LC/MS: $[M+H]^+=991.3$.

Step B—Synthesis of Intermediate 10 g

To a solution of 10f (3.6 g, 3.63 mmol) in acetonitrile (40 ml) was added piperidine (1.798 ml, 18.16 mmol) and the resulting solution was stirred at RT for 3 h. The mixture was diluted with acetonitrile (150 mL), washed twice with hexanes then concentrated to give 10 g. LC/MS: $[M+H]^+=770.1$.

Step C—Synthesis of Intermediate 10 h

To a solution of 10 g (2.79 g, 3.63 mmol) in DMF (20 ml) at 0° C. were added 18-(tert-butoxy)-18-oxooctadecanoic acid (1.748 g, 4.72 mmol), HATU (1.794 g, 4.72 mmol), and DIEA (2.54 ml, 14.51 mmol) then the resulting solution was stirred at RT for 40 min. The final mixture was diluted with brine and extracted with EtOAc. The organic layer was washed with brine, dried over Na2SO4 and filtered. The filtrate was concentrated and the residue was purified by MPLC over silica gel (eluting with a gradient of MeOH in DCM) to provide 10 h. LC/MS: $[M+H]^+=1121.4$.

Step D—Synthesis of Intermediate 10i

To a solution of 10 h (3.1 g, 2.76 mmol) in MeOH (100 ml) at RT was added 10% Pd/C (0.588 g, 0.553 mmol), and the mixture was degassed then hydrogenated using a balloon filled with hydrogen for 2 h. The final mixture was filtered over Celite and concentrated to give 10i. LC/MS: [M+H]$^+$=1031.7.

Step E—Synthesis of Intermediate 10j

To a solution of 10i (2.548 g, 2.471 mmol) and intermediate I (1.491 g, 2.96 mmol) in DMF (6 ml) and acetonitrile (30 ml) at 0° C. were added DIEA (2.158 ml, 12.35 mmol) and HATU (1.127 g, 2.96 mmol), then the resulting solution was stirred at RT for 1 h. The final mixture was concentrated, diluted with brine and extracted with DCM. The combined organic layers were washed with brine, dried over Na$_2$SO$_4$ and concentrated to give provide 10j. LC/MS: [M]$^+$=1351.9.

Step F—Synthesis of Intermediate 10k

To a solution of 10j (3.65 g, 2.467 mmol) in MeOH (100 ml) was added well shaken Raney Ni (25 ml, 2.467 mmol) then the resulting mixture was hydrogenated using a balloon filled with hydrogen for 8 h. The final mixture was filtered over Celite (rinsing with MeOH and DCM) and the filtrate was concentrated. The residue was purified by reverse phase MPLC over C18 (eluting with a gradient of acetonitrile (+0.05% TFA) in water (+0.05% TFA)) to give 10k. LC/MS: [M]$^+$=1261.8.

Step G—Synthesis of Intermediate 10l

Intermediate 10k (1.78 g, 1.294 mmol) was reacted with intermediate N and converted to 10l using conditions similar to those described in Example 9, Step C. LC/MS: [(M+H)/2]$^+$=1320.0.

Step H—Synthesis of Example 10 (Cl Salt)

Intermediate 10l (3.7 g, 1.289 mmol) was converted to Example 10 (Cl salt) using conditions similar to those described in Synthesis A of Example 4, Steps G and H. LC/MS: [(M+H)/2]$^+$=1235.9.

Synthesis of Example 11

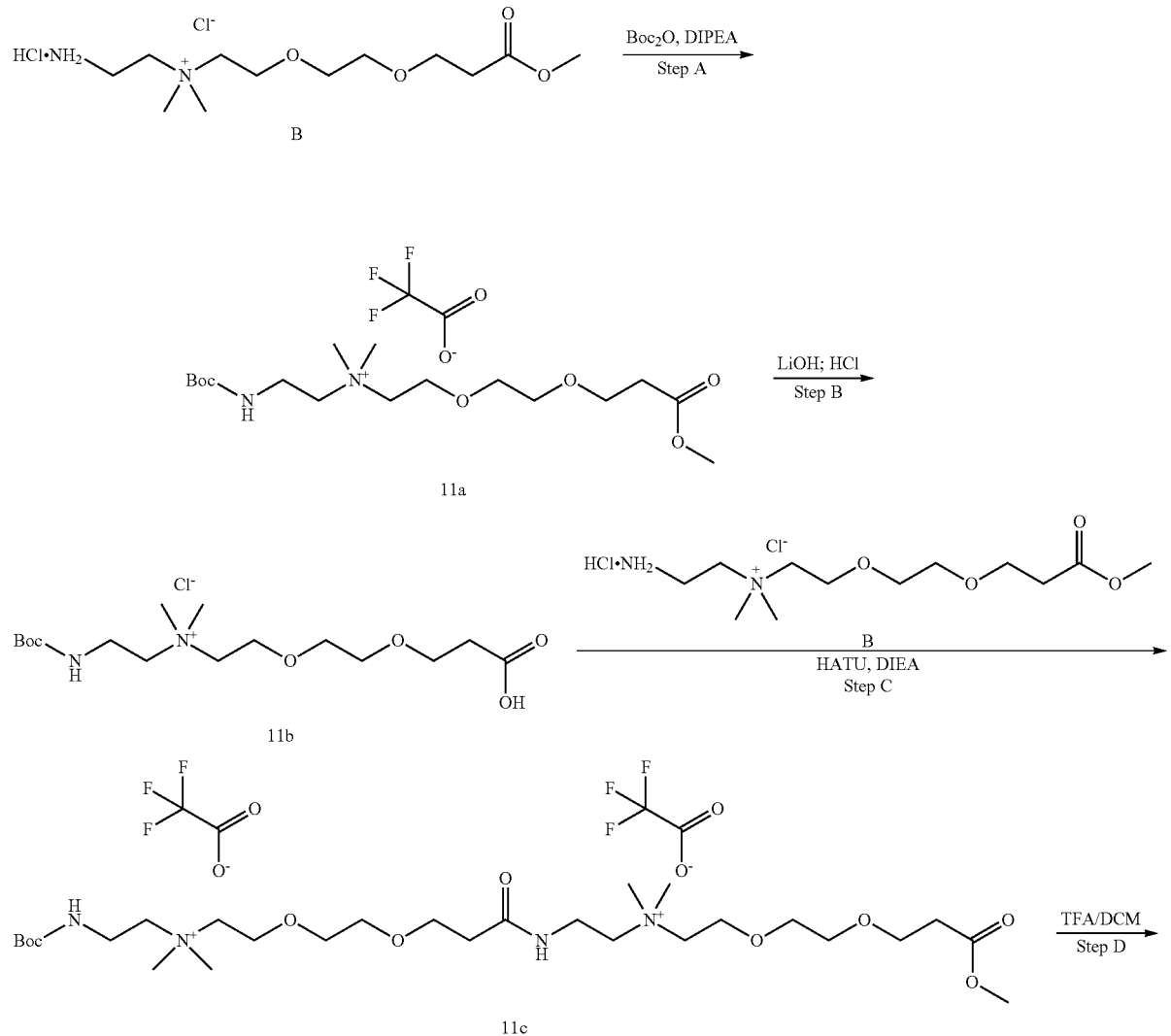

321 322
-continued
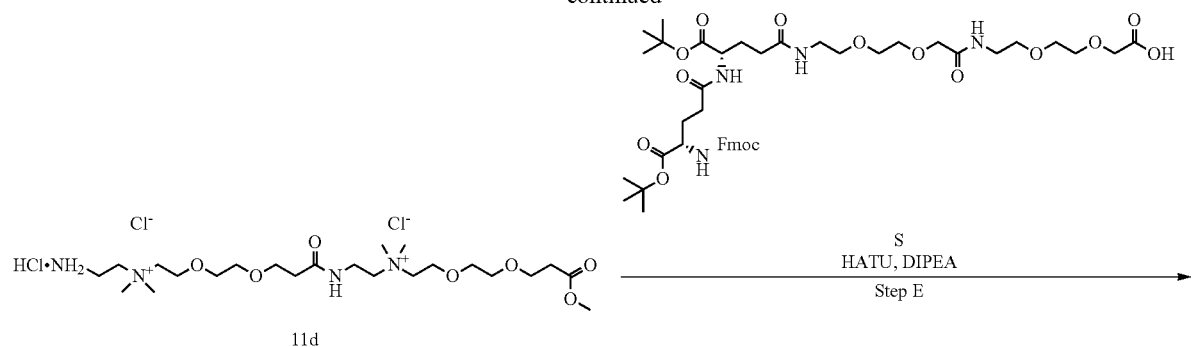
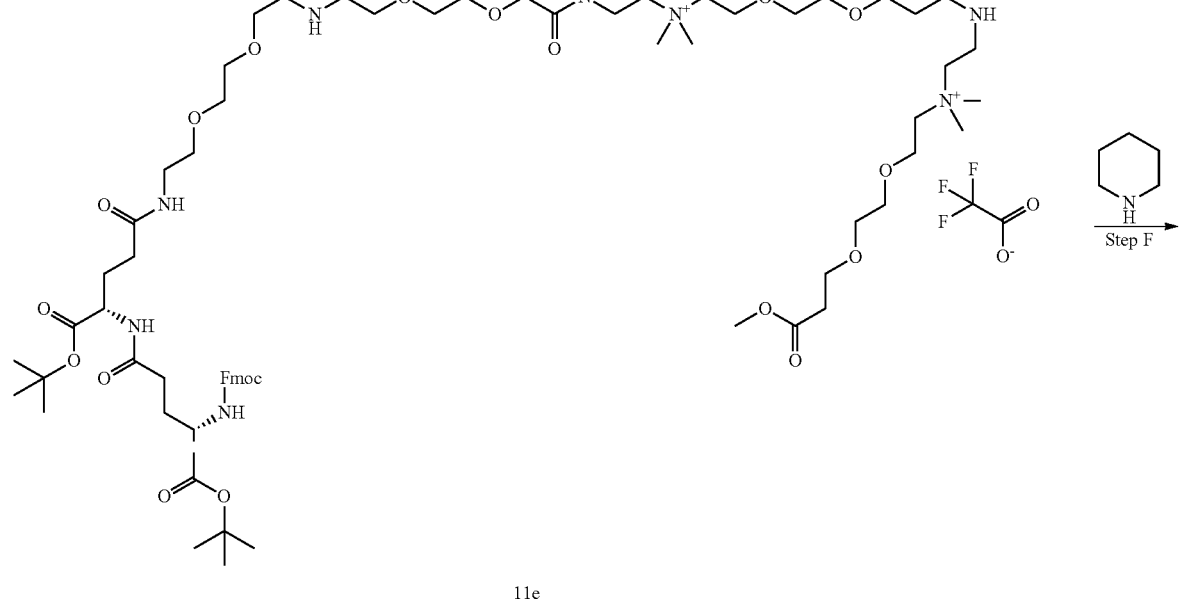
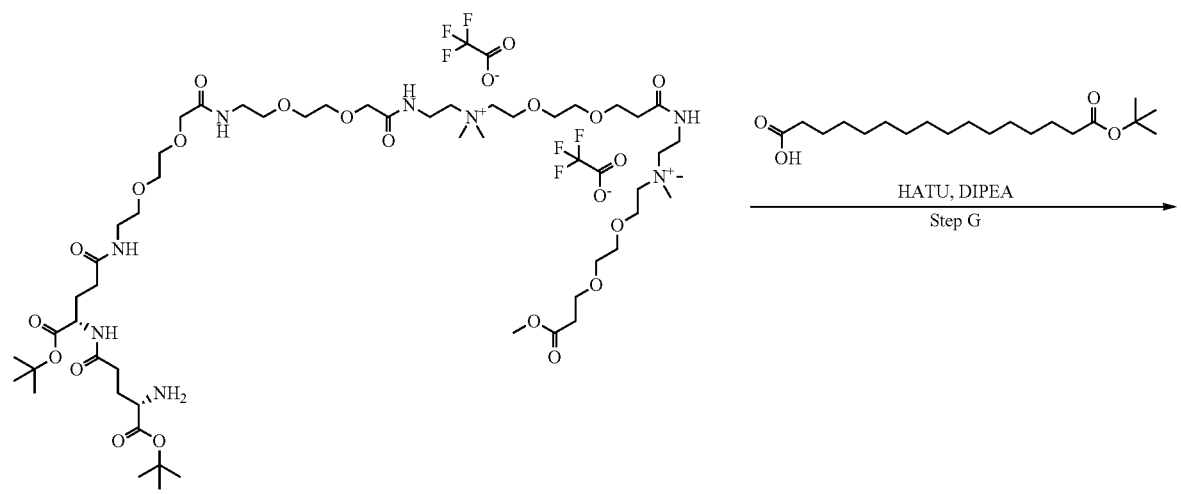

323
324
-continued
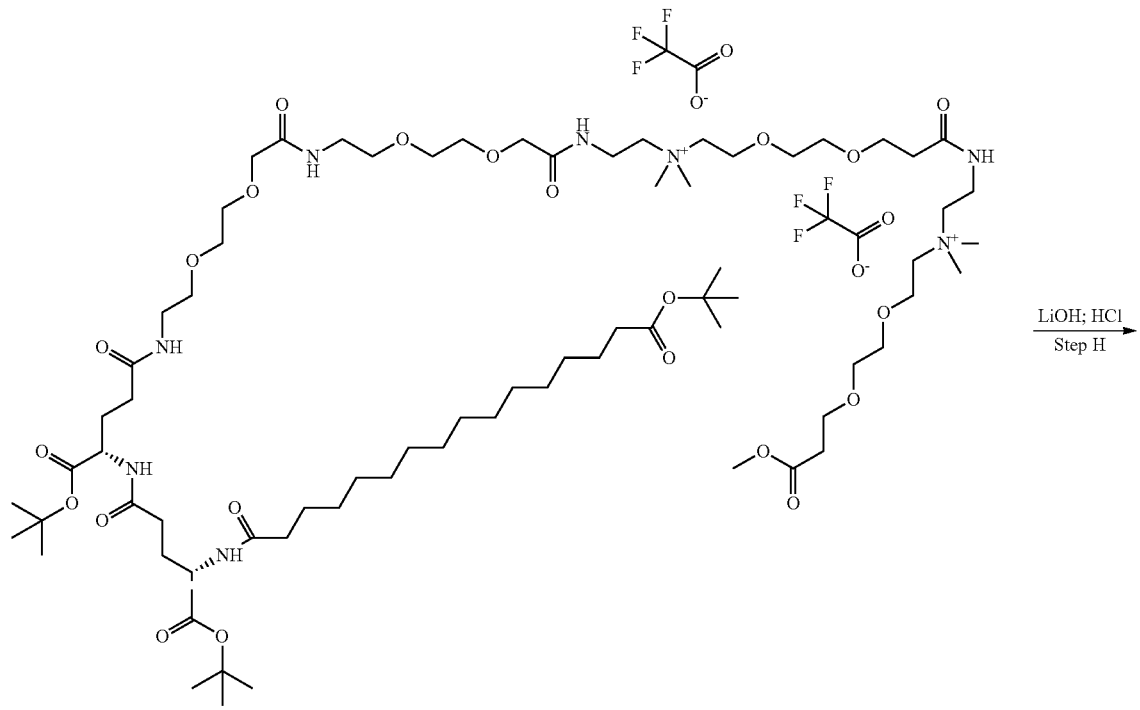
11g
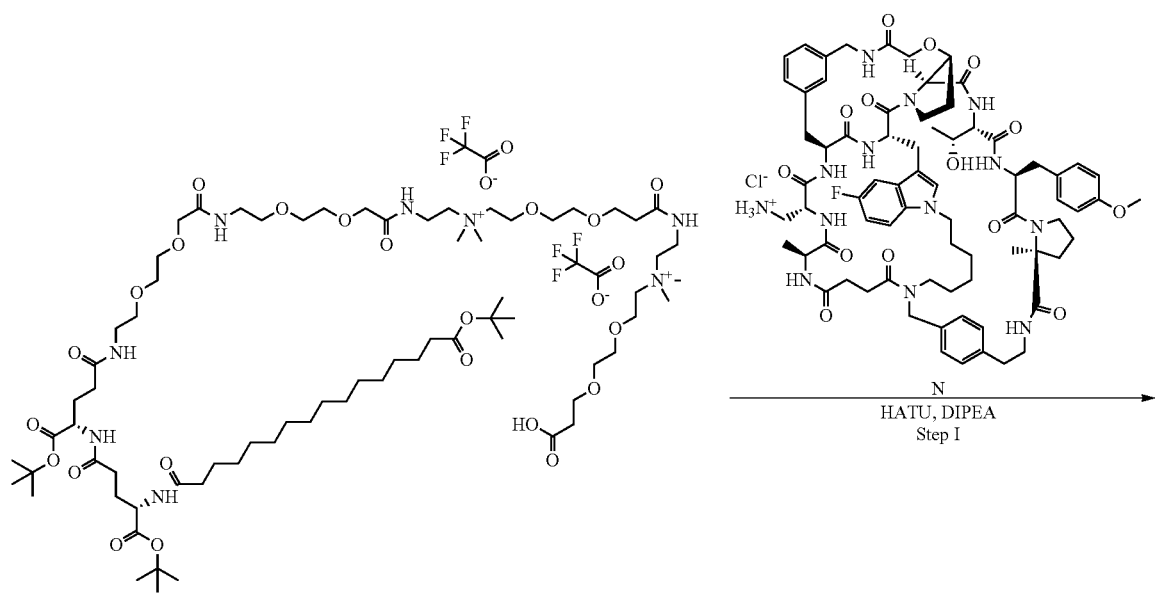
11h 325
326
-continued
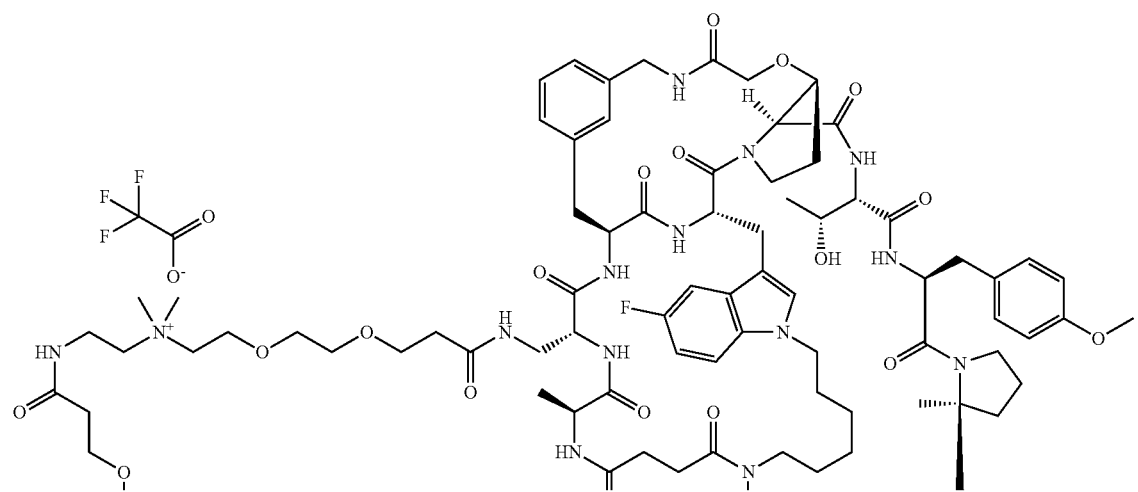
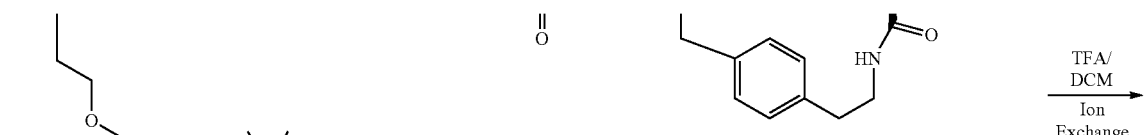
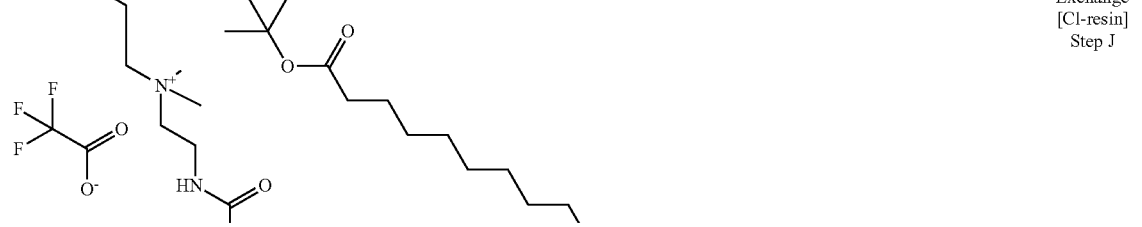
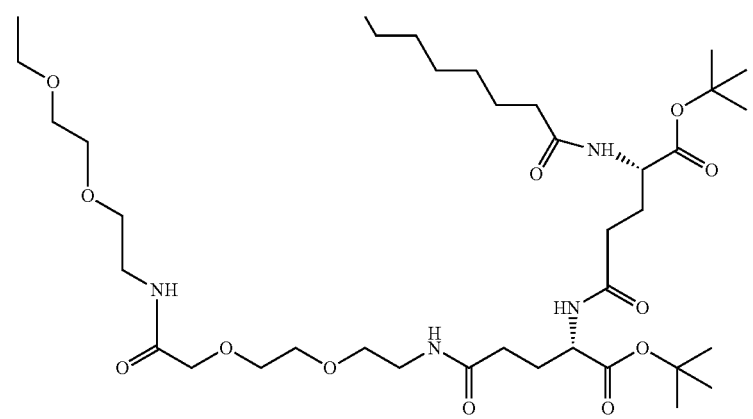
11i

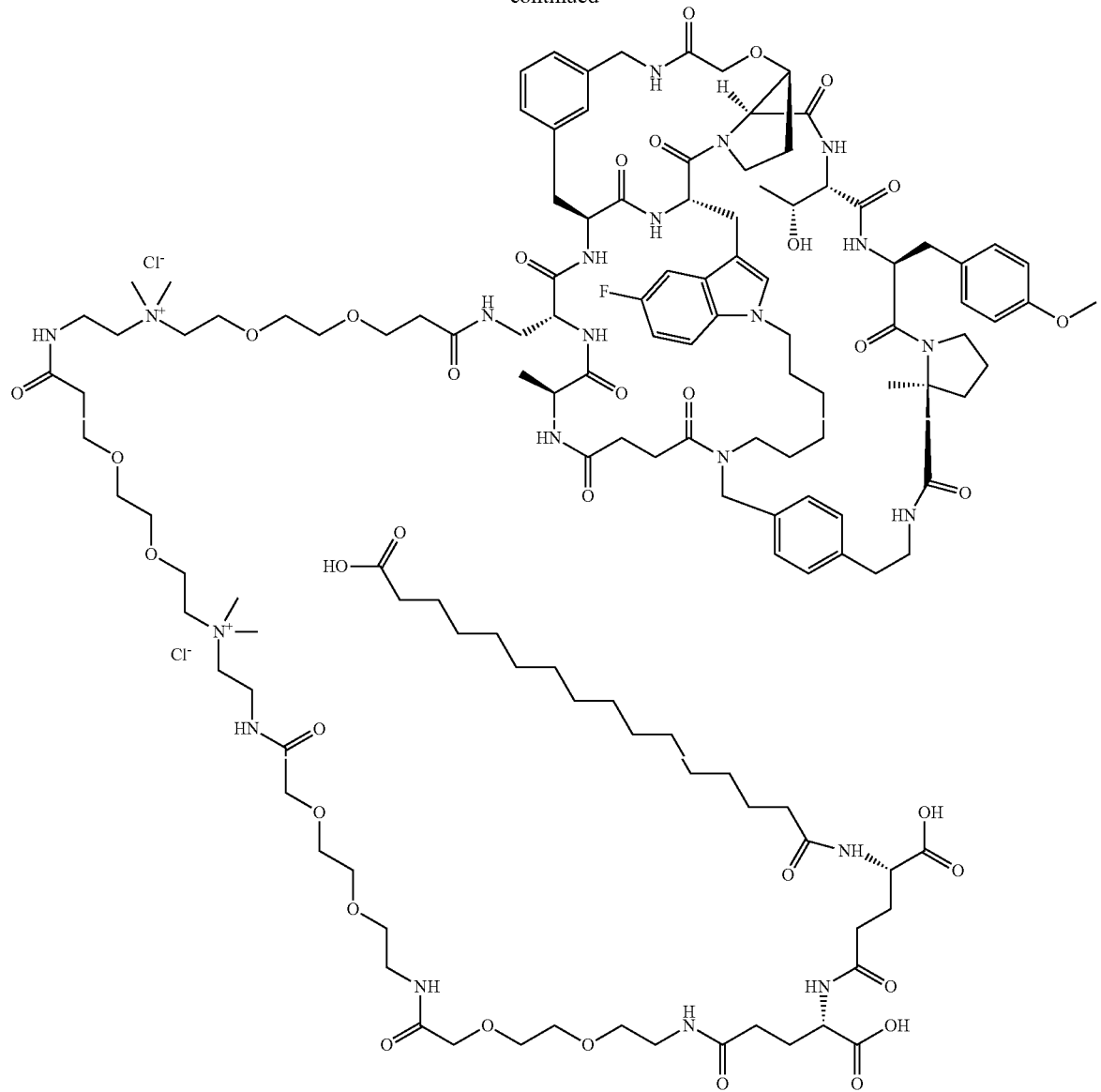

Example 11 (Cl salt)

Step A—Synthesis of Intermediate 11a

To a mixture of intermediate B (1.0 g, 2.358 mmol) in acetonitrile (20 ml) at RT were added DIEA (2.471 ml, 14.15 mmol) and Boc$_2$O (0.602 ml, 2.59 mmol) in DCM (10 mL) then the resulting solution was stirred at RT for 2 h. The solution was concentrated and the residue was purified by reverse phase MPLC over C18 (eluting with a gradient of acetonitrile (+0.05% TFA) in water (+0.05% TFA)) to give 11a. LC/MS: [M]$^+$=363.3.

Step B Synthesis of Intermediate 11b

To a solution of 11a (1.34 g, 2.90 mmol) in THF (10 ml), MeOH (3 ml), and water (3 ml) at 0° C. was added 1 N aqueous LiOH (11.61 ml, 11.61 mmol) then the resulting solution was stirred at RT for 2 h. The solution was concentrated, acidified to pH 3-4 with 1 N aqueous HCl, then lyophilized to give 11b. LC/MS: [M]$^+$=349.3.

Step C—Synthesis of Intermediate 11e

To a mixture of intermediate B (1.355 g, 3.20 mmol) and 11b (1.121 g, 2.90 mmol) in DMF (30 mL) at RT were added DIEA (5.07 ml, 29.0 mmol) and HATU (1.160 g, 3.05 mmol) then the resulting mixture was stirred at RT for 4 h. The final mixture was purified by reverse phase MPLC over C18 (eluting with a gradient of acetonitrile (+0.05% TFA) in water (+0.05% TFA)) to give 11c. LC/MS: [M/2]$^+$=297.3.

Step D—Synthesis of Intermediate 11d

To a solution of 11e (2.06 g, 2.60 mmol) in DCM (10 ml) was added TFA (10 ml, 130 mmol) and the resulting solution was stirred at RT for 50 min. The solution was concentrated, the residue was dissolved in acetonitrile (25 mL) and water (25 mL) and lyophilized, then the residue was re-dissolved in DCM/acetonitrile 3:1 (30 mL), treated with 4N HCl in dioxane (1.954 ml, 7.81 mmol) and concentrated to give 11d. LC/MS: [M/2]⁺=247.3.

Step E—Synthesis of Intermediate 11e

To a solution of intermediate S (150 mg, 0.166 mmol) and 11d (157 mg, 0.216 mmol) in DMF (4 ml) at RT were added HATU (66.5 mg, 0.175 mmol) and DIEA (0.174 ml, 0.999 mmol) then the resulting solution was stirred at RT for 1 h. The final solution was purified by reverse phase MPLC over C18 (eluting with a gradient of acetonitrile (+0.05% TFA) in water (+0.05% TFA)) to give 11e. LC/MS: [M/2]⁺=688.6.

Step F—Synthesis of Intermediate 11f

To a solution of 11e (191 mg, 0.121 mmol) in acetonitrile (2 ml) was added piperidine (0.036 ml, 0.364 mmol) and the resulting solution was stirred at RT for 2.5 h, then concentrated to give 11f.
LC/MS: [M/2]⁺=577.7

Step G—Synthesis of Intermediate 11 g

To a solution of 11f (174 mg, 0.129 mmol) and 16-(tert-butoxy)-16-oxohexadecanoic acid (66.1 mg, 0.193 mmol) in DMF (4.5 ml) at RT were added HATU (73.4 mg, 0.193 mmol) and DIEA (0.135 ml, 0.772 mmol) then the resulting solution was stirred at RT for 1.5 h. The final mixture was purified by reverse phase MPLC over C18 (eluting with a gradient of acetonitrile (+0.05% TFA) in water (+0.05% TFA)) to give 11 g. LC/MS: [M/2]⁺=739.7.

Step H Synthesis of Intermediate 11 h

To a solution of 11 g (163 mg, 0.097 mmol) in THF (2 ml) at 0° C. was added 1 N aqueous LiOH (0.224 ml, 0.224 mmol) and the resulting solution was stirred at 0° C. for 1 h. The final solution was quenched with 1 N aqueous HCl (200 μL), then concentrated, and the residue was purified by reverse phase MPLC over C18 (eluting with a gradient of acetonitrile (+0.05% TFA) in water (+0.05% TFA)) to give 11 h. LC/MS: [M/2]⁺=732.8.

Step I—Synthesis of Intermediate 11i

To a solution of intermediate N (52 mg, 0.036 mmol) and 11 h (66.4 mg, 0.040 mmol) in DMF (2 ml) and water (0.1 ml) at 0° C. were added HATU (15.20 mg, 0.040 mmol) and DIEA (0.051 ml, 0.291 mmol) and the solution was stirred at 0° C. for 90 min. The solution was purified by reverse phase MPLC over C18 (eluting with a gradient of acetonitrile (+0.05% TFA) in water (+0.05% TFA)) to give 11i. LC/MS: [M/2]⁺=1421.1.

Step J—Synthesis of Example 11 (Cl Salt)

Intermediate 11i (92 mg, 0.032 mmol) was converted to Example 11 (TFA salt) using tert-butyl ester deprotection conditions similar to those described in Synthesis A of Example 4, Step G. LC/MS: [M/2]⁺=1337.0. Example 11 (TFA salt) was then converted to Example 11 (Cl salt) using resin exchange conditions similar to those described in Synthesis A of Example 4, Step H. LC/MS: [M/2]⁺=1336.4.

Synthesis of Example 12

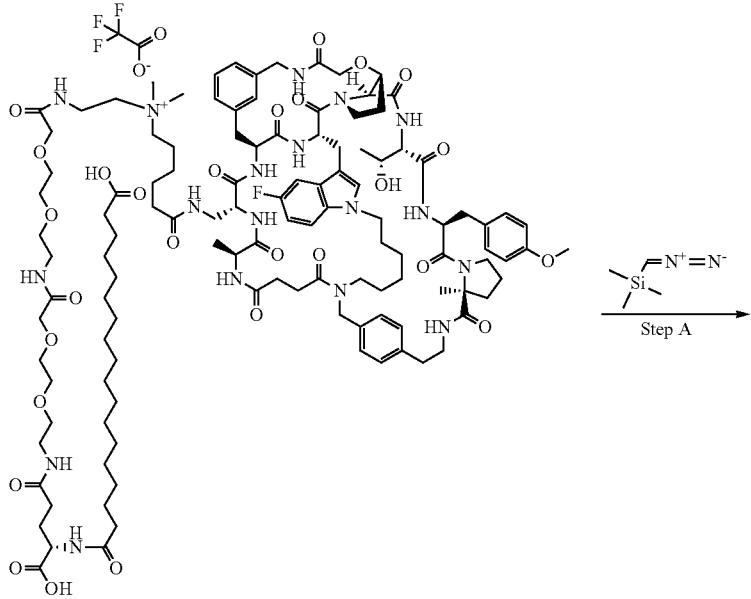

Example 2 (TFA salt)

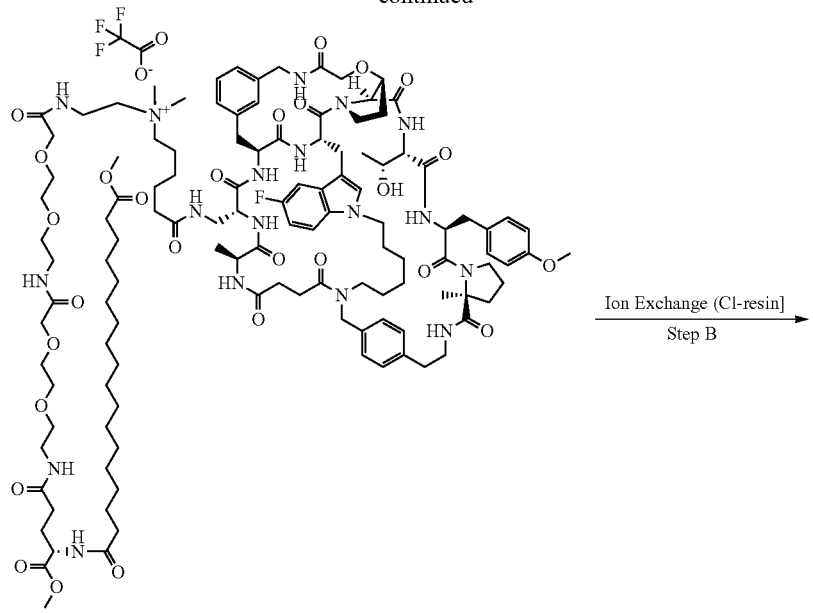

Example 12 (TFA salt)

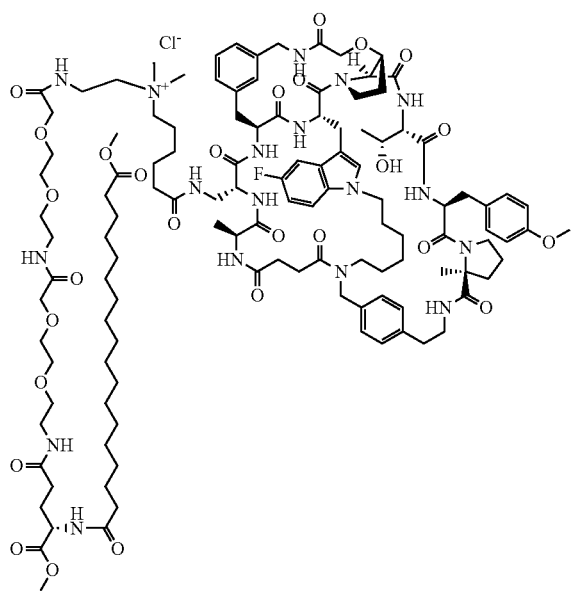

Example 12 (Cl salt)

Step A—Synthesis of Example 12 (TFA Salt)

To a solution of Example 2 (TFA salt) (103 mg, 0.043 mmol) in MeOH (10 ml) was added TMS-diazomethane (2.138 ml, 4.28 mmol) dropwise, and the resulting solution was stirred at RT for 10 min. The solution was quenched by addition of a few drops of acetic acid, concentrated then the residue was purified by reverse phase HPLC over C18 (eluting with a gradient of acetonitrile (+0.05% TFA) in water (+0.05% TFA)) to afford Example 12 (TFA salt). LC/MS: $[(M+H)/2]^+=1161.8$.

Step B—Synthesis of Example 12 (Cl Salt)

Example 12 (TFA salt) was converted to Example 12 (Cl salt) using resin exchange conditions similar to those described in Synthesis A of Example 4, Step H. LC/MS: $[(M+H)/2]^+=1161.9$.

Synthesis of Example 13
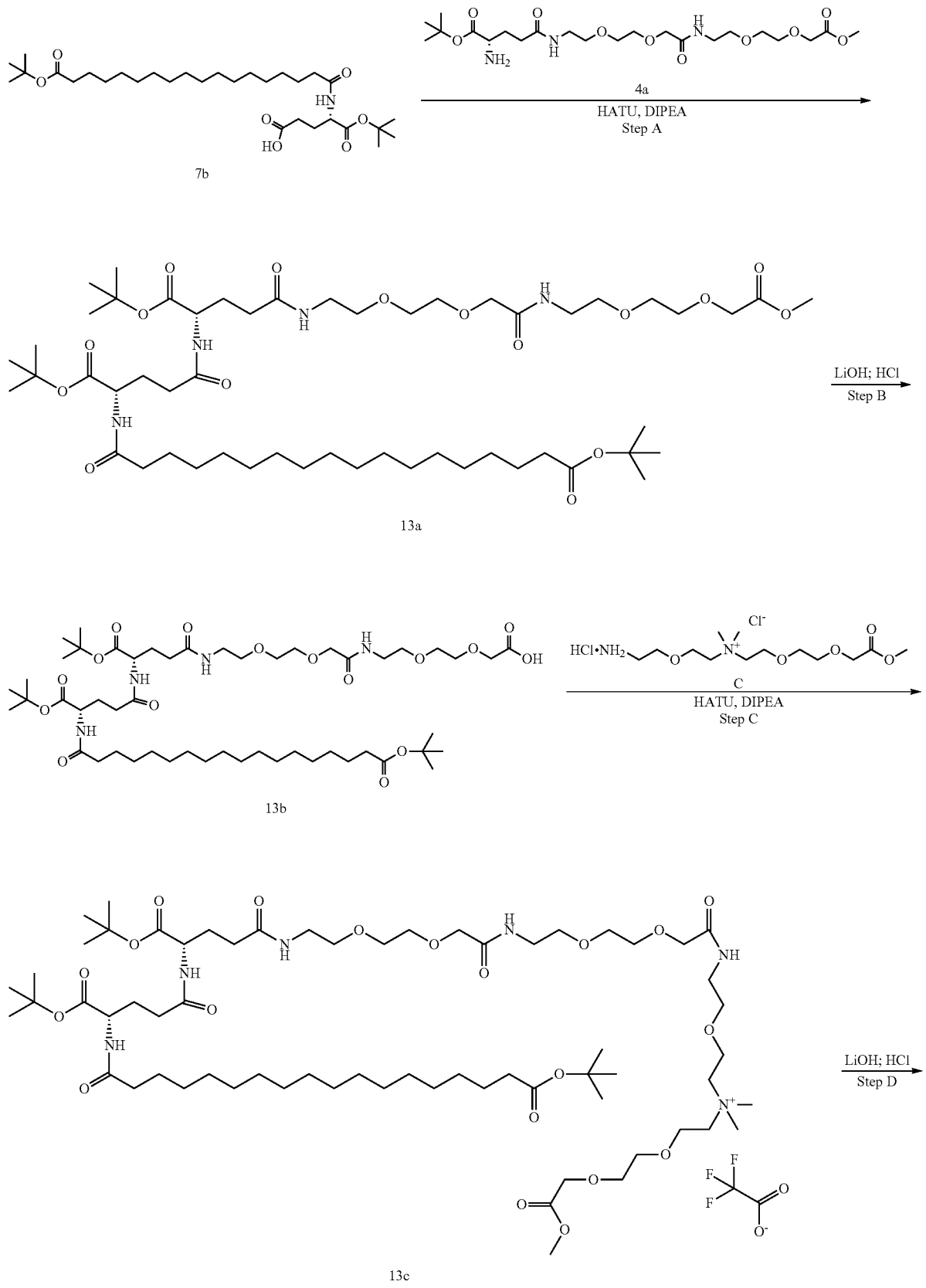

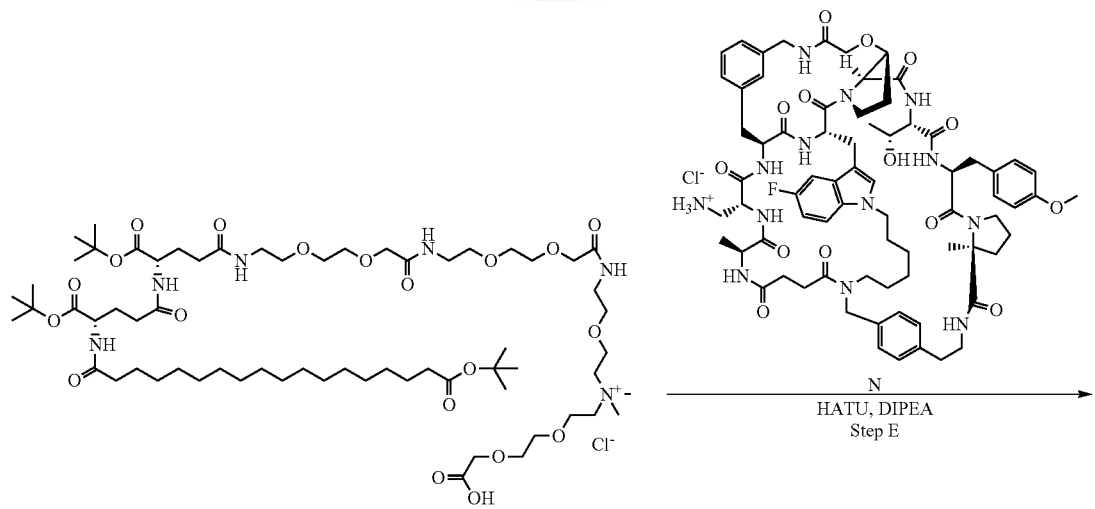
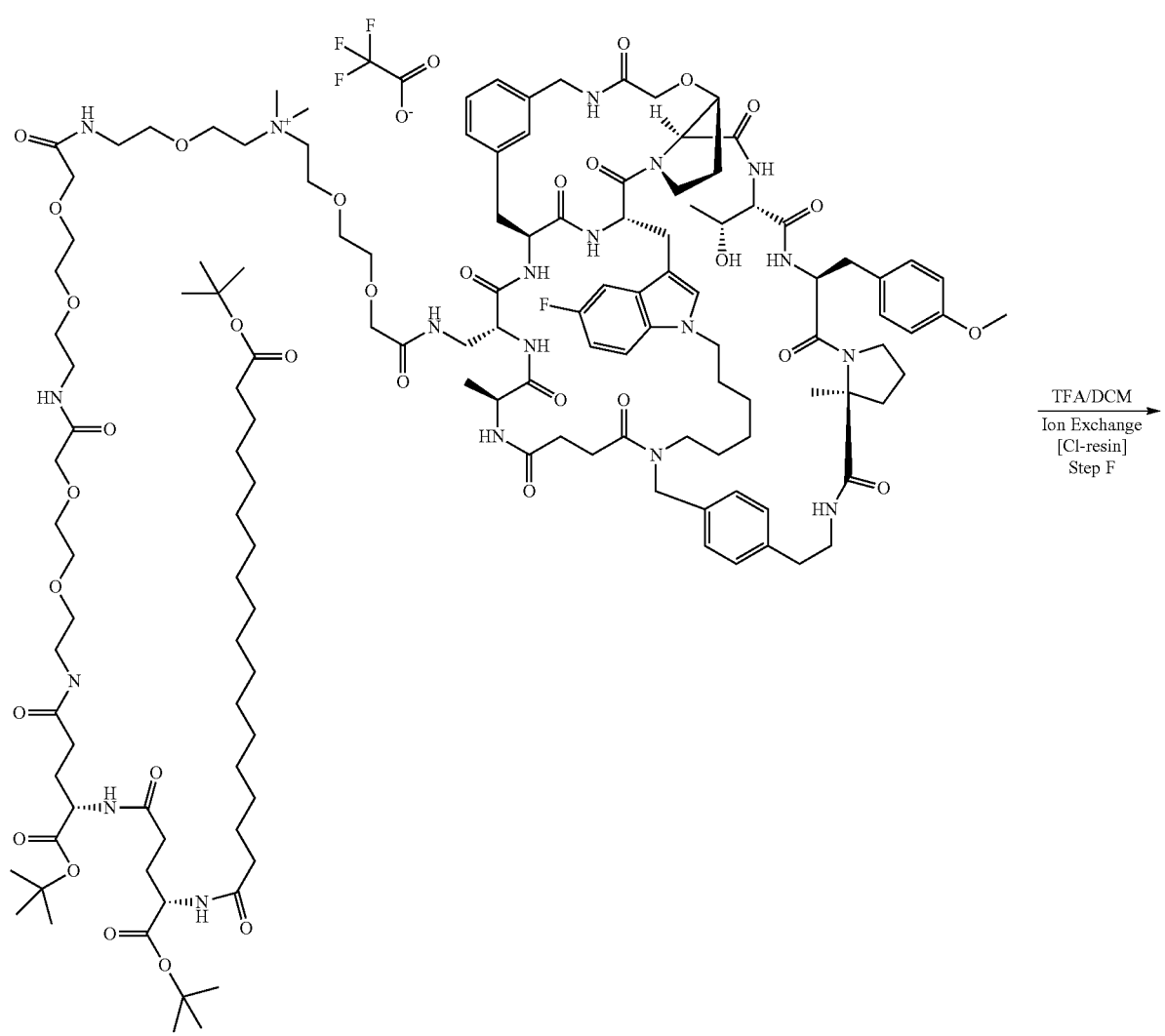

-continued

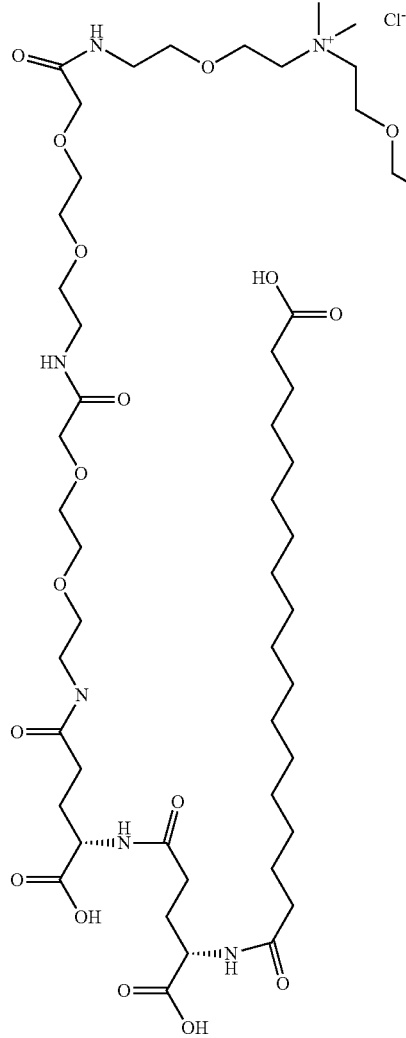
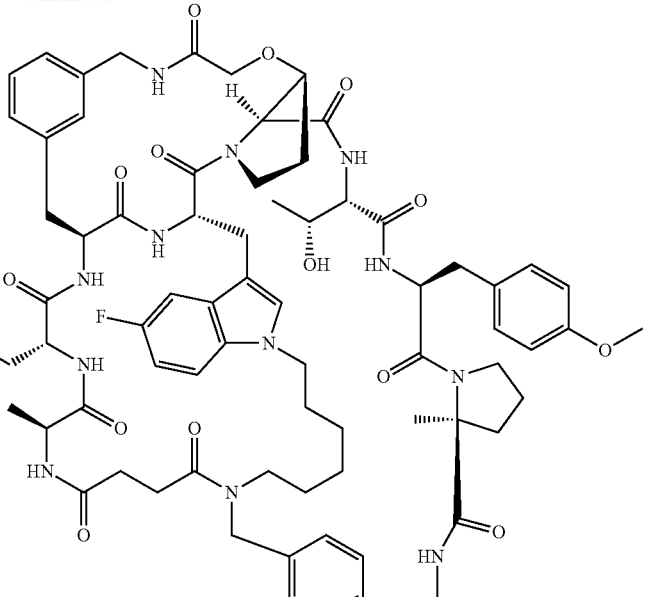

Example 13 (Cl salt)

Step A—Synthesis of Intermediate 13a

To a solution of 7b (1.2 g, 2.16 mmol) in DMF (15 mL) at 0° C. were added 4a (1.21 g, 2.38 mmol), HATU (0.90 g, 2.38 mmol) and DIEA (3.02 mL, 17.27 mmol) and the reaction mixture was stirred at 0° C. for 1 h. The solution was quenched with water (2 mL) and purified by reverse phase MPLC over C18 (eluting with a gradient of acetonitrile in water (+0.05% TFA)) to give 13a. LC/MS: $[M+Na]^+=1068.6$.

Step B—Synthesis of Intermediate 13b

To a solution of 13a (1.6 g, 1.53 mmol) in THF (16 mL) at 0° C. was added 1 M aqueous LiOH (3.06 mL, 3.06 mmol) and the reaction mixture was stirred at 0° C. for 1 h. The resulting solution was quenched with 1 M aqueous HCl (3.06 mL) and purified by reverse phase MPLC over C18 (eluting with a gradient of acetonitrile in water) to afford 13b. LC/MS: $[M+H]^+=1031.5$. $^1$H NMR (400 MHz, CD$_3$OD): δ 4.32-4.25 (m, 2H), 4.18 (s, 2H), 4.03 (s, 2H), 3.76-3.65 (m, 8H), 3.63-3.56 (m, 4H), 3.47 (t, J=5.5 Hz, 2H), 3.41 (t, J=5.8 Hz, 2H), 2.40-2.11 (m, 10H), 1.94-1.86 (m, 2H), 1.70-1.54 m, 4H), 1.51-1.44 (m, 27H), 1.37-1.29 (m, 24H).

Step C—Synthesis of Intermediate 13c

To a solution of 13b (200 mg, 0.194 mmol) in DMF (2 mL) and water (0.2 mL) at 0° C. were added HATU (88 mg, 0.233 mmol), DIEA (0.203 mL, 1.164 mmol) and intermediate C (142 mg, 0.388 mmol) and the mixture was stirred at −10° C. for 10 min. The final solution was quenched with water (200 μL) and purified by reverse phase MPLC over C18 (eluting with a gradient of acetonitrile in water (+0.05% TFA)). The fractions containing the desired product were combined and concentrated. The residue was re-dissolved in acetonitrile (10 mL) and water (10 mL) and lyophilized to afford 13c. LC/MS: $[M]^+=1305.8$.

Step D—Synthesis of Intermediate 13d

To a solution 13c (230 mg, 0.16 mmol) in THF (2.3 mL) at 0° C. was added 1 M aqueous LiOH (0.32 mL, 0.32 mmol) and the mixture was stirred at 0° C. for 1 h. The solution was quenched with 1 M aqueous HCl (0.33 mL) and purified by reverse phase MPLC over C18 (eluting with a gradient of acetonitrile in water (+0.05% TFA)). The fractions containing the desired product were combined and concentrated. The residue was re-dissolved in acetonitrile (5 mL) and water (5 mL), treated at 0° C. with 1 N aqueous HCl (0.17 mL) and lyophilized to afford 13d. LC/MS: [M]$^+$=1291.8.

Step E—Synthesis of Intermediate 13e

To a solution of 13d (91 mg, 0.068 mmol) in DMF (700 µL) and water (70 µL) at 0° C. were added intermediate N (70 mg, 0.05 mmol), HATU (37.2 mg, 0.10 mmol) and DIEA (50.6 mg, 0.39 mmol) and the mixture was stirred at 0° C. for 10 min. The final solution was quenched with water (500 µL) and purified by reverse phase MPLC over C18 (eluting with a gradient of acetonitrile in water (+0.05% TFA)) to provide 13e. LC/MS: [(M+H)/2)]$^+$=1335.0.

Step F—Synthesis of Example 13 (Cl Salt)

Intermediate 13e (95 mg, 0.034 mmol) was converted to Example 13 (TFA salt) using tert-butyl ester deprotection conditions similar to those described in Synthesis A of Example 4, Step G. LC/MS: [(M+H)/2)]$^+$=1250.7. Example 13 (TFA salt) was then converted to Example 13 (Cl salt) using resin exchange conditions similar to those described in Synthesis A of Example 4, Step H. LC/MS: [M]$^+$=2499.3.

Synthesis of Example 14

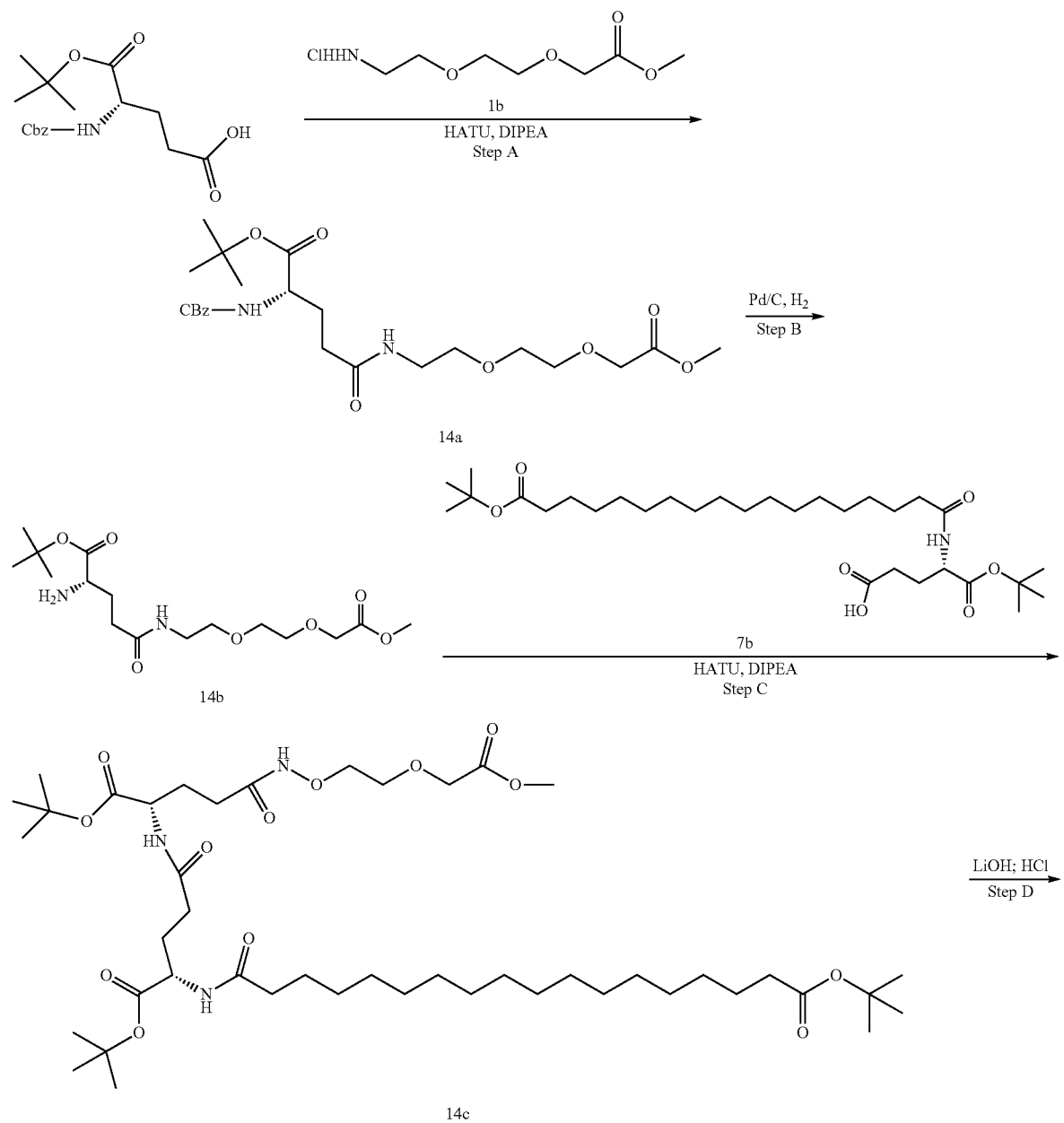

341 342
-continued
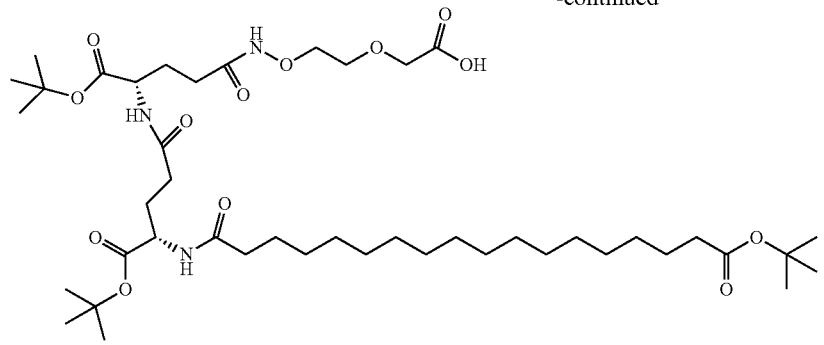
14d
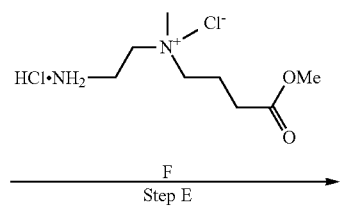
Step E
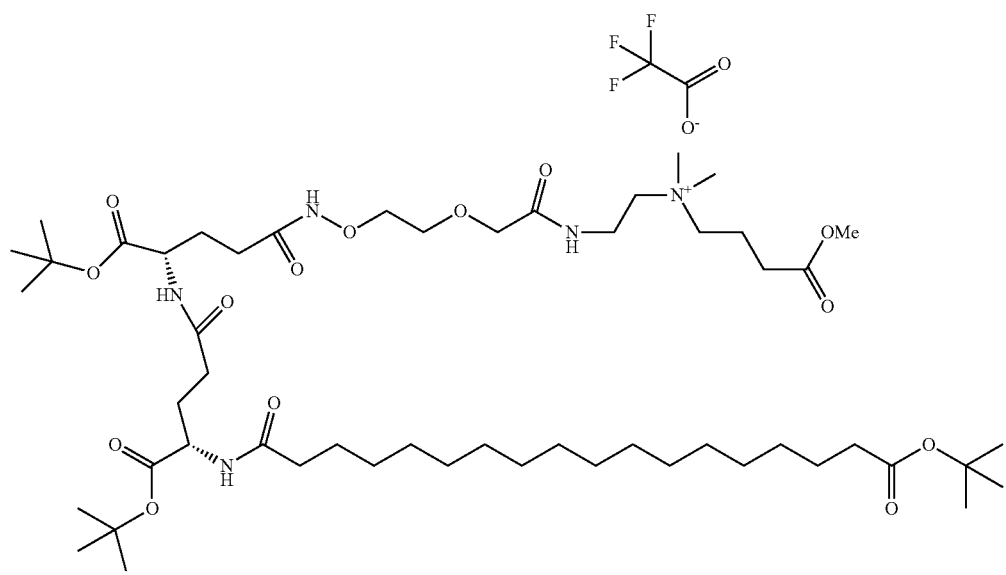
14e
LiOH; HCl
Step F
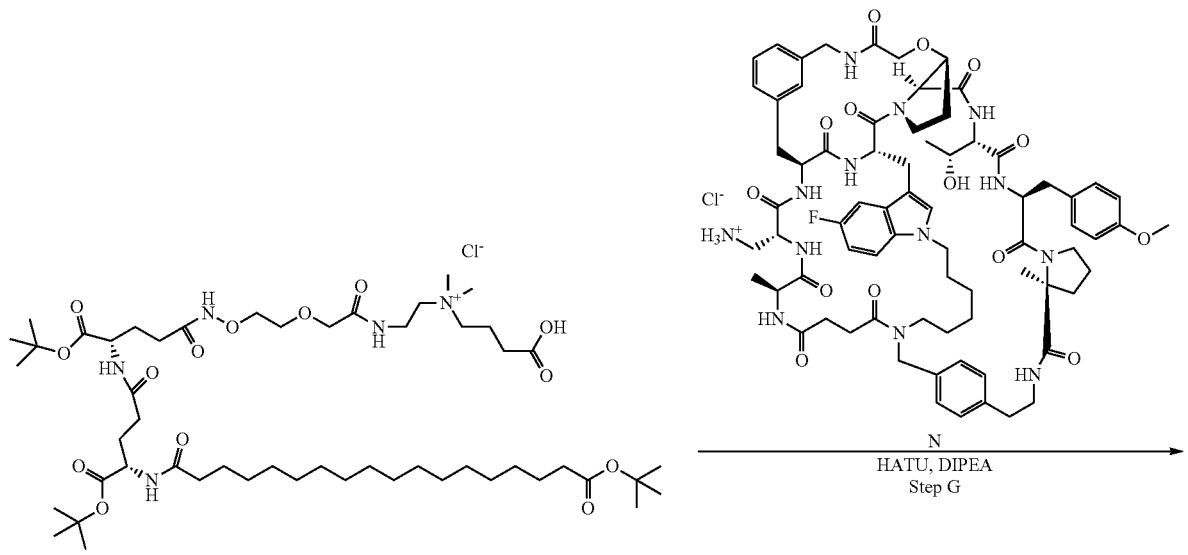
14f
HATU, DIPEA
Step G -continued

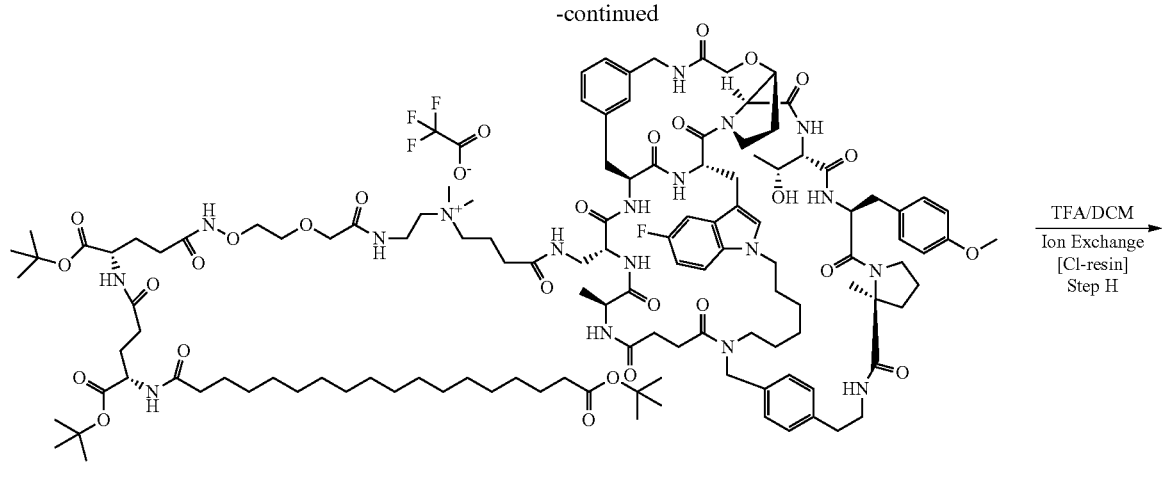

14g

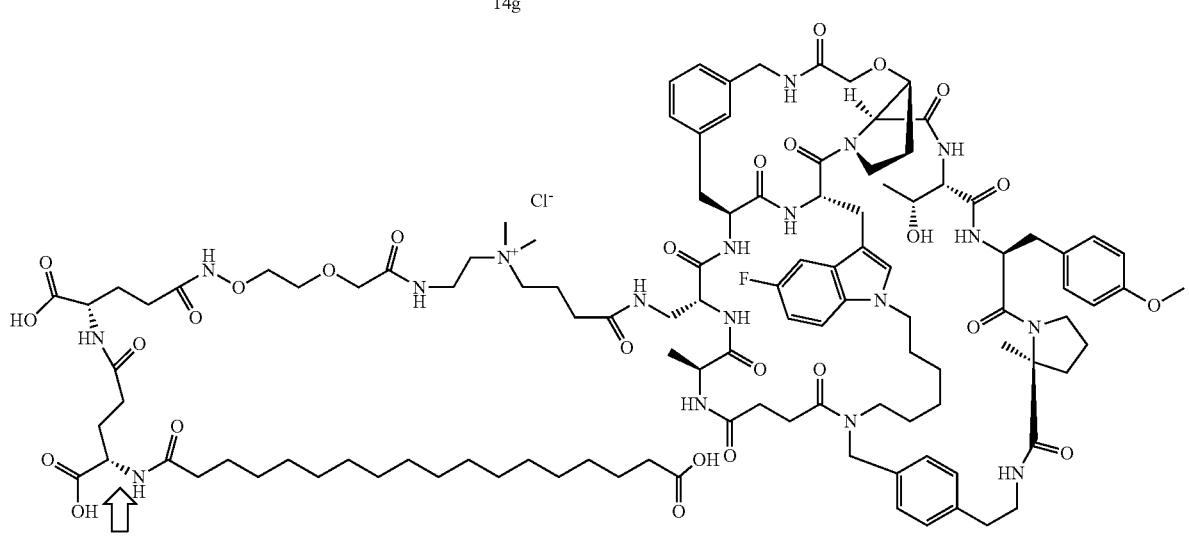

Example 14 (Cl salt)

Step A—Synthesis of Intermediate 14a

To a solution of (S)-4-(((benzyloxy)carbonyl)amino)-5-(tert-butoxy)-5-oxopentanoic acid (8.68 g, 25.7 mmol) in DMF (50 mL) at 0° C. were added HATU (10.68 g, 28.1 mmol), 1b (5 g, 23.40 mmol) and DIEA (32.7 mL, 187 mmol) and the reaction was stirred at 0° C. for 1 h. The final mixture was quenched with water (200 mL) and extracted with EtOAc (2×100 mL). The combined organic layers were washed with brine, dried over anhydrous $Na_2SO_4$ and filtered. The filtrate was concentrated under reduced pressure and the residue was purified by MPLC over silica gel (eluting with a gradient of 0%-30% EtOAc in PE) to provide 14a. LC/MS: $[M+H]^+$=497.2. $^1$H NMR (400 MHz, $CDCl_3$): δ 7.37-7.28 (m, 5H), 5.10 (s, 2H), 4.30-4.16 (m, 1H), 4.14 (s, 2H), 3.74 (s, 3H), 3.72-3.67 (m, 2H), 3.67-3.62 (m, 2H), 3.69-3.63 (m, 2H), 3.50-3.36 (m, 2H), 2.37-1.84 (m, 4H), 1.45 (s, 9H).

Step B—Synthesis of Intermediate 14b

To a solution of 14a (9 g, 18.13 mmol) in THF (150 mL) at RT was added 10% Pd/C (900 mg, 0.846 mmol). The mixture was degassed with hydrogen 3 times and stirred for 16 h at RT under hydrogen. The final mixture was filtered over Celite and the filtrate was concentrated under reduced pressure to provide 14b. LC/MS: $[M+H]^+$=363.2.

Step C—Synthesis of Intermediate 14c

To a solution of 7b (1 g, 1.80 mmol) in DMF (10 mL) at 0° C. were added 14b (0.72 g, 1.98 mmol), HATU (0.75 g, 1.98 mmol) and DIEA (1.57 mL, 9.00 mmol) and the reaction mixture was stirred at 0° C. for 1 h. The final solution was quenched with water (2 mL) and purified by reverse phase MPLC over C18 (eluting with a gradient of acetonitrile in water (+0.05% TFA)) to give 14c. LC/MS: $[M+H]^+$=900.6.

Step D—Synthesis of Intermediate 14d

To a solution of 14c (1.4 g, 1.56 mmol) in THF (14 mL) at 0° C. was added 1 M aqueous LiOH (3.11 mL, 3.11 mmol) and the reaction mixture was stirred at 0° C. for 1 h. The final mixture was quenched with 1 M aqueous HCl (3.1 mL) and purified by reverse phase MPLC over C18 (eluting with a gradient of acetonitrile in water) to provide 14d. LC/MS: $[M+H]^+$=886.7. $^1$H NMR (400 MHz, $CD_3OD$): δ 4.32-4.23 (m, 2H), 4.15 (s, 2H), 3.75-3.69 (m, 2H), 3.68-3.63 (m, 2H), 3.57 (t, J=5.4 Hz, 2H), 3.42-3.35 (m, 2H), 2.42-2.09 (m, 10H), 1.96-1.84 (m, 2H), 1.67-1.54 (m, 4H), 1.51-1.44 (m, 27H), 1.41-1.29 (m, 24H).

Step E—Synthesis of Intermediate 14e

To a solution of 14d (200 mg, 0.23 mmol) in DMF (2 mL) and water (0.2 mL) at 0° C. were added intermediate F (118 mg, 0.45 mmol), HATU (129 mg, 0.34 mmol) and DIEA (0.24 mL, 1.35 mmol) and the reaction was stirred at 0° C. for 1 h. The final solution was quenched with water (2 mL) and purified by reverse phase MPLC over C18 (eluting with a gradient of acetonitrile in water (+0.05% TFA)) to give 14e. LC/MS: [M]$^+$=1056.6.

Step F—Synthesis of Intermediate 14f

To a solution of 14e (180 mg, 0.15 mmol) in THF (2 mL) at 0° C. was added 1 M aqueous LiOH (0.31 mL, 0.31 mmol) and the reaction mixture was stirred at 0° C. for 1 h. The final solution was quenched with 1 M aqueous HCl (0.31 mL) and purified by reverse phase MPLC over C18 (eluting with a gradient of acetonitrile in water). The fractions containing the desired product were combined and concentrated. The residue was re-dissolved in acetonitrile (3 mL) and water (5 mL), treated at 0° C. with 1 N aqueous HCl (0.12 mL) and lyophilized to afford 14f. LC/MS: [M]$^+$=1043.6. $^1$H NMR (400 MHz, CD$_3$OD): δ 4.33-4.25 (m, 2H), 4.06 (s, 2H), 3.81-3.65 (m, 8H), 3.62-3.36 (m, 6H), 3.21 (s, 6H), 2.48 (t, J=6.8 Hz, 2H), 2.40-2.01 (m, 12H), 1.95-1.81 (m, 2H), 1.72-1.54 (m, 4H), 1.52-1.44 (m, 27H), 1.42-1.29 (m, 24H).

Step G—Synthesis of Intermediate 14 g

To a solution of intermediate N (50 mg, 0.035 mmol) in DMF (500 µL) and water (50 µL) at 0° C. were added 14f (52.8 mg, 0.049 mmol), HATU (26.6 mg, 0.07 mmol) and DIEA (36.1 mg, 0.28 mmol) and the reaction mixture was stirred at 0° C. for 1 h. The final mixture was quenched with water (300 µL) and purified by reverse phase MPLC over C18 (eluting with a gradient of acetonitrile in water (+0.05% TFA)) to give 14 g. LC/MS: [(M+H)/2)]$^+$=1210.4.

Step H—Synthesis of Example 14 (Cl Salt)

Intermediate 14 g (64 mg, 0.025 mmol) was converted to Example 14 (TFA salt) using tert-butyl ester deprotection conditions similar to those described in Synthesis A of Example 4, Step G. LC/MS: [(M+H)/2)]$^+$=1126.0. Example 14 (TFA salt) was then converted to Example 14 (Cl salt) using resin exchange conditions similar to those described in Synthesis A of Example 4, Step H. LC/MS: [M]$^+$=2250.2.

Synthesis of Example 15

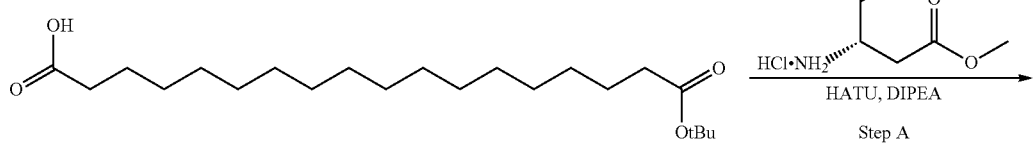

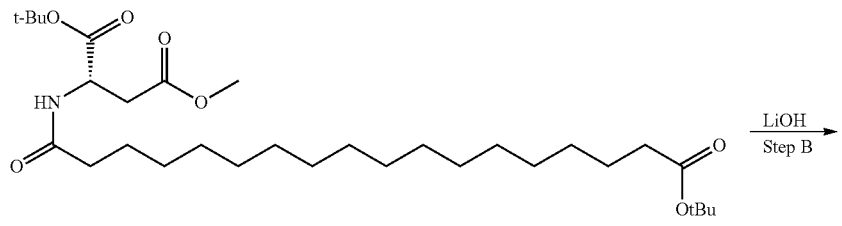

15a

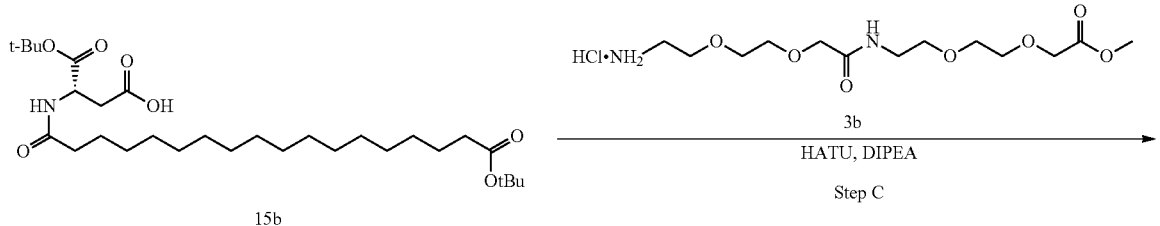

15b

-continued
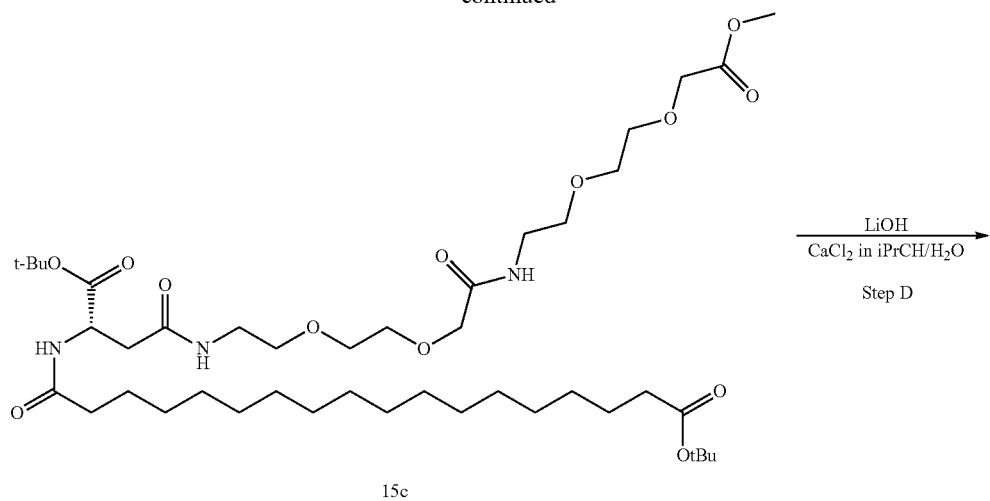
15c
Step D
LiOH
CaCl₂ in iPrCH/H₂O
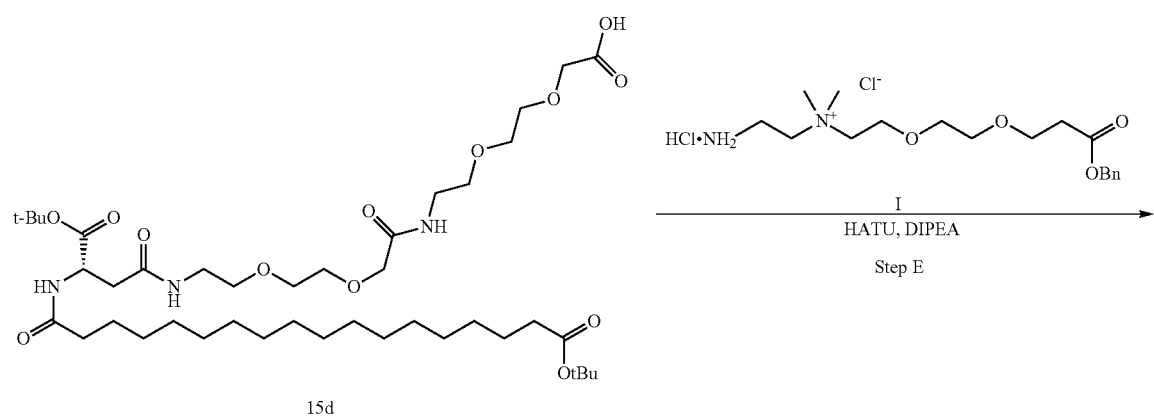
15d
Step E
HATU, DIPEA
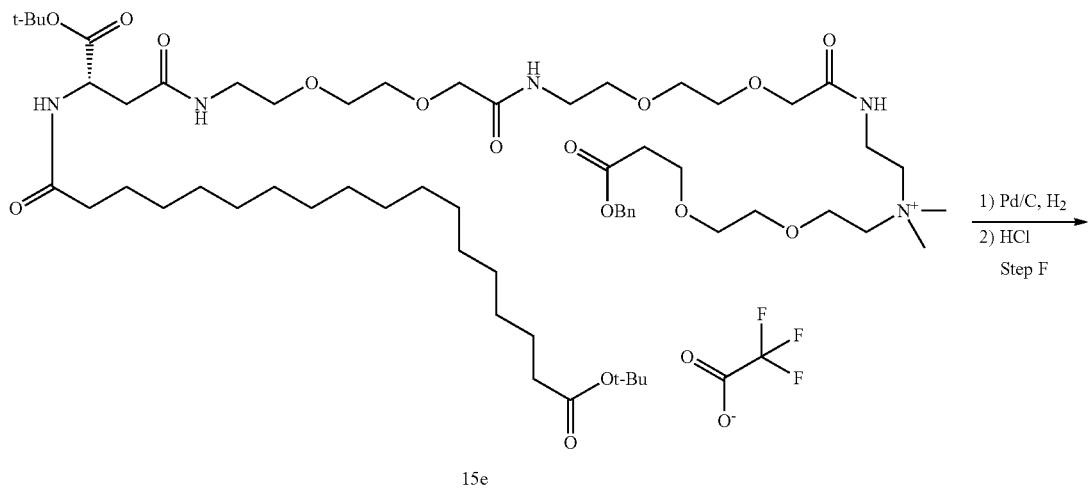
15e
Step F
1) Pd/C, H₂
2) HCl -continued
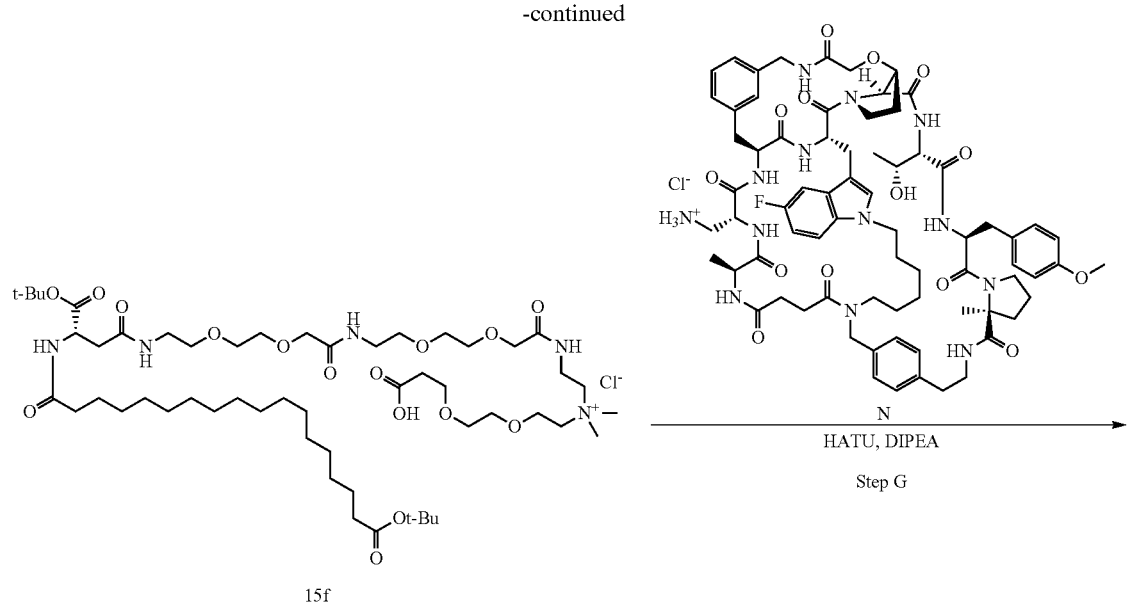
15f
HATU, DIPEA
Step G
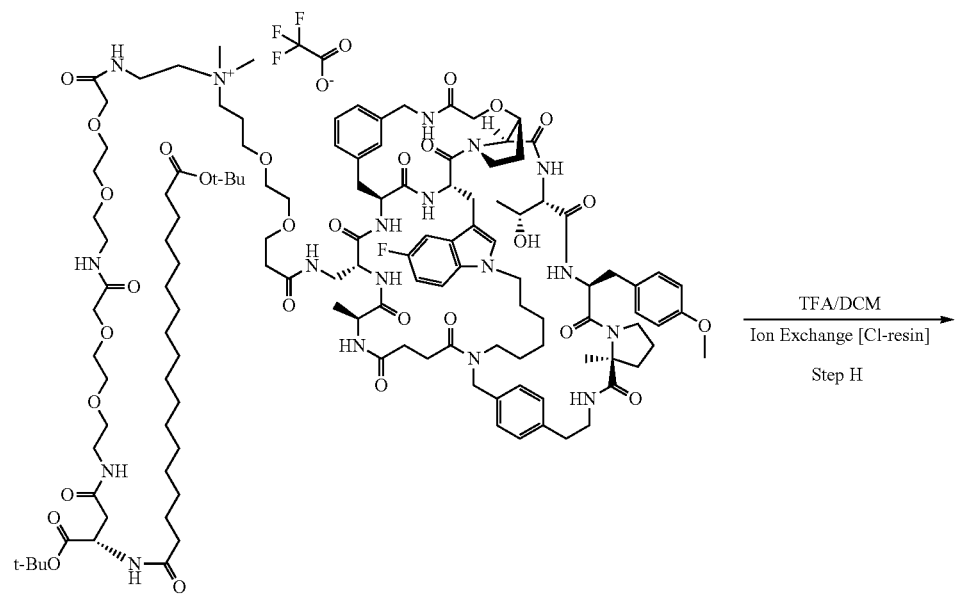
15g
TFA/DCM
Ion Exchange [Cl-resin]
Step H -continued

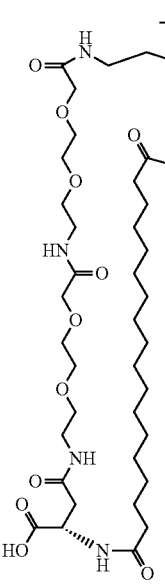
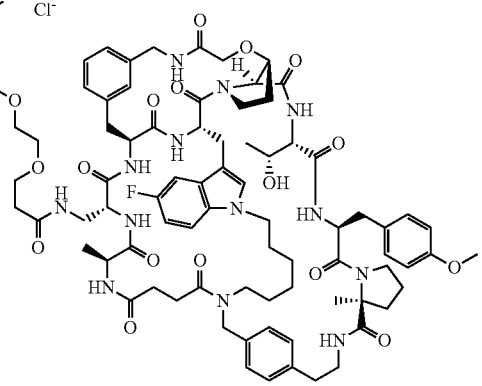

Example 15 (Cl salt)

Step A—Synthesis of Intermediate 15a

To a solution of 18-(tert-butoxy)-18-oxooctadecanoic acid (2 g, 5.40 mmol) in DMF (20 mL) at 0° C. were added HATU (2.25 g, 5.94 mmol), (S)-1-tert-butyl 4-methyl 2-aminosuccinate hydrochloride (1.55 g, 6.48 mmol) and DIEA (4.71 mL, 27.0 mmol) and the mixture was stirred at 0° C. for 1 h. The reaction solution was quenched with water (3 mL) and purified by reverse phase MPLC over C18 (eluting with a gradient of acetonitrile in water (+0.05% TFA)) to afford 15a. LC/MS: [M+Na]$^+$=578.5.

Step B—Synthesis of Intermediate 15b

To a solution of 15a (2.5 g, 4.50 mmol) in THF (25 mL) at 0° C. was added 1 M aqueous LiOH (9.00 mL, 9.00 mmol) and the mixture was stirred at 0° C. for 1 h. The reaction solution was quenched with 1 M aqueous HCl (9 mL) and purified by reverse phase MPLC over C18 (eluting with a gradient of acetonitrile in water (+0.05% TFA)) to provide 15b. LC/MS: [M+Na]$^+$=564.4.

Step C—Synthesis of Intermediate 15c

To a solution of 15b (300 mg, 0.554 mmol) in DMF (3 mL) at 0° C. were added HATU (232 mg, 0.609 mmol), 3b (397 mg, 1.11 mmol) and DIEA (0.484 mL, 2.77 mmol) and the mixture was stirred at 0° C. for 1 h. The reaction solution was quenched with water (1 mL) and purified by reverse phase MPLC over C18 (eluting with a gradient of acetonitrile in water (+0.1% TFA)) to provide 15c. LC/MS: [M+H]$^+$=846.5. $^1$H NMR (300 MHz, CD$_3$OD): δ 4.62-4.58 (m, 1H), 4.17 (s, 2H), 4.00 (s, 2H), 3.73 (s, 3H), 3.72-3.51 (m, 12H), 3.48-3.33 (m, 4H), 2.73-2.58 (m, 2H), 2.26-2.14 (m, 4H), 1.63-1.50 (m, 4H), 1.48-1.41 (m, 18H), 1.36-1.26 (m, 24H).

Step D—Synthesis of Intermediate 15d

To a solution of 0.8 M CaCl$_2$ in 2-propanol (4.2 mL) and water (1.8 mL) at 0° C. were added 15c (300 mg, 0.355 mmol) and 1 N aqueous LiOH (0.532 mL, 0.532 mmol) then the solution was stirred at RT for 1 h. The reaction was quenched with AcOH (0.3 mL), concentrated under reduced pressure and purified by reverse phase MPLC over C18 (eluting with a gradient of acetonitrile in water (+0.1% TFA)) to give 15d. LC/MS: [M+H]$^+$=832.5.

Step E—Synthesis of Intermediate 15e

To a solution of 15d (150 mg, 0.180 mmol) in DMF (800 μL) and water (804) at 0° C. were added HATU (82 mg, 0.216 mmol), DIEA (157 μL, 0.901 mmol) and intermediate I (148 mg, 0.361 mmol) and the mixture was stirred at 0° C. for 1 h. The reaction solution was quenched with water (0.5 mL) and purified by reverse phase MPLC over C18 (eluting with a gradient of acetonitrile in water (+0.1% TFA)) to give 15e. LC/MS: [M]$^+$=1152.6.

Step F—Synthesis of Intermediate 15f

To a solution of 15e (200 mg, 0.158 mmol) in THF (30 mL) was 10% Pd/C (20 mg, 0.019 mmol), and the mixture was degassed then hydrogenated using a balloon filled with hydrogen for 1 h. The final mixture was filtered over Celite and concentrated, then the residue was purified by reverse phase MPLC over C18 (eluting with a gradient of acetonitrile in water (+0.1% TFA)). The fractions containing the desired product were combined and concentrated under reduced pressure then the residue was re-dissolved in acetonitrile (3 mL) and water (6 mL), treated with 1 N aqueous HCl (0.16 mL) at 0° C. and lyophilized to afford 15f. LC/MS: [M]$^+$=1062.6.

Step G—Synthesis of Intermediate 15 g

To a solution of intermediate N (50 mg, 0.035 mmol) in DMF (500 μL) and water (50 μL) at −20° C. were added 15f (53.7 mg, 0.049 mmol), HATU (26.6 mg, 0.070 mmol) and DIEA (36.1 mg, 0.28 mmol) then the reaction mixture was stirred at 0° C. for 30 min. The resulting solution was quenched with water (300 μL) and purified by reverse phase MPLC over C18 (eluting with a gradient of acetonitrile in water (+0.1% TFA)) to give 15 g. LC/MS: [(M+H)/2)]$^+$=1220.2.

Step H—Synthesis of Example 15 (Cl Salt)

Intermediate 15 g (68 mg, 0.027 mmol) was converted to Example 15 (TFA salt) using tert-butyl ester deprotection conditions similar to those described in Synthesis A of Example 4, Step G. LC/MS: [(M+H)/2)]$^+$=1164.2. Example 15 (TFA salt) was then converted to Example 15 (Cl salt) using resin exchange conditions similar to those described in Synthesis A of Example 4, Step H. LC/MS: [M]$^+$=2326.3.

Synthesis of Example 16

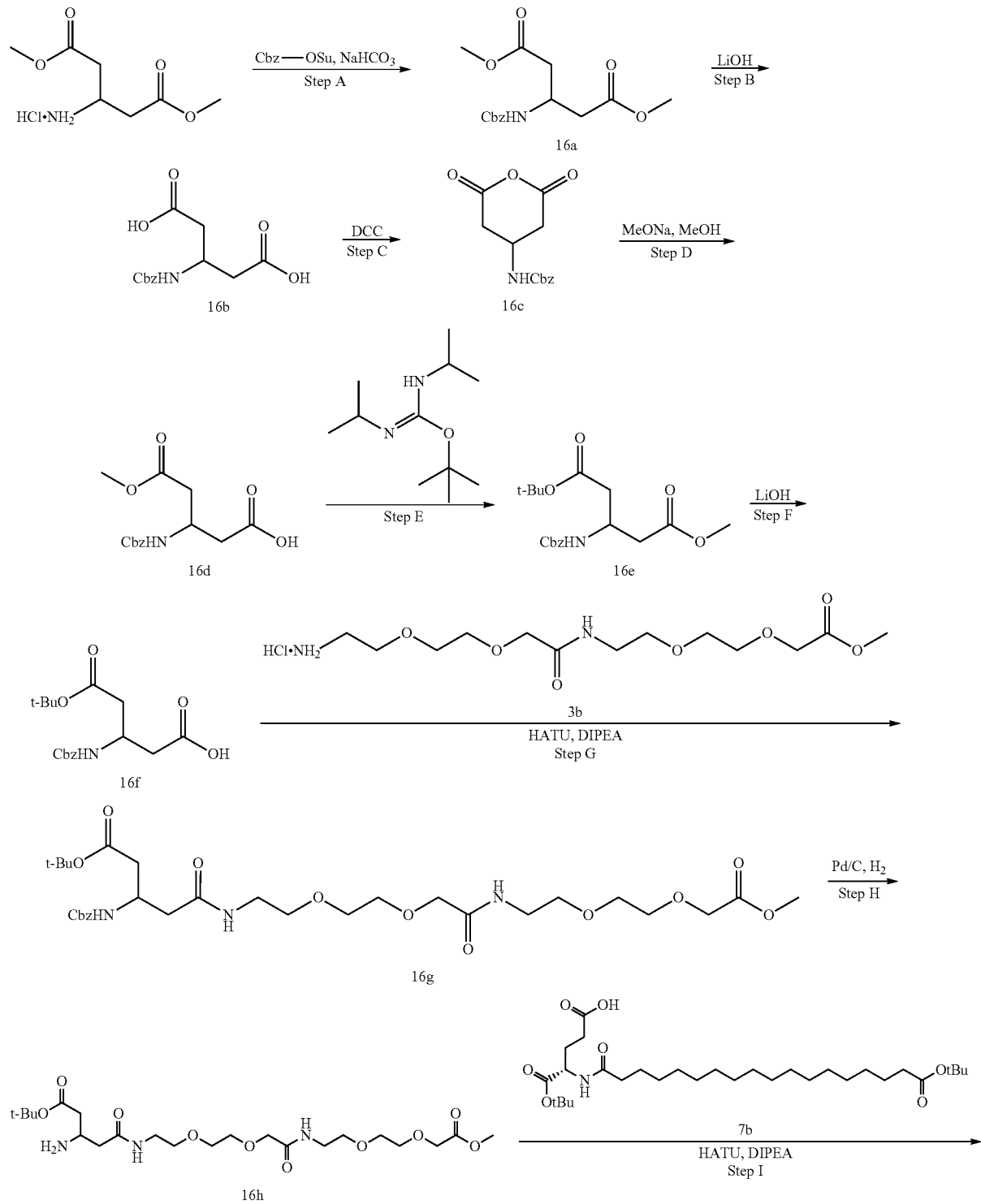

-continued
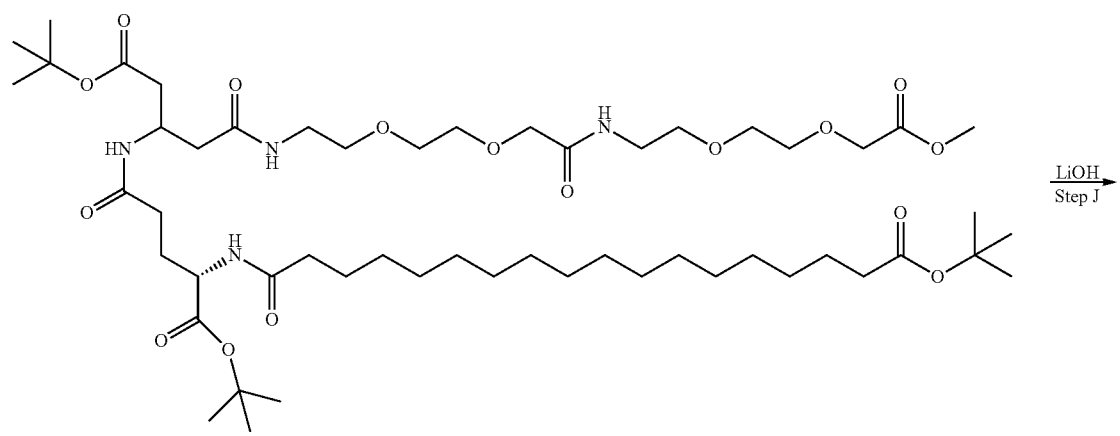
16i
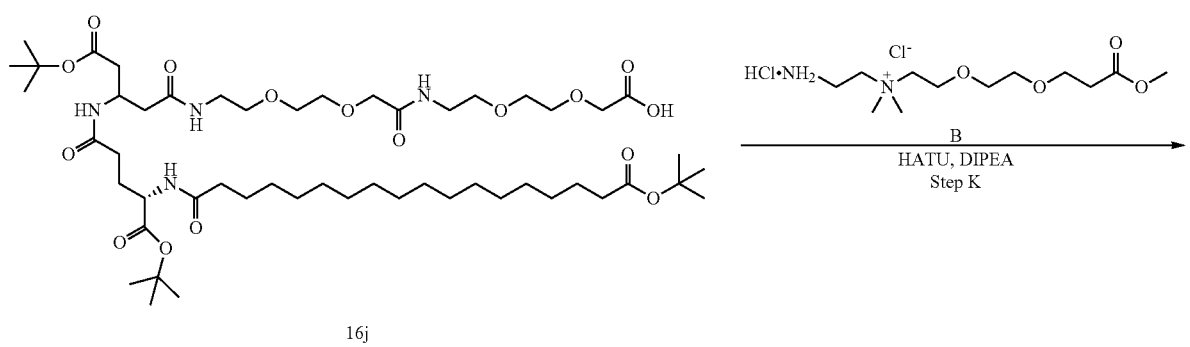
16j
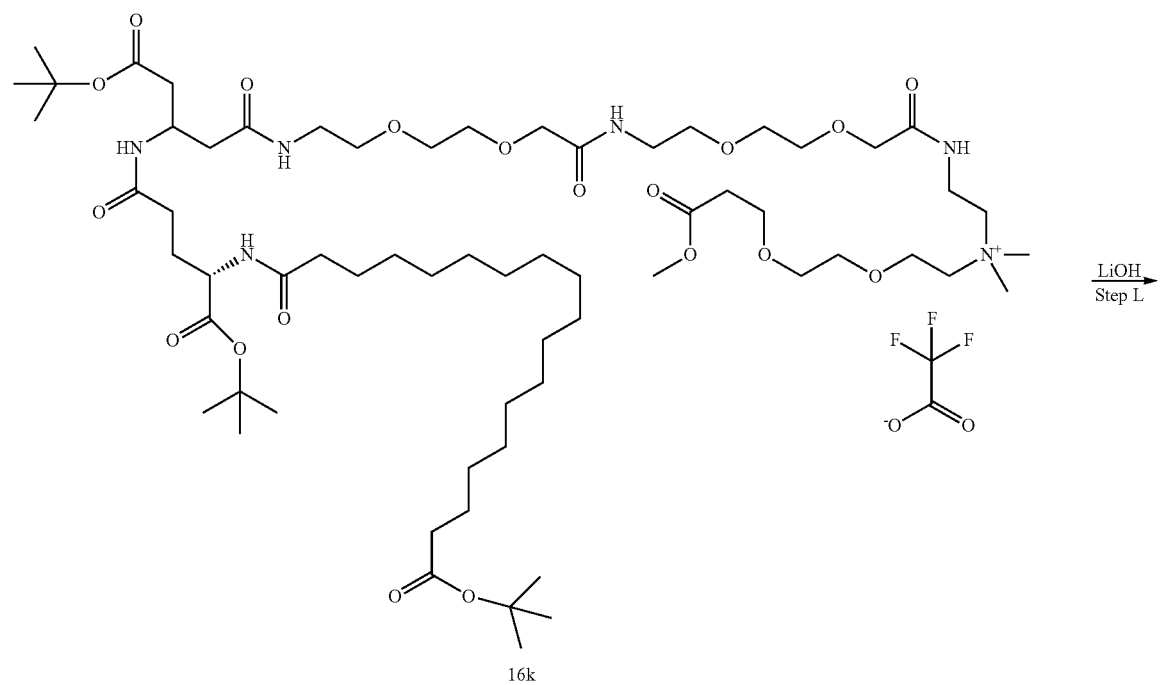
16k

357 -continued 358
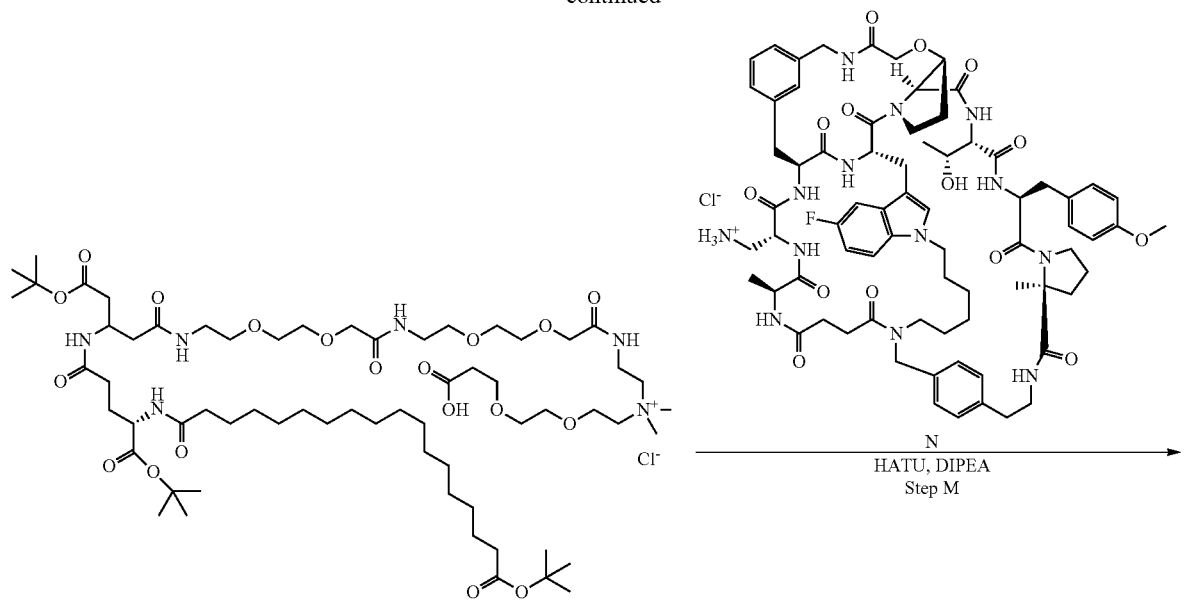
16l
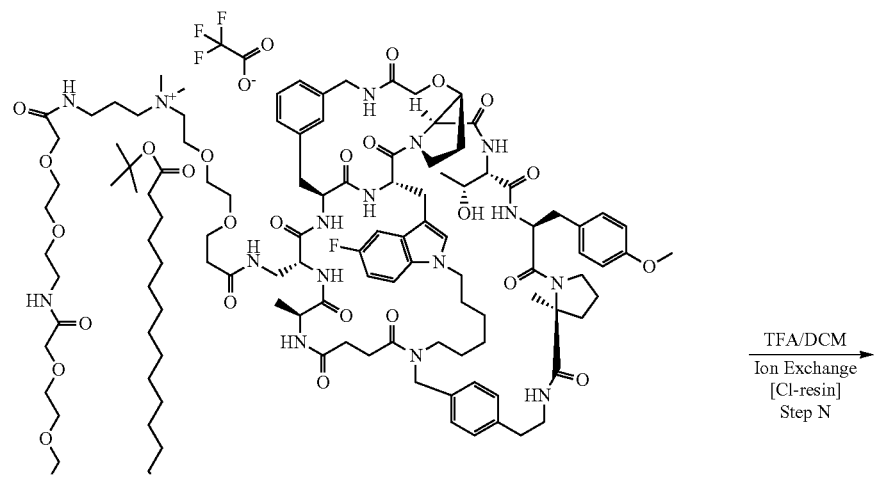
16m

-continued

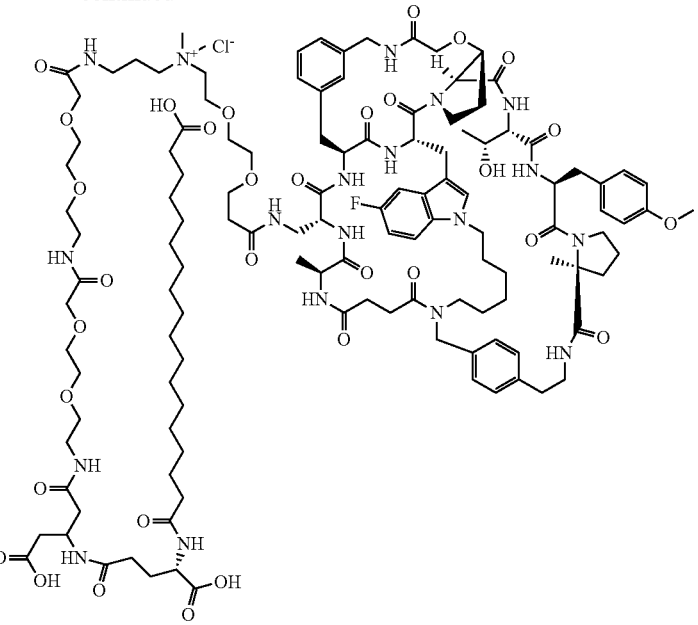

Example 16 (Cl salt)

Step A—Synthesis of Intermediate 16a

To a solution of dimethyl 3-aminopentanedioate hydrochloride (1 g, 4.72 mmol) in THF (10 mL) and water (10 mL) at 0° C. were added NaHCO$_3$ (1.588 g, 18.90 mmol) and Cbz-OSu (1.766 g, 7.09 mmol) then the reaction was stirred at RT for 2 h. The resulting mixture was diluted with water and extracted with EtOAc. The combined organic layers were washed with brine, dried over Na$_2$SO$_4$ and filtered. The filtrate was concentrated under reduced pressure and the residue was purified by MPLC over silica gel (eluting with a gradient of 1%-50% EtOAc in PE) to provide 16a. LC/MS: [M+H]$^+$=310.1.

Step B—Synthesis of Intermediate 16b

To a solution of 16a (1.3 g, 4.20 mmol) in THF (13 mL) at 0° C. was added 1 M aqueous LiOH (6.30 mL, 6.30 mmol) then the reaction mixture was stirred at RT for 1 h. The resulting solution was adjusted to pH 4-5 with 1N aqueous HCl and purified by reverse phase MPLC over C18 (eluting with a gradient of acetonitrile in water (+0.05% TFA)) to give 16b. LC/MS: [M+H]$^+$=282.1.

Step C—Synthesis of Intermediate 16c

To a solution of 16b (600 mg, 2.133 mmol) in EtOAc (10 mL) at 0° C. was added DCC (484 mg, 2.347 mmol) then the mixture was stirred at RT for 14 h. The resulting solution was filtered and the filtrate was concentrated under reduced pressure to afford 16c. LC/MS: [M+H]$^+$=264.1.

Step D—Synthesis of Intermediate 16d

To a solution of 16c (470 mg, 1.785 mmol) in MeOH (6 mL) at RT was added MeONa (1.929 mg, 0.036 mmol) then the mixture was stirred at 65° C. for 2 h. The resulting solution was purified by reverse phase MPLC over C18 (eluting with a gradient of acetonitrile in water (+0.05% TFA)) to give 16d. LC/MS: [M+Na]$^+$=318.1.

Step E—Synthesis of Intermediate 16e

To a solution of 16d (410 mg, 1.39 mmol) in DCM (5 mL) at RT was added tert-butyl N,N'-diisopropylcarbamimidate (1.39 g, 6.94 mmol) then the solution was stirred at 50° C. for 5 h. The resulting solution was concentrated under reduced pressure and the residue was purified by MPLC over silica gel (eluting with a gradient of 1%-30% EtOAc in PE) to provide 16e. LC/MS: [M+H]$^+$=352.2.

Step F—Synthesis of Intermediate 16f

To a solution of 16e (450 mg, 1.28 mmol) in THF (5 mL) at 0° C. was added 1 M aqueous LiOH (2.56 mL, 2.56 mmol) then the reaction was stirred at RT for 1 h. The resulting solution was quenched with 1 M aqueous HCl (2.56 mL) and purified by reverse phase MPLC over C18 (eluting with a gradient of acetonitrile in water (+0.1% TFA)) to provide 16f LC/MS: [M+Na]$^+$=360.0. $^1$H NMR (300 MHz, CD$_3$OD): δ 7.45-7.20 (m, 5H), 5.08 (S, 2H), 4.40-4.24 (m, 1H), 2.61-2.42 (m, 4H), 1.42 (s, 9H).

Step G—Synthesis of Intermediate 16 g

To a solution of 16f (200 mg, 0.593 mmol) in DMF (2 mL) at 0° C. were added 3b (234 mg, 0.652 mmol), HATU (248 mg, 0.652 mmol) and DIEA (0.828 mL, 4.74 mmol) and the reaction mixture was stirred at 0° C. for 1 h. The final solution was quenched with water (2 mL) and purified by reverse phase MPLC over C18 (eluting with a gradient of acetonitrile in water (+0.05% TFA)) to give 16 g. LC/MS: [M+H]$^+$=642.4.

Step H—Synthesis of Intermediate 16 h

To a stirred solution of 16 g (200 mg, 0.312 mmol) in THF (5 mL) at RT was added 10% Pd/C (33.2 mg, 0.031 mmol)

and the mixture was degassed then hydrogenated using a balloon filled with hydrogen for 2 h. The resulting mixture was filtered over Celite and the filtrate was concentrated to give 16 h. LC/MS: [M+H]$^+$=508.4.

Step I—Synthesis of Intermediate 16i

To a solution of 7b (150 mg, 0.27 mmol) in DMF (2 mL) at 0° C. were added 16 h (137 mg, 0.27 mmol), HATU (113 mg, 0.297 mmol) and DIEA (0.377 mL, 2.159 mmol) and the reaction mixture was stirred at 0° C. for 1 h. The resulting solution was quenched with water (2 mL) and purified by reverse phase MPLC over C18 (eluting with a gradient of acetonitrile in water (+0.05% TFA)) to provide 16i. LC/MS: [M+H]$^+$=1045.6.

Step J—Synthesis of Intermediate 16j

To a solution of 16i (260 mg, 0.249 mmol) in THF (3 mL) at 0° C. was added 1 M aqueous LiOH (0.497 mL, 0.497 mmol) and the reaction mixture was stirred at 0° C. for 1 h. The solution was quenched with 1 M aqueous HCl (0.5 mL) and purified by reverse phase MPLC over C18 (eluting with a gradient of acetonitrile in water (+0.05% TFA)) to afford 16j. LC/MS: [M+Na]$^+$=1053.4.

Step K—Synthesis of Intermediate 16k

To a solution of 16j (180 mg, 0.175 mmol) in DMF (2 mL) and water (0.2 mL) at 0° C. were added intermediate B (117 mg, 0.349 mmol), HATU (100 mg, 0.262 mmol) and DIEA (0.244 mL, 1.396 mmol) and the reaction mixture was stirred at 0° C. for 1 h. The resulting solution was quenched with water (0.5 mL) and purified by reverse phase MPLC over C18 (eluting with a gradient of acetonitrile in water (+0.05% TFA)) to give 16k. LC/MS: [M]$^+$=1276.7.

Step L—Synthesis of Intermediate 16l

To a solution of 16k (220 mg, 0.158 mmol) in THF (3 mL) at 0° C. was added 1 M aqueous LiOH (0.317 mL, 0.317 mmol) and the reaction mixture was stirred at 0° C. for 1 h. The resulting solution was quenched with 1 M aqueous HCl (0.32 mL) and purified by reverse phase MPLC over C18 (eluting with a gradient of acetonitrile in water (+0.05% TFA)).

The fractions containing the desired product were combined and concentrated. The residue was re-dissolved in acetonitrile (3 mL) and water (5 mL), treated with 1 N aqueous HCl (0.12 mL) at 0° C. and the solution was lyophilized to give 16l. LC/MS: [M]$^+$=1261.5.

Step M—Synthesis of Intermediate 16m

To a solution of intermediate N (50 mg, 0.035 mmol) in DMF (500 µL) and water (50 µL) at −20° C. were added 16l (63.5 mg, 0.049 mmol), HATU (26.6 mg, 0.07 mmol) and DIEA (36.1 mg, 0.280 mmol) and the reaction was stirred at 0° C. for 30 min. The final solution was quenched with water (300 µL) and purified by reverse phase MPLC over C18 (eluting with a gradient of acetonitrile in water (+0.1% TFA)) to give 16m. LC/MS: [(M+H)/2)]$^+$=1319.7.

Step N—Synthesis of Example 16 (Cl Salt)

Intermediate 16m (65 mg, 0.024 mmol) was converted to Example 16 (TFA salt) using tert-butyl ester deprotection conditions similar to those described in Synthesis A of Example 4, Step G. LC/MS: [(M+H)/2)]$^+$=1235.6. Example 16 (TFA salt) was then converted to Example 16 (Cl salt) using resin exchange conditions similar to those described in Synthesis A of Example 4, Step H. LC/MS: [M]$^+$=2469.3.

Synthesis of Example 17

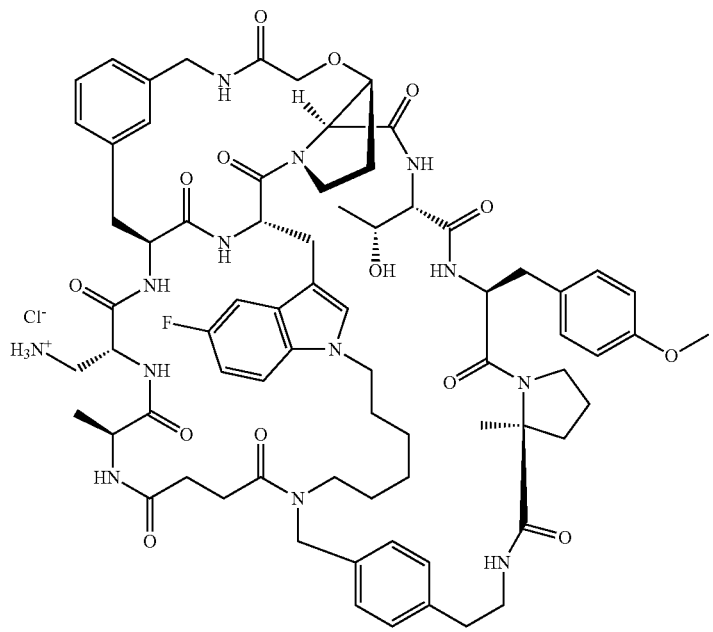

N

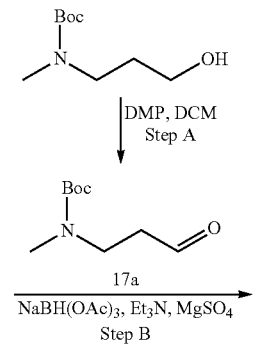

363
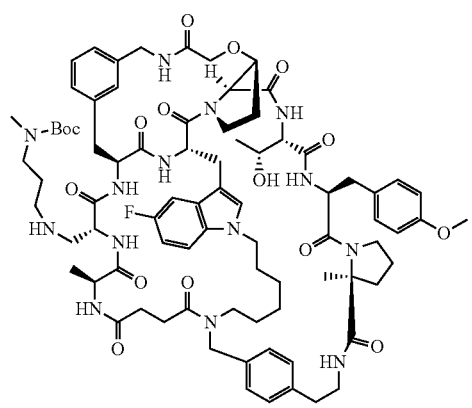
17b
364
-continued
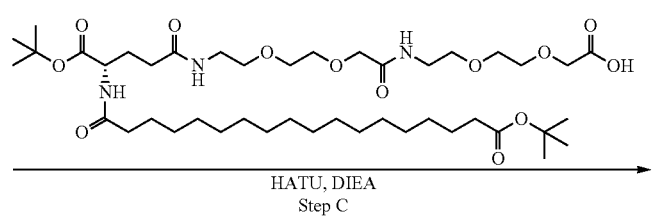
HATU, DIEA
Step C
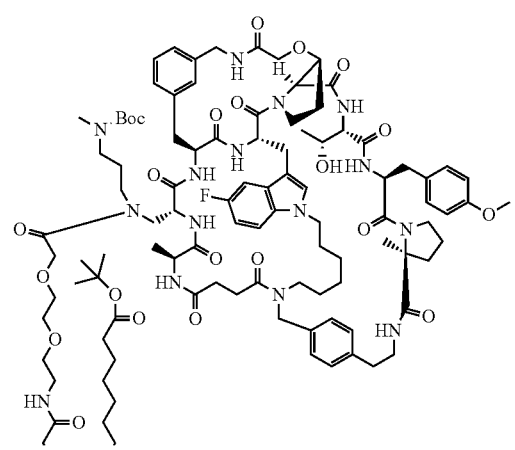
TFA, DCM
Step D
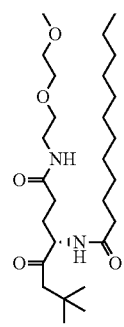
17c -continued
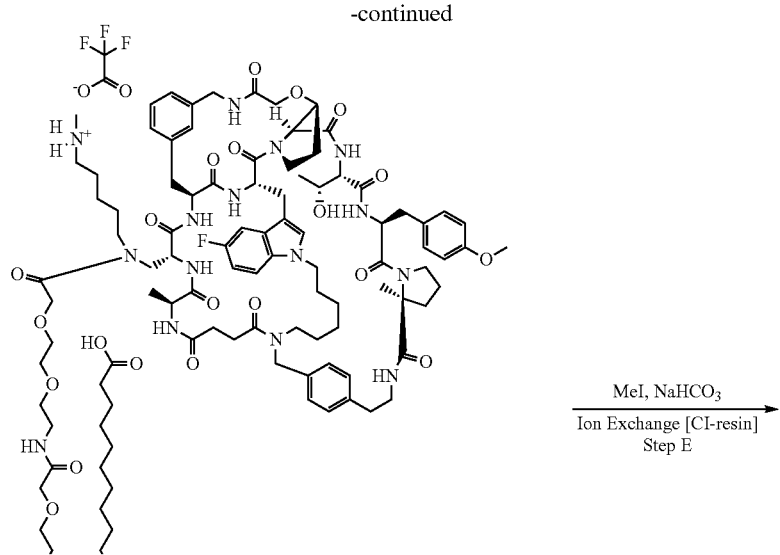
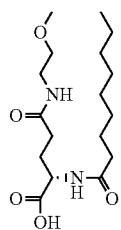
17d
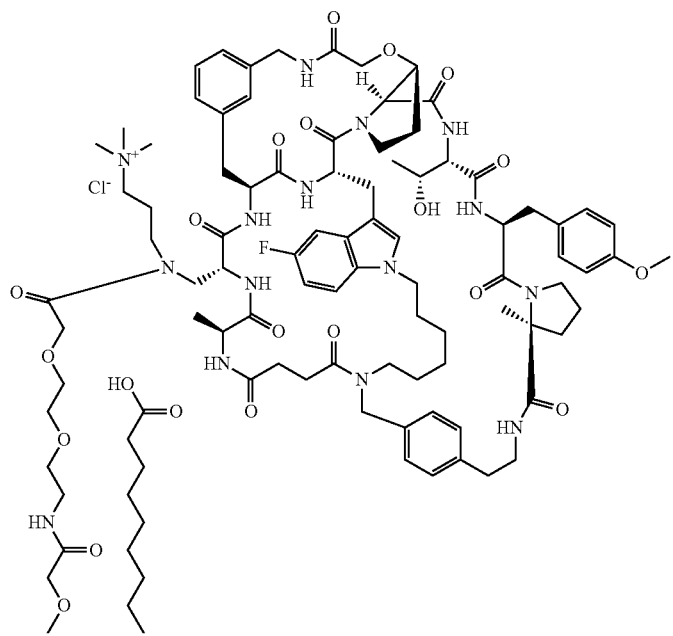

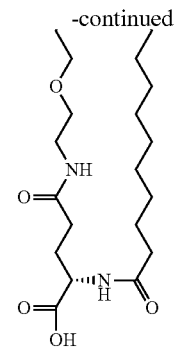

Example 17 (Cl salt)

Step A—Synthesis of Intermediate 17a

To a solution of tert-butyl (3-hydroxypropyl)(methyl) carbamate (1.00 g, 5.28 mmol) in DCM (10 mL) at 0° C. was added DMP (4.48 g, 10.6 mmol) then the reaction mixture was stirred at RT for 2 h. The final solution was quenched with saturated $Na_2S_2O_3$/$NaHCO_3$ solution (100 mL) and diluted with DCM (2×50 mL). The organic layer was washed by brine, dried over anhydrous $Na_2SO_4$ and filtered. The filtrate was concentrated under reduced pressure and the residue was purified by MPLC over silica gel (eluting with a gradient of 0%-40% EtOAc in PE) to provide 17a. $^1$H NMR (400 MHz, $CDCl_3$): δ 9.81 (t, J=1.8 Hz, 1H), 3.55 (t, J=6.7 Hz, 2H), 2.87 (s, 3H), 2.72-2.64 (m, 2H), 1.45 (s, 9H).

Step B—Synthesis of Intermediate 17b

To a solution of intermediate N (20 mg, 0.014 mmol) in DCE (300 μL) at RT were added 17a (1.31 mg, 6.99 μmol) and $Et_3N$ (4.24 mg, 0.042 mmol) and the solution was dried with excess anhydrous $MgSO_4$. After 30 min of stirring at RT, $NaBH(OAc)_3$ (8.89 mg, 0.042 mmol) was added and the mixture was stirred at RT for 16 h. The final solution was filtered, concentrated and the residue was purified by reverse phase MPLC over C18 (eluting with a gradient of acetonitrile in water (+0.1% TFA)) to give 17b. LC/MS: [(M+H)/2)]$^+$=783.8.

Step C—Synthesis of Intermediate 17c

To a solution of 17b (10.0 mg, 6.39 μmol) in DMF (300 μL) at −20° C. were added (S)-22-(tert-butoxycarbonyl)-43,43-dimethyl-10,19,24,41-tetraoxo-3,6,12,15,42-pentaoxa-9,18,23-triazatetratetracontan-1-oic acid (7.56 mg, 8.94 μmol, the synthesis of which is described in Example 9, page 90, of WO 2009/115469), HATU (4.86 mg, 0.013 mmol) and DIEA (6.60 mg, 0.051 mmol) then the reaction was stirred at 0° C. for 2 h. The resulting solution was quenched with water (100 μL) and purified by reverse phase MPLC over C18 (eluting with a gradient of acetonitrile in water (+0.1% TFA)) to provide 17c. LC/MS: [(M+H)/2)]$^+$=1197.8.

Step D—Synthesis of Intermediate 17d

To a solution of 17c (10 mg, 4.18 μmol) in DCM (2 mL) at 0° C. was added TFA (2 mL) then the mixture was stirred at RT for 3 h. The resulting solution was concentrated under reduced pressure to provide 17d. LC/MS: [(M+H)/2)]$^+$=1091.5.

Step E—Synthesis of Example 17 (Cl Salt)

To a solution of 17d (8.0 mg, 3.48 μmol) in acetonitrile (300 μL) and MeOH (300 μL) at RT were added Met (4.95 mg, 0.035 mmol) and $NaHCO_3$ (1.46 mg, 0.017 mmol) and the mixture was stirred for 14 h. The pH value of the solution was adjusted to 5 with 1 N aqueous HCl and the resulting solution was purified by reverse phase MPLC over C18 (eluting with a gradient of acetonitrile in water (+0.1% TFA)) to afford Example 17 (TFA salt). LC/MS: [(M+H)/2)]$^+$=1105.6. Example 17 (TFA salt) was then converted to Example 17 (Cl salt) using resin exchange conditions similar to those described in Synthesis A of Example 4, Step H. LC/MS: [M]$^+$=2209.2.

Using the synthetic schemes and intermediates described above and, as will be appreciated, in some instances with appropriate substitution of certain intermediates with different spacers apparent to those skilled in the art, the following compounds of the invention (Table 3) were prepared. Alternate salt forms of the compounds below may also be prepared.

TABLE 3
Additional Examples of the Invention.
| Ex-No | Structure | LC/MS Observed [M]⁺, [M/2]⁺, or [(M + H)/2)]⁺ |
|---|---|---|
| 18 | 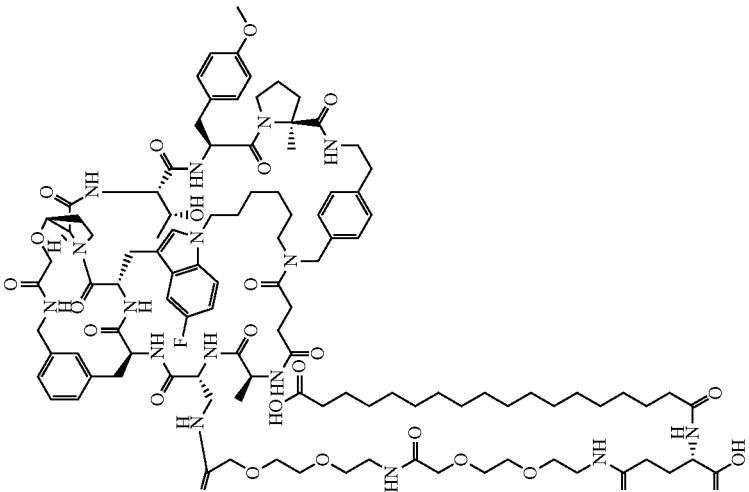 | 1055.9 |

TABLE 3-continued
Additional Examples of the Invention.
| Ex-No | Structure | LC/MS Observed [M]+, [M/2]+, or [(M + H)/2]+ |
|---|---|---|
| 19 | 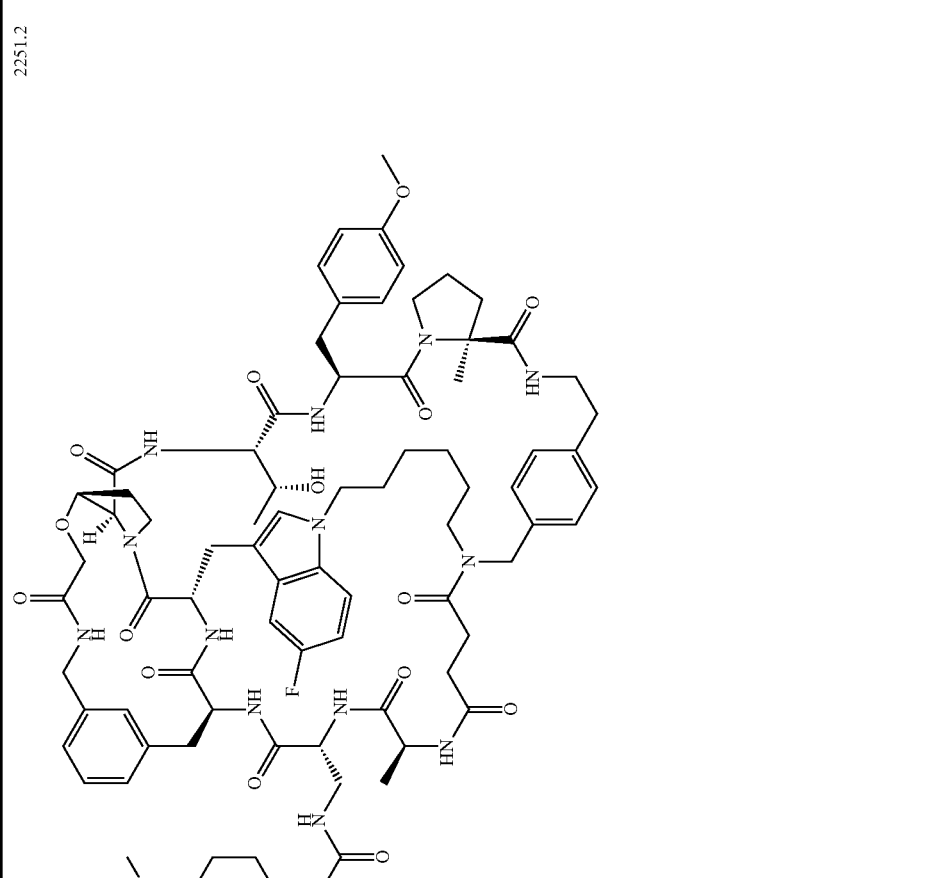 | 2251.2 |

TABLE 3-continued
Additional Examples of the Invention.
| Ex-No | Structure | LC/MS Observed [M]+, [M/2]+, or [(M + H)/2)]+ |
|---|---|---|
| 20 | 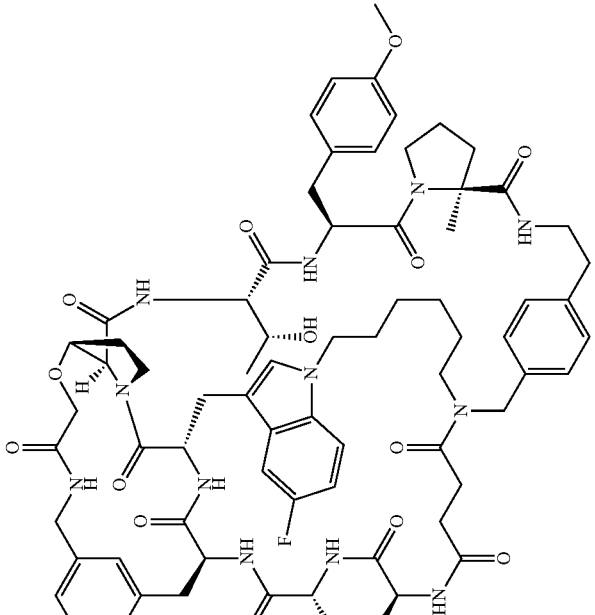 | 1878.1 |

TABLE 3-continued
Additional Examples of the Invention.
| Ex-No | Structure | LC/MS Observed [M]+, [M/2]+, or [(M + H)/2]+ |
|---|---|---|
| 21 | 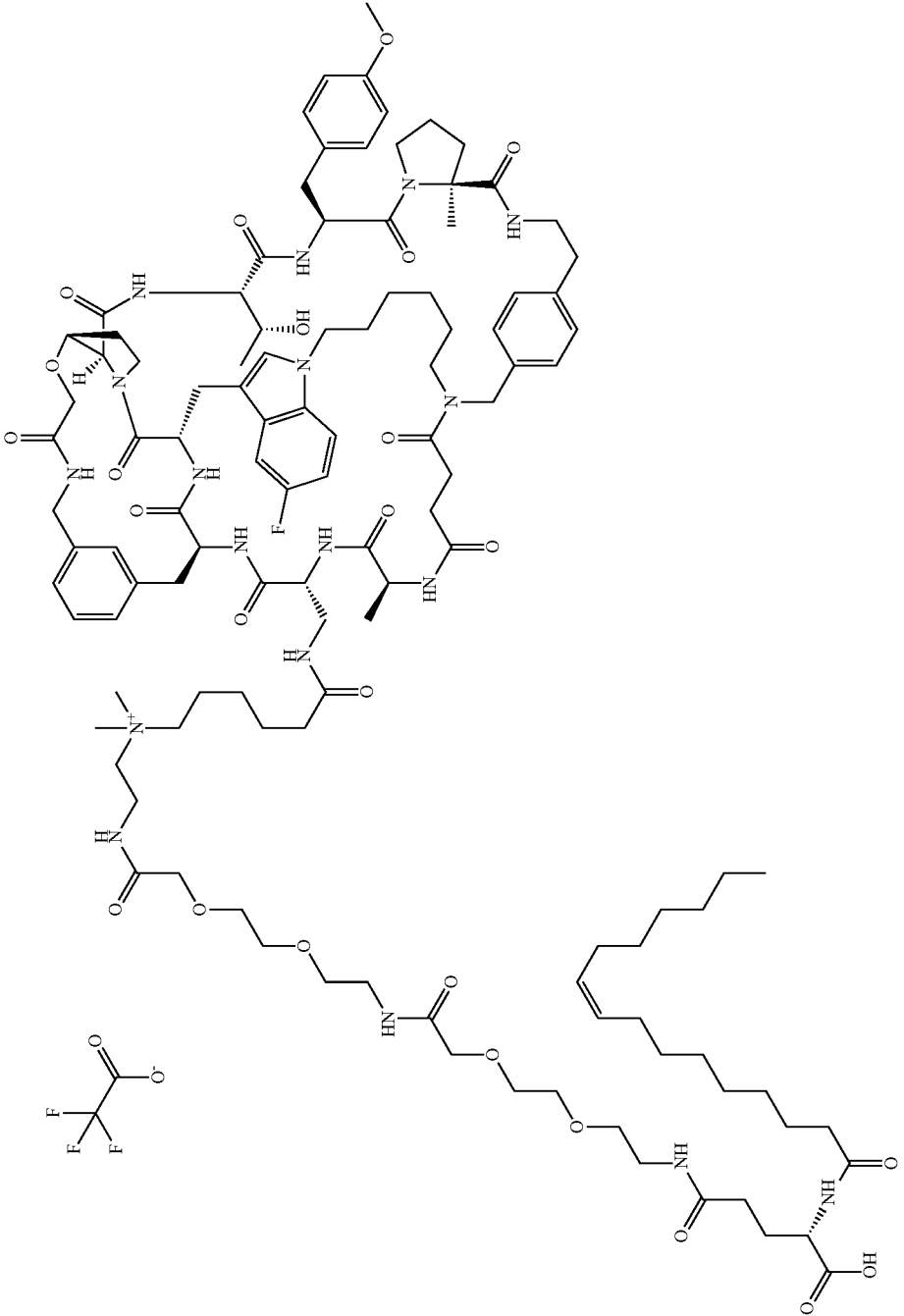 | 2234.3 |

TABLE 3-continued
Additional Examples of the Invention.
| Ex-No | Structure | LC/MS Observed [M]+, [M/2]+, or [(M + H)/2]+ |
|---|---|---|
| 22 | 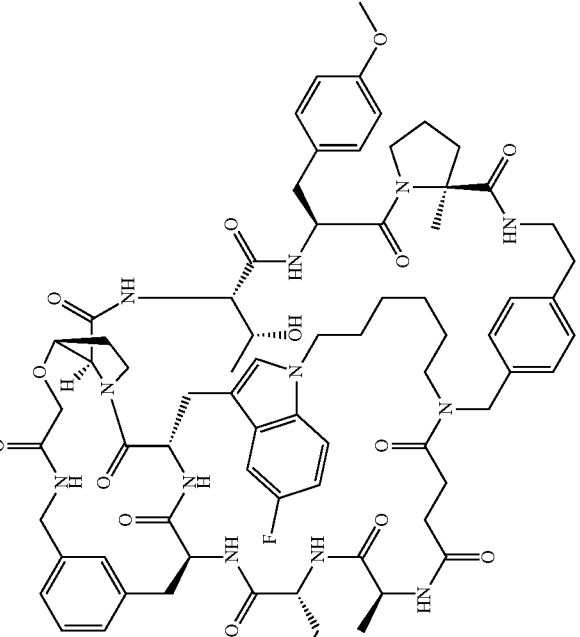 | 2340.3 |

TABLE 3-continued

Additional Examples of the Invention.

| Ex-No | Structure | LC/MS Observed [M]+, [M/2]+, or [(M + H)/2)]+ |
|---|---|---|
| 23 | 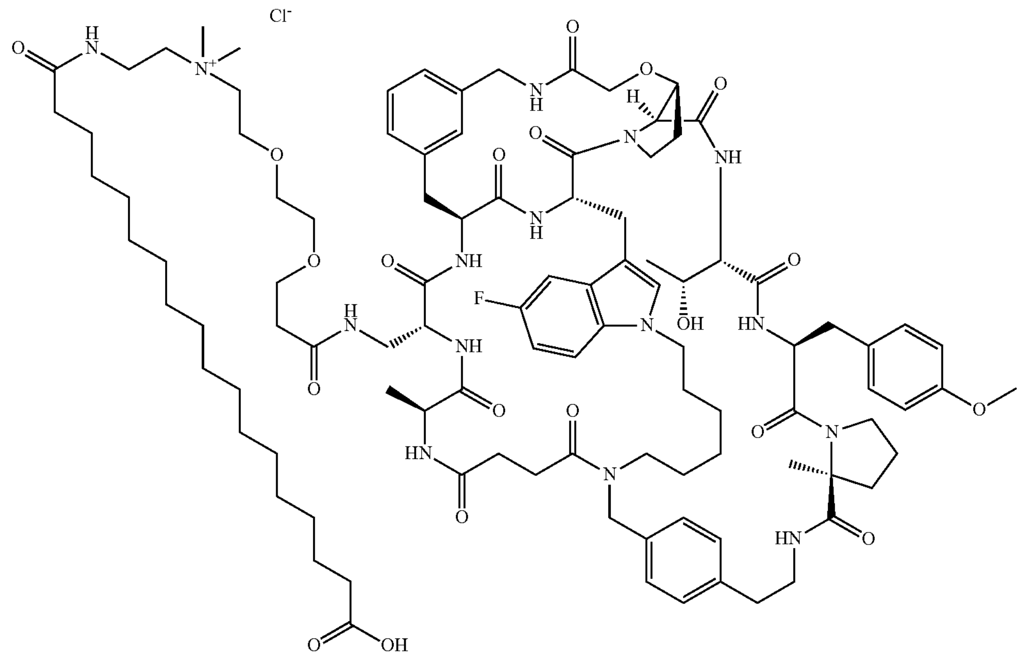 [SMILES: [Cl-] ; COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCOCCOCC[N+](C)(C)CCNC(=O)CCCCCCCCCCCCCCCCC(=O)O)C(=O)N[C@@H](Cc2cccc(c2)CNC(=O)CO4)C(=O)N3)cc1] | 1921.9 |

TABLE 3-continued

Additional Examples of the Invention.

| Ex-No | Structure | LC/MS Observed [M]+, [M/2]+, or [(M + H)/2]+ |
|---|---|---|
| 24 | 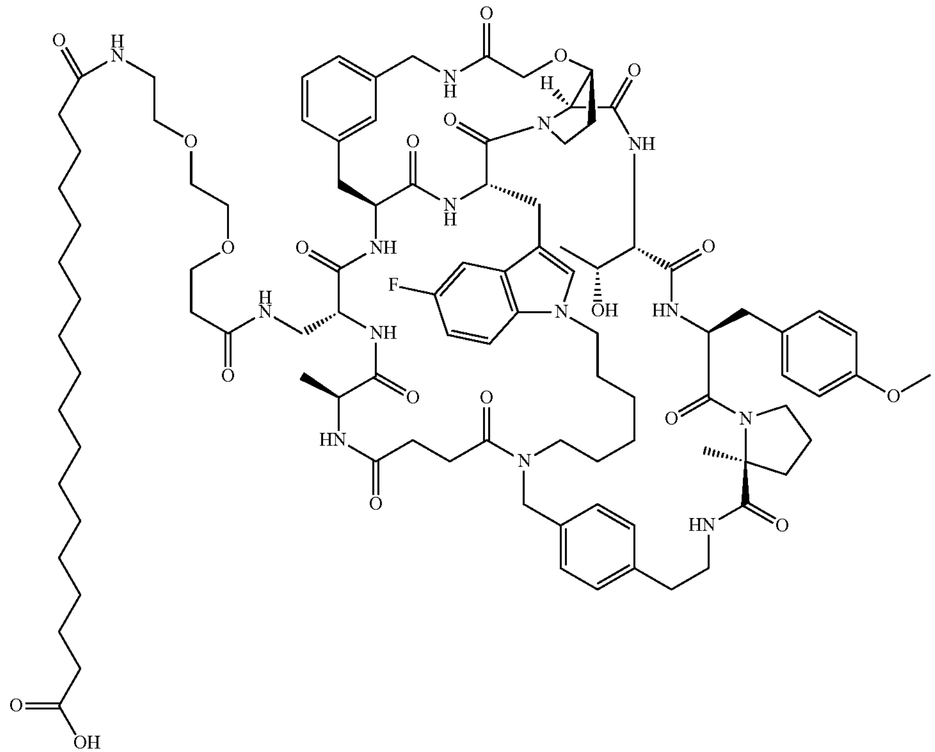 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCOCCOCCNC(=O)CCCCCCCCCCCCCCCCC(=O)O)C(=O)N[C@@H](Cc2cccc(c2)CNC(=O)CO4)C(=O)N3)cc1] | 1850.9 |

TABLE 3-continued

Additional Examples of the Invention.

| Ex-No | Structure | LC/MS Observed [M]+, [M/2]+, or [(M + H)/2]+ |
|---|---|---|
| 25 | 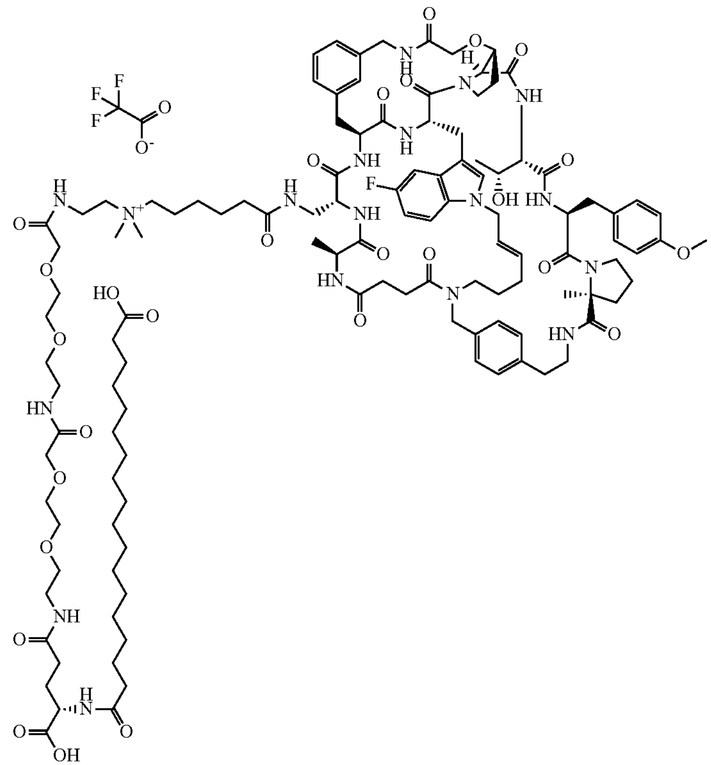 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)C/C=C/CCCN(Cc5ccc(cc5)CCNC(=O)[C@]5(C)CCCN5C2=O)C(=O)CCC(=O)N[C@@H](C)C(=O)N[C@H](CNC(=O)CCCCC[N+](C)(C)CCNC(=O)COCCOCCNC(=O)COCCOCCNC(=O)CC[C@H](NC(=O)CCCCCCCCCCCCCCCCC(=O)O)C(=O)O)C(=O)N[C@@H](Cc2cccc(c2)CNC(=O)CO4)C(=O)N3)cc1 ; O=C([O-])C(F)(F)F] | 1147.4 |

TABLE 3-continued
Additional Examples of the Invention.
| Ex-No | Structure | LC/MS Observed [M]+, [M/2]+, or [(M + H)/2)]+ |
|---|---|---|
| 26 | 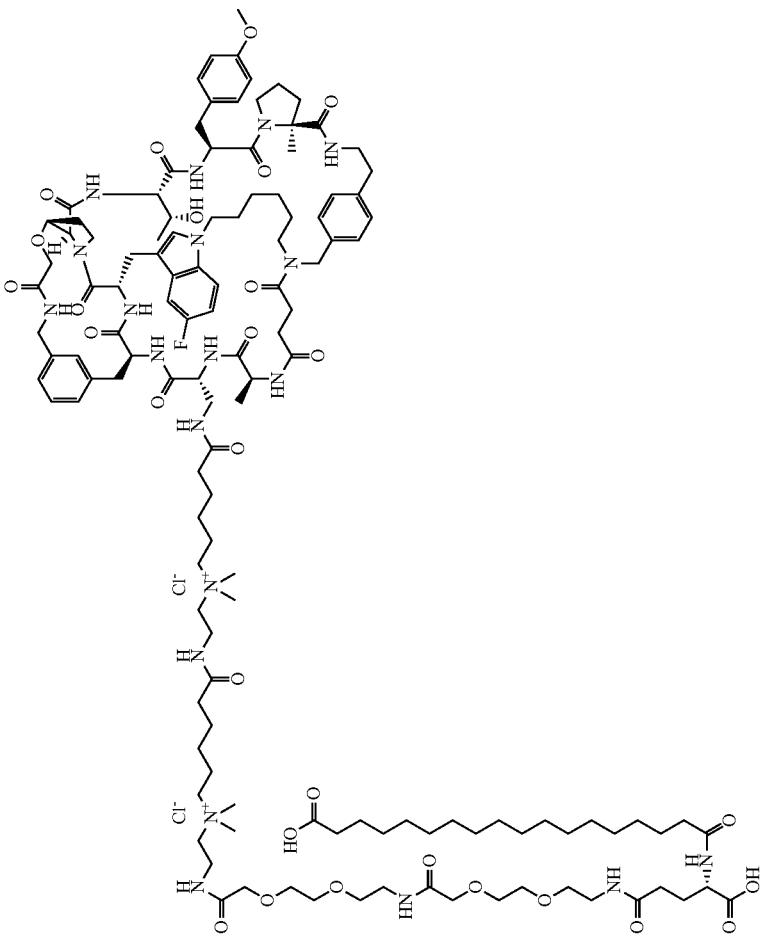 | 1240.5 |

TABLE 3-continued
Additional Examples of the Invention.
| Ex-No | Structure | LC/MS Observed [M]+, [M/2]+, or [(M + H)/2]+ |
|---|---|---|
| 27 | 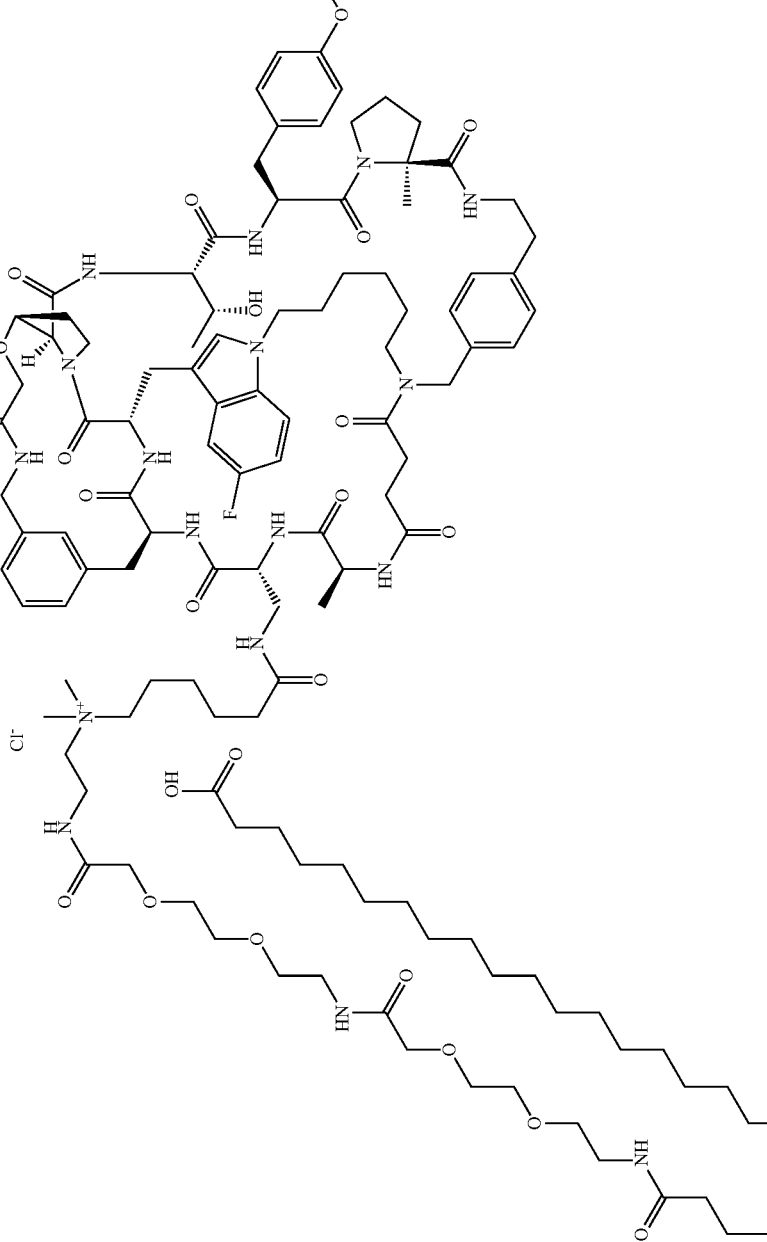 | 2322.3 |

TABLE 3-continued
Additional Examples of the Invention.
| Ex-No | Structure | LC/MS Observed [M]+, [M/2]+, or [(M + H)/2)]+ |
|---|---|---|
| 28 | 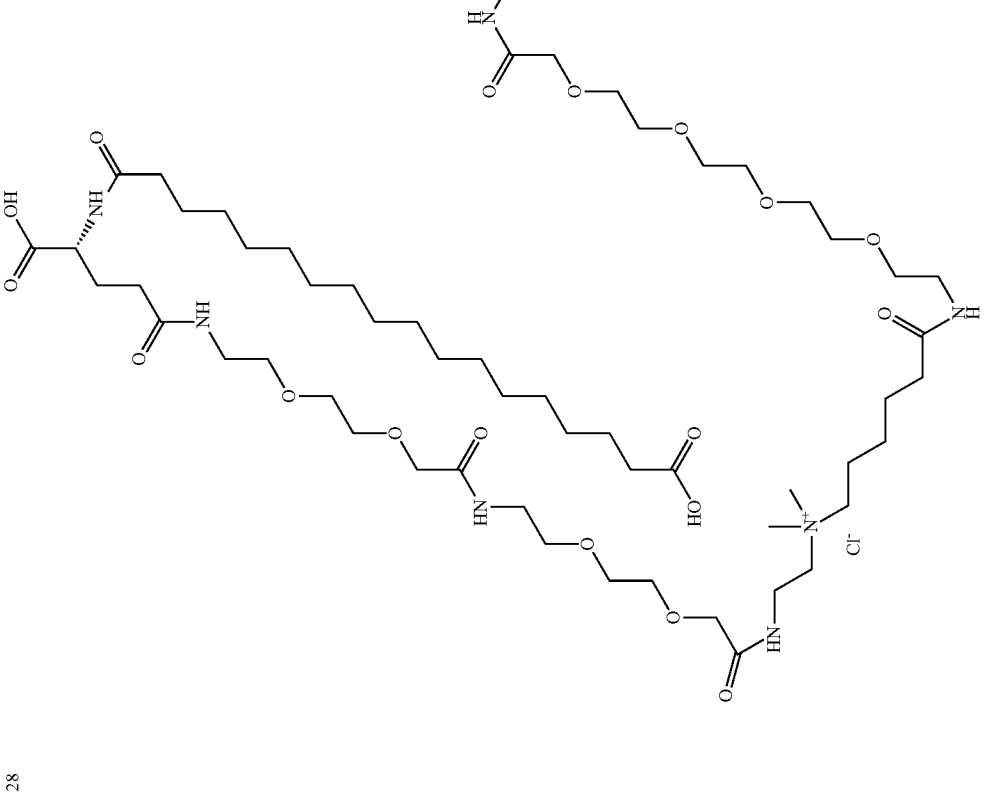 | 1264.5 |

TABLE 3-continued
Additional Examples of the Invention.
| Ex-No | Structure | LC/MS Observed [M]+, [M/2]+, or [(M + H)/2)]+ |
|---|---|---|
| 29 | 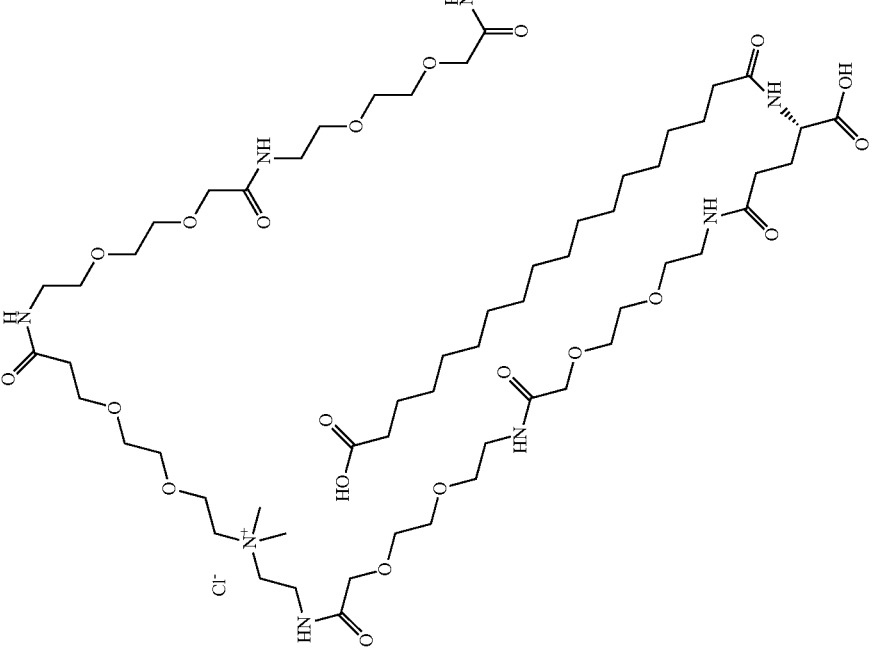 | 1316.0 |

TABLE 3-continued

Additional Examples of the Invention.

| Ex-No | Structure | LC/MS Observed [M]+, [M/2]+, or [(M + H)/2)]+ |
|---|---|---|
| 30 | 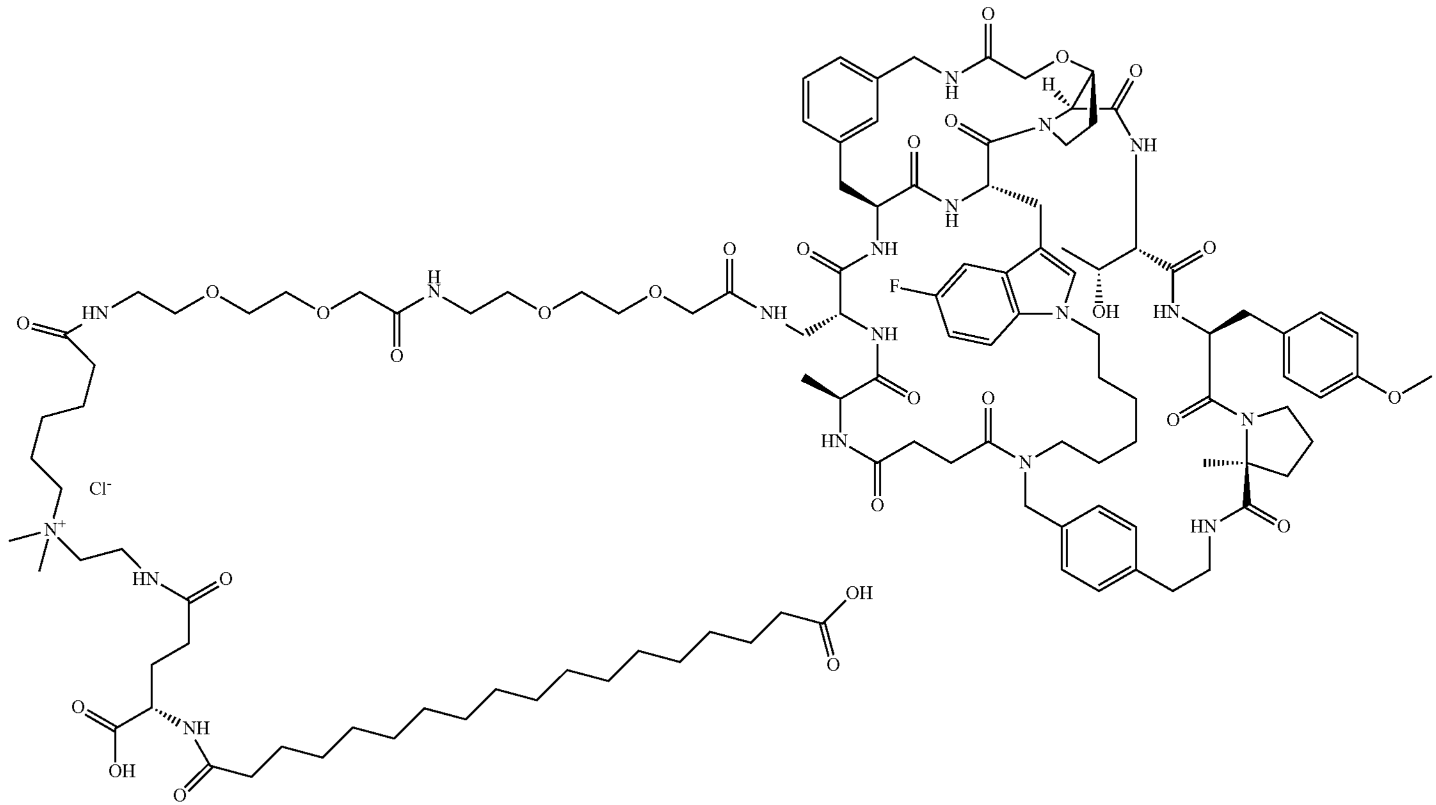 | 2294.3 |

TABLE 3-continued
Additional Examples of the Invention.
| Ex-No | Structure | LC/MS Observed [M]+, [M/2]+, or [(M + H)/2)]+ |
|---|---|---|
| 31 | 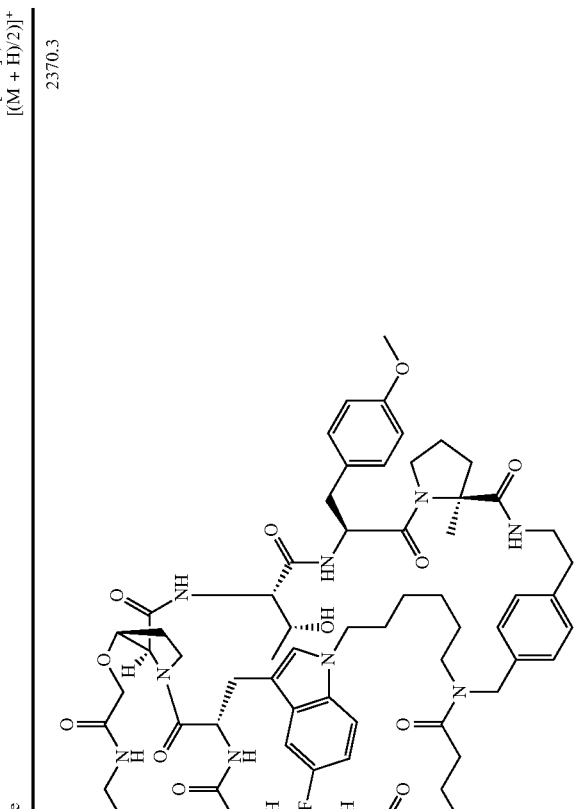 | 2370.3 |

TABLE 3-continued
Additional Examples of the Invention.
| Ex-No | Structure | LC/MS Observed [M]+, [M/2]+, or [(M + H)/2)]+ |
|---|---|---|
| 32 | 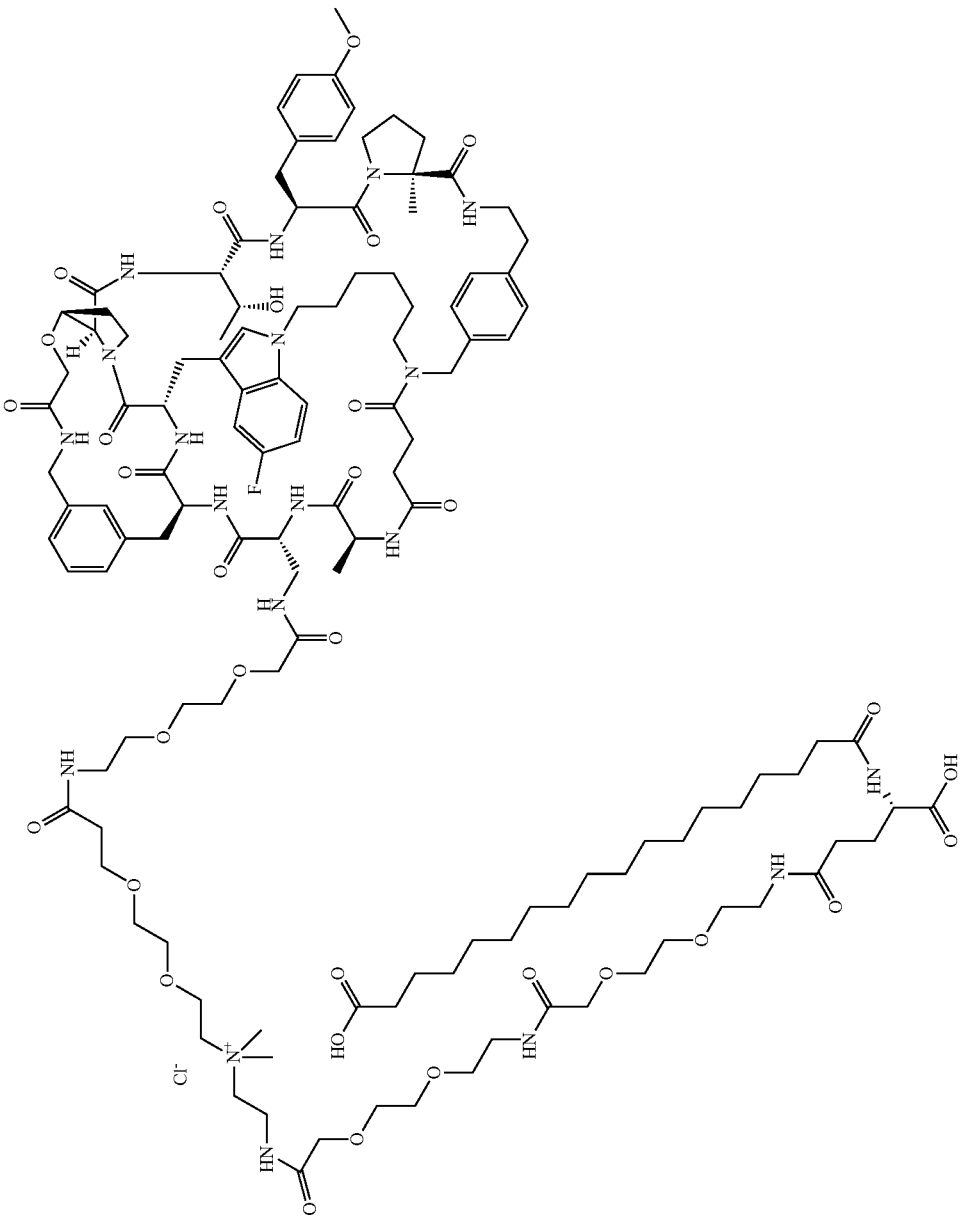 | 1243.4 |

TABLE 3-continued

Additional Examples of the Invention.

| Ex-No | Structure | LC/MS Observed [M]+, [M/2]+, or [(M + H)/2)]+ |
|---|---|---|
| 33 | 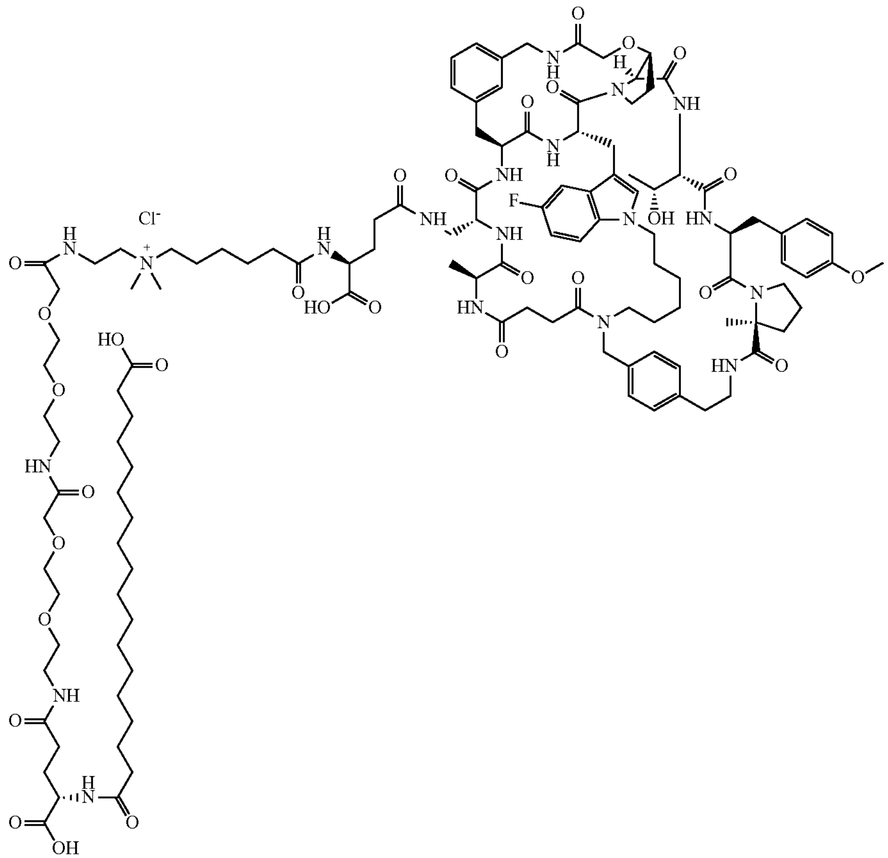 | 1212.8 |

TABLE 3-continued
Additional Examples of the Invention.
| Ex-No | Structure | LC/MS Observed [M]+, [M/2]+, or [(M + H)/2]+ |
|---|---|---|
| 34 | 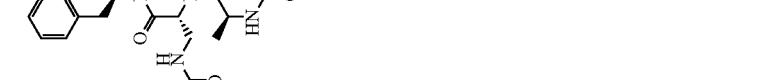 | 1221.3 |

TABLE 3-continued

Additional Examples of the Invention.

| Ex-No | Structure | LC/MS Observed [M]+, [M/2]+, or [(M + H)/2)]+ |
|---|---|---|
| 35 | 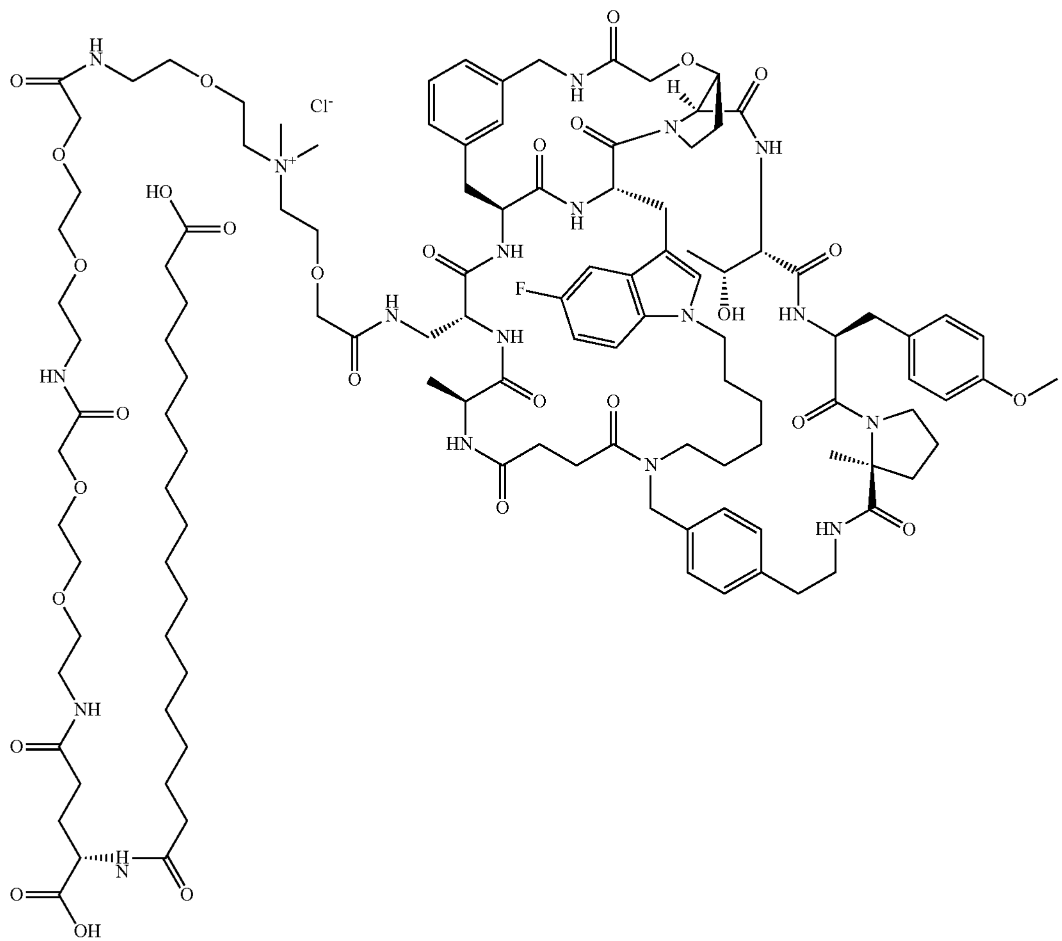 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)COCC[N+](C)(C)CCOCCNC(=O)COCCOCCNC(=O)COCCOCCNC(=O)CC[C@H](NC(=O)CCCCCCCCCCCCCCCCC(=O)O)C(=O)O)C(=O)N[C@@H](Cc2cccc(c2)CNC(=O)CO4)C(=O)N3)cc1 ; [Cl-]] | 2326.3 |

TABLE 3-continued

Additional Examples of the Invention.

| Ex-No | Structure | LC/MS Observed [M]+, [M/2]+, or [(M + H)/2)]+ |
|---|---|---|
| 36 | 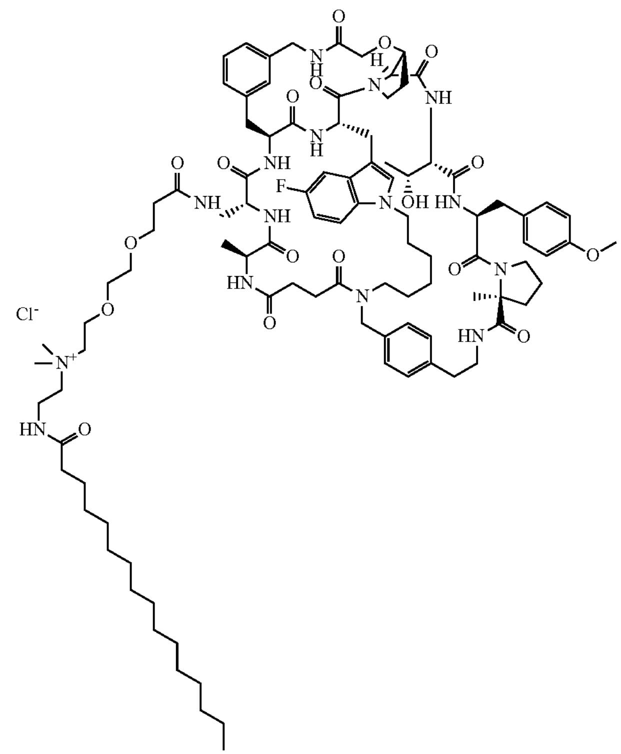 | 1864.0 |

TABLE 3-continued

Additional Examples of the Invention.

| Ex-No | Structure | LC/MS Observed [M]+, [M/2]+, or [(M + H)/2]+ |
|---|---|---|
| 37 | 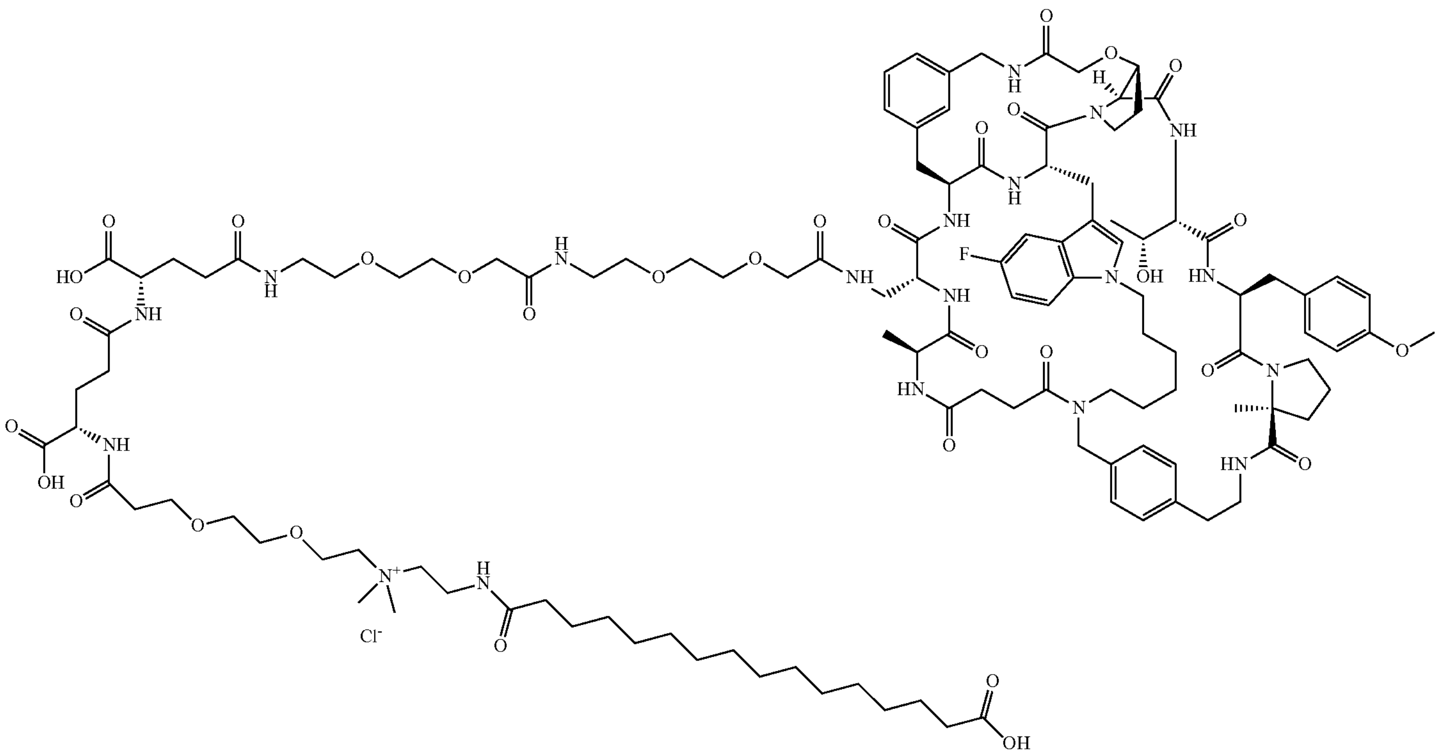 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)COCCOCCNC(=O)COCCOCCNC(=O)CC[C@H](NC(=O)CC[C@H](NC(=O)CCOCCOCC[N+](C)(C)CCNC(=O)CCCCCCCCCCCCCCC(=O)O)C(=O)O)C(=O)O)C(=O)N[C@@H](Cc2cccc(c2)CNC(=O)CO4)C(=O)N3)cc1 ; [Cl-]] | 1221.4 |

TABLE 3-continued

Additional Examples of the Invention.

| Ex-No | Structure | LC/MS Observed [M]+, [M/2]+, or [(M + H)/2]+ |
|---|---|---|
| 38 | 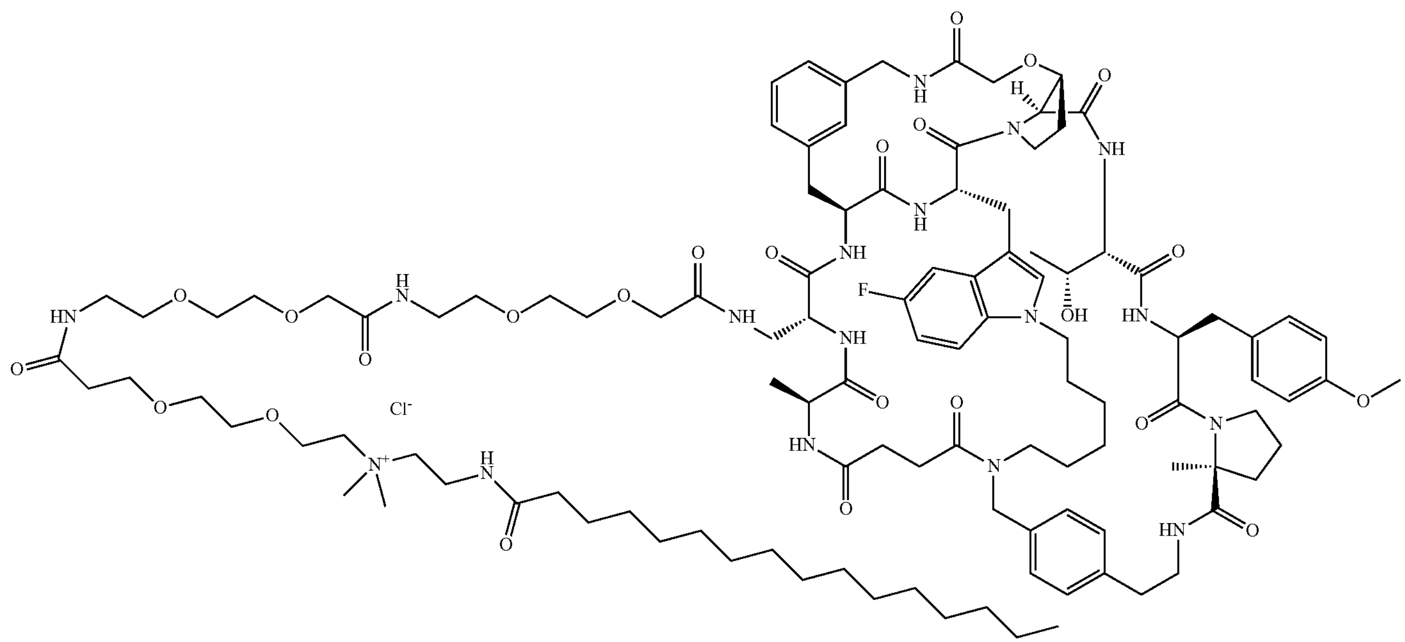 [SMILES: CCCCCCCCCCCCCCCC(=O)NCC[N+](C)(C)CCOCCOCCC(=O)NCCOCCOCC(=O)NCCOCCOCC(=O)NC[C@H]1NC(=O)[C@H](C)NC(=O)CCC(=O)N2CCCCCCn3cc(c4cc(F)ccc43)C[C@@H]3NC(=O)[C@H](Cc4cccc(c4)CNC(=O)CO[C@H]4CCN(C3=O)[C@@H]4C(=O)N[C@@H]([C@@H](C)O)C(=O)N[C@@H](Cc3ccc(OC)cc3)C(=O)N3CCC[C@@]3(C)C(=O)NCCc3ccc(cc3)C2)NC1=O ; [Cl-]] | 1077.5 |

TABLE 3-continued
Additional Examples of the Invention.
| Ex-No | Structure | LC/MS Observed [M]+, [M/2]+, or [(M + H)/2)]+ |
|---|---|---|
| 39 | 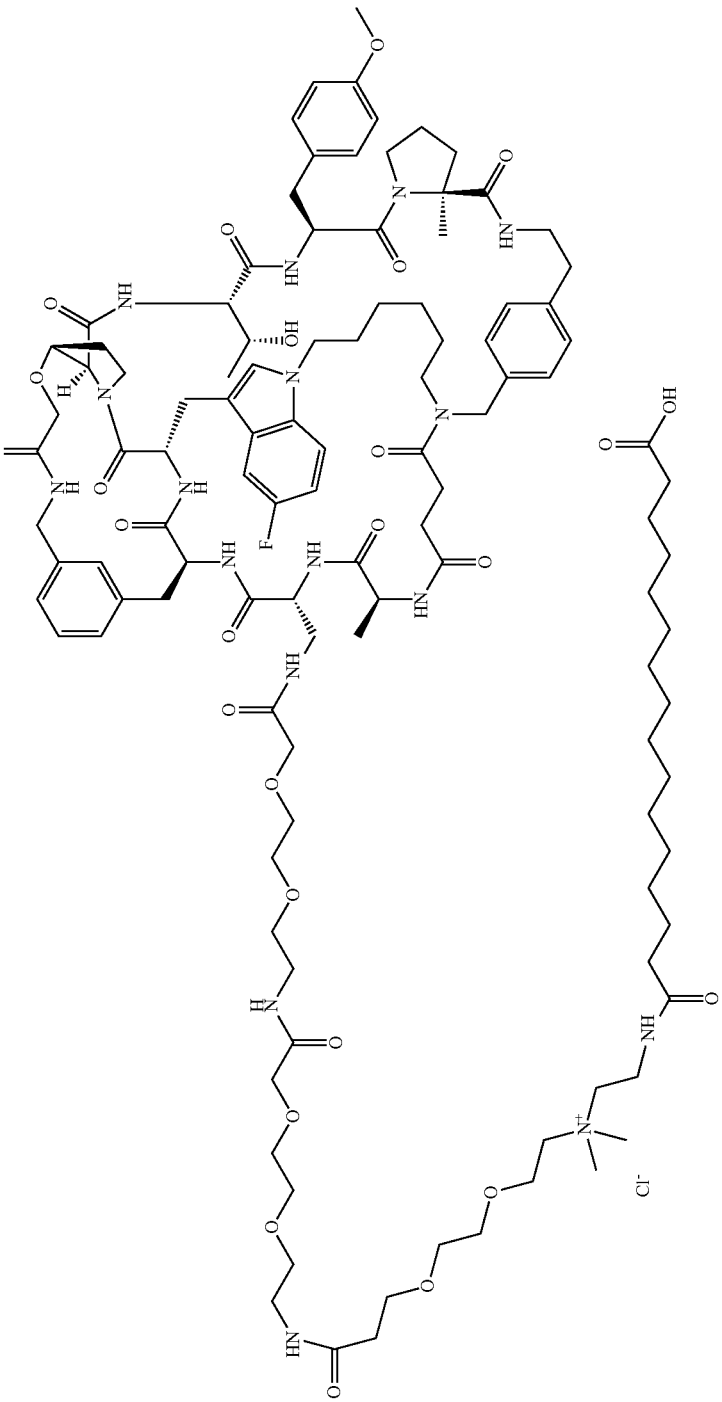 | 1092.4 |

TABLE 3-continued
Additional Examples of the Invention.
| Ex-No | Structure | LC/MS Observed [M]+, [M/2]+, or [(M + H)/2]+ |
|---|---|---|
| 40 | 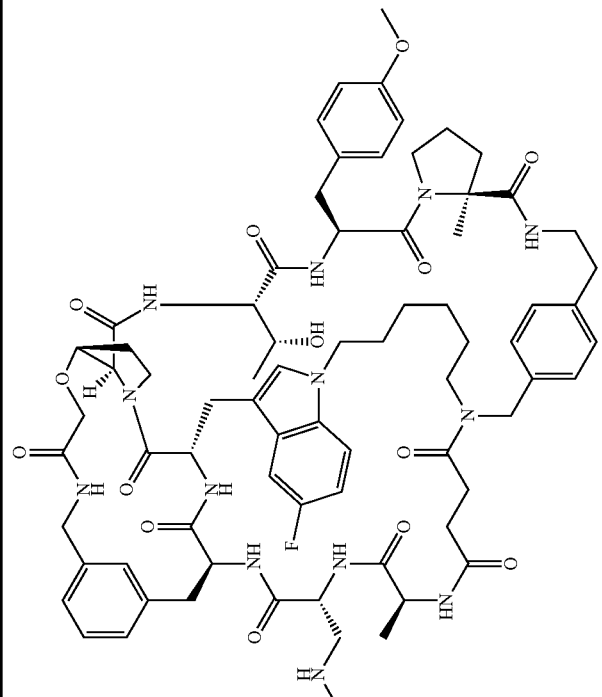 | 2326.3 |

TABLE 3-continued
Additional Examples of the Invention.
| Ex-No | Structure | LC/MS Observed [M]+, [M/2]+, or [(M + H)/2]+ |
|---|---|---|
| 41 | 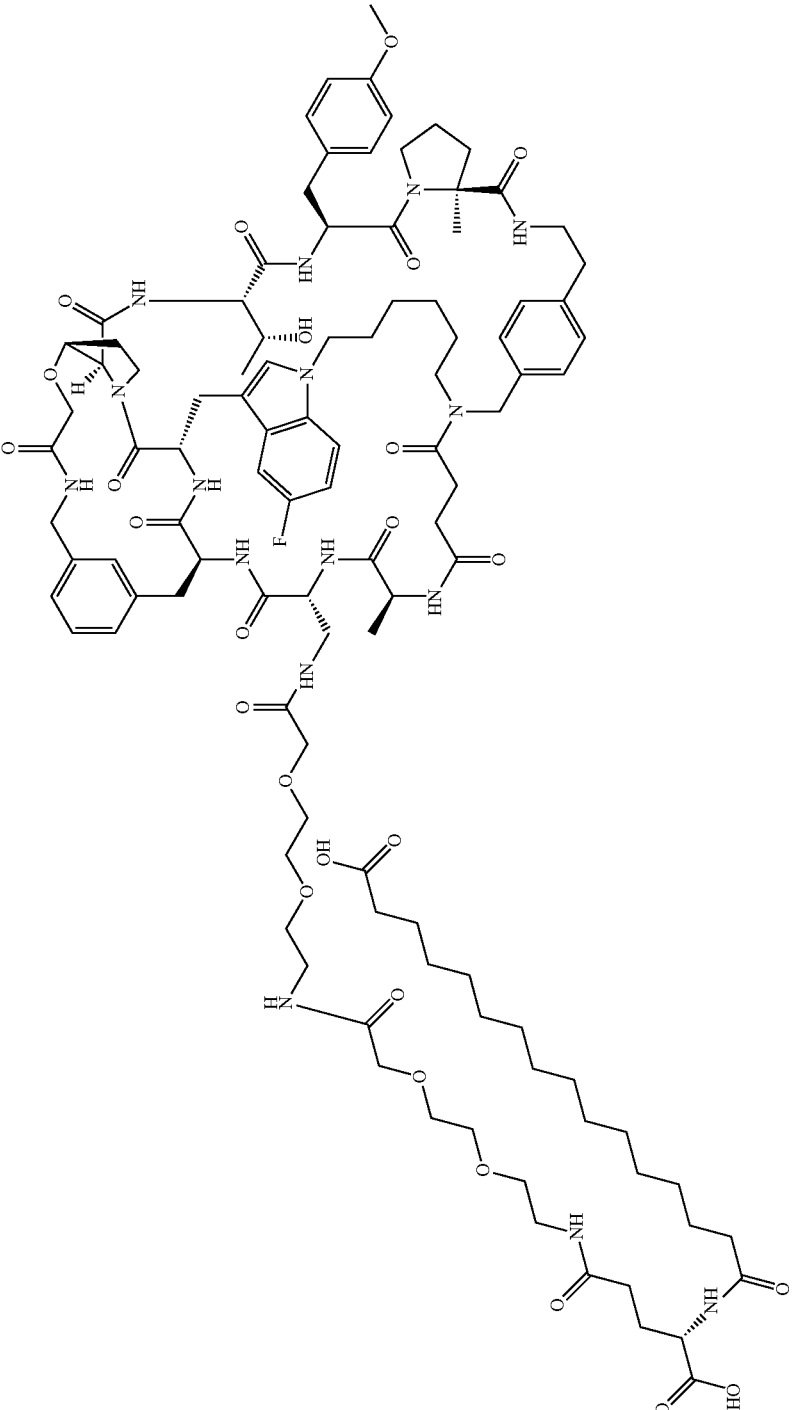 | 1042.2 |

TABLE 3-continued

Additional Examples of the Invention.

| Ex-No | Structure | LC/MS Observed [M]+, [M/2]+, or [(M + H)/2]+ |
|---|---|---|
| 42 | 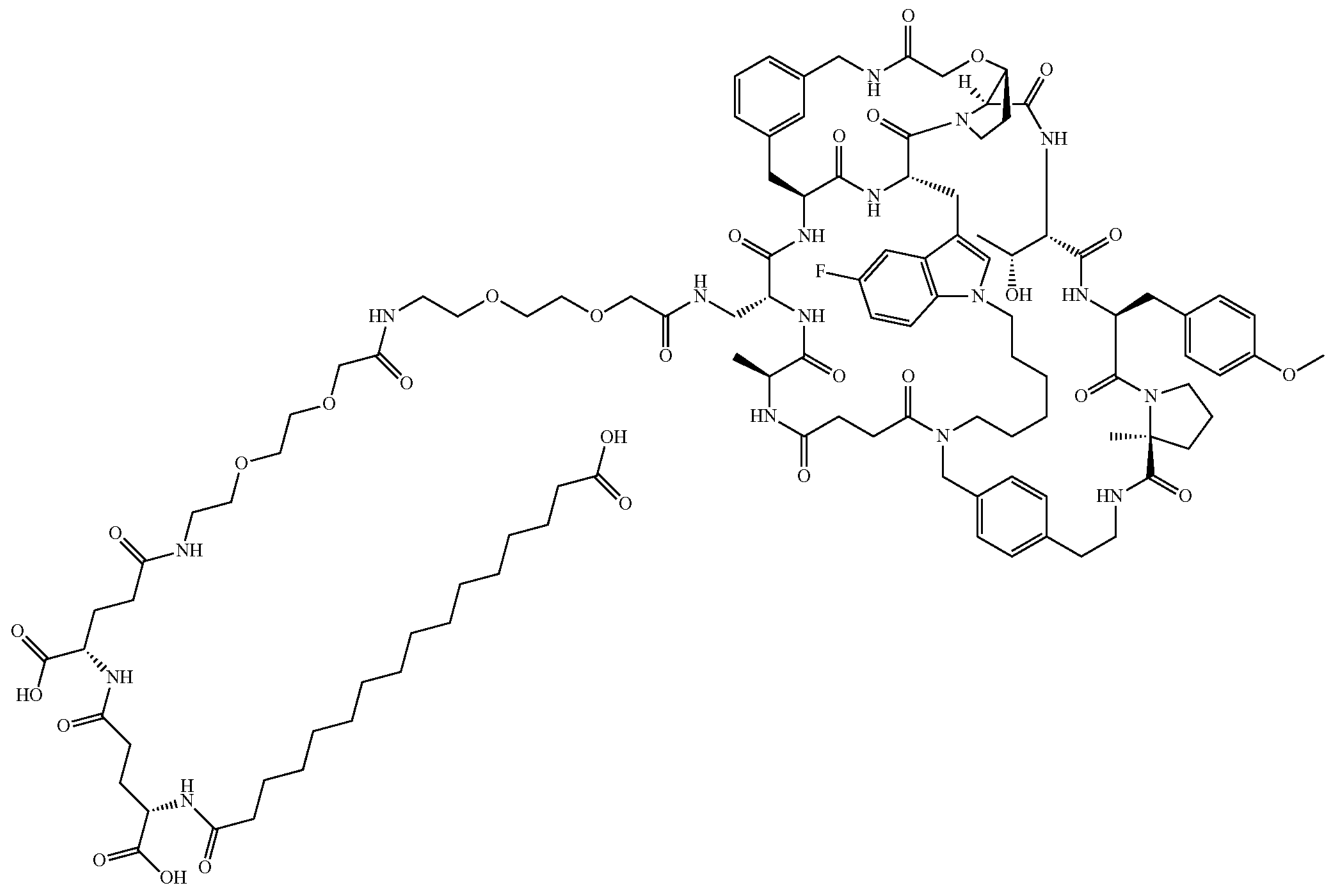 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)COCCOCCNC(=O)COCCOCCNC(=O)CC[C@H](NC(=O)CC[C@H](NC(=O)CCCCCCCCCCCCCCC(=O)O)C(=O)O)C(=O)O)C(=O)N[C@@H](Cc2cccc(c2)CNC(=O)CO4)C(=O)N3)cc1] | 1106.6 |

TABLE 3-continued
Additional Examples of the Invention.
| Ex-No | Structure | LC/MS Observed [M]+, [M/2]+, or [(M + H)/2)]+ |
|---|---|---|
| 43 | 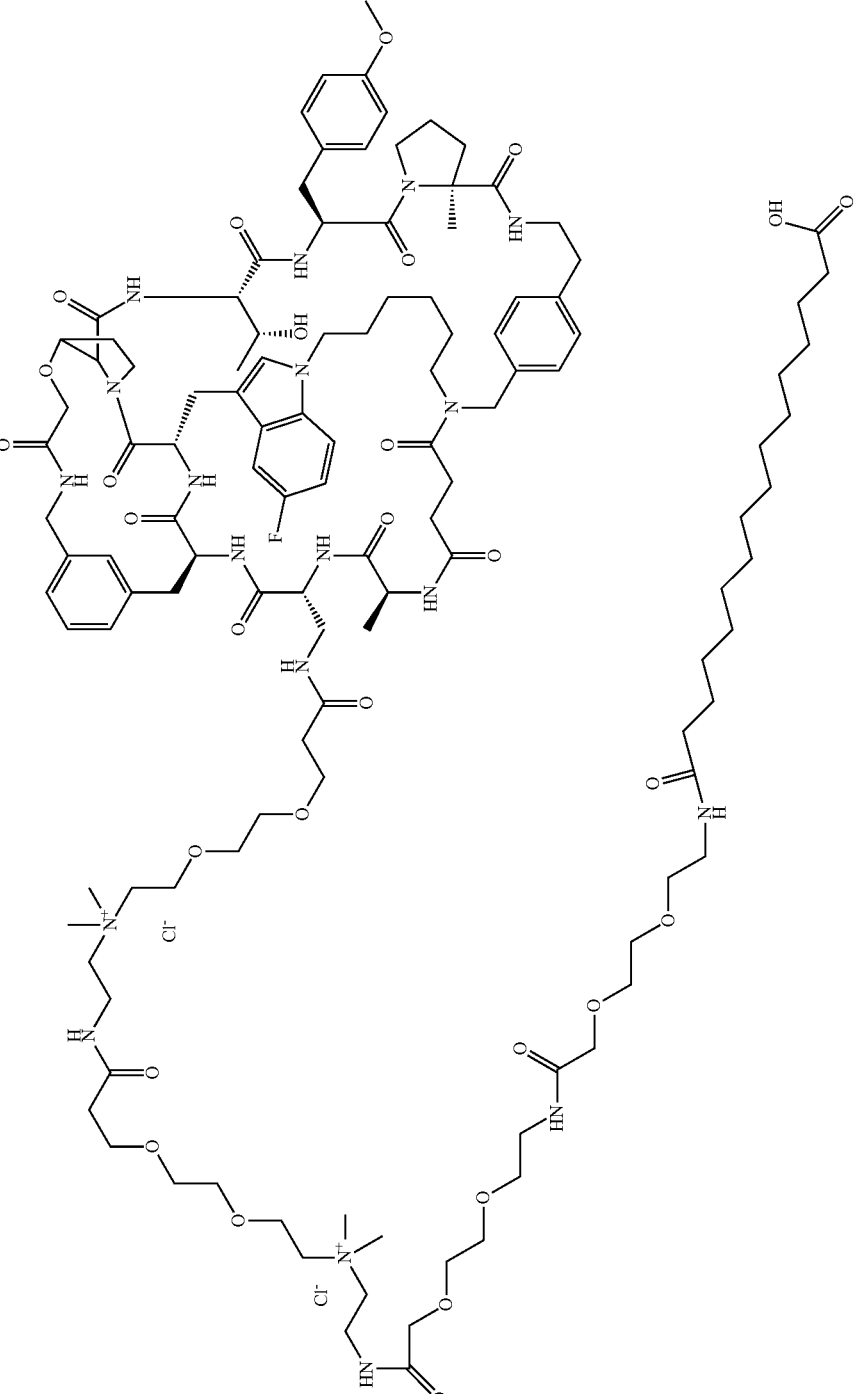 | 1207.4 |

TABLE 3-continued
Additional Examples of the Invention.
| Ex-No | Structure | LC/MS Observed [M]+, [M/2]+, or [(M + H)/2]+ |
|---|---|---|
| 44 | 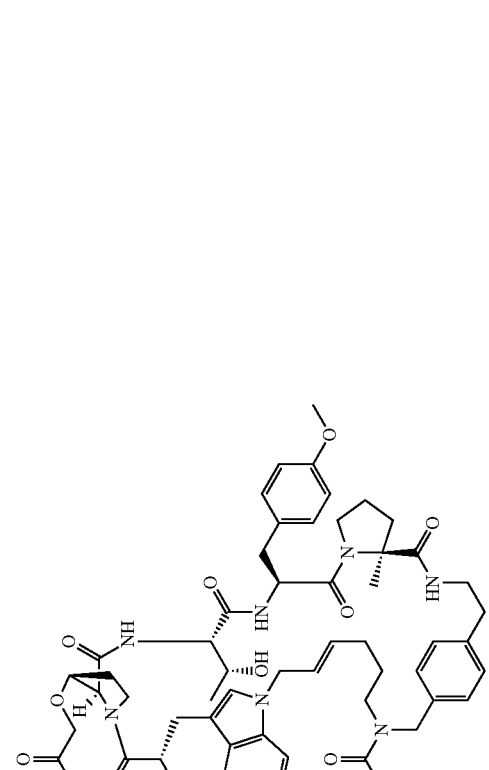 | 1234.3 |

TABLE 3-continued
Additional Examples of the Invention.
| Ex-No | Structure | LC/MS Observed [M]+, [M/2]+, or [(M + H)/2)]+ |
|---|---|---|
| 45 | 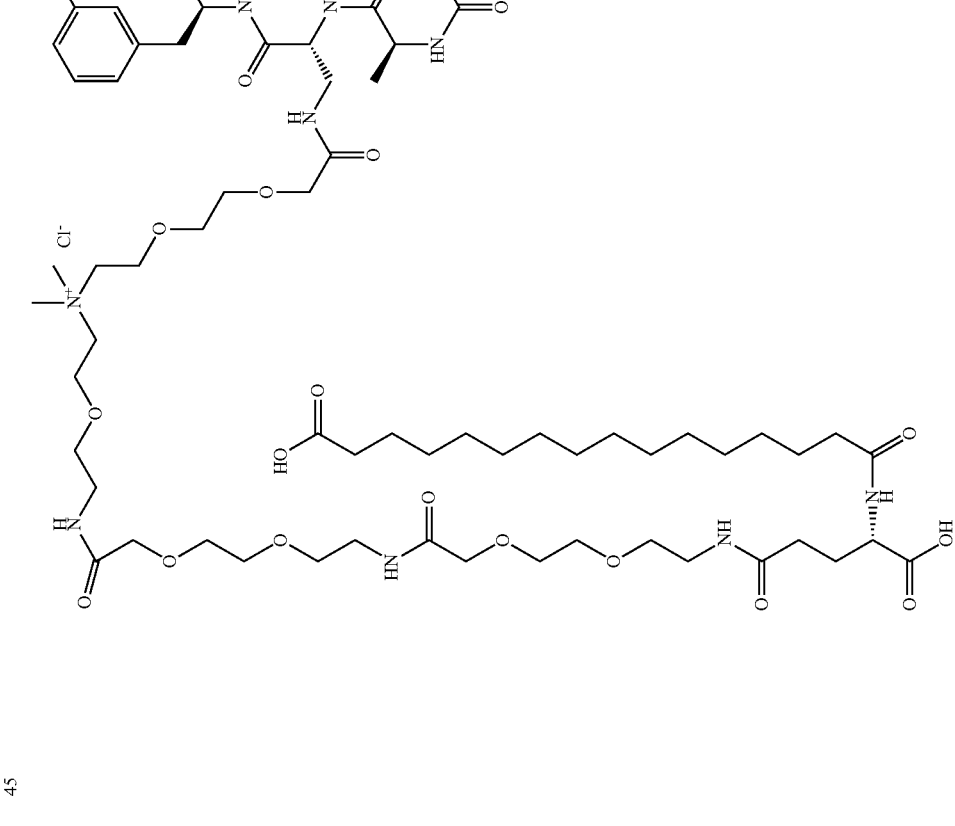 | 2342.3 |

TABLE 3-continued
Additional Examples of the Invention.
| Ex-No | Structure | LC/MS Observed [M]+, [M/2]+, or [(M + H)/2]+ |
|---|---|---|
| 46 | 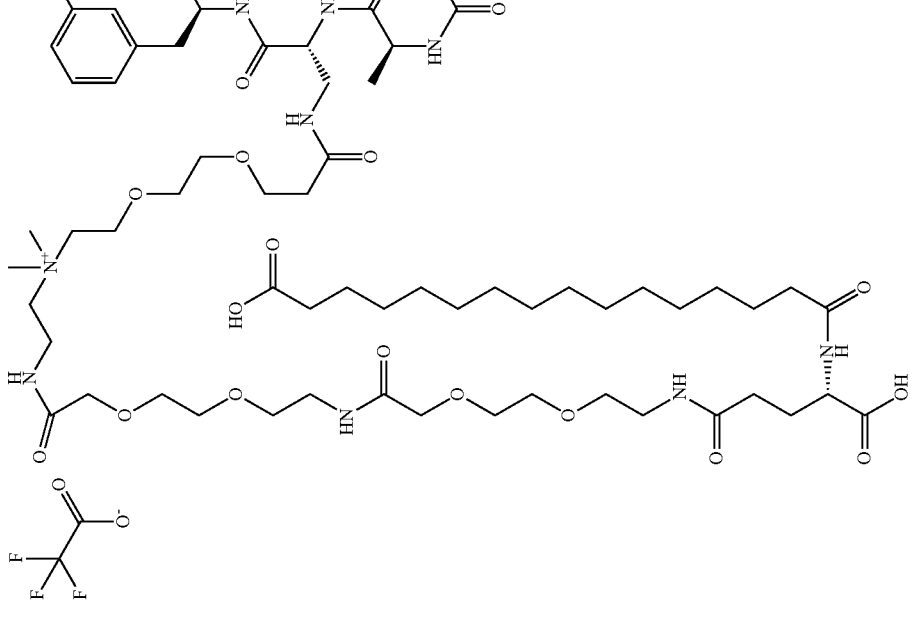 | 1156.2 |

TABLE 3-continued

Additional Examples of the Invention.

| Ex-No | Structure | LC/MS Observed [M]+, [M/2]+, or [(M + H)/2]+ |
|---|---|---|
| 47 | 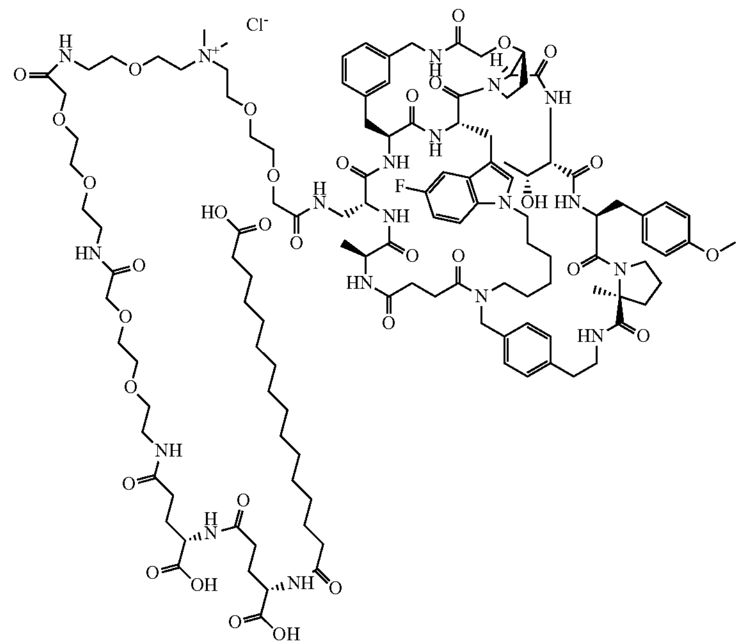 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)COCCOCC[N+](C)(C)CCOCCNC(=O)COCCOCCNC(=O)COCCOCCNC(=O)CC[C@H](NC(=O)CC[C@H](NC(=O)CCCCCCCCCCCCCCC(=O)O)C(=O)O)C(=O)O)C(=O)N[C@@H](Cc2cccc(c2)CNC(=O)CO4)C(=O)N3)cc1 ; [Cl-]] | 2471.3 |

TABLE 3-continued
Additional Examples of the Invention.
| Ex-No | Structure | LC/MS Observed [M]+, [M/2]+, or [(M + H)/2)]+ |
|---|---|---|
| 48 | 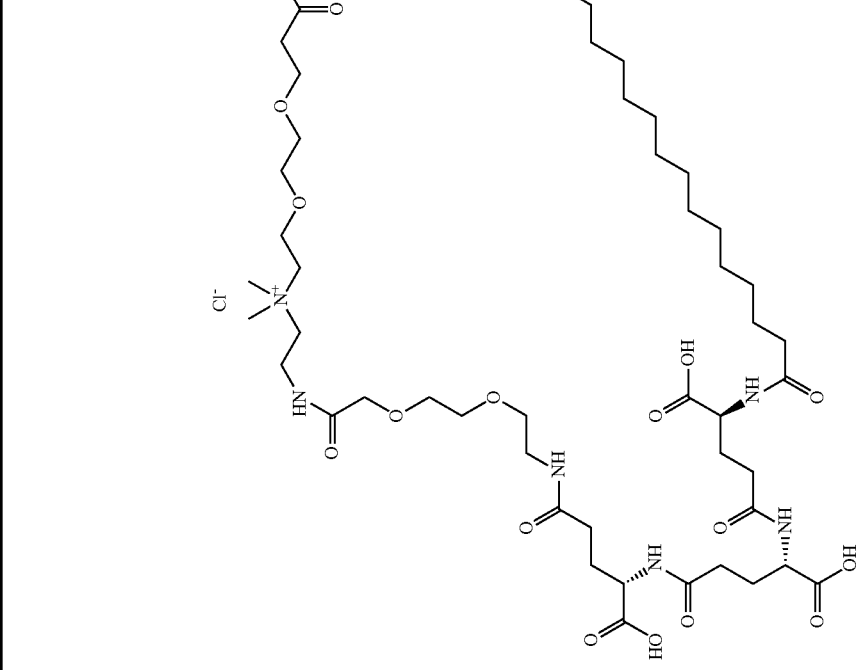 | 1227.4 |

TABLE 3-continued
Additional Examples of the Invention.
| Ex-No | Structure | LC/MS Observed $[M]^+$, $[M/2]^+$, or $[(M+H)/2]^+$ |
|---|---|---|
| 49 | 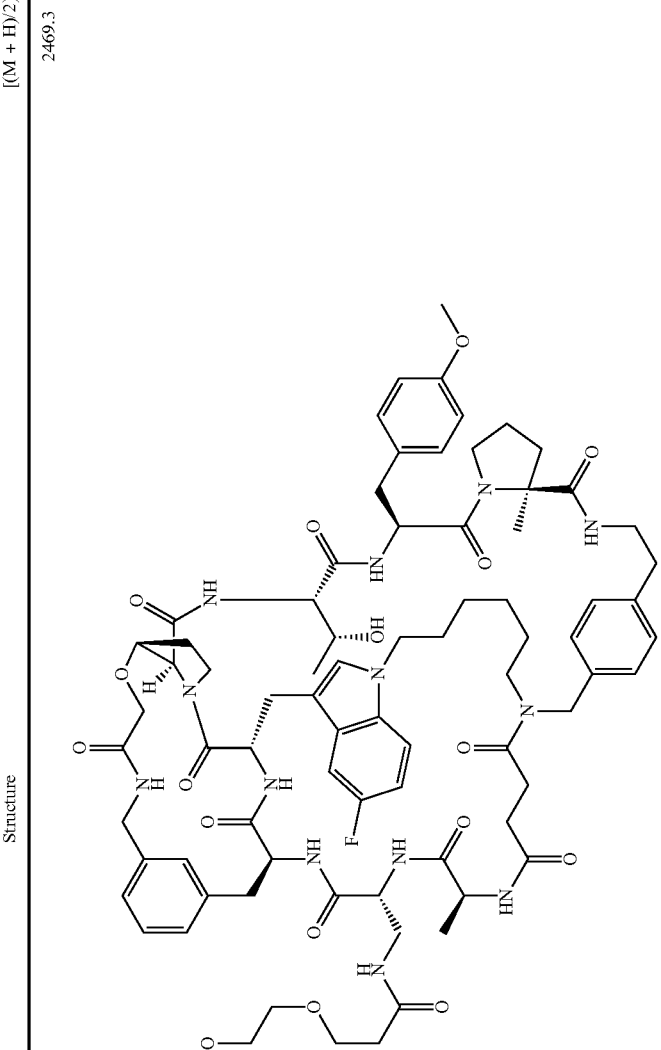 | 2469.3 |

TABLE 3-continued
Additional Examples of the Invention.
| Ex-No | Structure | LC/MS Observed [M]+, [M/2]+, or [(M + H)/2]+ |
|---|---|---|
| 50 | 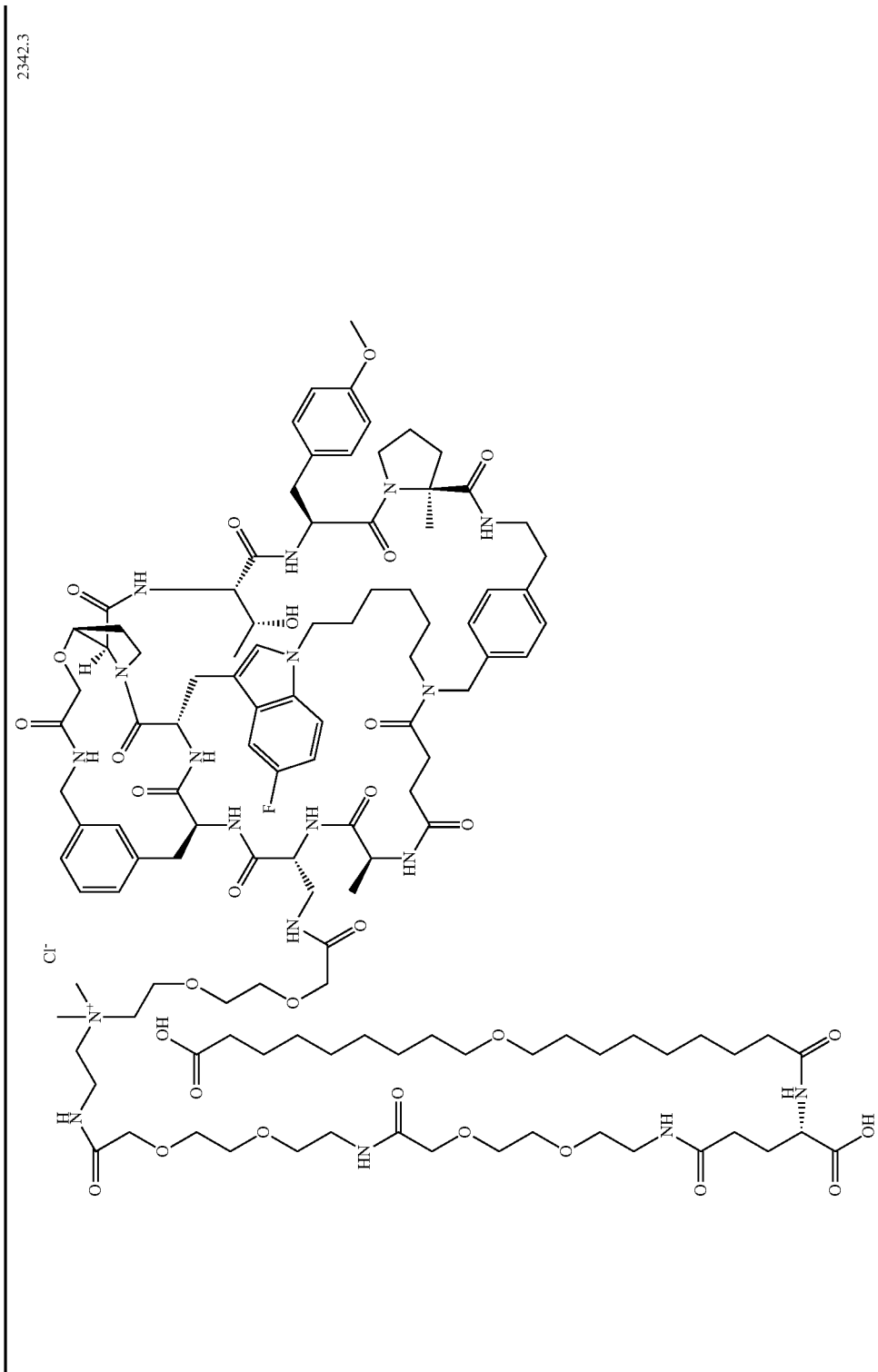 | 2342.3 |

TABLE 3-continued
Additional Examples of the Invention.
| Ex-No | Structure | LC/MS Observed [M]+, [M/2]+, or [(M + H)/2)]+ |
|---|---|---|
| 51 |  | 1228.7 |

TABLE 3-continued
Additional Examples of the Invention.
| Ex-No | Structure | LC/MS Observed [M]+, [M/2]+, or [(M + H)/2]+ |
|---|---|---|
| 52 | 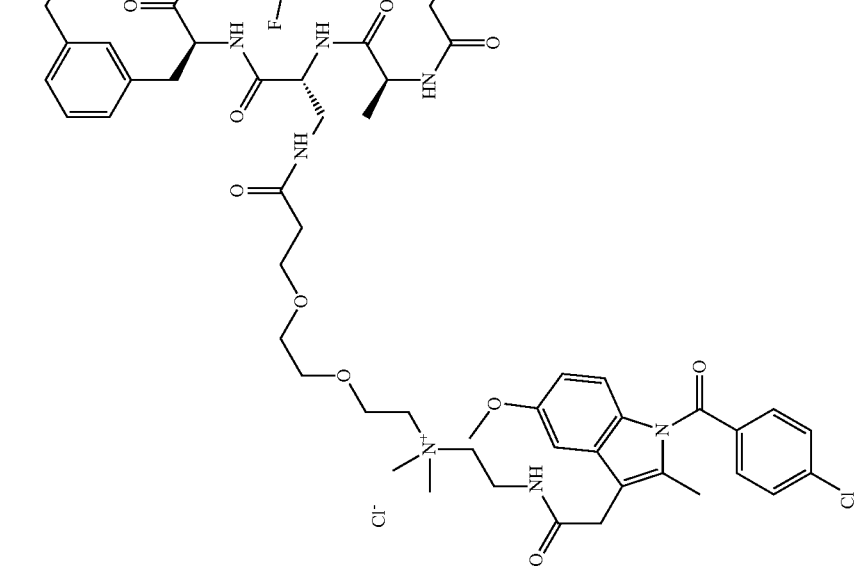 | 983.1 |

TABLE 3-continued
Additional Examples of the Invention.
| Ex-No | Structure | LC/MS Observed [M]+, [M/2]+, or [(M + H)/2)]+ |
|---|---|---|
| 53 | 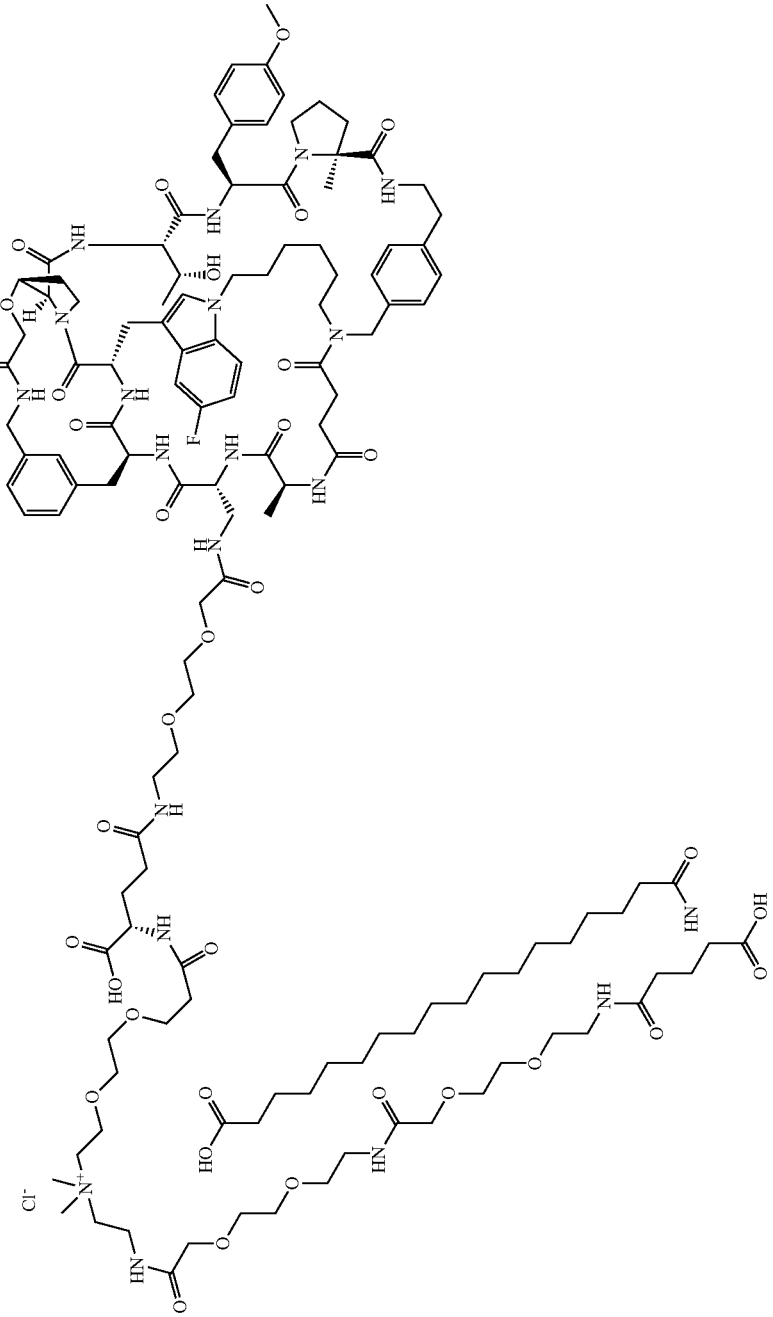 | 2614.4 |

TABLE 3-continued

Additional Examples of the Invention.

| Ex-No | Structure | LC/MS Observed [M]+, [M/2]+, or [(M + H)/2]+ |
|---|---|---|
| 54 | 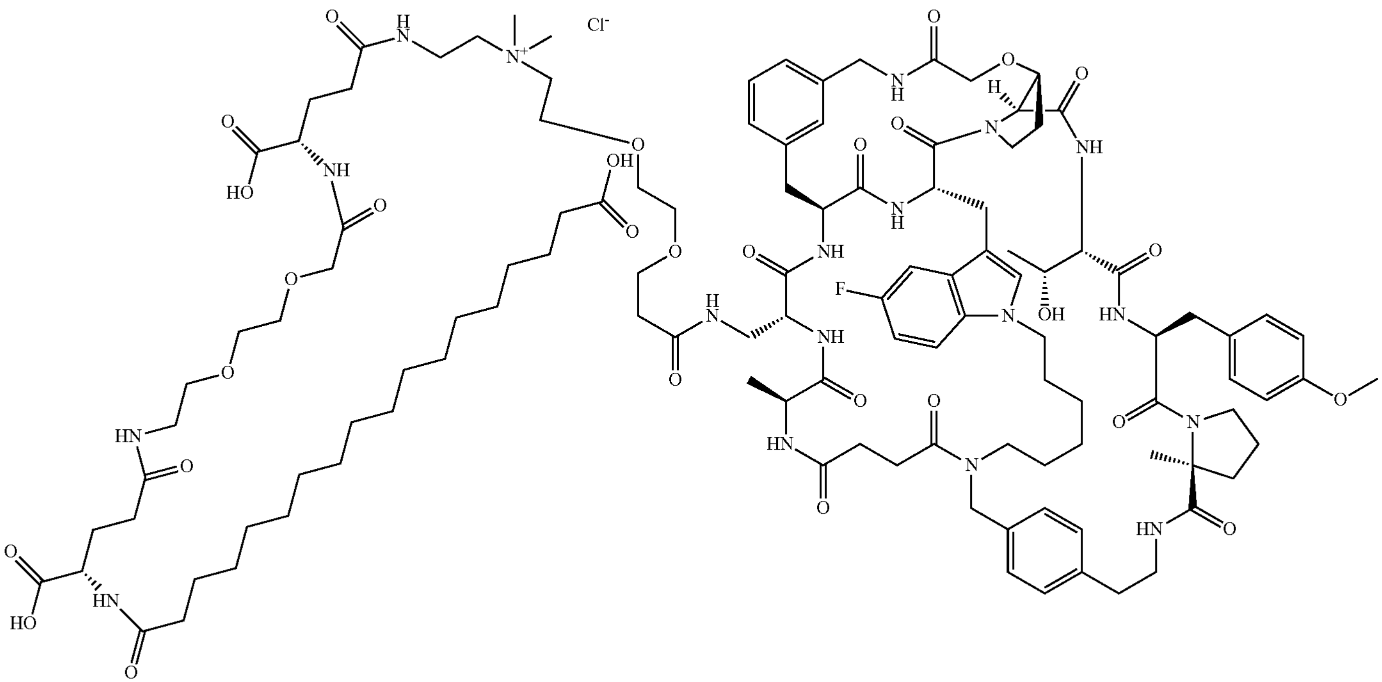 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCOCCOCC[N+](C)(C)CCNC(=O)CC[C@H](NC(=O)COCCOCCNC(=O)CC[C@H](NC(=O)CCCCCCCCCCCCCCCCC(=O)O)C(=O)O)C(=O)O)C(=O)N[C@@H](Cc2cccc(c2)CNC(=O)CO4)C(=O)N3)cc1 ; [Cl-]] | 2324.2 |

TABLE 3-continued
Additional Examples of the Invention.
| Ex-No | Structure | LC/MS Observed [M]+, [M/2]+, or [(M + H)/2)]+ |
|---|---|---|
| 55 | 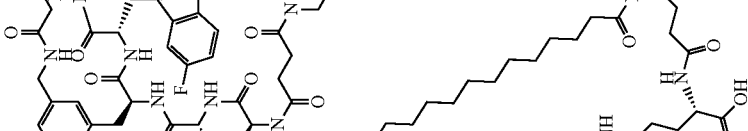 | 2409.3 |

TABLE 3-continued
Additional Examples of the Invention.
| Ex-No | Structure | LC/MS Observed [M]+, [M/2]+, or [(M + H)/2]+ |
|---|---|---|
| 56 | 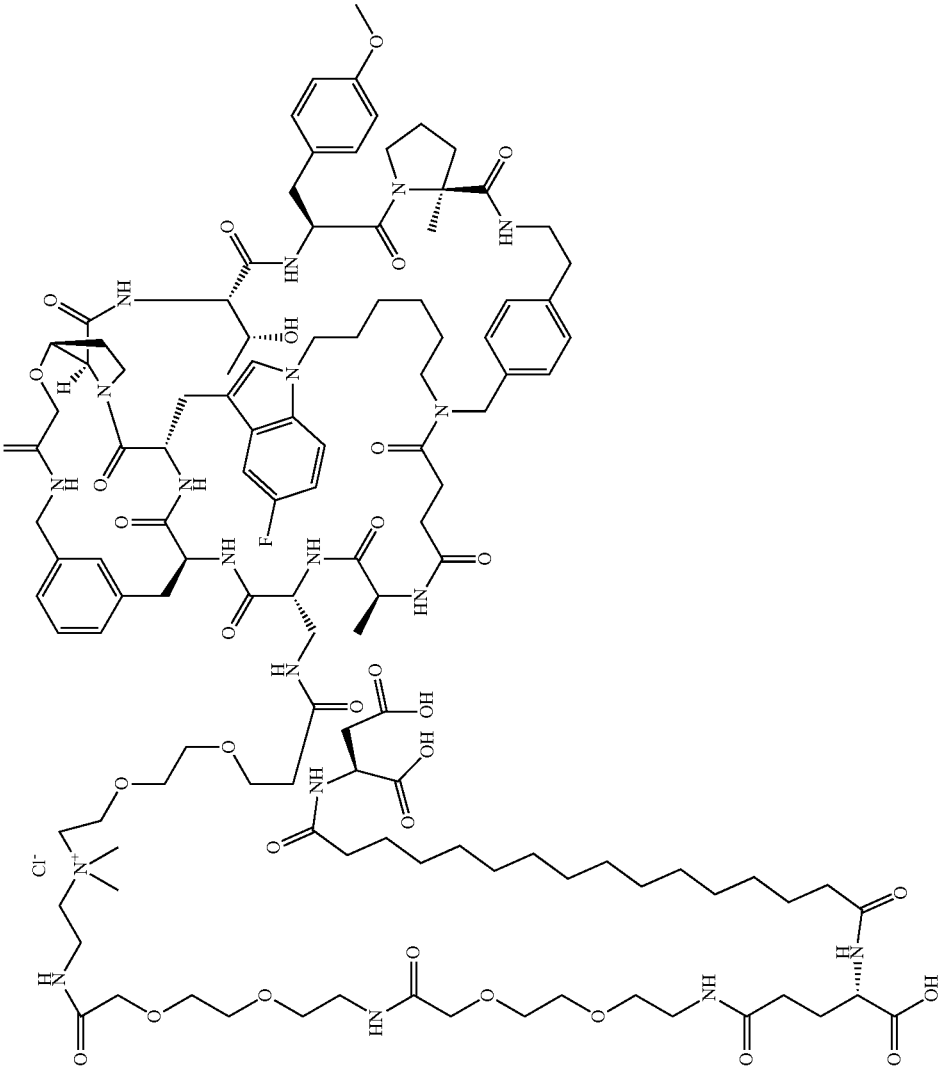 | 2427.3 |

TABLE 3-continued
Additional Examples of the Invention.
| Ex-No | Structure | LC/MS Observed [M]+, [M/2]+, or [(M + H)/2)]+ |
|---|---|---|
| 57 | 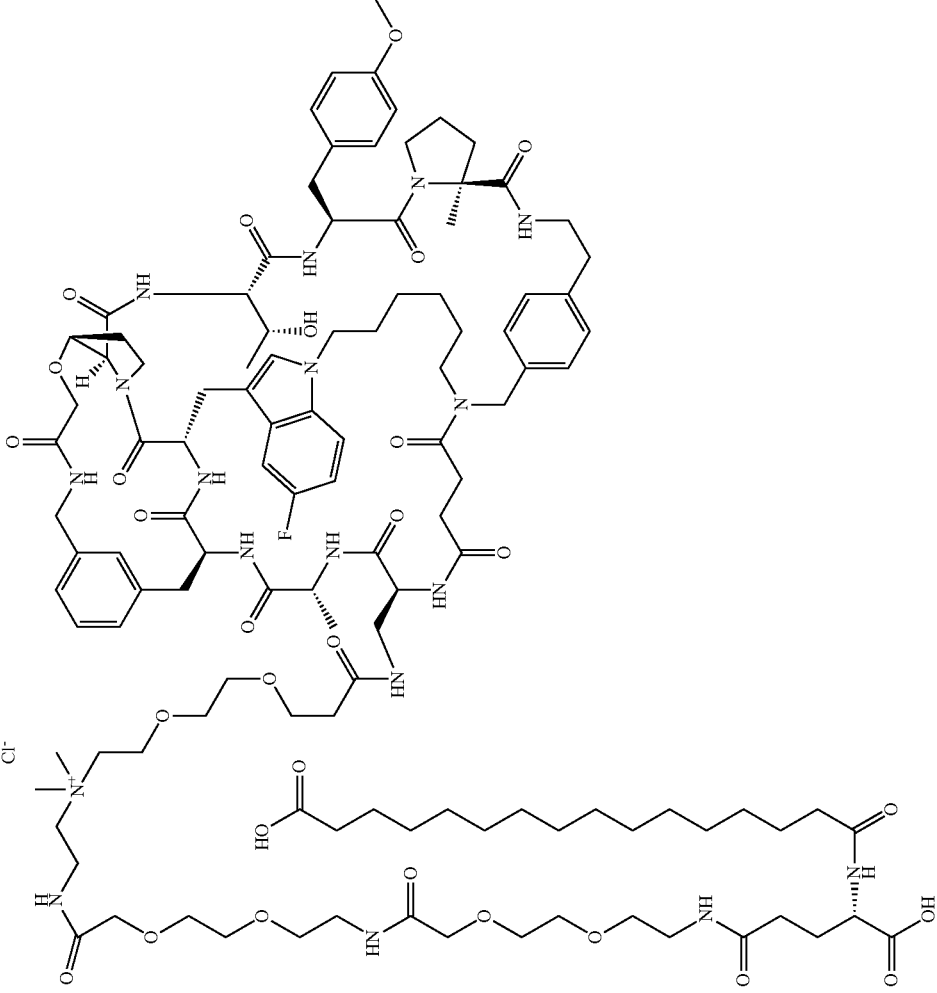 | 2312.3 |

TABLE 3-continued
Additional Examples of the Invention.
| Ex-No | Structure | LC/MS Observed [M]+, [M/2]+, or [(M + H)/2)]+ |
|---|---|---|
| 58 | 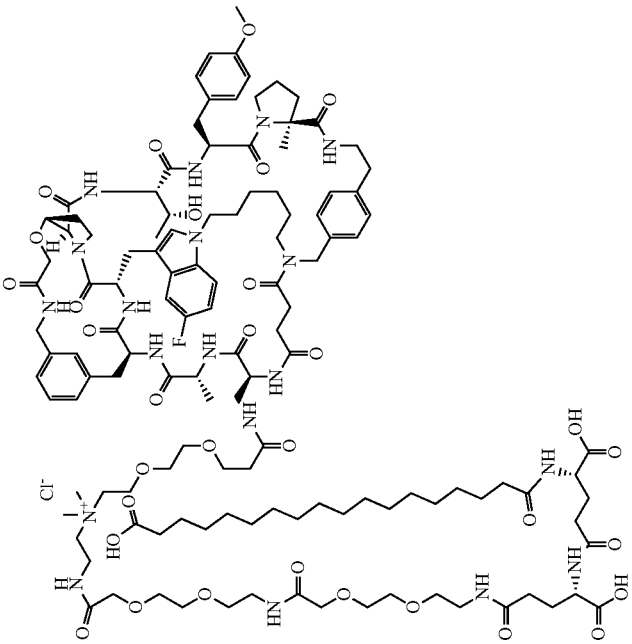 | 2469.3 |

TABLE 3-continued
Additional Examples of the Invention.
| Ex-No | Structure | LC/MS Observed [M]+, [M/2]+, or [(M + H)/2]+ |
|---|---|---|
| 59 | 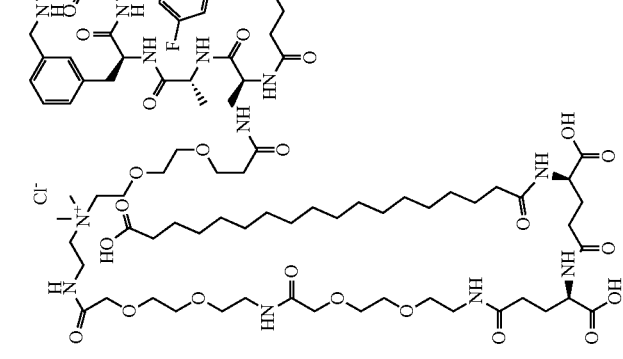 | 2469.3 |

TABLE 3-continued
Additional Examples of the Invention.
| Ex-No | Structure | LC/MS Observed [M]⁺, [M/2]⁺, or [(M + H)/2)]⁺ |
|---|---|---|
| 60 | 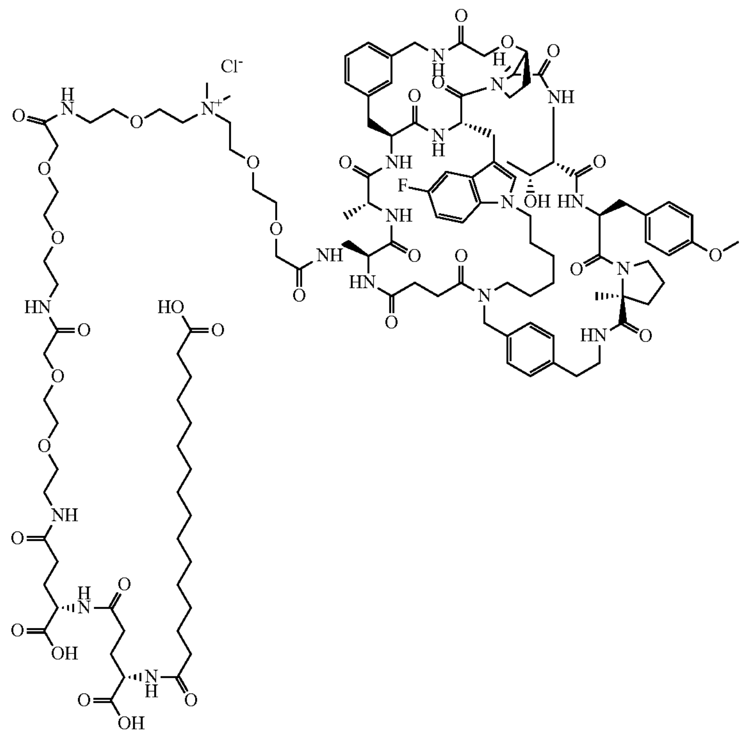 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](CNC(=O)COCCOCC[N+](C)(C)CCOCCNC(=O)COCCOCCNC(=O)COCCOCCNC(=O)CC[C@H](NC(=O)CC[C@H](NC(=O)CCCCCCCCCCCCCCC(=O)O)C(=O)O)C(=O)O)C(=O)N[C@H](C)C(=O)N[C@@H](Cc2cccc(c2)CNC(=O)CO4)C(=O)N3)cc1 ; [Cl-]] | 2471.3 |

TABLE 3-continued
Additional Examples of the Invention.
| Ex-No | Structure | LC/MS Observed [M]+, [M/2]+, or [(M + H)/2]+ |
|---|---|---|
| 61 | 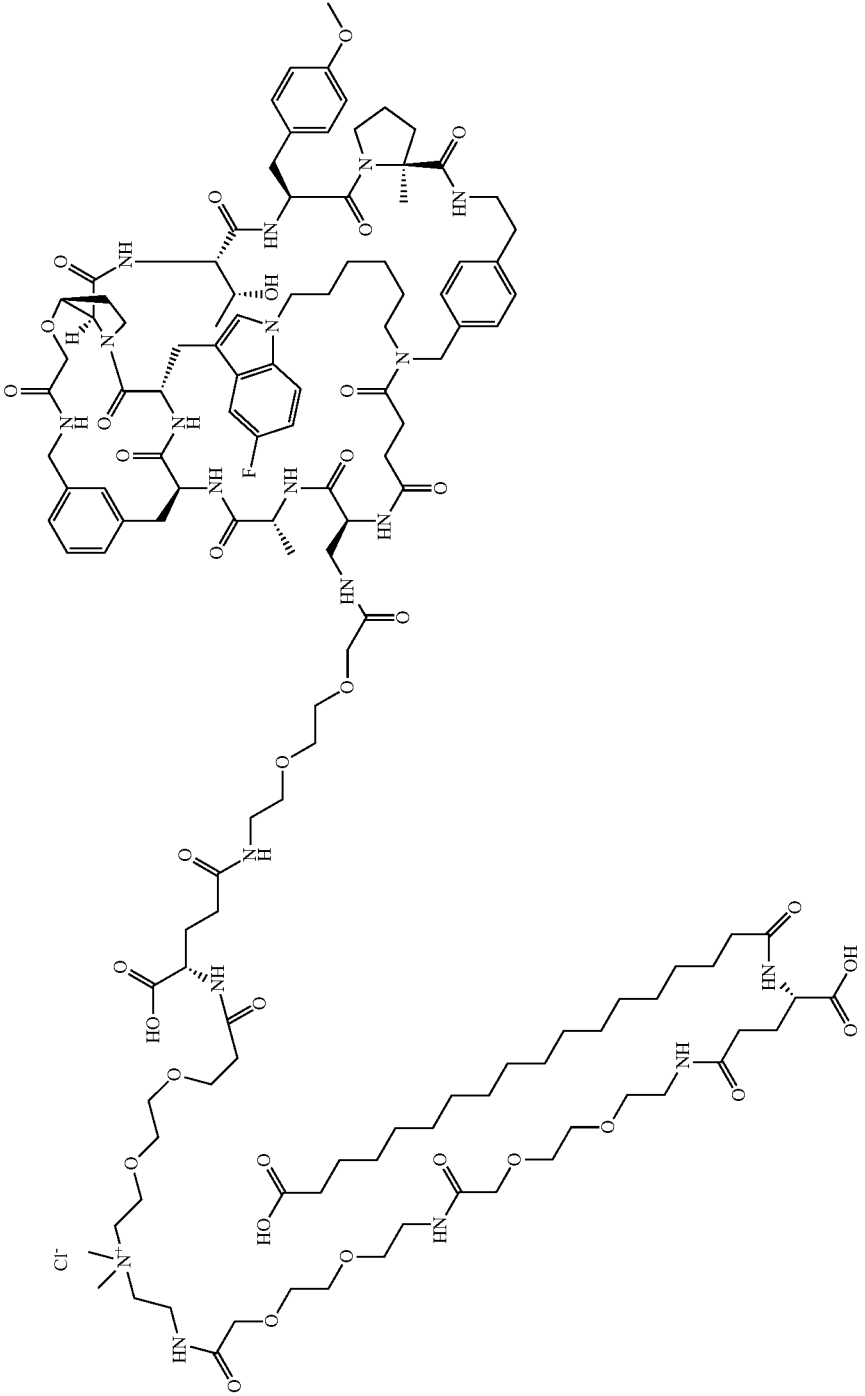 | 2614.4 |

TABLE 3-continued
Additional Examples of the Invention.
| Ex-No | Structure | LC/MS Observed [M]+, [M/2]+, or [(M + H)/2]+ |
|---|---|---|
| 62 | 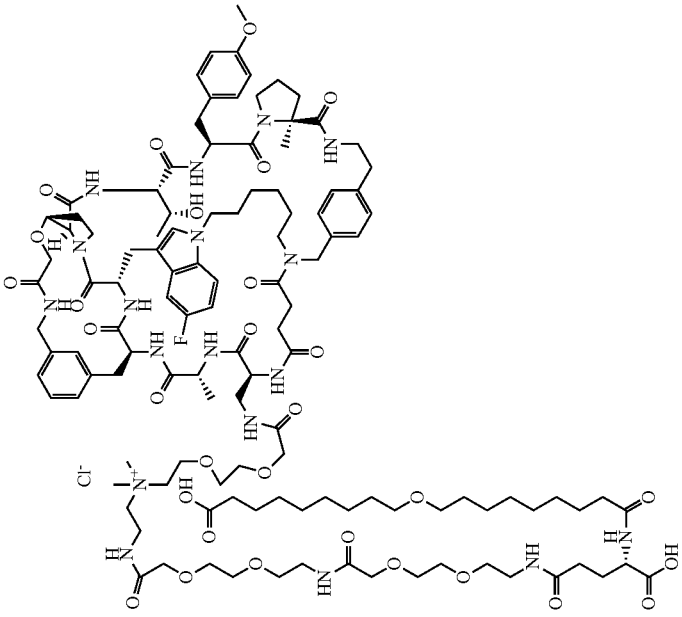 | 2342.3 |

TABLE 3-continued
Additional Examples of the Invention.
| Ex-No | Structure | LC/MS Observed [M]+, [M/2]+, or [(M + H)/2)]+ |
|---|---|---|
| 63 | 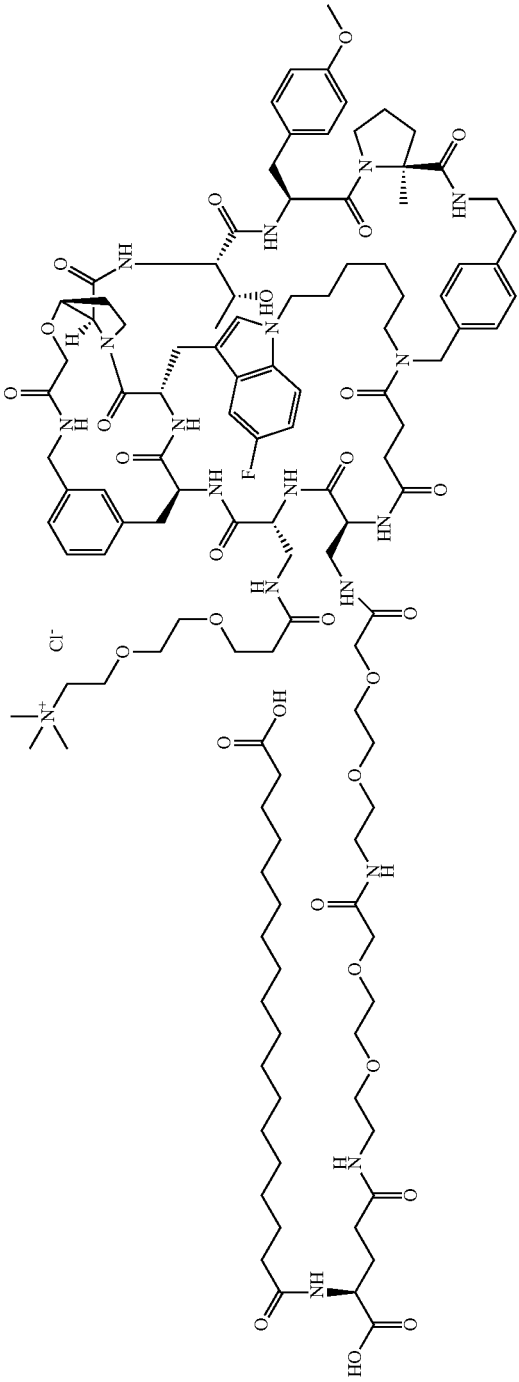 | 2327.3 |

TABLE 3-continued

Additional Examples of the Invention.

| Ex-No | Structure | LC/MS Observed [M]⁺, [M/2]⁺, or [(M + H)/2)]⁺ |
|---|---|---|
| 64 | 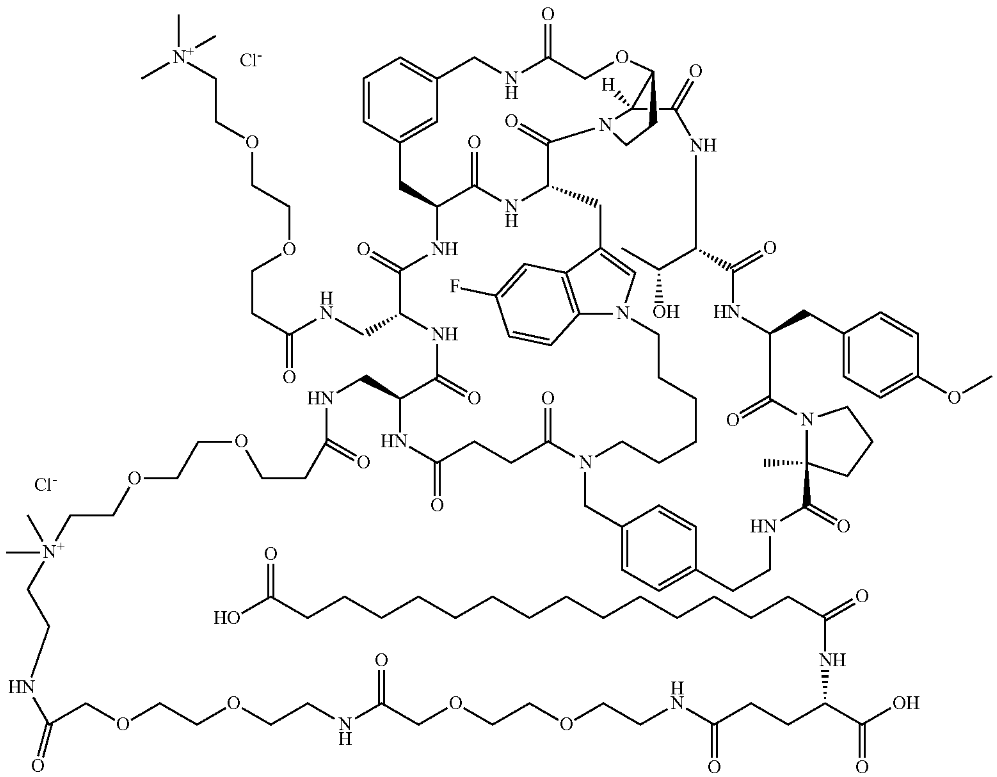 | 2529.4 |

TABLE 3-continued

Additional Examples of the Invention.

| Ex-No | Structure | LC/MS Observed [M]+, [M/2]+, or [(M + H)/2)]+ |
|---|---|---|
| 65 | 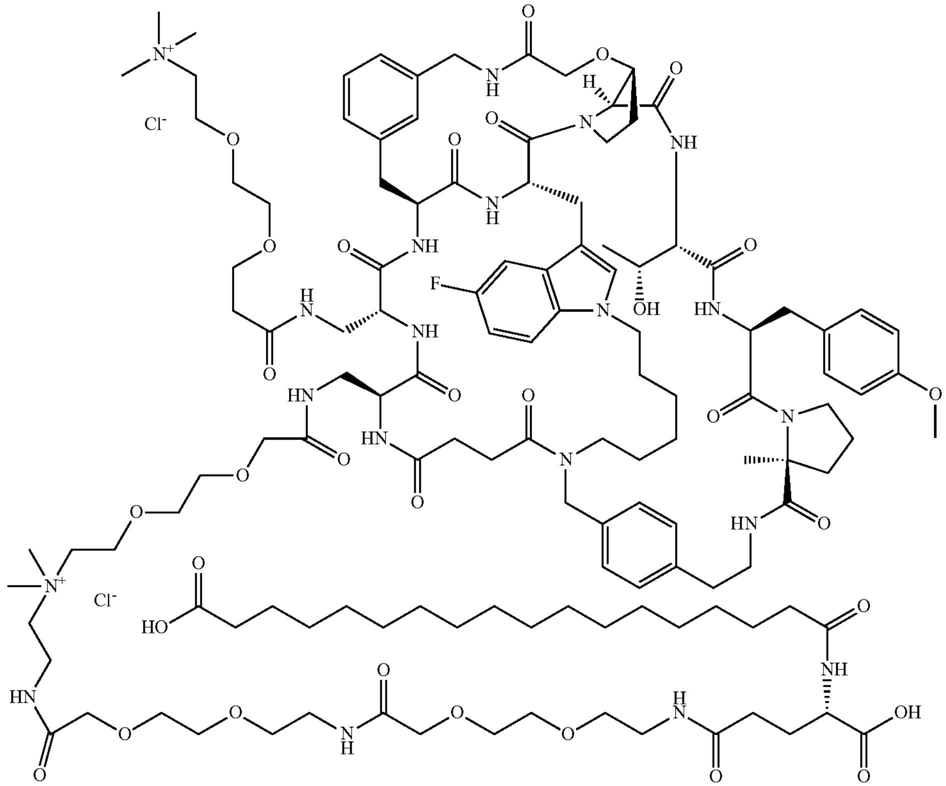 | 1271.7 |

TABLE 3-continued
Additional Examples of the Invention.
| Ex-No | Structure | LC/MS Observed [M]+, [M/2]+, or [(M + H)/2]+ |
|---|---|---|
| 66 | 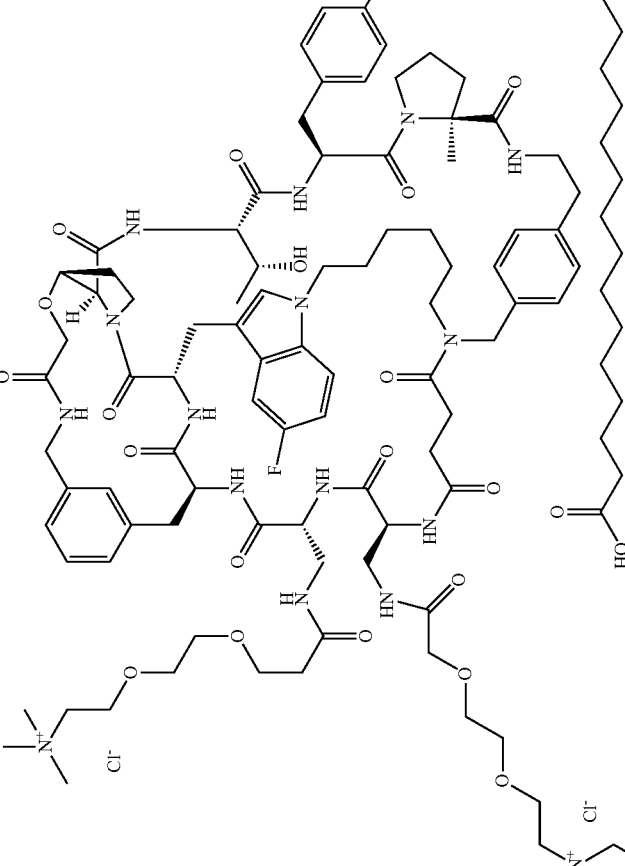 | 2687.5 |

TABLE 3-continued
Additional Examples of the Invention.
| Ex-No | Structure | LC/MS Observed [M]+, [M/2]+, or [(M + H)/2]+ |
|---|---|---|
| 67 | 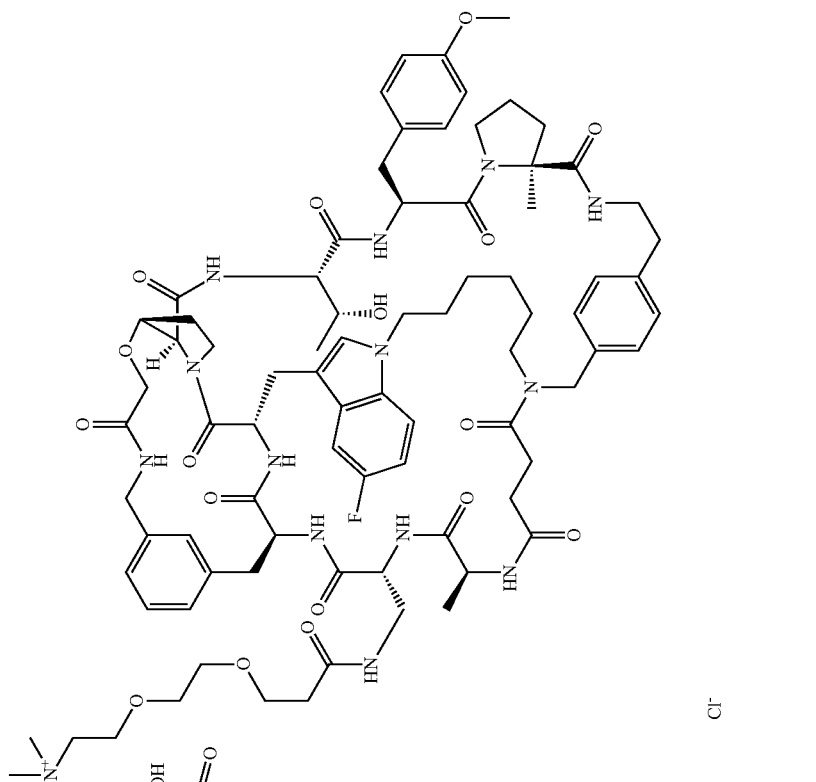 | 2390.3 |

TABLE 3-continued

Additional Examples of the Invention.

| Ex-No | Structure | LC/MS Observed [M]+, [M/2]+, or [(M + H)/2)]+ |
|---|---|---|
| 68 | 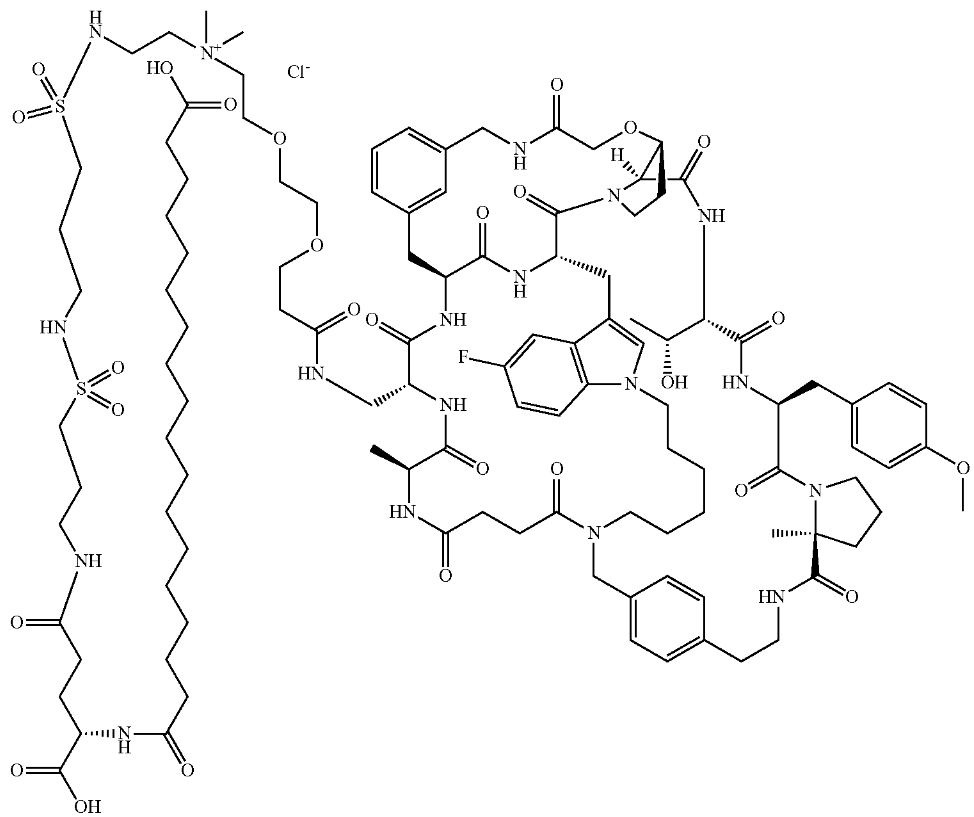 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCOCCOCC[N+](C)(C)CCNS(=O)(=O)CCCNS(=O)(=O)CCCNC(=O)CC[C@H](NC(=O)CCCCCCCCCCCCCCCCC(=O)O)C(=O)O)C(=O)N[C@@H](Cc2cccc(c2)CNC(=O)CO4)C(=O)N3)cc1 ; [Cl-]] | 2292.2 |

Activity Determination

Selected compounds of the invention were subjected to one or more of the following procedures to assay their activity for antagonism of PCSK9 activity.

The following is a description of the assays used to determine activity of compounds of the invention, and any comparator compounds reported, toward PCSK9 antagonism. Biotinylated PCSK9 was obtained commercially.

Alexa FRET Standard TR-FRET

The PCSK9 Alexa FRET Standard assay measures the interaction between PCSK9 and an AlexaFluor647 (AF) tagged cyclic peptide, Reagent A ($K_D$=83 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2, 0.01% BSA, and 0.01% Surfactant P20. A separate solution containing 40 nM of the AlexaFluor tagged cyclic peptide is made in the same buffer system. An Echo is used to transfer 0.750 ul of compound to an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 20 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the Ic50 and the $K_D$ of AF cyclic peptide. Counts (B-counts) of the europium-labeled PCSK9 are followed to observe if compounds are adversely PCSK9. A fall off of the B-counts likely indicates a false positive of inhibition. Data from this procedure is reported as "A='numerical value' (nanomolar)"

Reagent A was prepared in accordance with the following method:

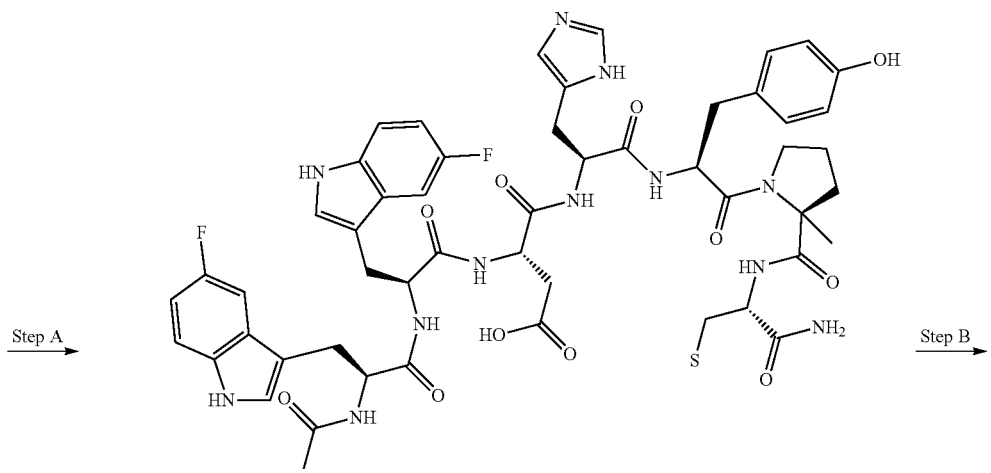

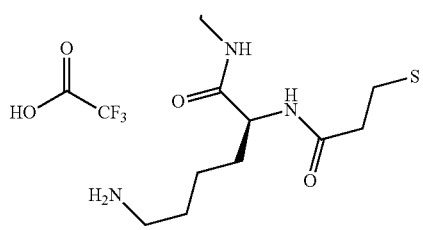

Int. A

-continued
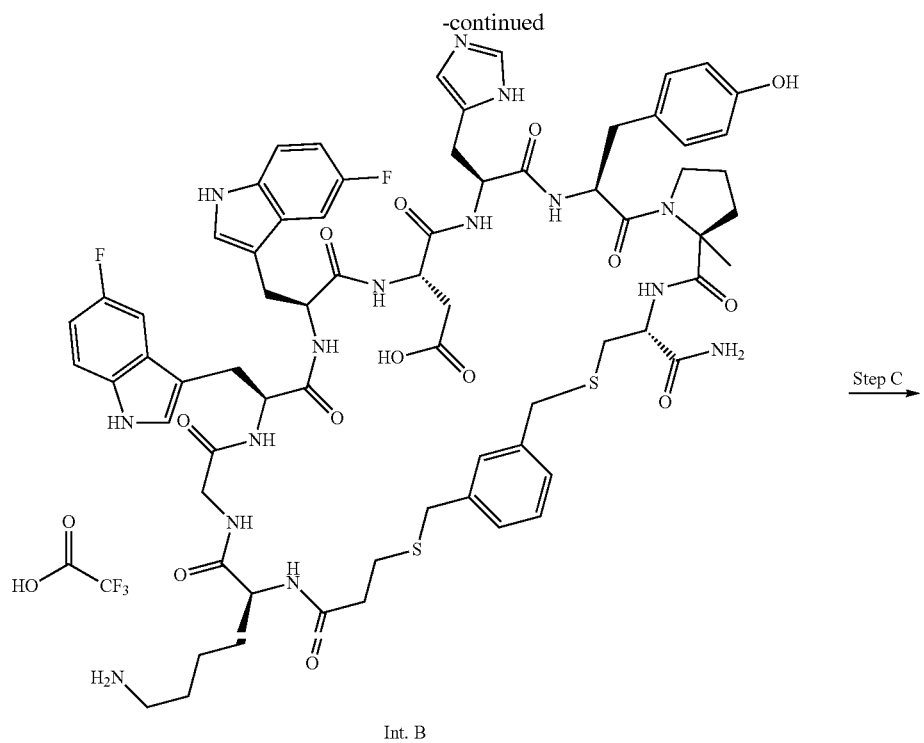
Int. B
Step C
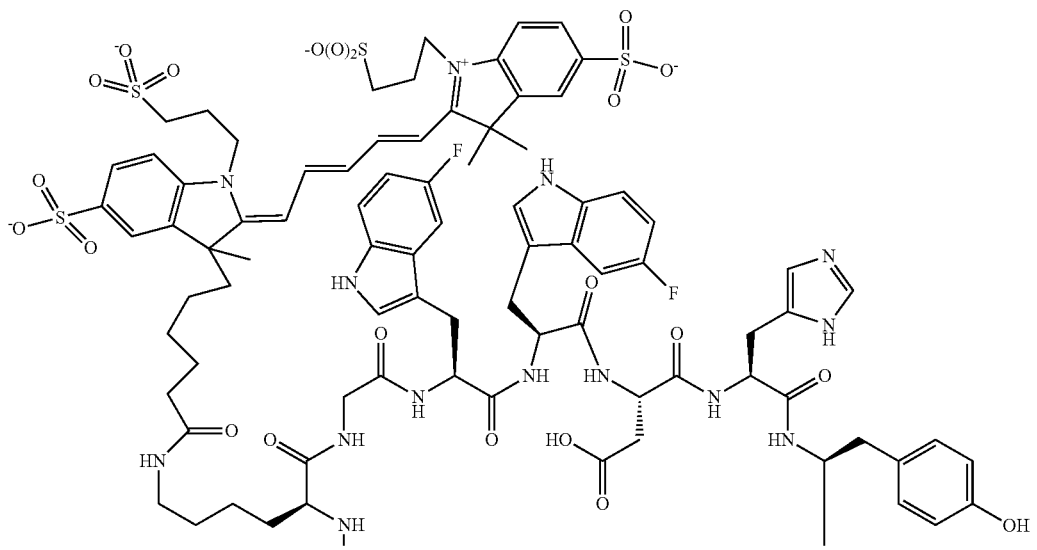
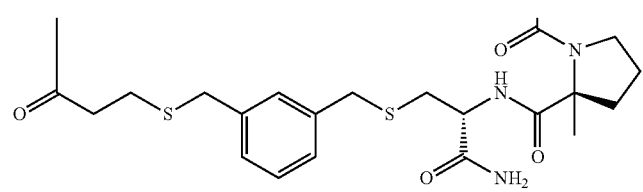
REAGENT A

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol g$^{-1}$. The assembly was performed using single-couplings using 4 eq of Fmoc protected amino acid 0.2M in DMF, 4 eq of 0.5M HATU in DMF, 4 eq of 2M DIPEA (double coupling for Tyr). Fmoc deprotection cycles were performed using 20% (V/V) piperidine in DMF.

The sequence of Fmoc protected amino acids and building blocks used are:
1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (((9H-fluoren-9-yl)methoxy)carbonyl)-L-tyrosine
4. N-(((9H-fluoren-9-yl)methoxy)carbonyl)-N-trityl-L-histidine
5. (S)-2-(4 (9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)glycine
9. N$^2$-(((9H-fluoren-9-yl)methoxy)carbonyl)-N$^6$-(tert-butoxycarbonyl)-L-lysine
10. 3-(tritylthio)propanoic acid At the end of the assembly, the resin was washed with DMF, MeOH, DCM, Et$_2$O. The peptide was cleaved from solid support using 50 ml of TFA solution (v/v) (91% TFA, 5% H$_2$O, 4% TIPS) for approximately 1.5 hours, at room temperature. The resin was filtered, washed with TFA and solution concentrated to dryness and lyophilized. Lyophilization afforded Intermediate Compound Int. A (399 mg), which was used as crude in the next step. LCMS anal. calcd. C61H75F2N15O13S2: 1328.48, found: 1328.2 (M+1)$^+$

Step B—Synthesis of Intermediate Compound Int-B: as Described for Reagent B

Purified by RP-HPLC (Waters Deltapak C4, double cartridge, 40×100 mm, 15 □m, 300 A; 15% to 35% ACN/water+0.1% TFA modifier over 20 min). Collected fractions lyophilized to afford 35 mg of Intermediate Compound Int-B. LCMS anal. calcd. for C69H81F2N15O13S2: 1430.62; found: 1430.9 (M+1)$^+$

Step C—Synthesis of Compound Reagent A: as Described for Reagent B

LCMS anal. calcd. for C105H122F2N17O26S6$^{3-}$: 2268.58; 1135.8 (M+2)$^{2+}$

Alexa FRET Plus TR-FRET

The PCSK9 Alexa FRET Plus assay measures the interaction between PCSK9 and an AlexaFluor647 (AF) tagged cyclic peptide, Reagent B (K$_D$=35 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2, 0.01% BSA, and 0.01% Surfactant P20. A separate solution containing 1920 nM of the AlexaFluor tagged cyclic peptide is made in the same buffer system. An Echo is used to transfer 0.075 ul of compound plus 0.675 ul of DMSO to each well of an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 960 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the Ic50 and the K$_D$ of AF cyclic peptide. Counts (B-counts) of the europium-labeled PCSK9 are followed to observe if compounds are adversely affecting PCSK9. A fall off of the B-counts is likely indicates a false positive of inhibition. Data from this procedure is reported as "P='numerical value' (nanomolar)"

Reagent B was Prepared by the Following Procedure.

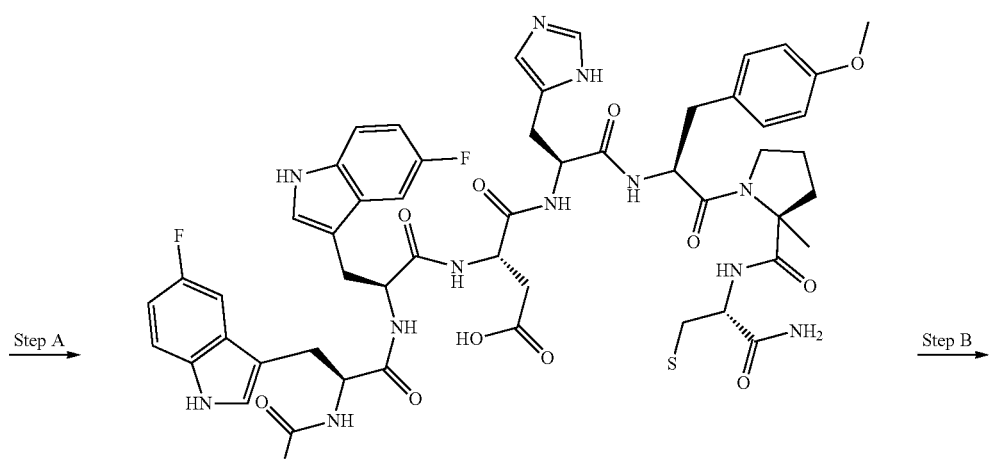

-continued
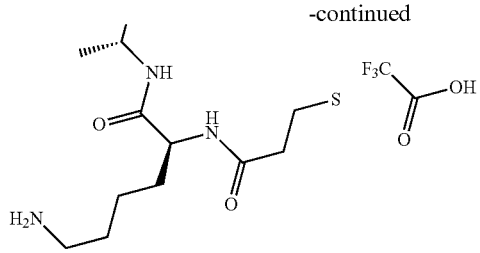
Int. A
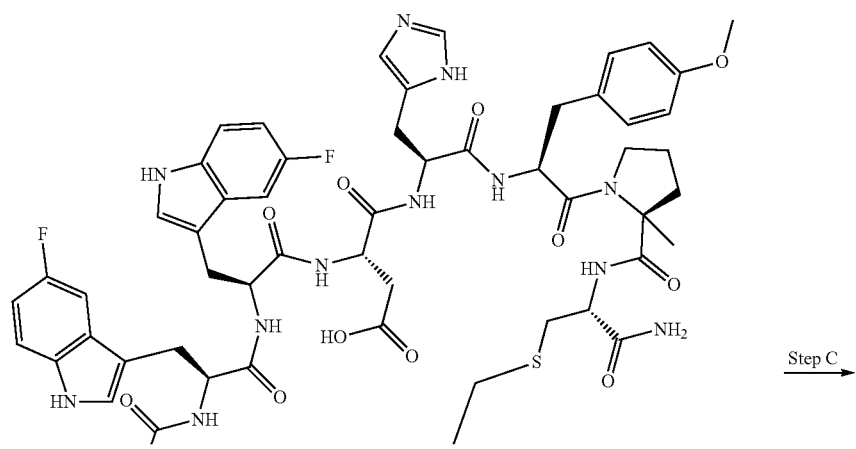
Step C
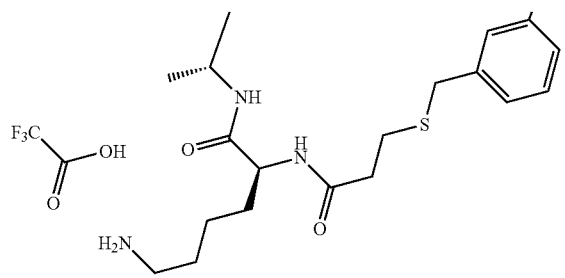
Int. B
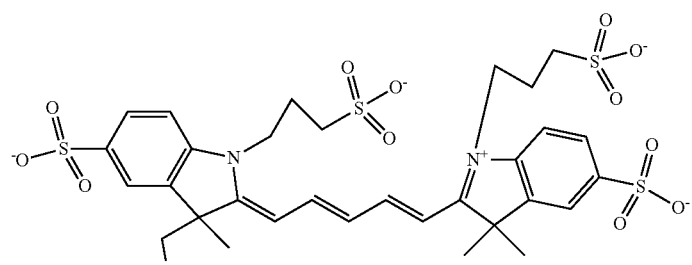

-continued

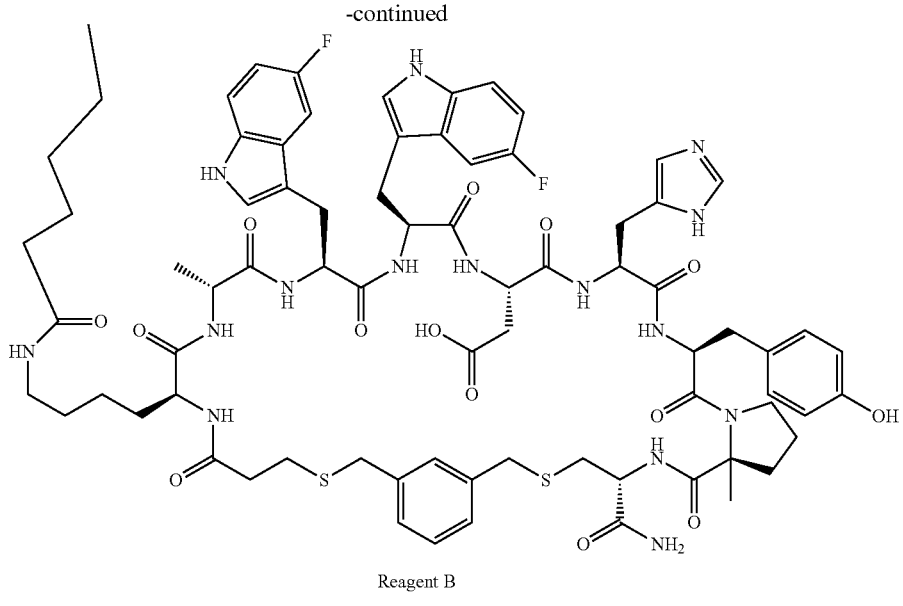

Reagent B

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol g$^{-1}$. The assembly was performed using single-couplings using 4eq of Fmoc protected amino acid 0.2M in DMF, 4 eq of 1M Oxyma in DMF, 4eq of 0.5M N,N-diisopropylcarbodiimide (DIC) (double coupling for Y01). Fmoc deprotection cycles were performed using 20% (V/V) piperidine in DMF.

The sequence of Fmoc protected amino acids and building blocks used are:
1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)-D-alanine
9. N$^2$-(((9H-fluoren-9-yl)methoxy)carbonyl)-N$^6$-(tert-butoxycarbonyl)-L-lysine
10. 3-(tritylthio)propanoic acid At the end of the assembly, the resin was washed with DMF, MeOH, DCM, Et$_2$O. The peptide was cleaved from solid support using 50 ml of TFA solution (v/v) (91% TFA, 5% H$_2$O, 4% TIPS) for approximately 1.5 hours, at room temperature. The resin was filtered, washed with TFA and solution concentrated to dryness and lyophilized. Lyophilization afforded Intermediate Compound Int. A (300 mg), which was used as crude in the next step. LCMS anal. calcd. C63H79F2N15O13S2: 1356.53, found: 1356.9 (M+1)+

Step B—Synthesis of Intermediate Compound Int-B

Crude Int-A (0.22 mmol) was dissolved in 24 ml of DMF. 6 ml of 1M aqueous solution of sodium bicarbonate was added to raise the pH to 7. Then 0.26 mmol of 1,3-bis(bromomethyl)benzene (0.1M in DMF) were added dropwise. Reaction was left under stirring at room temperature for 20 min, quenched with TFA (pH to 3-4) and then concentrated in vacuo to provide crude Int-B, which was purified by RP-HPLC (Waters XBridge, C18, 50×150 mm, □□m, 130 A; 25% to 40% ACN/water+0.1% TFA modifier over 20 min). Collected fractions were lyophilized to afford 35 mg of Intermediate Compound Int-B. LCMS anal. calcd. for C71H85F2N15O13S2: 1458.67; found: 1458.8 (M+1)$^+$

Step C—Synthesis of Compound Reagent B

Intermediate Compound Int-B (15 mg) was dissolved in 0.2 ml of dry DMSO. Then 15 mg of ALEXAFLUOR 647NHS Ester (A37566, Life technology) dissolved in 1.5 ml of dry DMSO were added. 20 uL of dry DIPEA were added. Reaction was left under stirring at room temperature for 12 h under Nitrogen atmosphere in the dark. Quenched with TFA (pH to 3-4) and purified by RP-HPLC (Dr Maish, Reprosil Gold C18, 250×20 mm, 120 Å, 10 μm; 20% to 35% of 0.1% TFA in ACN/0.1% TFA in H$_2$O, over 20 min, then 35% to 40% over 5 min at 20 mL/min flow rate). Collected fractions were lyophilized to afford 16.1 mg of Compound Reagent B. LCMS anal. for C107H126F2N17O26S6$^{3-}$: 2296.64; found: 1150.6 (M+2)$^{2+}$ Activity data obtained by one or both of the above-described procedures is reported for selected example compounds of the invention in the following format: Example No.: A (standard TR Fret)='numerical value'; P (Alexa Fret plus standard TR Fret)='numerical value'/, note that all values reported are nanomolar.

Alexa FRET Ultra TR-FRET

The PCSK9 Alexa FRET Ultra assay measures the interaction between PCSK9 and an AlexaFluor647 (AF) tagged cyclic peptide, Reagent B (K$_D$=0.99 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2, 0.01% BSA, and 0.01% Surfactant P20. A separate solution containing 1920 nM of the AlexaFluor tagged cyclic peptide is made in the same buffer system. An Echo is used to transfer 0.015 ul of compound plus 0.735 ul of DMSO to each well of an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 960 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the Ic50 and the $K_D$ of AF cyclic peptide. Counts (B-counts) of the europium-labeled PCSK9 are followed to observe if compounds are adversely affecting PCSK9. A fall off of the B-counts is likely indicates a false positive of inhibition. Data from this procedure is reported as "Ki Ultra='numerical value' (data reported is nanomolar)"

The following compounds were assessed using the protocol described above and the results are shown in Table 4.

TABLE 4

Activity Data for Examples of the Invention.

| Example | Alexa FRET Stdt TR-FRET, nM | Alexa FRET Plus TR-FRET, nM | Alexa FRET Ultra TR-FRET, nM |
|---|---|---|---|
| 1 | <1.26 | <0.006 | 0.007 |
| 2 | <1.26 | 0.014 | 0.006 |
| 3 | <1.26 | <0.006 | 0.005 |
| 4 | <1.26 | <0.006 | 0.003 |
| 5 | <1.26 | <0.006 | 0.007 |
| 6 | <1.26 | 0.009 | 0.012 |
| 7 | <1.26 | 0.008 | 0.013 |
| 8 | <1.26 | 0.016 | 0.008 |
| 9 | <1.26 | <0.006 | 0.007 |
| 10 | <1.26 | 0.008 | 0.006 |
| 11 | <1.26 | 0.007 | 0.006 |
| 12 | <1.26 | 0.014 | 0.007 |
| 13 | <1.26 | <0.006 | 0.003 |
| 14 | <1.26 | <0.006 | 0.005 |
| 15 | <1.26 | <0.006 | 0.005 |
| 16 | <1.26 | 0.014 | 0.008 |
| 17 | <1.26 | 0.016 | 0.018 |
| 18 | <1.26 | 0.023 | 0.021 |
| 19 | <1.26 | <0.006 | 0.001 |
| 20 | <1.26 | <0.006 | 0.001 |
| 21 | <1.26 | 0.010 | 0.001 |
| 22 | <1.26 | 0.015 | 0.004 |
| 23 | <1.26 | <0.006 | 0.007 |
| 24 | <1.26 | 0.009 | 0.018 |
| 25 | <1.26 | 0.006 | 0.009 |
| 26 | <1.26 | 0.006 | 0.008 |
| 27 | <1.26 | 0.014 | 0.006 |
| 28 | <1.26 | 0.013 | 0.010 |
| 29 | <1.26 | 0.011 | 0.013 |
| 30 | <1.26 | <0.006 | 0.004 |
| 31 | <1.26 | <0.006 | 0.006 |
| 32 | <1.26 | 0.009 | 0.011 |
| 33 | <1.26 | 0.014 | 0.016 |
| 34 | <1.26 | <0.006 | 0.003 |
| 35 | <1.26 | 0.007 | 0.009 |
| 36 | <1.26 | 0.044 | 0.016 |
| 37 | <1.26 | <0.006 | 0.006 |
| 38 | <1.26 | 0.013 | 0.012 |
| 39 | <1.26 | <0.006 | 0.003 |
| 40 | <1.26 | 0.008 | 0.004 |
| 41 | <1.26 | <0.006 | 0.005 |
| 42 | <1.26 | <0.006 | 0.010 |
| 43 | <1.26 | <0.006 | 0.002 |

TABLE 4-continued

Activity Data for Examples of the Invention.

| Example | Alexa FRET Stdt TR-FRET, nM | Alexa FRET Plus TR-FRET, nM | Alexa FRET Ultra TR-FRET, nM |
|---|---|---|---|
| 44 | <1.26 | <0.006 | 0.003 |
| 45 | <1.26 | <0.006 | 0.002 |
| 46 | <1.26 | <0.006 | 0.001 |
| 47 | <1.26 | <0.006 | 0.003 |
| 48 | <1.26 | <0.006 | 0.009 |
| 49 | <1.26 | <0.006 | 0.003 |
| 50 | <1.26 | <0.006 | 0.005 |
| 51 | <1.26 | 0.007 | 0.005 |
| 52 | <1.26 | <0.006 | 0.001 |
| 53 | <1.26 | 0.010 | 0.014 |
| 54 | <1.26 | 0.021 | 0.014 |
| 55 | <1.26 | 0.012 | 0.010 |
| 56 | <1.26 | <0.006 | 0.004 |
| 57 | <1.26 | 0.009 | 0.034 |
| 58 | <1.26 | 0.018 | 0.079 |
| 59 | <1.26 | 0.020 | 0.101 |
| 60 | <1.26 | 0.008 | 0.062 |
| 61 | <1.26 | 0.049 | 0.131 |
| 62 | <1.26 | <0.006 | 0.038 |
| 63 | <1.26 | <0.006 | 0.045 |
| 64 | <1.26 | 0.012 | 0.028 |
| 65 | <1.26 | <0.006 | 0.024 |
| 66 | <1.26 | 0.007 | 0.027 |
| 67 | <1.26 | <0.006 | 0.005 |
| 68 | <1.26 | <0.006 | 0.005 |

18. The method of claim 17, wherein the compound is:
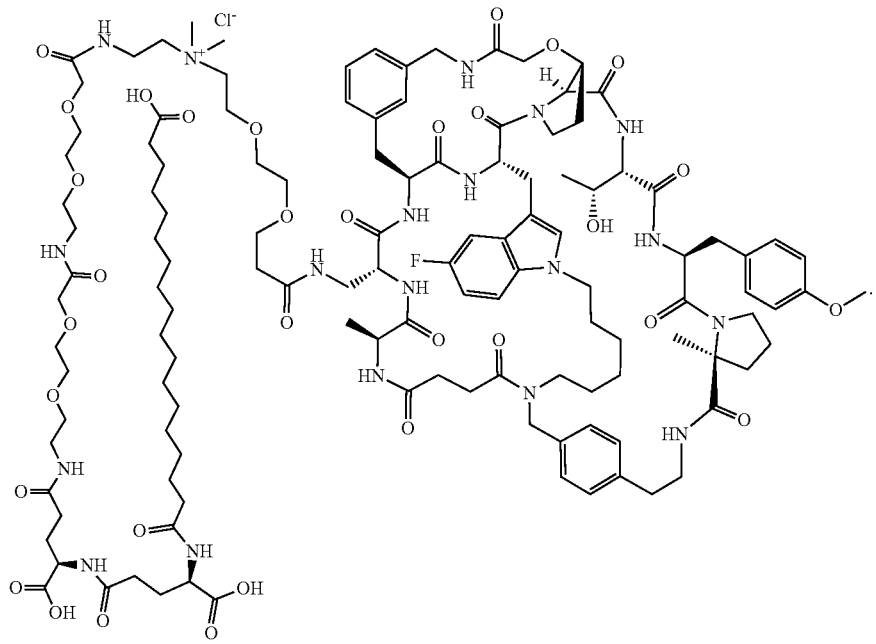

What is claimed is:

1. A method of treating hypercholesterolemia, comprising administering to a patient in need thereof a therapeutically effective amount of a compound of Formula A:

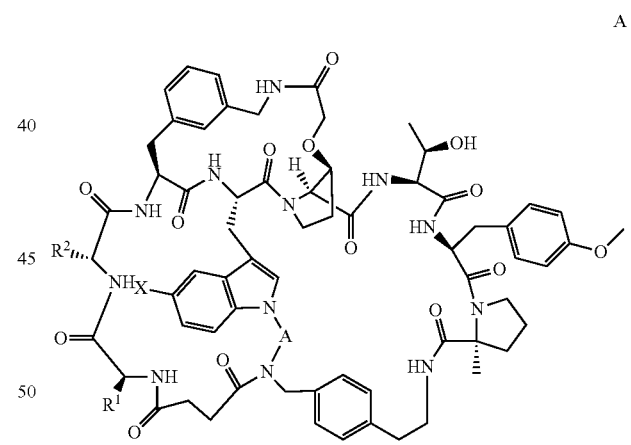

wherein:
X is H, F, Cl, or Br;
R is independently selected from H or $C_{1-6}$ alkyl;
$R^a$ is independently selected from H, —$CR_2$—$S(O)_2OR^9$, or —$C(O)OR^9$;
$R^b$ is independently selected from H, $C_{1-6}$ alkyl, or $C_{1-6}$ alkyl-$N^+(CH_3)_2$;
$R^d$ is independently selected from H or —$C(O)OR^9$;
$R^1$ is selected from:
(a) —H,
(b) $C_{1-6}$ alkyl,
(c) —$(CR_2)_z$—$NR^b$—$C(O)R^{10}$, and
(d) —$(CR_2)_z$—NR—C(O)—$(CR_2)_z[O(CR_2)_n]$—$N^+$ $(CH_3)_3$;

$R^2$ is selected from:
(a) —H
(b) $C_{1-6}$ alkyl,
(c) —$(CR_2)_z$—$NR^b$—$C(O)R^{10}$, and
(d) —$(CR_2)_z$—NR—C(O)—$(CR_2)_z[O(CR_2)_n]$—$N^+(CH_3)_3$;

provided that at least one of $R^1$ and $R^2$ is —$(CR_2)_z$—$NR^b$—$C(O)R^{10}$;

$R^4$ is

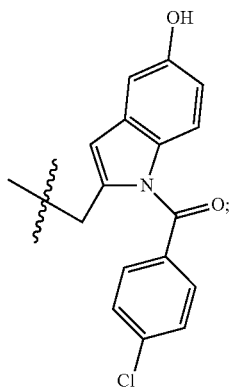 [SMILES: *Cc1cc2cc(O)ccc2n1C(=O)c1ccc(Cl)cc1]

$R^5$ is independently selected from —$(CR^a_2)_x$, —$(CR^a_2)_xO(CR^a_2)_x$—, and $C_{1-8}$ alkyl;

$R^6$ is independently selected from —$(CR^a_2)_x$NRC(O)—, —$(CR_2)_x$NRS(O)$_2$—, and —$(CR^a_2)_nO(CR^a_2)_q$NRC(O)—;

$R^9$ is independently selected from H or $C_{1-6}$ alkyl;

$R^{10}$ is independently selected from:
a) —$(R^5$—$N^+(CH_3)_2$—$R^6)_u$—$(R^{20})_n$—$(R^6)_m$—$R^{12}$,
b) —$(R^{20})_n$—$(R^6)_m$—$R^5$—$N^+(CH_3)_2$—$R^6$—$R^{12}$,
c) —$(R^{20})_n$—$R^5$—$N^+(CH_3)_2$—$(R^{20})_s$—$(R^6)_q$—$R^{12}$,
d) —$R^6$—$R^{20}$—$N^+(CH_3)_2$—$(R^{20})_n$—$(R^6)_m$—$R^{12}$,
e) —$R^{20}$—$N^+(CH_3)_2$—$(R^6)_m$—$(R^{20})_n$—$(R^6)_q$—$R^{12}$,
f) —$(R^{20})_n$—$(R^6)_m$—$R^{12}$,
g) —$R^5$—$N^+(CH_3)_2$—$(R^{20})_n$—$(R^6)_m$—$R^5$—$[NRC(O)$—$R^5]_q$,
h) —$R^{20}$—$N^+(CH_3)_2$—$(R^6)_m$—$R^5$,
i) —$R^5$—$N^+(CH_3)_2$—$(R^{20})_n$—$(R^6)_m$—$R^5$,
j) —$R^5$—$N^+(CH_3)_2$—$(R^{20})_n$—$(R^6)_m$—$R^{12}$,
k) —$(R^{20})_n$—$N^+(CH_3)_2$—$(R^{20})_n$—$(R^6)_q$—$R^{12}$,
l) —$R^6$—$R^5$—$N^+(CH_3)_2$—$(R^{20})_n$—$(R^6)_q$—$R^{12}$,
m) —$(R^{20})_n$—$N^+(CH_3)_2$—$(R^6)_q$—$R^{12}$,
n) —$(R^{20})_n$—$(R^6)_m$—$R^{20}$—$N^+(CH_3)_2$—$(R^{20})_s$—$(R^6)_q$—$R^{12}$,
o) —$R^{20}$—$N^+(CH_3)_2$—$(R^6)_m$—$R^4$,
p) —$(R^{20})_n$—$N^+(CH_3)_2$—$(R^6)_q$—$(R^{20})_n$—$(R^6)_m$—$R^{12}$,
q) —$R^{20}$—$N^+(CH_3)_2$—$(R^6)_m$—$(R^{20})_n$—$N^+(CH_3)_2$—$(R^{20})_n$—$(R^6)_q$—$R^{12}$,
r) —$R^5$—$N^+(CH_3)_2$—$(R^6)_m$—$R^5$—$N^+(CH_3)_2$—$(R^{20})_n$—$(R^6)_q$—$R^{12}$, and
s) —$CR^b_2$—$(R^{20})_n$—$(R^6)_m$—$R^{12}$;

$R^{12}$ is independently selected from —$C_{11-20}$ alkyl-$R^d$, —$(CR_2)_x$—O—$(CR_2)_x$—$R^d$, —$C_{11-20}$ alkyl-C(O)NR—$(CR^d_2)_2$H, and $C_{2-16}$ alkenyl;

$R^{20}$ is independently selected from
a) —$(CR^a_2)_tO(CR^a_2)_qO$—$(CR^a_2)_t$—,
b) —$(CR^a_2)_tO(CR^a_2)_qO$—$(CR^a_2)_t$—NRC(O)—,
c) —$(CR^a_2)_tO(CR^a_2)_q$—NRC(O)—$(CR^a_2)_n$O$(CR^a_2)_n$O—,
d) —$(CR^a_2)_t$—NRC(O)—$(CR^a_2)_qO(CR^a_2)_qO$—$(CR^a_2)_t$—,
e) —$(CR^a_2)_tO(CR^a_2)_qO$—$(CR^a_2)_t$—, and
f) —$(CR^a_2)_t$—O—$(CR^a_2)_qO(CR^a_2)_qO$—$(CR^a_2)_t$—;

A is selected from $C_{2-6}$ alkyl or $C_{2-6}$ alkenyl;
m is independently selected from 0, 1, 2, 3, or 4;
n is independently selected from 1, 2, or 3;
q is independently selected from 1, 2, 3, or 4;
r is independently selected from 0, 1, 2, 3, or 4;
s is independently selected from 0, 1, 2, or 3;
t is independently selected from 0, 1, 2, or 3;
u is 1 or 2;
x is independently selected from 1, 2, 3, 4, 5, 6, 7, or 8;
z is independently selected from 1, 2, 3, 4, 5, or 6;
or a pharmaceutically acceptable salt of any thereof.

2. The method of claim 1, wherein the compound has a structure of Formula I:

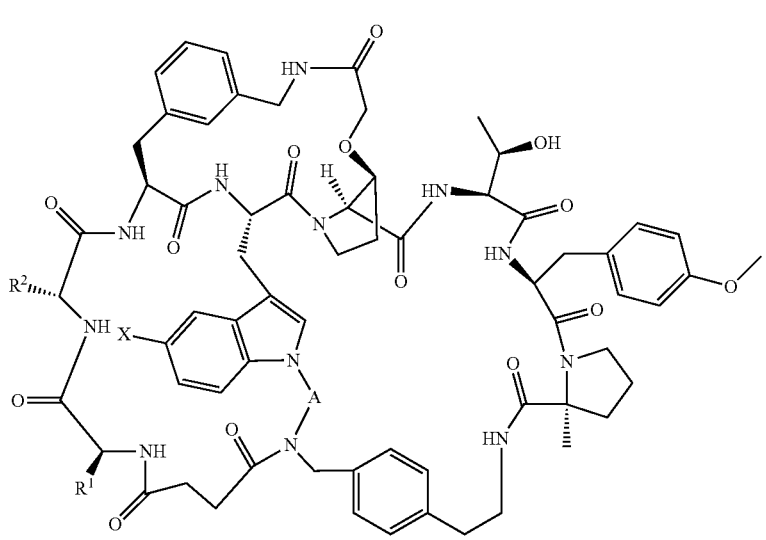

I wherein:
X is H, F, Cl or Br;
R is independently selected from H or $C_{1-6}$ alkyl;
$R^a$ is independently selected from H or $-C(O)OR^9$;
$R^b$ is independently selected from H, $C_{1-6}$ alkyl, or $C_{1-6}$ alkyl-$N^+(CH_3)_2$;
$R^d$ is independently selected from H or $-C(O)OR^9$;
$R^1$ is selected from:
  (a) $-H$,
  (b) $C_{1-6}$ alkyl,
  (c) $-(CR_2)_z-NR^b-C(O)R^{10}$, and
  (d) $-(CR_2)_z-NR-C(O)-(CR_2)_z[O(CR_2)_n]_t-N^+(CH_3)_3$;
$R^2$ is selected from:
  (a) $-H$,
  (b) $C_{1-6}$ alkyl,
  (c) $-(CR_2)_z-NR^b-C(O)R^{10}$, and
  (d) $-(CR_2)_z-NR-C(O)-(CR_2)_z[O(CR_2)_n]_t-N^+(CH_3)_3$;
provided that at least one of $R^1$ and $R^2$ is $-(CR_2)_z-NR^b-C(O)R^{10}$;
$R^4$ is

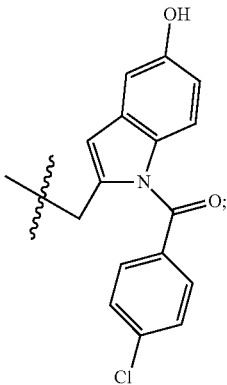 [SMILES: *Cc1cc2cc(O)ccc2n1C(=O)c1ccc(Cl)cc1]

$R^5$ is independently selected from $-(CR^a_2)_x$, $-(CR^a_2)_xO(CR^a_2)_x-$, and $C_{1-8}$ alkyl;
$R^6$ is independently selected from $-(CR^a_2)_xNRC(O)-$, $-(CR_2)_xNRS(O)_2-$, and $(CR^a_2)_nO(CR^a_2)_qNRC(O)-$;
$R^9$ is independently selected from H or $C_{1-6}$ alkyl;
$R^{10}$ is independently selected from:
  a) $-(R^5-N^+(CH_3)_2-R^6)_u-(R^{20})_n-(R^6)_m-R^{12}$,
  b) $-(R^{20})_n-(R^6)_m-R^5-N^+(CH_3)_2-R^6-R^{12}$,
  c) $-(R^{20})_n-R^5-N^+(CH_3)_2-(R^{20})_s-(R^6)_q-R^{12}$,
  d) $-R^6-R^{20}-N^+(CH_3)_2-(R^{20})_n-(R^6)_m-R^{12}$,
  e) $-R^{20}-N^+(CH_3)_2-(R^6)_m-(R^{20})_n-(R^6)_q-R^{12}$,
  f) $-(R^{20})_n-(R^6)_m-R^{12}$,
  g) $-R^5-N^+(CH_3)_2-(R^{20})_n-(R^6)_m-R^5-[NRC(O)-R^5]_q$,
  h) $-R^{20}-N^+(CH_3)_2-(R^6)_m-R^5$,
  i) $-R^5-N^+(CH_3)_2-(R^{20})_n-(R^6)_m-R^5$,
  j) $-R^5-N^+(CH_3)_2-(R^{20})_n-(R^6)_m-R^{12}$,
  k) $-(R^{20})_n-N^+(CH_3)_2-(R^{20})_n-(R^6)_q-R^{12}$,
  l) $-R^6-R^5-N^+(CH_3)_2-(R^{20})_n-(R^6)_q-R^{12}$,
  m) $-(R^{20})_n-N^+(CH_3)_2-(R^6)_q-R^{12}$,
  n) $-(R^{20})_n-(R^6)_m-R^{20}-N^+(CH_3)_2-(R^{20})_s-(R^6)_q-R^{12}$,
  o) $-R^{20}-N^+(CH_3)_2-(R^6)_m-R^4$,
  p) $-(R^{20})_n-N^+(CH_3)_2-(R^6)_q-(R^{20})_n-(R^6)_m-R^{12}$,
  q) $-R^{20}-N^+(CH_3)_2-(R^6)_m-(R^{20})_n-N^+(CH_3)_2-(R^{20})_n-(R^6)_q-R^{12}$,
  r) $-R^5-N^+(CH_3)_2-(R^6)_m-R^5-N^+(CH_3)_2-(R^{20})_n-(R^6)_q-R^{12}$, and
  s) $-CR^b_2-(R^{20})_n-(R^6)_m-R^{12}$;
$R^{12}$ is independently selected from $-C_{11-20}$ alkyl-$R^d$, $-(CR_2)_x-O-(CR_2)_x-R^d$, $-C_{11-20}$ alkyl-$C(O)NR-(CR^d_2)_2H$, and $C^{2-16}$ alkenyl;
$R^{20}$ is independently selected from
  a) $-(CR^a_2)_tO(CR^a_2)_qO-(CR^a_2)_t-$,
  b) $-(CR^a_2)_tO(CR^a_2)_qO-(CR^a_2)_t-NRC(O)-$,
  c) $-(CR^a_2)_tO(CR^a_2)_q-NRC(O)-(CR^a_2)_nO(CR^a_2)_nO-$,
  d) $-(CR^a_2)_t-NRC(O)-(CR^a_2)_qO(CR^a_2)_qO-(CR^a_2)_t-$,
  e) $-(CR^a_2)_tO(CR^a_2)_qO-(CR^a_2)_t-$, and
  f) $-(CR^a_2)_t-O-(CR^a_2)_qO(CR^a_2)_qO-(CR^a_2)_t-$;
A is selected from $C_{2-6}$ alkyl or $C_{2-6}$ alkenyl;
m is independently selected from 0, 1, 2, 3 or 4;
n is independently selected from 1, 2 or 3;
q is independently selected from 1, 2, 3 or 4;
r is independently selected from 0, 1, 2, 3 or 4;
s is independently selected from 0, 1, 2 or 3;
t is independently selected from 0, 1, 2 or 3;
u is 1 or 2;
x is independently selected from 1, 2, 3, 4, 5, 6, 7, or 8;
z is independently selected from 1, 2, 3, 4, 5 or 6;
or a pharmaceutically acceptable salt of any thereof.

3. The method of claim 2,
wherein
X is F;
R is independently selected from H or $C_{1-6}$ alkyl;
$R^a$ is independently selected from H or $-C(O)OR^9$;
$R^b$ is independently selected from H, $C_{1-6}$ alkyl, or $C_{1-6}$ alkyl-$N^+(CH_3)$ 2;
$R^d$ is independently selected from H or $-C(O)OR^9$;
$R^1$ is selected from:
  (a) H,
  (b) $C_{1-6}$ alkyl, and
  (c) $-(CR_2)_z-NR^b-C(O)R^{10}$;
$R^2$ is selected from:
  (a) $C_{1-6}$ alkyl, and
  (b) $-(CR_2)_z-NR^b-C(O)R^{10}$;
provided that at least one of $R^1$ and $R^2$ is $-(CR_2)_z-NR^b-C(O)R^{10}$;
$R^4$ is

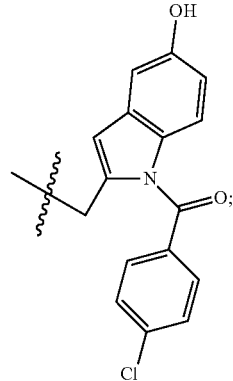 [SMILES: *Cc1cc2cc(O)ccc2n1C(=O)c1ccc(Cl)cc1]

$R^5$ is independently selected from $-(CR^a_2)_x$, $-(CR^a_2)_xO(CR^a_2)_x-$, and $C_{1-8}$ alkyl;

$R^6$ is independently selected from —$(CR^a_2)_x$NRC(O)— and —$(CR^a_2)_n$O$(CR^a_2)_q$NRC(O)—;

$R^9$ is independently selected from H or $C_{1-6}$ alkyl;

$R^{10}$ is selected from:
a) —$(R^5$—$N^+(CH_3)_2$—$R^6)_u$—$(R^{20})_n$—$(R^6)_m$—$R^{12}$,
b) —$(R^{20})_n$—$(R^6)_m$—$R^5$—$N^+(CH_3)_2$—$R^6$—$R^{12}$,
c) —$(R^{20})_n$—$R^5$—$N^+(CH_3)_2$—$(R^{20})_s$—$(R^6)_q$—$R^{12}$,
d) —$R^6$—$R^{20}$—$N^+(CH_3)_2$—$(R^{20})_n$—$(R^6)_m$—$R^{12}$,
e) —$R^{20}$—$N^+(CH_3)_2$—$(R^6)_m$—$(R^{20})_n$—$(R^6)_g$—$R^{12}$,
f) —$(R^{20})_n$—$(R^6)_m$—$R^{12}$,
g) —$R^5$—$N^+(CH_3)_2$—$(R^{20})_n$—$(R^6)_m$—$R^5$—[NRC(O)—$R^5]_q$,
h) —$R^{20}$—$N^+(CH_3)_2$—$(R^6)_m$—$R^5$,
i) —$R^5$—$N^+(CH_3)_2$—$(R^{20})_n$—$(R^6)_m$—$R^5$,
j) —$R^5$—$N^+(CH_3)_2$—$(R^{20})_n$—$(R^6)_m$—$R^{12}$,
k) —$(R^{20})_n$—$N^+(CH_3)_2$—$(R^{20})_n$—$(R^6)_q$—$R^{12}$,
l) —$R^6$—$R^5$—$N^+(CH_3)_2$—$(R^{20})_n$—$(R^6)_q$—$R^{12}$,
m) —$(R^{20})_n$—$N^+(CH_3)_2$—$(R^6)_q$—$R^{12}$,
n) —$(R^{20})_n$—$(R^6)_m$—$R^{20}$—$N^+(CH_3)_2$—$(R^{20})_s$—$(R^6)_q$—$R^{12}$,
o) —$R^{20}$—$N^+(CH_3)_2$—$(R^6)_m$—$R^4$,
p) —$(R^{20})_n$—$N^+(CH_3)_2$—$(R^6)_q$—$(R^{20})_n$—$(R^6)_m$—$R^{12}$,
q) —$R^{20}$—$N^+(CH_3)_2$—$(R^6)_m$—$(R^{20})_n$—$N^+(CH_3)_2$—$(R^{20})_n$—$(R^6)_q$—$R^{12}$,
r) —$R^5$—$N^+(CH_3)_2$—$(R^6)_m$—$R^5$—$N^+(CH_3)_2$—$(R^{20})_n$—$(R^6)_q$—$R^{12}$, and
s) —$CR^b_2$—$(R^{20})_n$—$(R^6)_m$—$R^{12}$;

$R^{12}$ is independently selected from —$C_{11-20}$ alkyl-$R^d$, —$(CR_2)_x$—O—$(CR_2)_x$—$R^d$, and —$C_{11-20}$ alkyl-C(O)NR—$(CR^d_2)_2$H;

$R^{20}$ is independently selected from
a) —$(CR^a_2)_t$O$(CR^a_2)_n$O—$(CR^a_2)_t$—,
b) —$(CR^a_2)_t$O$(CR^a_2)_n$O—$(CR^a_2)_t$—NRC(O)—,
c) —$(CR^a_2)_t$O$(CR^a_2)_n$—NRC(O)—$(CR^a_2)_n$O$(CR^a_2)_n$O—,
d) —$(CR^a_2)_t$—NRC(O)—$(CR^a_2)_n$O$(CR^a_2)_n$O—$(CR^a_2)_t$—,
e) —$(CR^a_2)_t$O$(CR^a_2)_n$O—,
f) —$(CR^a_2)_t$—O—$(CR^a_2)_n$O$(CR^a_2)_n$O—$(CR^a_2)_t$—, A is $C_{2-6}$ alkyl;
m is independently selected from 0, 1, 2, 3 or 4;
n is independently selected from 1, 2 or 3;
q is independently selected from 1, 2, 3 or 4;
r is independently selected from 0, 1, 2, 3 or 4;
s is independently selected from 0, 1 or 2;
t is independently selected from 0, 1, 2 or 3;
u is 1 or 2;
x is independently selected from 1, 2, 3, 4, 5, 6, 7, or 8;
z is independently selected from 1, 2, 3, 4, 5 or 6;
or a pharmaceutically acceptable salt of any thereof.

4. The method of claim 3, where the compound has the structure of Formula IA:

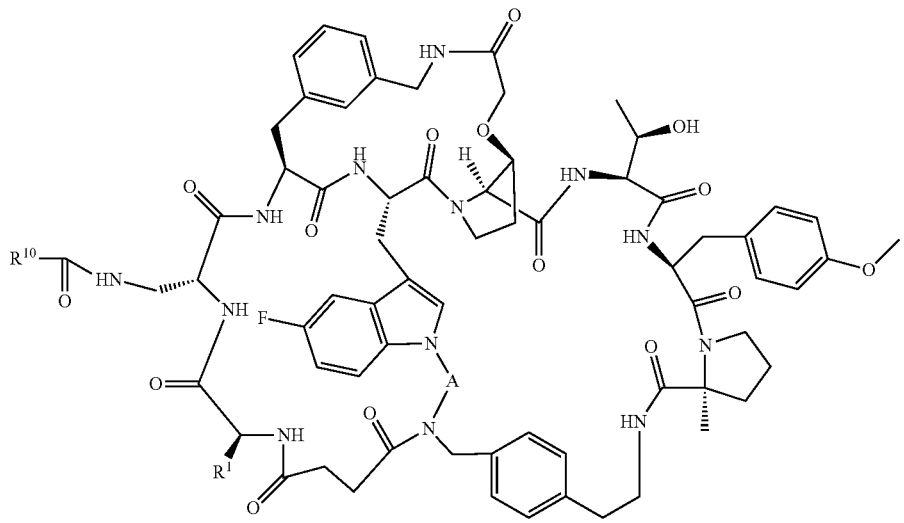

or a pharmaceutically acceptable salt thereof.

5. The method of claim 3, wherein the compound has the structure of Formula II:

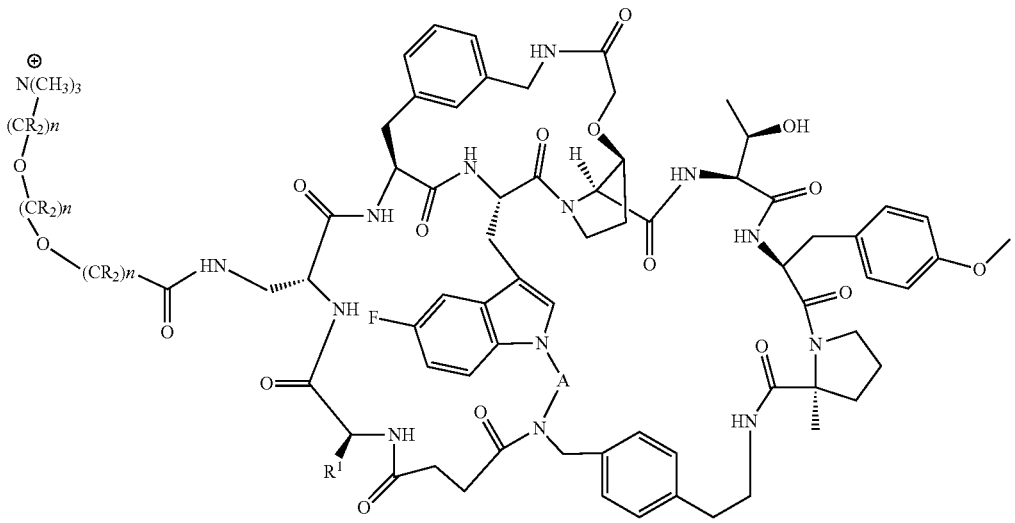

wherein
R¹ is —(CR₂)_z—NR^b—C(O)R¹⁰,
or a pharmaceutically acceptable salt thereof.

6. The method of claim 3, wherein the compound has the structure of Formula IIA:

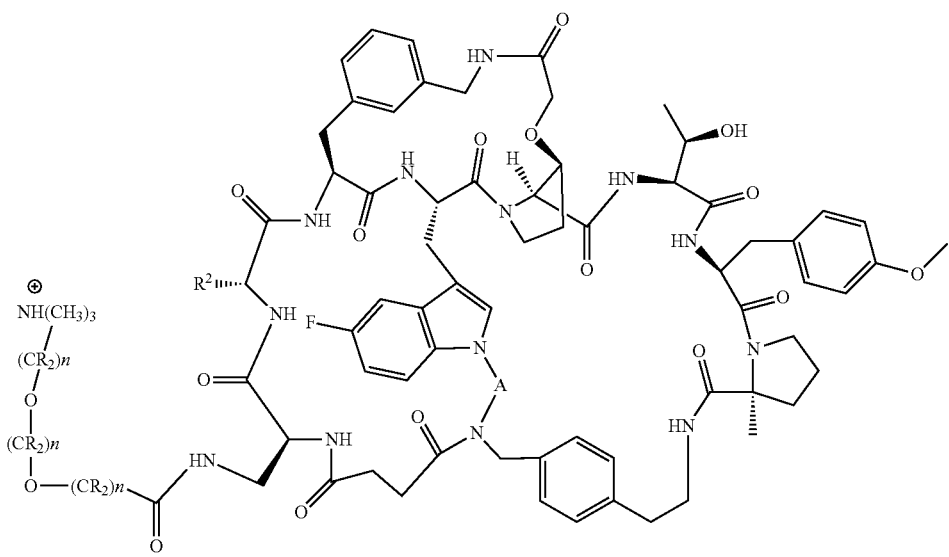

wherein
R² is —(CR₂)_z—NR^b—C(O)R¹⁰,
or a pharmaceutically acceptable salt thereof.

7. The method of claim 2, wherein R⁶ is (CR^a₂)_xNRC(O)—,
or a pharmaceutically acceptable salt thereof.

8. The method of claim 2, wherein R¹⁰ is selected from
a) —R⁶—R²⁰—N⁺(CH₃)₂—(R²⁰)_n—(R⁶)_m—R¹²,
b) —R²⁰—N⁺(CH₃)₂—(R⁶)_m—(R²⁰)_n—(R⁶)_q—R¹²,
c) —(R²⁰)_n—(R⁶)_m—R¹²,
d) —R⁵—N⁺(CH₃)₂—(R²⁰)_n—(R⁶)_m—R¹²,
e) —(R²⁰)_n—N⁺(CH₃)₂—(R²⁰)_n—(R⁶)_q—R¹²,
f) —(R²⁰)_n—N⁺(CH₃)₂—(R⁶)_q—R¹², and
g) —(R²⁰)_n—(R⁶)_m—R²⁰—N⁺(CH₃)₂—(R²⁰)_s—(R⁶)_q—R¹², or a pharmaceutically acceptable salt thereof.

9. The method of claim 1, wherein the compound is selected from the group consisting of:

| Ex No | Structure |
|---|---|
| Ex-1* | 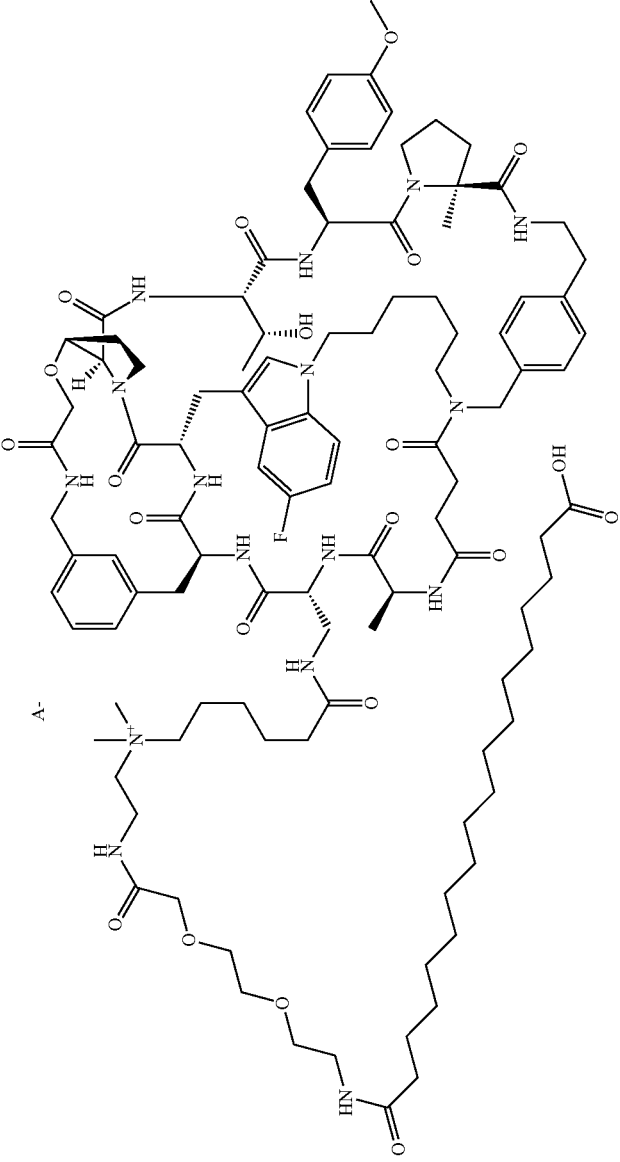 |

| Ex No | Structure |
|---|---|
| Ex-2* | 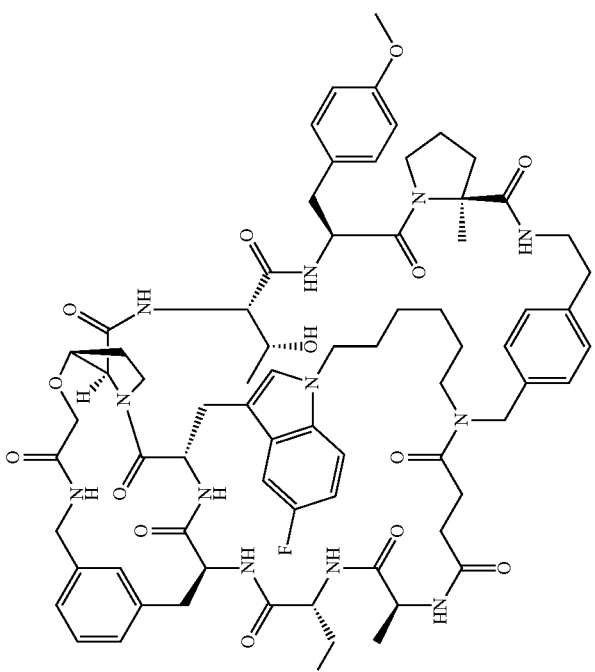 |

| Ex No | Structure |
|---|---|
| Ex-3* | 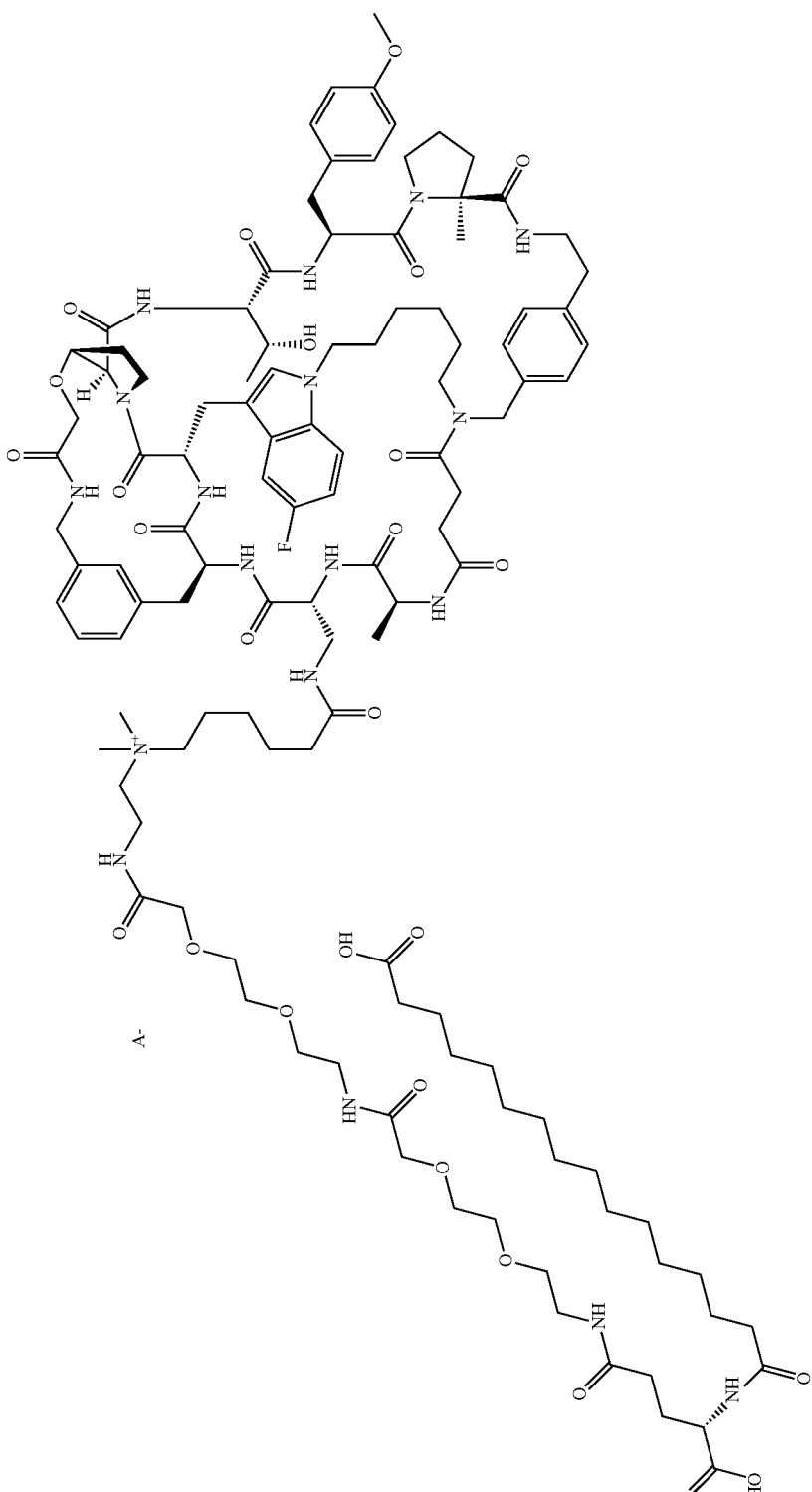 |

| Ex No | Structure |
|---|---|
| Ex-4* | A- (chemical structure) |

| Ex No | Structure |
|---|---|
| Ex-5* | 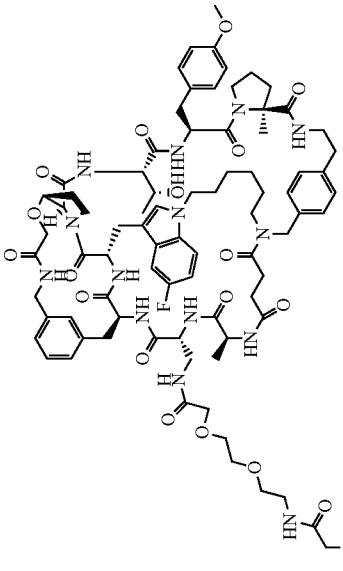 |

| Ex No | Structure |
|---|---|
| Ex-6* | 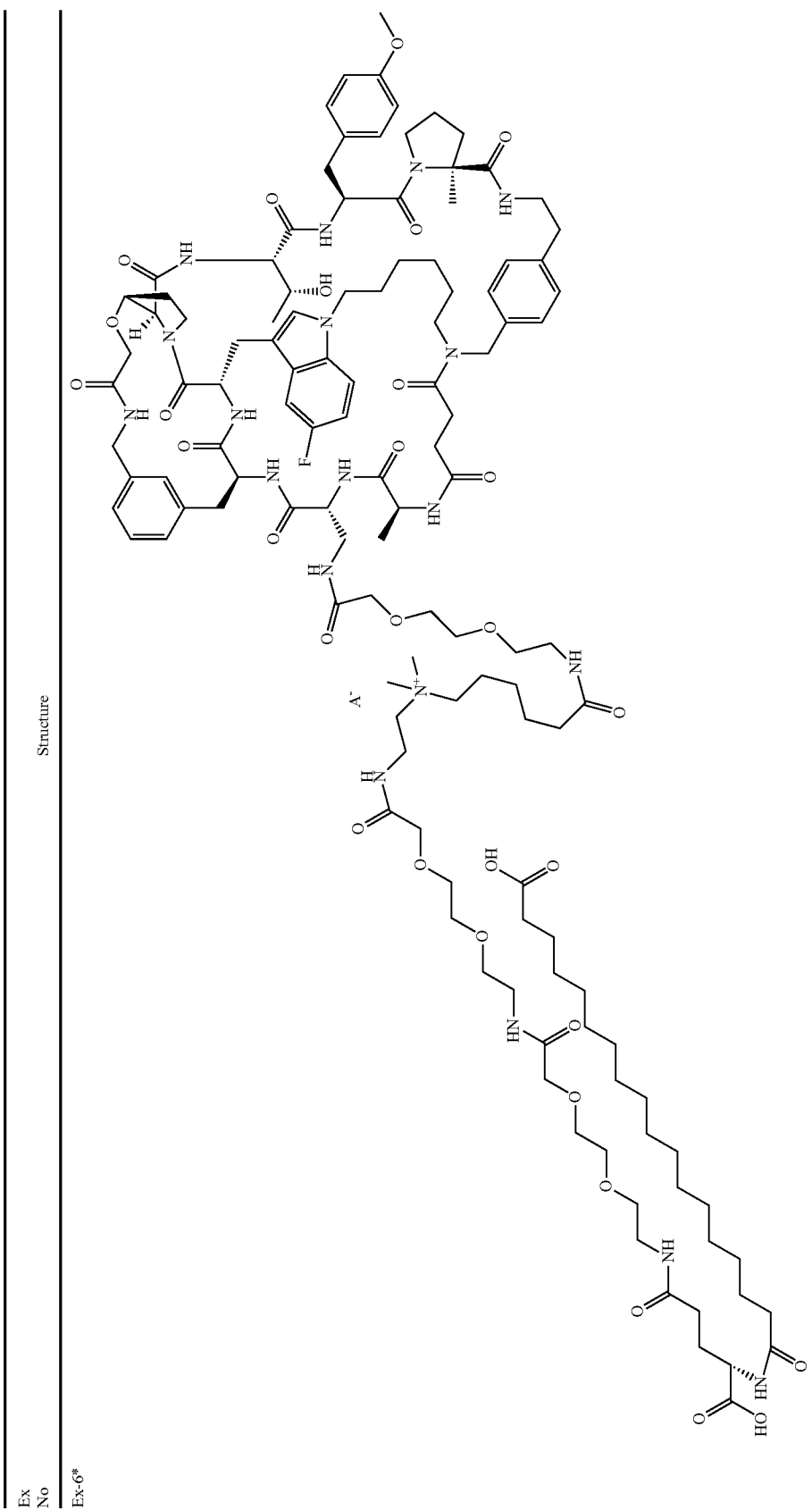 |

| Ex No | Structure |
|---|---|
| Ex-7* | 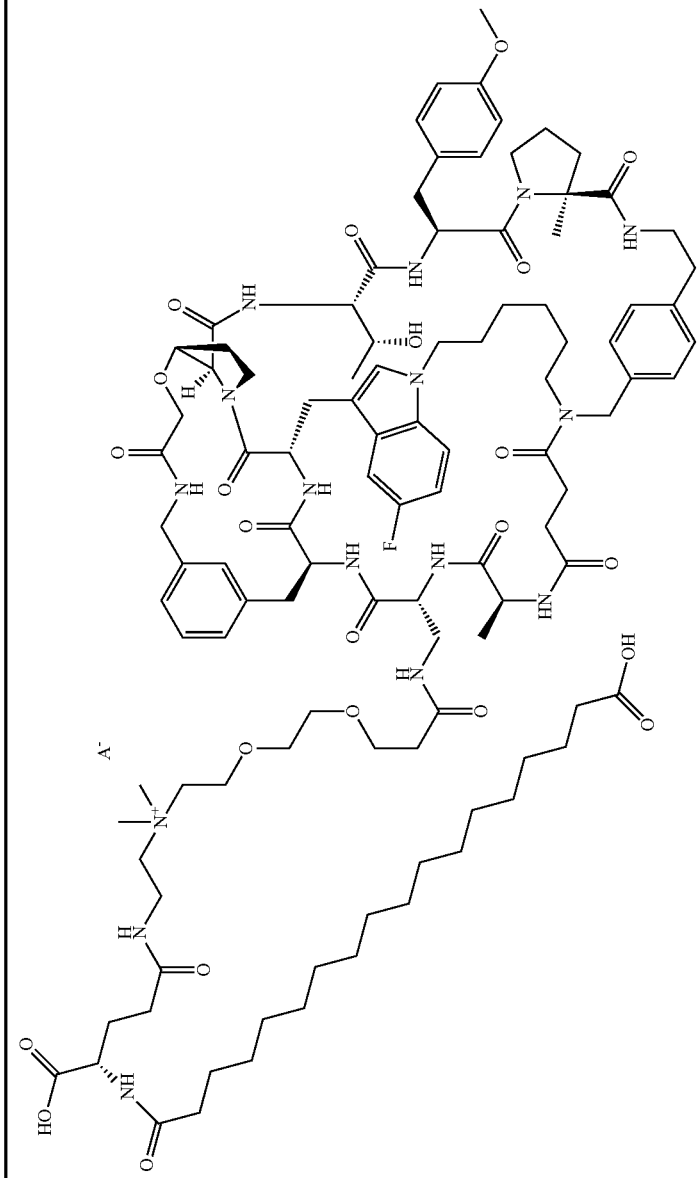 |

| Ex No | Structure |
|---|---|
| Ex-8* | 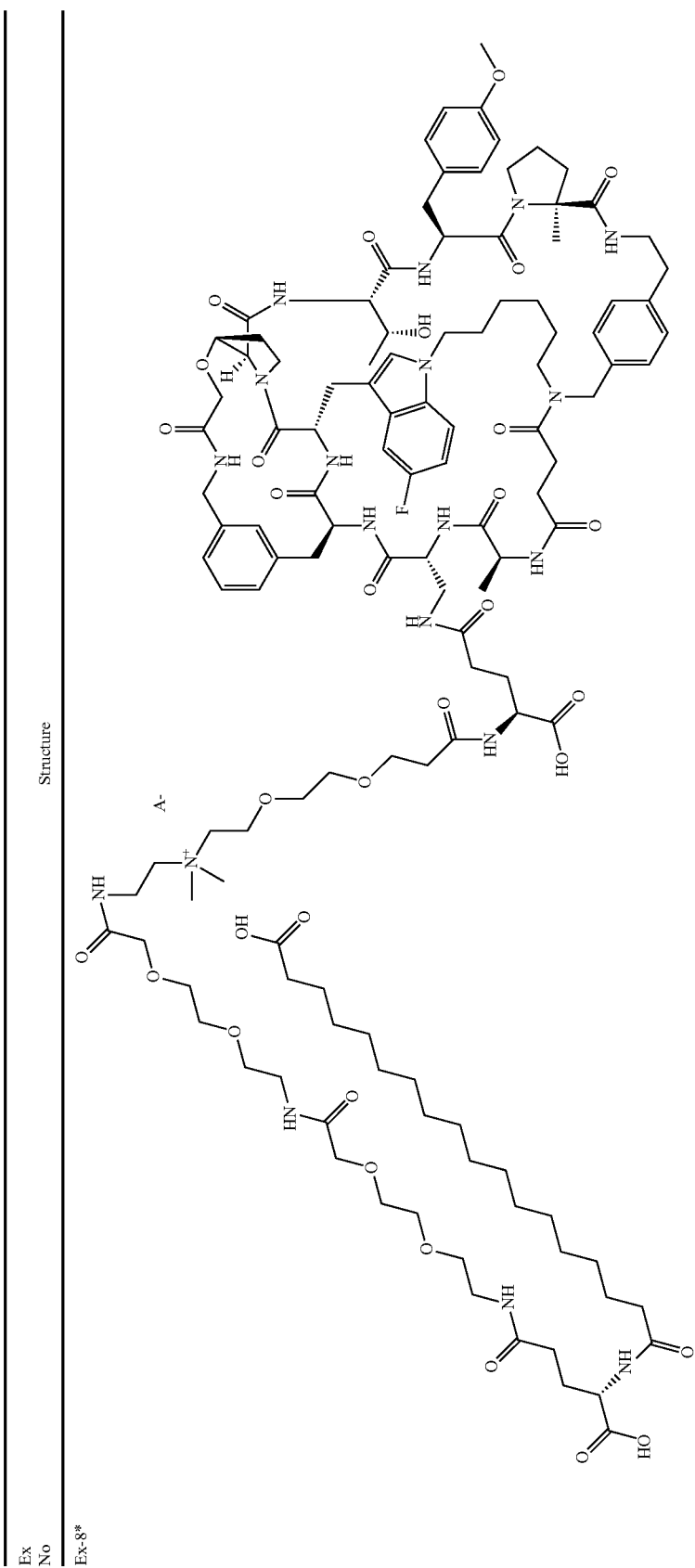 |

| Ex No | Structure |
|---|---|
| Ex-9* | 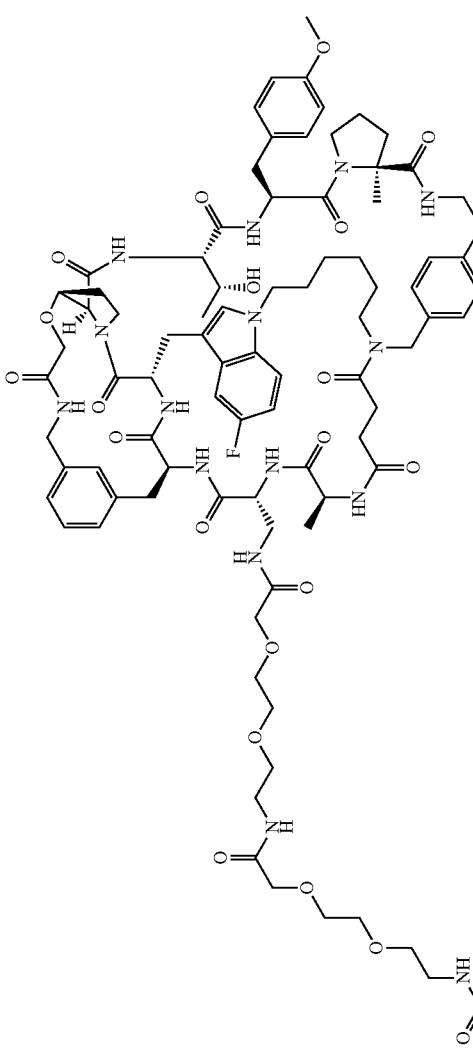 |

| Ex No | Structure |
|---|---|
| Ex-10* | 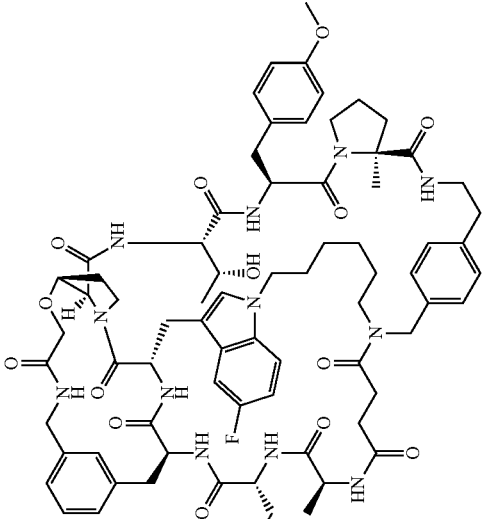 |

-continued
| Ex No | Structure |
|---|---|
| Ex-11* | 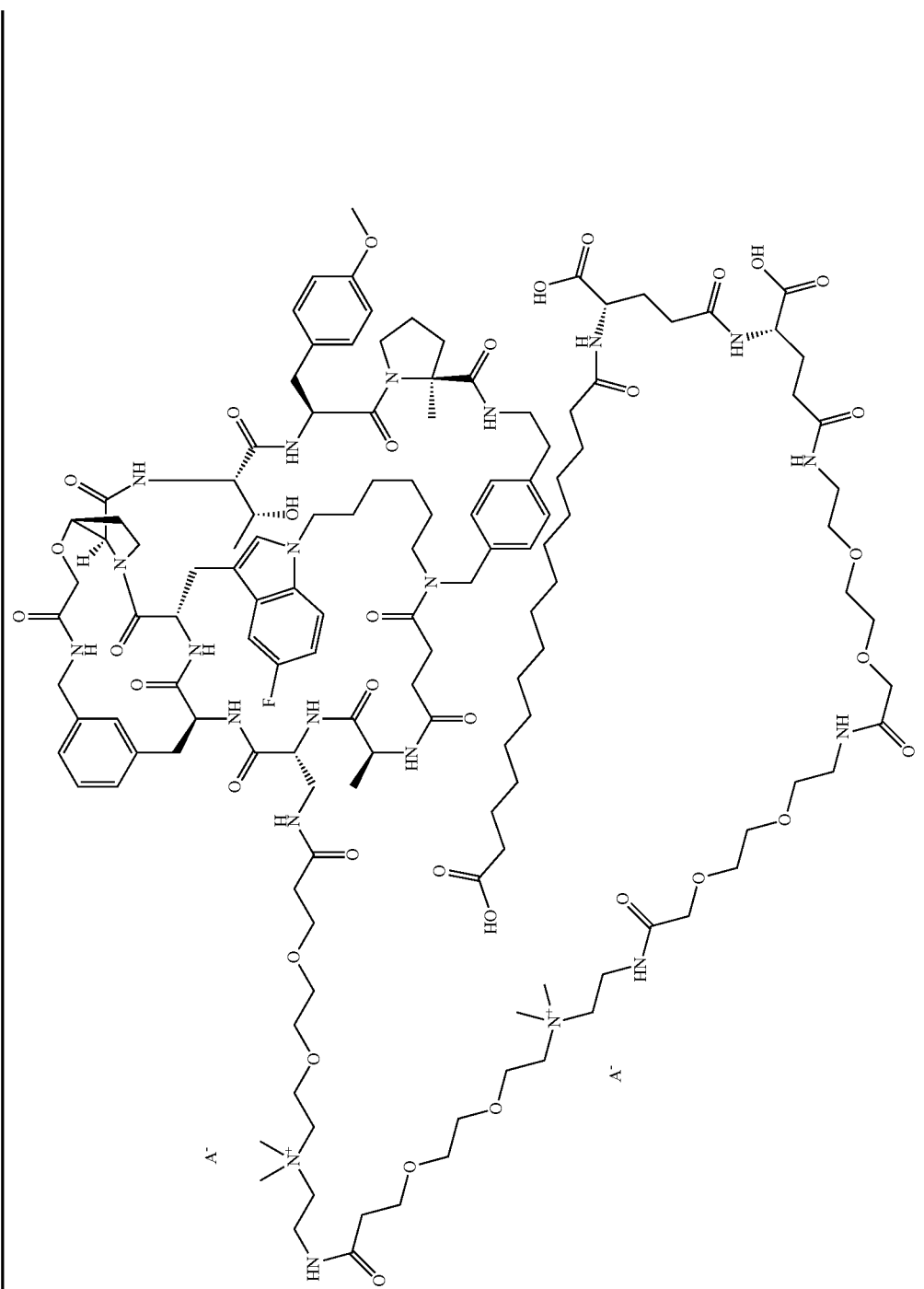 |

-continued
| Ex No | Structure |
|---|---|
| Ex-12* | 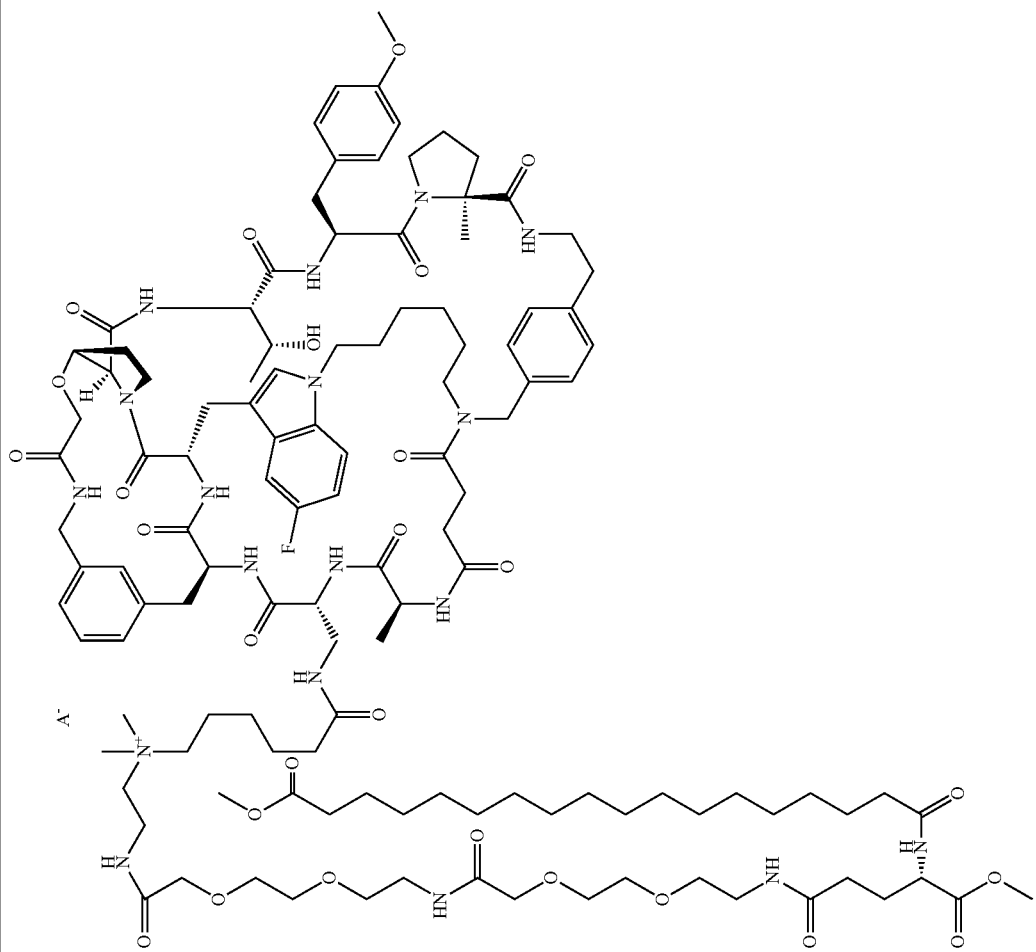 |

-continued
| Ex No | Structure |
|---|---|
| Ex-13* | 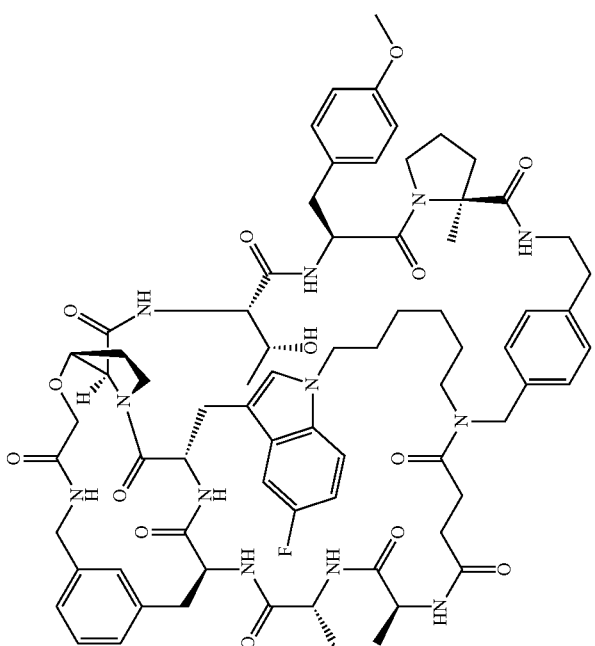 |

-continued
| Ex No | Structure |
|---|---|
| Ex-14* | 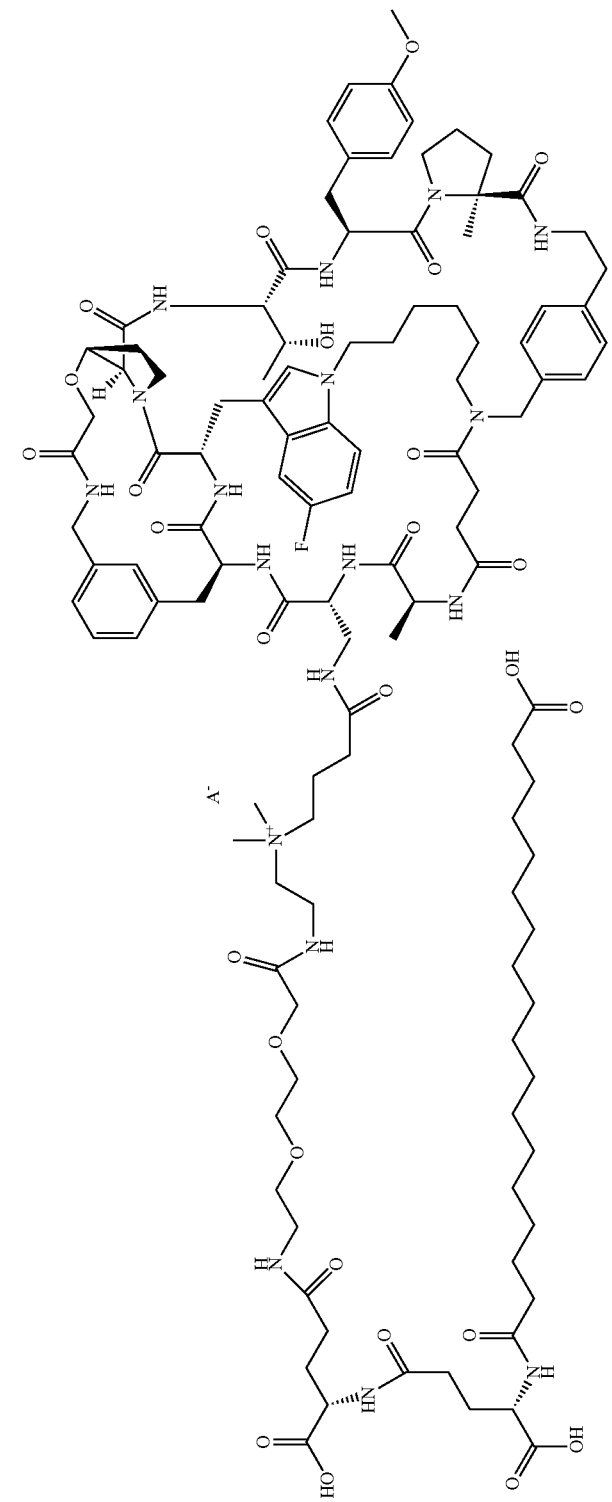 |

| Ex No | Structure |
|---|---|
| Ex-15* | 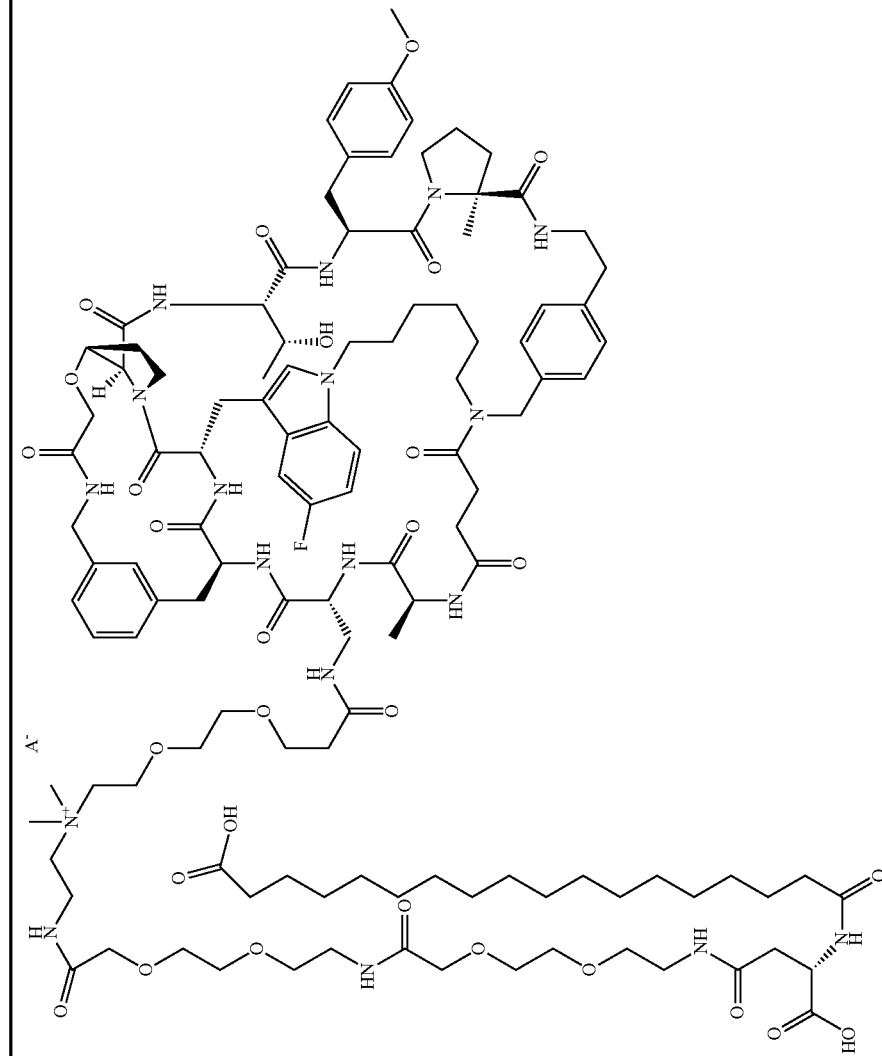 |

-continued
| Ex No | Structure |
|---|---|
| Ex-16* | 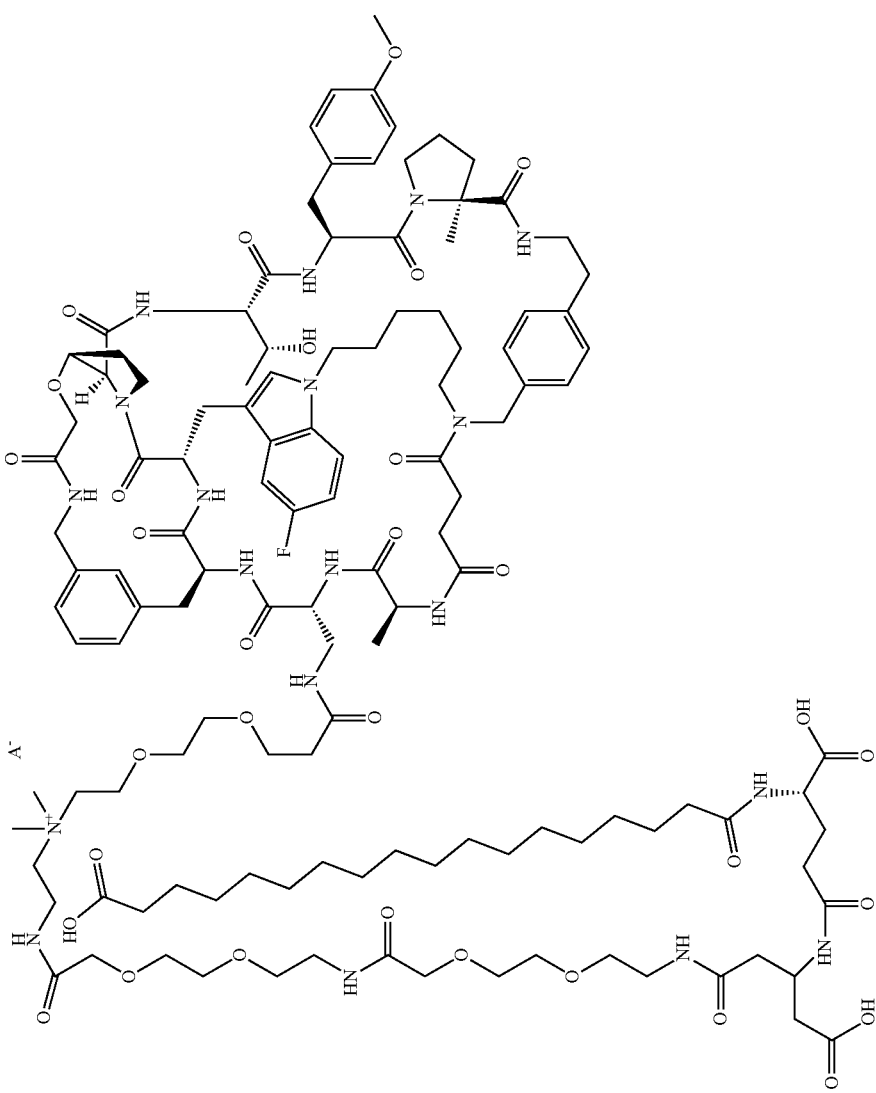 |

-continued
| Ex No | Structure |
|---|---|
| Ex-17* | 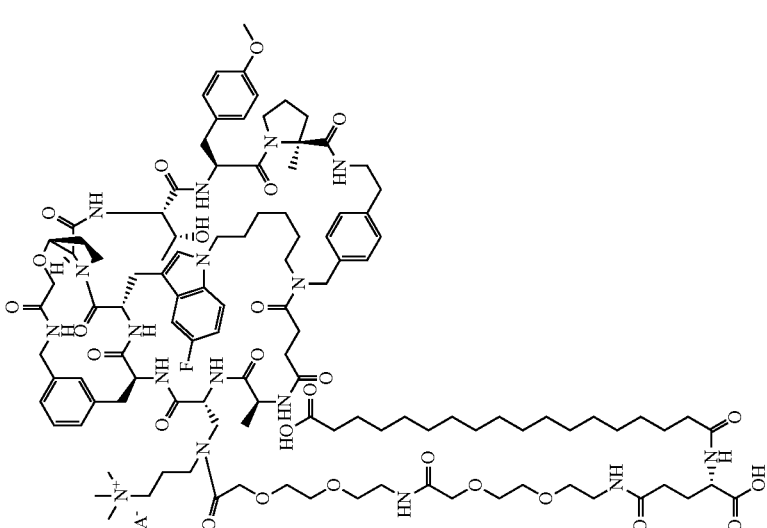 |

-continued
| Ex No | Structure |
|---|---|
| Ex-18 | 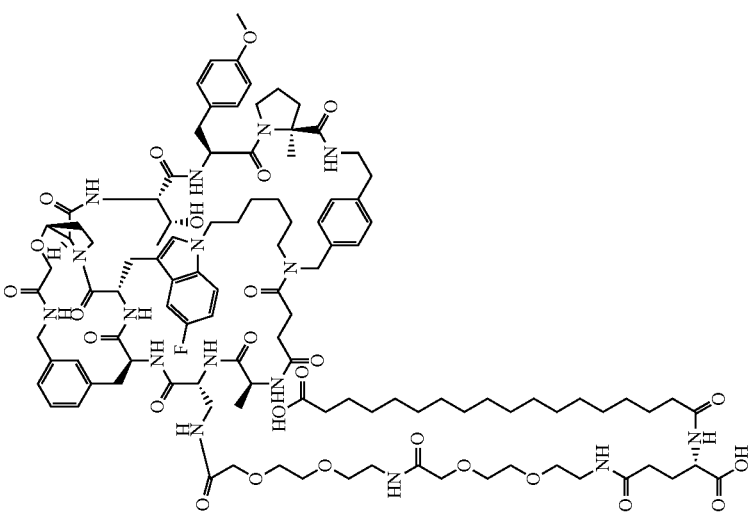 |

| Ex No | Structure |
|---|---|
| Ex-19* | 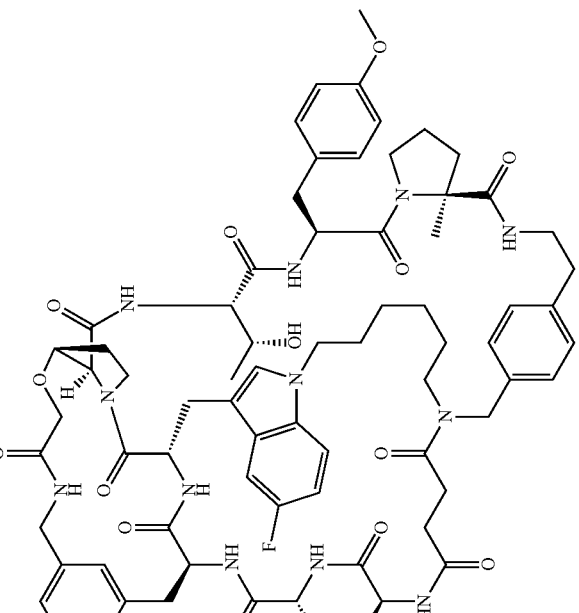 |

-continued
| Ex No | Structure |
|---|---|
| Ex-20* | 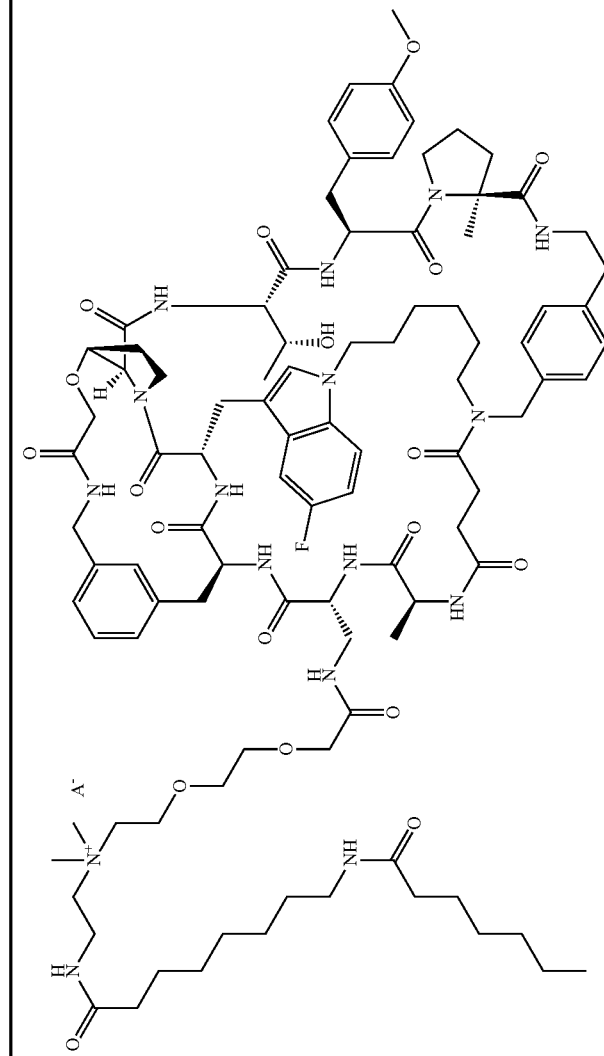 |

-continued
| Ex No | Structure |
|---|---|
| Ex-21* | 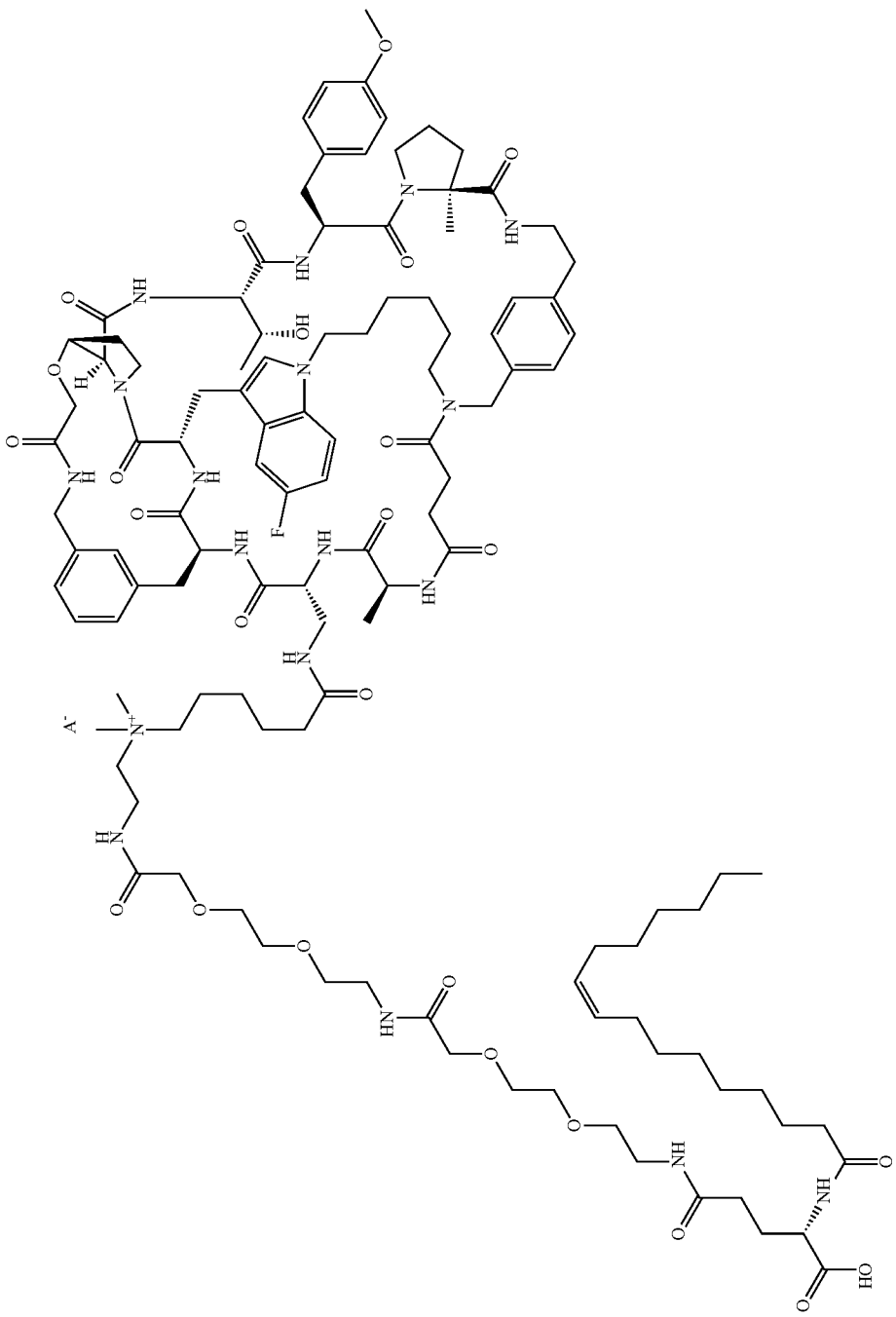 |

-continued
| Ex No | Structure |
|---|---|
| Ex-22* | 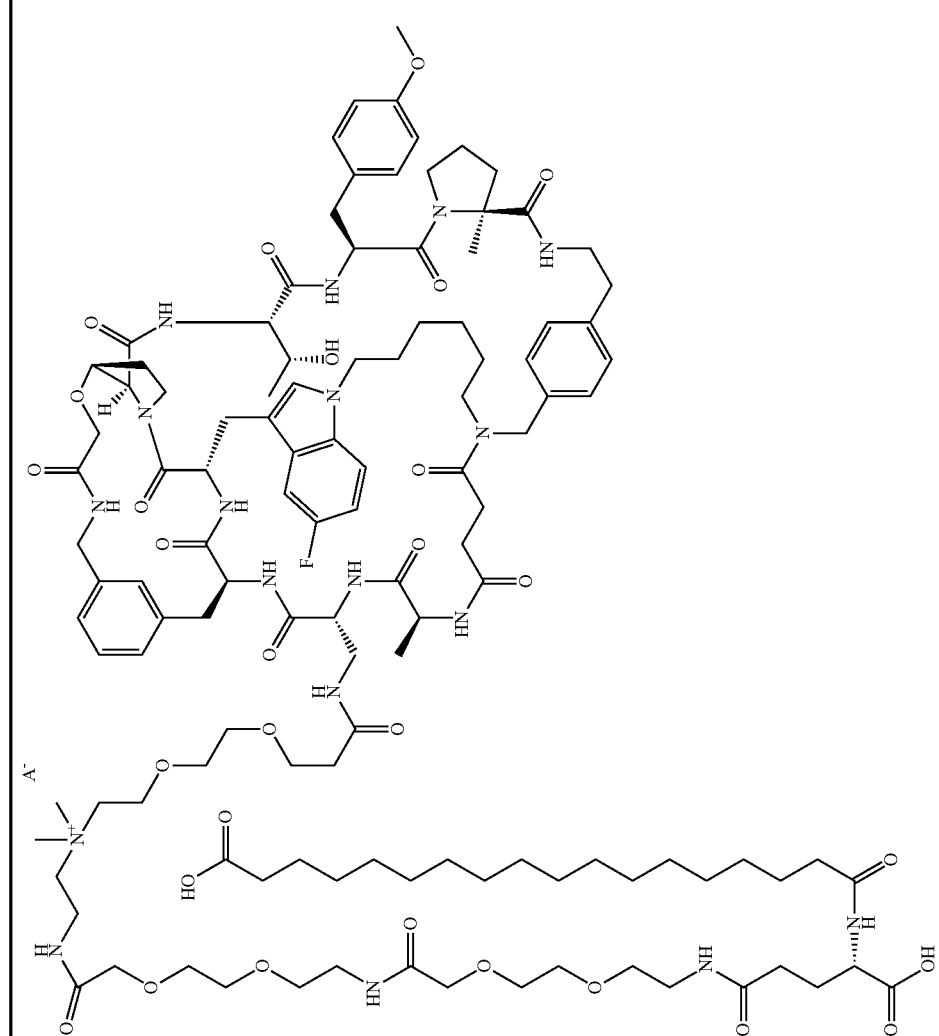 |

-continued
| Ex No | Structure |
|---|---|
| Ex-23* | 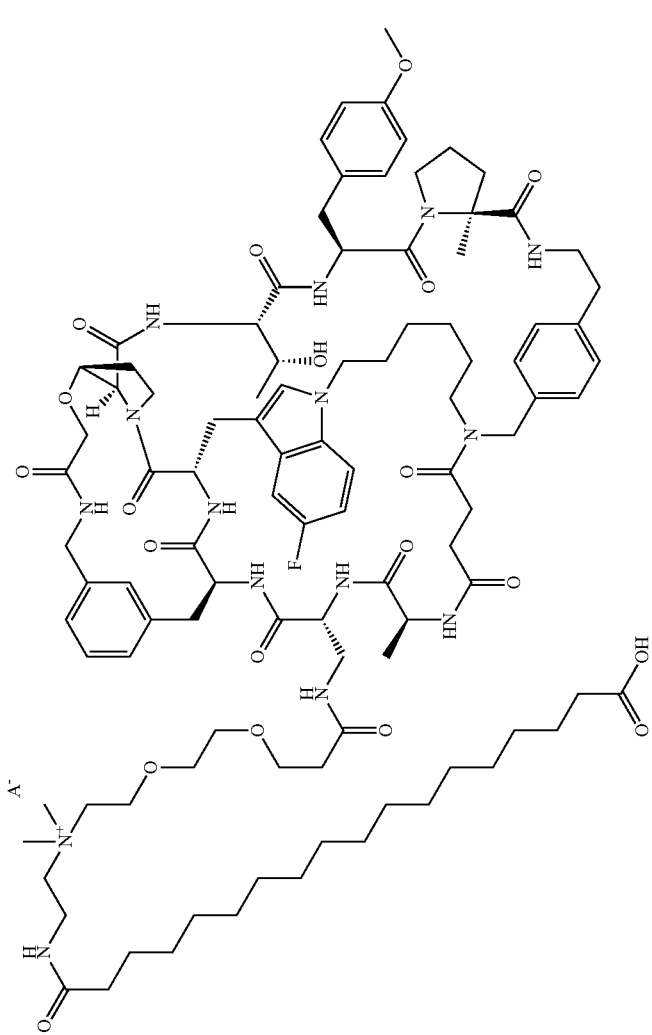 |

| Ex No | Structure |
|---|---|
| Ex-24 | 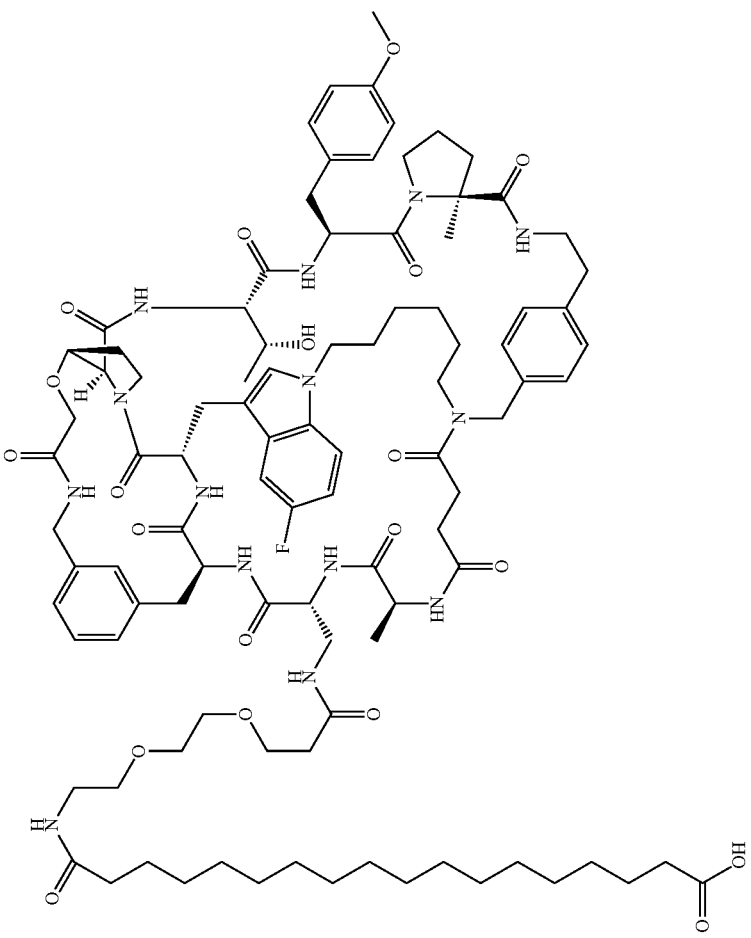 |

| Ex No | Structure |
|---|---|
| Ex-25* | 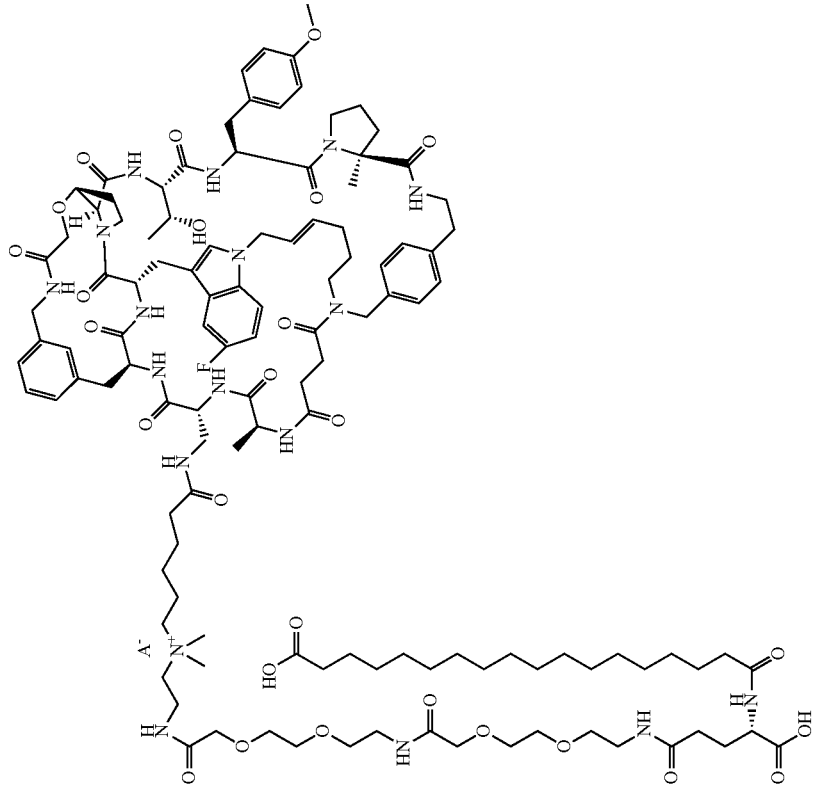 |
-continued

| Ex No | Structure |
|---|---|
| Ex-26* | 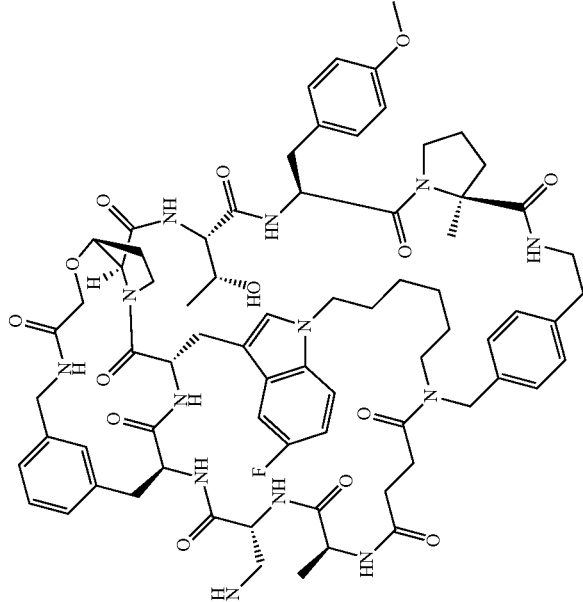 |
-continued

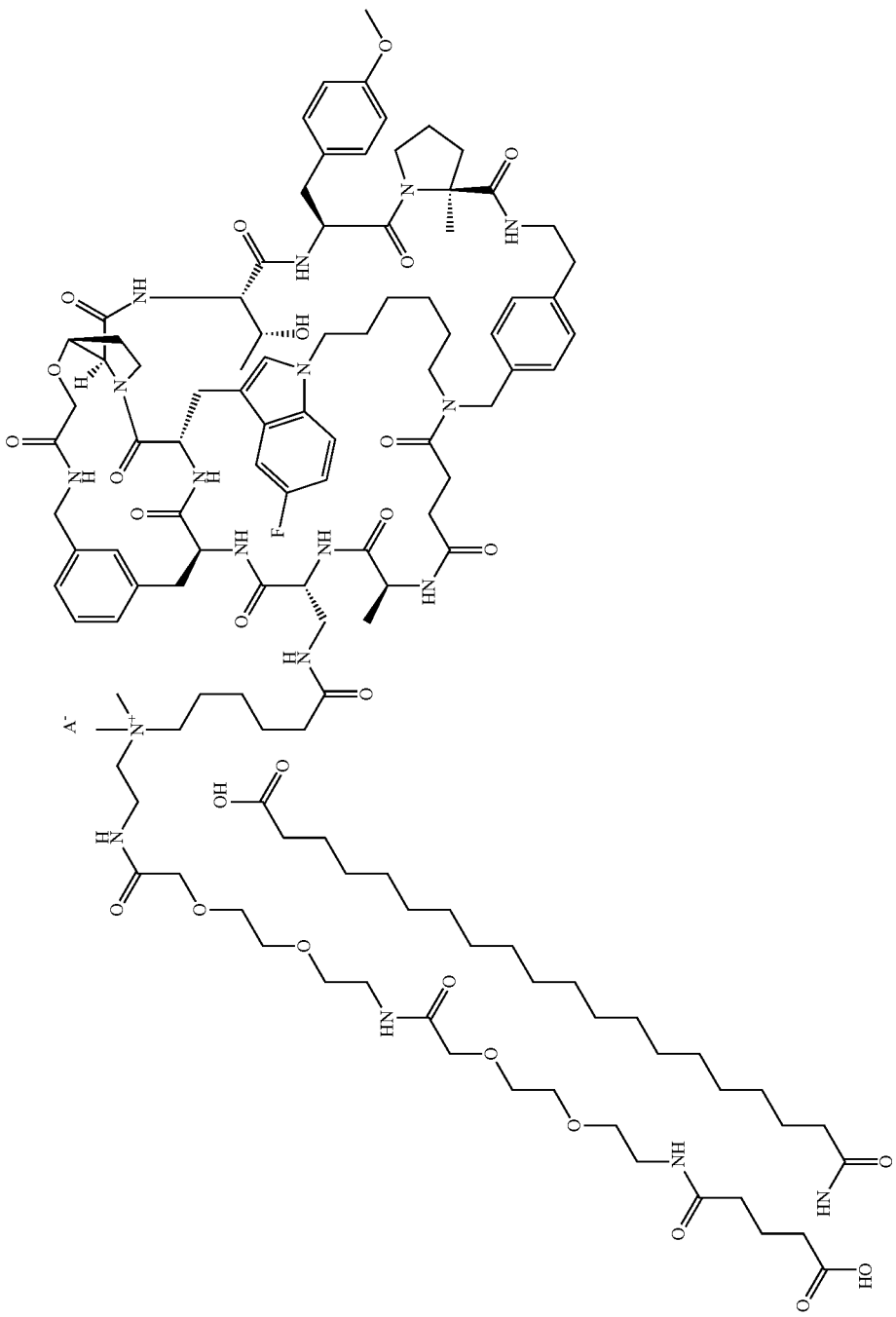

| Ex No | Structure |
|---|---|
| Ex-28* | 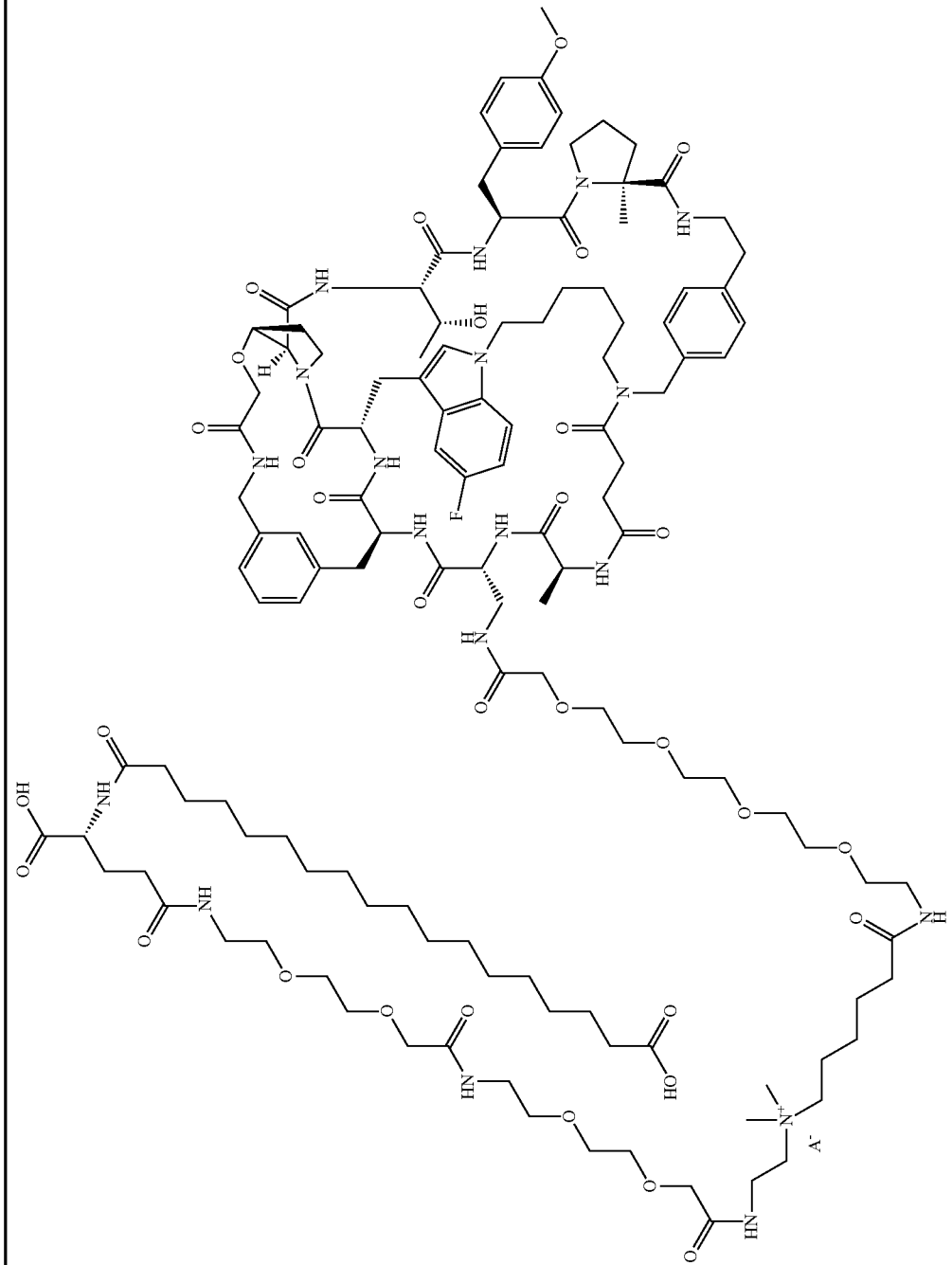 |

-continued
| Ex No | Structure |
|---|---|
| Ex-29* | 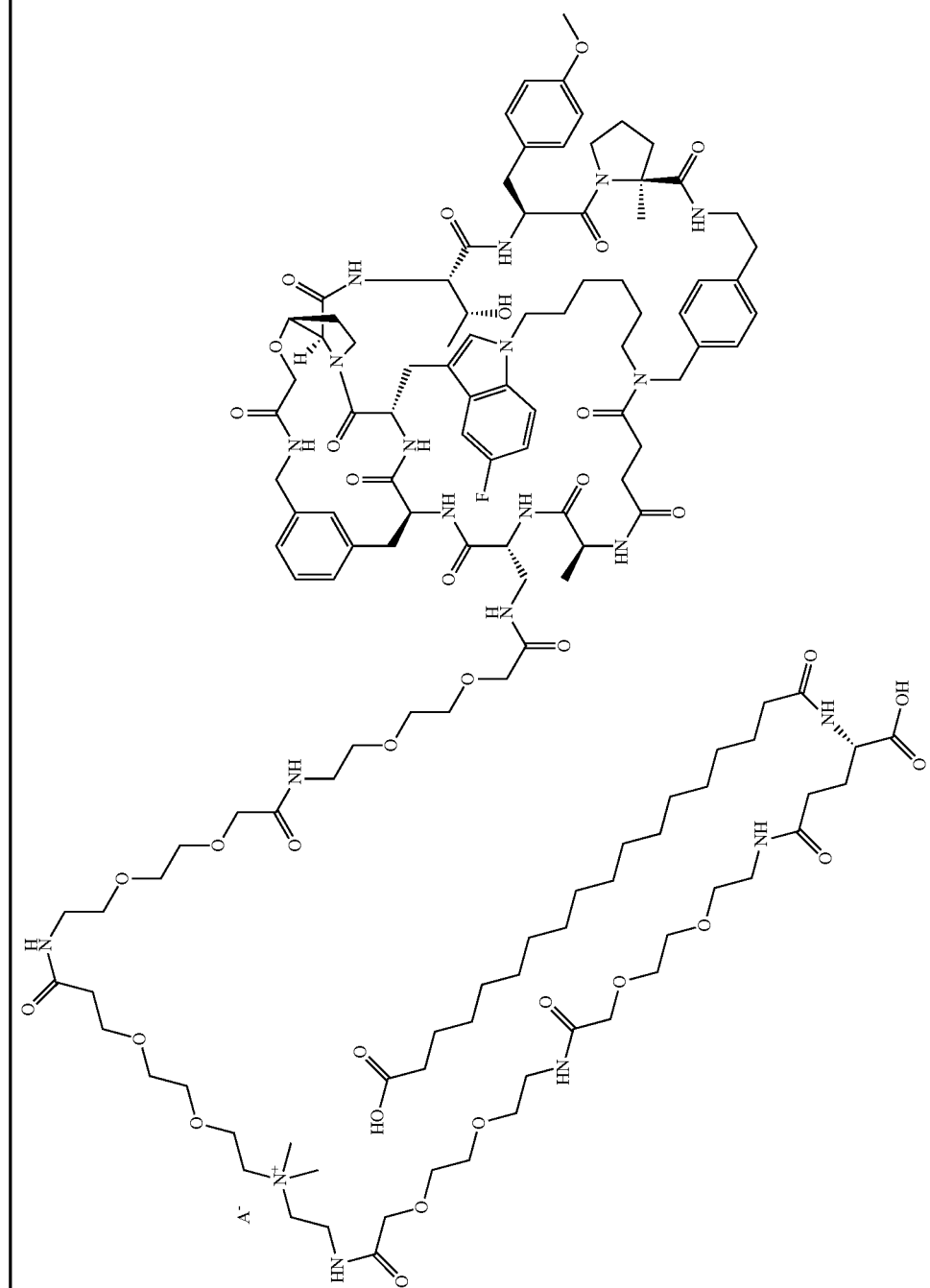 |

| Ex No | Structure |
|---|---|
| Ex-30* | 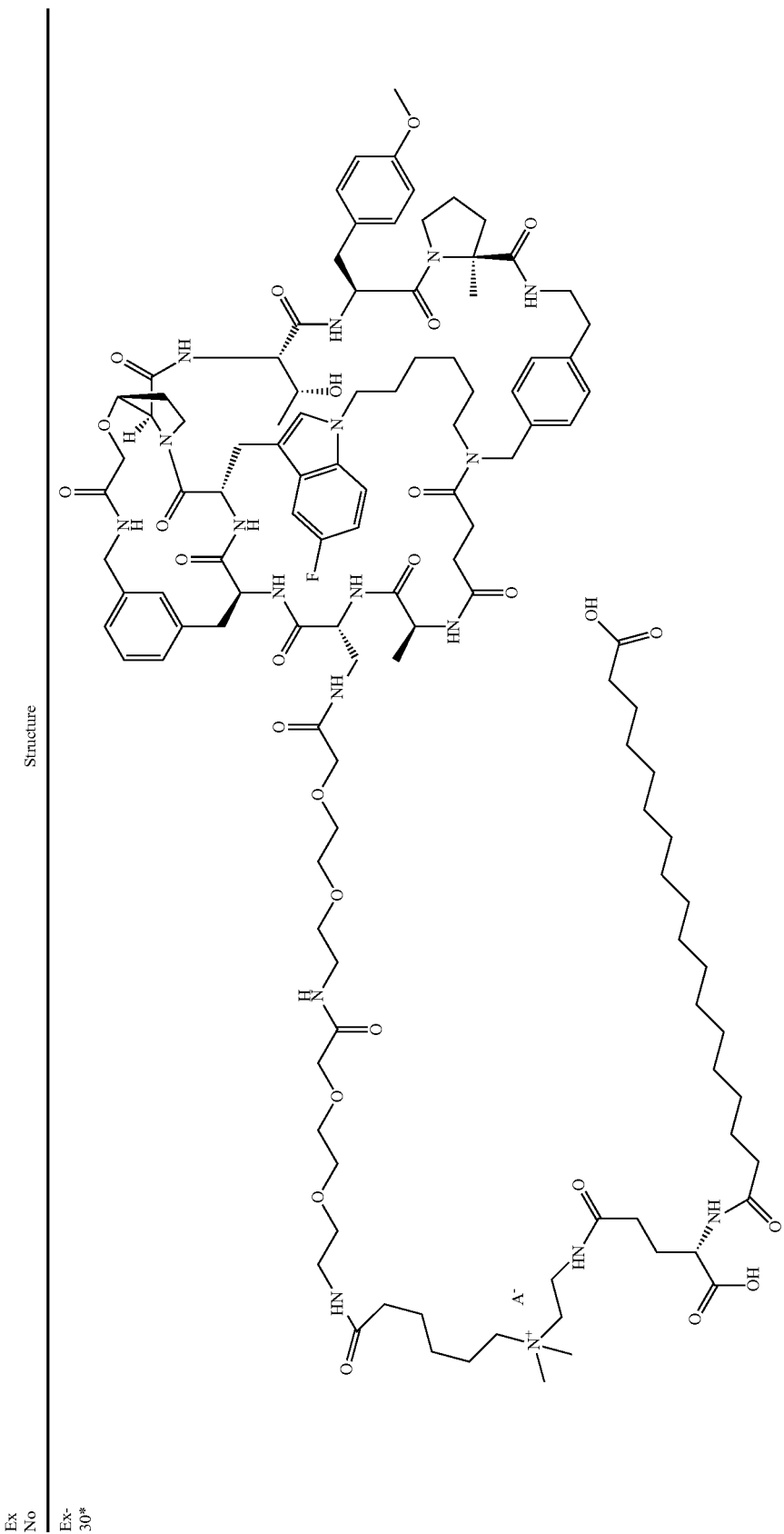 |

| Ex No | Structure |
|---|---|
| Ex31* | 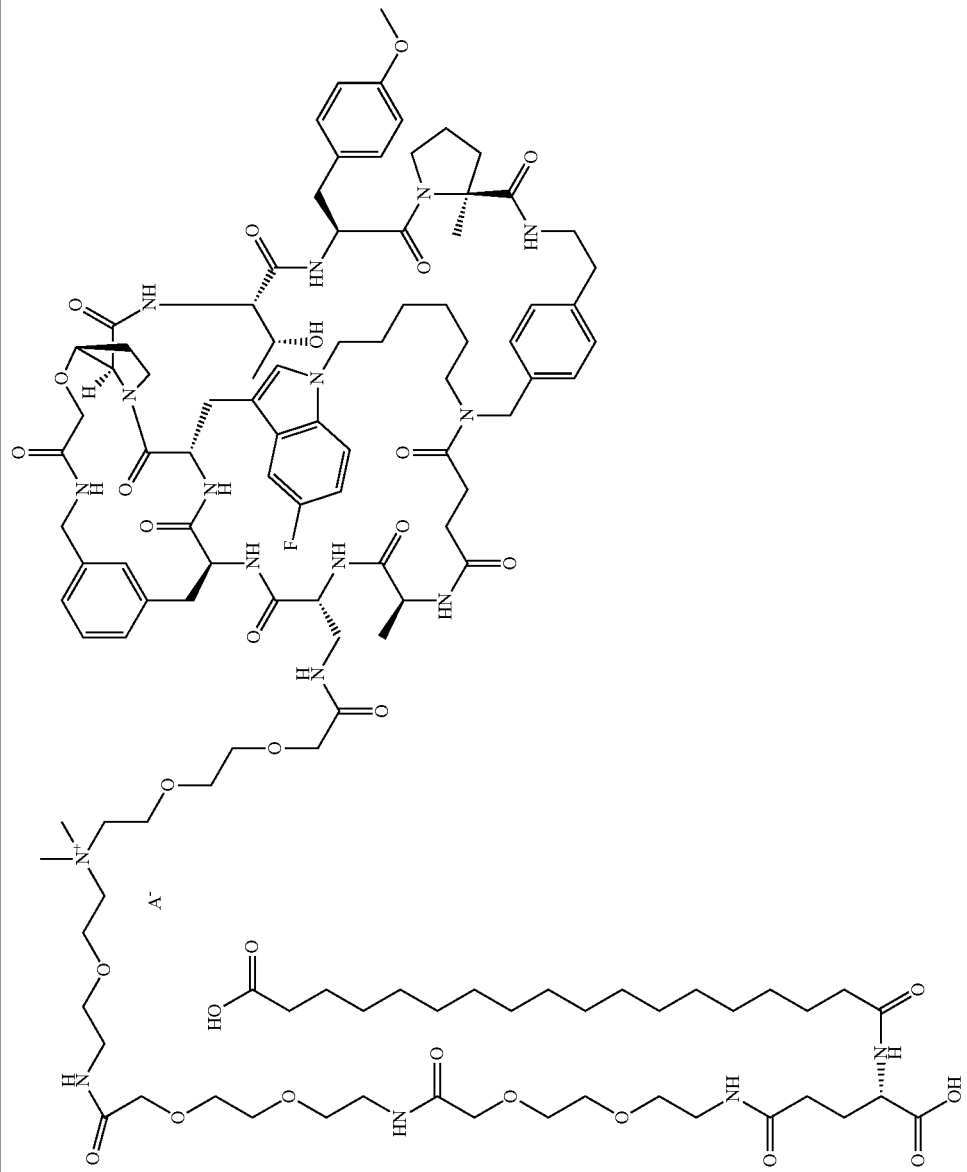 |
-continued

-continued
| Ex No | Structure |
|---|---|
| Ex-32* | 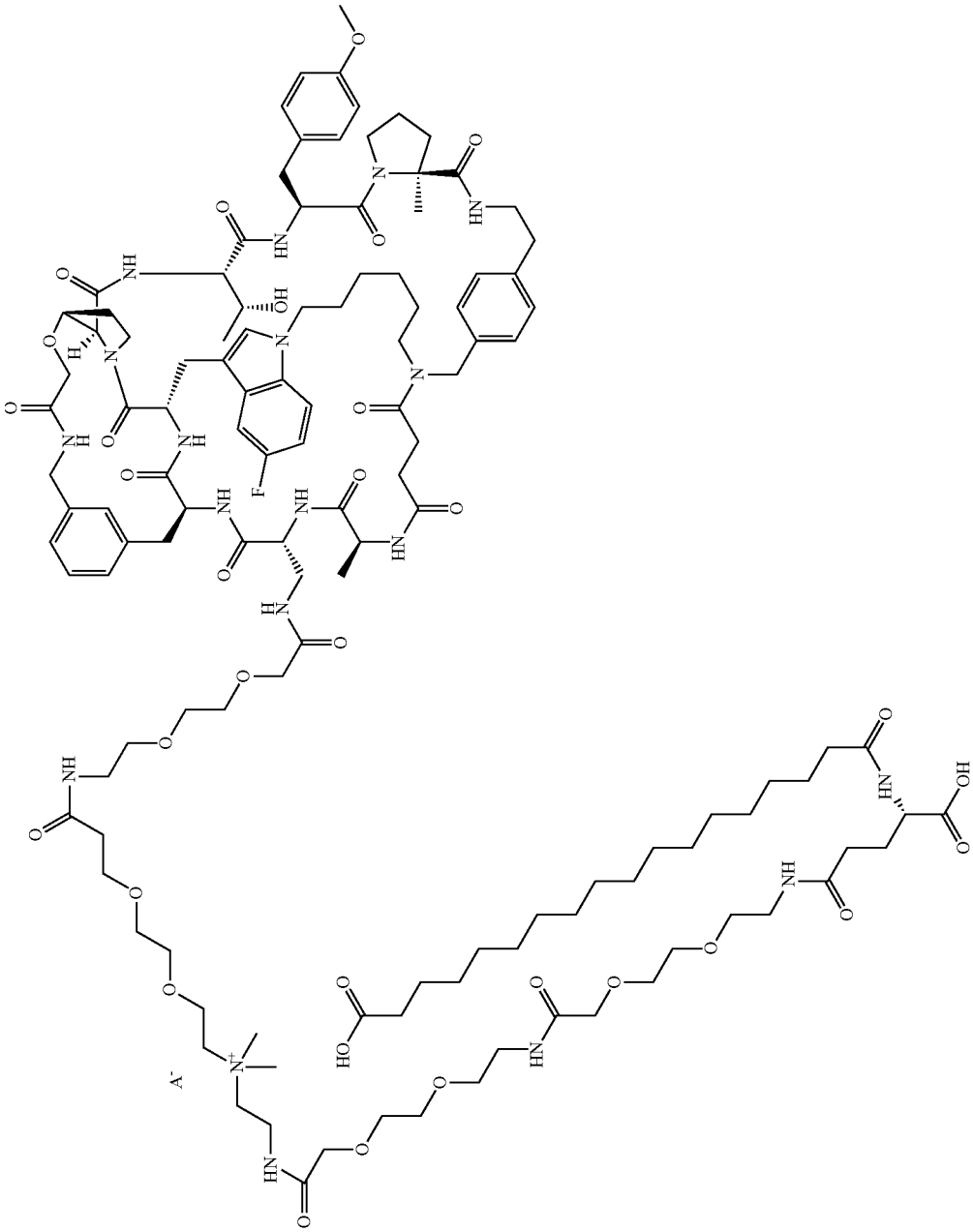 |

| Ex No | Structure |
|---|---|
| Ex-33* | 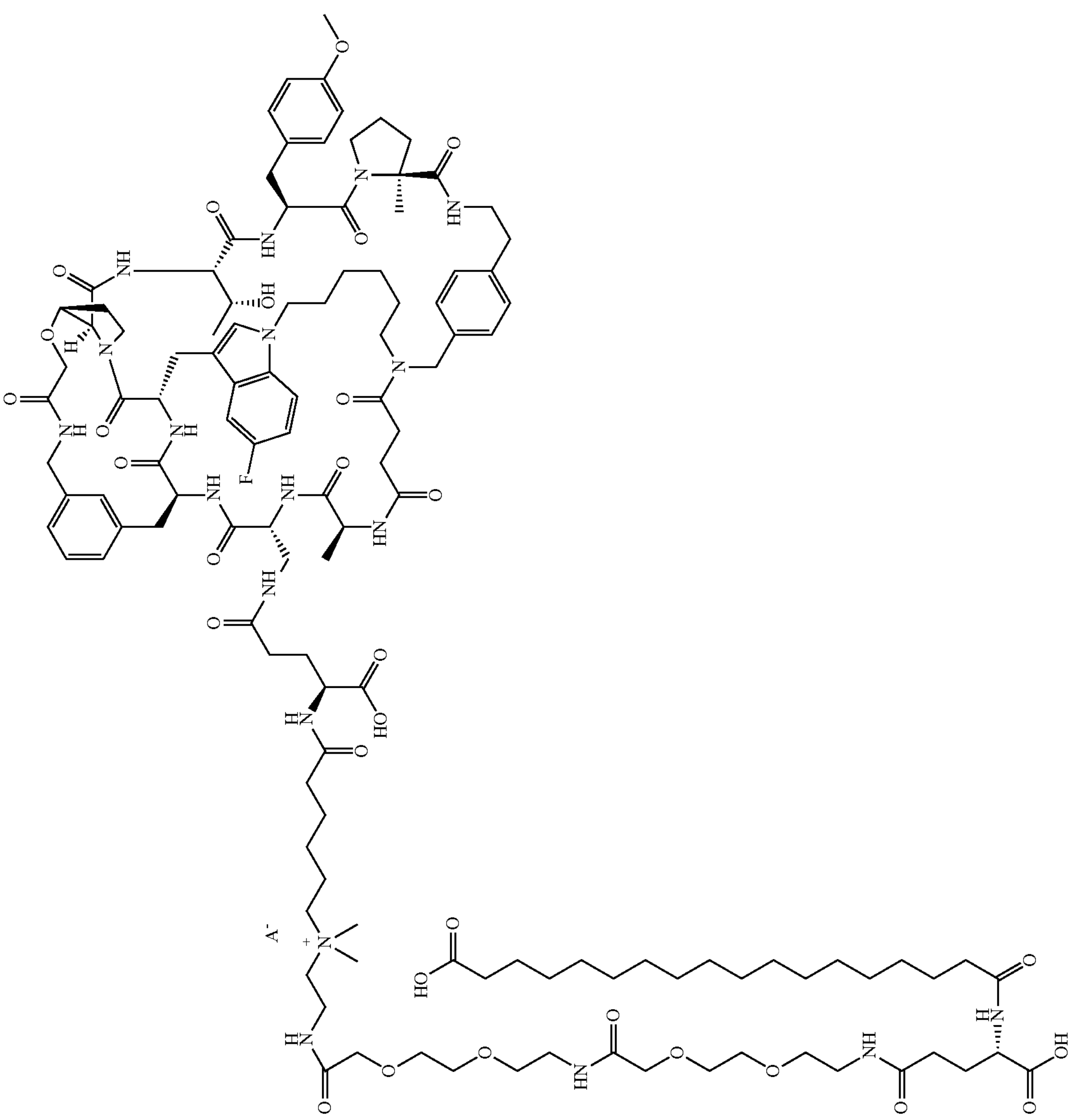 |

-continued
| Ex No | Structure |
|---|---|
| Ex-34* | 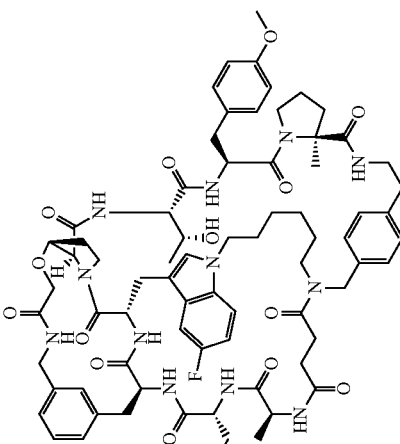 |

| Ex No | Structure |
|---|---|
| Ex-35* | 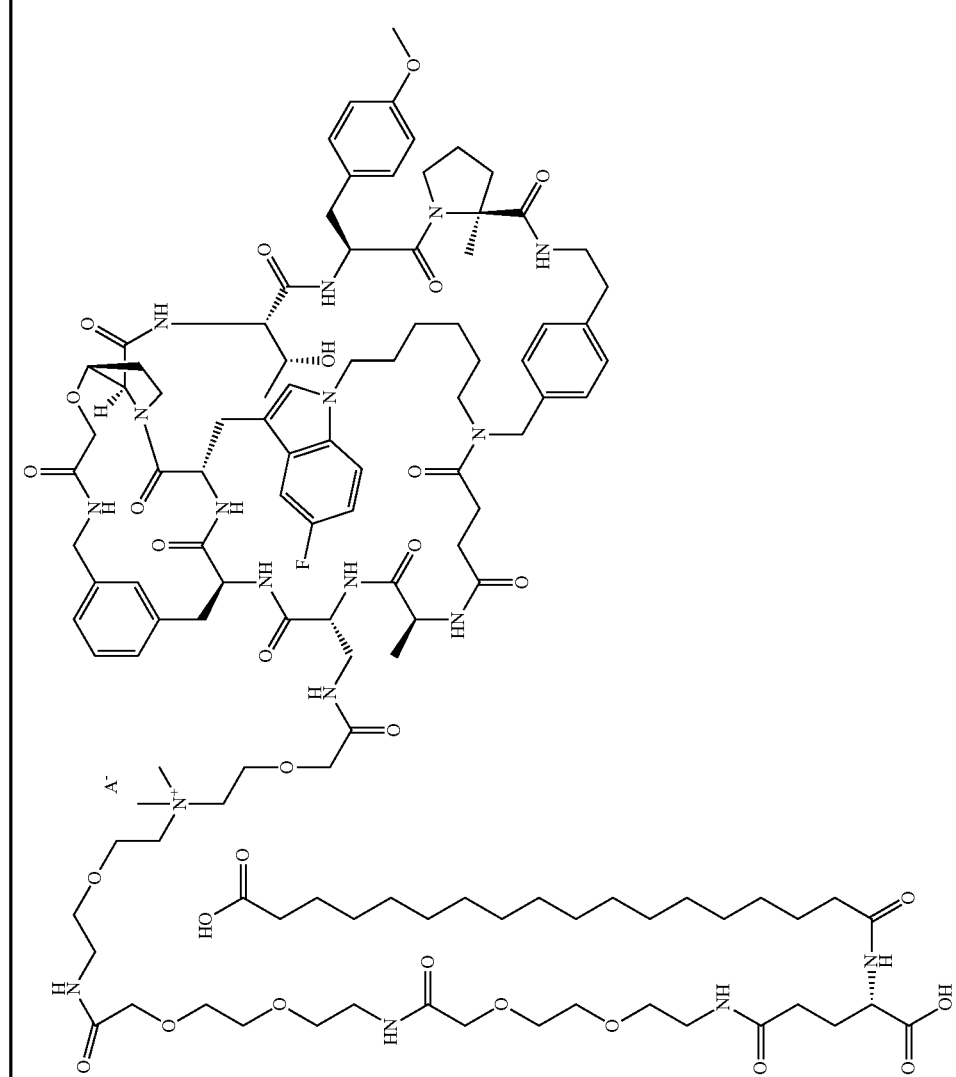 |

| Ex No | Structure |
|---|---|
| Ex-36* | 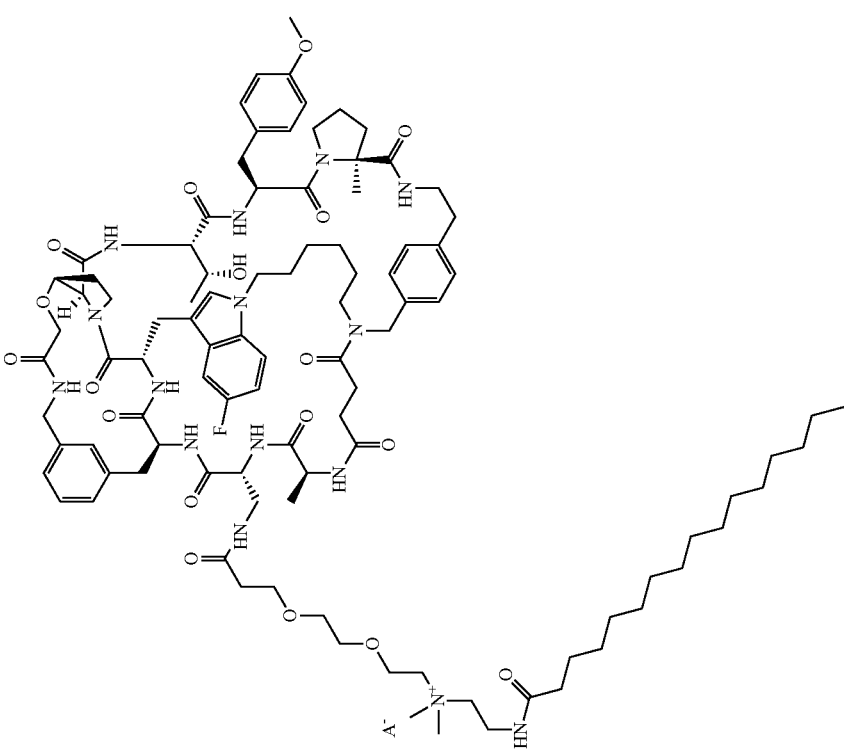 |

| Ex No | Structure |
|---|---|
| Ex-37* | 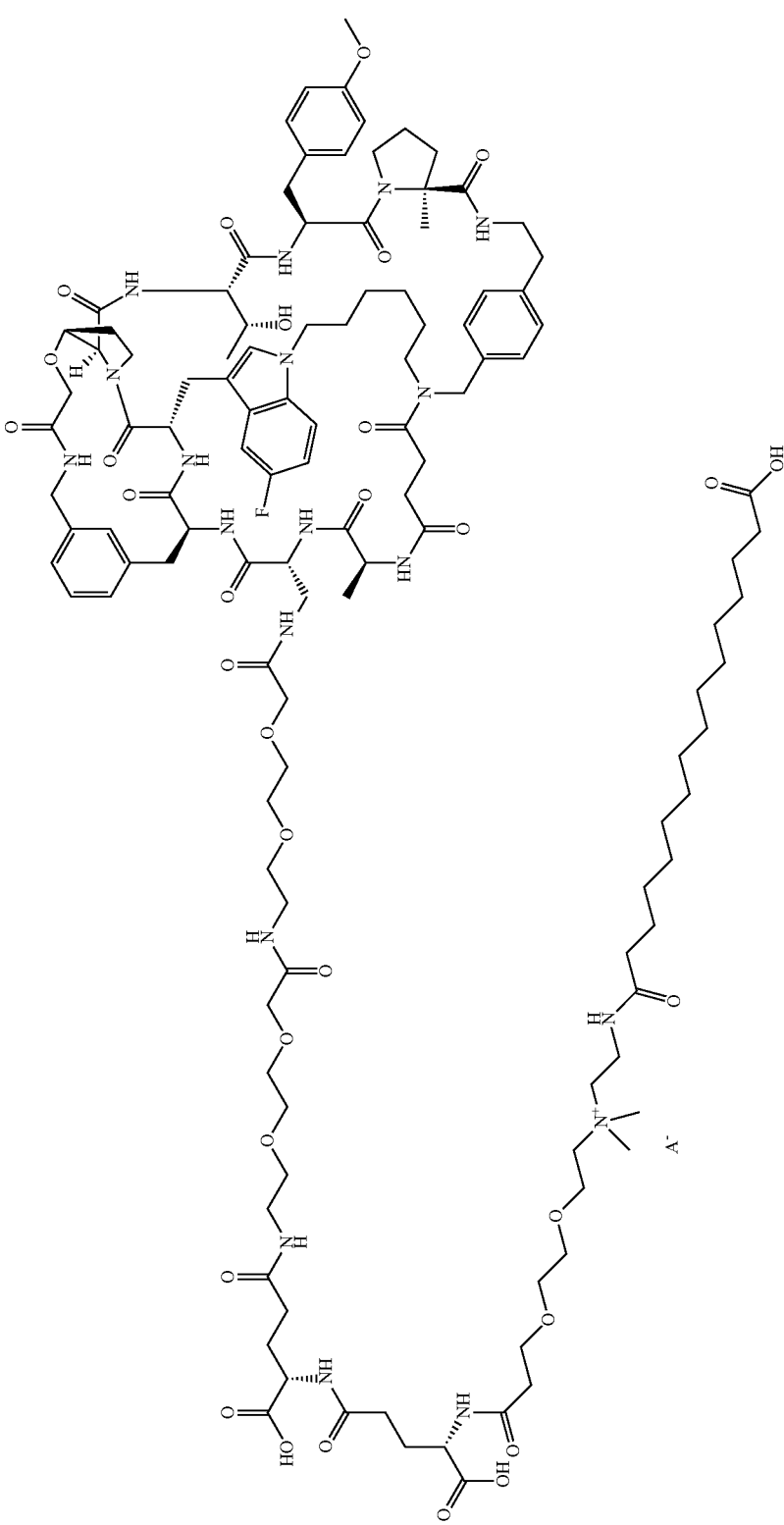 |

-continued
| Ex No | Structure |
|---|---|
| Ex-38* | 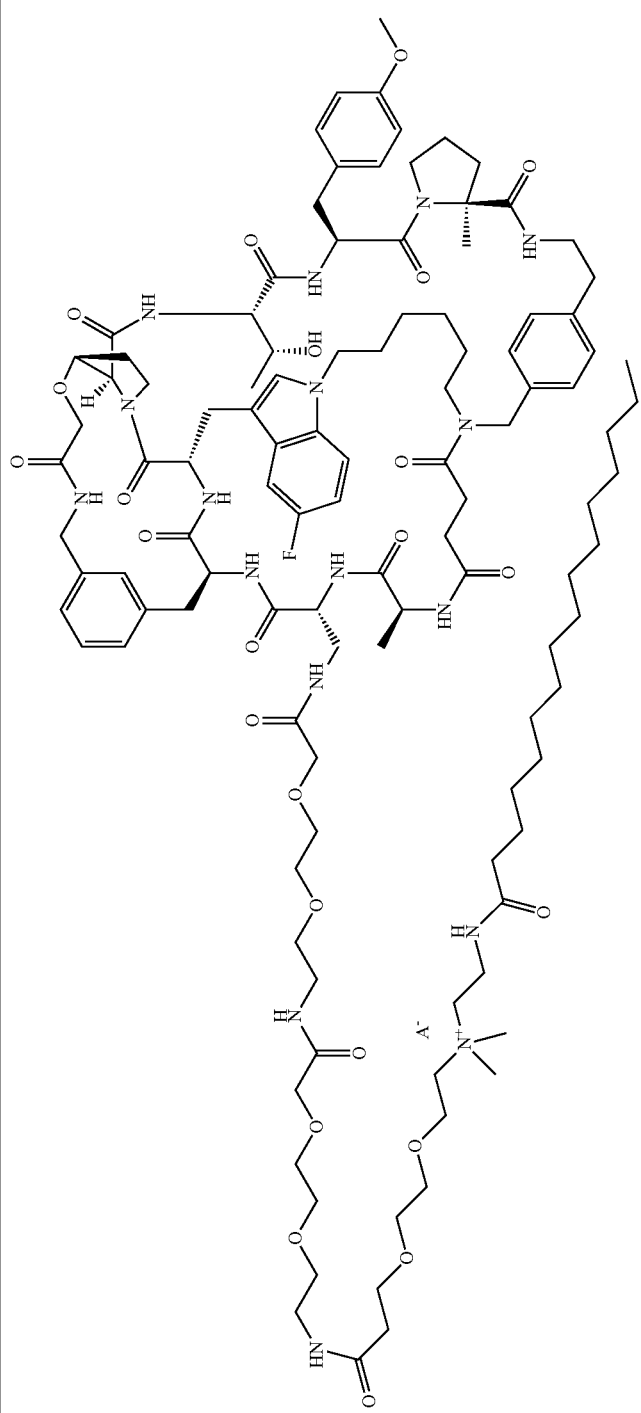 |

-continued
| Ex No | Structure |
|---|---|
| Ex-39* | 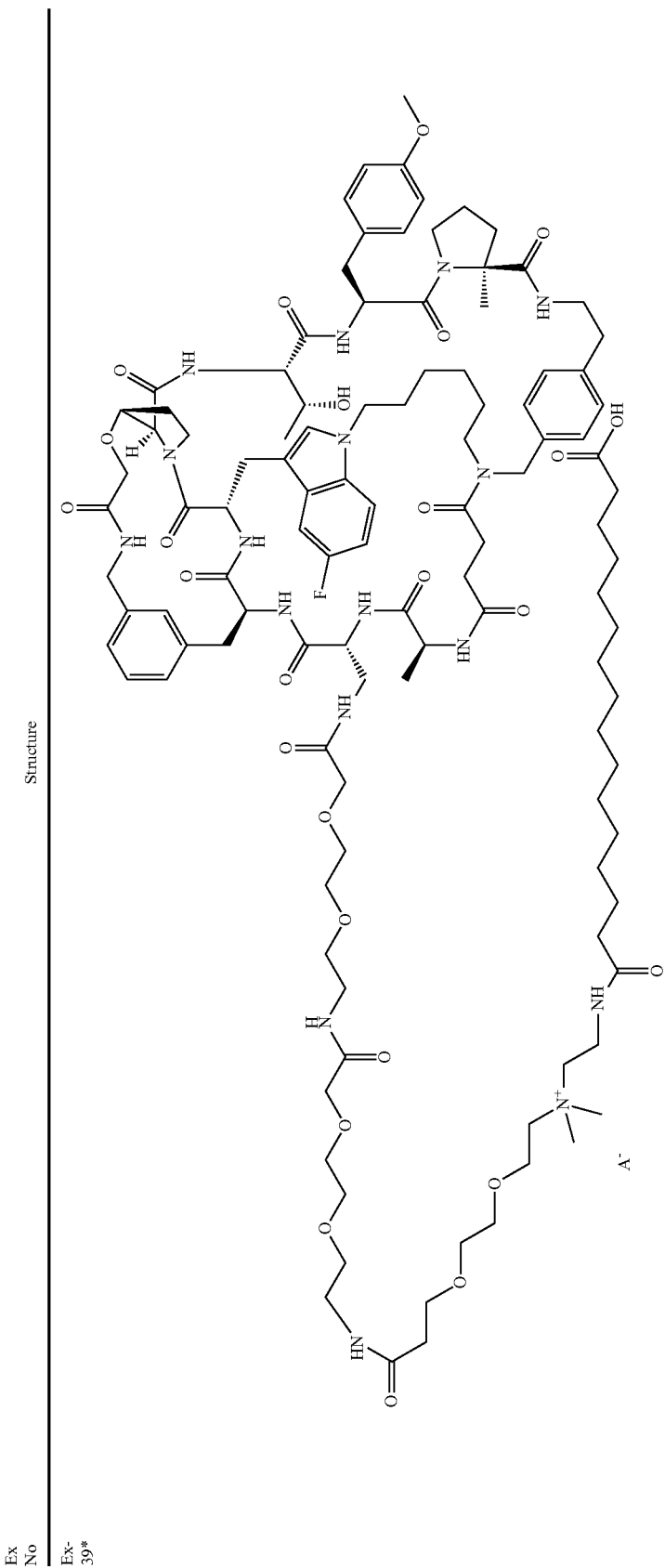 |

| Ex No | Structure |
|---|---|
| Ex-40* | 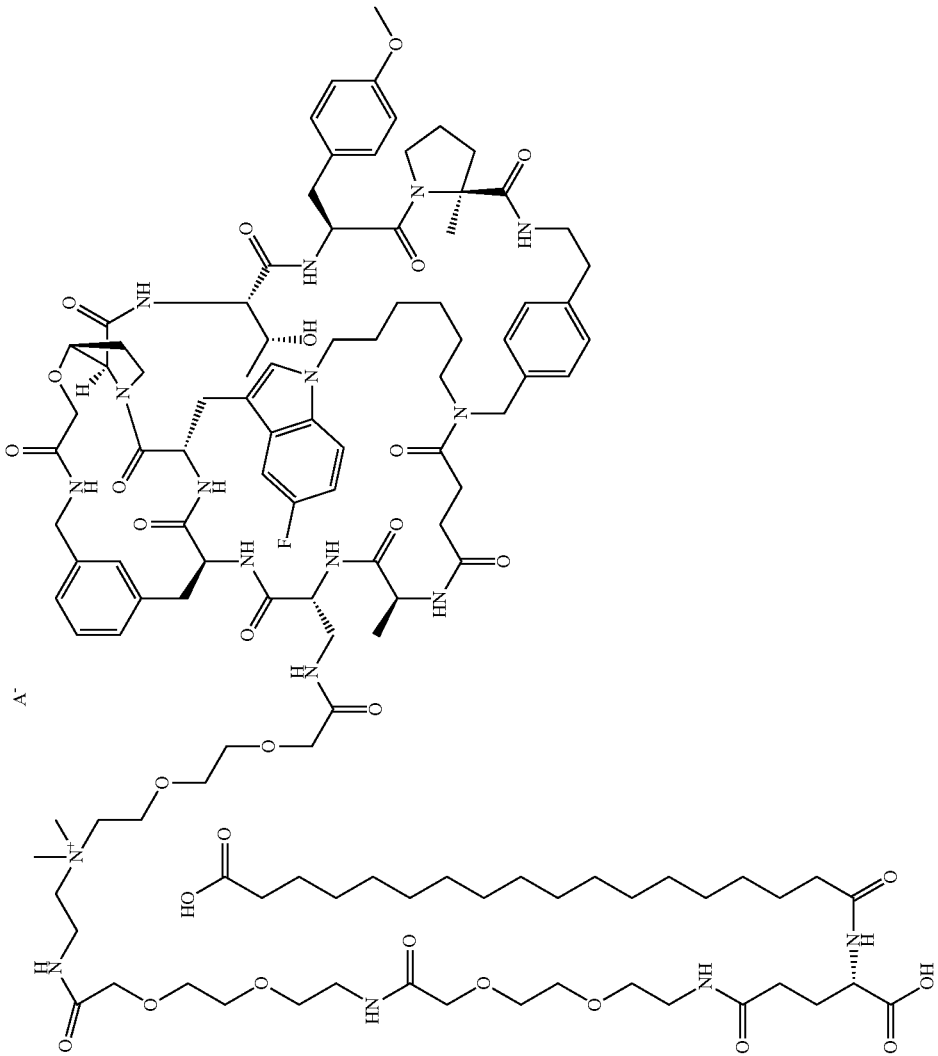 |

| Ex No | Structure |
|---|---|
| Ex-41 | 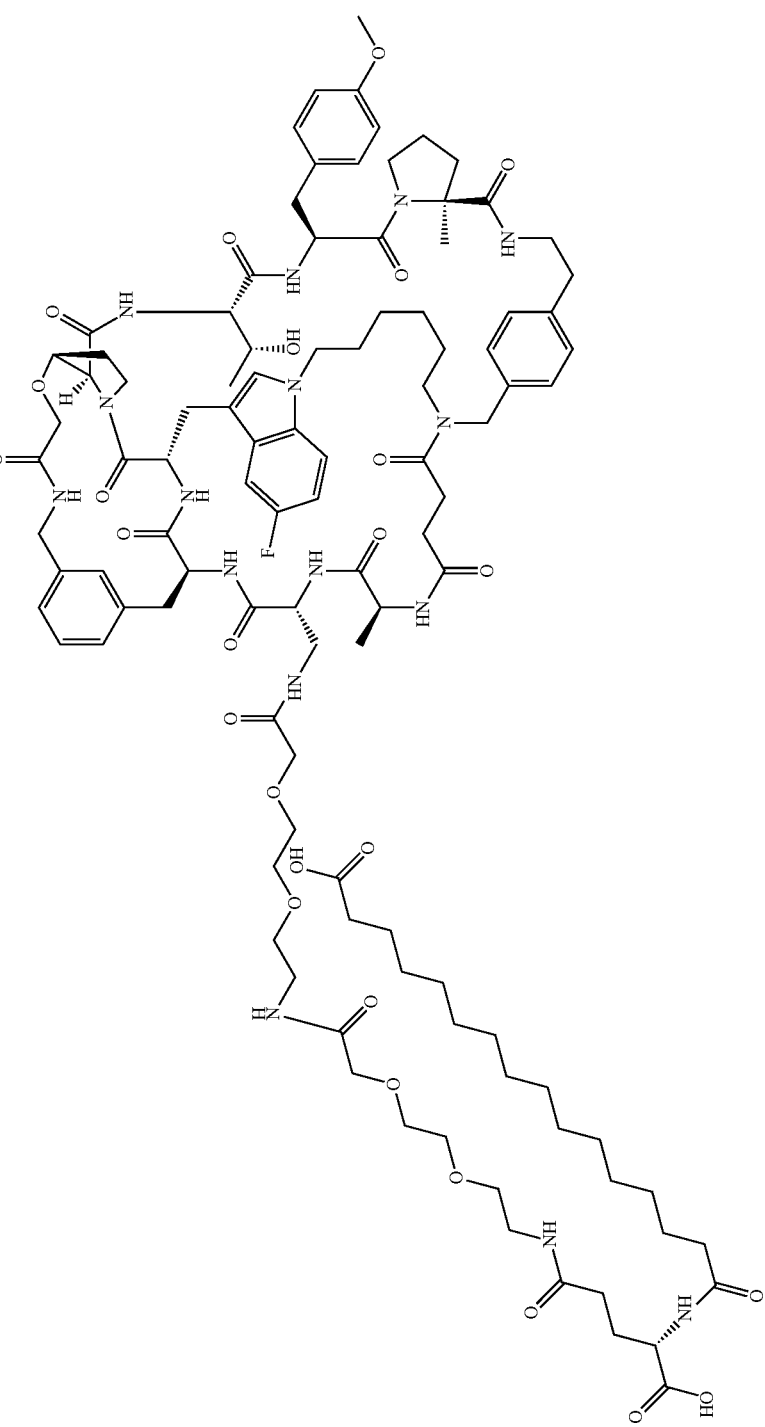 |

| Ex No | Structure |
|---|---|
| Ex-42 | 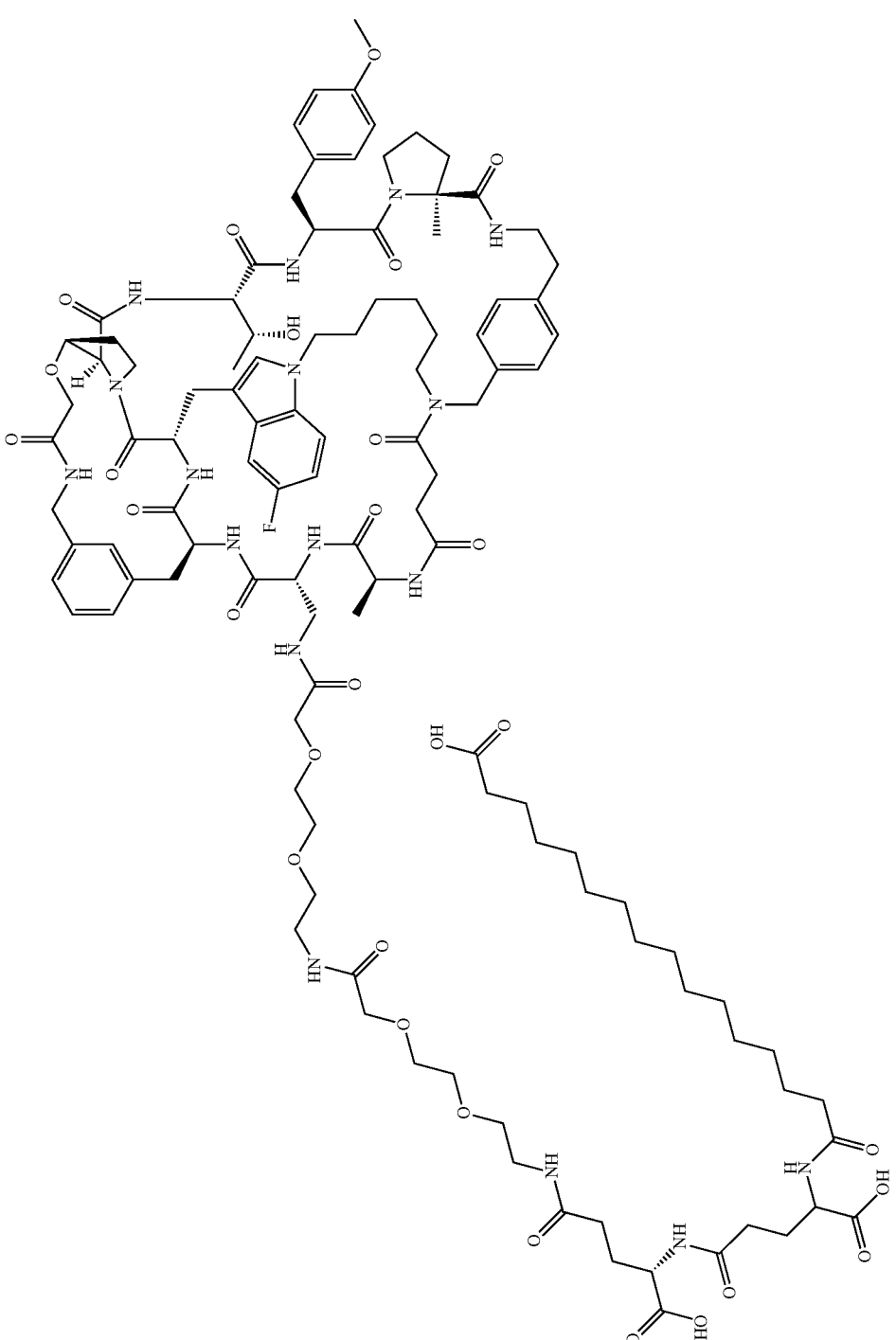 |

| Ex No | Structure |
|---|---|
| Ex-43* | 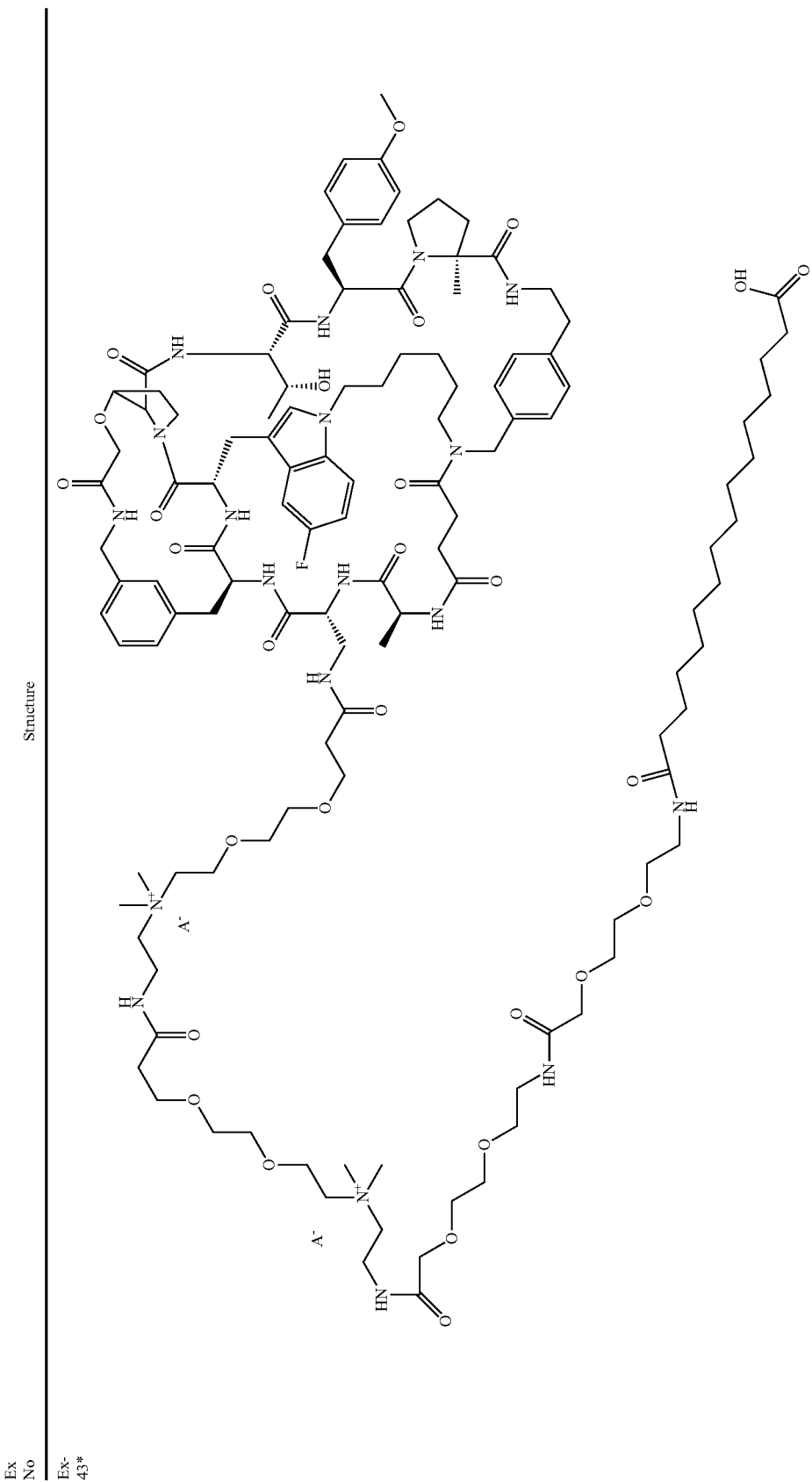 |

| Ex No | Structure |
|---|---|
| Ex-44* | 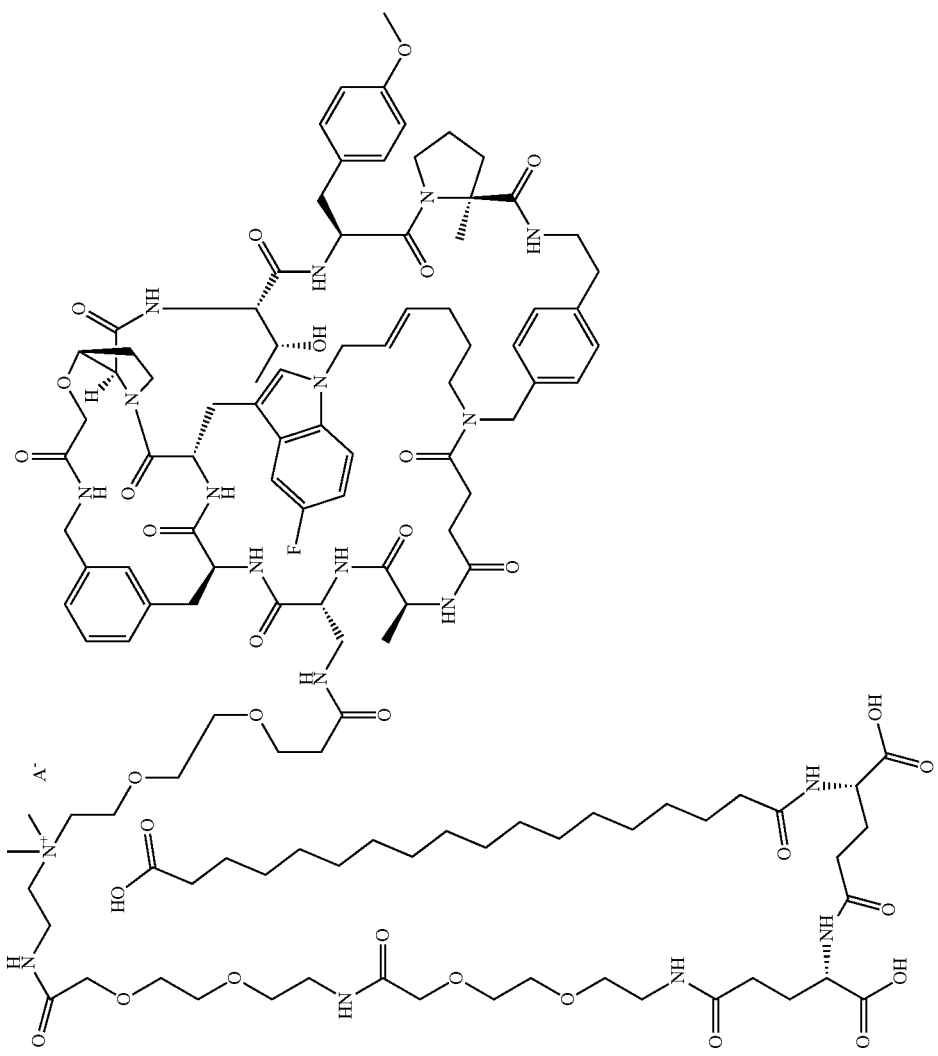 |

| Ex No | Structure |
|---|---|
| Ex-45* | 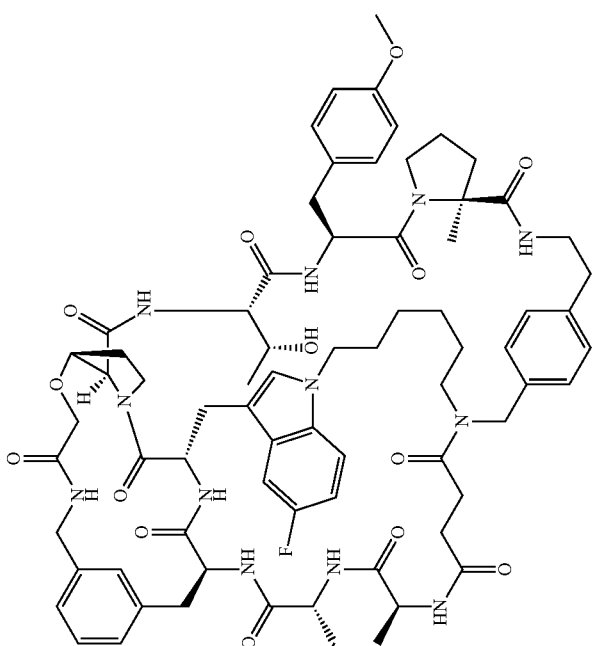 |

| Ex No | Structure |
|---|---|
| Ex-46* | 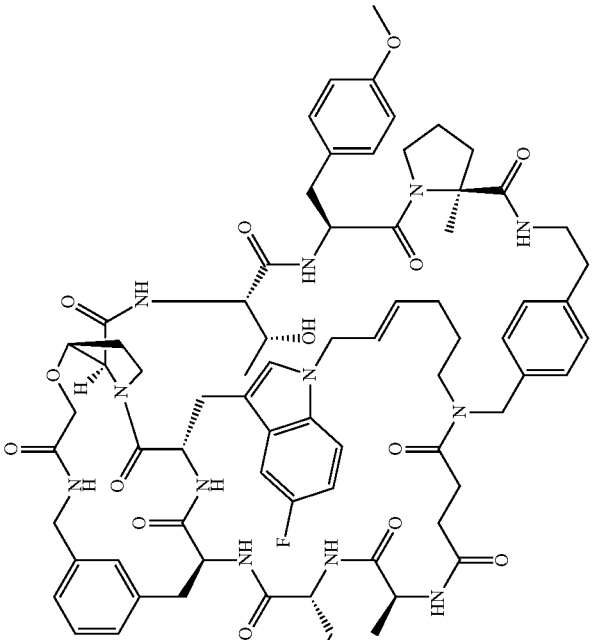 |

-continued
| Ex No | Structure |
|---|---|
| Ex-47* | 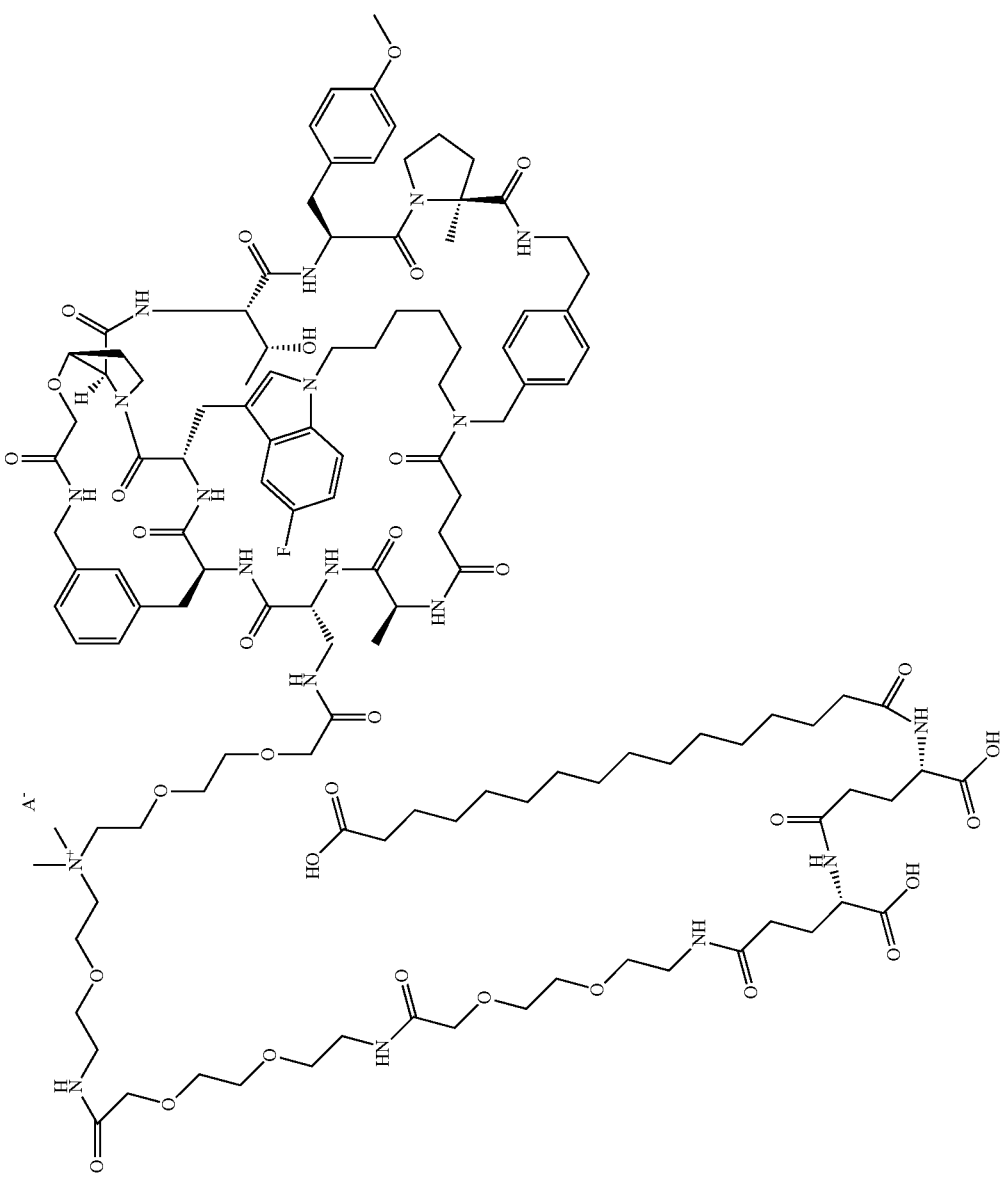 |

| Ex No | Structure |
|---|---|
| Ex-48* | 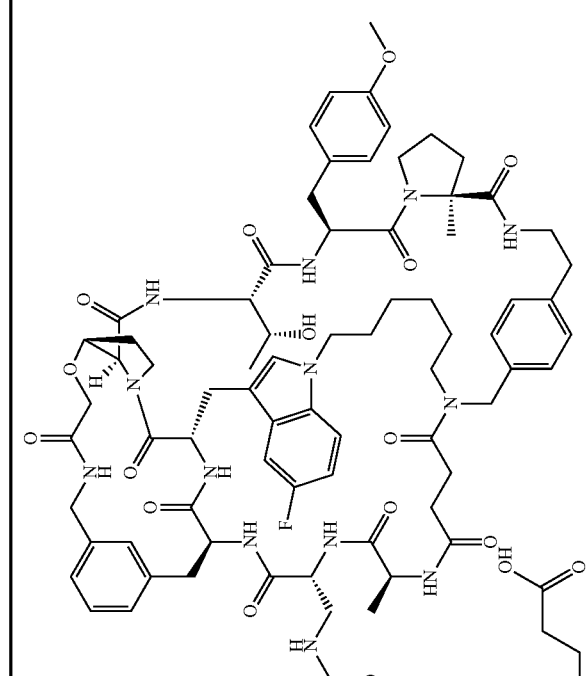 |

| Ex No | Structure |
|---|---|
| Ex-49* | 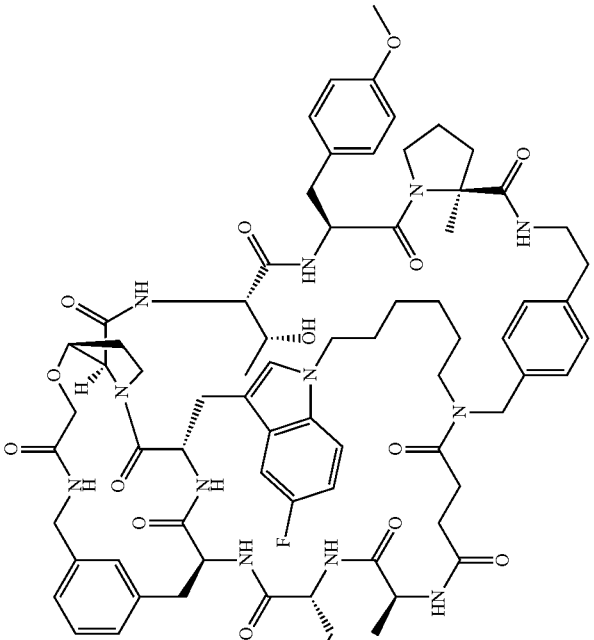 |

| Ex No | Structure |
|---|---|
| Ex-50* | 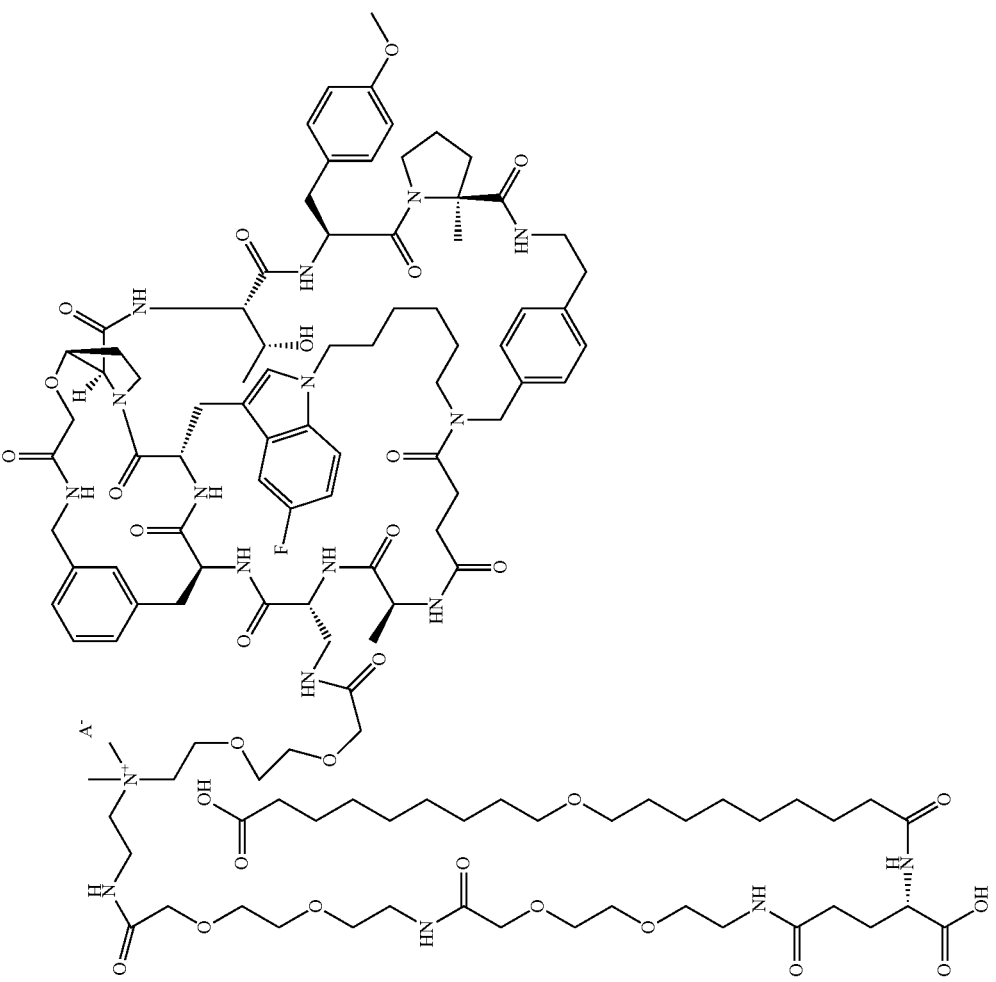 |

| Ex No | Structure |
|---|---|
| Ex-51* | 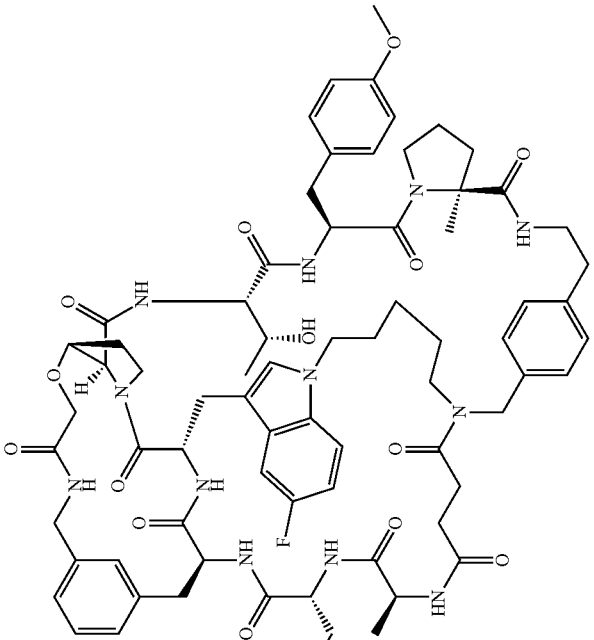 |

-continued
| Ex No | Structure |
|---|---|
| Ex-52* | 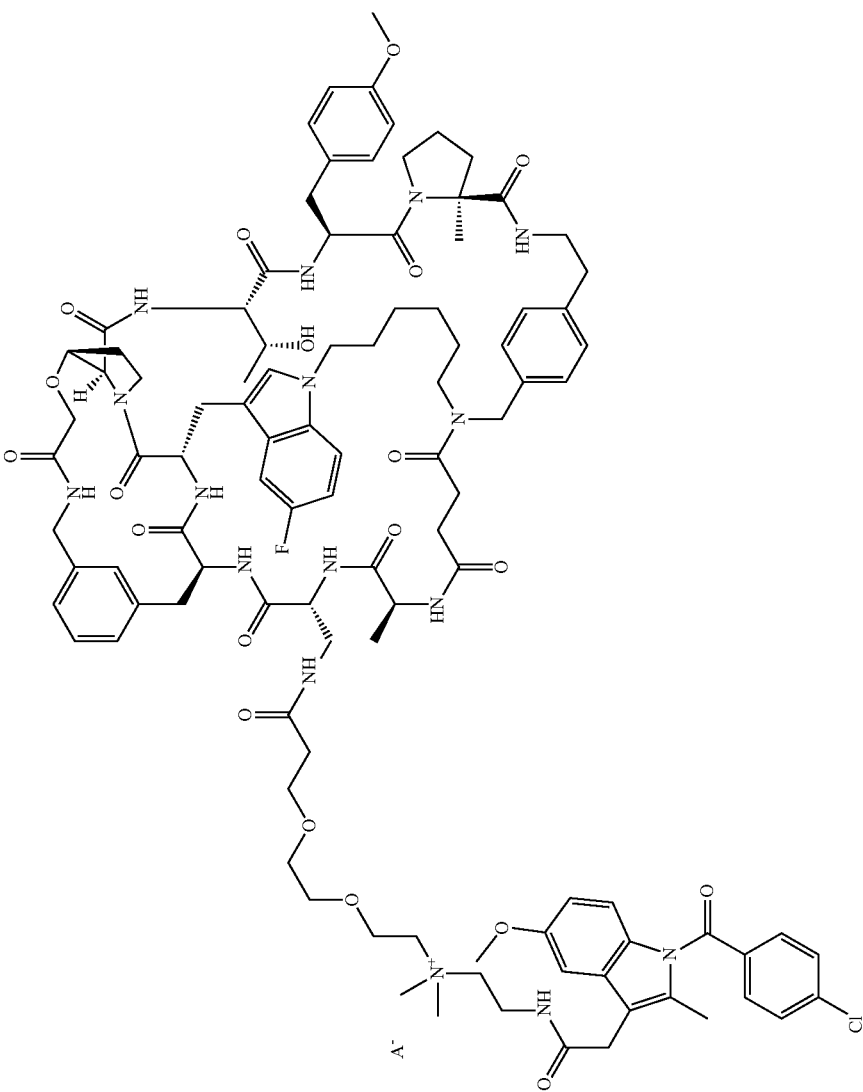 |

-continued
| Ex No | Structure |
|---|---|
| Ex-53* | 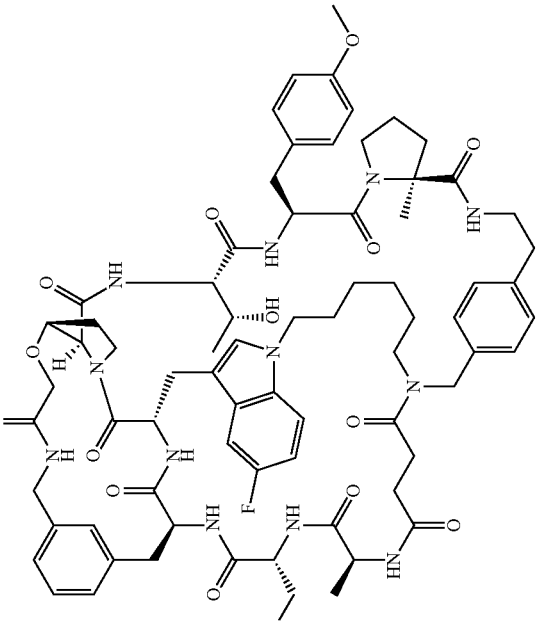 |

| Ex No | Structure |
|---|---|
| Ex-54* | 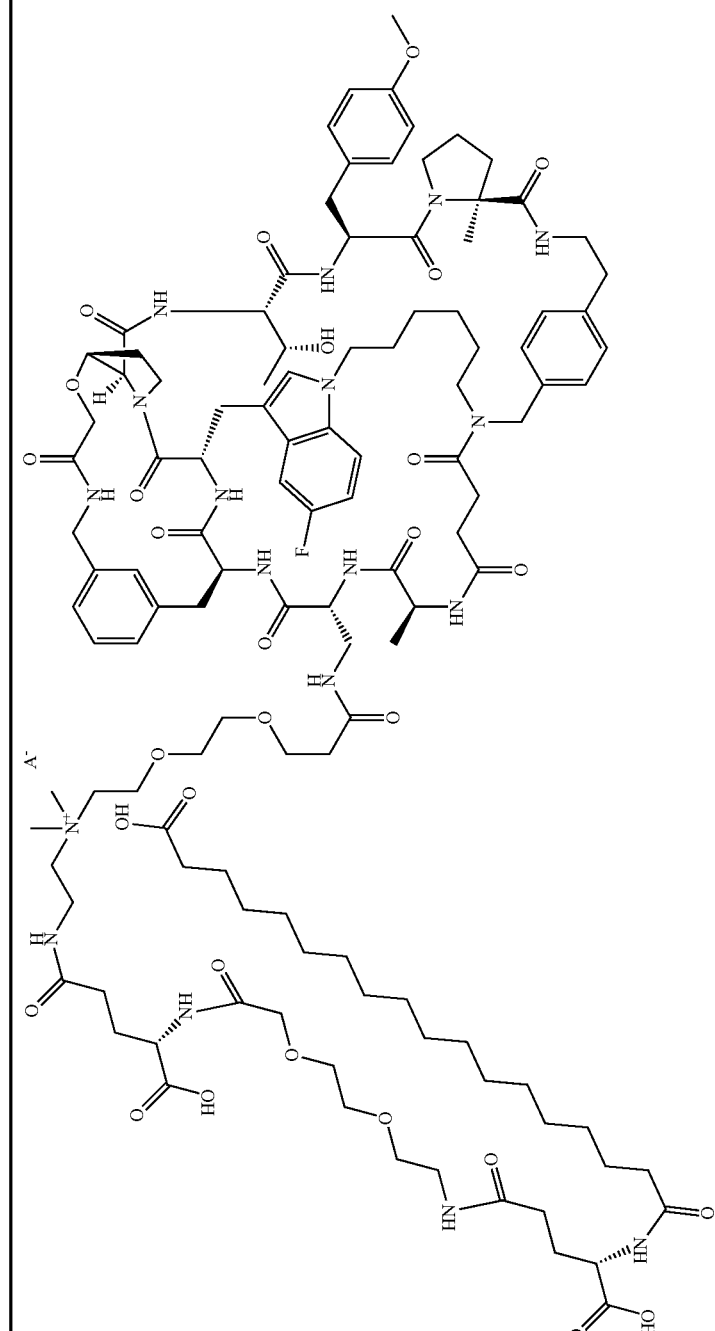 |

| Ex No | Structure |
|---|---|
| Ex-55* | 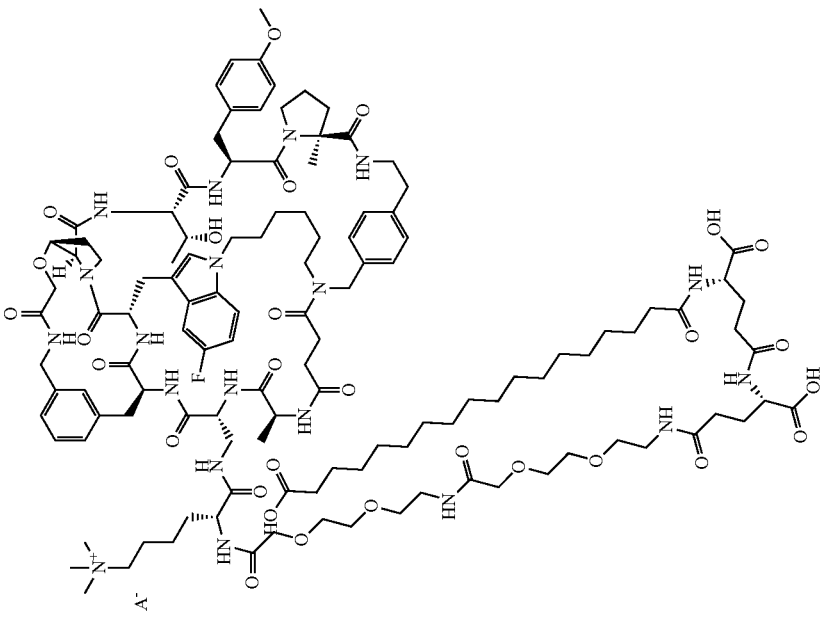 |

| Ex No | Structure |
|---|---|
| Ex-56* | 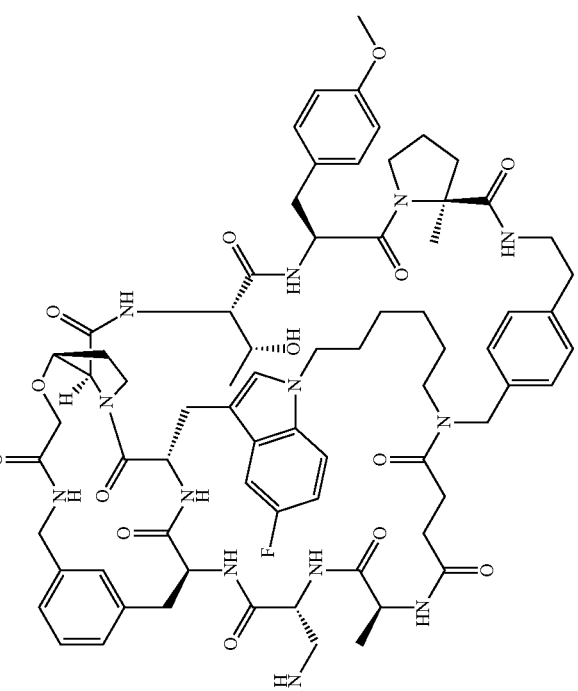 |

-continued
| Ex No | Structure |
|---|---|
| Ex-57* | 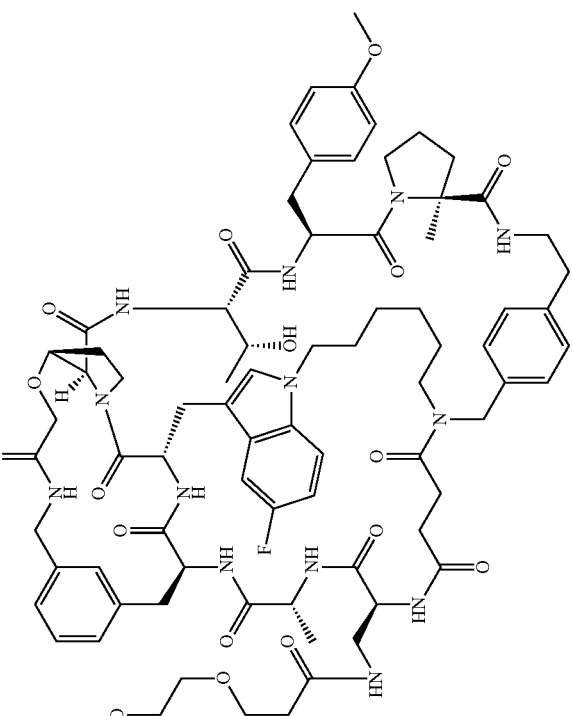 |

-continued
| Ex No | Structure |
|---|---|
| Ex-58* | 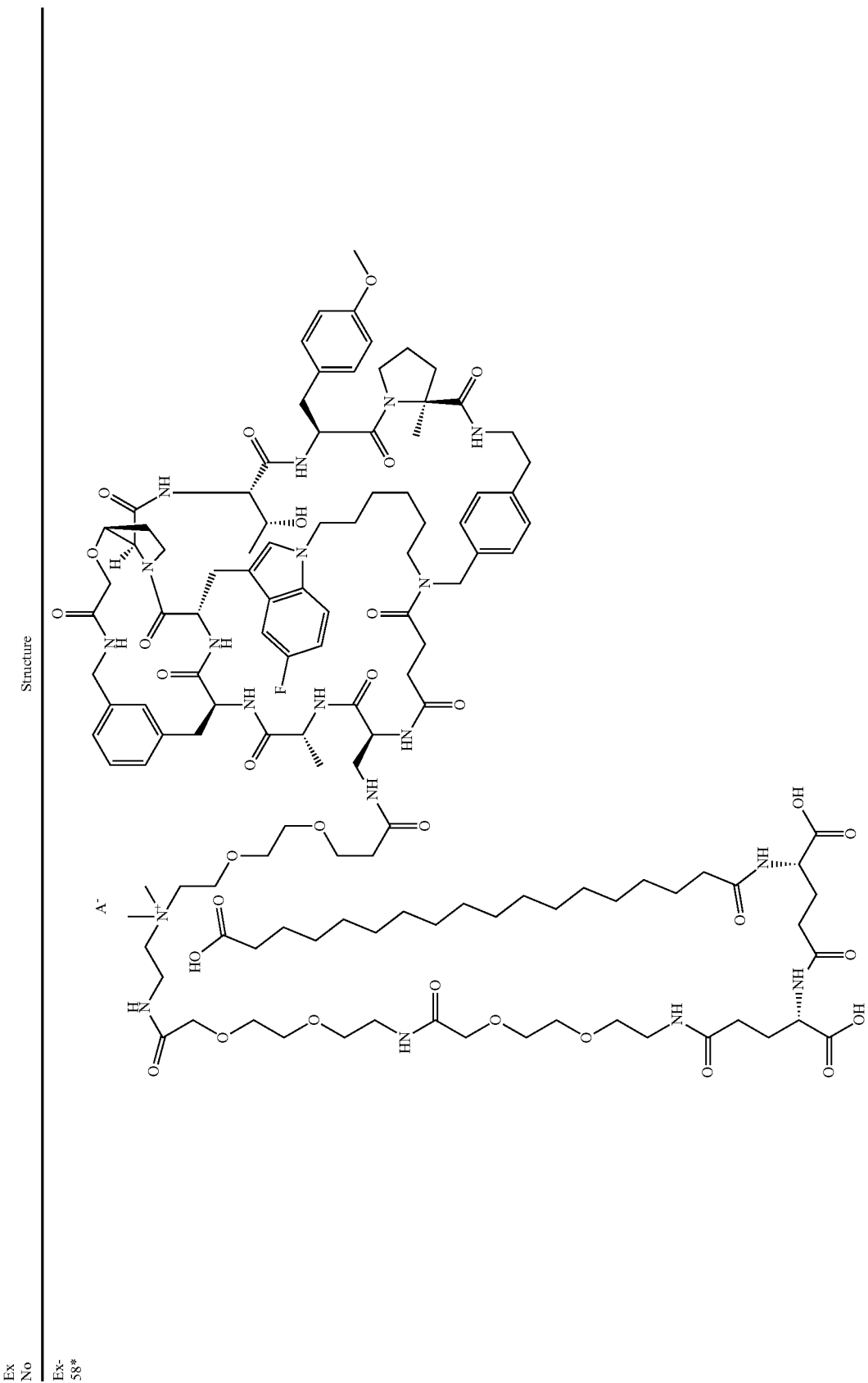 |

-continued
| Ex No | Structure |
|---|---|
| Ex-59* | 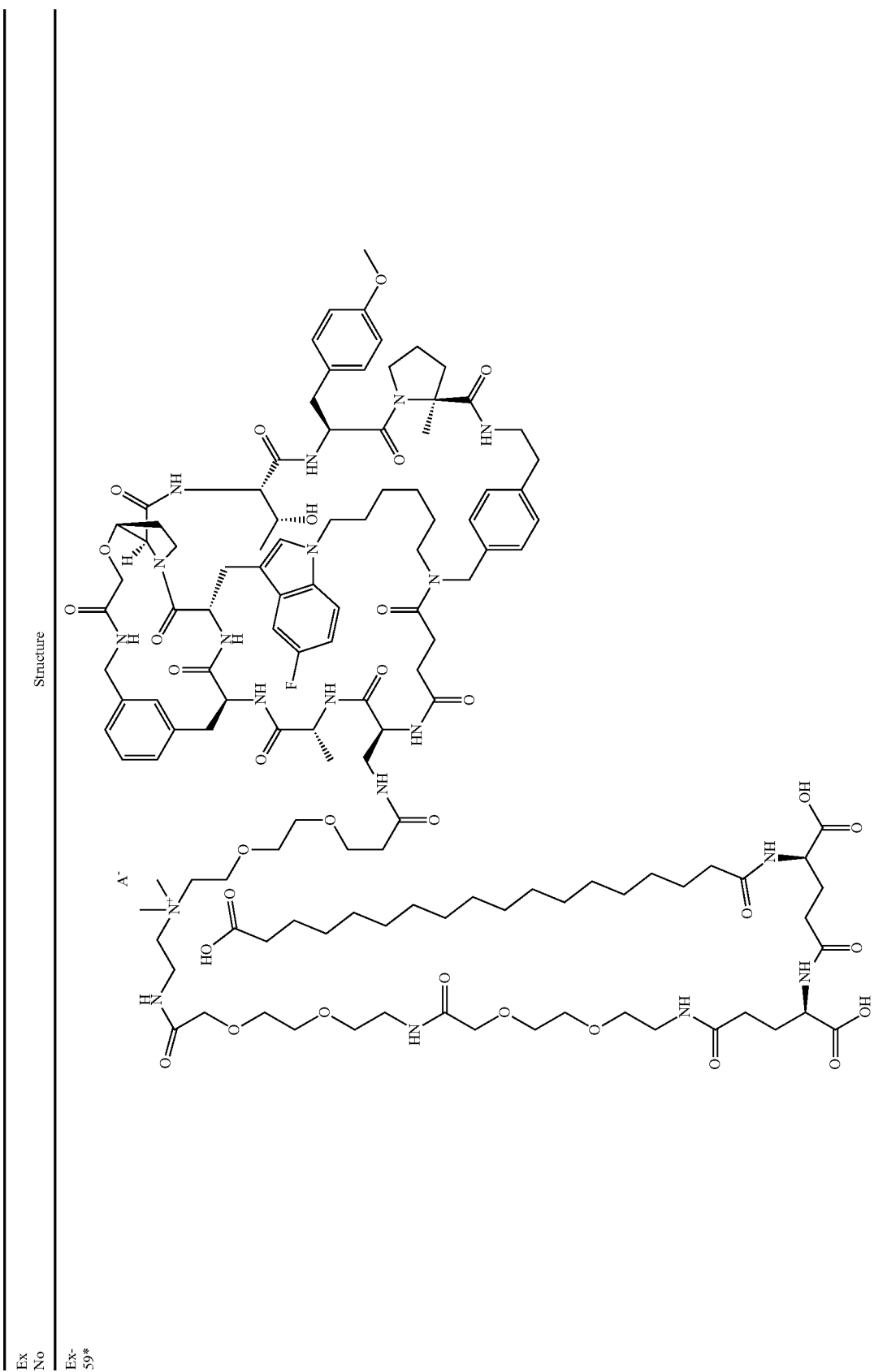 |

-continued
| Ex No | Structure |
|---|---|
| Ex-60* | 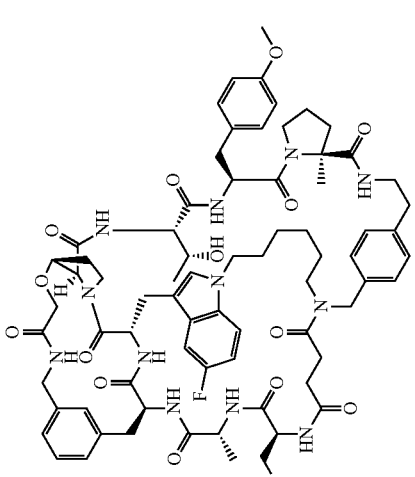 |

-continued
| Ex No | Structure |
|---|---|
| Ex-61* | 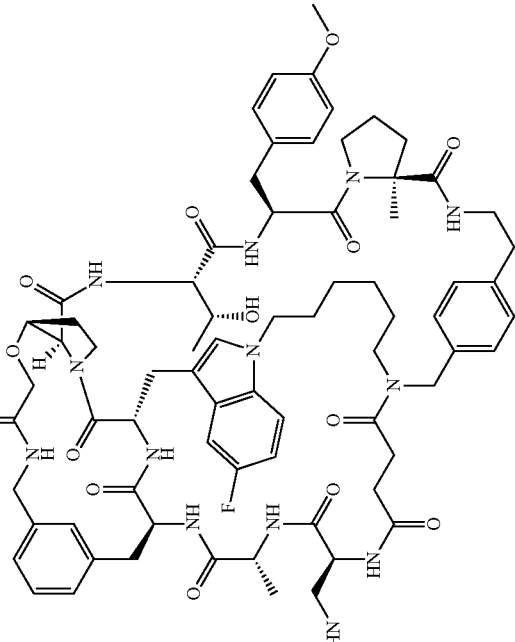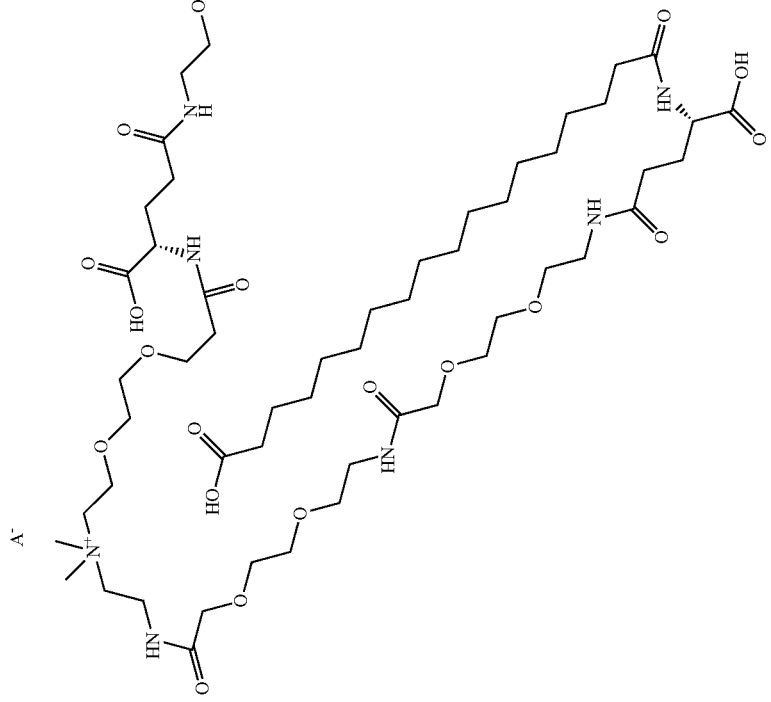 |

| Ex No | Structure |
|---|---|
| Ex-62* | 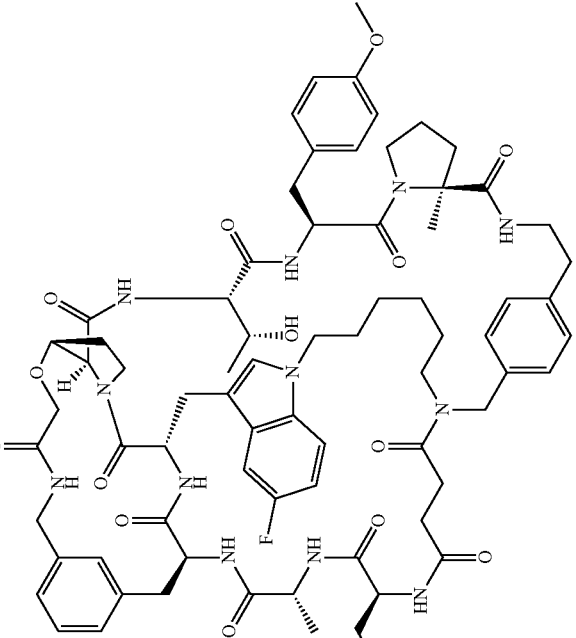 |

| Ex No | Structure |
|---|---|
| Ex-63* | 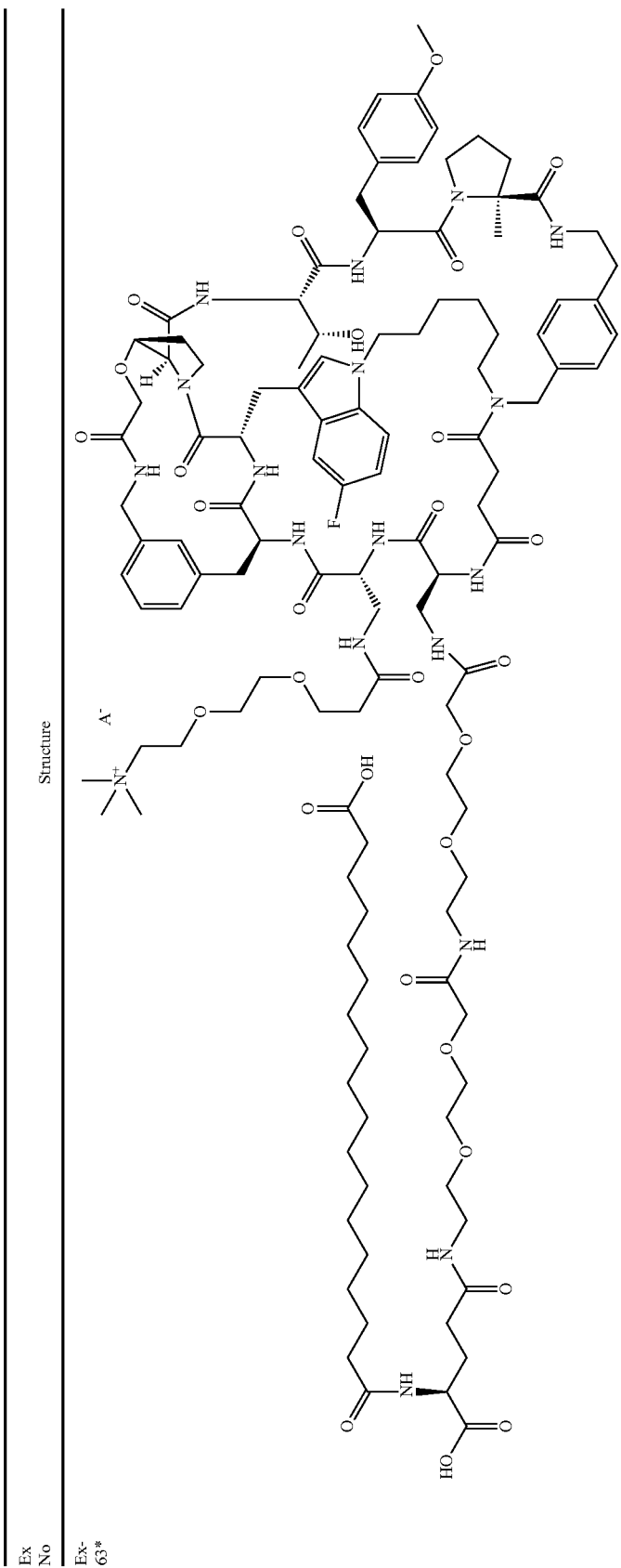 |

-continued
Structure
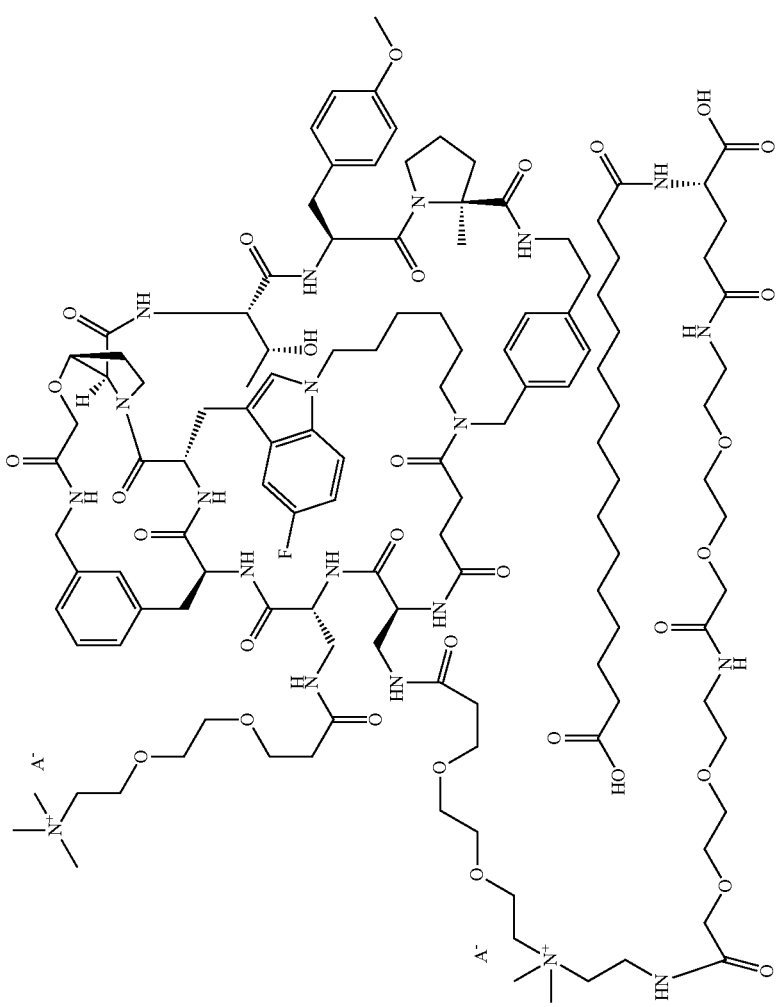
| Ex No |
|---|
| Ex-64* |

-continued
| Ex No | Structure |
|---|---|
| Ex-65 | 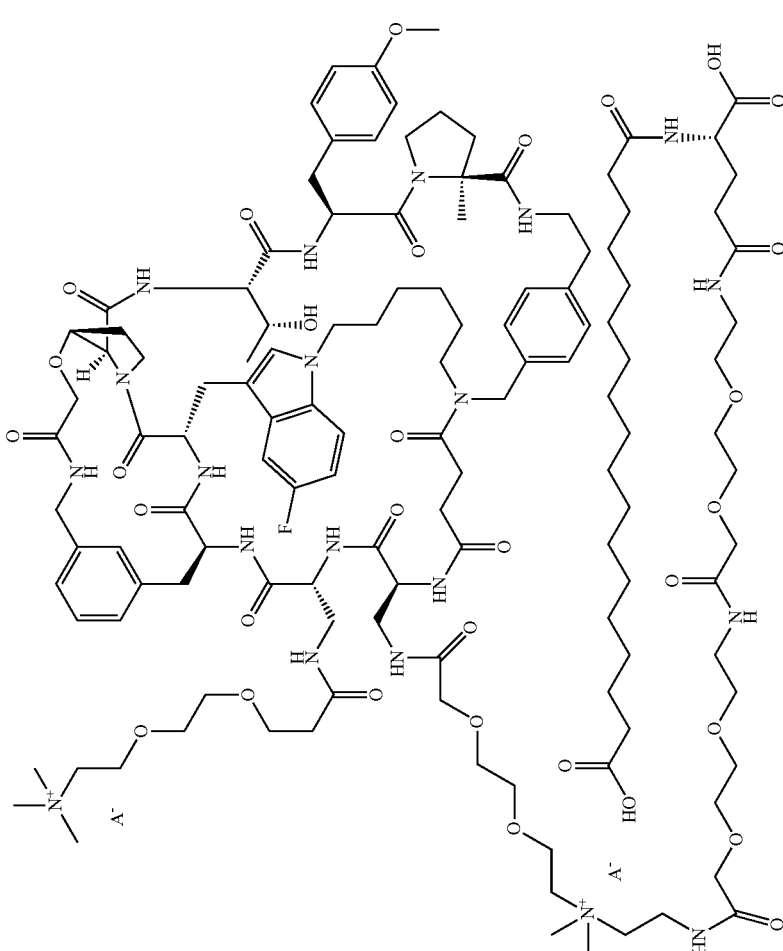 |

-continued
| Ex No | Structure |
|---|---|
| Ex-66 | 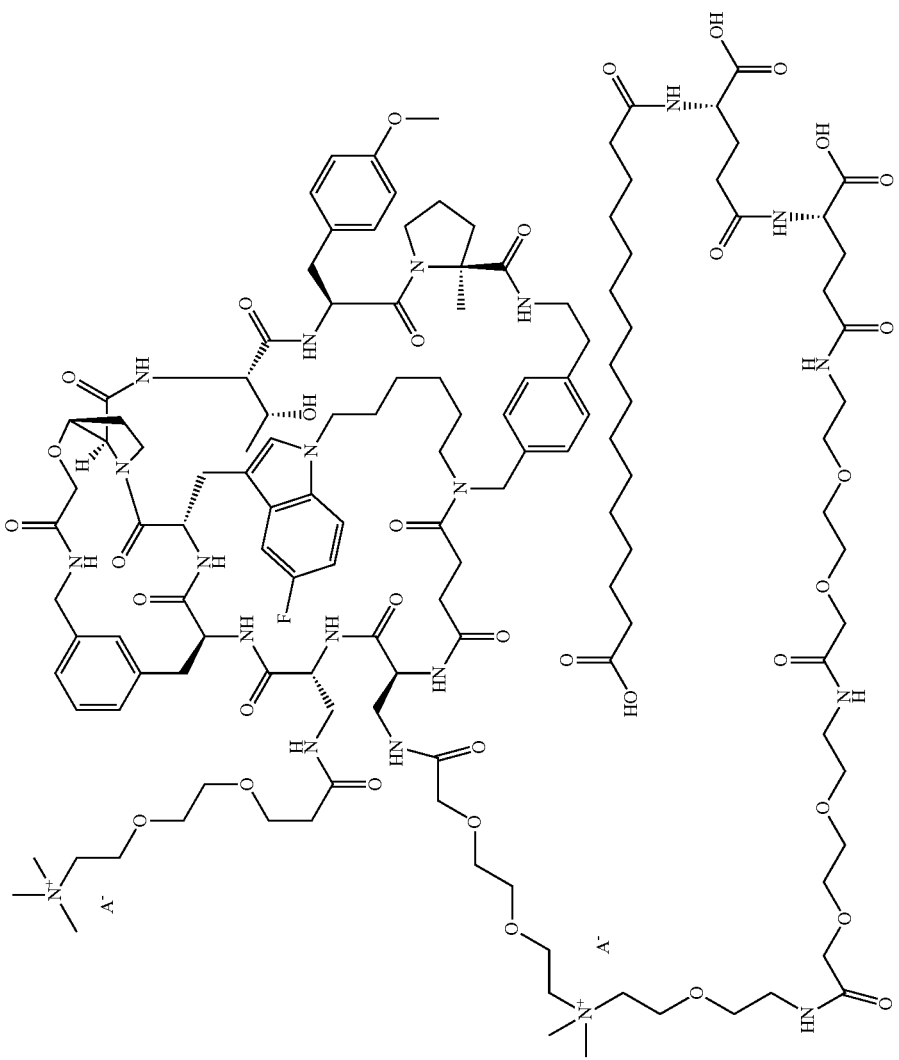 |

| Ex No | Structure |
|---|---|
| Ex-67 | 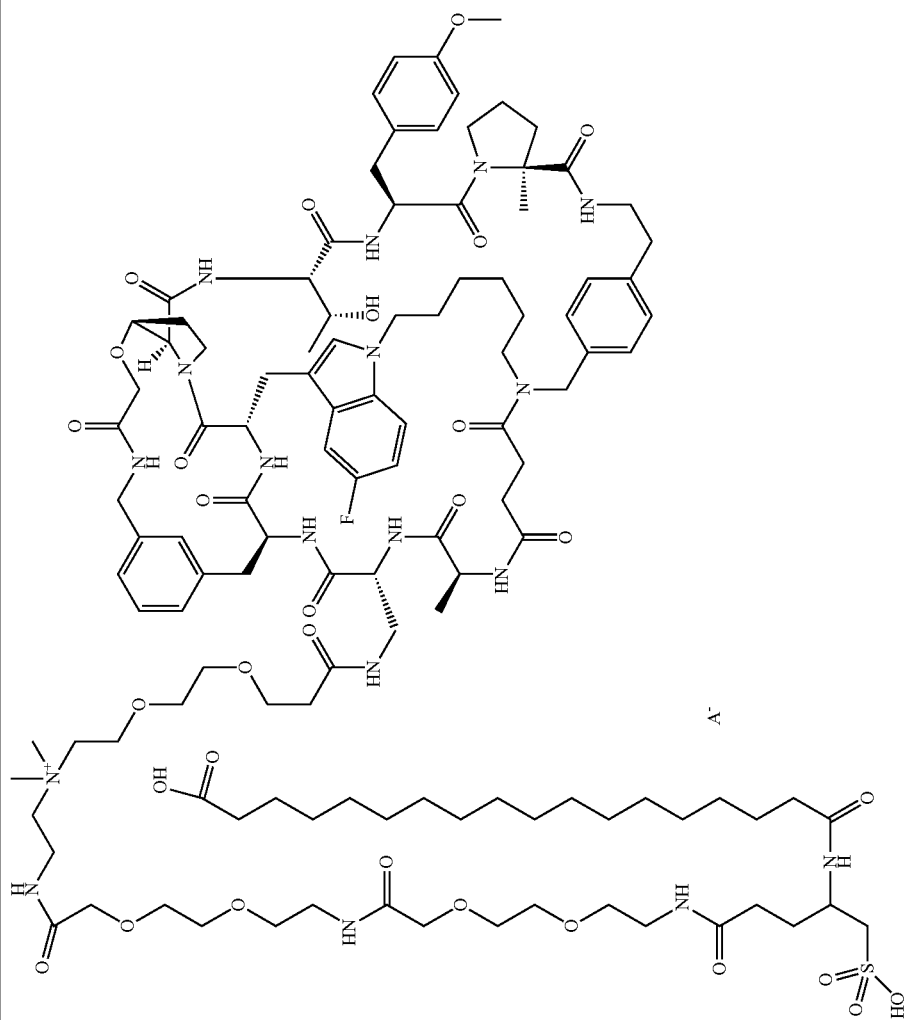 |

| Ex No | Structure |
|---|---|
| Ex-68 | 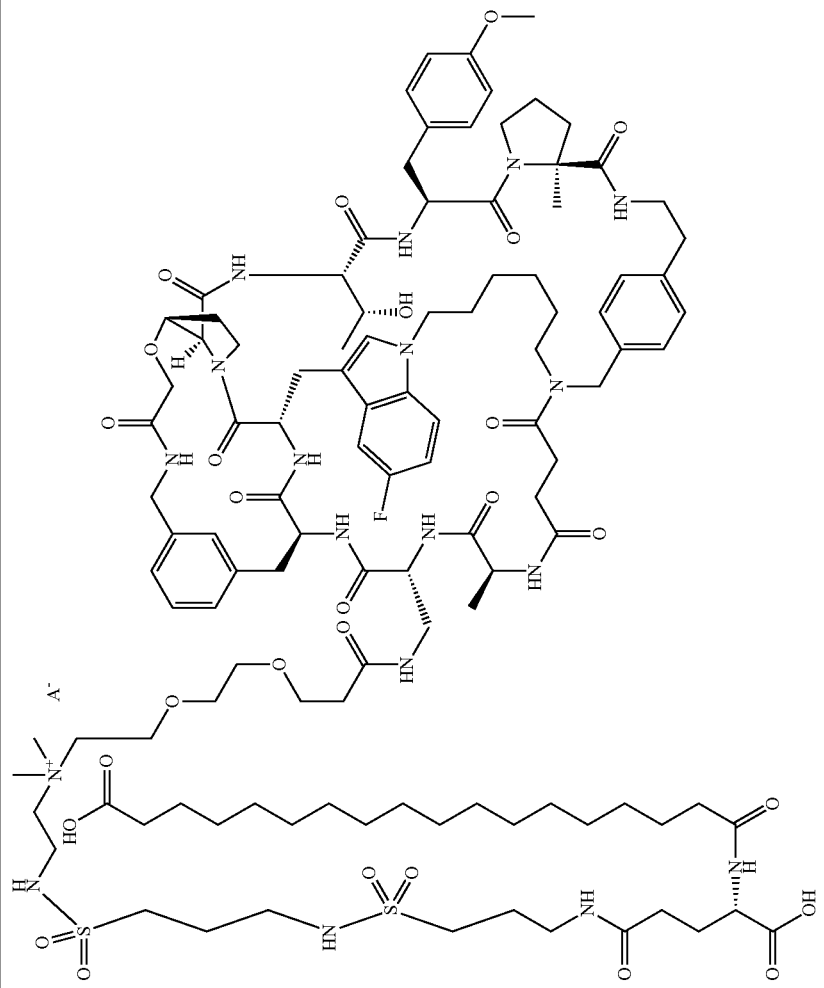 | wherein A⁻ is a pharmaceutically acceptable counter ion,
or a pharmaceutically acceptable salt thereof.

10. The method of claim 1, wherein the compound is selected from the group consisting of:

| Ex No | Structure |
|---|---|
| Ex-2 | 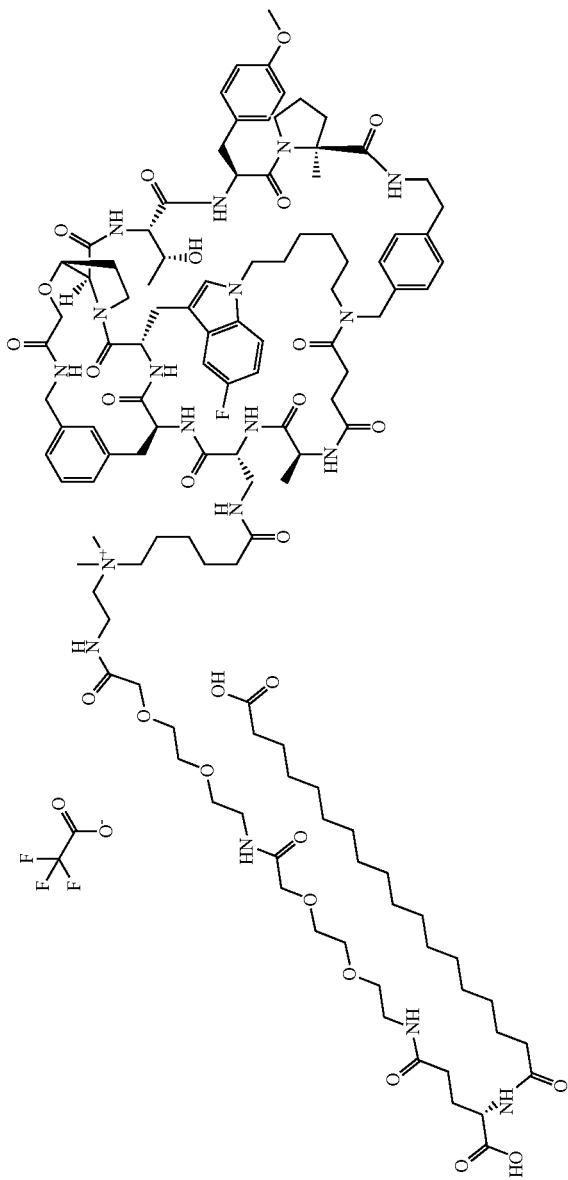 |

| Ex No | Structure |
|---|---|
| Ex-4 | 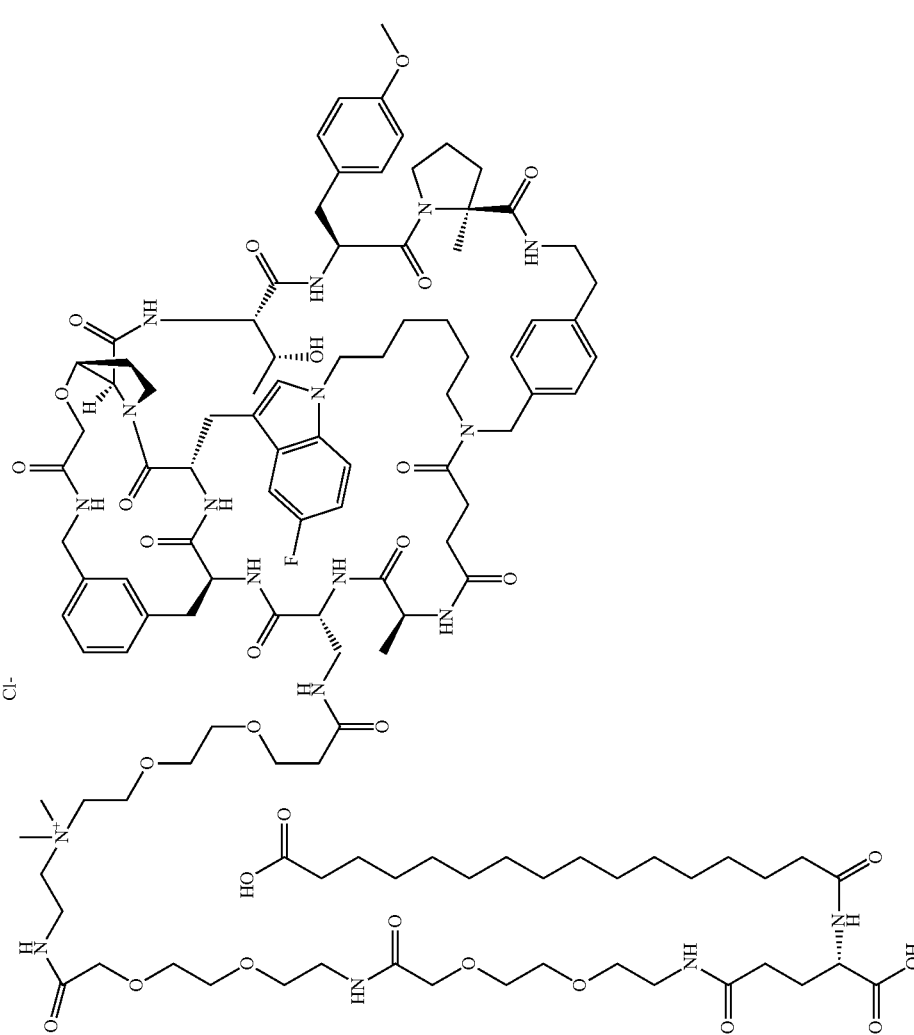 |

| Ex No | Structure |
|---|---|
| Ex-8 | 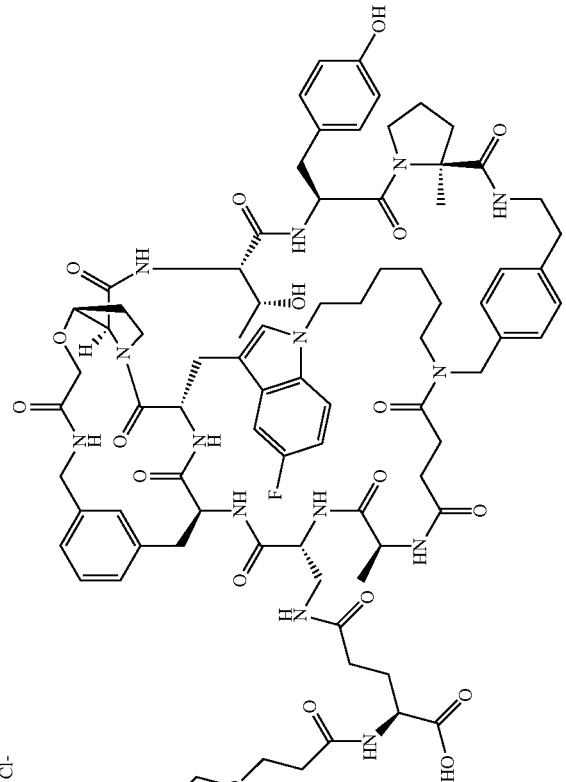 |

-continued
| Ex No | Structure |
|---|---|
| Ex-9 | 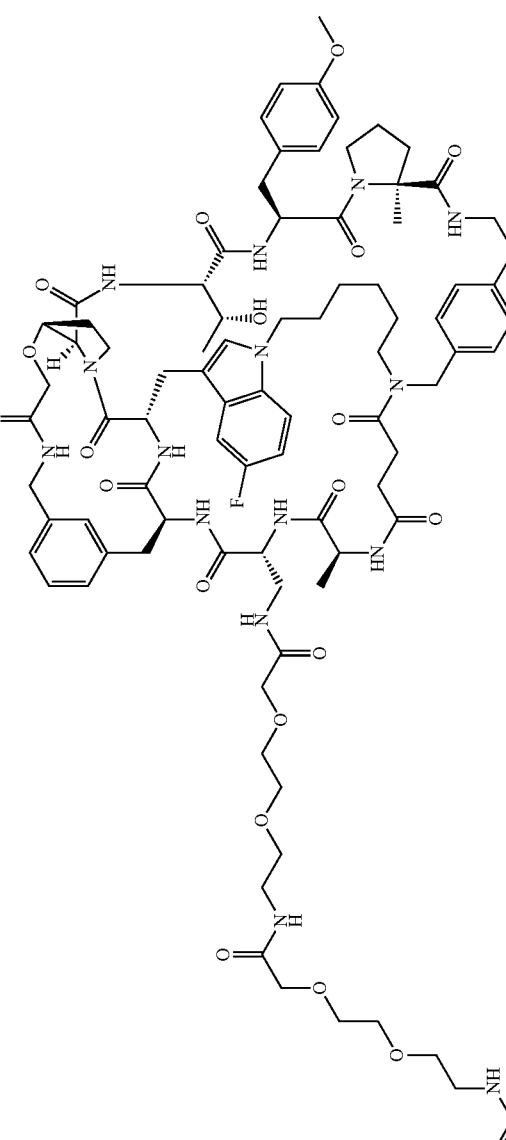 |

| Ex No | Structure |
|---|---|
| Ex-10 | 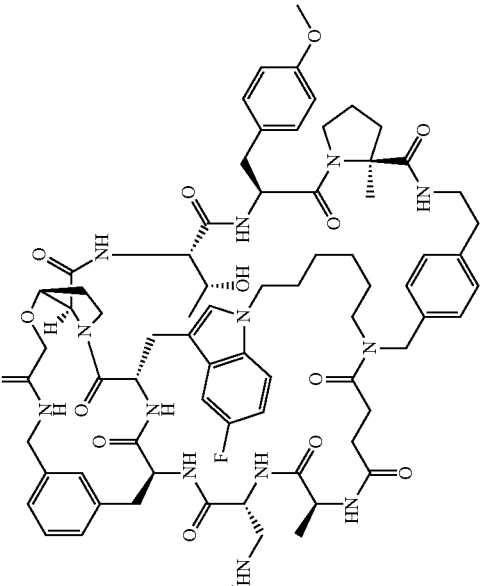 |

-continued
| Ex No | Structure |
|---|---|
| Ex-22 | 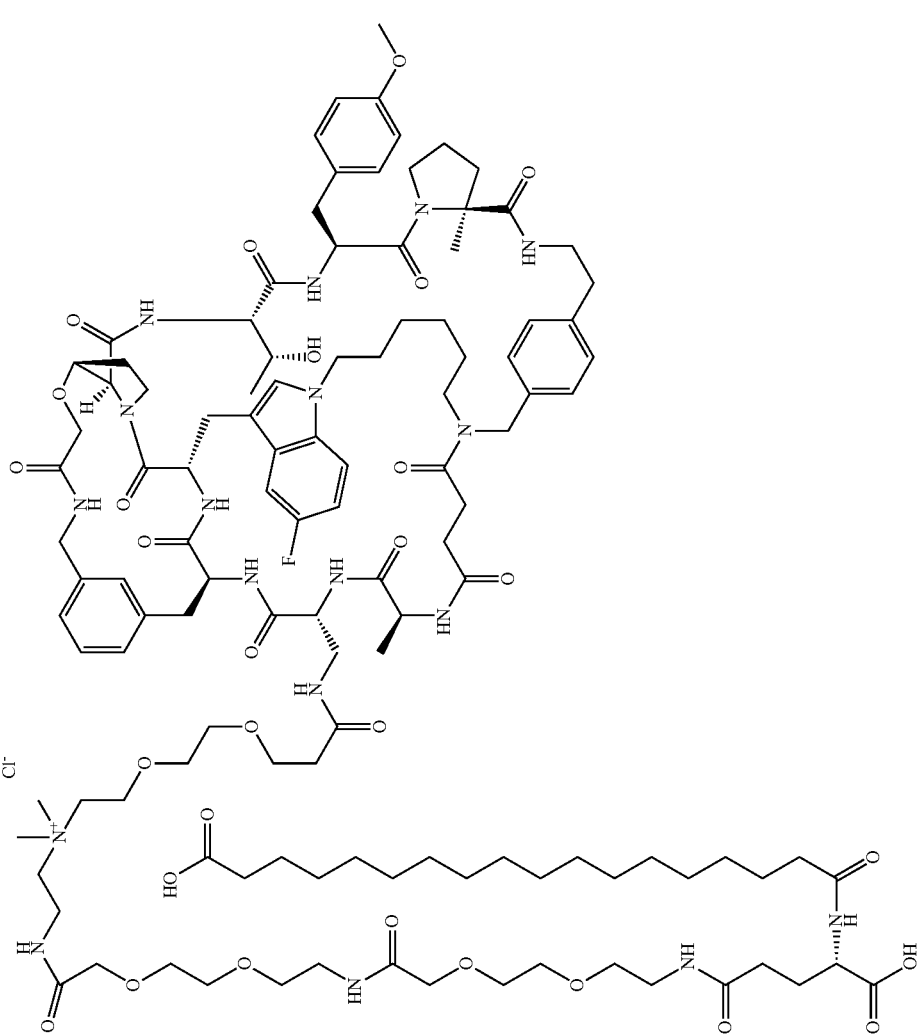 |

| Ex No | Structure |
|---|---|
| Ex-34 | 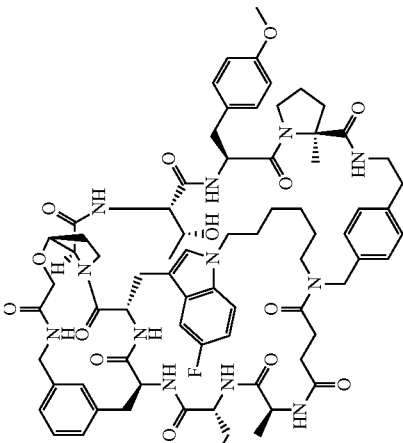 |

-continued
| Ex No | Structure |
|---|---|
| Ex-44 | 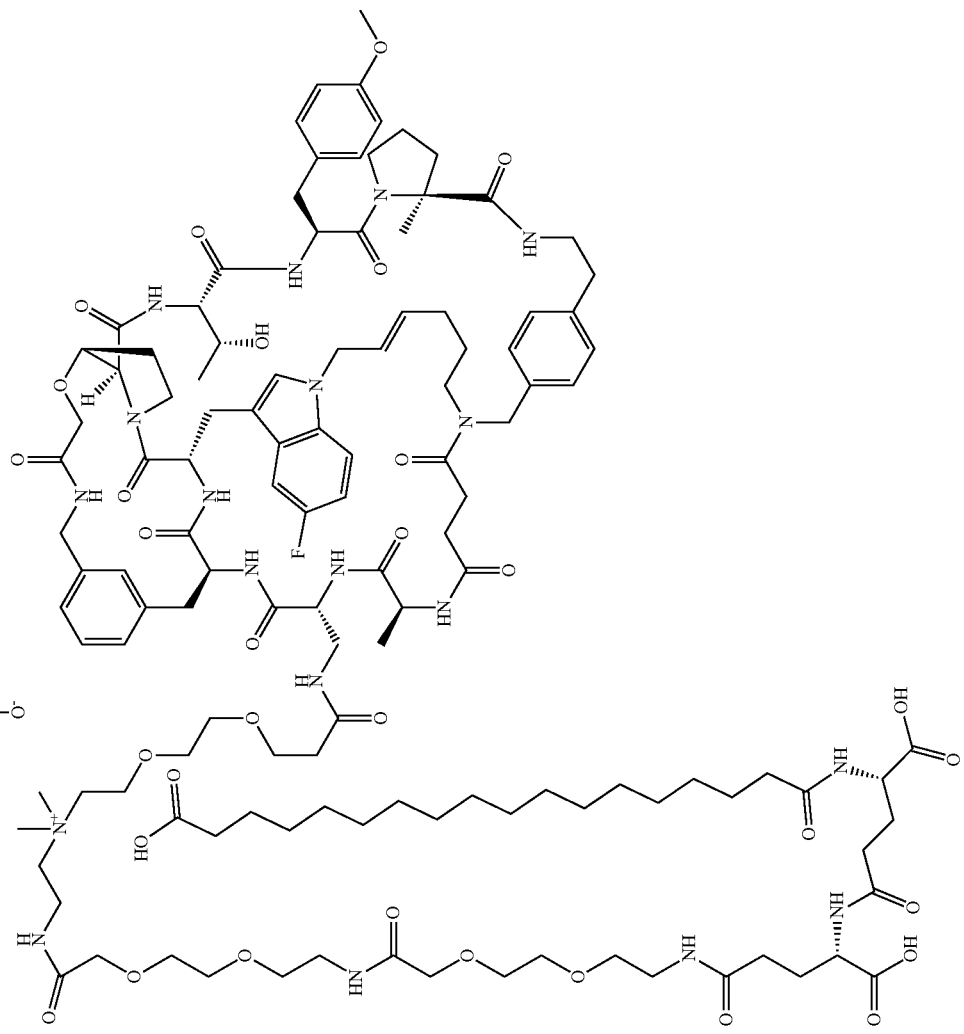 |

| Ex No | Structure |
|---|---|
| Ex-48 | 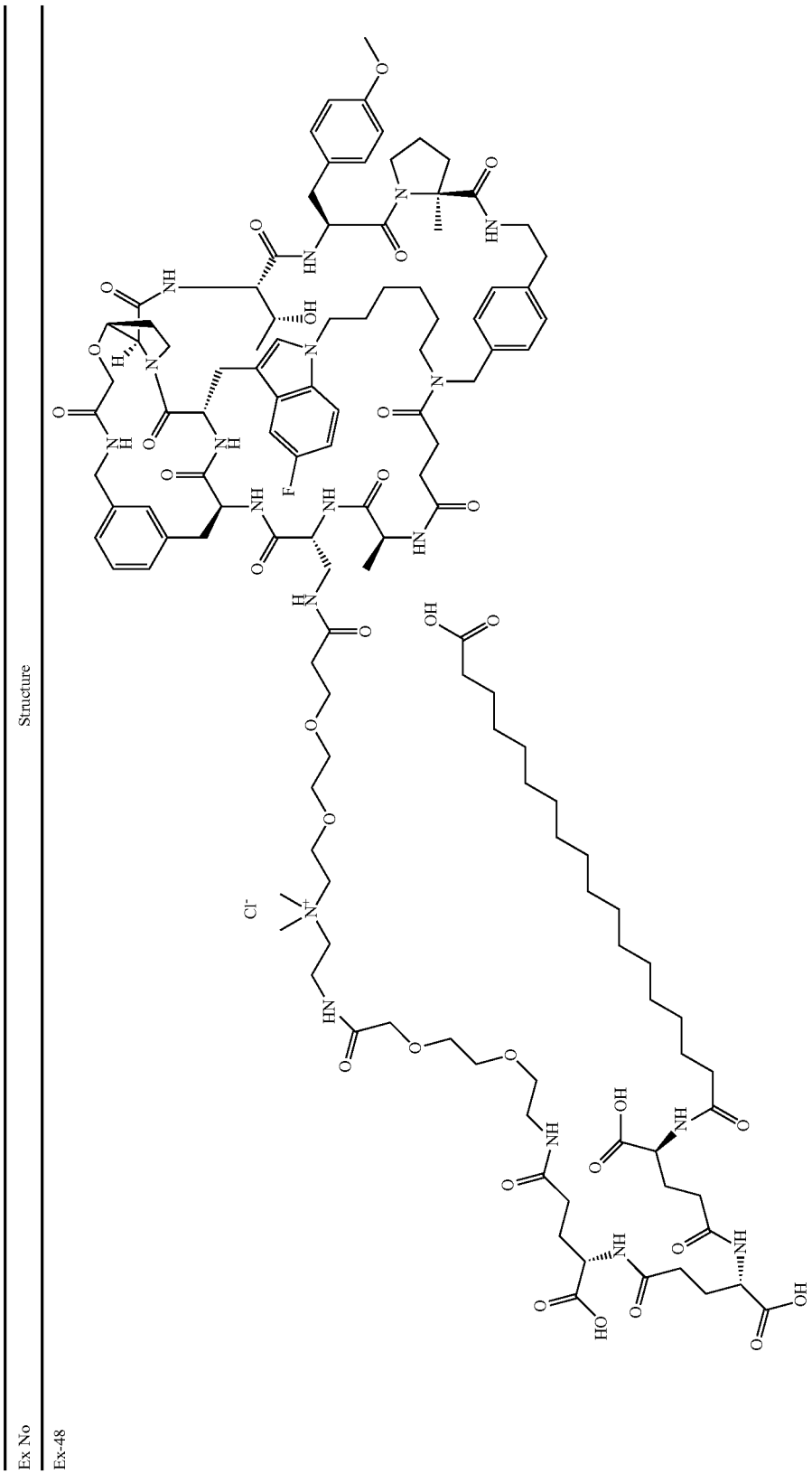 |

| Ex No | Structure |
|---|---|
| Ex-49 | *-continued* chemical structure |

| Ex No | Structure |
|---|---|
| Ex-58 | -continued | or a pharmaceutically acceptable salt thereof.

11. The method of claim 10, wherein the compound is selected from the group consisting of:

| Ex No | Structure |
|---|---|
| Ex-4 | 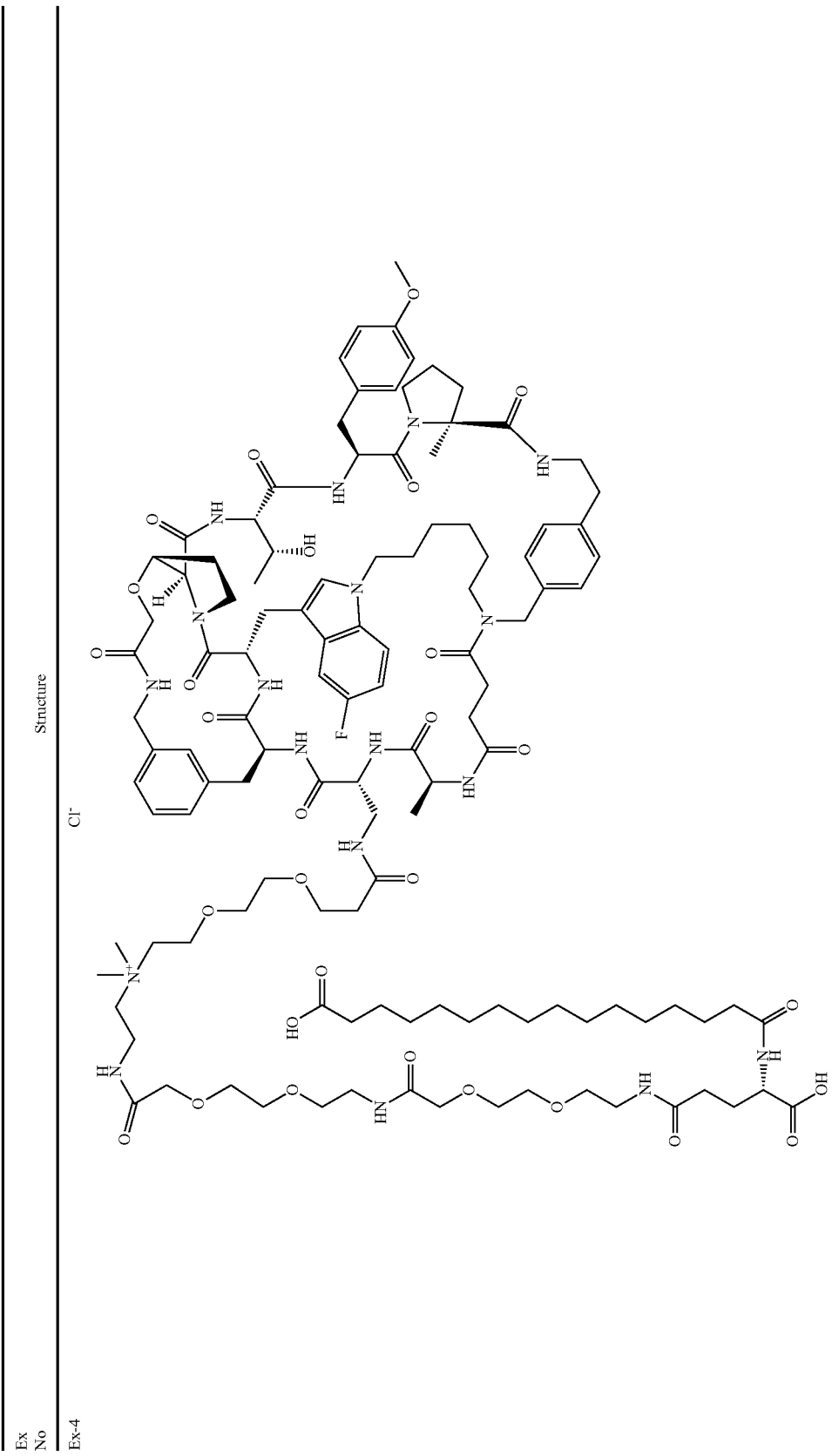 Cl⁻ |

-continued
| Ex No | Structure |
|---|---|
| Ex-8 | 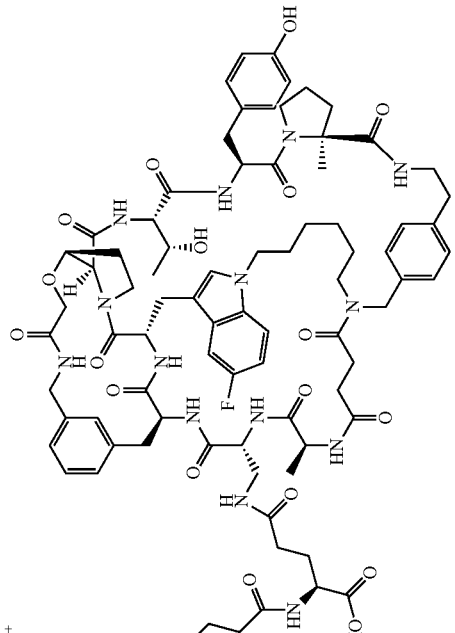 |

| Ex No | Structure |
|---|---|
| Ex-9 | 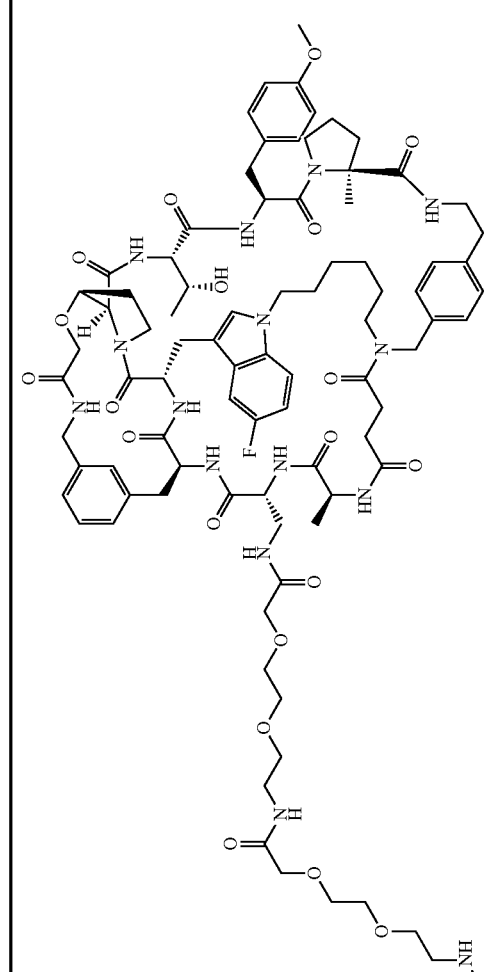 |

| Ex No | Structure |
|---|---|
| Ex-10 | 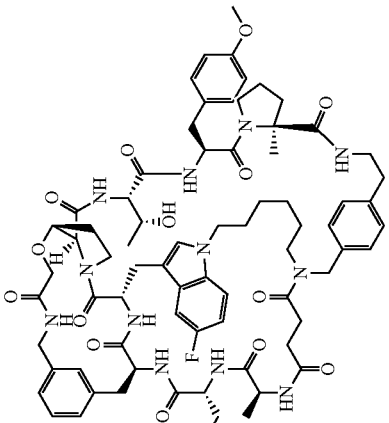 |

| Ex No | Structure |
|---|---|
| Ex-22 | *-continued* |

-continued
| Ex No | Structure |
|---|---|
| Ex-34 | 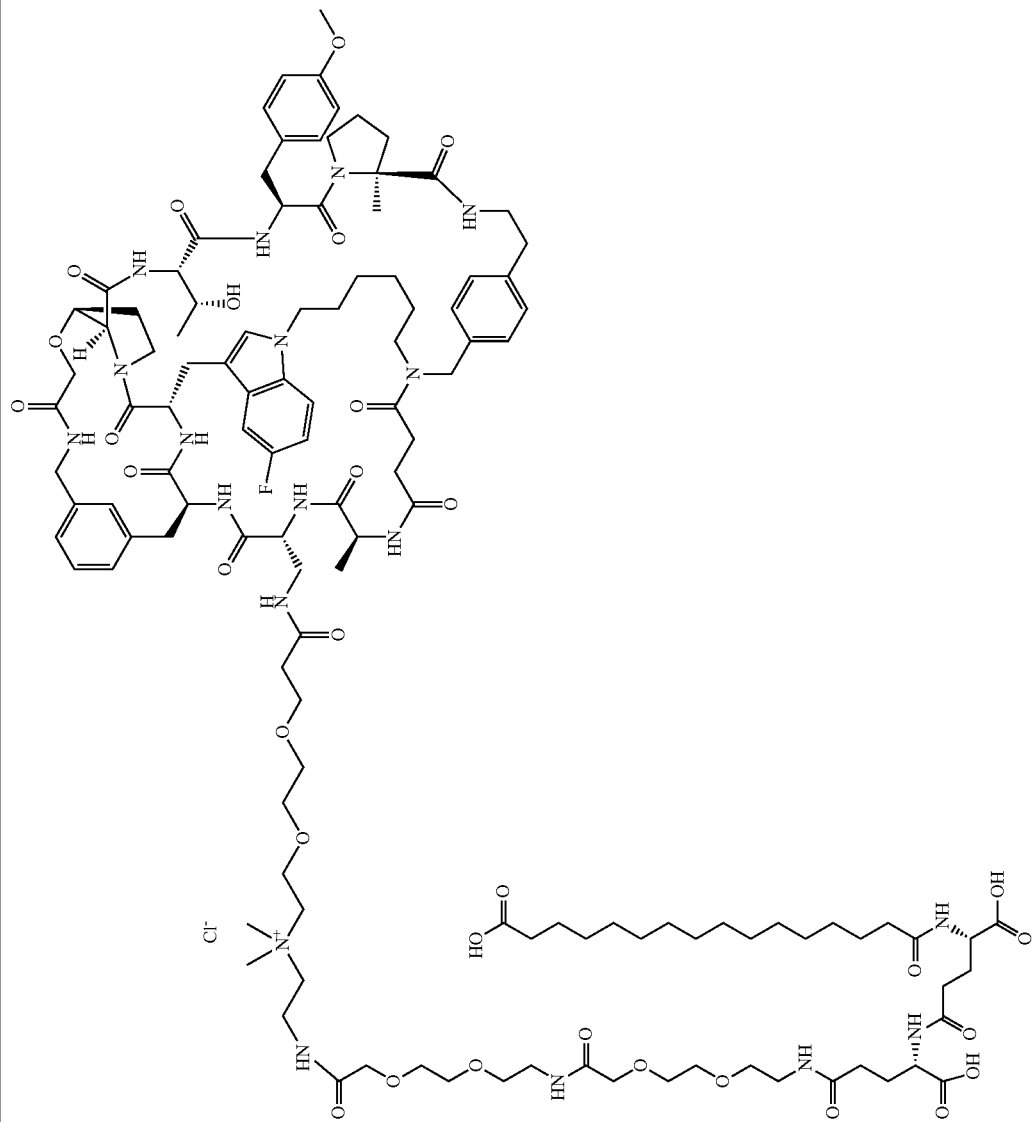 |

| Ex No | Structure |
|---|---|
| Ex-48 | -continued |

| Ex No | Structure |
|---|---|
| Ex-49 | 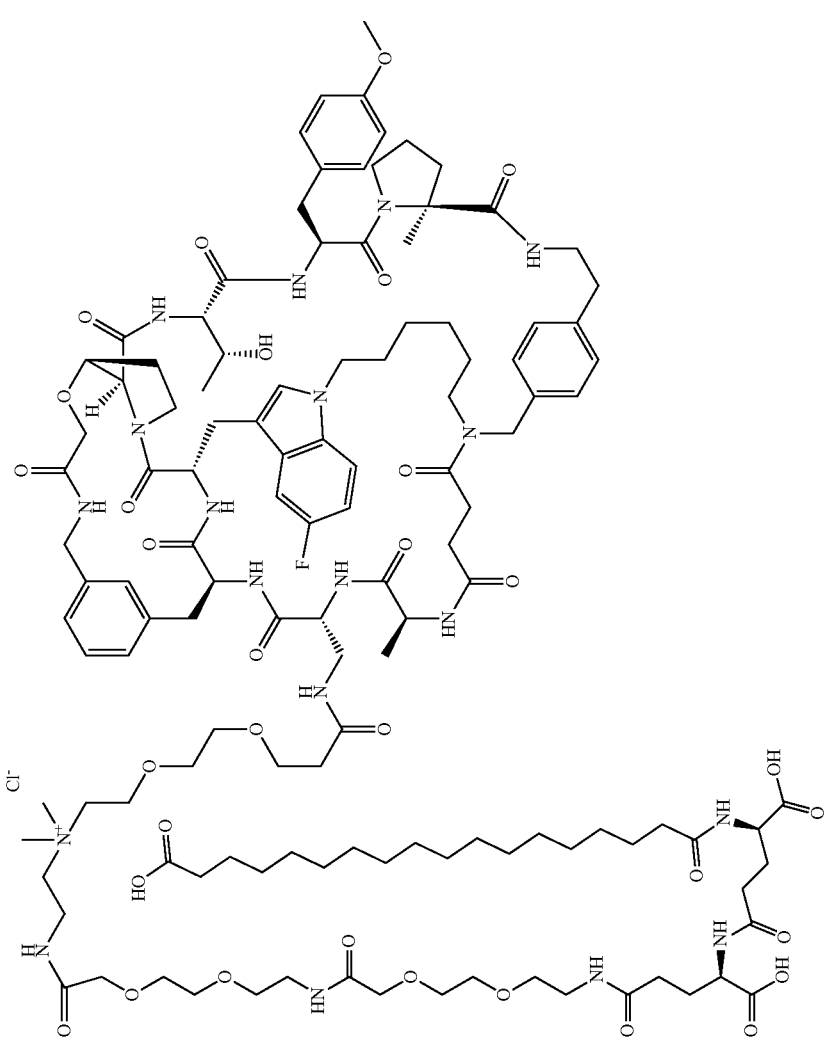 | or a pharmaceutically acceptable salt thereof.

12. A method of treating hypercholesterolemia, comprising administering to a patient in need thereof a therapeutically effective amount of a composition comprising at least one compound of claim 1, or a pharmaceutically acceptable salt thereof or freebase form thereof, and at least one pharmaceutically acceptable excipient.

13. The method of claim 1, wherein the compound has the structure:

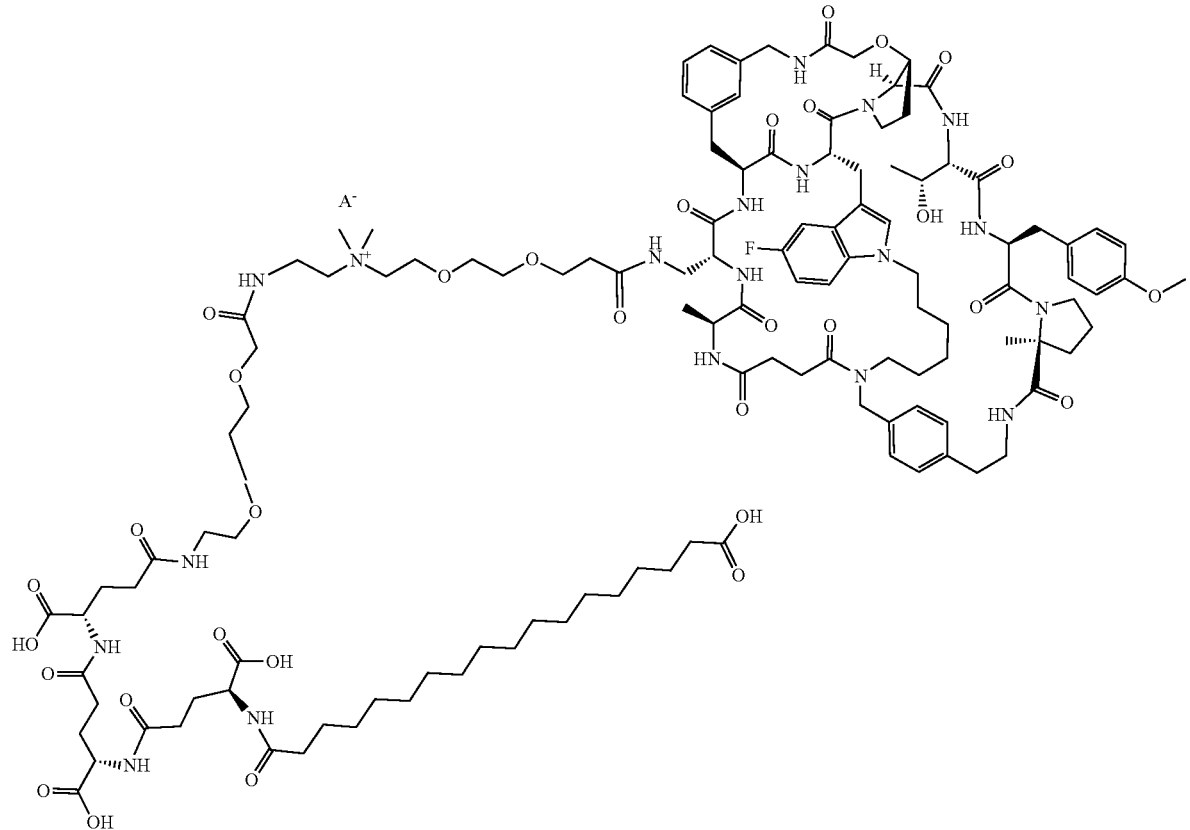

wherein A− is a pharmaceutically acceptable counter ion, or a pharmaceutically acceptable salt thereof.

14. The method of claim 13, wherein the compound is:

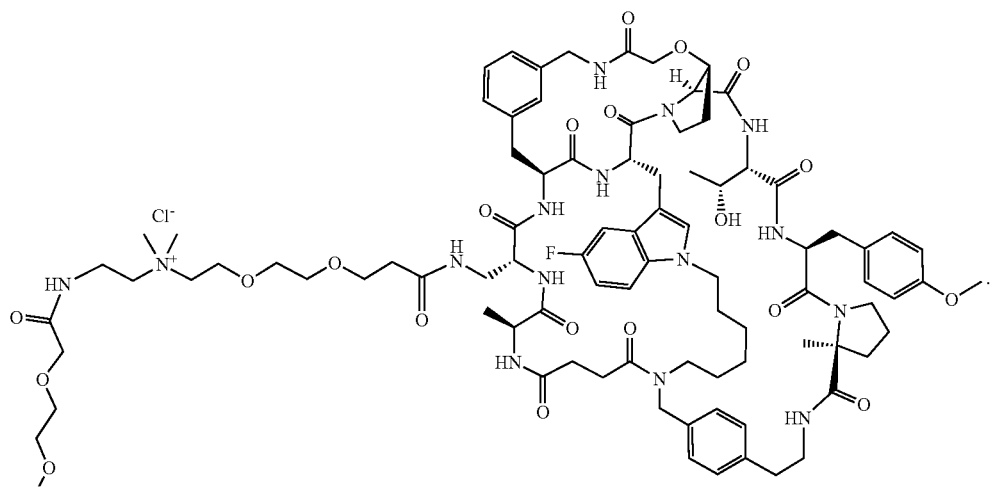

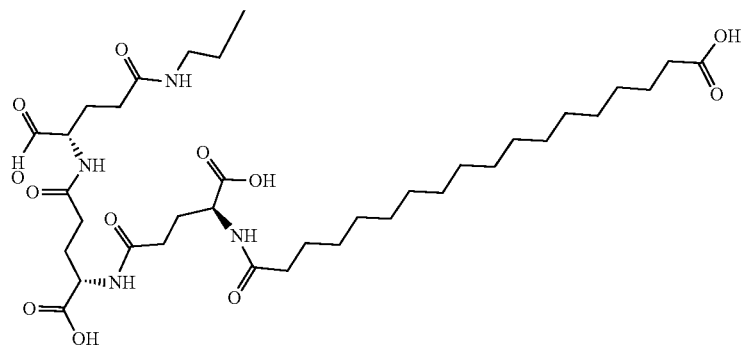
15. The method of claim 1, wherein the compound has the structure:
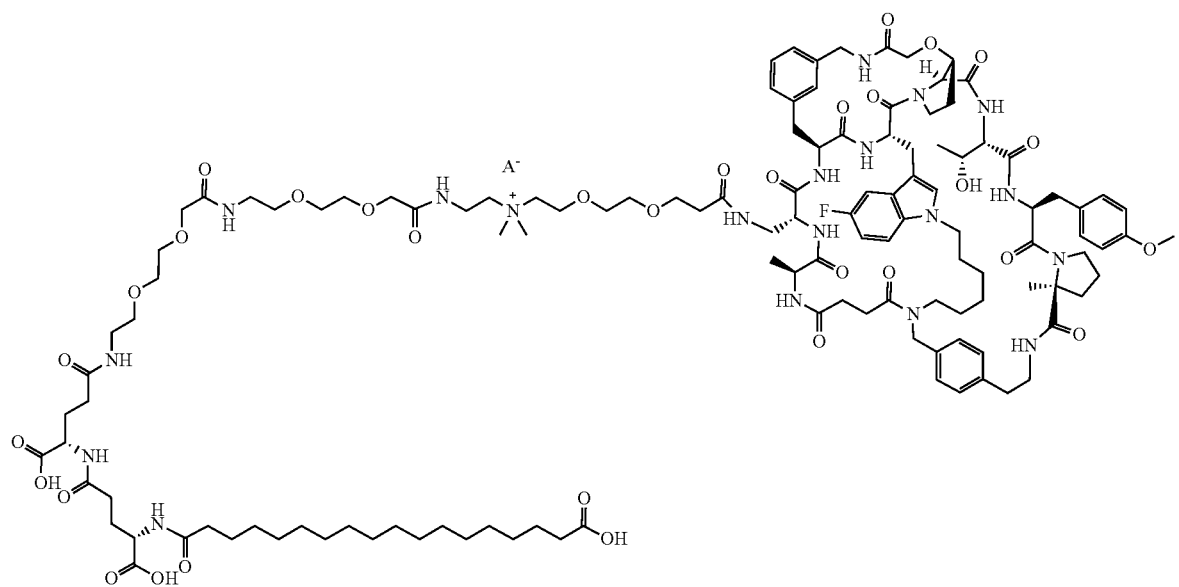
wherein A− is a pharmaceutically acceptable counter ion, or a pharmaceutically acceptable salt thereof.

16. The method of claim 15, wherein the compound is:
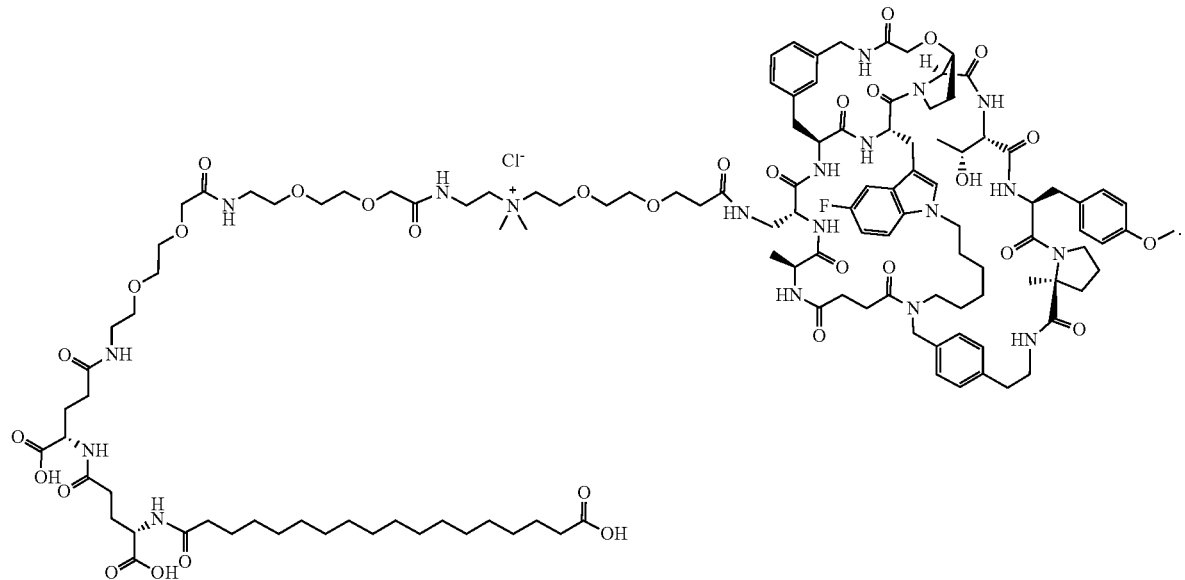 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCOCCOCC[N+](C)(C)CCNC(=O)COCCOCCNC(=O)COCCOCCNC(=O)CC[C@H](NC(=O)CC[C@H](NC(=O)CCCCCCCCCCCCCCCCC(=O)O)C(=O)O)C(=O)O)C(=O)N[C@@H](Cc2cccc(c2)CNC(=O)CO4)C(=O)N3)cc1 ; [Cl-]]
17. The method of claim 1, wherein the compound has the structure:
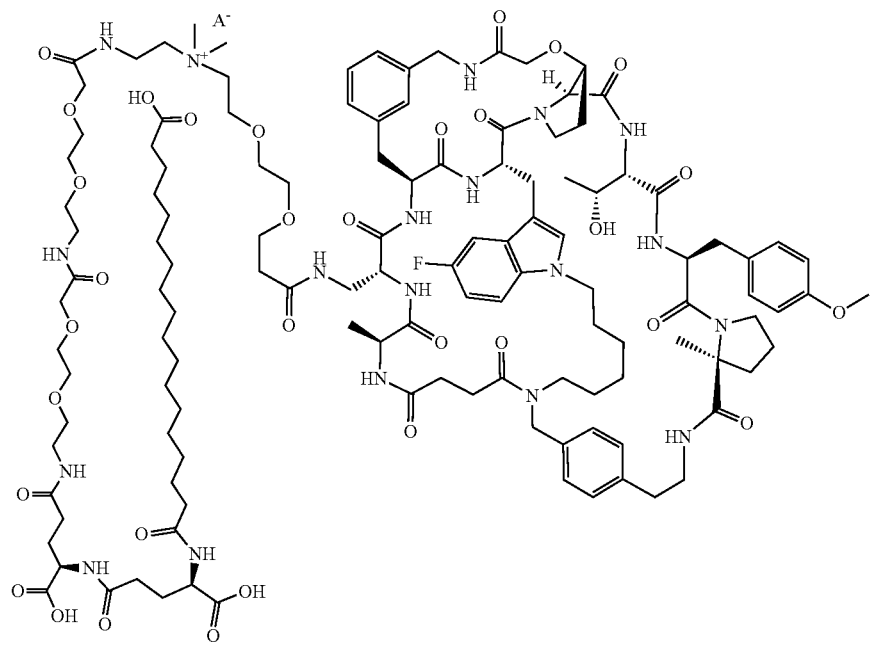
wherein A− is a pharmaceutically acceptable counter ion, or a pharmaceutically acceptable salt thereof.